US008222483B2

(12) United States Patent
Brugiere et al.

(10) Patent No.: US 8,222,483 B2
(45) Date of Patent: Jul. 17, 2012

(54) CYTOKININ OXIDASE SEQUENCES AND METHODS OF USE

(75) Inventors: Norbert Brugiere, Johnston, IA (US); Jeffrey E Habben, Urbandale, IA (US)

(73) Assignee: Pioneer Hi Bred International Inc, Johnston, IA (US)

( * ) Notice: Subject to any disclaimer, the term of this patent is extended or adjusted under 35 U.S.C. 154(b) by 543 days.

(21) Appl. No.: 12/165,935

(22) Filed: Jul. 1, 2008

(65) Prior Publication Data

US 2009/0165174 A1 Jun. 25, 2009

Related U.S. Application Data

(63) Continuation-in-part of application No. 11/094,917, filed on Mar. 31, 2005, now abandoned.

(60) Provisional application No. 60/559,252, filed on Apr. 2, 2004.

(51) Int. Cl.
*C12N 15/29* (2006.01)
*C12N 15/82* (2006.01)
*A01H 5/00* (2006.01)
*A01H 5/10* (2006.01)

(52) U.S. Cl. ...................................................... 800/278

(58) Field of Classification Search ........................ None
See application file for complete search history.

(56) References Cited

U.S. PATENT DOCUMENTS

| 6,229,066 B1 | 5/2001 | Morris |
| 6,310,271 B1 * | 10/2001 | Hanson et al. ................ 800/278 |
| 6,617,497 B1 | 9/2003 | Morris |
| 7,259,296 B2 * | 8/2007 | Schmulling et al. ........... 800/298 |
| 2002/0152500 A1 | 10/2002 | Niu et al. |
| 2003/0074698 A1 * | 4/2003 | Schmulling et al. ........... 800/287 |
| 2003/0163847 A1 | 8/2003 | Huang et al. |
| 2004/0031073 A1 | 2/2004 | Schmulling et al. |

FOREIGN PATENT DOCUMENTS

| WO | 0063401 | 10/2000 |
| WO | 0196580 | 12/2001 |
| WO | 03050287 | 6/2003 |

OTHER PUBLICATIONS

Bowie et al, Science 247:1306-1310, 1990.*
McConnell et al, Nature 411 (6838):709-713, 2001.*
Whitelaw et al (2003, NCBI Accession No. BZ709659).*
Houba-Herin, N., et al.; "Cytokinin oxidase from *Zea mays*: purification, cDNA cloning and expression in moss protoplasts"; The Plant Journal (1999) 17(6):615-626; Blackwell Publishing, Ltd.; Oxford, UK.
Bilyeu, K.D., et al.; "Molecular and Biochemical Characterization of a Cytokinin Oxidase from Maize"; Plant Physiology (Jan. 2001) 125:378-386; American Society of Plant Biologists (ASPB); Rockville, MD, US.
Werner, T., et al.; "Regulation of plant growth by cytokinin" PNAS (Aug. 28, 2001) 98(18):10487-10492; National Academy of Sciences; Washington, DC, US.
Bilyeu, K.D., et al.; "Dynamics of expression and distribution of cytokinin oxidase/dehydrogenase in developing maize kernels"; Plant Growth Regulation (2003) 39:195-203; Springer, The Netherlands.
Brugiere, N., et al.; "Cytokinin Oxidase Gene Expression in Maize is Localized to the Vasculature, and Is Induced by Cytokinins, Abscisic Acid, and Abiotic Stress"; Plant Physiology (Jul. 2003) 132:1228-1240; American Society of Plant Biologists (ASPB); Rockville, MD, US.
Werner, T., et al.; "Cytokinin-Deficient Transgenic *Arabidopsis* Plants Show Multiple Development Alterations Indicating Opposite Functions of Cytokinins in the Regulation of Shoot and Meristem Activity"; The Plant Cell (2003) 15:2532-2550; American Society of Plant Physiologists; Rockville, MD, US.
Buell, C.R., et al.; EMBL Accession No. Q8LNV6 (2002) "*Oryza sativa* putative cytokinin oxidase".
Houba-Herin, N., et al.; EMBL Accession No. AJ606942 (2003) "*Zea mays* mRNA for cytokinin oxidase 2."
Houba-Herin, N., et al.; (2001) Abstract No. 437; "Why So Many Cytokinins in Plants?"; 17th International Conference on Plant Growth Substances, Brno, Czech Republic.
Schmulling, T., et al.; (2003) "Structure and function of cytokinin oxidase/dehyrogenase genes of maize, rice, *Arabidopsis*, and other species"; J. Plant Res. 116:241-252; Springer, Japan.
Meilan, R. et al.; "Cloning the cytokinin oxidase gene"; Plant Physiology (1994) 105(S):68; American Society of Plant Biologists (ASPB); Rockville, MD, US.
Massoneau, et al.; NCBI Accession No. AJ606943 (2003) "*Zea mays* mRNA for cytokinin oxidase 3".

* cited by examiner

*Primary Examiner* — Stuart F. Baum
(74) *Attorney, Agent, or Firm* — Pioneer Hi-Bred Int'l Inc.

(57) ABSTRACT

Methods and compositions for modulating plant development are provided. Polynucleotide sequences and amino acid sequences encoding cytokinin oxidase polypeptides are provided. The sequences can be used in a variety of methods including modulating root development, modulating floral development, modulating leaf and/or shoot development, modulating seed size and/or weight, modulating tolerance under abiotic stress, and modulating resistance to pathogens. Polynucleotides comprising CKX promoters are also provided. The promoters can be used to regulate expression of a sequence of interest. Transformed plants, plant cells, tissues, and seed are also provided.

12 Claims, 58 Drawing Sheets

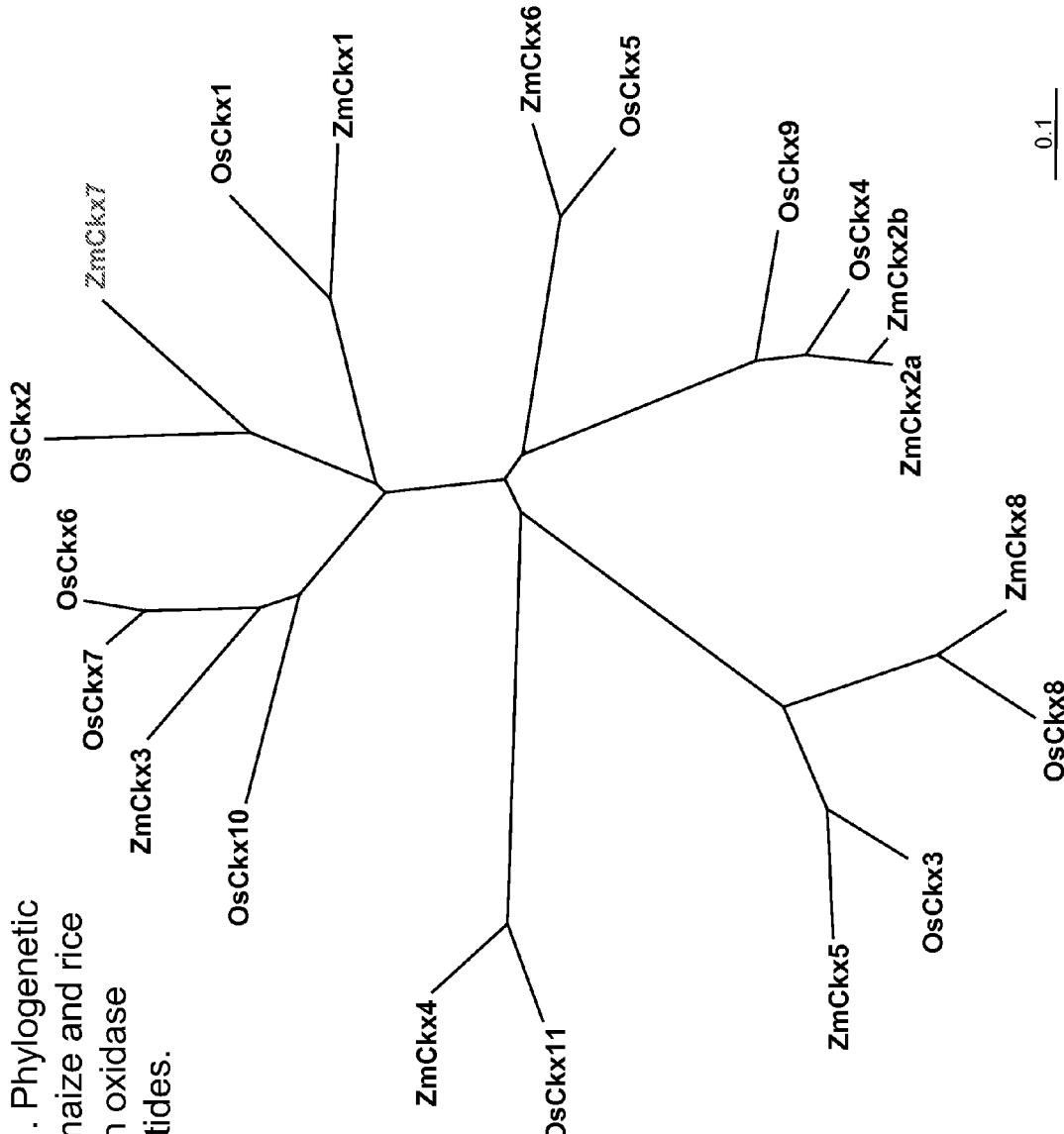
Figure 1. Phylogenetic tree of maize and rice cytokinin oxidase polypeptides.

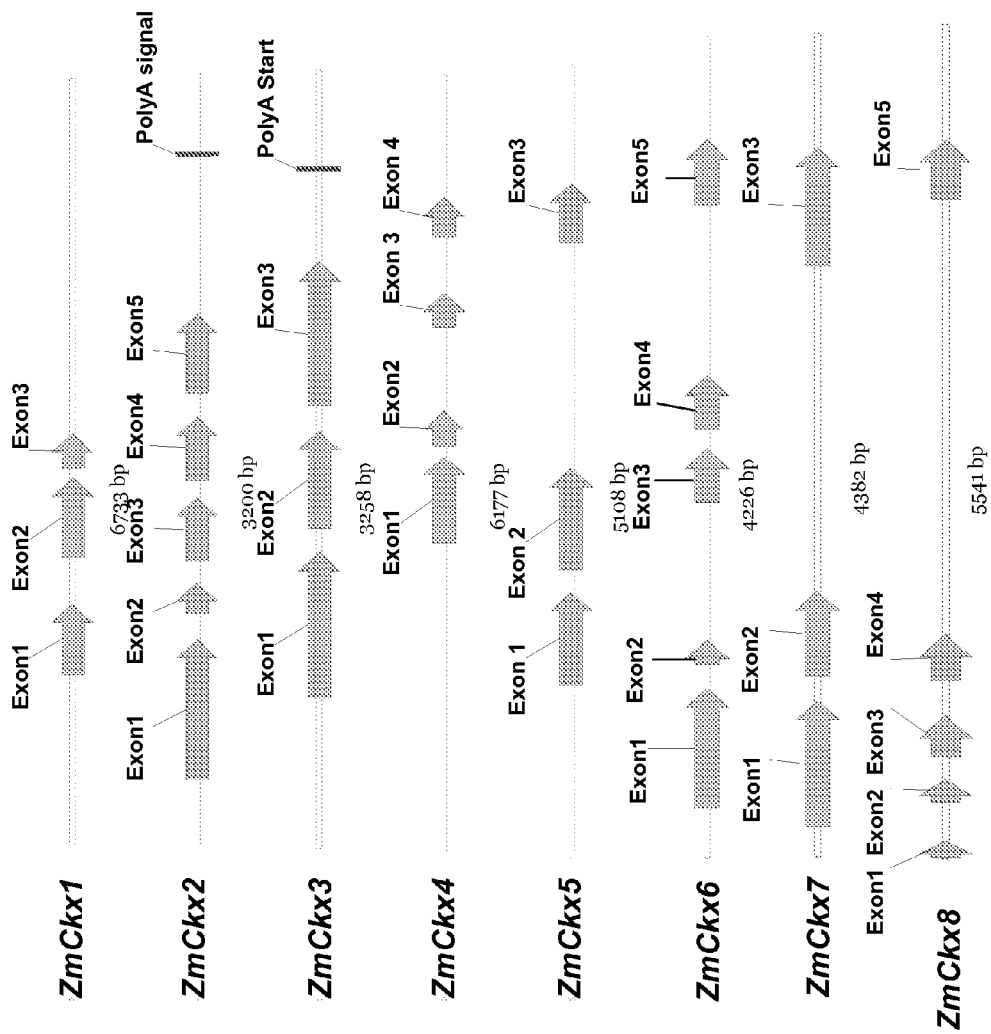
Figure 2. A multigene family of cytokinin oxidases in corn

| | Ckx2a # libr. | Ckx2a ppm | Ckx2b # libr. | Ckx2b ppm | Ckx3 # libr. | Ckx3 ppm | Ckx4 # libr. | Ckx4 ppm | Ckx5 # libr. | Ckx5 ppm | Ckx6 # libr. | Ckx6 ppm | Ckx7 # libr. | Ckx7 ppm | Ckx8 # libr. | Ckx8 ppm |
|---|---|---|---|---|---|---|---|---|---|---|---|---|---|---|---|---|
| Anther | | | | | | | 1 | 4.0 | | | 3 | 149.3 | 2 | 7.5 | | |
| Ear | 9 | 6.2 | 2 | 7.5 | | | 25 | 52.0 | 13 | 10.6 | 20 | 16.0 | 6 | 19.3 | | |
| Embryo | 6 | 5.8 | | | | | 17 | 13.8 | 2 | 5.0 | 17 | 13.1 | 1 | 12.0 | | |
| Endosperm | 6 | 6.5 | 1 | 5.0 | | | 7 | 6.6 | 2 | 3.5 | 15 | 34.3 | 10 | 120.8 | 2 | 18 |
| Endosperm; pericarp | | | | | | | | | | | 2 | 28.0 | 1 | 21.0 | | |
| Husk | 1 | 11.0 | | | | | 1 | 20.0 | | | 1 | 18.0 | | | | |
| Internode | | | | | | | 4 | 12.3 | | | | | | | | |
| Kernel | 5 | 6.8 | | | | | 13 | 24.7 | 6 | 15.8 | 16 | 66.1 | 10 | 23.0 | 1 | 5 |
| Leaf | 17 | 33.4 | 15 | 20.5 | | | 60 | 46.7 | 11 | 9.3 | 29 | 39.6 | 5 | 12.4 | 3 | 5.7 |
| Meristem | 5 | 25.4 | 1 | 3.0 | 1 | 8.0 | 36 | 36.5 | 10 | 7.9 | 12 | 18.0 | 4 | 4.5 | 7 | 14 |
| Pedicel | 1 | 131.0 | 1 | 29.0 | | | 11 | 16.0 | 7 | 12.3 | 10 | 129.2 | 9 | 61.2 | | |
| Pericarp | 3 | 4.7 | 1 | 7.0 | | | 7 | 20.1 | 1 | 9.0 | 7 | 49.1 | 3 | 19.7 | | |
| Root | 9 | 12.4 | 3 | 10.7 | 8 | 46.6 | 40 | 20.1 | 40 | 25.9 | 32 | 27.1 | 1 | 4.0 | 1 | 4 |
| Scutellum | 1 | 2.0 | | | | | 2 | 32.5 | | | 1 | 3.0 | | | | |
| Seed | | | | | | | | | 2 | 4.0 | | | | | | |
| Seedling | 5 | 47.0 | 4 | 25.8 | | | 11 | 39.4 | 3 | 3.0 | 9 | 16.2 | | | | |
| Shoot | | | | | | | 3 | 15.0 | 1 | 3.0 | 1 | 11.0 | | | | |
| Silk | 2 | 10.5 | 6 | 12.0 | | | 9 | 53.3 | 4 | 5.3 | 9 | 49.0 | 7 | 12.1 | | |
| Stalk | 15 | 31.3 | 2 | 15.5 | | | 17 | 25.1 | 8 | 14.6 | 21 | 38.7 | 5 | 4.8 | | |
| Stem; sheath | | | | | | | 1 | 21.0 | 1 | 4.0 | 1 | 20.0 | 1 | 7.0 | | |
| Tassel | 10 | 7.1 | 3 | 7.7 | | | 17 | 27.1 | 13 | 11.7 | 16 | 24.4 | 2 | 2.5 | 8 | 19.1 |
| Vascular bundles | 1 | 9.0 | | | | | 1 | 66.0 | 1 | 24.0 | 1 | 18.0 | | | | |
| Whorl | 4 | 17.3 | 1 | 9 | | | 2 | 21.5 | | | 2 | 23.0 | | | | |

Figure 3. Lynx expression profile data for maize cytokinin oxidase genes 2a, 2b, 3, 4, 5, 6, 7, and 8; for each, # of libraries in which tag was identified, and expression level in average adjusted parts per million.

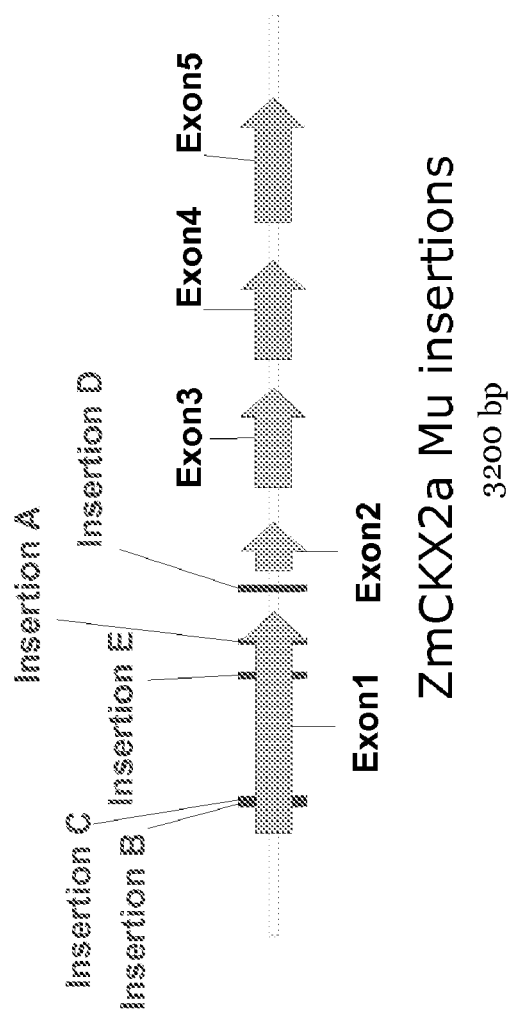
Figure 4A: Position of Mu insertions in *ZmCKX2a* mutants

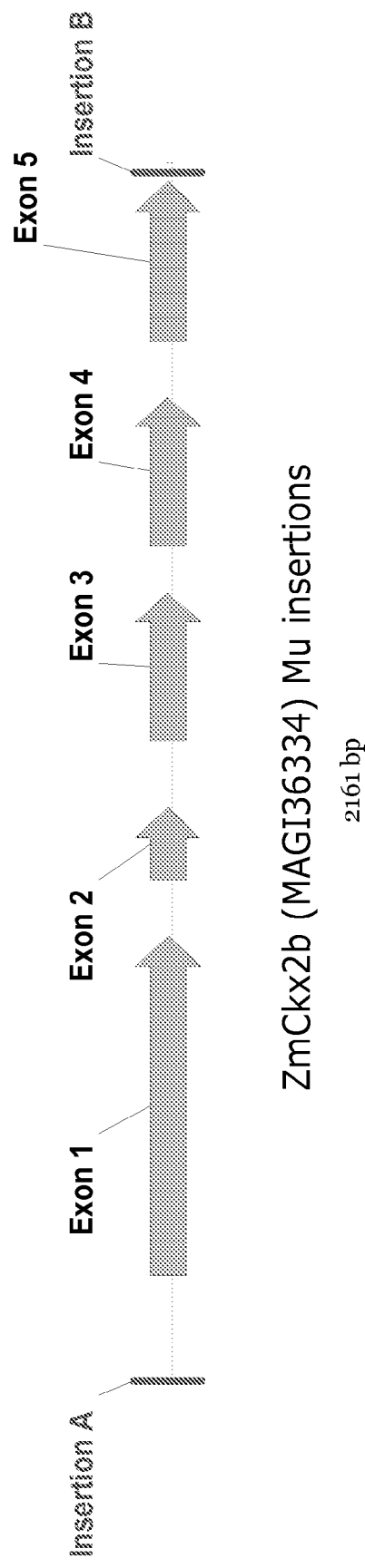
Figure 4B: Position of Mu insertions in *ZmCKX2b* mutants

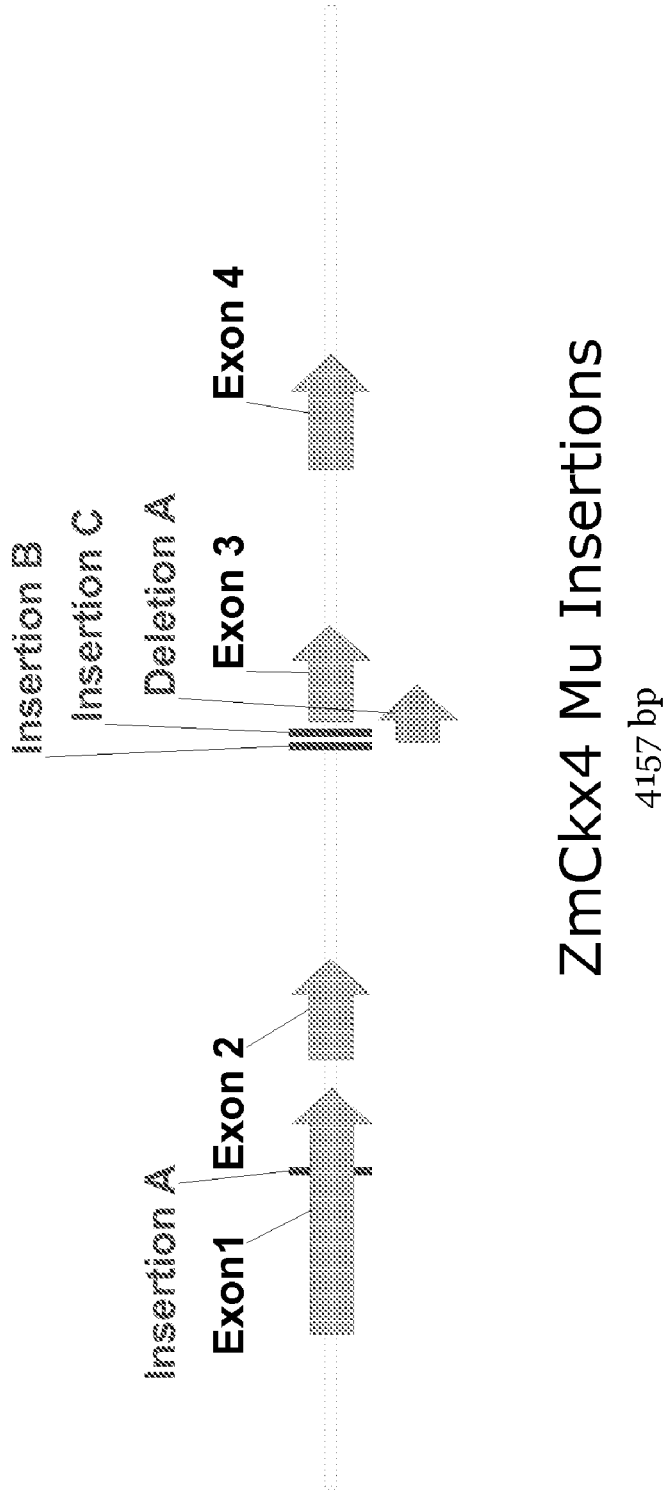
Figure 4C: Position of Mu insertions in *ZmCKX4* mutants

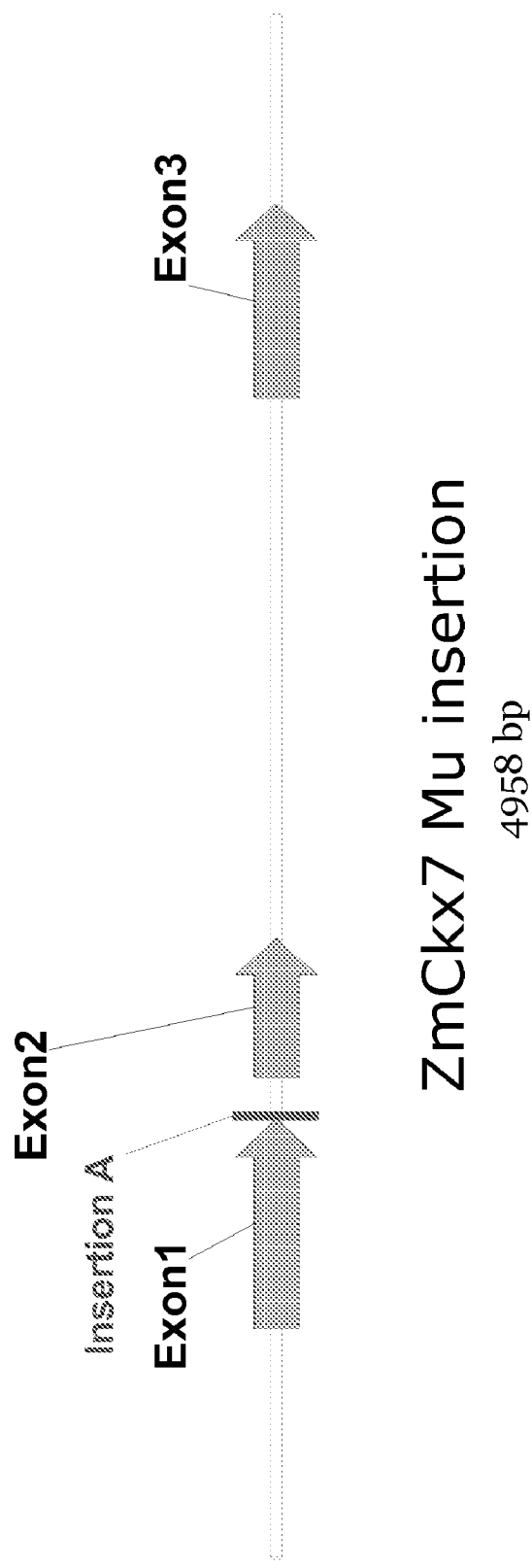
Figure 4D: Position of Mu insertion in *ZmCKX7* mutant

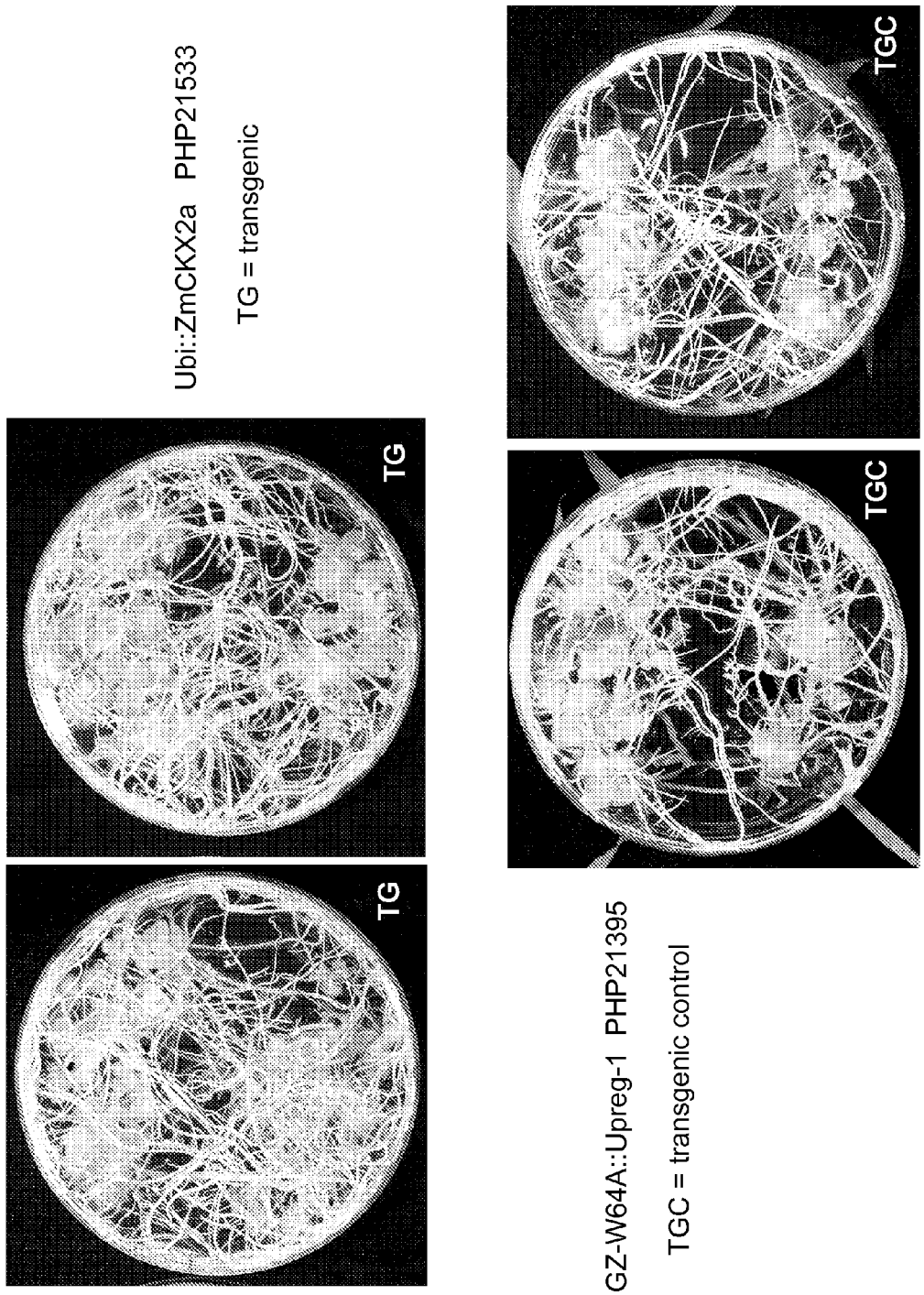
Figure 5. Ectopic over-expression of *ZmCkx2a* increases root formation *in vitro*.

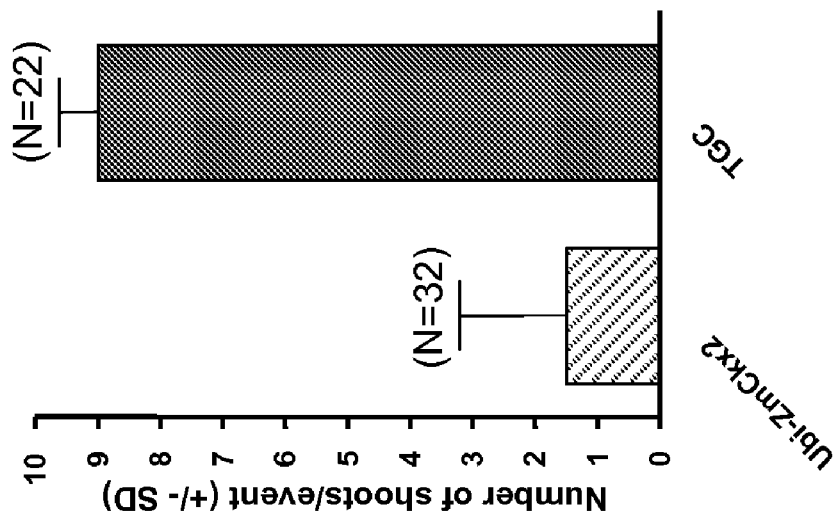
Figure 6: Number of shoots formed from Ubi::ZmCkx2 or transgenic control (TGC) calli during the regeneration process.

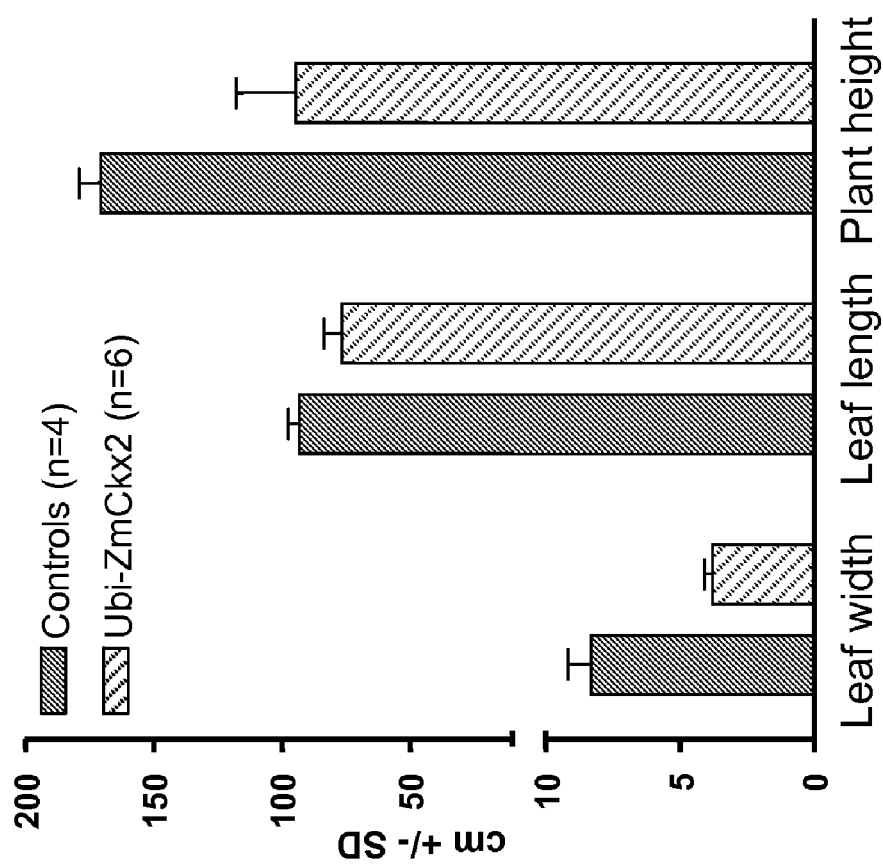
Figure 7: Phenotypic characteristics of Ubi::ZmCkx2 T0 plants.

```
Query sequence: ZmCkx2a

Scores for sequence family classification (score includes all domains):
Model          Description                                    Score    E-value   N
--------       -----------                                    -----    -------  ---
PF09265.1.fs   Cytokinin dehydrogenase 1, FAD and cyto        636.4    8.8e-202   1
PF09265.1.ls   Cytokinin dehydrogenase 1, FAD and cyto        638.2    6.3e-189   1
PF01565.13.fs  FAD binding domain                              62.9    3.4e-17    1
PF01565.13.ls  FAD binding domain                              61.5    2.6e-15    1

Parsed for domains:
Model          Domain  seq-f seq-t    hmm-f hmm-t     score  E-value
--------       ------  ----- -----    ----- -----     -----  -------
PF01565.13.ls   1/1       63   202 ..     1   144 []   61.5  2.6e-15
PF01565.13.fs   1/1       90   202 ..    25   144 .]   62.9  3.4e-17
PF09265.1.fs    1/1      234   509 ..     1   297 []  636.4  8.8e-202
PF09265.1.ls    1/1      234   509 ..     1   297 []  638.2  6.3e-189

Alignments of top-scoring domains:

PF01565.13.ls: domain 1 of 1, from 63 to 202: score 61.5, E = 2.6e-15
                   *->PaavvrPeseeevaaivrlAreh....gipvtprGgGhslsfGgavp
                      Paav+   +s+  ++aa+vr        ++++ + v++rG Ghsl  G++++
       ZmCkx2a    63   PAAVLH-GSVSDIAATVRHVFSLgegsPLTVAARGHGHSLM-GQSQA 107 lntgGvvldlsrklnriileiDpetdgtatveaGvtl.dLnralaakGlf
                   +   G+v+++ + l++     +    dg + + +G+ +  + r++  k+++
       ZmCkx2a   108 A--QGIVVRMES-LRG--ARLQVH-DGFVDAPGGELWiNVLRET-LKHGL 150 lpldpgsgipgtvGGaiatnagGygsekyGltrdnvlglevVladGevvr
                   +p ++  ++     tvGG++++ +    ++++G+ + nv  le+V++  G+vv+
       ZmCkx2a   151 APKSWTDYLHLTVGGTLSNAGVSGQAFRHGPQVSNVNQLEIVTGRGDVVT 200 ls<-*
                   +s
       ZmCkx2a   201 CS      202

PF01565.13.fs: domain 1 of 1, from 90 to 202: score 62.9, E = 3.4e-17
                   *->ipvtprGgGhslsfGgavplntgGvvldlsrklnriileiDpetdgt
                      + v++rG Ghsl  G+++++   G+v+++ + l++    +      dg
       ZmCkx2a    90    LTVAARGHGHSLM-GQSQAA--QGIVVRMES-LRG--ARLQVH-DGF 129 atveaGvtl.dLnralaakGlflpldpgsgipgtvGGaiatnagGygsek
                   + + +G+ +  + r++  k+++p ++ ++     tvGG++++ +     +++
       ZmCkx2a   130 VDAPGGELWiNVLRET-LKHGLAPKSWTDYLHLTVGGTLSNAGVSGQAFR 178 yGltrdnvlglevVladGevvrls<-*
                   +G+ + nv  le+V++  G+vv++s
       ZmCkx2a   179 HGPQVSNVNQLEIVTGRGDVVTCS     202

PF09265.1.fs: domain 1 of 1, from 234 to 509: score 636.4, E = 8.8e-202
                   *->PkrVRWvRvlYsDFaaFTkDQErLISkenggggakvGfDYVEGFvil
                      P +VRW+RvlYsDF++FT+DQE+LI++en+         fDY+EGFvi+
       ZmCkx2a   234    PEMVRWIRVLYSDFESFTEDQEMLIMAENS-------FDYIEGFVII 273 nrtglvnnwrssFFspsDpariasLasknnggvlYcLEvakyYdyadsda
                   nrtg++nnwr+s F+p+Dp+++++++s  +g+vlYcLE++k+++    d+
       ZmCkx2a   274 NRTGILNNWRAS-FKPQDPVQASHFQS--DGRVLYCLELTKNFN--SGDT 318 atvDqeveeLlrqLsfvpGflFstDVsYvdFLdRVhreElkLRskGlWdV
                   +t++qev +Ll++L+f++++lF+tDV+Y++FLdRVh+++ElkLR++ lW+V
       ZmCkx2a   319 DTMEQEVAVLLSRLRFIQSTLFHTDVTYLEFLDRVHTSELKLRAQSLWEV 368

PHPWLNLFVPkSrIldFdrgVFkgIlLkntnnsGPiLvYPmnrsKWDdrm
                   PHPWLNL++P+S+I  +F+++VF+  I  Lk++nn GPiL+YP+n+sKWD+ +
       ZmCkx2a   369 PHPWLNLLIPRSSIRRFATEVFGRI-LKDSNN-GPILLYPVNKSKWDNKT 416

SaviPdedEdVFYlVGlLrSAvPysagpgdleelenqNrrIlefCekaGI
                   S+viPd   E++FYlVG+L+SA++  +g+g++++   +++N +I+efCe+a+I
       ZmCkx2a   417 SVVIPD--EEIFYLVGFLSSAPSL-SGHGSIAHAMSLNSQIVEFCEEADI 463 gyKQYLPhYLtsqedNYWkrHFGAakWdrFvdRKarYDPkaILsPGQgIF
                   g+KQYL+hY t+qe+   Wk HFG a+W++F +RK+rYDP+aIL+PGQ+IF
       ZmCkx2a   464 GMKQYLAHY-TTQEQ--WKTHFG-ARWETFERRKHRYDPLAILAPGQRIF 509

<-*

ZmCkx2a     -       -
```

Figure 9

```
PF09265.1.1s: domain 1 of 1, from 234 to 509: score 638.2, E = 6.3e-189
              *->PkrVRWvRvlYsDFaaFTkDQErLISkengggakvGfDYVEGFvil
                 P +VRW+RvlYsDF++FT+DQE+LI++en+       fDY+EGFvi+
     ZmCkx2a  234  PEMVRWIRVLYSDFESFTEDQEMLIMAENS------FDYIEGFVII 273 nrtglvnnwrssFFspsDpariasLasknnggvlYcLEvakyYdyadsda
                 nrtg++nnwr+s F+p+Dp+++++++s  +g+vlYcLE++k+++   d+
     ZmCkx2a  274  NRTGILNNWRAS-FKPQDPVQASHFQS--DGRVLYCLELTKNFN--SGDT 318 atvDqeveeLlrqLsfvpGflFstDVsYvdFLdRVhreElkLRskGlWdV
                 +t++qev +Ll++L+f++++lF+tDV+Y++FLdRVh++ElkLR++ lW+V
     ZmCkx2a  319  DTMEQEVAVLLSRLRFIQSTLFHTDVTYLEFLDRVHTSELKLRAQSLWEV 368

PHPWLNLFVPkSrIldFdrgVFkgIlLkntnnsGPiLvYPmnrsKWDdrm
                 PHPWLNL++P+S+I +F+++VF+ I Lk++nn GPiL+YP+n+sKWD+ +
     ZmCkx2a  369  PHPWLNLLIPRSSIRRFATEVFGRI-LKDSNN-GPILLYPVNKSKWDNKT 416

SaviPdedEdVFYlVGlLrSAvPysagpgdleelenqNrrIlefCekaGI
                 S+viPd  E++FY1VG+L+SA++  +g+g++++ +++N +I+efCe+a+I
     ZmCkx2a  417  SVVIPD--EEIFYLVGFLSSAPSL-SGHGSIAHAMSLNSQIVEFCEEADI 463 gyKQYLPhYLtsqedNYWkrHFGAakWdrFvdRKarYDPkaILsPGQgIF
                 g+KQYL+hY t+qe+  Wk HFG a+W++F +RK+rYDP+aIL+PGQ+IF
     ZmCkx2a  464  GMKQYLAHY-TTQEQ--WKTHFG-ARWETFERRKHRYDPLAILAPGQRIF 509

<-*
     ZmCkx2a    -    -

Query sequence: ZmCkx2b

Scores for sequence family classification (score includes all domains):
Model          Description                                Score    E-value  N
--------       -----------                                -----    -------  ---
PF09265.1.fs   Cytokinin dehydrogenase 1, FAD and cyto     654.4   1.8e-207  1
PF09265.1.1s   Cytokinin dehydrogenase 1, FAD and cyto     656.2   2.4e-194  1
PF01565.13.fs  FAD binding domain                           65.8   5.3e-18   1
PF01565.13.1s  FAD binding domain                           67.8   3.3e-17   1

Parsed for domains:
Model          Domain  seq-f  seq-t      hmm-f hmm-t      score  E-value
--------       ------  -----  -----      ----- -----      -----  -------
PF01565.13.fs   1/1       64    209  ..      1   144 []    65.8  5.3e-18
PF01565.13.1s   1/1       64    209  ..      1   144 []    67.8  3.3e-17
PF09265.1.fs    1/1      241    516  ..      1   297 []   654.4  1.8e-207
PF09265.1.1s    1/1      241    516  ..      1   297 []   656.2  2.4e-194

Alignments of top-scoring domains:

PF01565.13.fs: domain 1 of 1, from 64 to 209: score 65.8, E = 5.3e-18
              *->PaavvrPeseeevaaivrlAreh....gipvtprGgGhslsfGgavp
                 Paav+ P+s+ ++aaivr     ++++ + v++rG Ghsl G++++
     ZmCkx2b   64  PAAVLHPGSVSDIAAIVRHVFSLgegsPLTVAARGHGHSLM-GQSQA 109 lntgGvvldlsrklnriileiDpe..tdgtatveaGvtl.dLnralaakG
                 +    G+v+++ + l+++ l++++++ +  + +G+ + r++  k+
     ZmCkx2b  110  A--QGIVVRMES-LRGPRLQVNDAgvSPPSVDAPGGELWiNVLRET-LKH 155 lflpldpgsgipgtvGGaiatnagGygsekyGltrdnvlglevVladGev
                 +++p ++ ++   tvGG++++ +   ++++G+ + nv  le+V++ G+v
     ZmCkx2b  156  GLAPKSWTDYLHLTVGGTLSNAGVSGQAFRHGPQVSNVNQLEIVTGRGDV 205 vrls<-*
                 v++s
     ZmCkx2b  206  VTCS    209

PF01565.13.1s: domain 1 of 1, from 64 to 209: score 67.8, E = 3.3e-17
              *->PaavvrPeseeevaaivrlAreh....gipvtprGgGhslsfGgavp
                 Paav+ P+s+ ++aaivr     ++++ + v++rG Ghsl G++++
     ZmCkx2b   64  PAAVLHPGSVSDIAAIVRHVFSLgegsPLTVAARGHGHSLM-GQSQA 109 lntgGvvldlsrklnriileiDpe..tdgtatveaGvtl.dLnralaakG
                 +    G+v+++ + l+++ l++++++ +  + +G+ + r++  k+
     ZmCkx2b  110  A--QGIVVRMES-LRGPRLQVNDAgvSPPSVDAPGGELWiNVLRET-LKH 155 lflpldpgsgipgtvGGaiatnagGygsekyGltrdnvlglevVladGev
                 +++p ++ ++   tvGG++++ +   ++++G+ + nv  le+V++ G+v
     ZmCkx2b  156  GLAPKSWTDYLHLTVGGTLSNAGVSGQAFRHGPQVSNVNQLEIVTGRGDV 205
```

Figure 9

```
                     vrls<-*
                     v++s
       ZmCkx2b   206 VTCS      209

PF09265.1.fs: domain 1 of 1, from 241 to 516: score 654.4, E = 1.8e-207
                 *->PkrVRWvRvlYsDFaaFTkDQErLISkengggakvGfDYVEGFvil
                    Pk+VRW+RvlYsDF++FT+DQE+LI++en+     fDYVEGFvi+
       ZmCkx2b   241  PKMVRWIRVLYSDFESFTEDQEMLIMAENS-------FDYVEGFVII 280 nrtglvnnwrssFFspsDpariasLasknnggvlYcLEvakyYdyadsda
                    nrtg++nnwr+s F+p+Dp+ +++++s  +g+vlYcLE++k+++     d+
       ZmCkx2b   281 NRTGVLNNWRAS-FKPQDPVEASHFQS--DGRVLYCLELTKNFN--SDDT 325 atvDqeveeLlrqLsfvpGflFstDVsYvdFLdRVhreElkLRskGlWdV
                    +t++qev +Ll++L+f+++1F+tDV+Y++FLdRVh++ElkLR++GlW+V
       ZmCkx2b   326 DTMEQEVTVLLSRLRFIQSTLFHTDVTYLEFLDRVHTSELKLRAQGLWEV 375

PHPWLNLFVPkSrIldFdrgVFkgIlLkntnnsGPiLvYPmnrsKWDdrm
                    PHPWLNL++P+S+I +F+++VF++I Lk++nn GPiL+YP+n+sKWD+r+
       ZmCkx2b   376 PHPWLNLLIPRSSIRRFAKEVFGKI-LKDSNN-GPILLYPVNKSKWDNRT 423

SaviPdedEdVFYlVGlLrSAvPysagpgdleelenqNrrIlefCekaGI
                    S+viPd   E++FYlVG+L+SA++  +g+g++++ +n+N++I+efCe+aGI
       ZmCkx2b   424 SVVIPD--EEIFYLVGFLSSAPSL-SGYGSIAHSMNLNKQIVEFCEEAGI 470 gyKQYLPhYLtsqedNYWkrHFGAakWdrFvdRKarYDPkaILsPGQgIF
                    g+KQYL+ Y t+q++  Wk+HFG a+W++F +RK+rYDP+aIL+PGQ+IF
       ZmCkx2b   471 GMKQYLAPY-TTQQQ--WKAHFG-ARWETFERRKHRYDPLAILAPGQRIF 516

<-*
       ZmCkx2b     -     -

PF09265.1.ls: domain 1 of 1, from 241 to 516: score 656.2, E = 2.4e-194
                 *->PkrVRWvRvlYsDFaaFTkDQErLISkengggakvGfDYVEGFvil
                    Pk+VRW+RvlYsDF++FT+DQE+LI++en+     fDYVEGFvi+
       ZmCkx2b   241  PKMVRWIRVLYSDFESFTEDQEMLIMAENS-------FDYVEGFVII 280 nrtglvnnwrssFFspsDpariasLasknnggvlYcLEvakyYdyadsda
                    nrtg++nnwr+s F+p+Dp+ +++++s  +g+vlYcLE++k+++     d+
       ZmCkx2b   281 NRTGVLNNWRAS-FKPQDPVEASHFQS--DGRVLYCLELTKNFN--SDDT 325 atvDqeveeLlrqLsfvpGflFstDVsYvdFLdRVhreElkLRskGlWdV
                    +t++qev +Ll++L+f+++1F+tDV+Y++FLdRVh++ElkLR++GlW+V
       ZmCkx2b   326 DTMEQEVTVLLSRLRFIQSTLFHTDVTYLEFLDRVHTSELKLRAQGLWEV 375

PHPWLNLFVPkSrIldFdrgVFkgIlLkntnnsGPiLvYPmnrsKWDdrm
                    PHPWLNL++P+S+I +F+++VF++I Lk++nn GPiL+YP+n+sKWD+r+
       ZmCkx2b   376 PHPWLNLLIPRSSIRRFAKEVFGKI-LKDSNN-GPILLYPVNKSKWDNRT 423

SaviPdedEdVFYlVGlLrSAvPysagpgdleelenqNrrIlefCekaGI
                    S+viPd   E++FYlVG+L+SA++  +g+g++++ +n+N++I+efCe+aGI
       ZmCkx2b   424 SVVIPD--EEIFYLVGFLSSAPSL-SGYGSIAHSMNLNKQIVEFCEEAGI 470 gyKQYLPhYLtsqedNYWkrHFGAakWdrFvdRKarYDPkaILsPGQgIF
                    g+KQYL+ Y t+q++  Wk+HFG a+W++F +RK+rYDP+aIL+PGQ+IF
       ZmCkx2b   471 GMKQYLAPY-TTQQQ--WKAHFG-ARWETFERRKHRYDPLAILAPGQRIF 516

<-*
       ZmCkx2b     -     -

Query sequence: ZmCkx3

Scores for sequence family classification (score includes all domains):
Model           Description                                Score     E-value  N
---------       -----------                                -----     -------  ---
PF09265.1.fs    Cytokinin dehydrogenase 1, FAD and cyto    579.5     9.2e-184  1
PF09265.1.ls    Cytokinin dehydrogenase 1, FAD and cyto    581.3     8.3e-172  1
PF01565.13.fs   FAD binding domain                          99.9     1.4e-27   1
PF01565.13.ls   FAD binding domain                         101.9     1.7e-27   1

Parsed for domains:
Model           Domain   seq-f  seq-t     hmm-f hmm-t       score   E-value
---------       ------   -----  -----     ----- -----       -----   -------
PF01565.13.fs    1/1       68    212  ..     1   144  []     99.9   1.4e-27
PF01565.13.ls    1/1       68    212  ..     1   144  []    101.9   1.7e-27
PF09265.1.fs     1/1      244    526  ..     1   297  []    579.5   9.2e-184
```

Figure 9

```
PF09265.1.ls    1/1     244  526 ..     1  297 []    581.3 8.3e-172
Alignments of top-scoring domains:
PF01565.13.fs: domain 1 of 1, from 68 to 212: score 99.9, E = 1.4e-27
                   *->PaavvrPeseeevaaivrlAr..ehgipvtprGgGhslsfGgavpln
                      P+av+ P++++++aa+vr+ +++++ +pv+prG Ghs+  G+a +
          ZmCkx3  68  PEAVFHPATPADIAALVRFSAtsAAPFPVAPRGQGHSWR-GQALA-- 111 tgGvvldlsrklnr...i.ileiDpetdgtatveaGvtl.dLnralaakG
                      gGvv+d+++ l r+++i++   +  +   +  +++    + d+ ra+ ++G
          ZmCkx3 112  PGGVVVDMGS-LGRgprInVSAVAGA-EPFVDAGGEQLWvDVLRATLRHG 159 lflpldpgsgipgtvGGaiatnagGygsekyGltrdnvlglevVladGev
                      l+      + ++   tvGG++++  ++G   ++++G+     nv++l+vV+++Ge+
          ZmCkx3 160  LAPR-VWTDYLRLTVGGTLSNAGIGGQAFRHGPQIANVHELDVVTGTGEM 208 vrls<-*
                      v++s
          ZmCkx3 209  VTCS    212

PF01565.13.ls: domain 1 of 1, from 68 to 212: score 101.9, E = 1.7e-27
                   *->PaavvrPeseeevaaivrlAr..ehgipvtprGgGhslsfGgavpln
                      P+av+ P++++++aa+vr+ +++++ +pv+prG Ghs+  G+a +
          ZmCkx3  68  PEAVFHPATPADIAALVRFSAtsAAPFPVAPRGQGHSWR-GQALA-- 111 tgGvvldlsrklnr...i.ileiDpetdgtatveaGvtl.dLnralaakG
                      gGvv+d+++ l r+++i++   +  +   +  +++    + d+ ra+ ++G
          ZmCkx3 112  PGGVVVDMGS-LGRgprInVSAVAGA-EPFVDAGGEQLWvDVLRATLRHG 159 lflpldpgsgipgtvGGaiatnagGygsekyGltrdnvlglevVladGev
                      l+      + ++   tvGG++++  ++G   ++++G+     nv++l+vV+++Ge+
          ZmCkx3 160  LAPR-VWTDYLRLTVGGTLSNAGIGGQAFRHGPQIANVHELDVVTGTGEM 208 vrls<-*
                      v++s
          ZmCkx3 209  VTCS    212

PF09265.1.fs: domain 1 of 1, from 244 to 526: score 579.5, E = 9.2e-184
                   *->PkrVRWvRvlYsDFaaFTkDQErLISkengggakvGfDYVEGFvil
                      PkrVRWvR++Y+D+a+FTkDQE LIS +++      +vGfDYVEG+v+l
          ZmCkx3 244  PKRVRWVRLAYTDVATFTKDQEFLISNRAS----QVGFDYVEGQVQL 286 nrtglvnnwrssFFspsDpariasLaskngggvlYcLEvakyYdyadsda
                      +r +++ + ++++FFs +D+ar+a+Las +    +Y++E+a+yY    +a
          ZmCkx3 287  SRSLVEGPKSTPFFSGADVARLAGLASRTGPAAIYYIEGAMYYT--KDTA 334 atvDqeveeLlrqLsfvpGflFstDVsYvdFLdRVhreElkLRskGlWdV
                      +vD+++++Ll+qLsf+pGf F++DV+  v+FLdRV++eE+ LRs+G W+V
          ZmCkx3 335  ISVDKKMKALLDQLSFEPGFAFTKDVTFVQFLDRVREEERVLRSAGAWEV 384

PHPWLNLFVPkSrIldFdrgVFkgIlLkntnnsGPiLvYPmnrsKWDdrm
                      PHPWLNLFVP+SrIldFd+gVFk+  Lk++n+ G iL+YPmn+++WDdrm
          ZmCkx3 385  PHPWLNLFVPRSRILDFDDGVFKAL-LKDSNPAGIILMYPMNKDRWDDRM 433

SaviPded.EdVFYlVGllLrSAvPysagpgdleelenqNrrIlefCekaG
                      a++P  d++d FY+V +L SA    +++d+ +le+ N+++l+fC+++G
          ZmCkx3 434  TAMTPATDdDDMFYAVSFLWSA----LSADDVPQLERWNKAVLDFCDRSG 479

IgyKQYLPhYLtsqedNYWkrHFGAakWdrFvdRKarYDPkaILsPGQgI
                      I +KQYLPhY tsq++  W+rHFG akW+r +++KarYDP+a+LsPGQ+I
          ZmCkx3 480  IECKQYLPHY-TSQDG--WRRHFG-AKWSRIAELKARYDPRALLSPGQRI 525

F<-*
                      F
          ZmCkx3 526  F       526

PF09265.1.ls: domain 1 of 1, from 244 to 526: score 581.3, E = 8.3e-172
                   *->PkrVRWvRvlYsDFaaFTkDQErLISkengggakvGfDYVEGFvil
                      PkrVRWvR++Y+D+a+FTkDQE LIS +++      +vGfDYVEG+v+l
          ZmCkx3 244  PKRVRWVRLAYTDVATFTKDQEFLISNRAS----QVGFDYVEGQVQL 286 nrtglvnnwrssFFspsDpariasLaskngggvlYcLEvakyYdyadsda
                      +r +++ + ++++FFs +D+ar+a+Las +    +Y++E+a+yY    +a
          ZmCkx3 287  SRSLVEGPKSTPFFSGADVARLAGLASRTGPAAIYYIEGAMYYT--KDTA 334 atvDqeveeLlrqLsfvpGflFstDVsYvdFLdRVhreElkLRskGlWdV
                      +vD+++++Ll+qLsf+pGf F++DV+  v+FLdRV++eE+ LRs+G W+V
          ZmCkx3 335  ISVDKKMKALLDQLSFEPGFAFTKDVTFVQFLDRVREEERVLRSAGAWEV 384
```

Figure 9

```
                PHPWLNLFVPkSrIldFdrgVFkqIlLkntnnsGPiLvYPmnrsKWDdrm
                PHPWLNLFVP+SrIldFd+gVFk + Lk++n+ G iL+YPmn+++WDdrm
    ZmCkx3  385 PHPWLNLFVPRSRILDFDDGVFKAL-LKDSNPAGIILMYPMNKDRWDDRM 433

SaviPded.EdVFY1VG1LrSAvPysagpgdleelenqNrrIlefCekaG
                a++P   d++d FY+V +L SA    +++d+ +le+ N+++l+fC+++G
    ZmCkx3  434 TAMTPATDdDDMFYAVSFLWSA----LSADDVPQLERWNKAVLDFCDRSG 479

IgyKQYLPhYLtsqedNYWkrHFGAakWdrFvdRKarYDPkaILsPGQgI
                I +KQYLPhY tsq++  W+rHFG akW+r +++KarYDP+a+LsPGQ+I
    ZmCkx3  480 IECKQYLPHY-TSQDG--WRRHFG-AKWSRIAELKARYDPRALLSPGQRI 525

F<-*
                F
    ZmCkx3  526 F  526

Query sequence: ZmCkx4

Scores for sequence family classification (score includes all domains):
Model          Description                              Score    E-value  N
---------      -----------                              -----    -------  ---
PF09265.1.fs   Cytokinin dehydrogenase 1, FAD and cyto  506.5   1.2e-160  1
PF09265.1.ls   Cytokinin dehydrogenase 1, FAD and cyto  508.3     8e-150  1
PF01565.13.fs  FAD binding domain                       114.9    8.9e-32  2
PF01565.13.ls  FAD binding domain                       110.2    5.6e-30  1

Parsed for domains:
Model          Domain  seq-f seq-t    hmm-f hmm-t      score  E-value
---------      ------  ----- -----    ----- -----      -----  -------
PF01565.13.fs   1/2      44    97 ..      1    57 [.    54.5  7.6e-15
PF01565.13.ls   1/1      44   196 ..      1   144 []   110.2  5.6e-30
PF01565.13.fs   2/2     123   196 ..     72   144 .]    60.3  1.8e-16
PF09265.1.fs    1/1     228   512 ..      1   297 []   506.5 1.2e-160
PF09265.1.ls    1/1     228   512 ..      1   297 []   508.3   8e-150

Alignments of top-scoring domains:

PF01565.13.fs: domain 1 of 2, from 44 to 97: score 54.5, E = 7.6e-15
                *->PaavvrPeseeevaaivrlAreh.gipvtprGgGhslsfGgavplnt
                   PaavvrP+s+++va ++r+A+  +++ v++rG+Ghs++ G+a++  +
    ZmCkx4   44 PAAVVRPASADDVASAIRAAALTpHLTVAARGNGHSVA-GQAMA--E 87 gGvvldlsrkl<-*
                gG+vld+++ l
    ZmCkx4   88 GGLVLDMRS-L  97

PF01565.13.ls: domain 1 of 1, from 44 to 196: score 110.2, E = 5.6e-30
                *->PaavvrPeseeevaaivrlAreh.gipvtprGgGhslsfGgavplnt
                   PaavvrP+s+++va ++r+A+  +++ v++rG+Ghs++ G+a++  +
    ZmCkx4   44 PAAVVRPASADDVASAIRAAALTpHLTVAARGNGHSVA-GQAMA--E 87 gGvvldls........rklnriileiDp.....etdgtatveaGvtl.dL
                gG+vld+++        ++++ +++    ++  +p++++++    a v +G+ ++++
    ZmCkx4   88 GGLVLDMRslaapsrrAQMQ--LVVQCPdgggR-RCFADVPGGALWeEV 134 nralaakGlflpldpgsgipgtvGGaiatnagGygsekyGltrdnvlgle
                +++   ++++p ++ ++ + tvGG++++++   s++yG+ + nv +le
    ZmCkx4  135 LHWAVDNHGLAPASWTDYLRLTVGGTLSNGGVSGQSFRYGPQVSNVAELE 184 vVladGevvrls<-*
                vV++dGe + +s
    ZmCkx4  185 VVTGDGERRVCS  196

PF01565.13.fs: domain 2 of 2, from 123 to 196: score 60.3, E = 1.8e-16
                *->atveaGvtl.dLnralaakGlflpldpgsgipgtvGGaiatnagGyg
                   a v +G+ ++++ +++   ++++p ++ ++ + tvGG++++++
    ZmCkx4  123 ADVPGGALWeEVLHWAVDNHGLAPASWTDYLRLTVGGTLSNGGVSGQ 169 sekyGltrdnvlglevVladGevvrls<-*
                s++yG+ + nv +levV++dGe + +s
    ZmCkx4  170 SFRYGPQVSNVAELEVVTGDGERRVCS  196

PF09265.1.fs: domain 1 of 1, from 228 to 512: score 506.5, E = 1.2e-160
                *->PkrVRWvRvlYsDFaaFTkDQErLISkengggakvGfDYVEGFvil
                   Pk VRW+Rv+Y++ a++T+D+E+L++++++ +    fDYVEGF ++
    ZmCkx4  228 PKAVRWTRVVYASIADYTADAEWLVTRPPDAA-----FDYVEGFAFV 269
```

Figure 9

```
                  nrtglvnnwrssFFspsDpariasLasknnggvlYcLEvakyYdya.dsd
                  n++++vn+w+s+ + p    + +sL ++++g vlYcLEva+y++ +++ d
   ZmCkx4    270 NSDDPVNGWPSV-PIPGGARFDPSLLPAGAGPVLYCLEVALYQYAHrPDD 318 aatvDqe...veeLlrqLsfvpGflFstDVsYvdFLdRVhreElkLRskG
                  ++ Dq    +v +++  L++v+G+ F+ DV YvdFL RV+r E+++R++G
   ZmCkx4    319 DDEEDQAavtVSRMMAPLKHVRGLEFAADVGYVDFLSRVNRVEEEARRNG 368 lWdVPHPWLNLFVPkSrIldFdrgVFkgIlLkntnnsGPiLvYPmnrsKW
                  Wd PHPWLNLFV+ ++I+dFdr+V+kg+ L+++ + GP+LvYPm++sKW
   ZmCkx4    369 SWDAPHPWLNLFVSARDIADFDRAVIKGM-LADGID-GPMLVYPMLKSKW 416

DdrmSaviPdedEdVFYlVGlLrSAvPysagpgdleelenqNrrIlefCe
                  D+++S+++P+   ++VFYlV+lLr++    ++g+   ++el++qN +Il++C+
   ZmCkx4    417 DPNTSVALPE--GEVFYLVALLRFC---RSGGPAVDELVAQNGAILRACR 461 kaGIgyKQYLPhYLtsqedNYWkrHFGAakWdrFvdRKarYDPkaILsPG
                  ++G++yK Y+P Y    +d   W rHFGAa+W rFvdRKarYDP+aIL+PG
   ZmCkx4    462 ANGYDYKAYFPSY-RGEAD--WARHFGAARWRRFVDRKARYDPLAILAPG 508

QgIF<-*
                  Q+IF
   ZmCkx4    509 QKIF    512

PF09265.1.ls: domain 1 of 1, from 228 to 512: score 508.3, E = 8e-150
                  *->PkrVRWvRvlYsDFaaFTkDQErLISkengggakvGfDYVEGFvil
                     Pk VRW+Rv+Y++ a++T+D+E+L++++++ +    fDYVEGF ++
   ZmCkx4    228    PKAVRWTRVVYASIADYTADAEWLVTRPPDAA-----FDYVEGFAFV 269 nrtglvnnwrssFFspsDpariasLasknnggvlYcLEvakyYdya.dsd
                  n++++vn+w+s+ + p    + +sL ++++g vlYcLEva+y++ +++ d
   ZmCkx4    270 NSDDPVNGWPSV-PIPGGARFDPSLLPAGAGPVLYCLEVALYQYAHrPDD 318 aatvDqe...veeLlrqLsfvpGflFstDVsYvdFLdRVhreElkLRskG
                  ++ Dq    +v +++  L++v+G+ F+ DV YvdFL RV+r E+++R++G
   ZmCkx4    319 DDEEDQAavtVSRMMAPLKHVRGLEFAADVGYVDFLSRVNRVEEEARRNG 368 lWdVPHPWLNLFVPkSrIldFdrgVFkgIlLkntnnsGPiLvYPmnrsKW
                  Wd PHPWLNLFV+ ++I+dFdr+V+kg+ L+++ + GP+LvYPm++sKW
   ZmCkx4    369 SWDAPHPWLNLFVSARDIADFDRAVIKGM-LADGID-GPMLVYPMLKSKW 416

DdrmSaviPdedEdVFYlVGlLrSAvPysagpgdleelenqNrrIlefCe
                  D+++S+++P+   ++VFYlV+lLr++    ++g+   ++el++qN +Il++C+
   ZmCkx4    417 DPNTSVALPE--GEVFYLVALLRFC---RSGGPAVDELVAQNGAILRACR 461 kaGIgyKQYLPhYLtsqedNYWkrHFGAakWdrFvdRKarYDPkaILsPG
                  ++G++yK Y+P Y    +d   W rHFGAa+W rFvdRKarYDP+aIL+PG
   ZmCkx4    462 ANGYDYKAYFPSY-RGEAD--WARHFGAARWRRFVDRKARYDPLAILAPG 508

QgIF<-*
                  Q+IF
   ZmCkx4    509 QKIF    512
```

Query sequence: ZmCkx5

```
Scores for sequence family classification (score includes all domains):
Model         Description                                 Score    E-value   N
--------      -----------                                 -----    -------   ---
PF09265.1.fs  Cytokinin dehydrogenase 1, FAD and cyto     447.8    4.6e-142  1
PF09265.1.ls  Cytokinin dehydrogenase 1, FAD and cyto     449.7    3.6e-132  1
PF01565.13.fs FAD binding domain                           86.8    6.8e-24   1
PF01565.13.ls FAD binding domain                           88.8    1.6e-23   1

Parsed for domains:
Model         Domain  seq-f seq-t    hmm-f hmm-t      score   E-value
--------      ------  ----- -----    ----- -----      -----   -------
PF01565.13.fs   1/1      59   207 ..      1   144 []   86.8   6.8e-24
PF01565.13.ls   1/1      59   207 ..      1   144 []   88.8   1.6e-23
PF09265.1.fs    1/1     239   527 ..      1   297 []  447.8   4.6e-142
PF09265.1.ls    1/1     239   527 ..      1   297 []  449.7   3.6e-132

Alignments of top-scoring domains:

PF01565.13.fs: domain 1 of 1, from 59 to 207: score 86.8, E = 6.8e-24
                  *->PaavvrPeseeevaaivrlAreh....gipvtprGgGhslsfGgavp
                     Paav+rP+s+ +++ ++ +    ++ +++ v++rG+Ghs   G+a++
   ZmCkx5     59    PAAVLRPQSPRDISMLLSFLSGSpslsRVTVAARGAGHSIH-GQAQA 104
```

Figure 9

```
                          lntgGvvldlsrklnriileiDp.......etdgtatveaGvtl.dLnra
                          +G+v+ +++ l +   e+   +++++++ + +a v++Gv + +L +
           ZmCkx5    105  --PDGIVVETRS-LPG-EMEFHHvrgggegR-ASYADVGGGVLWiELLER 149 laakGlflpldpgsgipgtvGGaiatnagGygsekyGltrdnvlqlevVl
                          + Gl+    ++ ++ + tvGG++++ ++    +k+G+   nvl levV+
           ZmCkx5    150  SLKLGLAPR-SWTDYLYLTVGGTLSNAGISGQTFKHGPQISNVLQLEVVT 198 adGevvrls<-*
                          + Ge+v++s
           ZmCkx5    199  GRGEIVECS    207

PF01565.13.ls: domain 1 of 1, from 59 to 207: score 88.8, E = 1.6e-23
                          *->PaavvrPeseeevaaivrlAreh....gipvtprGgGhslsfGgavp
                             Paav+rP+s+ +++ ++ +     ++ +++ v++rG+Ghs   G+a++
           ZmCkx5     59     PAAVLRPQSPRDISMLLSFLSGSpslsRVTVAARGAGHSIH-GQAQA 104 lntgGvvldlsrklnriileiDp.......etdgtatveaGvtl.dLnra
                          +G+v+ +++ l +   e+   +++++++ + +a v++Gv + +L +
           ZmCkx5    105  --PDGIVVETRS-LPG-EMEFHHvrgggegR-ASYADVGGGVLWiELLER 149 laakGlflpldpgsgipgtvGGaiatnagGygsekyGltrdnvlqlevVl
                          + Gl+    ++ ++ + tvGG++++ ++    +k+G+   nvl levV+
           ZmCkx5    150  SLKLGLAPR-SWTDYLYLTVGGTLSNAGISGQTFKHGPQISNVLQLEVVT 198 adGevvrls<-*
                          + Ge+v++s
           ZmCkx5    199  GRGEIVECS    207

PF09265.1.fs: domain 1 of 1, from 239 to 527: score 447.8, E = 4.6e-142
                          *->PkrVRWvRvlYsDFaaFTkDQErLISkenggggakvGfDYVEGFvil
                             P +V WvR++Y+D aFT+DQE+L+S++++       +DYVEGF++l
           ZmCkx5    239     PEKVTWVRAFYDDLGAFTRDQELLVSIPDS-------VDYVEGFMVL 278 nrtglvnnwrssFFspsDpariasLasknnggvlYcLEvakyYdyadsda
                          n+ +l+++++++   p+ +++ +++++ +   +++Yc E+a++ +      +
           ZmCkx5    279  NERSLHSSSIAF---PASVDFSPDFGTRSSPRIYYCVEFAVHHH--HGYQ 323 atvDqeveeLlrqLsfvpGflFstDVsYvdFLdRVhreElkLRskGlW.d
                          +    ve+++r++s+   + l+s++VsY+dFL+RV++eE++LRs+G+W++
           ZmCkx5    324  QQSQAAVEAISRRMSHMASQLYSVEVSYLDFLNRVRMEEVSLRSAGMWeE 373

VPHPWLNLFVPkSrIldFdrgVFkgIlLkntnnsGPiLvYPmnrsKWDdr
                          V+HPWLN+FVPk +++ F+++++++ +  +++ G+iL+YP++r+KWD++
           ZmCkx5    374  VHHPWLNMFVPKAGVAGFRDLLMDNV--SPDSFQGLILIYPLLRDKWDTN 421 mSaviPd....edEdVFYlVGlLrSAvP......ysagpgdleelenqNr
                          +S+viPd++++d+ V+Y+VG+LrSA+P+++++++++++ +l el++ +r
           ZmCkx5    422  TSVVIPDsgptADDPVMYVVGILRSANPgpeedgDGCSHRCLHELLRSHR 471 rIlefCekaGIgyKQYLPhYLtsqedNYWkrHFGAakWdrFvdRKarYDP
                          rI++++ +a +g+KQYLPh+ +++++  W+ H G ++W+rF+dRkar+DP
           ZmCkx5    472  RIADAA-EARLGAKQYLPHH-PTPAR--WQQHLG-RRWERFADRKARFDP 516 kaILsPGQgIF<-*
                          ++IL+PGQgIF
           ZmCkx5    517  LRILGPGQGIF   527

PF09265.1.ls: domain 1 of 1, from 239 to 527: score 449.7, E = 3.6e-132
                          *->PkrVRWvRvlYsDFaaFTkDQErLISkenggggakvGfDYVEGFvil
                             P +V WvR++Y+D aFT+DQE+L+S++++       +DYVEGF++l
           ZmCkx5    239     PEKVTWVRAFYDDLGAFTRDQELLVSIPDS-------VDYVEGFMVL 278 nrtglvnnwrssFFspsDpariasLasknnggvlYcLEvakyYdyadsda
                          n+ +l+++++++   p+ +++ +++++ +   +++Yc E+a++ +      +
           ZmCkx5    279  NERSLHSSSIAF---PASVDFSPDFGTRSSPRIYYCVEFAVHHH--HGYQ 323 atvDqeveeLlrqLsfvpGflFstDVsYvdFLdRVhreElkLRskGlW.d
                          +    ve+++r++s+   + l+s++VsY+dFL+RV++eE++LRs+G+W++
           ZmCkx5    324  QQSQAAVEAISRRMSHMASQLYSVEVSYLDFLNRVRMEEVSLRSAGMWeE 373

VPHPWLNLFVPkSrIldFdrgVFkgIlLkntnnsGPiLvYPmnrsKWDdr
                          V+HPWLN+FVPk +++ F+++++++ +  +++ G+iL+YP++r+KWD++
           ZmCkx5    374  VHHPWLNMFVPKAGVAGFRDLLMDNV--SPDSFQGLILIYPLLRDKWDTN 421 mSaviPd....edEdVFYlVGlLrSAvP......ysagpgdleelenqNr
                          +S+viPd++++d+ V+Y+VG+LrSA+P+++++++++++ +l el++ +r
           ZmCkx5    422  TSVVIPDsgptADDPVMYVVGILRSANPgpeedgDGCSHRCLHELLRSHR 471
```

Figure 9

```
                 rIlefCekaGIgyKQYLPhYLtsqedNYWkrHFGAakWdrFvdRKarYDP
                 rI++++ +a +g+KQYLPh+ +++++  W+ H G ++W+rF+dRKar+DP
   ZmCkx5    472 RIADAA-EARLGAKQYLPHH-PTPAR--WQQHLG-RRWERFADRKARFDP 516 kaILsPGQgIF<-*
                 ++IL+PGQgIF
   ZmCkx5    517 LRILGPGQGIF      527
```

Query sequence: ZmCkx6

```
Scores for sequence family classification (score includes all domains):
Model           Description                              Score    E-value  N
--------        -----------                              -----    -------  ---
PF09265.1.fs    Cytokinin dehydrogenase 1, FAD and cyto  629.6   1.2e-199  1
PF09265.1.ls    Cytokinin dehydrogenase 1, FAD and cyto  631.4   6.8e-187  1
PF01565.13.fs   FAD binding domain                        64.2    1.5e-17  1
PF01565.13.ls   FAD binding domain                        66.2    9.9e-17  1

Parsed for domains:
Model           Domain  seq-f seq-t    hmm-f hmm-t      score  E-value
--------        ------- ----- -----    ----- -----      -----  -------
PF01565.13.fs    1/1       65   215 ..     1   144 []   64.2   1.5e-17
PF01565.13.ls    1/1       65   215 ..     1   144 []   66.2   9.9e-17
PF09265.1.fs     1/1      247   528 ..     1   297 []  629.6   1.2e-199
PF09265.1.ls     1/1      247   528 ..     1   297 []  631.4   6.8e-187

Alignments of top-scoring domains:

PF01565.13.fs: domain 1 of 1, from 65 to 215: score 64.2, E = 1.5e-17
                 *->PaavvrPeseeevaaivrlAr..ehgipvtprGgGhslsfGgavpln
                    P av+ P+ + +va +v +A ++++g++v +rG Ghs s G+a+++
   ZmCkx6     65    PMAVFHPRAAGDVAGLVGAAFrsARGFRVSARGHGHSIS-GQAQAA- 109 tgGvvldls..........rklnriileiDpetdgtatveaGvtl.dLnr
                 gGvv+d+s++++++     r l   +++     ++++ v +G+  + d+
   ZmCkx6    110 -GGVVVDMSrgrgpgaavaRALP--VHSAALG-GHYVDVWGGELWvDVLN 155 alaakGlflpldpgsgipgtvGGaiatnagGygsekyGltrdnvlglevV
                 ++  +G+++p ++ ++ + +vGG++++ ++     ++ +G+   nv +l+vV
   ZmCkx6    156 WTLSHGGLAPRSWTDYLYLSVGGTLSNAGISGQAFHHGPQISNVYELDVV 205 ladGevvrls<-*
                 ++ Gevv++s
   ZmCkx6    206 TGKGEVVTCS      215

PF01565.13.ls: domain 1 of 1, from 65 to 215: score 66.2, E = 9.9e-17
                 *->PaavvrPeseeevaaivrlAr..ehgipvtprGgGhslsfGgavpln
                    P av+ P+ + +va +v +A ++++g++v +rG Ghs s G+a+++
   ZmCkx6     65    PMAVFHPRAAGDVAGLVGAAFrsARGFRVSARGHGHSIS-GQAQAA- 109 tgGvvldls..........rklnriileiDpetdgtatveaGvtl.dLnr
                 gGvv+d+s++++++     r l   +++     ++++ v +G+  + d+
   ZmCkx6    110 -GGVVVDMSrgrgpgaavaRALP--VHSAALG-GHYVDVWGGELWvDVLN 155 alaakGlflpldpgsgipgtvGGaiatnagGygsekyGltrdnvlglevV
                 ++  +G+++p ++ ++ + +vGG++++ ++     ++ +G+   nv +l+vV
   ZmCkx6    156 WTLSHGGLAPRSWTDYLYLSVGGTLSNAGISGQAFHHGPQISNVYELDVV 205 ladGevvrls<-*
                 ++ Gevv++s
   ZmCkx6    206 TGKGEVVTCS      215

PF09265.1.fs: domain 1 of 1, from 247 to 528: score 629.6, E = 1.2e-199
                 *->PkrVRWvRvlYsDFaaFTkDQErLISkengggakvGfDYVEGFvil
                    P +VRW+R+lYs+F++FT+DQErLIS   +ggg    fDYVEGFv+
   ZmCkx6    247    P-KVRWIRALYSNFSEFTADQERLISL-GSGGGRR--FDYVEGFVVA 289 nrtglvnnwrssFFspsDpariasLasknnggvlYcLEvakyYdyadsda
                 +gl nnwrssFFsp++p++++sL++   +++vlYcLEv+k+Yd  d++a
   ZmCkx6    290 A-EGLINNWRSSFFSPQNPVKLTSLKH--HSSVLYCLEVTKNYD--DETA 334 atvDqeveeLlrqLsfvpGflFstDVsYvdFLdRVhreElkLRskGlWdV
                 +vDq+v++Ll++L+f+pG++F+tD++YvdFLdRVh++ElkLR+kG+W+V
   ZmCkx6    335 GSVDQDVDTLLGELNFLPGTVFTTDLPYVDFLDRVHKAELKLRAKGMWEV 384

PHPWLNLFVPkSrIldFdrgVFkgIlLkntnn..sGPiLvYPmnrsKWDd
                 PHPWLNLFVP SrI+dFdrgVF+g+ L++++++  GP+L+YPmn++KWD+
   ZmCkx6    385 PHPWLNLFVPASRIADFDRGVFRGV-LGGRTAgaGGPVLIYPMNKHKWDP 433
```

Figure 9

```
                        rmSaviPdedEdVFYlVGlLrSAvPysagpgdleelenqNrrIlefCeka
                        r+Sav+Pd  E+VFYlV++LrSA P+   +p +le+l +qN+rIl+fC +a
        ZmCkx6     434  RSSAVTPD--EEVFYLVAFLRSALPG--APESLEALARQNQRILDFCAGA 479

GIgyKQYLPhYLtsqedNYWkrHFGAakWdrFvdRKarYDPkaILsPGQg
                        GIg+KQYLP++ +++  +   W +HFGAa+WdrF+++Ka++DP+aIL+ GQg
        ZmCkx6     480  GIGAKQYLPGH-KARHE--WAEHFGAARWDRFARLKAEFDPRAILAAGQG 526

IF<-*
                        IF
        ZmCkx6     527  IF       528

PF09265.1.ls: domain 1 of 1, from 247 to 528: score 631.4, E = 6.8e-187
                        *->PkrVRWvRvlYsDFaaFTkDQErLISkenggggakvGfDYVEGFvil
                           P +VRW+R+lYs+F++FT+DQErLIS   +ggg    fDYVEGFv+
        ZmCkx6     247     P-KVRWIRALYSNFSEFTADQERLISL-GSGGGRR--FDYVEGFVVA 289 nrtglvnnwrssFFspsDpariasLasknnggvlYcLEvakyYdyadsda
                        +gl nnwrssFFsp++p++++sL++   +++vlYcLEv+k+Yd  d++a
        ZmCkx6     290  A-EGLINNWRSSFFSPQNPVKLTSLKH--HSSVLYCLEVTKNYD--DETA 334 atvDqeveeLlrqLsfvpGflFstDVsYvdFLdRVhreElkLRskGlWdV
                        +vDq+v++Ll++L+f+pG++F+tD++YvdFLdRVh+++ElkLR+kG+W+V
        ZmCkx6     335  GSVDQDVDTLLGELNFLPGTVFTTDLPYVDFLDRVHKAELKLRAKGMWEV 384

PHPWLNLFVPkSrIldFdrgVFkgIlLkntnns..GPiLvYPmnrsKWDd
                        PHPWLNLFVP SrI+dFdrgVF+g+ L+++++   +GP+L+YPmn++KWD+
        ZmCkx6     385  PHPWLNLFVPASRIADFDRGVFRGV-LGGRTAGaqGPVLIYPMNKHKWDP 433 rmSaviPdedEdVFYlVGlLrSAvPysagpgdleelenqNrrIlefCeka
                        r+Sav+Pd  E+VFYlV++LrSA P+   +p +le+l +qN+rIl+fC +a
        ZmCkx6     434  RSSAVTPD--EEVFYLVAFLRSALPG--APESLEALARQNQRILDFCAGA 479

GIgyKQYLPhYLtsqedNYWkrHFGAakWdrFvdRKarYDPkaILsPGQg
                        GIg+KQYLP++ +++  +   W +HFGAa+WdrF+++Ka++DP+aIL+ GQg
        ZmCkx6     480  GIGAKQYLPGH-KARHE--WAEHFGAARWDRFARLKAEFDPRAILAAGQG 526

IF<-*
                        IF
        ZmCkx6     527  IF       528
```

Query sequence: ZmCkx7

```
Scores for sequence family classification (score includes all domains):
Model           Description                               Score    E-value  N
---------       -----------                               -----    -------  ---
PF09265.1.fs    Cytokinin dehydrogenase 1, FAD and cyto   510.2   8.3e-162  1
PF09265.1.ls    Cytokinin dehydrogenase 1, FAD and cyto   512.0     6e-151  1
PF01565.13.fs   FAD binding domain                         91.6    3.1e-25  2
PF01565.13.ls   FAD binding domain                         85.3    1.7e-22  1

Parsed for domains:
Model           Domain   seq-f  seq-t    hmm-f hmm-t       score  E-value
---------       ------   -----  -----    ----- -----       -----  -------
PF01565.13.fs    1/2        74    128 ..      1    57 [.    38.1  3.1e-10
PF01565.13.ls    1/1        74    232 ..      1   144 []    85.3  1.7e-22
PF01565.13.fs    2/2       151    232 ..     62   144 .]    53.5  1.5e-14
PF09265.1.fs     1/1       264    575 ..      1   297 []   510.2 8.3e-162
PF09265.1.ls     1/1       264    575 ..      1   297 []   512.0   6e-151

Alignments of top-scoring domains:
PF01565.13.fs: domain 1 of 2, from 74 to 128: score 38.1, E = 3.1e-10
                        *->PaavvrPeseeevaaivrlAreh..gipvtprGgGhslsfGgavpln
                           Paav++P ++++aa++r+  +  + +pv +rG Ghs+  G+a++
        ZmCkx7      74     PAAVFYPSCAADIAALLRASSASasPFPVSARGRGHSTR-GQATA-- 117 tgGvvldlsrkl<-*
                        gGvv+d+++ l
        ZmCkx7     118  PGGVVVDMAS-L       128

PF01565.13.ls: domain 1 of 1, from 74 to 232: score 85.3, E = 1.7e-22
                        *->PaavvrPeseeevaaivrlAreh..gipvtprGgGhslsfGgavpln
                           Paav++P ++++aa++r+  +  + +pv +rG Ghs+  G+a++
        ZmCkx7      74     PAAVFYPSCAADIAALLRASSASasPFPVSARGRGHSTR-GQATA-- 117 tgGvvldlsrklnri.ileiDp.................etdgtatveaG
                        gGvv+d+++ l      ++ ++++ ++++ + +  + + ++++ +++
        ZmCkx7     118  PGGVVVDMAS-LAVAaGRDETAttnasstsasarlavsvD-GRYIDAGGE 165
```

Figure 9

```
                    vtl.dLnralaakGlflpldpgsgipgtvGGaiatnagGygsekyGltrd
                      + d+ +a+ a+Gl+    ++ ++ + tvGG++++ ++    ++++G+
       ZmCkx7   166 QLWvDVLHAALAHGLTPR-SWTDYLRLTVGGTLSNAGISGQAFRHGPQIS 214 nvlglevVladGevvrls<-*
                    nvl+l+vV+++G++v++s
       ZmCkx7   215 NVLELDVVTGTGDMVTCS    232

PF01565.13.fs: domain 2 of 2, from 151 to 232: score 53.5, E = 1.5e-14
                    *->leiDpetdgtatveaGvtl.dLnralaakGlflpldpgsgipgtvGG
                       l +  + ++++ +++   + d+ +a+ a+Gl+    ++ ++ + tvGG
       ZmCkx7   151    LAVSVD-GRYIDAGGEQLWvDVLHAALAHGLTPR-SWTDYLRLTVGG 195 aiatnagGygsekyGltrdnvlglevVladGevvrls<-*
                    ++++ ++    ++++G+    nvl+l+vV+++G++v++s
       ZmCkx7   196 TLSNAGISGQAFRHGPQISNVLELDVVTGTGDMVTCS    232

PF09265.1.fs: domain 1 of 1, from 264 to 575: score 510.2, E = 8.3e-162
                    *->PkrVRWvRvlYsDFaaFTkDQErLISkengggakvG.fDYVEGFvi
                       P+r+RW R+lY+   a+ T+DQErLI+ ++  gga  G +DYVEG+v+
       ZmCkx7   264    PARARWLRLLYTGAADLTADQERLIADDERRGGALAGlMDYVEGSVV 310 ln.rtglvnnwrss.......FFspsDpariasLasknnggvlYcLEvak
                    + ++gl ++wrss+++++++++F+s +D aria+La + +ggvlY+LE+a+
       ZmCkx7   311 TDlQQGLIGSWRSQpppssssFYSATDAARIAALAEE-AGGVLYFLEGAV 359 yYdya.dsdaatvDqeveeLlrqLsfvpGflFstDVsYvdFLdRVhreEl
                    yY +a+d+++aa+vD++v+++lr+L++  +Gf++++DVsY +FLdRV  +E+
       ZmCkx7   360 YYGGAsDTTAADVDKRVDVMLRELRYARGFAYVQDVSYEQFLDRVSAGER 409 kLRskGlWdVPHPWLNLFVPksrIldFdrgVFkgIlLkntnn....sGPi
                    LR  GlWdVPHPWLNLF P+SrIldF++gVF+g+lL  ++++++ GP+
       ZmCkx7   410 RLRGEGLWDVPHPWLNLFLPRSRILDFAAGVFHGVLLPTRAggggGGPV 459

LvYPmnrsKWDdrmSaviP....ded.EdVFYlVGlLrSAvPysagpgdl
                    LvYPmnr KWD  +Sav+P +++d+d+++VFY+VG+LrSA   ++ gdl
       ZmCkx7   460 LVYPMNRGKWDGATSAVLPyddgDGDgDEVFYTVGILRSA----VADGDL 505 eelenqNrrIlefCekaGIgyKQYLPhYLtsqedNYW.krHFGAa....k
                    ++e+qN+++++fCe+aGI + QYLP Y ++q+d  W  rHFG + ++++
       ZmCkx7   506 RRMEEQNAEVARFCEAAGIPCTQYLPSY-ATQAD--WaARHFG-PagsgR 551

WdrFvdRKarYDPkaILsPGQgIF<-*
                    Wd+F +RK +YDP+aILs+GQ+IF
       ZmCkx7   552 WDTFLRRKRKYDPMAILSRGQRIF    575

PF09265.1.ls: domain 1 of 1, from 264 to 575: score 512.0, E = 6e-151
                    *->PkrVRWvRvlYsDFaaFTkDQErLISkengggakvG.fDYVEGFvi
                       P+r+RW R+lY+   a+ T+DQErLI+ ++  gga  G +DYVEG+v+
       ZmCkx7   264    PARARWLRLLYTGAADLTADQERLIADDERRGGALAGlMDYVEGSVV 310 ln.rtglvnnwrss.......FFspsDpariasLasknnggvlYcLEvak
                    + ++gl ++wrss+++++++++F+s +D aria+La + +ggvlY+LE+a+
       ZmCkx7   311 TDlQQGLIGSWRSQpppssssFYSATDAARIAALAEE-AGGVLYFLEGAV 359 yYdya.dsdaatvDqeveeLlrqLsfvpGflFstDVsYvdFLdRVhreEl
                    yY +a+d+++aa+vD++v+++lr+L++  +Gf++++DVsY +FLdRV  +E+
       ZmCkx7   360 YYGGAsDTTAADVDKRVDVMLRELRYARGFAYVQDVSYEQFLDRVSAGER 409 kLRskGlWdVPHPWLNLFVPksrIldFdrgVFkgIlLkntnns....GPi
                    LR  GlWdVPHPWLNLF P+SrIldF++gVF+g+lL  +++ ++++GP+
       ZmCkx7   410 RLRGEGLWDVPHPWLNLFLPRSRILDFAAGVFHGVLLPTRAGgggGPV 459

LvYPmnrsKWDdrmSaviP....ded.EdVFYlVGlLrSAvPysagpgdl
                    LvYPmnr KWD  +Sav+P +++d+d+++VFY+VG+LrSA   ++ gdl
       ZmCkx7   460 LVYPMNRGKWDGATSAVLPyddgDGDgDEVFYTVGILRSA----VADGDL 505 eelenqNrrIlefCekaGIgyKQYLPhYLtsqedNYW.krHFGAa....k
                    ++e+qN+++++fCe+aGI + QYLP Y ++q+d  W  rHFG + ++++
       ZmCkx7   506 RRMEEQNAEVARFCEAAGIPCTQYLPSY-ATQAD--WaARHFG-PagsgR 551

WdrFvdRKarYDPkaILsPGQgIF<-*
                    Wd+F +RK +YDP+aILs+GQ+IF
       ZmCkx7   552 WDTFLRRKRKYDPMAILSRGQRIF    575
```

Query sequence: ZmCkx8

Figure 9

```
Scores for sequence family classification (score includes all domains):
Model           Description                               Score    E-value  N
-------         -----------                               -----    -------  ---
PF09265.1.fs    Cytokinin dehydrogenase 1, FAD and cyto   482.1    6.6e-153  1
PF09265.1.ls    Cytokinin dehydrogenase 1, FAD and cyto   483.9    1.8e-142  1
PF01565.13.fs   FAD binding domain                         96.2    1.5e-26   1
PF01565.13.ls   FAD binding domain                         98.2    2.3e-26   1

Parsed for domains:
Model           Domain  seq-f seq-t    hmm-f hmm-t     score  E-value
-------         ------  ----- -----    ----- -----     -----  -------
PF01565.13.fs   1/1        55   205 ..     1   144 []   96.2  1.5e-26
PF01565.13.ls   1/1        55   205 ..     1   144 []   98.2  2.3e-26
PF09265.1.fs    1/1       237   518 ..     1   297 []  482.1  6.6e-153
PF09265.1.ls    1/1       237   518 ..     1   297 []  483.9  1.8e-142

Alignments of top-scoring domains:

PF01565.13.fs: domain 1 of 1, from 55 to 205: score 96.2, E = 1.5e-26
                   *->PaavvrPeseeevaaivrlAreh......gipvtprGgGhslsfGga
                      + av +P+s+++a+++ +       +++++++ +v++rG+Ghsl  G+a
         ZmCkx8  55  AIAVMQPGSPADIARLLGALSSTgpgpgpKAAVAARGAGHSLH-GQA 100 vplntgGvvldlsrklnriileiDpe......tdgtatveaGvtl.dLnr
                    ++   gG+v+ ++  l r ++e+ +++++++++ +a v++G+ + ++ +
         ZmCkx8 101  QA--RGGIVVETRA-LPR-LVEVVRRgdgdggGAAYADVGGGALWvEVLE 146 alaakGlflpldpgsgipgtvGGaiatnagGygsekyGltrdnvlglevV
                    ++ ++Gl+    ++ ++ + tvGG+++++++    ++k+G+   nvl levV
         ZmCkx8 147  ECLRAGLAPR-SWTDYLYLTVGGTLSNGGISGQAFKHGPQISNVLQLEVV 195 ladGevvrls<-*
                    +++Gevv++s
         ZmCkx8 196  TGTGEVVTCS    205

PF01565.13.ls: domain 1 of 1, from 55 to 205: score 98.2, E = 2.3e-26
                   *->PaavvrPeseeevaaivrlAreh......gipvtprGgGhslsfGga
                      + av +P+s+++a+++ +       +++++++ +v++rG+Ghsl  G+a
         ZmCkx8  55  AIAVMQPGSPADIARLLGALSSTgpgpgpKAAVAARGAGHSLH-GQA 100 vplntgGvvldlsrklnriileiDpe......tdgtatveaGvtl.dLnr
                    ++   gG+v+ ++  l r ++e+ +++++++++ +a v++G+ + ++ +
         ZmCkx8 101  QA--RGGIVVETRA-LPR-LVEVVRRgdgdggGAAYADVGGGALWvEVLE 146 alaakGlflpldpgsgipgtvGGaiatnagGygsekyGltrdnvlglevV
                    ++ ++Gl+    ++ ++ + tvGG+++++++    ++k+G+   nvl levV
         ZmCkx8 147  ECLRAGLAPR-SWTDYLYLTVGGTLSNGGISGQAFKHGPQISNVLQLEVV 195 ladGevvrls<-*
                    +++Gevv++s
         ZmCkx8 196  TGTGEVVTCS    205

PF09265.1.fs: domain 1 of 1, from 237 to 518: score 482.1, E = 6.6e-153
                   *->PkrVRWvRvlYsDFaaFTkDQErLISkenggggakvGfDYVEGFvil
                      P +VRWvR++Y++F++FTkDQE+L+S+++        +DYVEGF++l
         ZmCkx8 237  PPKVRWVRAFYDSFETFTKDQELLVSMPEL-------VDYVEGFMVL 276 nrtglvnnwrssFFspsDpariasLask..nnggv..lYcLEvakyYdya
                    n+++l +++ ++   p+++++ ++++s+++n++v   +Yc+E+a++++
         ZmCkx8 277  NEQSLRSSSVAF---PAQVNFRPDFGSDdgTNKKVcyYYCIEFAVHDF-- 321 dsdaatvDqeveeLlrqLsfvpGflFstDVsYvdFLdRVhreElkLRskG
                    +    + D++v+ ++++Ls+++++++s++V+Y dFL+RV++eE++LR++G
         ZmCkx8 322  QRQDSAADHVVDLVSGKLSYLRPHAYSVEVAYWDFLNRVRMEEESLRRRG 371 lWdVPHPWLNLFVPkSrIldFdrgVFkgIlLkntnnsGPiLvYPmnrsKW
                    lWdVPHPWLNLFVP++++++F ++++ +I  ++++++GP+LvYP+++++W
         ZmCkx8 372  LWDVPHPWLNLFVPRHGVARFMDLLMATI--AQGDFEGPVLVYPLLTHRW 419

DdrmSaviPdedEdVFYlVGlLrSAvPysagpgdleelenqNrrIlefCe
                    D +mSav+P +++ V+Y++ +LrS++P+++g+ + e++++q+rr+++ +
         ZmCkx8 420  DGNMSAVVPAAPDGVMYVFSVLRSTDPARCGRACMERILEQHRRVADEA- 468 kaGIgyKQYLPhYLtsqedNYwkrHFGAakWdrFvdRKarYDPkaILsPG
                    +  +g+KQYL+++  +s +    W++HFG a WdrFv RKar+DP+ +L+PG
         ZmCkx8 469  CRRLGAKQYLARQ-PSLAH--WRDHFG-ASWDRFVARKARFDPMNVLGPG 514

QgIF<-*
                    QgIF
```

Figure 9

```
            ZmCkx8    515 QGIF      518
PF09265.1.ls: domain 1 of 1, from 237 to 518: score 483.9, E = 1.8e-142
                  *->PkrVRWvRvlYsDFaaFTkDQErLISkengggakvGfDYVEGFvil
                     P +VRWvR++Y++F++FTkDQE+L+S+++         +DYVEGF++l
            ZmCkx8    237 PPKVRWVRAFYDSFETFTKDQELLVSMPEL------VDYVEGFMVL 276 nrtglvnnwrssFFspsDpariasLask..nnggv..lYcLEvakyYdya
                     n+++l +++ ++    p+++++ ++++s++++n++v  +Yc+E+a++++
            ZmCkx8    277 NEQSLRSSSVAF---PAQVNFRPDFGSDdgTNKKVcyYYCIEFAVHDF-- 321 dsdaatvDqeveeLlrqLsfvpGflFstDVsYvdFLdRVhreElkLRskG
                     +   +   D++v+ ++++Ls++++++s++V+Y dFL+RV++eE++LR++G
            ZmCkx8    322 QRQDSAADHVVDLVSGKLSYLRPHAYSVEVAYWDFLNRVRMEEESLRRRG 371 lWdVPHPWLNLFVPkSrIldFdrgVFkgIlLkntnnsGPiLvYPmnrsKW
                     lWdVPHPWLNLFVP++++++F ++++ +I  +++++GP+LvYP+++++W
            ZmCkx8    372 LWDVPHPWLNLFVPRHGVARFMDLLMATI--AQGDFEGPVLVYPLLTHRW 419

DdrmSaviPdedEdVFYlVGlLrSAvPysagpgdleelenqNrrIlefCe
                     D +mSav+P +++ V+Y++ +LrS++P+++g+ + e++++q+rr+++ +
            ZmCkx8    420 DGNMSAVVPAAPDGVMYVFSVLRSTDPARCGRACMERILEQHRRVADEA- 468 kaGIgyKQYLPhYLtsqedNYWkrHFGAakWdrFvdRKarYDPkaILsPG
                     + +g+KQYL+++ +s +    W++HFG a WdrFv RKar+DP+ +L+PG
            ZmCkx8    469 CRRLGAKQYLARQ-PSLAH--WRDHFG-ASWDRFVARKARFDPMNVLGPG 514

QgIF<-*
                     QgIF
            ZmCkx8    515 QGIF      518
```

Figure 9

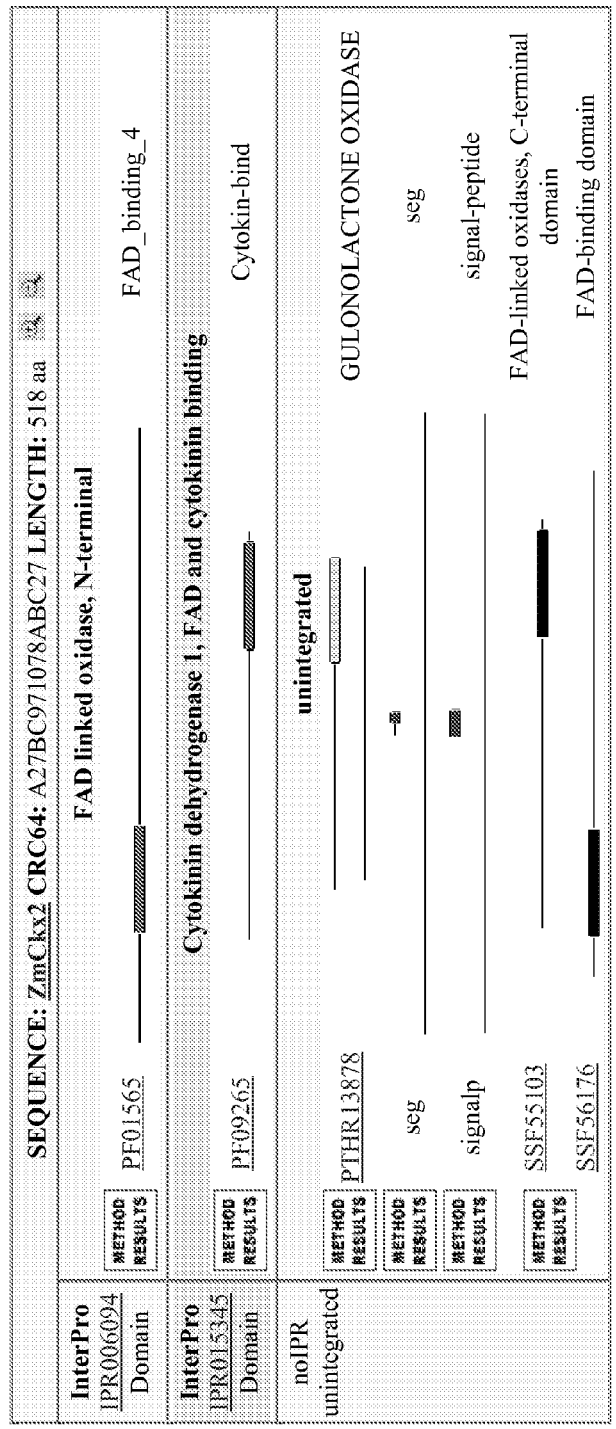
Figure 10.   InterPro Scan Data for ZmCkx 2-8

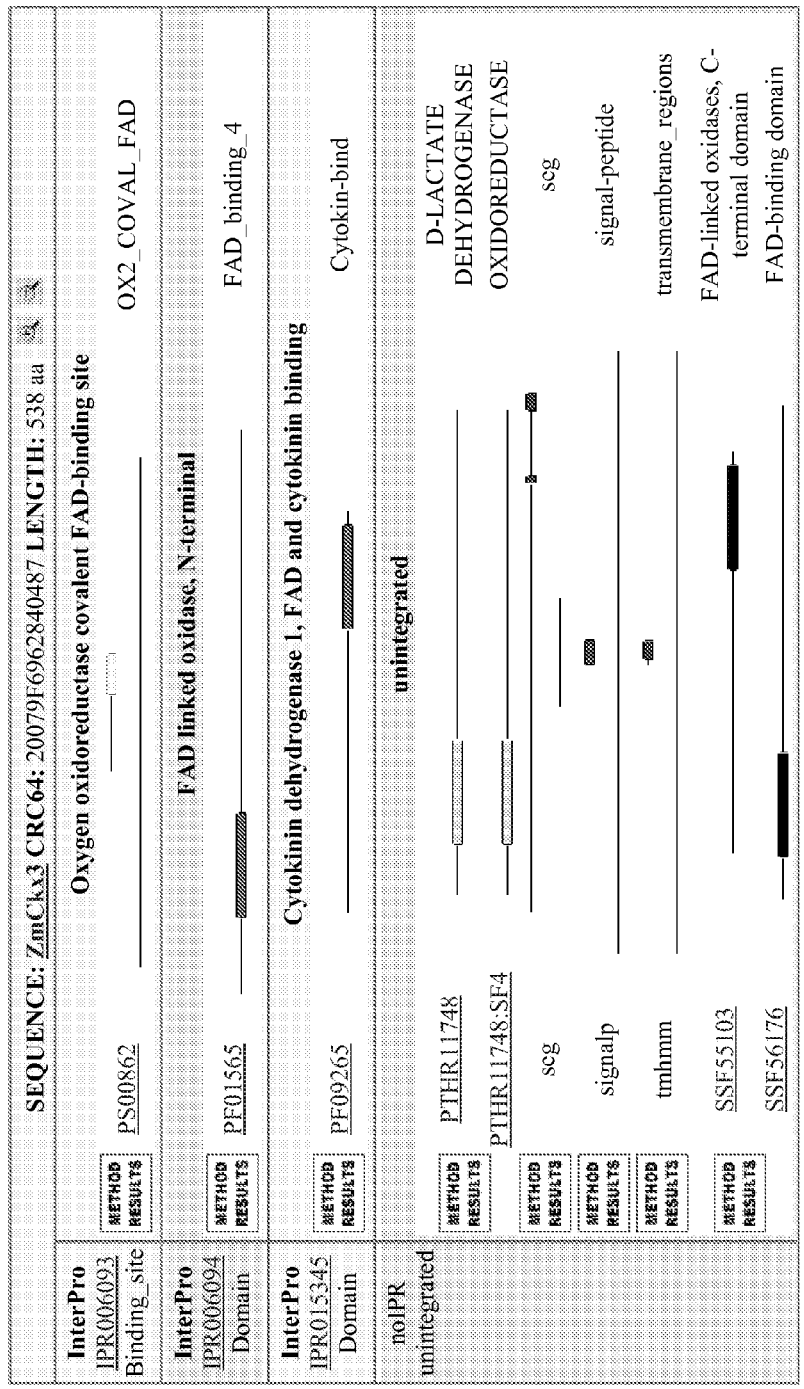
Figure 10.    InterPro Scan Data for ZmCkx 2-8

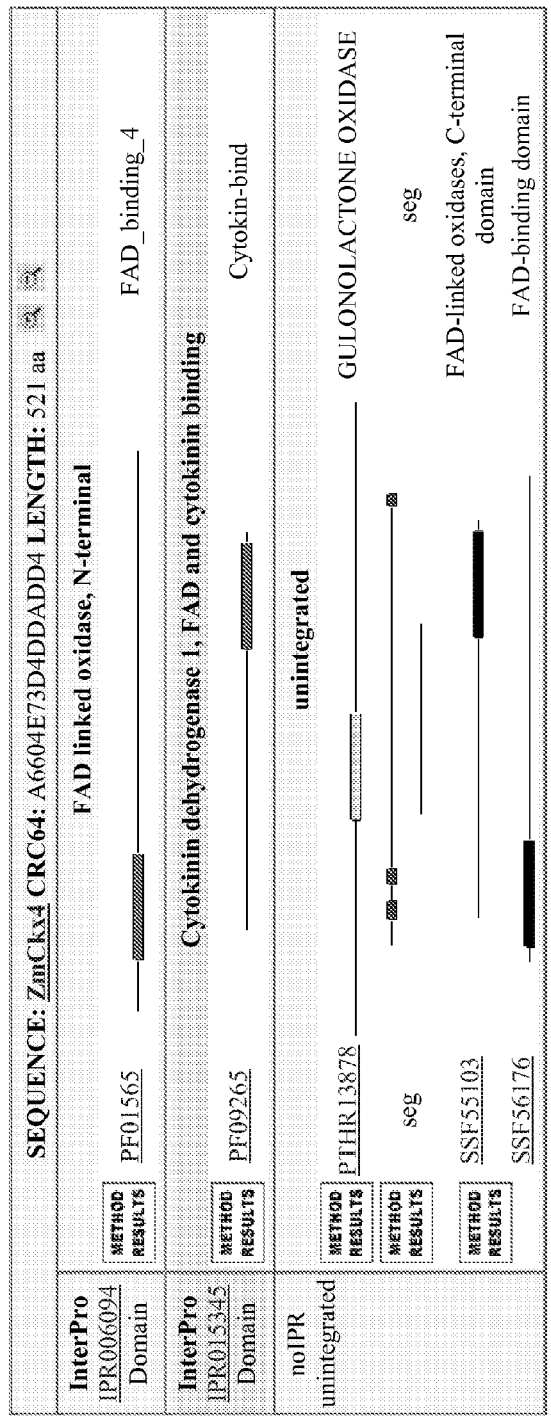
Figure 10.　　InterPro Scan Data for ZmCkx 2-8

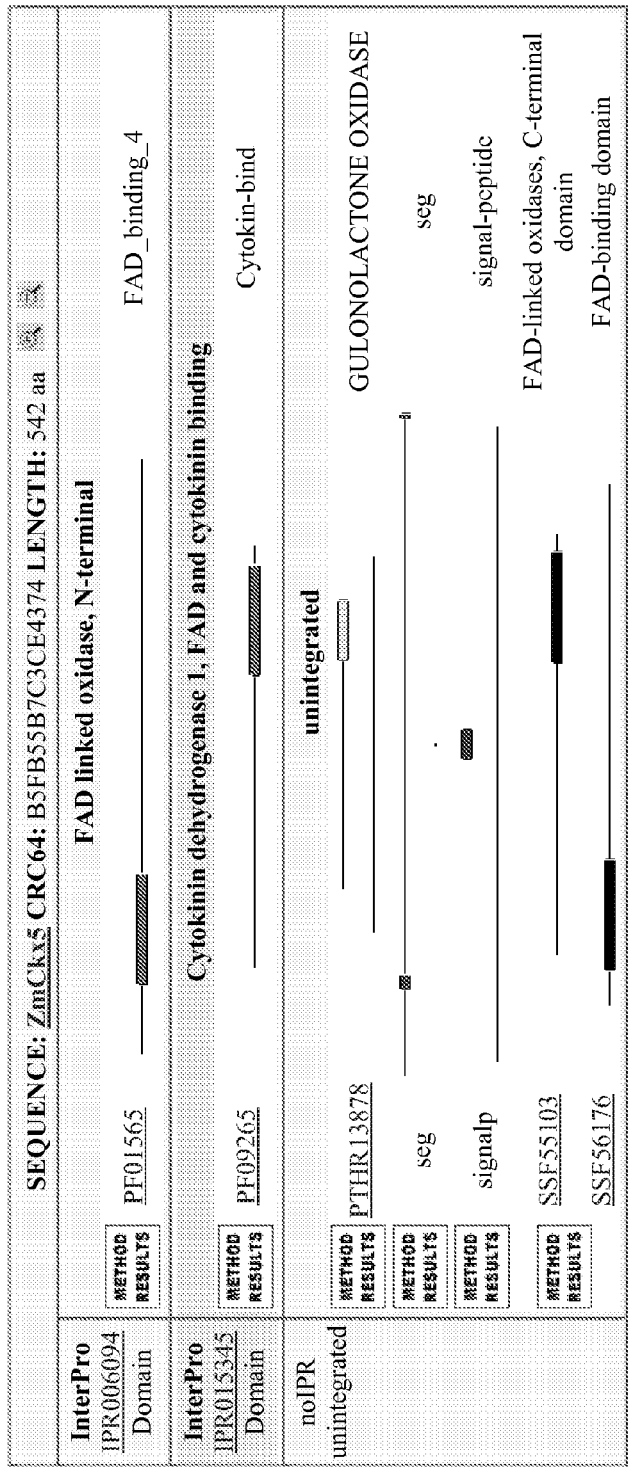
Figure 10. InterPro Scan Data for ZmCkx 2-8

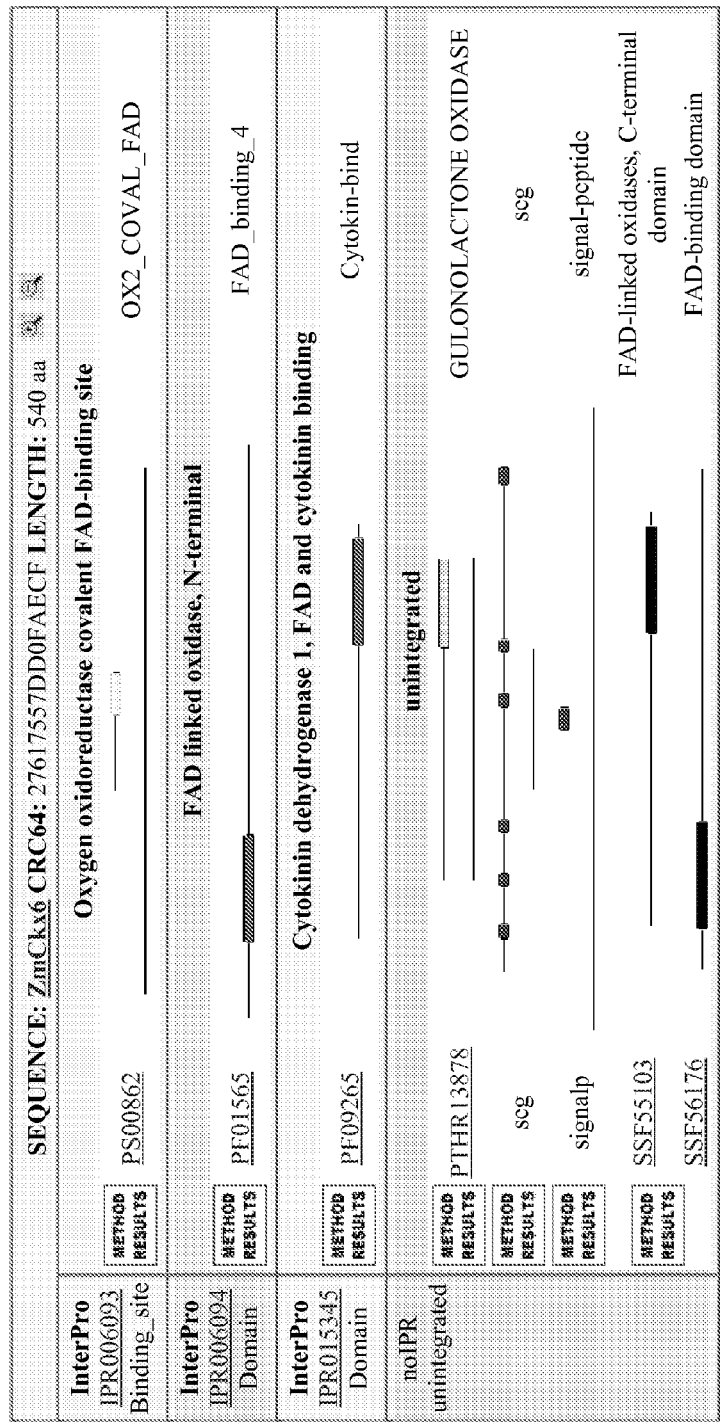
Figure 10. InterPro Scan Data for ZmCkx 2-8

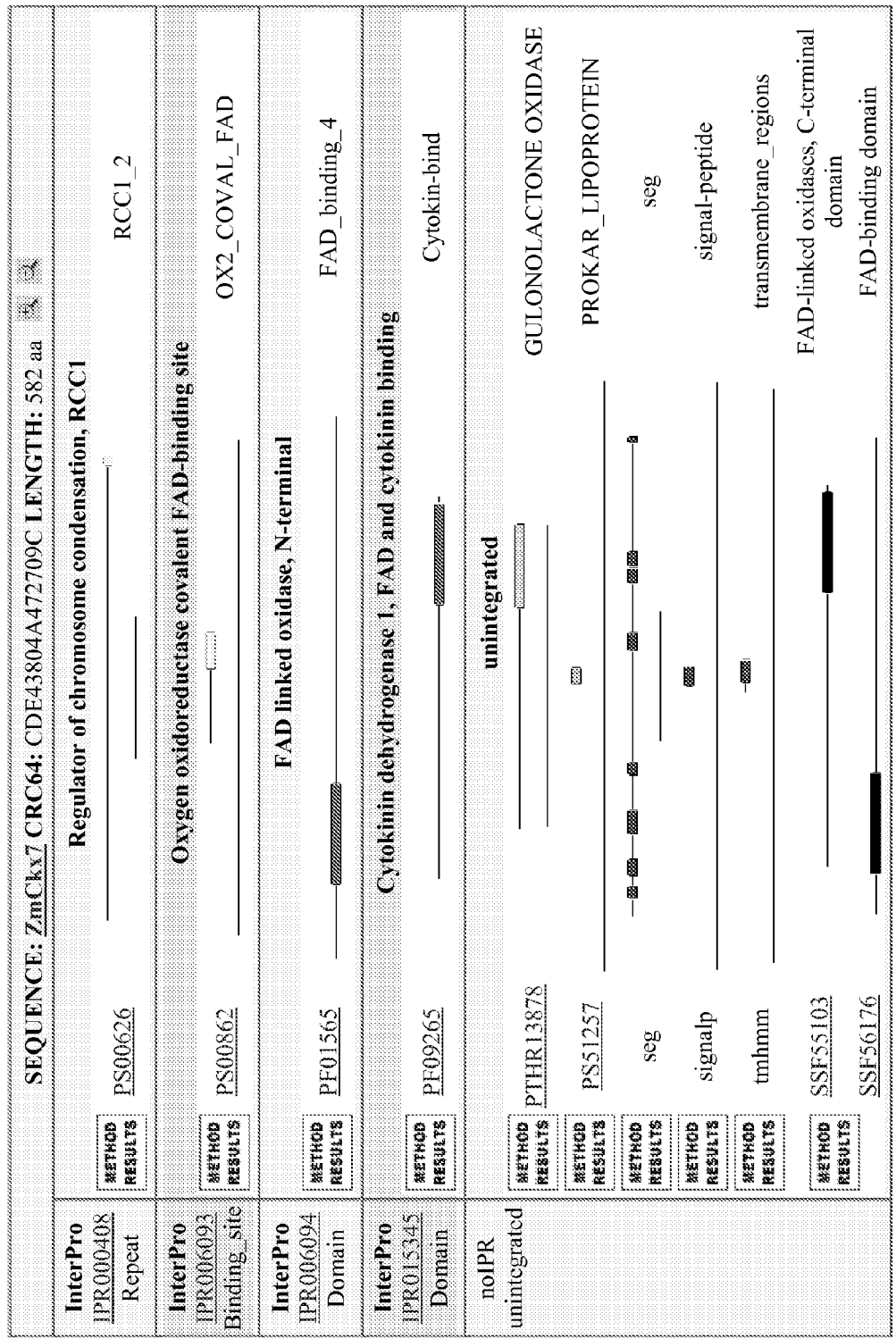
Figure 10. InterPro Scan Data for ZmCkx 2-8

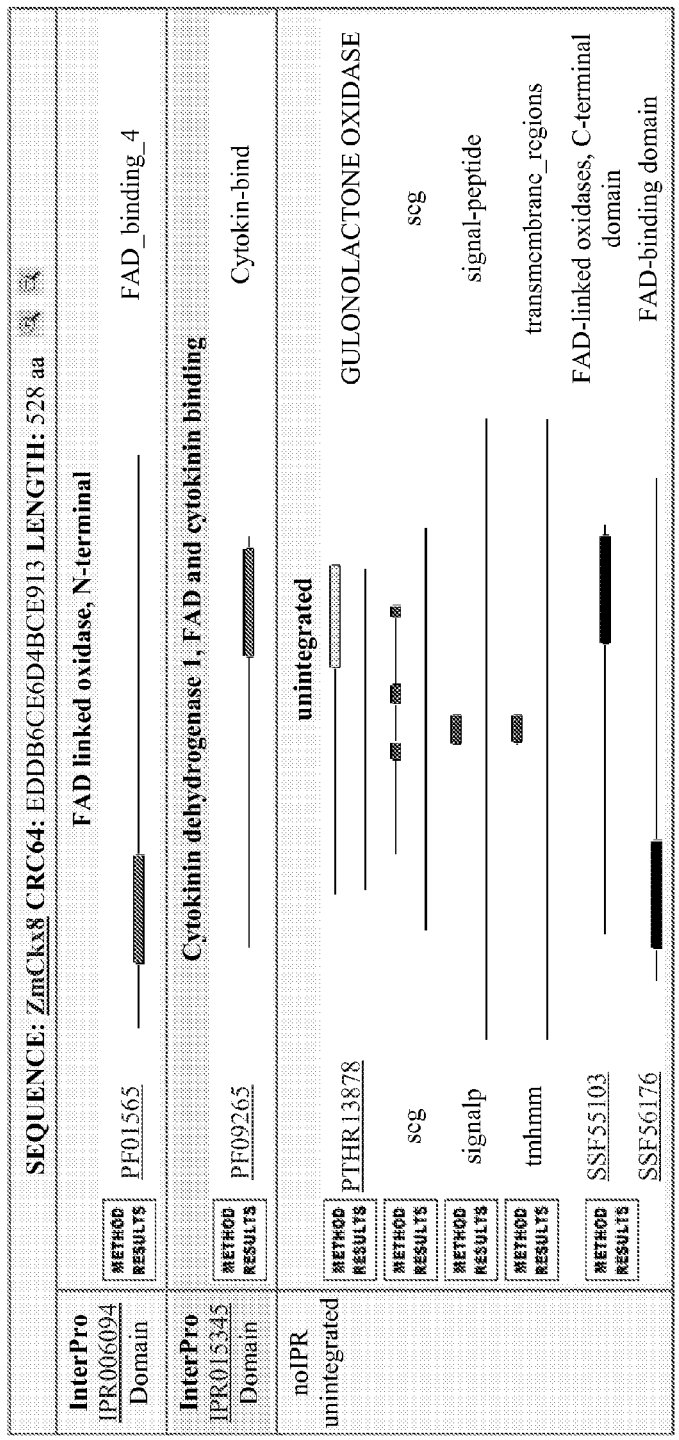
Figure 10.     InterPro Scan Data for ZmCkx 2-8

```
                1                                                        50
    AtCKX1      MGLTSSLRFH RQNNKTFLGI FMILVLSCIP GRTNLCSNHS ..VSTPKELP
    AtCKX2      .......... .....MANLR LMITLITVLM ITK.....SS NGIKIDLPKS
    AtCKX3      .......MAS YNLRSQVRLI AITIVIIITL STPITTNTSP QPWNILSHNE
    AtCKX4      .......... ...MTNTLCL SLITLITFFI SLTPTLIKSD EGIDVFLPIS
    AtCkx5      .......... .....MIAYI EPYFLENDAE AASAATAAGK STDGVSESLN
    AtCKX6      .........M NREMTSSFLL LTFAICKLII AVGLNVGP.. SELLRIGAID
    AtCKX7      .......... ....MLIVRS FTILLLSCIA FKLACCFSSS ..ISSLKALP
    DsCkx1      ....MNLHAM PPFLNPTSLL LTTTLMSILI QSP......N SLPTNLLTHP
    HvCkx2      .......... ..MRQLLLQY LKLFLLLGLG AVTAEHVLKH DVLASLGTLP
    HvCkx3      .......... ..MKQLLLQY LKLFLLLGLS RVTTEHVPKY DVLASLGTLP
    OsCKx1      ........MA AIYLLIAALI ASSHALAAHG AGGGVPLAAA APLPFPGDLA
    OsCkx2      .......MKQ EQVRMAVLLM LNCFVKATAP PPWPPSASSA SFLDDLGDLG
    OsCkx3      .......... MEVAMVCTR. VNLLILILSL CSPYKFIQSP ..........
    OsCkx4      .......MRG AMKPS.IVHC LKLLMLLALG GVTMHVPDED DVVASLGALR
    OsCkx5      .......... ..MAWCLVF. MVFLIYCLIS TVGLPVAPAD EAAMQLGG.V
    OsCkx6      .......... ........MA ARCSIAFMVM ASCLSVVVSG GLPGDLFAHS
    OsCkx7      .......... ........MA ARCSIAFMIM ASCLSVVVSG GLPGDLFALS
    OsCkx8      .......... MELKAMYLY. ..AAVLAVLL CSSVNFIQSP T.........
    OsCkx9      .......... ..MRPSLLQY LKLLLLLALG GVTTMHVPKQ DVPSSLEELT
    OsCkx10     ........M MPRAQLTTFL IVTSFLSTVP YLRAPVHGGV LTSYDVSSLD
    OsCkx11     .......... ....MMLAYM DHAAAAAEPD AGAEP..... ..........
    ZmCkx1      .......MAV VYYLLLAGLI ACSHALAAGT PALGDDRGRP WPASLA.ALA
    ZmCkx2a     .......... MKPPS.LVHC FKLLVLLALA RLTMHVPDED .MLSPLGALR
    ZmCkx2b     .......... MKPPSSLVHY FKLLVLLALA RLTMHVPDED .VLLSLGALR
    ZmCkx3      ........M ARRTRFVAIA ALLTSFLNVA AGHSRPLSGA GLPGDLFGLG
    ZmCkx4      .......... ....MMLAYM DRATAAAEPE DAGR...... ..........
    ZmCkx5      .......... MEVAMVVSAR ASLLILVLSL CSPYKFIQSP ..........
    ZmCkx6      .......... ..MTRCLMFT LLFLVSSLIS TVGLPVEPPA ELLQLGGGDV
    ZmCkx7      ......MARA TTSTVAALCF LLSCVSATPS TLAASSAIIH DIIRGLADT.
    ZmCkx8      .......... MEGKVLCTY. ..AGIVALLL CSSVNFIQSP S.........

51                                                       100
    AtCKX1      SSNPSDIRSS LVSLDLEGYI SFDDVHNVAK DFGN...... ..RYQLPPLA
    AtCKX2      .......... ...LNLTLST DPSIISAASH DFGN...... ..ITTVTPGG
    AtCKX3      .......... ...FAGKLTS SSSSVESAAT DFGH...... ..VTKIFPSA
    AtCKX4      .......... ...LNLTVLT DPFSISAASH DFGN...... ..ITDENPGA
    AtCkx5      .......... ...IQGEILC GGAAADIAGR DFGG...... ..MNCVKPLA
    AtCKX6      .......... ...VDGHFTV HPSDLASVSS DFGMLKSP.. .....EEPLA
    AtCKX7      .......... .....LVGHL EFEHVHHASK DFGN...... ..RYQLIPLA
    DsCkx1      .......... ...TSTHLRF DSLSLSAASS DFGD...... ..IIHSLPSA
    HvCkx2      .......... .....LDGHF SFHDLSAAAM DFGN...... ..LSSFPPVA
    HvCkx3      .......... .....LDGHF SFHDLPAAAR DFGN...... ..LSSFPPVA
    OsCKx1      .......... ...ASGKLRT DPNATVPASM DFGN...... ..ITAALPAA
    OsCkx2      .......... ...IAPLIRA DEAGTARASA DFGNLSVAGV GAPRLAAAAA
    OsCkx3      .......... .MDFGPLNLL PTTTTASS.. DFGRILFHS. ........PSA
    OsCkx4      .......... .....LDGHF SFDDAHAAAR DFGN...... ..RCSLLPAA
    OsCkx5      .......... ...GGGRLSV EPSDVMEASL DFGRLTS... .....AEPLA
    OsCkx6      .......... ...VASKLRV DRDTTARASS DFGR...... ..IVAAAPEA
    OsCkx7      .......... ...VASKLRV DRNSTARASS DFGR...... ..IVAAAPEA
    OsCkx8      .......... .DVLGPVALL EPTPSSAR.. DFGAVVSDA. ........PFA
    OsCkx9      .......... .....LDGHF SFHDVSAAAQ DFGN...... ..LSSFPPVA
    OsCkx10     .......... ...IMSKIHT DHDATTKASS DFGH...... ..IVHATPNG
```

FIGURE 11
Page 1 of 9

```
 OsCkx11    .......... ......AVAA VDAAEFAAAM DFGG...... ...LVSARPAA
  ZmCkx1    .......... ...LDGKLRT DSNATAAAST DFGN...... ...ITSALPAA
 ZmCkx2a    .......... .....LDGHF SFHDVSAMAR DFGN...... ...QCSFLPAA
 ZmCkx2b    .......... .....LDGHF SFHDVSAMAR DFGN...... ...QCSFLPAA
  ZmCkx3    .......... ...IASRIRT DSNSTAKAAT DFGQ...... ...MVRAAPEA
  ZmCkx4    .......... ......EPAT MAGGCAAAAT DFGG...... ...LGSAMPAA
  ZmCkx5    .......... .MDLGPLNLL PTTSTAAASS DFGRILFRA. ........PAA
  ZmCkx6    .......... ...GGGRLSV DASDIAEASR DFGGVAR... .....AEPMA
  ZmCkx7    .......... ...TAARVRT DAEATARAST DFG....TNA TADDATRPAA
  ZmCkx8    .......... .DVFGPVALL EPTASAAR.. DFGGVVSEA. .......AIA 101                                                 150
  AtCKX1    ILHPRSVFDI SSMMKHIVHL GST....... .SNLTVAARG HGHSLQGQAL
  AtCKX2    VICPSSTADI SRLLQYAANG K......... .STFQVAARG QGHSLNGQAS
  AtCKX3    VLIPSSVEDI TDLIKLSFDS Q......... .LSFPLAARG HGHSHRGQAS
  AtCKX4    VLCPSSTTEV ARLLRFANGG FSYNKGSTSP ASTFKVAARG QGHSLRGQAS
  AtCkx5    VVRPVGPEDI AGAVKAALRS DK........ ...LTVAARG NGHSINGQAM
  AtCKX6    VLHPSSAEDV ARLVRTAYGS AT........ ..AFPVSARG HGHSINGQAA
  AtCKX7    VLHPKSVSDI ASTIRHIWMM GTH....... .SQLTVAARG RGHSLQGQAQ
  DsCkx1    VFLPSSPSDI ATLLRLSHFS P......... .HSFTVSARG LGHSTRGQAQ
  HvCkx2    VLHPGSVADI ATTVRHVFLM GEH....... .SALTVAARG HGHSLYGQSQ
  HvCkx3    VLHPGSVADI ARTVRHVFLM GEH....... .STLTVAARG HGHSLYGQSQ
  OsCKx1    VLFPGSPGDV AELLRAAYAA PGR....... ..PFTVSFRG RGHSTMGQAL
  OsCkx2    VLYPSRPADI AALLRASCAR PA........ ..PFAVSARG CGHSVHGQAS
  OsCkx3    VLKPQAPRDI SLLLSFLSAS P......... LGKVTVAARG AGHSIHGQAQ
  OsCkx4    VLHPGSVSDV AATVRRVFQL GRS....... .SPLTVAARG HGHSLLGQSQ
  OsCkx5    VFHPRGAGDV AALVKAAYGS AS........ ..GIRVSARG HGHSISGQAQ
  OsCkx6    VLHPATPAEI AELVRFSASS PS........ ..PFPVAPRG QGHSARGQSL
  OsCkx7    VLHPATPAEI AELVRFSASS PS........ ..PFPVAPRG QGHSARGQSL
  OsCkx8    VMRPESPDDI ALLLGALSST APS......P ..RATVAAVG AGHSLHGQAQ
  OsCkx9    VLHPGSVADI ATTIRHVFLM GEH....... .STLTVAARG HGHSLYGQSQ
 OsCkx10    VFRPTFPADI AALIRLSLSQ PT........ ..PFTVAPRG KGHSSRGQAF
 OsCkx11    VVRPASSDDV ASAIRAAART AH........ ...LTVAARG NGHSVAGQAM
  ZmCkx1    VLYPSSTGDL VALLSAANST PGW....... ..PYTIAFRG RGHSLMGQAF
 ZmCkx2a    VLHPGSVSDI AATVRHVFSL GEG....... .SPLTVAARG HGHSLMGQSQ
 ZmCkx2b    VLHPGSVSDI AAIVRHVFSL GEG....... .SPLTVAARG HGHSLMGQSQ
  ZmCkx3    VFHPATPADI AALVRFSATS AA........ ..PFPVAPRG QGHSWRGQAL
  ZmCkx4    VVRPASADDV ASAIRAAALT PH........ ...LTVAARG NGHSVAGQAM
  ZmCkx5    VLRPQSPRDI SMLLSFLSGS PS........ LSRVTVAARG AGHSIHGQAQ
  ZmCkx6    VFHPRAAGDV AGLVGAAFRS AR........ ..GFRVSARG HGHSISGQAQ
  ZmCkx7    VFYPSCAADI AALLRASSAS AS........ ..PFPVSARG RGHSTRGQAT
  ZmCkx8    VMQPGSPADI ARLLGALSST GPG......P GPKAAVAARG AGHSLHGQAQ 151                                                 200
  AtCKX1    AHQ.GVVIKM ESLRSP.... .......... DIRIYKGKQ. ........PY
  AtCKX2    VSG.GVIVNM TCITD..... .......... .....VVVSK DK......KY
  AtCKX3    AKD.GVVVNM RSMVN..RD. .......... ...RGIKVSR TC......LY
  AtCKX4    APG.GVVVNM TCLAMAAKP. .......... ...AAVVISA DG......TY
  AtCkx5    AEG.GLVVDM STTAEN.... .......... ..HFEVGYLS GG...DATAF
  AtCKX6    AGRNGVVVEM NHG....... ..........V TGTPKPLVRP DE......MY
  AtCKX7    TRH.GIVIHM ESLHPQ.... .......... KLQVYSVDSP A.......PY
  DsCkx1    AFG.GIVINM PSLDG..... .......... ....GITVSI DG......MF
  HvCkx2    AAG.GIVIRM ESLRSV.... .......... KMQVHPG... AS......PY
  HvCkx3    AAG.GIVIRM ESLQSV.... .......... KMQVHPG... AS......PY
```

FIGURE 11

```
OsCKx1    AAG.GVVVHM QSMGGGGAP. .......... ....RINVSA DG......AY
OsCkx2    APD.GVVVDM ASLGRLQG.. .......... GGARRLAVSV EG......RY
OsCkx3    ALD.GIVVEM SSLPSEIEFY RR........ .......... ...GEGDVSY
OsCkx4    AAG.GIVVKM ESLAAA.... .......... AARAVRVHGG AS......PH
OsCkx5    AAG.GVVVDM SHG.WRAEAA .........E RTLPVYSPAL GG......HY
OsCkx6    APG.GVVVDM RALAARRGR. .......... .VNVSAGGAG AA......PY
OsCkx7    APG.GVVVDM RALASRRGR. .......... .VNVSAG... AA......PY
OsCkx8    ARD.GIVVET RALPRDVHVV SAR....... ......AHGG DD.DATVRAY
OsCkx9    AAE.GIIISM ESLQSN.... .......... TMRVNPG... VS......PY
OsCkx10   APG.GIVVDM SALGDHGHH. .......... .TSHRIDVSV DR......MY
OsCkx11   ARG.GLVLDM RALPR..... .......... ..RMQLVVAP SG.....EKF
ZmCkx1    APG.GVVVNM ASLGDAAAPP .......... ....RINVSA DG......RY
ZmCkx2a   AAQ.GIVVRM ESLRGA.... .......... RLQVHDG... .........F
ZmCkx2b   AAQ.GIVVRM ESLRGP.... .......... RLQVNDAGV. SP......PS
ZmCkx3    APG.GVVVDM GSLG.RGPR. .......... .INVSAVAG. AE......PF
ZmCkx4    AEG.GLVLDM RSLAAPSRR. .......... .AQMQLVVQC PDGGGGRRCF
ZmCkx5    APD.GIVVET RSLPGEMEFH HVR....... .......... GG.GEGRASY
ZmCkx6    AAG.GVVVDM SRGRGPGAAV .........A RALPVHSAAL GG......HY
ZmCkx7    APG.GVVVDM ASLAVAAGRD ETATTNASST SASARLAVSV DG......RY
ZmCkx8    ARG.GIVVET RALPRLVEVV RR........ .........G DG.DGGGAAY 201                                                 250
AtCKX1    VDVSGGEIWI NILRETLKYG .LSPKSWTDY LHLTVGGTLS NAGISGQAFK
AtCKX2    ADVAAGTLWV DVLKKTAEKG .VSPVSWTDY LHITVRGTLS NGGIGGQVFR
AtCKX3    VDVDAAWLWI EVLNKTLELG .LTPVSWTDY LYLTVGGTLS NGGISGQTFR
AtCKX4    ADVAAGTMWV DVLKAAVDRG .VSPVTWTDY LYLSVGGTLS NAGIGGQTFR
AtCkx5    VDVSGGALWE DVLKRCVSEY GLAPRSWTDY LGLTVGGTLS NAGVSGQAFR
AtCKX6    VDVWGGELWV DVLKKTLEHG .LAPKSWTDY LYLTVGGTLS NAGISGQALH
AtCKX7    VDVSGGELWI NILHETLKYG .LAPKSWTDY LHLTVGGTLS NAGISGQAFR
DsCkx1    VDAGAEQMWI DVLRETLRHG .LTPKSWTDY LYLTLGGTLS NGGISGQAFL
HvCkx2    VDASGGELWI NVLNKTLKYG .LAPKSWTDY LHLTVGGTLS NAGVSGQTFR
HvCkx3    VDASGGELWI NVLNKTLKYG .LAPKSWTDY LHLTVGGTLS NAGVSGQTFR
OsCKx1    VDAGGEQLWV DVLRAALARG .VAPRSWTDY LHLTVGGTLS NAGVSGQTYR
OsCkx2    VDAGGEQLWV DVLRASMAHG .LTPVSWTDY LHLTVGGTLS NAGISGQAFR
OsCkx3    ADVGGGIMWI ELLEQSLKLG .LAPRSWTDY LYLTIGGTLS NAGISGQTFK
OsCkx4    VDAPGGELWI NVLHETLKHG .LAPKSWTDY LHLTVGGTLS NAGVSGQAFR
OsCkx5    IDVWGGELWI DVLNWTLEHG GLAPRSWTDY LYLSVGGTLS NAGISGQAFH
OsCkx6    VDAGGEQLWA DVLRATLEHG .LAPRVWTDY LRITVAGTLS NAGIGGQAFR
OsCkx7    VDAGGEQLWA DVLRATLEHG .LAPRVWTDY LRITVAGTLS NAGIGGQAFR
OsCkx8    ADVGAGALWV EVLEECLKLG .LAPPSWTDY LYLTVGGTLS NGGISGQTFK
OsCkx9    VDASGGELWI NVLHETLKYG .LAPKSWTDY LHLTVGGTLS NAGVSGQTFR
OsCkx10   VDAGGEQLWI DVLHTALKHG .LTPRVWTDY LRITVGGTLS NAGIGGQAFR
OsCkx11   ADVPGGALWE EVLHWAVSKH GLAPASWTDY LRLTVGGTLS NGGVSGQSFR
ZmCkx1    VDAGGEQVWI DVLRASLARG .VAPRSWNDY LYLTVGGTLS NAGISGQAFR
ZmCkx2a   VDAPGGELWI NVLRETLKHG .LAPKSWTDY LHLTVGGTLS NAGVSGQAFR
ZmCkx2b   VDAPGGELWI NVLRETLKHG .LAPKSWTDY LHLTVGGTLS NAGVSGQAFR
ZmCkx3    VDAGGEQLWV DVLRATLRHG .LAPRVWTDY LRLTVGGTLS NAGIGGQAFR
ZmCkx4    ADVPGGALWE EVLHWAVDNH GLAPASWTDY LRLTVGGTLS NGGVSGQSFR
ZmCkx5    ADVGGGVLWI ELLERSLKLG .LAPRSWTDY LYLTVGGTLS NAGISGQTFK
ZmCkx6    VDVWGGELWV DVLNWTLSHG GLAPRSWTDY LYLSVGGTLS NAGISGQAFH
ZmCkx7    IDAGGEQLWV DVLHAALAHG .LTPRSWTDY LRLTVGGTLS NAGISGQAFR
ZmCkx8    ADVGGGALWV EVLEECLRAG .LAPRSWTDY LYLTVGGTLS NGGISGQAFK 251                                                 300
```

FIGURE 11

```
AtCKX1    HGPQINNVYQ LEIVTGKGEV VTCSEKRNSE LFFSVLGGLG QFGIITRARI
AtCKX2    NGPLVSNVLE LDVITGKGEM LTCSRQLNPE LFYGVLGGLG QFGIITRARI
AtCKX3    YGPQITNVLE MDVITGKGEI ATCSKDMNSD LFFAVLGGLG QFGIITRARI
AtCKX4    HGPQISNVHE LDVITGKGEM MTCSPKLNPE LFYGVLGGLG QFGIITRARI
AtCkx5    YGPQTSNVTE LDVVTGNGDV VTCSEIENSE LFFSVLGGLG QFGIITRARV
AtCKX6    HGPQISNVLE LDVVTGKGEV MRCSEEENTR LFHGVLGGLG QFGIITRARI
AtCKX7    HGPQISNVHQ LEIVTGKGEI LNCTKRQNSD LFNGVLGGLG QFGIITRARI
DsCkx1    HGPQISNVHE LDIVTGKGEM VTCSESNNPD LFFSVLGGLG QFGIITRARI
HvCkx2    HGPQISNVNE LEIVTGRGDI VTCSPEQNSD LFRAALGGLG QFGIITRARI
HvCkx3    HGPQISNVNE LEIVTGRGDI ITCSPEQNSD LFHAALGGLG QFGIITRARI
OsCKx1    HGPQISNVLE LDVITGHGET VTCSKAVNSD LFDAVLGGLG QFGVITRARV
OsCkx2    HGPQISNVLE LDVITGVGEM VTCSKEKAPD LFDAVLGGLG QFGVITRARI
OsCkx3    HGPQISNVLQ LEVVTGRGEI VTCSPTKDAE LFNAVLGGLG QFGIITRARI
OsCkx4    HGPQVSNVNQ LEIVTGRGEV VTCSHEVNSD LFYAALGGLG QFGIITRARI
OsCkx5    HGPQISNVYE LDVVTGKGEV VTCSESNNPD LFFGALGGLG QLGIITRARI
OsCkx6    HGPQIANVLE LDVITGRGDM VTCSRDKEPD LFFAVLGGLG QFGIITRARI
OsCkx7    HGPQIANVLE LDVITGTGDM VTCSRDKDSD LFFAVLGGLG QFGIITRARI
OsCkx8    HGPQISNVLQ LEVVTGKGEV VTCSPTEIPE LFFAVLGGLG QFGIITRARI
OsCkx9    HGPQISNVNE LEIVTGRGDV ITCSPEQNSD LFHAALGGLG QFGVITRARI
OsCkx10   HGPQISNVHE LDVVTGMGEM ITCSPEVNSA LFFAVLGGLG QFGVITRARI
OsCkx11   YGPQVSNVAQ LEVVTGDGEC HVCSRSADPD LFFAVLGGLG QFGVITRARI
ZmCkx1    HGPQISNVLE MDVITGHGEM VTCSKQLNAD LFDAVLGGLG QFGVITRARI
ZmCkx2a   HGPQVSNVNQ LEIVTGRGDV VTCSPEDNSD LFYAALGGLG QFGIITRARI
ZmCkx2b   HGPQVSNVNQ LEIVTGRGDV VTCSPDDNAD LFYAALGDLG QFGIITRARI
ZmCkx3    HGPQIANVHE LDVVTGTGEM VTCSMDVNSD LFMAALGGLG QFGVITRARI
ZmCkx4    YGPQVSNVAE LEVVTGDGER RVCSPSSHPD LFFAVLGGLG QFGVITRARI
ZmCkx5    HGPQISNVLQ LEVVTGRGEI VECSPSKEAD LFNAVLGGLG QFGIITRARI
ZmCkx6    HGPQISNVYE LDVVTGKGEV VTCSETENPD LFFGVLGGLG QFGIITRARI
ZmCkx7    HGPQISNVLE LDVVTGTGDM VTCSKEKDAD LFDAVLGGLG QFGIITRARI
ZmCkx8    HGPQISNVLQ LEVVTGTGEV VTCSPTQSPE LFFAVLGGLG QFGIITRARI 301                                                 350
AtCKX1    SLEPAPHMVK WIRVLYSDFS AFSRDQEYLI SKE....... ..KTFDYVEG
AtCKX2    VLDHAPKRAK WFRMLYSDFT TFTKDQERLI SMAND..... ..IGVDYLEG
AtCKX3    KLEVAPKRAK WLRFLYIDFS EFTRDQERVI SKT....... ..DGVDFLEG
AtCKX4    ALDHAPTRVK WSRILYSDFS AFKRDQERLI SMTND..... ..LGVDFLEG
AtCkx5    LLQPAPDMVR WIRVVYTEFD EFTQDAEWLV SQKNE..... ..SSFDYVEG
AtCKX6    SLEPAPQRVR WIRVLYSSFK VFTEDQEYLI SMH..GQ... ..LKFDYVEG
AtCKX7    ALEPAP.... .......... ..TMDQEQLI SAQG...... ..HKFDYIEG
DsCkx1    ALEKAPQSVR WMRLMYTDFE LFTKDQELLI SIKAEGEG.. ..WKLNYVEG
HvCkx2    ALEPAPQMVR WIRVLYLDFM SFTEDQEMLI SAE....... ..KTFDYIEG
HvCkx3    ALEPAPQMVR WIRVLYLDFM SLTEDQEMLI SAE....... ..KTFDYIEG
OsCKx1    AVEPAPARAR WVRLYADFA AFSADQERLV AARPDG.... SHGPWSYVEG
OsCkx2    PLAPAPARAR WVRFVYTTAA AMTADQERLI AVDRAGGAGA VGGLMDYVEG
OsCkx3    LLQEAPQKVK WVRAFYDDFA TFTKDQELLV SMP....... ..VLVDYVEG
OsCkx4    ALEPAPKMVR WIRVLYSDFE TFTEDQEKLI ASE....... ..KTFDYIEG
OsCkx5    ALEPAPHRVR WIRALYSNFT EFTADQERLI SLQHGG.... ..RRFDYVEG
OsCkx6    GLEPAPKRVR WVRLAYSDVV TFTRDQELLI SKRASEAG.. ....FDYVEG
OsCkx7    GLMPAPKRVR WVRLAYSDVA TFTKDQELLI SKRASEAG.. ....FDYVEG
OsCkx8    PLQLAPPKVR WVRAFYDSFE TFTGDQELLV SMP....... ..EQVDYVEG
OsCkx9    PLEPAPKMVR WLRVLYLDFT SFTEDQEMLI SAE....... ..KTFDYIEG
OsCkx10   RLEPAPKRVK WVRIAYSDVH PFTTDQELLI SKWASGSG.. ....FDYVEG
OsCkx11   PLSPAPQTVR WTRVVYASFA DYAADAEWLV TRPPH..... ..EAFDYVEG
ZmCkx1    AVEPAPARAR WVRFVYTDFA AFSADQERLT APRPGGGG.A SFGPMSYVEG
```

FIGURE 11

```
ZmCkx2a    ALEPAPEMVR  WIRVLYSDFE  SFTEDQEMLI  MAE.......  ..NSFDYIEG
ZmCkx2b    ALEPAPKMVR  WIRVLYSDFE  SFTEDQEMLI  MAE.......  ..NSFDYVEG
 ZmCkx3    RLEPAPKRVR  WVRLAYTDVA  TFTKDQEFLI  SNRASQVG..  ....FDYVEG
 ZmCkx4    PLHRAPKAVR  WTRVVYASIA  DYTADAEWLV  TRPPD.....  ..AAFDYVEG
 ZmCkx5    LLQEAPEKVT  WVRAFYDDLG  AFTRDQELLV  SIP.......  ..DSVDYVEG
 ZmCkx6    ALERAP.KVR  WIRALYSNFS  EFTADQERLI  SLGSGGG...  ..RRFDYVEG
 ZmCkx7    PLAPAPARAR  WLRLLYTGAA  DLTADQERLI  ADDERRGG.A  LAGLMDYVEG
 ZmCkx8    PLQVAPPKVR  WVRAFYDSFE  TFTKDQELLV  SMP.......  ..ELVDYVEG 351                                                     400
 AtCKX1    FVIINRTDLL  N.......N.  ........WRS  SFSPNDSTQA  SRFKS.....
 AtCKX2    QIFLSNGVVD  ..........  ........TS  FFPPSDQSKV  ADLVK.....
 AtCKX3    SIMVDHGPPD  N.......W.  ........RST  YYPPSDHLRI  ASMVK.....
 AtCKX4    QLMMSNGFVD  ..........  ........TS  FFPLSDQTRV  ASLVN.....
 AtCkx5    FVFVNGADPV  NG........  ........WPT  VPLHPDHEFD  PTRLPQS...
 AtCKX6    FVIVDEGLVN  N.........  ........WRSS  FFSPRNPVKI  SSVSS.....
 AtCKX7    FVIINRTGLL  N.......S.  ........WRL  SFTAEEPLEA  SQFKF.....
 DsCkx1    SLLMEHSLKS  N.......W.  ........RSP  FFSEKDLKKI  KKLASG....
 HvCkx2    FVIINRTGIL  N.......N.  ........WRS  SFNPQDPERA  SRFET.....
 HvCkx3    FVSINRTGIL  N.......N.  ........WRS  SFNPQDPERA  SQFET.....
 OsCKx1    AVYLAGRGLA  VALKSSGG..  ..........  FFSDADAARV  VALAAAR...
 OsCkx2    SVH..LNQGL  VETWRTQPQP  PSPSSSSSSS  FFSDADEARV  AALAKEA...
 OsCkx3    FIVLNEQSLH  S.........  ........SS  IAFPTNVDFN  PDFGTKN...
 OsCkx4    FVIINRTGIL  N.......N.  ........WRT  SFKPQDPVQA  SQFQS.....
 OsCkx5    FVVAAEGLIN  N.........  .......WRSS  FFSPQNPVKL  SSLKH.....
 OsCkx6    QVQLN..RTL  TEGPKSTP..  ..........  FFSRFDIDRL  AGLASES...
 OsCkx7    QVQLN..RTL  TEGPKSTP..  ..........  FFSSSDIGRL  AGLASKS...
 OsCkx8    FMVLNEQSLH  S.........  ........SS  VAFPAQLNFS  PDFGSKG...
 OsCkx9    FVIINRTGIL  N.......N.  ........WRS  SFNPQDPVRS  SQFES.....
OsCkx10    QVQLN..RTL  TQGRRSSS..  ..........  FFSATDLARL  TGLAIDT...
OsCkx11    FAFVRSDDPV  NG........  ........WPT  VPIPDGAHFD  ASLLPAN...
 ZmCkx1    SVFVN.QSLA  TDLANTG...  ..........  FFTDADVARI  VALAGER...
ZmCkx2a    FVIINRTGIL  N.......N.  ........WRA  SFKPQDPVQA  SHFQS.....
ZmCkx2b    FVIINRTGVL  N.......N.  ........WRA  SFKPQDPVEA  SHFQS.....
 ZmCkx3    QVQLS..RSL  VEGPKSTP..  ..........  FFSGADVARL  AGLASRT...
 ZmCkx4    FAFVNSDDPV  NG........  ........WPS  VPIPGGARFD  PSLLPAG...
 ZmCkx5    FMVLNERSLH  S.........  ........SS  IAFPASVDFS  PDFGTRS...
 ZmCkx6    FVVAAEGLIN  N.........  ......WRSS  FFSPQNPVKL  TSLKH.....
 ZmCkx7    SVVTDLQQGL  IGSWRSQP.P  PS.....SSS  FYSATDAARI  AALAEEA...
 ZmCkx8    FMVLNEQSLR  S.........  ........SS  VAFPAQVNFR  PDFGSDDGTN 401                                                     450
 AtCKX1    .DGKTLYCLE  VVKYFNP...  .....EEASS  MDQETGKLLS  ELNYIPSTLF
 AtCKX2    .QHGIIYVLE  VAKYYDD...  .....PNLPI  ISKVIDTLTK  TLSYLPGFIS
 AtCKX3    .RHRVIYCLE  VVKYYDE...  .....TSQYT  VNEEMEELSD  SLNHVRGFMY
 AtCKX4    .DHRIIYVLE  VAKYYDR...  .....TTLPI  IDQVIDTLSR  TLGFAPGFMF
 AtCkx5    .CGSVLYCLE  LGLHYRDS..  .....DSNST  IDKRVERLIG  RLRFNEGLRF
 AtCKX6    .NGSVLYCLE  ITKNYHD...  .....SDSEI  VDQEVEILMK  KLNFIPTSVF
 AtCKX7    .DGRTLYCLE  LAKYLKQ...  .....DNKDV  INQEVKETLS  ELSYVTSTLF
 DsCkx1    .NEGVIYCLE  ASFYYDYGHE  MNFSRADKAQ  MDQDIEELLR  KLSFVSGFAF
 HvCkx2    .DRKVLFCLE  MTKNFNP...  .....EEADI  MEQEVHALLS  QLRYTPASLF
 HvCkx3    .DRKVLFCLE  MTKNFNP...  .....EEAGI  MEQ.IHALLS  QLRYTPPSLF
 OsCKx1    .NATAVYSIE  ATLNYA....  ...ANATPSS  VDAAVAAALG  DLHFEEGFSF
 OsCkx2    .GGVLYFLEG  AIYFGGA...  ...AGPSAAD  VDKRMDVLRR  ELRHERGFVF
```

```
OsCkx3    .NPKIYYCIE FAVHDYQ...  .....NKNIN VEQVVEVISR QMSHIASHLY
OsCkx4    .DGRVLYCLE LTMNFNH...   .....DEADI MEQEVGALLS RLRYISSTLF
OsCkx5    .NSGVLYCLE VTKNYDD...   .....STAVT VDQDVEALLG ELNFIPGTVF
OsCkx6    .VSGVIYFIE GAMYYN....   ....ESTTAS VDQKLTSVLE QLSFDKGFVF
OsCkx7    .VSGVIYVIE GTMYYN....   ....ESTSTT MDQKLESILG QLSFEEGFVF
OsCkx8    .RKKVYYCIE FAVHDFQ...   .....QDSSR ADHVVKLVSA KLSYLRPHVY
OsCkx9    .DGKVLFCLE MTKNFNP...   .....DEADV MEQEVNTLLS QLRYMPSSLF
OsCkx10   .GSVAIYYIE GAMYYD....   ....DNTAAS VDQKLDALLE ELSFVRGFVF
OsCkx11   .AGPVLYCLE VALYQRGG..   ..GGDGGGDD MDKRVGEMMR QLKYVRGLEF
ZmCkx1    .NATTVYSIE ATLNYDN...   ...ATAAAAA VDQELASVLG TLSYVEGFAF
ZmCkx2a   .DGRVLYCLE LTKNFNS...   .....GDTDT MEQEVAVLLS RLRFIQSTLF
ZmCkx2b   .DGRVLYCLE LTKNFNS...   .....DDTDT MEQEVTVLLS RLRFIQSTLF
ZmCkx3    .GPAAIYYIE GAMYYT....   ....KDTAIS VDKKMKALLD QLSFEPGFAF
ZmCkx4    .AGPVLYCLE VALYQYAHR.   .PDDDDEEDQ AAVTVSRMMA PLKHVRGLEF
ZmCkx5    .SPRIYYCVE FAVHHHH...   .....GYQQQ SQAAVEAISR RMSHMASQLY
ZmCkx6    .HSSVLYCLE VTKNYDD...   .....ETAGS VDQDVDTLLG ELNFLPGTVF
ZmCkx7    .GGVLYFLEG AVYYGGA...   ...SDTTAAD VDKRVDVMLR ELRYARGFAY
ZmCkx8    KKVCYYYCIE FAVHDFQ...   .....RQDSA ADHVVDLVSG KLSYLRPHAY 451                                                  500
AtCKX1    SSEVPYIEFL DRVHIAERKL RAKGLW.EVP HPWLNLLIPK SSIYQFATEV
AtCKX2    MHDVAYFDFL NRVHEENKL  RSLGLW.ELP HPWLNLYVPK SRILDFHNGV
AtCKX3    EKDVTYMDFL NRVRTGELNL KSKGQW.DVP HPWLNLFVPK TQISKFDDGV
AtCKX4    VQDVPYFDFL NRVRNEEDKL RSLGLW.EVP HPWLNIFVPG SRIQDFHDGV
AtCkx5    EVDLPYVDFL LRVKRSEEIA KENGTW.ETP HPWLNLFVSK RDIGDFNRTV
AtCKX6    TTDLQYVDFL DRVHKAELKL RSKNLW.EVP HPWLNLFVPK SRISDFDKGV
AtCKX7    TTEVAYEAFL DRVHVSEVKL RSKGQW.EVP HPWLNLLVPR SKINEFARGV
DsCkx1    RNDVSYMGFL NRVHDGELKL RAMGLW.DVP HPWLNLFVSK SNIMDFHIGV
HvCkx2    HTDVTYIEFL DRVHSSEMKL RAKGLW.EVP HPWLNLIIPR STIHTFAEQV
HvCkx3    HTDVTYMEFL DRVHSSEIKL RAKGLW.EVP HPWLNLIIPR STVHTFAKQV
OsCKx1    SRDVTYEEFL DRVYGEEEAL EKAGLW.RVP HPWLNLFVPG SRIADFDRGV
OsCkx2    AQDVAYAGFL DRVHDGELKL RAAGLW.DVP HPWLNLFLPR SGVLAFADGV
OsCkx3    SVEVSYFDFL NRVMEEMSL  RNSGLW.EVH HPWLNMFVPS AGISDFRDLL
OsCkx4    YTDVTYLEFL DRVHTSELKL RAQGLW.EVP HPWLNLLIPR STVHKFAKEV
OsCkx5    TTDLPYVDFL DRVHKAELKL RGKGMW.EVP HPWLNLFVPA SRIADFDRGV
OsCkx6    TKDVSYVQFL DRVREEERIL RSIGMW.DVP HPWLNLFVPQ SRILDFDTGV
OsCkx7    TKDVRYVQFL DRVREEERVL RSIGMW.DVP HPWLNLFVPR SRILDFDAGV
OsCkx8    SVEVSYFDFL NRVMEEESL  RSRGLW.DVP HPWLNVFVPK HGITQFKGLL
OsCkx9    HTDVTYIEFL DRVHSSEMKL RAKGMW.EVP HPWLNIIIPR SMIHKFAKEV
OsCkx10   VRDASYVEFL DRVGREEQNL RSAGAW.DVP HPWLNLFVPR SRILHFDAAV
OsCkx11   AAGVGYVDFL SRVNRVEDEA RRNGSW.AAP HPWLNFISS  RDIAAFDRAV
ZmCkx1    QRDVAYAAFL DRVHGEEVAL NKLGLW.RVP HPWLNMFVPR SRIADFDRGV
ZmCkx2a   HTDVTYLEFL DRVHTSELKL RAQSLW.EVP HPWLNLLIPR SSIRRFATEV
ZmCkx2b   HTDVTYLEFL DRVHTSELKL RAQGLW.EVP HPWLNLLIPR SSIRRFAKEV
ZmCkx3    TKDVTFVQFL DRVREEERVL RSAGAW.EVP HPWLNLFVPR SRILDFDDGV
ZmCkx4    AADVGYVDFL SRVNRVEEEA RRNGSW.DAP HPWLNLFVSA RDIADFDRAV
ZmCkx5    SVEVSYLDFL NRVMEEVSL  RSAGMWEEVH HPWLNMFVPK AGVAGFRDLL
ZmCkx6    TTDLPYVDFL DRVHKAELKL RAKGMW.EVP HPWLNLFVPA SRIADFDRGV
ZmCkx7    VQDVSYEQFL DRVSAGERRL RGEGLW.DVP HPWLNLFLPR SRILDFAAGV
ZmCkx8    SVEVAYWDFL NRVMEEESL  RRRGLW.DVP HPWLNLFVPR HGVARFMDLL 501                                                  550
AtCKX1    FNNILTSNNN GP......IL IYPVNQSKWK KHTSLITP.. .....NEDIF
AtCKX2    VKDILLKQKS ASG....LAL LYPTNRNKWD NRMSAMIPE. ....IDEDVI
```

FIGURE 11

```
AtCKX3    FKGIILRNNI TSG....PVL VYPMNRNKWN DRMSAAIP.. .....EEDVF
AtCKX4    INGLLLNQTS TSG....VTL FYPTNRNKWN NRMSTMTP.. .....DEDVF
AtCkx5    FKELVKNGVN GP......ML VYPLLRSRWD DRTSVVIPEE ......GEIF
AtCKX6    FKGILGNKTS GP......IL IYPMNKDKWD ERSSAVTP.. .....DEEVF
AtCKX7    FGNILTDTSN GP......VI VYPVNKSKWD NQTSAVTP.. .....EEEVF
DsCkx1    FKGIMKNSK. SMG....PIL VYPTKRSKWD KRMSTSIP.. .....DEEVF
HvCkx2    FGKILEDNNN GP......IL LYPVKKSRWD NRTSVVIP.. .....DEEVF
HvCkx3    FGKILEDNNN GP......IL LYPVNKSRWD NRTSVVLP.. .....DEEVS
OsCKx1    FKGILQTATD IAG....PLI IYPVNKSKWD AAMSAVTPEG EEE.....VF
OsCkx2    FHGILSRTPA MG.....PVL IYPMNRNKWD SNMSAVITDD DGD....EVF
OsCkx3    MDSISPDNFE GL......IL IYPLLRHKWD TNTSVVLPDS G...STDQVM
OsCkx4    FGKILKDSNN GP......IL LYPVNRTKWD NRTSVVIP.. .....DEEIF
OsCkx5    FRGVLGSRTA GG.....PIL IYPMNRHKWD PRSSVVTP.. .....EEDVF
OsCkx6    LKGVFVGANP VG.....VIL MYPMNRNMWD DRMTAVS... ..G..NDDMF
OsCkx7    FKGVFAGANP VG.....VIL MYPMNTNMWD DCMMAVA... ..S..DDDVF
OsCkx8    MDTVSADDFE GP......IL VYPLLTDKWD GNTSAVVPAA P.....DGVM
OsCkx9    FGKILKDSNN GP......IL LYPVNKSRWD NRTSVVIP.. .....DEEVF
OsCkx10   FKGILRNANP VG.....LIL MYPMNKDMWD DRMTAMTP.. .....DEDVF
OsCkx11   LNGMLADGVD GP......ML IYPMLKSKWD PATSVALPN. ......GEIF
ZmCkx1    FKGILQG.TD IVG....PLI VYPLNKSMWD DGMSAATP.. SED.....VF
ZmCkx2a   FGRILKDSNN GP......IL LYPVNKSKWD NKTSVVIP.. .....DEEIF
ZmCkx2b   FGKILKDSNN GP......IL LYPVNKSKWD NRTSVVIP.. .....DEEIF
ZmCkx3    FKALLKDSNP AG.....IIL MYPMNKDRWD DRMTAMTPA. .TD..DDDMF
ZmCkx4    IKGMLADGID GP......ML VYPMLKSKWD PNTSVALPE. ......GEVF
ZmCkx5    MDNVSPDSFQ GL......IL IYPLLRDKWD TNTSVVIPDS GPT.ADDPVM
ZmCkx6    FRGVLGGRTA GAGG...PVL IYPMNKHKWD PRSSAVTP.. .....DEEVF
ZmCkx7    FHGVLLPTRT AGGGGGGPVL VYPMNRGKWD GATSAVLPYD DGDGDGDEVF
ZmCkx8    MATIAQGDFE GP......VL VYPLLTHRWD GNMSAVVPAA P.....DGVM 551                                                600
AtCKX1    YLVAFLPSAV PNS......S GKNDLEYLLK QNQRVMNFCA AAN......L
AtCKX2    YIIGLLQSAT P......... ..KDLPEVES VNEKIIRFCK DSG......I
AtCKX3    YAVGFLRSAG F......... ..DNWEAFDQ ENMEILKFCE DAN......M
AtCKX4    YVIGLLQSAG GS........ ..QNWQELEN LNDKVIQFCE NSG......I
AtCkx5    YIVALLRFVP P.C......A KVSSVEKMVA QNQEIVHWCV KNG......I
AtCKX6    YLVALLRSAL TDG......E ETQKLEYLKD QNRRILEFCE QAK......I
AtCKX7    YLVAILTSAS PGS......A GKDGVEEILR RNRRILEFSE EAG......I
DsCkx1    YSIGILLSSE M......... ..NDLEHLES HNAEILKFCD QQG......M
HvCkx2    YLVGFLSSA. .........I GPHSIEHTLN LNNQIIEFSN KAS......I
HvCkx3    YLVGFLPSA. .........M GPHSIKRTLN LNNQIIEFSN KAS......I
OsCkx1    YVVSLLFSAV AN........ ...DVAALEA QNRRILRFCD LAG......I
OsCkx2    YTVGILRSAA AAG....... ...DVGRLEE QNDEILGFCE VAG......I
OsCkx3    YAVGILRSAN P.....DDGC SHHCLQELLL RHRRLAGAAA SG.......L
OsCkx4    YLVGFLSSAP .SS......S GHGSVEHAMN LNNKIVDFCE KNG......V
OsCkx5    YLVAFLRSAV PGST.....D PAQSLEALER QNREILEFCD EAG......I
OsCkx6    YVVGLLRSAV VPG....... ...DVERLER ENEAVLAFCD NEG......I
OsCkx7    YAVGLLRSAA VIG....... ...DVERLEK ENEAVLAFCH NED......I
OsCkx8    YIFGVLRSTD P......ARC GRACVDSIMA RHRRVADEAC RDGGGGGRGI
OsCkx9    YLVAFLSSA. .........L GPHNIKHTLD LNYRIIEFSD KAG......I
OsCkx10   YAVGLLRSAV AGGS...... .GGDVEQLER ENAAVLELCD LAGGG....I
OsCkx11   YLVALLRFCR PYP......G GGPPVDELVA QNNAIIDACR SNG......Y
ZmCkx1    YAVSLLFSSV APN....... ...DLARLQE QNRRILRFCD LAG......I
ZmCkx2a   YLVGFLSSAP .SL......S GHGSIAHAMS LNSQIVEFCE EAD......I
ZmCkx2b   YLVGFLSSAP .SL......S GYGSIAHSMN LNKQIVEFCE EAG......I
```

```
ZmCkx3    YAVSFLWSAL SAD....... ...DVPQLER WNKAVLDFCD RSG.......I
ZmCkx4    YLVALLRFCR .........S GGPAVDELVA QNGAILRACR ANG.......Y
ZmCkx5    YVVGILRSAN PGPEEDGDGC SHRCLHELLR SHRRIADAAE AR........L
ZmCkx6    YLVAFLRSAL PG........ APESLEALAR QNQRILDFCA GAG.......I
ZmCkx7    YTVGILRSAV ADG....... ...DLRRMEE QNAEVARFCE AAG.......I
ZmCkx8    YVFSVLRSTD P......ARC GRACMERILE QHRRVADEAC RR........L 601                                                   650
AtCKX1    NVKQYLPHYE TQKEWKSHFG .....KRWET FAQRKQAYDP LAILAPGQRI
AtCKX2    KIKQYLMHYT SKEDWIEHFG .....SKWDD FSKRKDLFDP KKLLSPGQDI
AtCKX3    GVIQYLPYHS SQEGWVRHFG .....PRWNI FVERKYKYDP KMILSPGQNI
AtCKX4    KIKEYLMHYT RKEDWVKHFG .....PKWDD FLRKKIMFDP KRLLSPGQDI
AtCkx5    DYKLYLPHYK SQEEWIRHFG .....NRWSR FVDRKAMFDP MAILSPGQKI
AtCKX6    NVKQYLPHHA TQEEWVAHFG .....DKWDR FRSLKAEFDP RHILATGQRI
AtCKX7    GLKQYLPHYT TREEWRSHFG .....DKWGE FVRRKSRYDP LAILAPGHRI
DsCkx1    NYKQYLPHYT SIEDWKKHFG .....KKWER FVEMKSRYDP KAILSPGQKI
HvCkx2    GVKQYLPNYT TEPEWKAHYG .....ARWDA FQQRKNTYDP LAILAPGQKI
HvCkx3    GVKQYLPHYS TEPEWKAHYG .....ARWDA FQQRKNTYDP LAILAPGQRI
OsCKx1    GYKAYLAHYD SRGDWVRHFG .AK....WDR FVQRKDKYDP KKLLSPGQDI
OsCkx2    AYKQYLPYYG SQAEWQKRHF GAN...LWPR FVQRKSKYDP KAILSRGQGI
OsCkx3    GAKQYLAHHP TPAGWRRHFG .....RRWER FADRKARFDP RCILGPGQGI
OsCkx4    GMKQYLAPYT TQKQWKAHFG .....ARWET FERRKHTYGP LAILAPGQRI
OsCkx5    GAKQYLPNHK AQREWEAHFG .....ARWAR FARLKAEFDP RAMLATGQGI
OsCkx6    GCKQYLPHYA SQDGWRSHFG .....AKWSR VTELKVKYDP YGILSPGQRI
OsCkx7    GCKQYLPYYT SQDGWQRHFG .....AKWSR VADLKAKYDP HRILSPGQRI
OsCkx8    GAKQYLARQP SPARWRDHFG .....AGWGR FAARKARFDP LHVLGPGQGI
OsCkx9    GVKQYLPNYT TEQEWQSHFG .....ARWDT FQQRKKAYDP LAILAPGQRI
OsCkx10   GCRQYLPHHA SRDGWRRHFG .....AKWGR VADLKARYDP RAILSPGQGI
OsCkx11   DYKIYFPSYH AQSDWSRHFG .....AKWSR FVDRKARYDP LAILAPGQNI
ZmCkx1    QYKTYLARHT DRSDWVRHFG AAK....WNR FVEMKNKYDP KRLLSPGQDI
ZmCkx2a   GMKQYLAHYT TQEQWKTHFG .....ARWET FERRKHRYDP LAILAPGQRI
ZmCkx2b   GMKQYLAPYT TQQQWKAHFG .....ARWET FERRKHRYDP LAILAPGQRI
ZmCkx3    ECKQYLPHYT SQDGWRRHFG .....AKWSR IAELKARYDP RALLSPGQRI
ZmCkx4    DYKAYFPSYR GEADWARHFG A....ARWRR FVDRKARYDP LAILAPGQKI
ZmCkx5    GAKQYLPHHP TPARWQQHLG .....RRWER FADRKARFDP LRILGPGQGI
ZmCkx6    GAKQYLPGHK ARHEWAEHFG A....ARWDR FARLKAEFDP RAILAAGQGI
ZmCkx7    PCTQYLPSYA TQADWAARHF GPAGSGRWDT FLRRKRKYDP MAILSRGQRI
ZmCkx8    GAKQYLARQP SLAHWRDHFG .....ASWDR FVARKARFDP MNVLGPGQGI 651                          687
AtCKX1    FQKTTGKLSP IQLAKSKATG SPQRYHYASI LPKPRTV
AtCKX2    F......... .......... .......... .......
AtCKX3    FQKINSS... .......... .......... .......
AtCKX4    FN........ .......... .......... .......
AtCkx5    FNRSL..... .......... .......... .......
AtCKX6    FQNPSLSLFP PSSSSSSAAS W......... .......
AtCKX7    FQKAVSYS.. .......... .......... .......
DsCkx1    FTHLVDELCL SDH....... .......... .......
HvCkx2    FQKKPASLPL SSLQYLL... .......... .......
HvCkx3    FQKTPASLPL SS........ .......... .......
OsCKx1    FN........ .......... .......... .......
OsCkx2    FTSPLA.... .......... .......... .......
OsCkx3    FPRDSSSSNG AFASYS.... .......... .......
OsCkx4    FPKASLPMSL .......... .......... .......
```

FIGURE 11
Page 8 of 9

```
OsCkx5   FD......SP  PLLAES....  ..........  .......
OsCkx6   FSSLTPMALV  AM........  ..........  .......
OsCkx7   FSSPASMVVV  SM........  ..........  .......
OsCkx8   FPRTDSAGSM  ..........  ..........  .......
OsCkx9   FQKASASLPL  PS........  ..........  .......
OsCkx10  FPPPPPPSPP  PPAAGEPITA  S.........  .......
OsCkx11  FARTPSSVAA  AAAVIV....  ..........  .......
ZmCkx1   FN........  ..........  ..........  .......
ZmCkx2a  FPKASLPLSL  ..........  ..........  .......
ZmCkx2b  FPKASLPLPL  ..........  ..........  .......
ZmCkx3   FPVPVEASGI  ASA.......  ..........  .......
ZmCkx4   FPRVPASVAV  ..........  ..........  .......
ZmCkx5   FPRTAQDAAA  AAAYGS....  ..........  .......
ZmCkx6   FRPP...GSP  ALAADS....  ..........  .......
ZmCkx7   FSSPLLAS..  ..........  ..........  .......
ZmCkx8   FPWTDSSSSP  M.........  ..........  .......
```

FIGURE 11

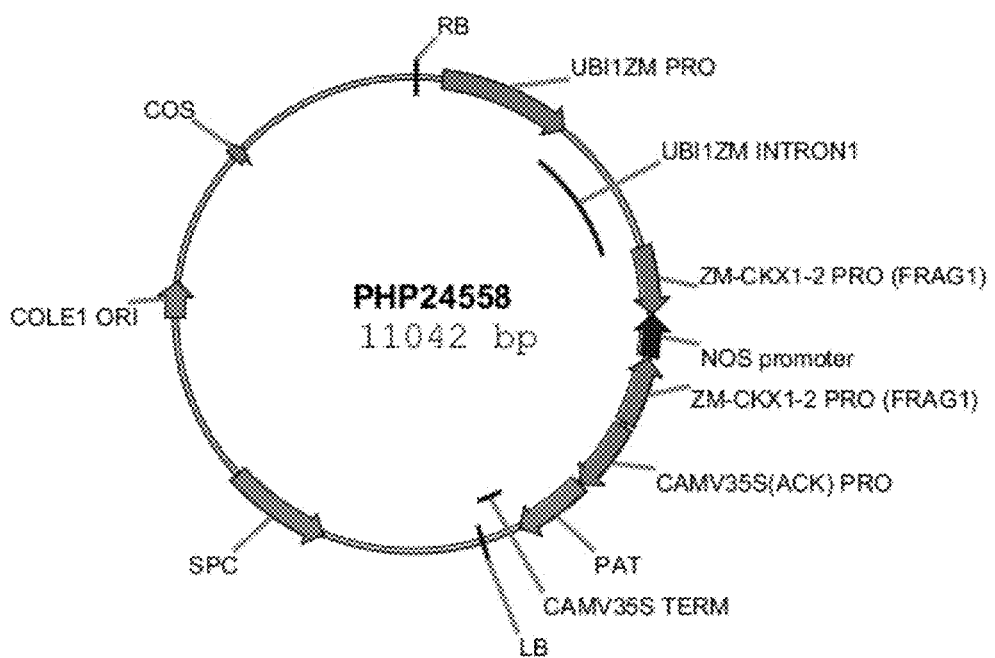
Figure 12A: Map of PHP24558 showing the "head-to-tail" arrangement of the *Ubi-ZmCkx1 PRO* inverted repeat construct relative to the 35S promoter of the cauliflower mosaic virus (CaMV).

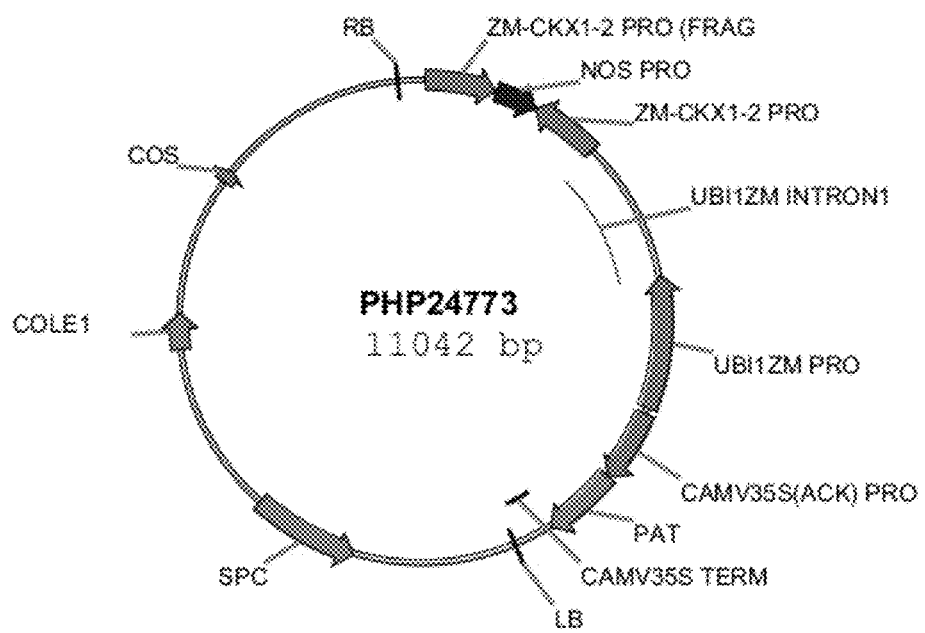
Figure 12B: Map of PHP24773 plasmid showing the "head-to-head" arrangement of the *Ubi-ZmCkx1 PRO* inverted repeat construct relative to the *35S* promoter of the cauliflower mosaic virus (CaMV).

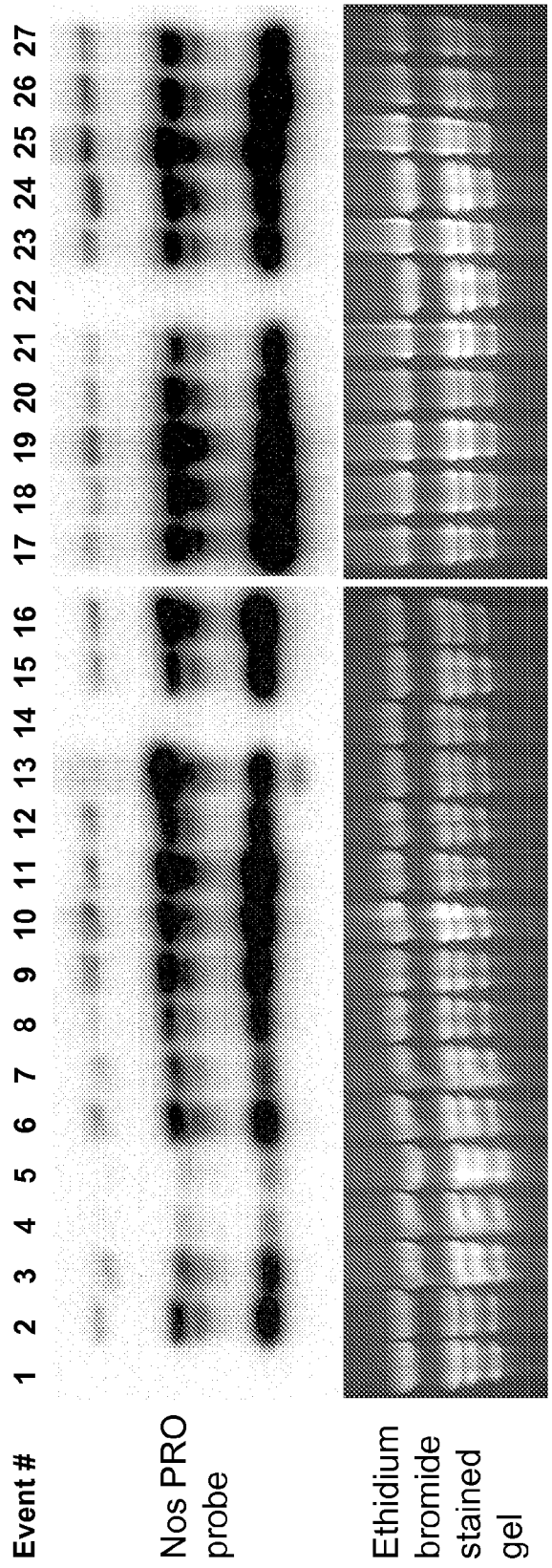
Figure 13. Northern analysis of ZmCkx1 promoter hairpin events.

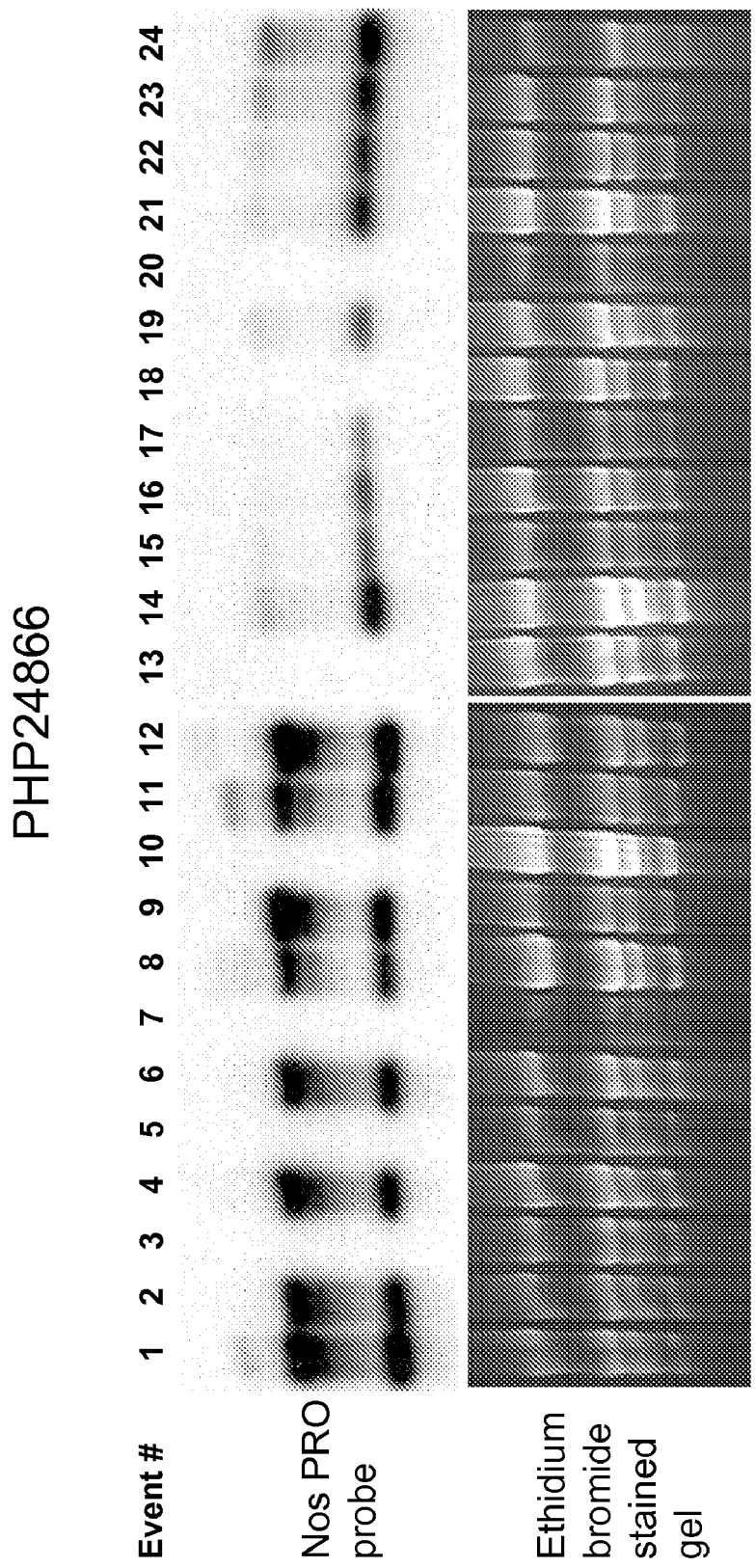
Figure 14. Northern analysis of ZmCkx1 promoter hairpin events.

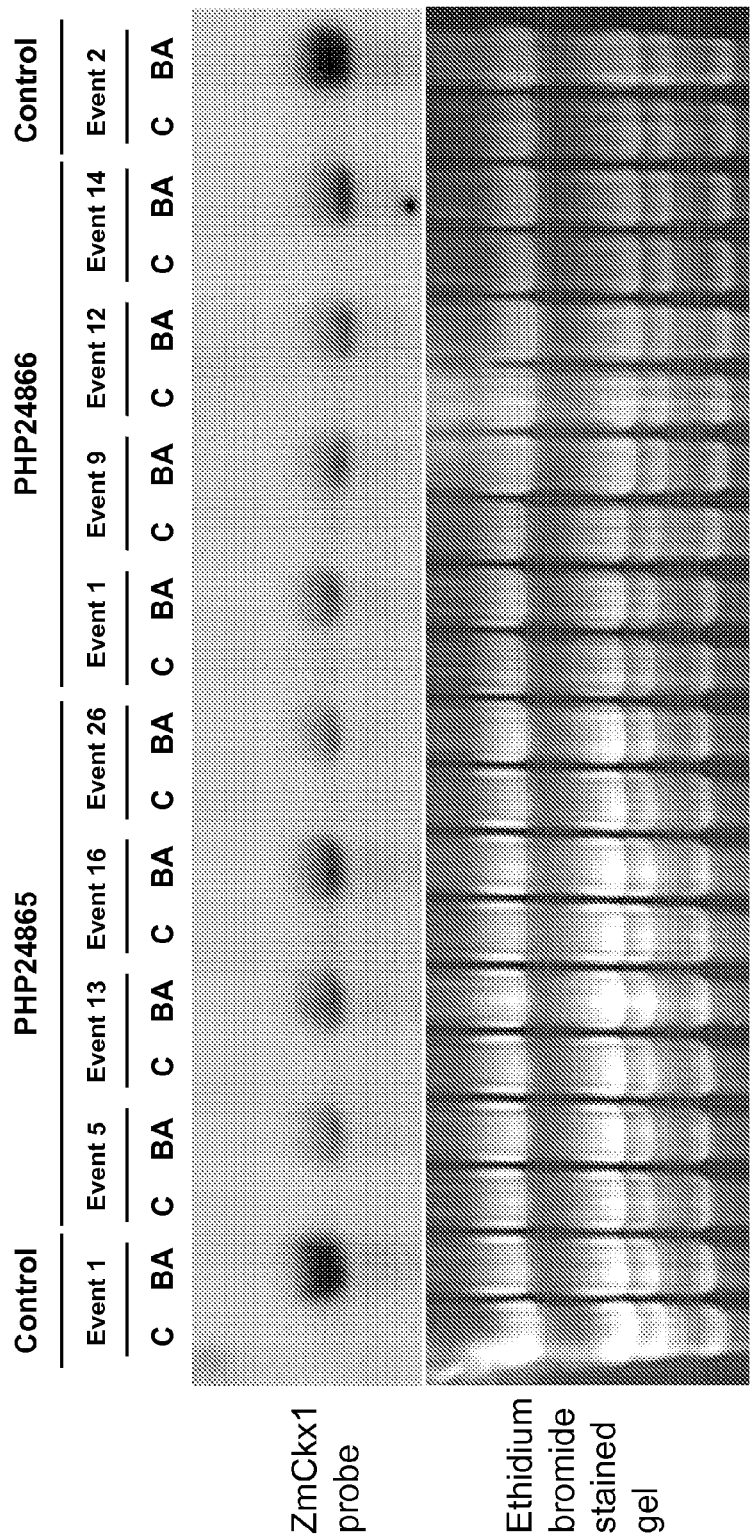
Figure 15. Northern analysis of BA-induced ZmCkx1 expression in leaf discs of transgenic plants

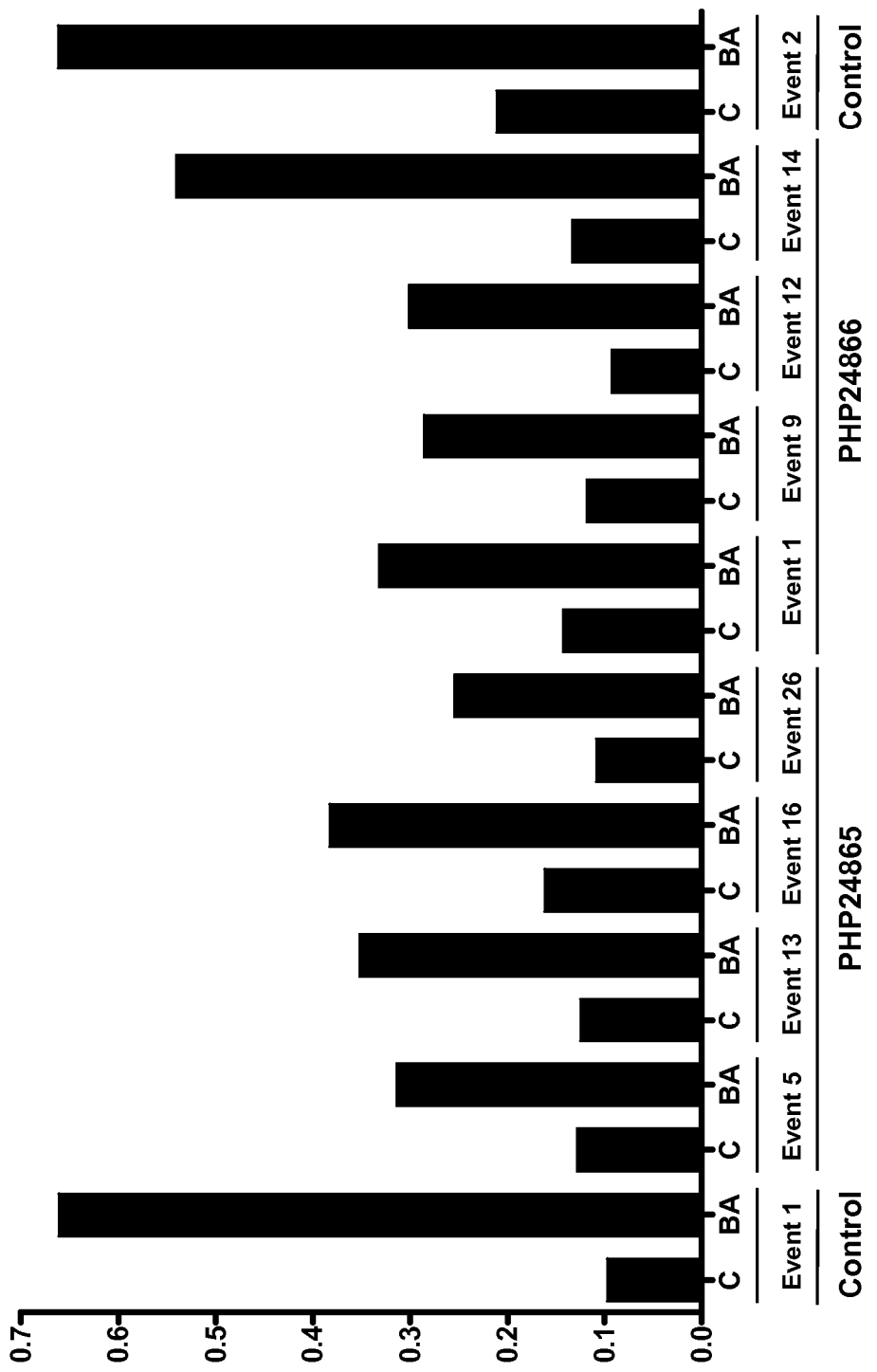
Figure 16. ZmCkx1 expression relative to 18S-RNA expression

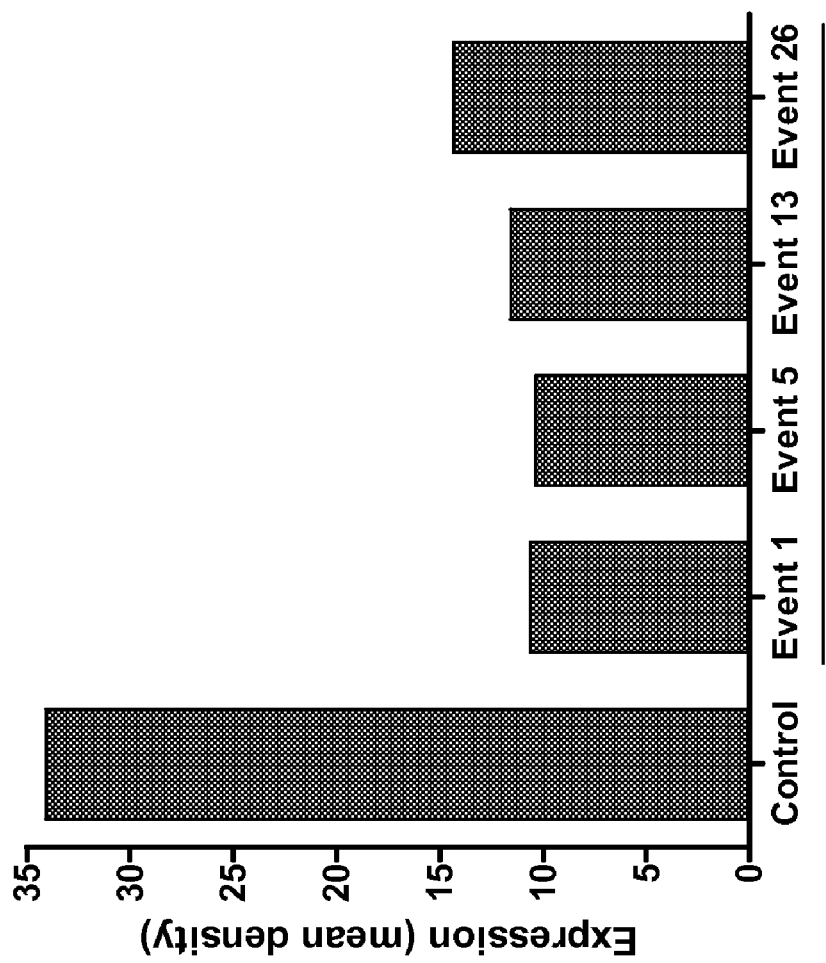
Figure 17. RT-PCR analysis of ZmCkx1 expression in PHP24865 events.

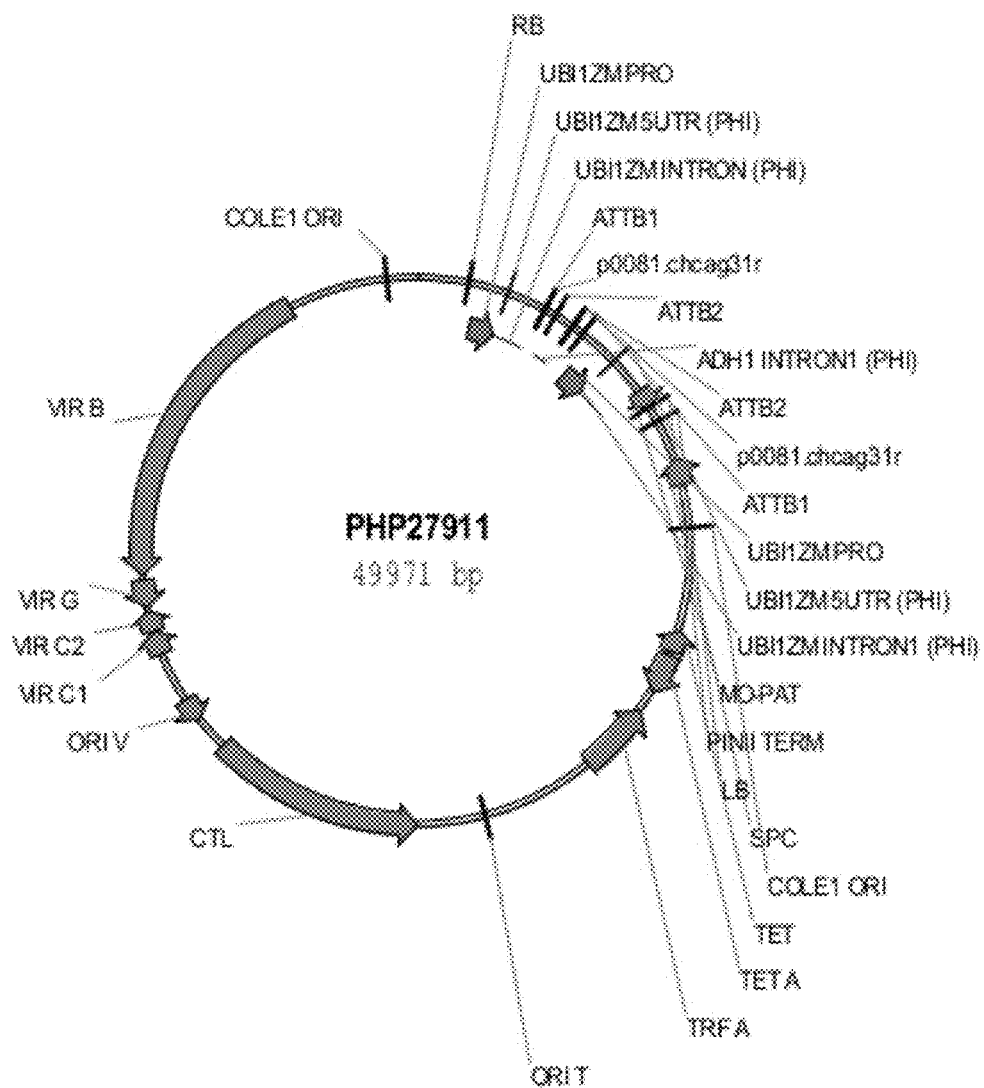
Figure 18. Plasmid comprising hairpin construct for ZmCkx2b 3' UTR (p0081.chcag31r).

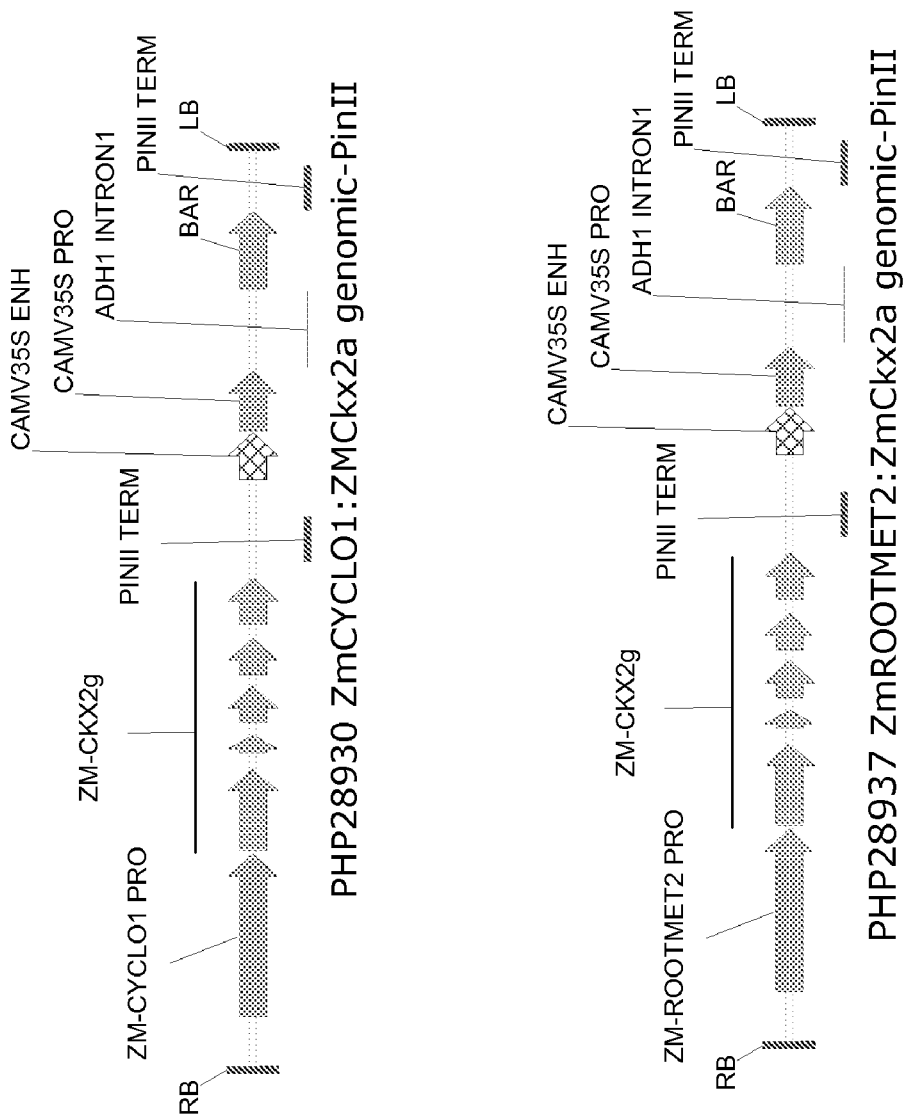
Figure 19. Expression cassettes for root-preferred overexpression of ZmCkx2a.

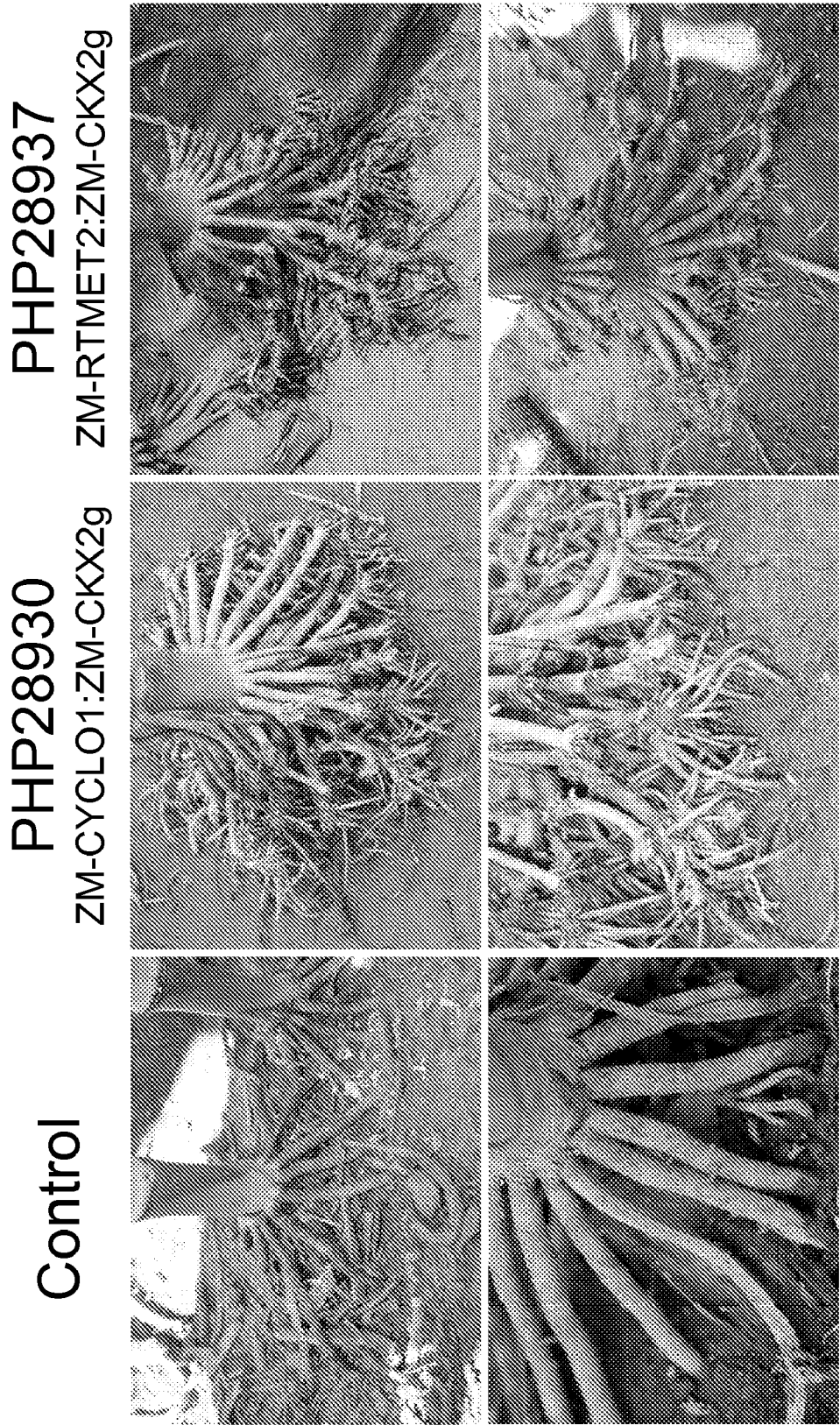
Figure 20A. Increased branching of brace roots on PHP28930 and PHP 28937 T1 plants

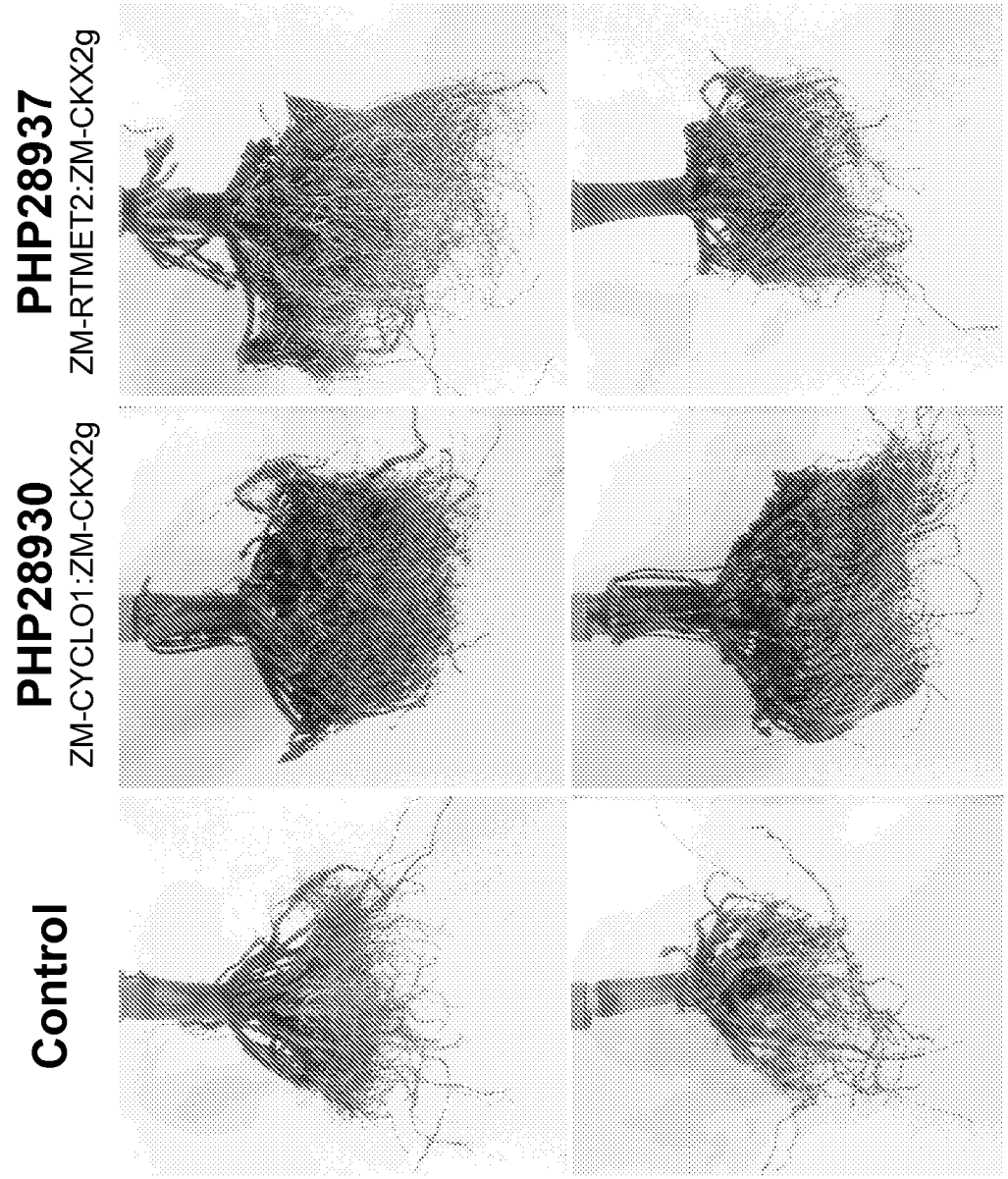
Figure 20B. PHP28930 and PHP28937 root growth in T1 plants

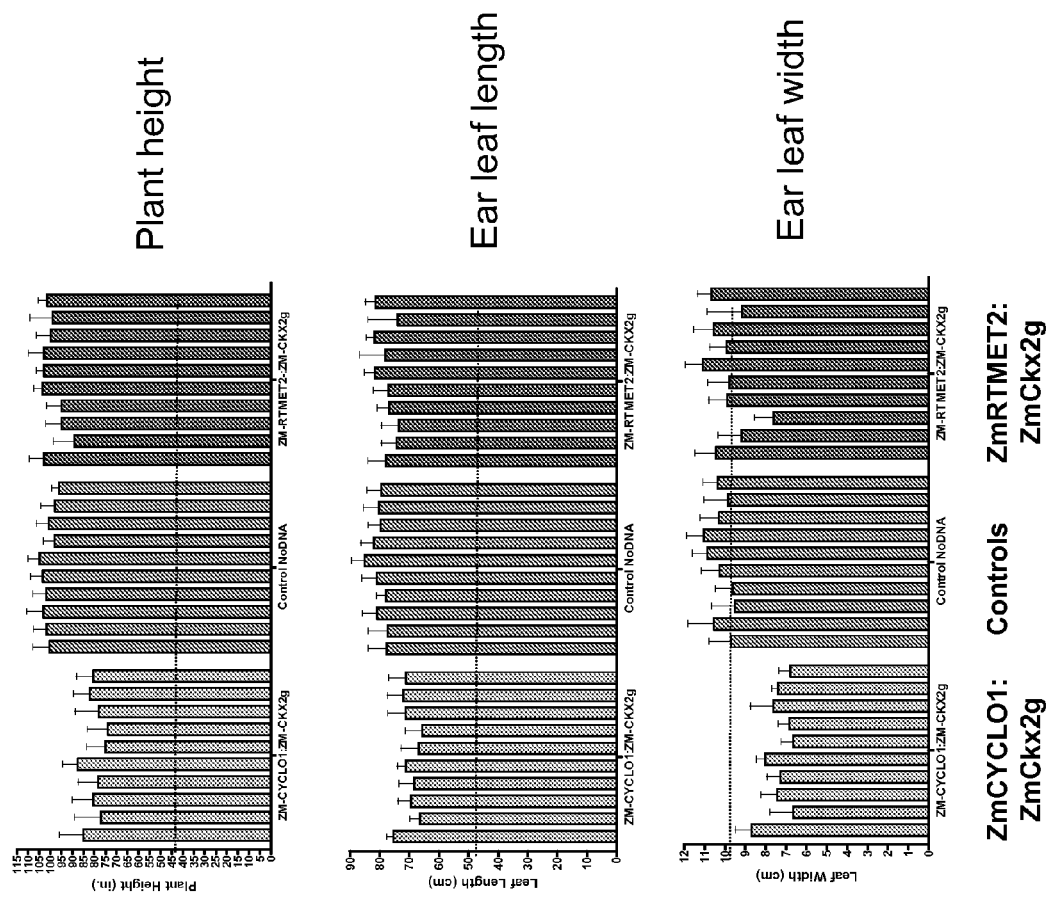
Figure 21. Effect of root-preferred ZmCkx2 overexpression on plant height, leaf length, and leaf width.

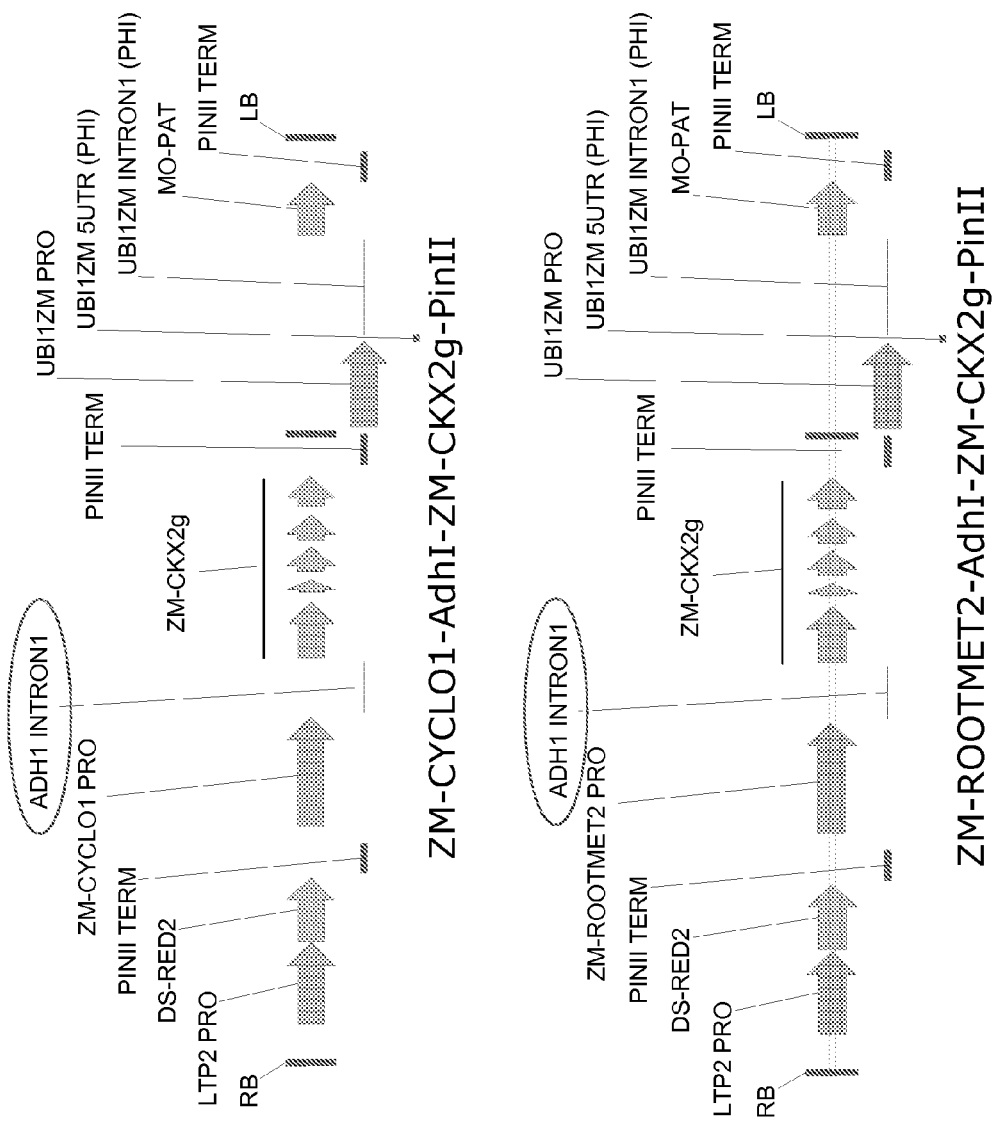
Figure 22. Optimized root-specific over-expression of *ZmCkx2* to increase root development

|  | OsCkx2 | OsCkx3 | OsCkx4 | OsCkx5 | OsCkx6 | OsCkx7 | OsCkx8 | OsCkx9 | OsCkx10 | OsCkx11 |
|---|---|---|---|---|---|---|---|---|---|---|
| OsCKx1 | 53.6 | 39.1 | 44.2 | 48.6 | 49.8 | 51.6 | 38.8 | 42.7 | 49.6 | 41 |
| OsCkx2 | - | 39.2 | 44.6 | 46.8 | 50 | 50.6 | 39.8 | 42.7 | 48.8 | 41.2 |
| OsCkx3 | - | - | 41.8 | 42.7 | 41.7 | 42.1 | 60.9 | 41.1 | 42.2 | 39.1 |
| OsCkx4 | - | - | - | 50.7 | 45.5 | 45.1 | 41.5 | 72.2 | 43.6 | 43.3 |
| OsCkx5 | - | - | - | - | 50 | 49.7 | 41.5 | 49.2 | 47.7 | 43.4 |
| OsCkx6 | - | - | - | - | - | 88 | 42.3 | 43.3 | 62.1 | 40.6 |
| OsCkx7 | - | - | - | - | - | - | 41.4 | 43.3 | 61.7 | 40.7 |
| OsCkx8 | - | - | - | - | - | - | - | 40.1 | 41.7 | 42 |
| OsCkx9 | - | - | - | - | - | - | - | - | 44.1 | 40.6 |
| OsCkx10 | - | - | - | - | - | - | - | - | - | 39.8 |

|  | ZmCkx2a | ZmCkx2b | ZmCkx3 | ZmCkx4 | ZmCkx5 | ZmCkx6 | ZmCkx7 | ZmCkx8 |
|---|---|---|---|---|---|---|---|---|
| ZmCkx1 | 43 | 43.6 | 51 | 42.7 | 38.2 | 46.8 | 49.5 | 41.1 |
| ZmCkx2a |  | 93 | 44.4 | 42.6 | 42.1 | 49.7 | 42.6 | 40.6 |
| ZmCkx2b | - | - | 45.7 | 42.8 | 41.9 | 50.4 | 42 | 41.5 |
| ZmCkx3 | - | - | - | 41.2 | 39.8 | 49.4 | 50.8 | 42.2 |
| ZmCkx4 | - | - | - | - | 41 | 43.8 | 41.3 | 43.1 |
| ZmCkx5 | - | - | - | - | - | 42.2 | 38.4 | 57.7 |
| ZmCkx6 | - | - | - | - | - | - | 48.8 | 43.7 |
| ZmCkx7 | - | - | - | - | - | - | - | 41 |

|  | ZmCkx1 | ZmCkx2a | ZmCkx2b | ZmCkx3 | ZmCkx4 | ZmCkx5 | ZmCkx6 | ZmCkx7 | ZmCkx8 |
|---|---|---|---|---|---|---|---|---|---|
| OsCKx1 | 70.8 | 44.4 | 44.1 | 53.9 | 41.8 | 38.5 | 47.8 | 49.2 | 40.4 |
| OsCkx2 | 52.2 | 44.5 | 42.7 | 51.5 | 41.7 | 40.5 | 48.2 | 63.7 | 42.1 |
| OsCkx3 | 40 | 41 | 41.2 | 41.1 | 39.5 | 76.4 | 43 | 39.3 | 60.7 |
| OsCkx4 | 43 | 81.9 | 81.9 | 45.7 | 42.4 | 42.5 | 49.8 | 42.9 | 41.4 |
| OsCkx5 | 46 | 50 | 50.8 | 48.1 | 43.9 | 41.8 | 80.9 | 47.5 | 42.4 |
| OsCkx6 | 49.5 | 43.1 | 44.8 | 67.8 | 41.2 | 42.4 | 48.7 | 50.6 | 42.8 |
| OsCkx7 | 50 | 44.2 | 44.4 | 68.5 | 40.3 | 41.5 | 48.8 | 50.1 | 44.1 |
| OsCkx8 | 38.3 | 41.3 | 42.2 | 41.3 | 42.3 | 60.5 | 42.6 | 40.6 | 78.5 |
| OsCkx9 | 41.8 | 73 | 74.2 | 44.3 | 42.9 | 41.8 | 48.3 | 41.5 | 40.6 |
| OsCkx10 | 48.8 | 43.9 | 44.5 | 63.4 | 39.4 | 41.6 | 50.1 | 49.5 | 39.7 |
| OsCkx11 | 41.2 | 41.9 | 41.7 | 41.4 | 78 | 39.4 | 43.6 | 39.5 | 42.2 |

FIGURE 23

Figure 24. Summary of Zscore data for UbiZM:CKX2-RNAi events

| Eu id | Growth Estimate | | | Yield Estimate | | |
|---|---|---|---|---|---|---|
| | Early | Late | Both | | | |
| | Zscore rt half maxvol | Zscore rt maxvolume | Zscore>1 | Zscore yield estimate | Zscore seed weight | Both Zscores>1 |
| 61249796 | 1.28535 | 0.97013 | | -0.32449 | 1.88058 | |
| 61249797 | 1.80194 | 1.01268 | Yes | 1.88084 | 0.42599 | |
| 61249798 | 0.87126 | 0.2811 | | -0.1932 | -0.21065 | |
| 61249799 | 2.33911 | 2.36765 | Yes | 0.09083 | -1.61472 | |
| 61249800 | 1.10081 | 1.6706 | Yes | 2.0872 | 1.86726 | Yes |
| 61249801 | 1.46182 | 1.31805 | Yes | | | |
| 61249802 | 0.37195 | -0.22262 | | 0.59404 | 0.25266 | |
| 61249803 | 1.22785 | 1.58464 | Yes | 1.02156 | 2.08739 | Yes |
| 61249804 | 1.52183 | 1.71536 | Yes | 1.483 | 0.21151 | |
| 61249805 | 0.96306 | 1.89905 | | 1.62907 | -0.59656 | |

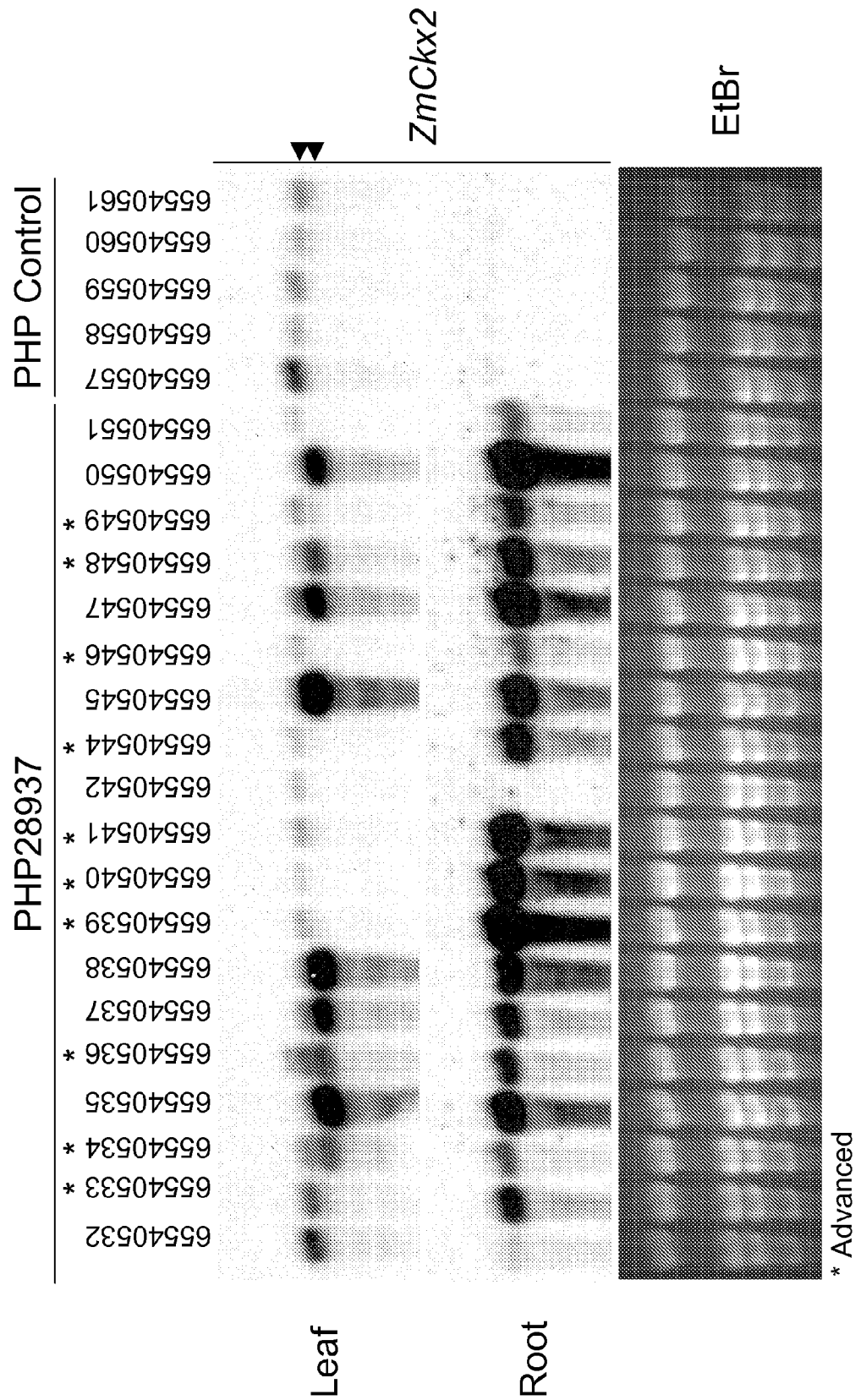
Figure 25A. Molecular characterization of PHP28937, ZmROOTMET2:ZmCKX2a (GENOMIC)
* Advanced

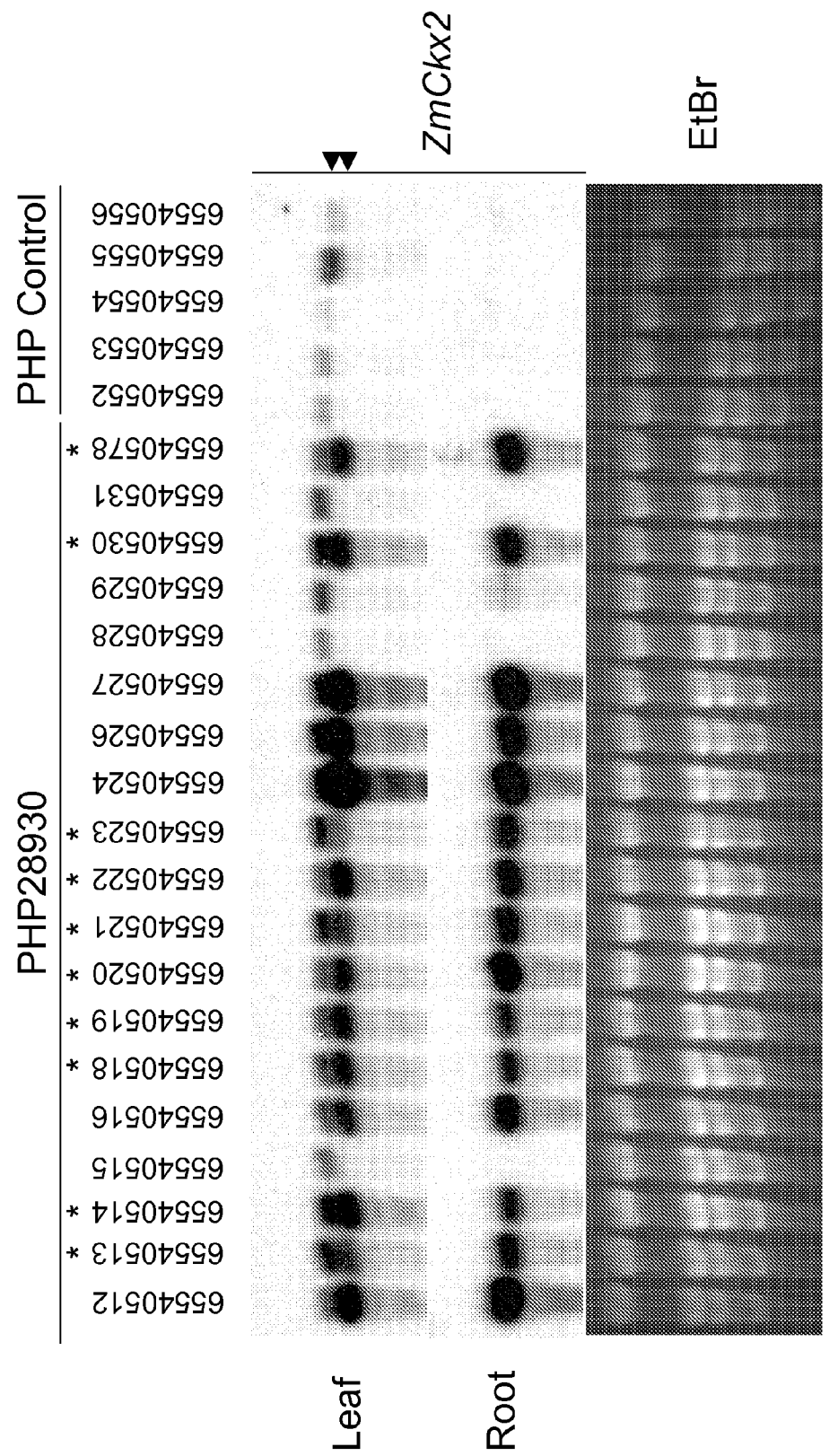
Figure 25B. Molecular characterization of PHP28930, ZmCYCLO1:ZmCKX2a (GENOMIC)

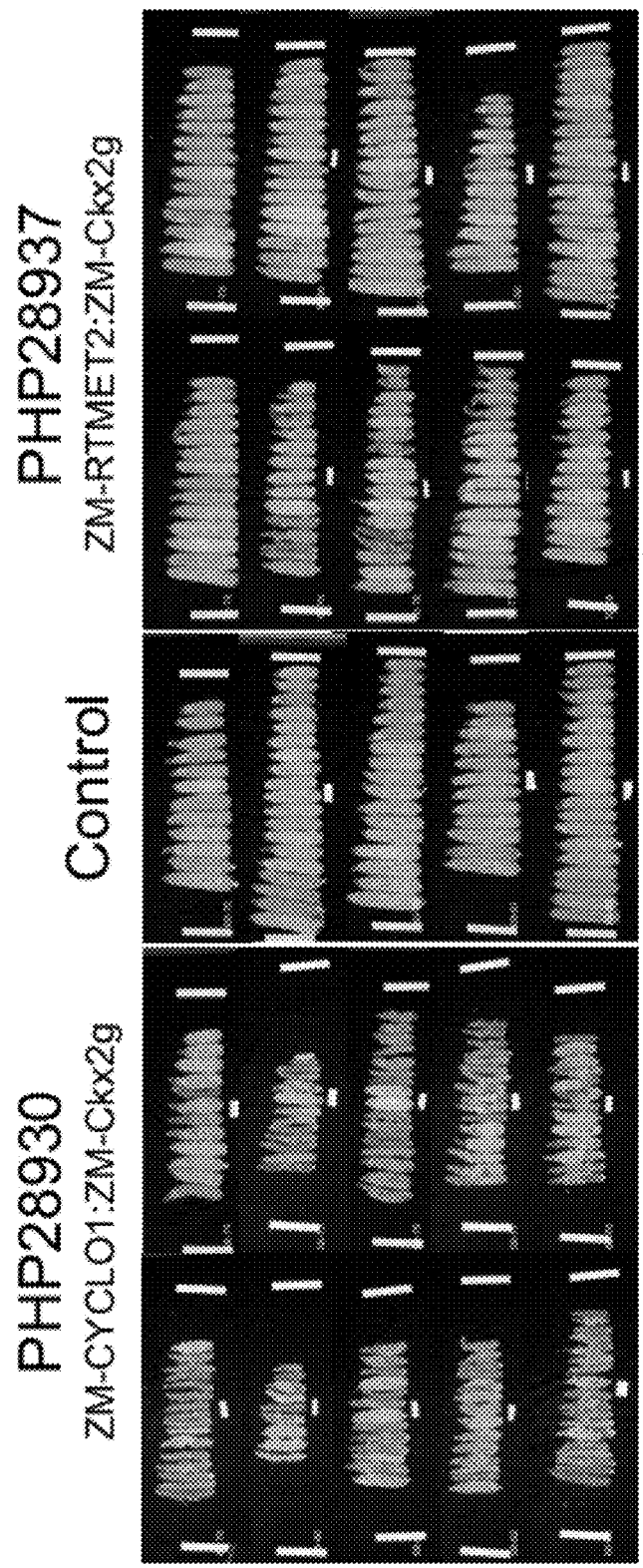
Figure 26. PHP28930 and PHP28937 ear phenotypes

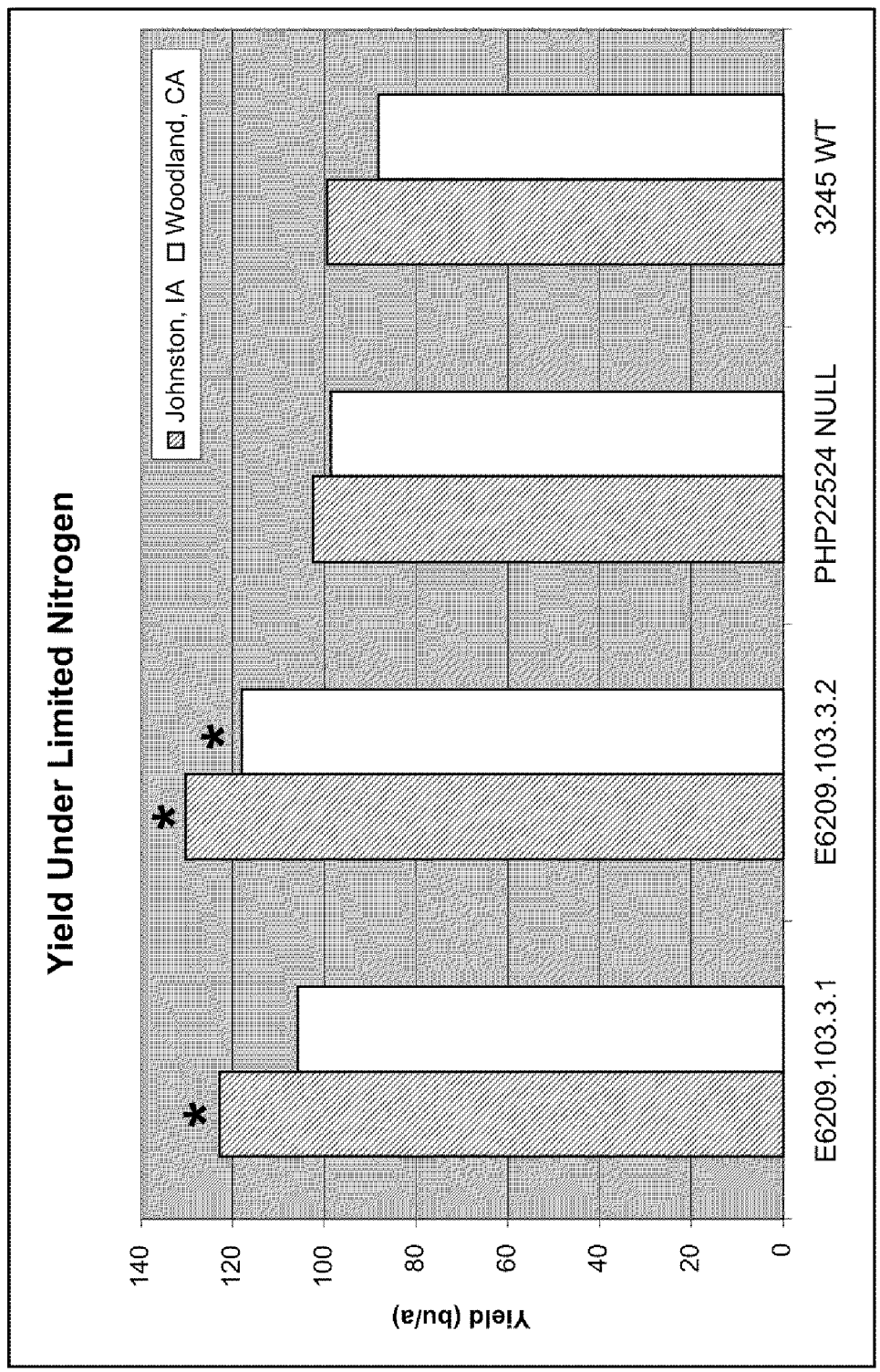
Figure 27. Yield of two events of PHP22514.

SEQUENCE LISTING

```
<160> NUMBER OF SEQ ID NOS: 112

<210> SEQ ID NO 1
<211> LENGTH: 3200
<212> TYPE: DNA
<213> ORGANISM: Zea mays
<220> FEATURE:
```

```
<221> NAME/KEY: exon
<222> LOCATION: (267)...(849)
<220> FEATURE:
<221> NAME/KEY: exon
<222> LOCATION: (957)...(1084)
<220> FEATURE:
<221> NAME/KEY: exon
<222> LOCATION: (1175)...(1435)
<220> FEATURE:
<221> NAME/KEY: exon
<222> LOCATION: (1509)...(1771)
<220> FEATURE:
<221> NAME/KEY: exon
<222> LOCATION: (1871)...(2195)
<220> FEATURE:
<221> NAME/KEY: polyA_signal
<222> LOCATION: (2859)...(2864)
<220> FEATURE:
<221> NAME/KEY: misc_feature
<222> LOCATION: (0)...(0)
<223> OTHER INFORMATION: Genomic sequence for ZmCkx2

<400> SEQUENCE: 1
cctatataga gaggccccct ccctccccct gcatggacag ccaccgcctt cttcaaccct      60
ccttccgtct tcctcctcta gtcttacctc gttgcacctc aagaaacttg gcgcgcaacc     120
aggaaacccc ctcttctctc tctctctctc tctctctctc tgccttctga ttccaagctc     180
cccaactgcc cagcaccaac ctgccgaact cccctccttt tgttggtttt gtcgaattat     240
aaattgagcc cggccggctg actaccatga agccgccatc actggtgcac tgcttcaagc     300
tgctggtcct gctggcgctc gccaggctga ccatgcacgt cccgacgag gacatgctat      360 cgccctcgg cgcgctgcgc ctcgacggtc atttcagctt ccatgacgtc tccgccatgg     420
cgcgggactt cggcaaccag tgcagcttcc tgccggccgc cgtgctccac ccaggctcgg     480
tctccgatat cgccgccacc gtgaggcacg tcttctccct gggcgagggc tcgccgctca     540
ccgtcgcggc gcgcgggcat ggacactccc tcatgggtca gtcccaggcc gcccagggga     600
tcgtggtcag gatggagtcg ctccggggcg ctaggctcca ggtccacgac ggctttgtcg     660
atgcccccgg aggagagctc tggatcaatg tcctgcgtga cgctgaag cacggcctgg       720 cacccaagtc gtggacggac tatctccatc tcacggtcgg tggcacctg tctaatgcgg      780 gggtcagcgg ccaggcgttc cgccacggac cgcaggtcag caatgtcaat caactggaga     840
ttgtgacagg tctcaaacga actcacaaag cattcaatca actagcttgg agcatacata     900
acgaaacata aaaaaaaaca gtcgctgatc gtaataatcg taaaaaccaa atgcaggaag     960
gggagacgtc gttacctgct cacccgagga taactctgat ctcttctatg ctgctctcgg    1020
cggtcttggt cagttcggga tcataaccag agcaaggatt gcacttgagc ctgctccaga    1080
gatggtaagt catcagacaa gcgattcagt taaatgaaat ctccagacag catgcagtca    1140
tttagtaaat ggatgtatat atatacaatg acaggtgagg tggataagag ttctttactc    1200
ggattttgaa agcttcaccg aagaccagga gatgttgatc atggcagaga actcctttga    1260
ctacattgaa ggttttgtca tcataaacag gacaggcatc ctcaacaact ggagggcgtc    1320
cttcaagcca caggacccag tccaagcaag ccatttccag tcagatggaa gagtgctata    1380
ctgcctcgaa ctaaccaaga acttcaatag tggcgacact gataccatgg aacaggtgag    1440
cctgttattt cactttgcac caagatatta gactccaatg ataataactg taaattttat    1500
gtttacagga agttgctgta ctgctatctc ggcttagatt catacagtct actctattcc    1560
acaccgatgt cacgtacctg gagttttttgg acagggtgca cacctctgag ctgaagctga    1620
gggcacaaag cctctgggaa gttccacacc cttggttgaa tcttctgata ccgaggagct    1680
```

|  |  |
|---|---|
| caatccgcag atttgctacg gaagtctttg gcaggatcct gaaagatagc aacaatggtc | 1740 |
| ctatattgct ttatccagtg aacaaatcaa agtaacttcc ttcacttgca aaaattactg | 1800 |
| tcacaaataa taagttaatc tagttgcgca cggttaaggt agctcaattc gtctgttcgt | 1860 |
| tctgatgcag gtgggacaac aaaacgtcag tggtcatacc agatgaggaa attttctacc | 1920 |
| tagtgggatt cctttcttca gcaccgtctc tctcaggtca cggcagcatt gcacatgcga | 1980 |
| tgagcctgaa cagccaaata gtagagttct gtgaagaggc tgatattggg atgaaacagt | 2040 |
| atctagcaca ctacaccaca caggagcagt ggaaaaccca ctttggagca aggtgggaga | 2100 |
| catttgaacg gaggaaacac agatatgatc ccctagccat cctagcacca ggacagagaa | 2160 |
| tattcccaaa ggcgtcactc ccattgtctt tgtgacggtt cctgctattt aaaggcttct | 2220 |
| gtagagcata cattgtacaa aagtgtaggt aaaagtatcc cctgtaaaga caatatctac | 2280 |
| ggaaggtagc tagcctgaag aacacagcat agcgactttt tcagtggcca agataccctc | 2340 |
| aaagcagtac ttcaatgtgg agcaacgtca cctgaaccct gaaggtggtg agtgcaactt | 2400 |
| tggaggcaat cactggtagt ggagcctgga gggttgtagc ggtccaagga acctgtctgt | 2460 |
| tgttacagcg ttgagatgag ctgtgctgat caactgatca ctaaccagtg tcccgaggaa | 2520 |
| atcatgttgg tctgtatgta ttttccgtta acaacagtgc agaagtttgc atgagggtag | 2580 |
| tgcattgatt agcaaatagc actgcctgtt atttcacttg taactggcat ctcatctcaa | 2640 |
| ggagagcctg cgtaactgta gcaggttata ttgttttcca tgagtcagaa actcagaata | 2700 |
| ttaatgctcg tgcaaaaaca gtgtagtcgc ttatcaatca tggtgttcag aaacagaaaa | 2760 |
| actcttggaa ttctctcaac ttgttcatta aatgttagca acctatagtg tgagcttgga | 2820 |
| taacaaataa gaaatcaaga gcgcaaatat tgaaactgaa taaatgttaa atgataattt | 2880 |
| tctaaagtcc aatcaagcag aattataagt ttgcaagata acttgataac tgacatctca | 2940 |
| gtttttttgta tcaagcaaat gtgctgtcaa aaacaaaagc aaatacaccc ttttcagtta | 3000 |
| gtgggccata ctgtggtctt aatcagacct ttgtttccgc aataaggtgt tcatggaact | 3060 |
| gcatgtgcga tacagcttct gctcatgata caaccaacat aagatctcaa tagagaagta | 3120 |
| ttcatatccc gtaacagcgc aatgttcaaa gatatttgcc tggttcaaat acgggcatgc | 3180 |
| agttcttcac gatcgtggta | 3200 |

```
<210> SEQ ID NO 2
<211> LENGTH: 1560
<212> TYPE: DNA
<213> ORGANISM: Zea mays
<220> FEATURE:
<221> NAME/KEY: CDS
<222> LOCATION: (1)...(1560)
<220> FEATURE:
<221> NAME/KEY: misc_feature
<222> LOCATION: (0)...(0)
<223> OTHER INFORMATION: ZmCkx2a cDNA

<400> SEQUENCE: 2
```

|  |  |
|---|---|
| atg aag ccg cca tca ctg gtg cac tgc ttc aag ctg ctg gtc ctg ctg<br>Met Lys Pro Pro Ser Leu Val His Cys Phe Lys Leu Leu Val Leu Leu<br>1                  5                       10                    15 | 48 |
| gcg ctc gcc agg ctg acc atg cac gtc ccc gac gag gac atg cta tcg<br>Ala Leu Ala Arg Leu Thr Met His Val Pro Asp Glu Asp Met Leu Ser<br>              20                      25                     30 | 96 |
| ccc ctc ggc gcg ctg cgc ctc gac ggt cat ttc agc ttc cat gac gtc<br>Pro Leu Gly Ala Leu Arg Leu Asp Gly His Phe Ser Phe His Asp Val<br>35                       40                       45 | 144 |
| tcc gcc atg gcg cgg gac ttc ggc aac cag tgc agc ttc ctg ccg gcc | 192 |

```
Ser Ala Met Ala Arg Asp Phe Gly Asn Gln Cys Ser Phe Leu Pro Ala
    50                  55                  60 gcc gtg ctc cac cca ggc tcg gtc tcc gat atc gcc gcc acc gtg agg      240
Ala Val Leu His Pro Gly Ser Val Ser Asp Ile Ala Ala Thr Val Arg
 65                  70                  75                  80 cac gtc ttc tcc ctg ggc gag ggc tcg ccg ctc acc gtc gcg gcg cgc      288
His Val Phe Ser Leu Gly Glu Gly Ser Pro Leu Thr Val Ala Ala Arg
                 85                  90                  95 ggg cat gga cac tcc ctc atg ggt cag tcc cag gcc gcc cag ggg atc      336
Gly His Gly His Ser Leu Met Gly Gln Ser Gln Ala Ala Gln Gly Ile
             100                 105                 110 gtg gtc agg atg gag tcg ctc cgg ggc gct agg ctc cag gtc cac gac      384
Val Val Arg Met Glu Ser Leu Arg Gly Ala Arg Leu Gln Val His Asp
         115                 120                 125 ggc ttt gtc gat gcc ccc gga gga gag ctc tgg atc aat gtc ctg cgt      432
Gly Phe Val Asp Ala Pro Gly Gly Glu Leu Trp Ile Asn Val Leu Arg
     130                 135                 140 gag acg ctg aag cac ggc ctg gca ccc aag tcg tgg acg gac tat ctc      480
Glu Thr Leu Lys His Gly Leu Ala Pro Lys Ser Trp Thr Asp Tyr Leu
145                 150                 155                 160 cat ctc acg gtc ggt ggc acc ttg tct aat gcg ggg gtc agc ggc cag      528
His Leu Thr Val Gly Gly Thr Leu Ser Asn Ala Gly Val Ser Gly Gln
                165                 170                 175 gcg ttc cgc cac gga ccg cag gtc agc aat gtc aat caa ctg gag att      576
Ala Phe Arg His Gly Pro Gln Val Ser Asn Val Asn Gln Leu Glu Ile
            180                 185                 190 gtg aca gga agg gga gac gtc gtt acc tgc tca ccc gag gat aac tct      624
Val Thr Gly Arg Gly Asp Val Val Thr Cys Ser Pro Glu Asp Asn Ser
        195                 200                 205 gat ctc ttc tat gct gct ctc ggc ggt ctt ggt cag ttc ggg atc ata      672
Asp Leu Phe Tyr Ala Ala Leu Gly Gly Leu Gly Gln Phe Gly Ile Ile
    210                 215                 220 acc aga gca agg att gca ctt gag cct gct cca gag atg gtg agg tgg      720
Thr Arg Ala Arg Ile Ala Leu Glu Pro Ala Pro Glu Met Val Arg Trp
225                 230                 235                 240 ata aga gtt ctt tac tcg gat ttt gaa agc ttc acc gaa gac cag gag      768
Ile Arg Val Leu Tyr Ser Asp Phe Glu Ser Phe Thr Glu Asp Gln Glu
                245                 250                 255 atg ttg atc atg gca gag aac tcc ttt gac tac att gaa ggt ttt gtc      816
Met Leu Ile Met Ala Glu Asn Ser Phe Asp Tyr Ile Glu Gly Phe Val
            260                 265                 270 atc ata aac agg aca ggc atc ctc aac aac tgg agg gcg tcc ttc aag      864
Ile Ile Asn Arg Thr Gly Ile Leu Asn Asn Trp Arg Ala Ser Phe Lys
        275                 280                 285 cca cag gac cca gtc caa gca agc cat ttc cag tca gat gga aga gtg      912
Pro Gln Asp Pro Val Gln Ala Ser His Phe Gln Ser Asp Gly Arg Val
    290                 295                 300 cta tac tgc ctc gaa cta acc aag aac ttc aat agt ggc gac act gat      960
Leu Tyr Cys Leu Glu Leu Thr Lys Asn Phe Asn Ser Gly Asp Thr Asp
305                 310                 315                 320 acc atg gaa cag gaa gtt gct gta ctg cta tct cgg ctt aga ttc ata     1008
Thr Met Glu Gln Glu Val Ala Val Leu Leu Ser Arg Leu Arg Phe Ile
                325                 330                 335 cag tct act cta ttc cac acc gat gtc acg tac ctg gag ttt ttg gac     1056
Gln Ser Thr Leu Phe His Thr Asp Val Thr Tyr Leu Glu Phe Leu Asp
            340                 345                 350 agg gtg cac acc tct gag ctg aag ctg agg gca caa agc ctc tgg gaa     1104
Arg Val His Thr Ser Glu Leu Lys Leu Arg Ala Gln Ser Leu Trp Glu
        355                 360                 365 gtt cca cac cct tgg ttg aat ctt ctg ata ccg agg agc tca atc cgc     1152
```

```
Val Pro His Pro Trp Leu Asn Leu Leu Ile Pro Arg Ser Ser Ile Arg
    370                 375                 380 aga ttt gct acg gaa gtc ttt ggc agg atc ctg aaa gat agc aac aat      1200
Arg Phe Ala Thr Glu Val Phe Gly Arg Ile Leu Lys Asp Ser Asn Asn
385                 390                 395                 400 ggt cct ata ttg ctt tat cca gtg aac aaa tca aag tgg gac aac aaa      1248
Gly Pro Ile Leu Leu Tyr Pro Val Asn Lys Ser Lys Trp Asp Asn Lys
                405                 410                 415 acg tca gtg gtc ata cca gat gag gaa att ttc tac cta gtg gga ttc      1296
Thr Ser Val Val Ile Pro Asp Glu Glu Ile Phe Tyr Leu Val Gly Phe
        420                 425                 430 ctt tct tca gca ccg tct ctc tca ggt cac ggc agc att gca cat gcg      1344
Leu Ser Ser Ala Pro Ser Leu Ser Gly His Gly Ser Ile Ala His Ala
            435                 440                 445 atg agc ctg aac agc caa ata gta gag ttc tgt gaa gag gct gat att      1392
Met Ser Leu Asn Ser Gln Ile Val Glu Phe Cys Glu Glu Ala Asp Ile
        450                 455                 460 ggg atg aaa cag tat cta gca cac tac acc aca cag gag cag tgg aaa      1440
Gly Met Lys Gln Tyr Leu Ala His Tyr Thr Thr Gln Glu Gln Trp Lys
465                 470                 475                 480 acc cac ttt gga gca agg tgg gag aca ttt gaa cgg agg aaa cac aga      1488
Thr His Phe Gly Ala Arg Trp Glu Thr Phe Glu Arg Arg Lys His Arg
                485                 490                 495 tat gat ccc cta gcc atc cta gca cca gga cag aga ata ttc cca aag      1536
Tyr Asp Pro Leu Ala Ile Leu Ala Pro Gly Gln Arg Ile Phe Pro Lys
        500                 505                 510 gcg tca ctc cca ttg tct ttg tga                                      1560
Ala Ser Leu Pro Leu Ser Leu
            515

<210> SEQ ID NO 3
<211> LENGTH: 519
<212> TYPE: PRT
<213> ORGANISM: Zea mays

<400> SEQUENCE: 3

Met Lys Pro Pro Ser Leu Val His Cys Phe Lys Leu Leu Val Leu Leu
1               5                   10                  15

Ala Leu Ala Arg Leu Thr Met His Val Pro Asp Glu Asp Met Leu Ser
            20                  25                  30

Pro Leu Gly Ala Leu Arg Leu Asp Gly His Phe Ser Phe His Asp Val
        35                  40                  45

Ser Ala Met Ala Arg Asp Phe Gly Asn Gln Cys Ser Phe Leu Pro Ala
    50                  55                  60

Ala Val Leu His Pro Gly Ser Val Ser Asp Ile Ala Ala Thr Val Arg
65                  70                  75                  80

His Val Phe Ser Leu Gly Glu Gly Ser Pro Leu Thr Val Ala Ala Arg
                85                  90                  95

Gly His Gly His Ser Leu Met Gly Gln Ser Gln Ala Ala Gln Gly Ile
            100                 105                 110

Val Val Arg Met Glu Ser Leu Arg Gly Ala Arg Leu Gln Val His Asp
        115                 120                 125

Gly Phe Val Asp Ala Pro Gly Gly Glu Leu Trp Ile Asn Val Leu Arg
    130                 135                 140

Glu Thr Leu Lys His Gly Leu Ala Pro Lys Ser Trp Thr Asp Tyr Leu
145                 150                 155                 160

His Leu Thr Val Gly Gly Thr Leu Ser Asn Ala Gly Val Ser Gly Gln
                165                 170                 175
```

Ala Phe Arg His Gly Pro Gln Val Ser Asn Val Asn Gln Leu Glu Ile
            180                 185                 190

Val Thr Gly Arg Gly Asp Val Val Thr Cys Ser Pro Glu Asp Asn Ser
        195                 200                 205

Asp Leu Phe Tyr Ala Ala Leu Gly Gly Leu Gly Gln Phe Gly Ile Ile
    210                 215                 220

Thr Arg Ala Arg Ile Ala Leu Glu Pro Ala Pro Glu Met Val Arg Trp
225                 230                 235                 240

Ile Arg Val Leu Tyr Ser Asp Phe Glu Ser Phe Thr Glu Asp Gln Glu
                245                 250                 255

Met Leu Ile Met Ala Glu Asn Ser Phe Asp Tyr Ile Glu Gly Phe Val
            260                 265                 270

Ile Ile Asn Arg Thr Gly Ile Leu Asn Asn Trp Arg Ala Ser Phe Lys
        275                 280                 285

Pro Gln Asp Pro Val Gln Ala Ser His Phe Gln Ser Asp Gly Arg Val
    290                 295                 300

Leu Tyr Cys Leu Glu Leu Thr Lys Asn Phe Asn Ser Gly Asp Thr Asp
305                 310                 315                 320

Thr Met Glu Gln Glu Val Ala Val Leu Leu Ser Arg Leu Arg Phe Ile
                325                 330                 335

Gln Ser Thr Leu Phe His Thr Asp Val Thr Tyr Leu Glu Phe Leu Asp
            340                 345                 350

Arg Val His Thr Ser Glu Leu Lys Leu Arg Ala Gln Ser Leu Trp Glu
        355                 360                 365

Val Pro His Pro Trp Leu Asn Leu Leu Ile Pro Arg Ser Ser Ile Arg
    370                 375                 380

Arg Phe Ala Thr Glu Val Phe Gly Arg Ile Leu Lys Asp Ser Asn Asn
385                 390                 395                 400

Gly Pro Ile Leu Leu Tyr Pro Val Asn Lys Ser Lys Trp Asp Asn Lys
                405                 410                 415

Thr Ser Val Val Ile Pro Asp Glu Glu Ile Phe Tyr Leu Val Gly Phe
            420                 425                 430

Leu Ser Ser Ala Pro Ser Leu Ser Gly His Gly Ser Ile Ala His Ala
        435                 440                 445

Met Ser Leu Asn Ser Gln Ile Val Glu Phe Cys Glu Glu Ala Asp Ile
    450                 455                 460

Gly Met Lys Gln Tyr Leu Ala His Tyr Thr Thr Gln Glu Gln Trp Lys
465                 470                 475                 480

Thr His Phe Gly Ala Arg Trp Glu Thr Phe Glu Arg Arg Lys His Arg
                485                 490                 495

Tyr Asp Pro Leu Ala Ile Leu Ala Pro Gly Gln Arg Ile Phe Pro Lys
            500                 505                 510

Ala Ser Leu Pro Leu Ser Leu
        515

```
<210> SEQ ID NO 4
<211> LENGTH: 3258
<212> TYPE: DNA
<213> ORGANISM: Zea mays
<220> FEATURE:
<221> NAME/KEY: misc_feature
<222> LOCATION: (0)...(0)
<223> OTHER INFORMATION: Genomic sequence for ZmCkx3
<220> FEATURE:
<221> NAME/KEY: TATA_signal
<222> LOCATION: (500)...(507)
<220> FEATURE:
<221> NAME/KEY: exon
```

```
<222> LOCATION: (630)...(1239)
<220> FEATURE:
<221> NAME/KEY: exon
<222> LOCATION: (1340)...(1746)
<220> FEATURE:
<221> NAME/KEY: exon
<222> LOCATION: (1853)...(2452)
<220> FEATURE:
<221> NAME/KEY: misc_feature
<222> LOCATION: 11, 13
<223> OTHER INFORMATION: n = A,T,C or G

<400> SEQUENCE: 4
```

| | | | | | |
|---|---|---|---|---|---|
| aaaaaatgtt | ntncagatat | atgtataaaa | atgtgtacct | agtacctacg | catgtcttag | 60 |
| ttcaacatac | ttgatagctg | tagttttctg | aaacctgttc | aaattaacct | ttttcctacc | 120 |
| tgatggtgaa | tagagagaaa | agctttacct | ttgtctgaat | aagaaaacta | acagaaagct | 180 |
| tacattttgg | ccactctacc | tgcccgagta | ttttctaagc | aagcaaaggc | gcatgaaaat | 240 |
| tttctcggaa | tccatgacct | tttacgcgca | tgaaaatttt | gaccaatgat | cattttgata | 300 |
| ctctccacaa | gtcaacatct | caaaaccaca | agatggggcc | catcaacata | agttcacgag | 360 |
| tgtgccttca | ggtacattgt | tctttttttt | tgttttgcta | aagtcaatca | gctgcaaaat | 420 |
| attcagaaca | atttcaataa | cccgaaaggc | tgttgtgcct | ccatttgtca | acgtttgcga | 480 |
| ggccaaatgg | taccccgct | ataaatacca | tggaagttct | tggcctctag | acacacaag | 540 |
| cgatctctcc | tcctatagtt | tctataaccc | cacaaagcgt | ccaggtcccg | tagtcacctc | 600 |
| cgattgcatt | gcgttgccgc | aagacaagca | tggcaagaag | gactcgtttc | gtggccatcg | 660 |
| ccgccctcct | cacaagcttc | ctcaacgtcg | cagccgggca | ttcccggcca | ctgtccggtg | 720 |
| ccggcctccc | gggcgatctt | ttcgggctgg | gcatcgcgtc | gaggatccgc | acggacagca | 780 |
| actcgacggc | gaaggcggcg | acggacttcg | gccagatggt | gagggccgcg | ccggaggccg | 840 |
| tgttccaccc | cgccacgccg | gccgacatcg | ccgcgctcgt | ccggttctcc | gccacgtcgg | 900 |
| cggcgccgtt | cccgttgcg | ccgcgcgggc | agggccactc | ctggcgcggc | caggcgctcg | 960 |
| ccccgggcgg | cgtcgtcgtg | gacatgggct | cgctggggcg | cggcccccgc | atcaacgtgt | 1020 |
| ccgccgtggc | cggcgcggag | ccgttcgtcg | acgccgcgg | ggagcagctg | tgggtcgacg | 1080 |
| tcctccgcgc | cacgctgcga | cacggcctgg | cgccccgcgt | gtggaccgac | tacctccggc | 1140 |
| tcaccgtcgg | cggcacgctc | tccaacgcgg | gaatcggcgg | gcaggcgttc | cgacacggtc | 1200 |
| cgcagatcgc | caacgtgcat | gaactcgacg | tcgtcacagg | tatcgaccga | tcgatggtta | 1260 |
| cactcccagt | gacaattaca | taagcagcta | atcacacacg | aatgctaata | atagtttata | 1320 |
| catgcgatga | aaaatgtagg | cacaggtgag | atggtgacat | gctccatgga | cgtgaactcg | 1380 |
| gacctgttca | tggcggctct | aggcgggtta | ggccagttcg | gggtcataac | cagagcacgg | 1440 |
| atccggcttg | agccggcgcc | caagagggtg | cgctgggttc | gacttgccta | caccgacgtc | 1500 |
| gctactttca | ccaaggatca | ggagtttctc | atatcaaacc | gggctagcca | agtcgggttc | 1560 |
| gactacgtcg | aaggccaggt | ccagctcagc | cggtccttgg | tcgaaggccc | caaatcaaca | 1620 |
| cccttcttct | ccggcgccga | tgttgctagg | cttgctggac | tcgcgtccag | gaccggacct | 1680 |
| gctgcaatct | actacatcga | aggcgccatg | tactacacca | aggacaccgc | catatctgtg | 1740 |
| gacaaggtac | agatcagctt | gaacacacac | acaaaaaaac | gaactttatt | attgctttca | 1800 |
| atgctttgga | cgaaaggaaa | ttcattcgtt | gttgctatat | gaaacgttgc | agaaaatgaa | 1860 |
| ggcactcctg | gatcagctga | gcttcgagcc | agggtttgcg | ttcaccaagg | acgtgacgtt | 1920 |
| cgtgcagttc | ctcgatcggg | tgcgcgagga | ggagagggtg | ctccggtcag | ccggcgcgtg | 1980 |

```
ggaggtgccg cacccatggc tgaacctctt cgtcccacgg tcgcgcatcc tcgacttcga      2040
cgacggagtg ttcaaggctc tgctcaagga ctccaaccca gctgggatca tcctcatgta      2100
ccccatgaac aaggataggt gggacgaccg gatgacagcg atgaccccag ccacggacga      2160
cgacgacatg ttctatgccg ttagtttcct ttggtcagca ctgtccgcag acgacgtgcc      2220
ccagctcgag agatggaaca aggcagtgct ggacttctgt gatcggtcag gaatagaatg      2280
caagcagtac ctgccacact acacatctca gacgggtgg cgacggcatt tcggggcgaa      2340
atggagcagg atcgctgagc tgaaggccag atatgaccct cgggcattgt tgtcgccggg      2400
ccagaggatt tttccggtgc cagtagaggc atctggcatt gcttctgcct gattgcccgg      2460
tctcgtagtc tcgaagcaaa cataaatgat tttcttgtgt agattgtaga atgtacatga      2520
taggtctttt tcattgtaag aaagataggc cttattttgt acataatttt tcttttgggt      2580
tgctagcacg gacggagggg ccattgtggc tagagaaagg taataatagt cacaaattat      2640
ataattcaca tctcacccttt taagtattaa gaagtcattt aaaaagaagg atagacaaat      2700
gcaattgcct tagtctctaa gatttatata gcaaaattat cagtataact ttgtattgtg      2760
tattatttac cccgcatatg tttcttaaca gtttattctt attttagaca atattctatt      2820
ttatacaatt tttttacagt agaatcccac ggtacactcg aaactaggat ggggctccaa      2880
atcggagcag gttttaatat aagagatggg aaagaagaac cagattaata ctaccctctc      2940
ctatcaaata aatttgcatt ccattaaaaa aattgaaaaa ctgaaaaaaa atcagtacaa      3000
gtagagccaa gatttgaatt tgcaaatac ttataaaaca ttttgaggca ttgatatgtt      3060
agctagaggc cgagagccaa gtatgtcgga tggtaaatcg agaagcgggc agtttgctaa      3120
aatatctttg ttttatttttt gtcatttaaa ctagggatga caatgggat ttttccgtcg      3180 gggaatggct ccccatcccc gtcctcgtgg ggtggaaaat tcctcgtccc cgtccccgcg      3240
aacacccacg ggaagctt                                                    3258

<210> SEQ ID NO 5
<211> LENGTH: 2635
<212> TYPE: DNA
<213> ORGANISM: Zea mays
<220> FEATURE:
<221> NAME/KEY: misc_feature
<222> LOCATION: (0)...(0)
<223> OTHER INFORMATION: ZmCkx3 cDNA
<220> FEATURE:
<221> NAME/KEY: CDS
<222> LOCATION: (630)...(2246)
<220> FEATURE:
<221> NAME/KEY: misc_feature
<222> LOCATION: 11, 13
<223> OTHER INFORMATION: n = A,T,C or G

<400> SEQUENCE: 5
aaaaaatgtt ntncagatat atgtataaaa atgtgtacct agtacctacg catgtcttag       60
ttcaacatac ttgatagctg tagttttctg aaacctgttc aaattaacct ttttcctacc      120
tgatggtgaa tagagagaaa agctttacct ttgtctgaat aagaaaacta acagaaagct      180 tacatttttgg ccactctacc tgcccgagta ttttctaagc aagcaaaggc gcatgaaaat      240
tttctcggaa tccatgacct tttacgcgca tgaaaatttt gaccaatgat cattttgata      300
ctctccacaa gtcaacatct caaaaccaca agatggggcc catcaacata agttcacgag      360
tgtgccttca ggtacattgt tctttttttt tgttttgcta aagtcaatca gctgcaaaat      420
attcagaaca atttcaataa cccgaaaggc tgttgtgcct ccatttgtca acgtttgcga      480
ggccaaatgg tacccccgct ataaatacca tggaagttct tggcctctag gacacacaag      540
```

```
cgatctctcc tcctatagtt tctataaccc cacaaagcgt ccaggtcccg tagtcacctc      600
cgattgcatt gcgttgccgc aagacaagc atg gca aga agg act cgt ttc gtg       653
                                Met Ala Arg Arg Thr Arg Phe Val
                                 1               5 gcc atc gcc gcc ctc ctc aca agc ttc ctc aac gtc gca gcc ggg cat       701
Ala Ile Ala Ala Leu Leu Thr Ser Phe Leu Asn Val Ala Ala Gly His
     10              15                  20 tcc cgg cca ctg tcc ggt gcc ggc ctc ccg ggc gat ctt ttc ggg ctg       749
Ser Arg Pro Leu Ser Gly Ala Gly Leu Pro Gly Asp Leu Phe Gly Leu
 25              30                  35                      40 ggc atc gcg tcg agg atc cgc acg gac agc aac tcg acg gcg aag gcg       797
Gly Ile Ala Ser Arg Ile Arg Thr Asp Ser Asn Ser Thr Ala Lys Ala
             45                  50                  55 gcg acg gac ttc ggc cag atg gtg agg gcc gcg ccg gag gcc gtg ttc       845
Ala Thr Asp Phe Gly Gln Met Val Arg Ala Ala Pro Glu Ala Val Phe
                 60                  65                  70 cac ccc gcc acg ccg gcc gac atc gcc gcg ctc gtc cgg ttc tcc gcc       893
His Pro Ala Thr Pro Ala Asp Ile Ala Ala Leu Val Arg Phe Ser Ala
             75                  80                  85 acg tcg gcg gcg ccg ttc ccc gtt gcg ccg cgc ggg cag ggc cac tcc       941
Thr Ser Ala Ala Pro Phe Pro Val Ala Pro Arg Gly Gln Gly His Ser
         90                  95                 100 tgg cgc ggc cag gcg ctc gcc ccg ggc ggc gtc gtc gtg gac atg ggc       989
Trp Arg Gly Gln Ala Leu Ala Pro Gly Gly Val Val Val Asp Met Gly
105                 110                 115                 120 tcg ctg ggg cgc ggc ccc cgc atc aac gtg tcc gcc gtg gcc ggc gcg      1037
Ser Leu Gly Arg Gly Pro Arg Ile Asn Val Ser Ala Val Ala Gly Ala
                125                 130                 135 gag ccg ttc gtc gac gcc ggc ggg gag cag ctg tgg gtc gac gtc ctc      1085
Glu Pro Phe Val Asp Ala Gly Gly Glu Gln Leu Trp Val Asp Val Leu
            140                 145                 150 cgc gcc acg ctg cga cac ggc ctg gcg ccc cgc gtg tgg acc gac tac      1133
Arg Ala Thr Leu Arg His Gly Leu Ala Pro Arg Val Trp Thr Asp Tyr
                155                 160                 165 ctc cgg ctc acc gtc ggc ggc acg ctc tcc aac gcg gga atc ggc ggg      1181
Leu Arg Leu Thr Val Gly Gly Thr Leu Ser Asn Ala Gly Ile Gly Gly
    170                 175                 180 cag gcg ttc cga cac ggt ccg cag atc gcc aac gtg cat gaa ctc gac      1229
Gln Ala Phe Arg His Gly Pro Gln Ile Ala Asn Val His Glu Leu Asp
185                 190                 195                 200 gtc gtc aca ggc aca ggt gag atg gtg aca tgc tcc atg gac gtg aac      1277
Val Val Thr Gly Thr Gly Glu Met Val Thr Cys Ser Met Asp Val Asn
                205                 210                 215 tcg gac ctg ttc atg gcg gct cta ggc ggg tta ggc cag ttc ggg gtc      1325
Ser Asp Leu Phe Met Ala Ala Leu Gly Gly Leu Gly Gln Phe Gly Val
            220                 225                 230 ata acc aga gca cgg atc cgg ctt gag ccg gcg ccc aag agg gtg cgc      1373
Ile Thr Arg Ala Arg Ile Arg Leu Glu Pro Ala Pro Lys Arg Val Arg
                235                 240                 245 tgg gtt cga ctt gcc tac acc gac gtc gct act ttc acc aag gat cag      1421
Trp Val Arg Leu Ala Tyr Thr Asp Val Ala Thr Phe Thr Lys Asp Gln
    250                 255                 260 gag ttt ctc ata tca aac cgg gct agc caa gtc ggg ttc gac tac gtc      1469
Glu Phe Leu Ile Ser Asn Arg Ala Ser Gln Val Gly Phe Asp Tyr Val
265                 270                 275                 280 gaa ggc cag gtc cag ctc agc cgg tcc ttg gtc gaa ggc ccc aaa tca      1517
Glu Gly Gln Val Gln Leu Ser Arg Ser Leu Val Glu Gly Pro Lys Ser
                285                 290                 295 aca ccc ttc ttc tcc ggc gcc gat gtt gct agg ctt gct gga ctc gcg      1565
Thr Pro Phe Phe Ser Gly Ala Asp Val Ala Arg Leu Ala Gly Leu Ala
```

```
        Thr Pro Phe Phe Ser Gly Ala Asp Val Ala Arg Leu Ala Gly Leu Ala
                    300                 305                 310 tcc agg acc gga cct gct gca atc tac tac atc gaa ggc gcc atg tac      1613
Ser Arg Thr Gly Pro Ala Ala Ile Tyr Tyr Ile Glu Gly Ala Met Tyr
            315                 320                 325 tac acc aag gac acc gcc ata tct gtg gac aag aaa atg aag gca ctc      1661
Tyr Thr Lys Asp Thr Ala Ile Ser Val Asp Lys Lys Met Lys Ala Leu
        330                 335                 340 ctg gat cag ctg agc ttc gag cca ggg ttt gcg ttc acc aag gac gtg      1709
Leu Asp Gln Leu Ser Phe Glu Pro Gly Phe Ala Phe Thr Lys Asp Val
345                 350                 355                 360 acg ttc gtg cag ttc ctc gat cgg gtg cgc gag gag gag agg gtg ctc      1757
Thr Phe Val Gln Phe Leu Asp Arg Val Arg Glu Glu Glu Arg Val Leu
                365                 370                 375 cgg tca gcc ggc gcg tgg gag gtg cca cac cca tgg ctg aac ctc ttc      1805
Arg Ser Ala Gly Ala Trp Glu Val Pro His Pro Trp Leu Asn Leu Phe
            380                 385                 390 gtc cca cgg tcg cgc atc ctc gac ttc gac gac gga gtg ttc aag gct      1853
Val Pro Arg Ser Arg Ile Leu Asp Phe Asp Asp Gly Val Phe Lys Ala
        395                 400                 405 ctg ctc aag gac tcc aac cca gct ggg atc atc ctc atg tac ccc atg      1901
Leu Leu Lys Asp Ser Asn Pro Ala Gly Ile Ile Leu Met Tyr Pro Met
410                 415                 420 aac aag gat agg tgg gac gac cgg atg aca gcg atg acc cca gcc acg      1949
Asn Lys Asp Arg Trp Asp Asp Arg Met Thr Ala Met Thr Pro Ala Thr
                425                 430                 435                 440 gac gac gac gac atg ttc tat gcc gtt agt ttc ctt tgg tca gca ctg      1997
Asp Asp Asp Asp Met Phe Tyr Ala Val Ser Phe Leu Trp Ser Ala Leu
                    445                 450                 455 tcc gca gac gac gtg ccc cag ctc gag aga tgg aac aag gca gtg ctg      2045
Ser Ala Asp Asp Val Pro Gln Leu Glu Arg Trp Asn Lys Ala Val Leu
            460                 465                 470 gac ttc tgt gat cgg tca gga ata gaa tgc aag cag tac ctg cca cac      2093
Asp Phe Cys Asp Arg Ser Gly Ile Glu Cys Lys Gln Tyr Leu Pro His
        475                 480                 485 tac aca tct caa gac ggg tgg cga cgg cat ttc ggg gcg aaa tgg agc      2141
Tyr Thr Ser Gln Asp Gly Trp Arg Arg His Phe Gly Ala Lys Trp Ser
490                 495                 500 agg atc gct gag ctg aag gcc aga tat gac cct cgg gca ttg ttg tcg      2189
Arg Ile Ala Glu Leu Lys Ala Arg Tyr Asp Pro Arg Ala Leu Leu Ser
505                 510                 515                 520 ccg ggc cag agg att ttt ccg gtg cca gta gag gca tct ggc att gct      2237
Pro Gly Gln Arg Ile Phe Pro Val Pro Val Glu Ala Ser Gly Ile Ala
                525                 530                 535 tct gcc tga ttgcccggtc tcgtagtctc gaagcaaaca taaatgattt              2286
Ser Ala tcttgtgtag attgtagaat gtacatgata ggtctttttc attgtaagaa agataggtct    2346
tattttgtac ataattttc ttttgggttg ctagcacgga cggagggcc attgtggcta      2406 gagaaaggta ataatagtca caaattatat aattcacatc tcaccttta agtattaaga    2466 agtcatttaa aaagaaggat agacaaatgc aattgcctta gtctctaaga tttatatagc    2526
aaaattatca gtataacttt gtattgtgta ttatttaccc cgcatatgtt tcttaacagt    2586
ttattcttat tttagacaat attctatttt atacaattt tttacagta                2635

<210> SEQ ID NO 6
<211> LENGTH: 538
<212> TYPE: PRT
<213> ORGANISM: Zea mays
```

<400> SEQUENCE: 6

```
Met Ala Arg Arg Thr Arg Phe Val Ala Ile Ala Ala Leu Leu Thr Ser
 1               5                  10                  15

Phe Leu Asn Val Ala Ala Gly His Ser Arg Pro Leu Ser Gly Ala Gly
             20                  25                  30

Leu Pro Gly Asp Leu Phe Gly Leu Gly Ile Ala Ser Arg Ile Arg Thr
         35                  40                  45

Asp Ser Asn Ser Thr Ala Lys Ala Ala Thr Asp Phe Gly Gln Met Val
     50                  55                  60

Arg Ala Ala Pro Glu Ala Val Phe His Pro Ala Thr Pro Ala Asp Ile
 65                  70                  75                  80

Ala Ala Leu Val Arg Phe Ser Ala Thr Ser Ala Ala Pro Phe Pro Val
                 85                  90                  95

Ala Pro Arg Gly Gln Gly His Ser Trp Arg Gly Gln Ala Leu Ala Pro
            100                 105                 110

Gly Gly Val Val Asp Met Gly Ser Leu Gly Arg Gly Pro Arg Ile
            115                 120                 125

Asn Val Ser Ala Val Ala Gly Ala Glu Pro Phe Val Asp Ala Gly Gly
        130                 135                 140

Glu Gln Leu Trp Val Asp Val Leu Arg Ala Thr Leu Arg His Gly Leu
145                 150                 155                 160

Ala Pro Arg Val Trp Thr Asp Tyr Leu Arg Leu Thr Val Gly Gly Thr
                165                 170                 175

Leu Ser Asn Ala Gly Ile Gly Gly Gln Ala Phe Arg His Gly Pro Gln
            180                 185                 190

Ile Ala Asn Val His Glu Leu Asp Val Val Thr Gly Thr Gly Glu Met
        195                 200                 205

Val Thr Cys Ser Met Asp Val Asn Ser Asp Leu Phe Met Ala Ala Leu
    210                 215                 220

Gly Gly Leu Gly Gln Phe Gly Val Ile Thr Arg Ala Arg Ile Arg Leu
225                 230                 235                 240

Glu Pro Ala Pro Lys Arg Val Arg Trp Val Arg Leu Ala Tyr Thr Asp
                245                 250                 255

Val Ala Thr Phe Thr Lys Asp Gln Glu Phe Leu Ile Ser Asn Arg Ala
            260                 265                 270

Ser Gln Val Gly Phe Asp Tyr Val Glu Gly Gln Val Gln Leu Ser Arg
        275                 280                 285

Ser Leu Val Glu Gly Pro Lys Ser Thr Pro Phe Phe Ser Gly Ala Asp
    290                 295                 300

Val Ala Arg Leu Ala Gly Leu Ala Ser Arg Thr Gly Pro Ala Ala Ile
305                 310                 315                 320

Tyr Tyr Ile Glu Gly Ala Met Tyr Tyr Thr Lys Asp Thr Ala Ile Ser
                325                 330                 335

Val Asp Lys Lys Met Lys Ala Leu Leu Asp Gln Leu Ser Phe Glu Pro
            340                 345                 350

Gly Phe Ala Phe Thr Lys Asp Val Thr Phe Val Gln Phe Leu Asp Arg
        355                 360                 365

Val Arg Glu Glu Glu Arg Val Leu Arg Ser Ala Gly Ala Trp Glu Val
    370                 375                 380

Pro His Pro Trp Leu Asn Leu Phe Val Pro Arg Ser Arg Ile Leu Asp
385                 390                 395                 400

Phe Asp Asp Gly Val Phe Lys Ala Leu Leu Lys Asp Ser Asn Pro Ala
                405                 410                 415
```

-continued

```
Gly Ile Ile Leu Met Tyr Pro Met Asn Lys Asp Arg Trp Asp Asp Arg
            420                 425                 430

Met Thr Ala Met Thr Pro Ala Thr Asp Asp Asp Met Phe Tyr Ala
            435                 440                 445

Val Ser Phe Leu Trp Ser Ala Leu Ser Ala Asp Asp Val Pro Gln Leu
450                 455                 460

Glu Arg Trp Asn Lys Ala Val Leu Asp Phe Cys Asp Arg Ser Gly Ile
465                 470                 475                 480

Glu Cys Lys Gln Tyr Leu Pro His Tyr Thr Ser Gln Asp Gly Trp Arg
                485                 490                 495

Arg His Phe Gly Ala Lys Trp Ser Arg Ile Ala Glu Leu Lys Ala Arg
                500                 505                 510

Tyr Asp Pro Arg Ala Leu Leu Ser Pro Gly Gln Arg Ile Phe Pro Val
            515                 520                 525

Pro Val Glu Ala Ser Gly Ile Ala Ser Ala
            530                 535

<210> SEQ ID NO 7
<211> LENGTH: 6177
<212> TYPE: DNA
<213> ORGANISM: Zea mays
<220> FEATURE:
<221> NAME/KEY: misc_feature
<222> LOCATION: (0)...(0)
<223> OTHER INFORMATION: Genomic sequence for ZmCkx4
<220> FEATURE:
<221> NAME/KEY: TATA_signal
<222> LOCATION: (2320)...(2323)
<220> FEATURE:
<221> NAME/KEY: exon
<222> LOCATION: (2449)...(3138)
<220> FEATURE:
<221> NAME/KEY: exon
<222> LOCATION: (3220)...(3501)
<220> FEATURE:
<221> NAME/KEY: exon
<222> LOCATION: (4874)...(5195)

<400> SEQUENCE: 7
ctttatgttg tagccaagga aagtatactg ttaagatcag aatgaacctt ataggagttg      60
tatgggcata aagccagcaa gtatagccaa aggtacacaa ggctaatata gtcaagttgt     120
tgatgtgtga gacgttcaag gaagtgaact attggaggag tcgactaaaa gtacgattaa     180
taaggtagac atgatggtaa aatctttgat ctagaattta agtggtatgg atgcgagggt     240
gagaatggca agcacaactt caaatatagg gtgatgctta tgcttggctg agccatttca     300
ttcatgagca taggaacatg agacatggtg ggatatggat acttgcacaa aaaaaggaat     360
taagtttatg atattcacct cccagtcagt ttgcatggta aaaaaattcc tatcaatttg     420
gttctcaact agggcctaaa attctcaaaa tatctgttgg ggaccattat cgtcgacgat     480
cctcagaatc tgttattacc aaattaaaag gtgtgtttca ggtactgtgc aaagcagcag     540
cgaagctatc cttcgtcaaa agtggctcaa tgaaccaggt ggagaagcta tggagcttcg     600
tctgcgtaga gcgtgccgga ggaggaagct tggctctga atgcatcgac ttacgaagca     660
tgggagaaga agactcagaa ggcttgtcca gcgtgggaat aaaaaggaga aaatacaatt     720 ttgccccttgt gggatttgta aatcatgtgc aaggctcatg gatatgtttg taattttata     780
tgatatgttt gtaaatcatg gatatgtttt gtaaatcagg tggactagag gagagggagg     840
gtggacatag tgacttgcat cttgatcatg gtagagtggg catggtagag ggaaaggggt     900
aggtcaattc tggagtgcgg ccacggtggc ttgagtgtcg gccacggtag gggaaagggg     960
```

```
tagcccaatt ctagggccgg catcggagaa ggccgacatg tgcacgtcag gaggtagtgt    1020
tagaggtttg aacggaaaaa attgaacatg ttagtatgat gagttgtgta attgctggga    1080
attgtggata atttccactt aactacggcc ctgtttattt acccctagat tataaaatcc    1140
aacttaaaaa agttgagatg taaacaaaca acacatatta ttaggtggat tatgttatct    1200
agaaatctgg atgataataa tttataagtc ggttaatagg tgtttacata atcgataagc    1260
tggattatat aatcctggaa cacggctttc gcgagagcgt attaaaacag gattccgtga    1320
agcacactat ctgaggagct ccaccaaaag ctgaatctag cccgcactct tttttggagg    1380
attcaaattt ggtgtcactg gagcattcgg cattttgttt catggcgtga agctattttt    1440
actaattaca gaagctgttt caaatagacc tttaaatgat ggctgagtat aaaaggaggc    1500
aattttttta tctcgccgat ggagccaggt cgcgtcgcgc cgcggccgtg ctgcgctctc    1560
gacgcgatct agcggcgatg tgcacagtac agttttgcca tgccattggt taagcctgca    1620
tacaacacac cagcgtactg ccctgcacaa gatctcctcg gctcggcctc tcctgatgga    1680
acgttcagct tgaacagcgg agcgtggggg catcccgggg atgggcgccg cggccgagaa    1740
attttgcaac ctggcaaatc tgccctgtcg catactacca tccacctcca ggcgccaaga    1800
acgcctccga gtttcaggct tgcagctcag ctctgtgttg aattggaacg ggcggagttt    1860
ctgggttcca gacttccagt acaaggcgat caattggtag ggcgaattac ttgcaggccc    1920
agatgcatgg cccatctatc tggttctcta tcggttgctt ttacttgcac aatagtggca    1980
gacaaactac aagtcagatc cgatcctatc catccatcca tctcgcagcg cgatgcaaat    2040
atgcaatcgt ctgtggaact cgaaaaaaaa cagaggtccg gcctcgcacg aggttaaggg    2100
aaaaaaaacg aagcgtttgg aactttggtt ggcattcgca gcatgctgtg ctgccaccgt    2160 atgttttat ttttgctttg tttgtcttct ttgagaaacg tgagggagcc gcgtgtccgc    2220
tcgttataaa accccccggg cgacccaaac taccacgagc tcaagcctca agcctcaagc    2280
ctcaagcaag cagagcgccg tgacatcacg aaacaaacat atagagctag ctgctctgcc    2340
tctgcttcac caatcacctg cttggccgcg cggaggggag ggtttccccc tttgacacag    2400
ctgagctccc ctccatcagc agccagctcc tcgtcgcaaa gcaagaagat gatgctcgcg    2460
tacatggacc gcgcgacggc ggccgccgag ccagaggacg ccggccgcga gcccgccacc    2520
atggcgggcg ggtgcgcggc ggcggcgacg gatttcggcg ggctggggag cgccatgccc    2580
gcggccgtgg tccgcccggc gagcgcggac gacgtggcca gcgccatccg cgcggcggcg    2640
ctgacgccgc acctcaccgt ggccgcccgc gggaacgggc actcggtggc cggccaggcc    2700
atggccgagg gcgggctggt cctcgacatg cgctcgctcg cggcgccgtc ccggcgcgcg    2760
cagatgcagc tcgtcgtgca gtgccccgac ggcggcggcg gccgccgctg cttcgccgac    2820
gtccccggcg gcgcgctctg ggaggaggtg ctccactggg ccgtcgacaa ccacgggctc    2880
gccccggcgt cctggacgga ctacctccgc ctcaccgtgg gcgcacgct ctccaatggc    2940 ggcgtcagcg gccagtcctt ccgctacggg ccccaggtgt ccaacgtggc cgagctcgag    3000
gtggtcaccg cgcgacggcga gcgccgcgtc tgctcgccct cctcccaccc ggacctcttc    3060
ttcgccgtgc tcggcgggct cggccagttt ggcgtcatca cgcgcgcccg catcccgctc    3120
cacagggcgc caaggcggt gagcgcgcgg acatcggggg cgaaagctaa agcttgcttt    3180
ttgcttgggc actactaact gactgacgtt gccattcagg tgcggtggac gcgcgtggtg    3240
tacgcgagca tcgcggacta cacggcggac gcggagtggc tggtgacgcg gccccccgac    3300
gcggcgttcg actacgtgga gggcttcgcg ttcgtgaaca gcgacgaccc cgtgaacggc    3360
```

```
tggccgtccg tgcccatccc cggcggcgcc cgcttcgacc cgtccctcct ccccgccggc   3420
gccggccccg tcctctactg cctggaggtg gccctgtacc agtacgcgca ccggcccgac   3480
gacgacgacg aggaggacca ggtaggtagc agtaattgcc aacctctccc cccgcttggc   3540
gcattcccgt acttgacccc ctcgcccgct ctggcgtgta cttttccgcg ggcagggcat   3600
gtctgactcg cctcgtcgtg tatctcccgc tggattcggt gacggggtg ctgcgtcctg    3660 ccaaaccaaa ccaccctaga ctagacagac ccccaggggc aggggtcgcg ccattggccg   3720
cacgcgggga ccggcgccag tgagtgcgcc gcgccgcacg gccgcgcccc gatctcgctc   3780
gctcgctcgc tggtgatcga atcggcgcgt acaatgcggc atggcccga gccccacacc    3840 cgcagtggcc gtgacgcgat tgcgctgcct ccggtccggc ccatgaccca gcggatcgcg   3900
tcgcgtcttt tggcaacgcc cgcgtcatca tatcgcgctc tttgtcgtcc ccacggagca   3960
cagcgcagcg cagcgcagcg cagccaacct tttctccgcc acgcacgctt cggcggcatt   4020
cattatttgg attttgttcc taccggtcga tccgcgtccg tccgtgcact gcaggcggct   4080
accgtcatgc tgaccaaccc attgccattg gttttgtttc ttctctctct ctccctctcg   4140
ttggttatgg ttcgtgcgtg cctgcaggcg cggtgaccg tgagccggat gatggcgccg    4200
ctcaagcacg tgcggggcct ggagttcgcg gcggacgtcg ggtacgtgga cttcctgtcc   4260
cgcgtgaacc gggtggagga ggaggccggg cgcaacggca gctgggacgc gccgcacccg   4320
tggctcaacc tcttcgtctc cgcgcgcgac atcgccgact cgaccgcgc cgtcatcaag    4380 ggcatgctcg ccgacggcat cgacgggccc atgctcgtct accctatgct caagagcaag   4440
tgagttgccc tccgctccgc tccttcgcac tgcgtgcagt agtacagtac aggagtggct   4500
gagtggtggt actgccattc agtgtgcagt tgccgttttgc ggcccgccaa gctagctagg   4560
ggccgggacg catgtgagcc gccctgcctt ctctctgctc gtcgtgtcac tgacgcctgg   4620
tcctccggga cagttgctga gccggcccgt acgtacctgt aagacgacgg tcccgagcct   4680
ccaccgccgc ttctgttttg gatttagccg tgtcacacag atcttacgga ggaggaggag   4740
tactatgatt gacaaattat tgcttcgccc gacccgaggc tagcgcacag tccatgtcat   4800
gtgggcctgg ctgtgtggtt tccgtcctga tgctgatgcc tgaagggaac tgcgtgcgtg   4860
tgcgtgcgtg caggtgggac cccaacacgt cggtggcgct gccggagggc gaggtcttct   4920
acctggtggc gctgctgcgg ttctgccgga cggcgggcc ggcggtggac gagctggtgg    4980
cgcagaacgg cgccatcctc cgcgcctgcc gcgccaacgg ctacgactac aaggcctact   5040
tcccgagcta ccgcggcgag gccgactggg cgcgccactt cggcgccgcc aggtggaggc   5100
gcttcgtgga ccgcaaggcc cggtacgacc cgctggcgat cctcgcgccg ggccagaaga   5160
tcttccctcg ggtcccggcg tccgtcgccg tgtagagcaa gggggagga ccagccagct    5220 gccagccaag acaggaggag gaggagggga ggctgatgga tcgccgctgc tgttgccggt   5280
aatgatggcg attacgctgc tgatcctggt gatgatgatg gacgatcgag gaagccgcag   5340
ggccgggcaa tgatggcgat agggccaccg ttaggtgtgc atccgggggc acaaattaaa   5400
gggattgctg tgtggagatc tgcacgagtt tttgctccat gcatgcttgc cgttcgtgtc   5460
cgcgtgtccc tctccccctt gttattattc cttcgcccgc cgaggccgag cgagcgggtg   5520
gtggcgacgc tggatttgtc tgctctgctc tgctccgccg ccgtgccac cccggtggcg     5580 tgcgcccgca agctgttcct tccgcgcgct tctgttccgt tcggttcccc cgtggtagct   5640
tccccccctc gccgtcctgg tcccccgcc gcccgcgcac cccacgtggc acaccagccc    5700
gatccaaacg ccgcgaccgc gacgcgcggg gccgttggtt cgcgttcccg ttccgtagca   5760
```

-continued

```
gcttgcccgc agcacacgac gaccgcgaac aaagcgcggc caaaaccgac gggtctcgcc    5820
gccgccgccg cggacgcgcc cacgggacag gaggaatatc actctggggc catccgcgcg    5880
ggaccataga actggtcggg tcgatgtcga tcgatatcgg cactctgtgc tggctggcga    5940
cgcggaccga gcggcaggga cgtgacggtt gctgccgccc gagcgcgacg gcgaccgtcc    6000
ttcgtctctg gggcggggcg gcgtttcgt ttggaaaatt tgtggacttc tacttgtata    6060
taaaaaaaca cgatcggcgc acgtatacaa ccagtcttcc tttccctgtc gtgcccagtc    6120
gcattccgtg atgcgagccg atcgcgacg gaagcggctc aacgagcgtc gtccctg       6177
```

<210> SEQ ID NO 8
<211> LENGTH: 1816
<212> TYPE: DNA
<213> ORGANISM: Zea mays
<220> FEATURE:
<221> NAME/KEY: misc_feature
<222> LOCATION: (0)...(0)
<223> OTHER INFORMATION: cDNA for ZmCkx4
<220> FEATURE:
<221> NAME/KEY: CDS
<222> LOCATION: (1)...(1566)

<400> SEQUENCE: 8

```
atg atg ctc gcg tac atg gac cgc gcg acg gcg gcc gcc gag cca gag      48
Met Met Leu Ala Tyr Met Asp Arg Ala Thr Ala Ala Ala Glu Pro Glu
1               5                   10                  15 gac gcc ggc cgc gag ccc gcc acc atg gcg ggc ggg tgc gcg gcg gcg      96
Asp Ala Gly Arg Glu Pro Ala Thr Met Ala Gly Gly Cys Ala Ala Ala
            20                  25                  30 gcg acg gat ttc ggg ggg ctg ggg agc gcc atg ccc gcg gcc gtg gtc     144
Ala Thr Asp Phe Gly Gly Leu Gly Ser Ala Met Pro Ala Ala Val Val
        35                  40                  45 cgc ccg gcg agc gcg gac gac gtg gcc agc gcc atc cgc gcg gcg gcg     192
Arg Pro Ala Ser Ala Asp Asp Val Ala Ser Ala Ile Arg Ala Ala Ala
    50                  55                  60 ctg acg ccg cac ctc acc gtg gcc gcc cgc ggg aac ggg cac tcg gtg     240
Leu Thr Pro His Leu Thr Val Ala Ala Arg Gly Asn Gly His Ser Val
65                  70                  75                  80 gcc ggc cag gcc atg gcc gag ggc ggg ctg gtc ctc gac atg cgc tcg     288
Ala Gly Gln Ala Met Ala Glu Gly Gly Leu Val Leu Asp Met Arg Ser
                85                  90                  95 ctc gcg gcg ccg tcc cgg cgc gcg cag atg cag ctc gtc gtg cag tgc     336
Leu Ala Ala Pro Ser Arg Arg Ala Gln Met Gln Leu Val Val Gln Cys
            100                 105                 110 ccc gac ggc ggc ggc cgc cgc tgc ttc gcc gac gtc ccc ggc ggc         384
Pro Asp Gly Gly Gly Arg Arg Cys Phe Ala Asp Val Pro Gly Gly
        115                 120                 125 gcg ctc tgg gag gag gtg ctc cac tgg gcc gtc gac aac cac ggg ctc     432
Ala Leu Trp Glu Glu Val Leu His Trp Ala Val Asp Asn His Gly Leu
    130                 135                 140 gcc ccg gcg tcc tgg acg gac tac ctc cgc ctc acc gtg ggc ggc acg     480
Ala Pro Ala Ser Trp Thr Asp Tyr Leu Arg Leu Thr Val Gly Gly Thr
145                 150                 155                 160 ctc tcc aat ggc ggc gtc agc ggc cag tcc ttc cgc tac ggg ccc cag     528
Leu Ser Asn Gly Gly Val Ser Gly Gln Ser Phe Arg Tyr Gly Pro Gln
                165                 170                 175 gtg tcc aac gtg gcc gag ctc gag gtg gtc acc ggc gac ggc gag cgc     576
Val Ser Asn Val Ala Glu Leu Glu Val Val Thr Gly Asp Gly Glu Arg
            180                 185                 190 cgc gtc tgc tcg ccc tcc tcc cac ccg gac ctc ttc ttc gcc gtg ctc     624
Arg Val Cys Ser Pro Ser Ser His Pro Asp Leu Phe Phe Ala Val Leu
        195                 200                 205
```

```
ggc ggg ctc ggc cag ttt ggc gtc atc acg cgc gcc cgc atc ccg ctc      672
Gly Gly Leu Gly Gln Phe Gly Val Ile Thr Arg Ala Arg Ile Pro Leu
    210                 215                 220 cac agg gcg ccc aag gcg gtg cgg tgg acg cgc gtg gtg tac gcg agc      720
His Arg Ala Pro Lys Ala Val Arg Trp Thr Arg Val Val Tyr Ala Ser
225                 230                 235                 240 atc gcg gac tac acg gcg gac gcg gag tgg ctg gtg acg cgg ccc ccc      768
Ile Ala Asp Tyr Thr Ala Asp Ala Glu Trp Leu Val Thr Arg Pro Pro
                245                 250                 255 gac gcg gcg ttc gac tac gtg gag ggc ttc gcg ttc gtg aac agc gac      816
Asp Ala Ala Phe Asp Tyr Val Glu Gly Phe Ala Phe Val Asn Ser Asp
            260                 265                 270 gac ccc gtg aac ggc tgg ccg tcc gtg ccc atc ccc ggc ggc gcc cgc      864
Asp Pro Val Asn Gly Trp Pro Ser Val Pro Ile Pro Gly Gly Ala Arg
        275                 280                 285 ttc gac ccg tcc ctc ctc ccc gcc ggc gcc ggc ccc gtc ctc tac tgc      912
Phe Asp Pro Ser Leu Leu Pro Ala Gly Ala Gly Pro Val Leu Tyr Cys
    290                 295                 300 ctg gag gtg gcc ctg tac cag tac gcg cac cgg ccc gac gac gac gac      960
Leu Glu Val Ala Leu Tyr Gln Tyr Ala His Arg Pro Asp Asp Asp Asp
305                 310                 315                 320 gag gag gac cag gcg gcg gtg acc gtg agc cgg atg atg gcg ccg ctc     1008
Glu Glu Asp Gln Ala Ala Val Thr Val Ser Arg Met Met Ala Pro Leu
                325                 330                 335 aag cac gtg cgg ggc ctg gag ttc gcg gcg gac gtg ggg tac gtg gac     1056
Lys His Val Arg Gly Leu Glu Phe Ala Ala Asp Val Gly Tyr Val Asp
            340                 345                 350 ttc ctg tcc cgc gtg aac cgg gtg gag gag gag gcc cgg cgc aac ggc     1104
Phe Leu Ser Arg Val Asn Arg Val Glu Glu Glu Ala Arg Arg Asn Gly
        355                 360                 365 agc tgg gac gcg ccg cac ccg tgg ctc aac ctc ttc gtc tcc gcg cgc     1152
Ser Trp Asp Ala Pro His Pro Trp Leu Asn Leu Phe Val Ser Ala Arg
    370                 375                 380 gac atc gcc gac ttc gac cgc gcc gtc atc aag ggc atg ctc gcc gac     1200
Asp Ile Ala Asp Phe Asp Arg Ala Val Ile Lys Gly Met Leu Ala Asp
385                 390                 395                 400 ggc atc gac ggg ccc atg ctc gtc tac cct atg ctc aag agc aag tgg     1248
Gly Ile Asp Gly Pro Met Leu Val Tyr Pro Met Leu Lys Ser Lys Trp
                405                 410                 415 gac ccc aac acg tcg gtg gcg ctg ccg gag ggc gag gtc ttc tac ctg     1296
Asp Pro Asn Thr Ser Val Ala Leu Pro Glu Gly Glu Val Phe Tyr Leu
            420                 425                 430 gtg gcg ctg ctg cgg ttc tgc cgg agc ggc ggg ccg gcg gtg gac gag     1344
Val Ala Leu Leu Arg Phe Cys Arg Ser Gly Gly Pro Ala Val Asp Glu
        435                 440                 445 ctg gtg gcg cag aac ggc gcc atc ctc cgc gcc tgc cgc gcc aac ggc     1392
Leu Val Ala Gln Asn Gly Ala Ile Leu Arg Ala Cys Arg Ala Asn Gly
    450                 455                 460 tac gac tac aag gcc tac ttc ccg agc tac cgc ggc gag gcc gac tgg     1440
Tyr Asp Tyr Lys Ala Tyr Phe Pro Ser Tyr Arg Gly Glu Ala Asp Trp
465                 470                 475                 480 gcg cgc cac ttc ggc gcc gcc agg tgg agg cgc ttc gtg gac cgc aag     1488
Ala Arg His Phe Gly Ala Ala Arg Trp Arg Arg Phe Val Asp Arg Lys
                485                 490                 495 gcc cgg tac gac ccg ctg gcg atc ctc gcg ccg ggc cag aag atc ttc     1536
Ala Arg Tyr Asp Pro Leu Ala Ile Leu Ala Pro Gly Gln Lys Ile Phe
            500                 505                 510 cct cgg gtc ccg gcg tcc gtc gcc gtg tag agcaaggggg gaggaccagc       1586
Pro Arg Val Pro Ala Ser Val Ala Val
        515                 520
```

```
cagctgccag ccaagacagg aggaggagga ggaggggagg ctgatggatc gccgctgctg    1646
ttgccggtaa tgatggcgat tacgctgctg atcctggtga tgatgatgga cgatcgagga    1706
agccgcaggg ccgggcaatg atggcgatag ggccaccgtt aggtgtgcat ccggggcgc     1766 aaattaaagg gattgctgtg tggagatctg cacgagtttt tgctccatgc                1816
```

<210> SEQ ID NO 9
<211> LENGTH: 521
<212> TYPE: PRT
<213> ORGANISM: Zea mays

<400> SEQUENCE: 9

```
Met Met Leu Ala Tyr Met Asp Arg Ala Thr Ala Ala Glu Pro Glu
  1               5                  10                  15

Asp Ala Gly Arg Glu Pro Ala Thr Met Ala Gly Gly Cys Ala Ala
                 20                  25                  30

Ala Thr Asp Phe Gly Gly Leu Gly Ser Ala Met Pro Ala Ala Val Val
             35                  40                  45

Arg Pro Ala Ser Ala Asp Asp Val Ala Ser Ala Ile Arg Ala Ala Ala
 50                  55                  60

Leu Thr Pro His Leu Thr Val Ala Ala Arg Gly Asn Gly His Ser Val
 65                  70                  75                  80

Ala Gly Gln Ala Met Ala Glu Gly Leu Val Leu Asp Met Arg Ser
                 85                  90                  95

Leu Ala Ala Pro Ser Arg Arg Ala Gln Met Gln Leu Val Val Gln Cys
                100                 105                 110

Pro Asp Gly Gly Gly Gly Arg Arg Cys Phe Ala Asp Val Pro Gly Gly
                115                 120                 125

Ala Leu Trp Glu Glu Val Leu His Trp Ala Val Asp Asn His Gly Leu
130                 135                 140

Ala Pro Ala Ser Trp Thr Asp Tyr Leu Arg Leu Thr Val Gly Gly Thr
145                 150                 155                 160

Leu Ser Asn Gly Gly Val Ser Gly Gln Ser Phe Arg Tyr Gly Pro Gln
                165                 170                 175

Val Ser Asn Val Ala Glu Leu Glu Val Val Thr Gly Asp Gly Glu Arg
                180                 185                 190

Arg Val Cys Ser Pro Ser Ser His Pro Asp Leu Phe Phe Ala Val Leu
                195                 200                 205

Gly Gly Leu Gly Gln Phe Gly Val Ile Thr Arg Ala Arg Ile Pro Leu
210                 215                 220

His Arg Ala Pro Lys Ala Val Arg Trp Thr Arg Val Val Tyr Ala Ser
225                 230                 235                 240

Ile Ala Asp Tyr Thr Ala Asp Ala Glu Trp Leu Val Thr Arg Pro Pro
                245                 250                 255

Asp Ala Ala Phe Asp Tyr Val Glu Gly Phe Ala Phe Val Asn Ser Asp
                260                 265                 270

Asp Pro Val Asn Gly Trp Pro Ser Val Pro Ile Pro Gly Gly Ala Arg
                275                 280                 285

Phe Asp Pro Ser Leu Leu Pro Ala Gly Ala Gly Pro Val Leu Tyr Cys
                290                 295                 300

Leu Glu Val Ala Leu Tyr Gln Tyr Ala His Arg Pro Asp Asp Asp
305                 310                 315                 320

Glu Glu Asp Gln Ala Ala Val Thr Val Ser Arg Met Met Ala Pro Leu
                325                 330                 335
```

```
Lys His Val Arg Gly Leu Glu Phe Ala Ala Asp Val Gly Tyr Val Asp
                340                 345                 350

Phe Leu Ser Arg Val Asn Arg Val Glu Glu Glu Ala Arg Arg Asn Gly
            355                 360                 365

Ser Trp Asp Ala Pro His Pro Trp Leu Asn Leu Phe Val Ser Ala Arg
    370                 375                 380

Asp Ile Ala Asp Phe Arg Ala Val Ile Lys Gly Met Leu Ala Asp
385                 390                 395                 400

Gly Ile Asp Gly Pro Met Leu Val Tyr Pro Met Leu Lys Ser Lys Trp
                405                 410                 415

Asp Pro Asn Thr Ser Val Ala Leu Pro Glu Gly Glu Val Phe Tyr Leu
            420                 425                 430

Val Ala Leu Leu Arg Phe Cys Arg Ser Gly Gly Pro Ala Val Asp Glu
        435                 440                 445

Leu Val Ala Gln Asn Gly Ala Ile Leu Arg Ala Cys Arg Ala Asn Gly
    450                 455                 460

Tyr Asp Tyr Lys Ala Tyr Phe Pro Ser Tyr Arg Gly Glu Ala Asp Trp
465                 470                 475                 480

Ala Arg His Phe Gly Ala Ala Arg Trp Arg Arg Phe Val Asp Arg Lys
                485                 490                 495

Ala Arg Tyr Asp Pro Leu Ala Ile Leu Ala Pro Gly Gln Lys Ile Phe
            500                 505                 510

Pro Arg Val Pro Ala Ser Val Ala Val
        515                 520

<210> SEQ ID NO 10
<211> LENGTH: 5108
<212> TYPE: DNA
<213> ORGANISM: Zea mays
<220> FEATURE:
<221> NAME/KEY: misc_feature
<222> LOCATION: (0)...(0)
<223> OTHER INFORMATION: Genomic sequence for ZmCkx5
<220> FEATURE:
<221> NAME/KEY: exon
<222> LOCATION: (1117)...(1711)
<220> FEATURE:
<221> NAME/KEY: exon
<222> LOCATION: (1858)...(2512)
<220> FEATURE:
<221> NAME/KEY: exon
<222> LOCATION: (3961)...(4339)

<400> SEQUENCE: 10
atcccgaata acaaatgaa gtaggtcctc agtcacccct gccctgttag ctgcaagaga      60
gctcatggtt ccagccaca caatcagtcc atggctcctt cttcttggcc taagtggtgg    120
ccaatcattg tgggtgatcg agtcttgggc cctctgaaca gtattacaca acagtaatcc    180
tgcaaaagat ttggtatatc tagattctag agtgagcgcc gtgttgtgcc cagctaggaa    240
tgggttgtca agtgcaacag gaggaggacc caggatggtc aggtgtaata ggctctcatt    300
aaaagactgt tcagatggat tagagcaacg acggggaagc cgggaaaaaa tggttggttc    360
tgctttcctc tcgctccccg gccgggttca tatatgaatc tgagaacgat atttttttgct    420 tcatttttca tttgctatat atttaaactg ttttttttgtg tgtgtgtgtg tgttcattga    480
gctcaatact tgaggcttga tagggagagg agtgaggcag ctgatcacat ggacctccat    540
ctgaggacag ttcctcttcc gaaacagaaa ggagagtgca gggaccagcg tggcctgtac    600
agtattgtgt ttgccctttt cctttggcag ggacagagag cttcaggctt gtcctcttta    660
tgtatgctgc tcgcctgctt cagagtcaga gcttccccctt ctcacttctc agagagagag    720
```

```
agagagaaga gagagagagg agagccctcc acagctcccc tgtcctgccc tcaggcattc    780
tttgtcacag ggggcgaggg ctgaagatca tcacatggtg gcctttttg ggtctgtggc    840 ctttggtctt ttagtgcttc ttccttttac ctcctcatga catgaacccc cttttaaac    900 ctccctcaaa atcaaatcac cctccttctc ctttaagagc cctcaacccc ttcccctcat    960
tttccttcat ccctcagcct ttgcacaaag ggcaagaata acgcagtatg atcatctgat   1020
catactcccg ccgccatcac aatcccacac gaacgtgaga caaaggtaac agacgcaaga   1080
agctagcagc tgcaggagat tgctcagccc atctccatgg aggttgccat ggtcgtgagc   1140
gcaagagcca gcctgctgat cctcgtcctc tccctctgct ctccgtacaa attcatacag   1200
agccccatgg acctgggccc cctgaacctg ctccccacca ccagcaccgc ggccgcgtcc   1260
agcgacttcg gcaggatact cttccgcgcc ccggccgcgg tgctgaggcc ccagtcgccg   1320
agggacatct ccatgctgct cagcttcctc tccggctcgc cctcgctgag cagggtcacg   1380
gtggcggcca ggggggcagg ccactccatc cacgggcagg cgcaggcccc ggacggcatt   1440
gtggtggaga cgcgctcctt gcccggcgag atggagttcc accacgtccg cggggaggc    1500 gaagggcgtg cctcctacgc cgacgtgggc ggcggggttc tgtggatcga gctcctggag   1560
cggagcctga agcttgggct ggctcccagg tcctggaccg actacctcta cctcactgtc   1620
ggcgggacgc tgtccaatgc cggcatcagc gggcagacgt tcaagcacgg gccacagatc   1680
agcaacgtcc tccagctgga ggtagtcaca ggtgagacac acgcacgcat gcatgcgtgc   1740
atgcatggta catagatgaa acacaaagat cagattttt tttctgcctc tctttcttga   1800
ccaacaaaca acctctctct ctctctctct ctctctctct ctctctataa caaacaggac   1860
gaggggagat tgtggaatgc tcacccagca aggaggccga cctgttcaat gccgtcctgg   1920
gaggcctagg ccagttcggc atcataacca gggccaggat cctgctgcag gaggctccgg   1980
agaaggtgac gtgggtgagg gccttctacg acgacttggg cgccttcacc agggaccagg   2040
agctgctggt gtcgattccg gattcgtgg actacgtgga agggttcatg gtcctgaacg   2100
agcggtccct ccacagctcc tccatcgcct tcccgcgag cgtggacttc agcccggatt   2160
tcggcaccag gagcagccct aggatctact actgcgtcga gttcgcggtc caccaccacc   2220
acggttacca gcagcagtct caggcggccg tggaggccat ctcgaggcgg atgagccaca   2280
tggcgtccca gctgtacagc gtggaggtgt cctacttgga cttcctgaac cgggtcagga   2340
tggaggaggt gagcctgcgg agcgccggga tgtgggagga ggtgcaccac ccgtggctca   2400
acatgttcgt gcccaaggcc ggggtcgctg gcttcaggga tctgctcatg gacaacgtct   2460
cgccggatag cttccaggc ctcatcctca tctacccact cctcagagac aagtaagtac    2520
cactcttcta ataataataa taataatgat gatgacacaa aagctatata gtagtacatc   2580
catgaagata cgcctacact ttcggctttt ctcaaagcaa agcttatctg ctttattaat   2640
cccggcctct tccggccgtc ctcacttcat attagcttac aagaagtcca agttgggcaa   2700
gcaagcattt ctttgcatta tccacagcaa gttgcctcct tgcgctgcct acagtggtaa   2760
cgacatgggt agggtttggt tttggagtaa tagcgggata tgaagccttt ccgctcttaa   2820
tttgttgttt ttagattgat tttatatagg acatagtgac acttaaaaaa tatatgttca   2880
aatattgaac cattttggtt tcagaaaatc tcttggaacg agccgttcta gccgttctct   2940
ctctagaacg gagtcgctcc atcctaacta gcttcacaat caaacattac cttggatgac   3000
gacgaagcgc cgagaaaagt ggtcactcat cgtgcgtgca ttagggatga tagatcccct   3060
ttgcttaatt agcatgttgg tttgtttttt ccctatgtcc agcaaaggcg ctcgtgggac   3120
```

```
ccacgccgtc gtatagaggc gaatatgggt tgttctatcg tgtgtttgta ctagtggtcc  3180
ctcggatagc atcacatctg cgtcatcatc agcattgtat gaatcagcta aaactgtaga  3240
tgagctcaat cagtcagtag catcaacctt gagagtggcg acagggaaat tataaaacat  3300
agtagtagct agctgatctg ctttggaatt agtcttcgtt tttcttcttt tttcacctaa  3360
gggctagttt aggaacacaa ttttctcaaa aaaaaaattg aactaattac tcttaagaaa  3420
atggaaattc ctagaaaaaa aatgaggttg ccaaactagg cttaaaagat ttttttaaca  3480
ggtgcaaaca acgtcgtaaa cttgtaatcg atagcacaag ttattcagtt acaagcgtct  3540
tgttatgtgt tcataccctc cgaataaatt tagacaagtt tacatggatg caaaaggggt  3600
ttaaatatgt gtatgtgcta gatcgcatcc cagtgtcaac tctgaactga ttgagcttta  3660
acaaaagatg aagtcgtcac ccaaagttcc acgttcaccg cactggacta gtgtatatat  3720
aatctacagg cccaacagag acctctgact tgcctcagga aaaaccacta aaccaaaagt  3780
ctctctctct cgagagagag tcagaatacg ctgaactgca gaatgtcagc tacaccaccc  3840
atacacaaat tcctgctacc gcttatttga aattcacagc gtctcgtcag caagctctaa  3900
aaaactgttt gttgctgtct tcatcctttc tttttttta tttgatttga ttgacgacag  3960
gtgggacacc aacacgtcgg tcgtgatccc ggactccggg cccaccgcgg acgacccggt  4020
gatgtacgtg gtcggcatcc tcaggtccgc gaaccctggt ccagaagaag acggtgacgg  4080
ctgctcccac cgctgcctgc acgagctcct ccgcagccac cgccggatcg ccgacgccgc  4140
ggaggcgcgc ctcggcgcca agcagtacct gcctcaccac ccgaccccgg cccgctggca  4200
gcagcacctg ggccggcgct gggagcgctt cgcggaccgc aaggcccggt tcgacccgct  4260
gcgcatcctg gggcccggcc agggcatatt ccctcggacg gcccaggatg ctgccgccgc  4320
tgctgcgtac gggagctagc attttatata tatacggcat gaaacagtat agattattaa  4380
ttatcagctg actagctagg atgcgatctt cttctttcttt cttcttctct cttcagtttc  4440
ctctgcattt tgagggcatg tggggccggt tgttgggtta ttctgtgagg ctctggcctc  4500
cggggcactt tgagaggacc tgatggtggt ggtggtggtg gtgattggtg attggtgaat  4560
gtcactggga attttggaac ttttgtacag gttgatggag gaagcacagg ctttaagttt  4620
ataagggaat agacatagcg cttctattcg gtctctctat tccttgttcg atatggccat  4680
tgctagtgtc actattgtcc tcggtaattc cgtttctagg ctgataaatt ccttccactt  4740
tgtcagagcc atcttcttta ggagaagtgg tgacaacgtg ccagagccct ttgggttagc  4800
tcgagatcag aatgtagtcc atggatgagg ggccatgggt gctagattta cagtgaattt  4860
gatccgtccc caatgttccg ttagctaaaa tgcatgcggt gaagtcgtac aagcatgcat  4920
gatgcatgcc cttttttttct ggagtacccg tcattttgcc ttctgaaact ccggaagccc  4980
ttgcattgac cgtttgacac aattatgaag tgaagatgat aagtcgtgaa tggattcatg  5040
acagatcaac acgtggcacc tccgtacata caaacacgcg cccgaagttc cctctaggaa  5100
acttcaat                                                           5108
```

<210> SEQ ID NO 11
<211> LENGTH: 1629
<212> TYPE: DNA
<213> ORGANISM: Zea mays
<220> FEATURE:
<221> NAME/KEY: misc_feature
<222> LOCATION: (0)...(0)
<223> OTHER INFORMATION: cDNA for ZmCkx5
<220> FEATURE:
<221> NAME/KEY: CDS

<222> LOCATION: (1)...(1629)

<400> SEQUENCE: 11

| | | | | | | | | | | | | | | | | |
|---|---|---|---|---|---|---|---|---|---|---|---|---|---|---|---|---|
| atg | gag | gtt | gcc | atg | gtc | gtg | agc | gca | aga | gcc | agc | ctg | ctg | atc | ctc | 48 |
| Met | Glu | Val | Ala | Met | Val | Val | Ser | Ala | Arg | Ala | Ser | Leu | Leu | Ile | Leu | |
| 1 | | | | 5 | | | | | 10 | | | | | 15 | | |
| gtc | ctc | tcc | ctc | tgc | tct | ccg | tac | aaa | ttc | ata | cag | agc | ccc | atg | gac | 96 |
| Val | Leu | Ser | Leu | Cys | Ser | Pro | Tyr | Lys | Phe | Ile | Gln | Ser | Pro | Met | Asp | |
| | | | 20 | | | | | 25 | | | | | 30 | | | |
| ctg | ggc | ccc | ctg | aac | ctg | ctc | ccc | acc | acc | agc | acc | gcg | gcc | gcg | tcc | 144 |
| Leu | Gly | Pro | Leu | Asn | Leu | Leu | Pro | Thr | Thr | Ser | Thr | Ala | Ala | Ala | Ser | |
| | | 35 | | | | | 40 | | | | | 45 | | | | |
| agc | gac | ttc | ggc | agg | ata | ctc | ttc | cgc | gcc | ccg | gcc | gcg | gtg | ctg | agg | 192 |
| Ser | Asp | Phe | Gly | Arg | Ile | Leu | Phe | Arg | Ala | Pro | Ala | Ala | Val | Leu | Arg | |
| | 50 | | | | | 55 | | | | | 60 | | | | | |
| ccc | cag | tcg | ccg | agg | gac | atc | tcc | atg | ctg | ctc | agc | ttc | ctc | tcc | ggc | 240 |
| Pro | Gln | Ser | Pro | Arg | Asp | Ile | Ser | Met | Leu | Leu | Ser | Phe | Leu | Ser | Gly | |
| 65 | | | | | 70 | | | | | 75 | | | | | 80 | |
| tcg | ccc | tcg | ctg | agc | agg | gtc | acg | gtg | gcg | gcc | agg | ggg | gca | ggc | cac | 288 |
| Ser | Pro | Ser | Leu | Ser | Arg | Val | Thr | Val | Ala | Ala | Arg | Gly | Ala | Gly | His | |
| | | | | 85 | | | | | 90 | | | | | 95 | | |
| tcc | atc | cac | ggg | cag | gcg | cag | gcc | ccg | gac | ggc | att | gtg | gtg | gag | acg | 336 |
| Ser | Ile | His | Gly | Gln | Ala | Gln | Ala | Pro | Asp | Gly | Ile | Val | Val | Glu | Thr | |
| | | | 100 | | | | | 105 | | | | | 110 | | | |
| cgc | tcc | ttg | ccc | ggc | gag | atg | gag | ttc | cac | cac | gtc | cgc | ggg | gga | ggc | 384 |
| Arg | Ser | Leu | Pro | Gly | Glu | Met | Glu | Phe | His | His | Val | Arg | Gly | Gly | Gly | |
| | | 115 | | | | | 120 | | | | | 125 | | | | |
| gaa | ggg | cgt | gcc | tcc | tac | gcc | gac | gtg | ggc | ggg | ggg | gtt | ctg | tgg | atc | 432 |
| Glu | Gly | Arg | Ala | Ser | Tyr | Ala | Asp | Val | Gly | Gly | Gly | Val | Leu | Trp | Ile | |
| | 130 | | | | | 135 | | | | | 140 | | | | | |
| gag | ctc | ctg | gag | cgg | agc | ctg | aag | ctt | ggg | ctg | gct | ccc | agg | tcc | tgg | 480 |
| Glu | Leu | Leu | Glu | Arg | Ser | Leu | Lys | Leu | Gly | Leu | Ala | Pro | Arg | Ser | Trp | |
| 145 | | | | | 150 | | | | | 155 | | | | | 160 | |
| acc | gac | tac | ctc | tac | ctc | act | gtc | ggc | ggg | acg | ctg | tcc | aat | gcc | ggc | 528 |
| Thr | Asp | Tyr | Leu | Tyr | Leu | Thr | Val | Gly | Gly | Thr | Leu | Ser | Asn | Ala | Gly | |
| | | | | 165 | | | | | 170 | | | | | 175 | | |
| atc | agc | ggg | cag | acg | ttc | aag | cac | ggg | cca | cag | atc | agc | aac | gtc | ctc | 576 |
| Ile | Ser | Gly | Gln | Thr | Phe | Lys | His | Gly | Pro | Gln | Ile | Ser | Asn | Val | Leu | |
| | | | 180 | | | | | 185 | | | | | 190 | | | |
| cag | ctg | gag | gta | gtc | aca | gga | cga | ggg | gag | att | gtg | gaa | tgc | tca | ccc | 624 |
| Gln | Leu | Glu | Val | Val | Thr | Gly | Arg | Gly | Glu | Ile | Val | Glu | Cys | Ser | Pro | |
| | | 195 | | | | | 200 | | | | | 205 | | | | |
| agc | aag | gag | gcc | gac | ctg | ttc | aat | gcc | gtc | ctg | gga | ggc | cta | ggc | cag | 672 |
| Ser | Lys | Glu | Ala | Asp | Leu | Phe | Asn | Ala | Val | Leu | Gly | Gly | Leu | Gly | Gln | |
| | 210 | | | | | 215 | | | | | 220 | | | | | |
| ttc | ggc | atc | ata | acc | agg | gcc | agg | atc | ctg | ctg | cag | gag | gct | ccg | gag | 720 |
| Phe | Gly | Ile | Ile | Thr | Arg | Ala | Arg | Ile | Leu | Leu | Gln | Glu | Ala | Pro | Glu | |
| 225 | | | | | 230 | | | | | 235 | | | | | 240 | |
| aag | gtg | acg | tgg | gtg | agg | gcc | ttc | tac | gac | gac | ttg | ggc | gcc | ttc | acc | 768 |
| Lys | Val | Thr | Trp | Val | Arg | Ala | Phe | Tyr | Asp | Asp | Leu | Gly | Ala | Phe | Thr | |
| | | | | 245 | | | | | 250 | | | | | 255 | | |
| agg | gac | cag | gag | ctg | ctg | gtg | tcg | att | ccg | gat | tcg | gtg | gac | tac | gtg | 816 |
| Arg | Asp | Gln | Glu | Leu | Leu | Val | Ser | Ile | Pro | Asp | Ser | Val | Asp | Tyr | Val | |
| | | | 260 | | | | | 265 | | | | | 270 | | | |
| gaa | ggg | ttc | atg | gtc | ctg | aac | gag | cgg | tcc | ctc | cac | agc | tcc | tcc | atc | 864 |
| Glu | Gly | Phe | Met | Val | Leu | Asn | Glu | Arg | Ser | Leu | His | Ser | Ser | Ser | Ile | |
| | | 275 | | | | | 280 | | | | | 285 | | | | |
| gcc | ttc | ccc | gcg | agc | gtg | gac | ttc | agc | ccg | gat | ttc | ggc | acc | agg | agc | 912 |
| Ala | Phe | Pro | Ala | Ser | Val | Asp | Phe | Ser | Pro | Asp | Phe | Gly | Thr | Arg | Ser | |
| | 290 | | | | | 295 | | | | | 300 | | | | | |

```
agc cct agg atc tac tac tgc gtc gag ttc gcg gtc cac cac cac cac    960
Ser Pro Arg Ile Tyr Tyr Cys Val Glu Phe Ala Val His His His His
305                 310                 315                 320 ggt tac cag cag cag tct cag gcg gcc gtg gag gcc atc tcg agg cgg    1008
Gly Tyr Gln Gln Gln Ser Gln Ala Ala Val Glu Ala Ile Ser Arg Arg
                325                 330                 335 atg agc cac atg gcg tcc cag ctg tac agc gtg gag gtg tcc tac ttg    1056
Met Ser His Met Ala Ser Gln Leu Tyr Ser Val Glu Val Ser Tyr Leu
            340                 345                 350 gac ttc ctg aac cgg gtc agg atg gag gag gtg agc ctg cgg agc gcc    1104
Asp Phe Leu Asn Arg Val Arg Met Glu Glu Val Ser Leu Arg Ser Ala
        355                 360                 365 ggg atg tgg gag gag gtg cac cac ccg tgg ctc aac atg ttc gtg ccc    1152
Gly Met Trp Glu Glu Val His His Pro Trp Leu Asn Met Phe Val Pro
370                 375                 380 aag gcc ggg gtc gct ggc ttc agg gat ctg ctc atg gac aac gtc tcg    1200
Lys Ala Gly Val Ala Gly Phe Arg Asp Leu Leu Met Asp Asn Val Ser
385                 390                 395                 400 ccg gat agc ttc cag ggc ctc atc ctc atc tac cca ctc ctc aga gac    1248
Pro Asp Ser Phe Gln Gly Leu Ile Leu Ile Tyr Pro Leu Leu Arg Asp
                405                 410                 415 aag tgg gac acc aac acg tcg gtc gtg atc ccg gac tcc ggg ccc acc    1296
Lys Trp Asp Thr Asn Thr Ser Val Val Ile Pro Asp Ser Gly Pro Thr
                420                 425                 430 gcg gac gac ccg gtg atg tac gtg gtc ggc atc ctc agg tcc gcg aac    1344
Ala Asp Asp Pro Val Met Tyr Val Val Gly Ile Leu Arg Ser Ala Asn
            435                 440                 445 cct ggt cca gaa gaa gac ggt gac ggc tgc tcc cac cgc tgc ctg cac    1392
Pro Gly Pro Glu Glu Asp Gly Asp Gly Cys Ser His Arg Cys Leu His
        450                 455                 460 gag ctc ctc cgc agc cac cgc cgg atc gcc gac gcc gcg gag gcg cgc    1440
Glu Leu Leu Arg Ser His Arg Arg Ile Ala Asp Ala Ala Glu Ala Arg
465                 470                 475                 480 ctc ggc gcc aag cag tac ctg cct cac cac ccg acc ccg gcc cgc tgg    1488
Leu Gly Ala Lys Gln Tyr Leu Pro His His Pro Thr Pro Ala Arg Trp
                485                 490                 495 cag cag cac ctg ggc cgg cgc tgg gag cgc ttc gcg gac cgc aag gcc    1536
Gln Gln His Leu Gly Arg Arg Trp Glu Arg Phe Ala Asp Arg Lys Ala
                500                 505                 510 cgg ttc gac ccg ctg cgc atc ctg ggg ccc ggc cag ggc ata ttc cct    1584
Arg Phe Asp Pro Leu Arg Ile Leu Gly Pro Gly Gln Gly Ile Phe Pro
            515                 520                 525 cgg acg gcc cag gat gct gcc gcc gct gcg tac ggg agc tag           1629
Arg Thr Ala Gln Asp Ala Ala Ala Ala Ala Tyr Gly Ser
        530                 535                 540

<210> SEQ ID NO 12
<211> LENGTH: 542
<212> TYPE: PRT
<213> ORGANISM: Zea mays

<400> SEQUENCE: 12

Met Glu Val Ala Met Val Val Ser Ala Arg Ala Ser Leu Leu Ile Leu
1               5                   10                  15

Val Leu Ser Leu Cys Ser Pro Tyr Lys Phe Ile Gln Ser Pro Met Asp
            20                  25                  30

Leu Gly Pro Leu Asn Leu Leu Pro Thr Thr Ser Thr Ala Ala Ala Ser
        35                  40                  45

Ser Asp Phe Gly Arg Ile Leu Phe Arg Ala Pro Ala Ala Val Leu Arg
    50                  55                  60
```

```
Pro Gln Ser Pro Arg Asp Ile Ser Met Leu Leu Ser Phe Leu Ser Gly
65                  70                  75                  80

Ser Pro Ser Leu Ser Arg Val Thr Val Ala Arg Gly Ala Gly His
                85                  90                  95

Ser Ile His Gly Gln Ala Gln Ala Pro Asp Gly Ile Val Val Glu Thr
            100                 105                 110

Arg Ser Leu Pro Gly Glu Met Glu Phe His His Val Arg Gly Gly Gly
            115                 120                 125

Glu Gly Arg Ala Ser Tyr Ala Asp Val Gly Gly Val Leu Trp Ile
            130                 135                 140

Glu Leu Leu Glu Arg Ser Leu Lys Leu Gly Leu Ala Pro Arg Ser Trp
145                 150                 155                 160

Thr Asp Tyr Leu Tyr Leu Thr Val Gly Gly Thr Leu Ser Asn Ala Gly
                165                 170                 175

Ile Ser Gly Gln Thr Phe Lys His Gly Pro Gln Ile Ser Asn Val Leu
            180                 185                 190

Gln Leu Glu Val Val Thr Gly Arg Gly Glu Ile Val Glu Cys Ser Pro
            195                 200                 205

Ser Lys Glu Ala Asp Leu Phe Asn Ala Val Leu Gly Gly Leu Gly Gln
210                 215                 220

Phe Gly Ile Ile Thr Arg Ala Arg Ile Leu Leu Gln Glu Ala Pro Glu
225                 230                 235                 240

Lys Val Thr Trp Val Arg Ala Phe Tyr Asp Asp Leu Gly Ala Phe Thr
                245                 250                 255

Arg Asp Gln Glu Leu Leu Val Ser Ile Pro Asp Ser Val Asp Tyr Val
            260                 265                 270

Glu Gly Phe Met Val Leu Asn Glu Arg Ser Leu His Ser Ser Ser Ile
            275                 280                 285

Ala Phe Pro Ala Ser Val Asp Phe Ser Pro Asp Phe Gly Thr Arg Ser
            290                 295                 300

Ser Pro Arg Ile Tyr Tyr Cys Val Glu Phe Ala Val His His His His
305                 310                 315                 320

Gly Tyr Gln Gln Gln Ser Gln Ala Ala Val Glu Ala Ile Ser Arg Arg
            325                 330                 335

Met Ser His Met Ala Ser Gln Leu Tyr Ser Val Glu Val Ser Tyr Leu
            340                 345                 350

Asp Phe Leu Asn Arg Val Arg Met Glu Glu Val Ser Leu Arg Ser Ala
            355                 360                 365

Gly Met Trp Glu Glu Val His His Pro Trp Leu Asn Met Phe Val Pro
            370                 375                 380

Lys Ala Gly Val Ala Gly Phe Arg Asp Leu Leu Met Asp Asn Val Ser
385                 390                 395                 400

Pro Asp Ser Phe Gln Gly Leu Ile Leu Ile Tyr Pro Leu Leu Arg Asp
                405                 410                 415

Lys Trp Asp Thr Asn Thr Ser Val Val Ile Pro Asp Ser Gly Pro Thr
            420                 425                 430

Ala Asp Asp Pro Val Met Tyr Val Val Gly Ile Leu Arg Ser Ala Asn
            435                 440                 445

Pro Gly Pro Glu Glu Asp Gly Asp Gly Cys Ser His Arg Cys Leu His
450                 455                 460

Glu Leu Leu Arg Ser His Arg Arg Ile Ala Asp Ala Ala Glu Ala Arg
465                 470                 475                 480

Leu Gly Ala Lys Gln Tyr Leu Pro His His Pro Thr Pro Ala Arg Trp
                485                 490                 495
```

Gln Gln His Leu Gly Arg Arg Trp Glu Arg Phe Ala Asp Arg Lys Ala
            500                 505                 510

Arg Phe Asp Pro Leu Arg Ile Leu Gly Pro Gly Gln Gly Ile Phe Pro
        515                 520                 525

Arg Thr Ala Gln Asp Ala Ala Ala Ala Ala Tyr Gly Ser
        530                 535                 540

<210> SEQ ID NO 13
<211> LENGTH: 3003
<212> TYPE: DNA
<213> ORGANISM: Zea mays
<220> FEATURE:
<221> NAME/KEY: misc_feature
<222> LOCATION: (0)...(0)
<223> OTHER INFORMATION: ZmCkx2 promoter

<400> SEQUENCE: 13

```
ctgccatcct catgcagatg agacggagag aagatgagaa agtacaaga tcccagaagc      60
aagcagcagg atggggccat ccccccccc cccactggg ccccacgggc cgaaagccac     120
cggcgaaaat gtccagaagg ccacgtgggg catgggtccc cggagtccac ttccgcgcga    180
tctcgaggcc gggccgcacc ggcaatcgct ctccggccac ctccctgctt cctcaggtcc    240
ggtctcccat agtccaatgc atgcatgcac gagcatcccc tcagaacgct ggcagtgagt    300
gtcttgctcg cacatcagct tggccagtca gtgcgagaac acagcagcaa caacaacaac    360
aacacctgtg cacaatggcg tctatcattg gtaccatctc aatcggctga cttgtctata    420
actactgtta acggaggtcc cttgtgcatc atgcagtttt agaagagcac ctcgatcgca    480
agcgcctcat tattatcatc attctcttaa actggtcaga aaactgacca tcagctaaag    540
tgatactgac atactgtatc tttgtagata attaaatgga gaaaaatctc cttctgttcc    600
gtctggccgt taaatgccga atccatgcat atataaatct gtacgtaggc tcaaagcaca    660
gtgtgcattt tggctttcca gctagcatac atacatgtga ctgctgacga tgaattgtgt    720
ggaccacatt ggcacaacgg tgcattgcaa cggacgggcg ccgtcaaggt caaacgcata    780
aaaggctgtc atttggcaac acaatgaatc agtggcgcca cgccatccgt ccacgatcca    840
ccgttcttgg tgtagtggtt ggtcccagcg cttgaaggcc aggccgaggc cgtgttctgg    900
aaggtggcct gtggtgagca ctaaacatgt gtgtgctttt gcctttccaa gccagagggc    960
cggtctctta atatacataa catacacacc acttttttcat tttgttcatt attacggtct   1020
aatgcaaaca aagccatttg cagaatgtgc tacatagcag gtatgtttct cttttttttcc  1080
ctgtaaaatt tgtagactta tcacaagaat aagtttaacc attactagaa tagttcctca   1140
catgtttgtt taccatcggg gcgggaacag cttgcattgc aaaagctgcg caagtattag   1200
ggccctctag attttttttaa tagtagtagt atatataata tataggtgtt actatttgag  1260
ttgttaggcc atctgcggca gattttctat gacatccctt atttcaaact ttattttgca   1320
aacagttgtc atataccccta ttttaggcga atcactgaag acaggtaagt tttggcacgg  1380
atgaggtgga gagtggacaa gaatctccgt tgtggagtct gcctaccagt accaggcaaa   1440
gtaatgcatg cgcgcggaca ggatggacgg tcgaagtggc ctccctgcct ccaccccgac   1500
gacgacgcat gggctccgtc cccttcgctt gcttcctgct ccagctagct ccatcgccta   1560
gtgctccgct ccgccgcaca ggaacggaac ggaacggacc gaaccacttg gtcgcatccc   1620
gatgcgttgc cgtctgccgg tgtccatcgt gtcggtttca cctctgcact agcataaatt   1680
ccttgacacc aacagcgagc gacatcatcg gctcagccct acaagtcacg agtgttctga   1740
```

-continued

```
ctgaccagct agcaatagca atctgctgct ctgcttgact tgctcggacg atccgccgct    1800
gcttgcgttc ggctccagta ggctatcctc cgcgacgtcg tcgatctgga ctccatggcg    1860
tccacacaga atcgacacga gcttggtgtg ccgcgtacgc atgtgtgcgt atgtatgcct    1920
cgtcttccac atgcaaacat acgcagagga aggggaaagg cggcagcaaa cgcgacggtc    1980
caagtcgtac cacagaagtg gtcgcgcatg tgtgcccaag ttgccatcac ccggatgcta    2040
ttagatttcc agaaactaac ttgtgaggac ccctggtgtc tgctagctgc tctccaactc    2100
caacctgtca atcaattccc agacggacaa gctgagctca cagctcaagc tcaacaacga    2160
tggccggccg ggtcaccatg gaactgatcc tctacagtac aggcatggga aaatggagga    2220
ggagagcagg gcagtgaggc cacagaatca gaggctgatt agtgttggtg agctccaatc    2280
caacagcata tgaccagcga gcagaacata gggatgtcct gtgggcttgc ccagggacag    2340
acgcatgcaa gccatgtgac tgtccggaga gagagccggt gatactggaa cagaggatcc    2400
gatcctgccc cccttctttt gcctctccct ctctcacaca cacagtctca cctatatgtg    2460
gctatgtcgt ctccattagg ctgttaacta gccaacacat gttccccgt tgcttaagac     2520 agcagctaca aagcgagaac atcatgctct aaaaagaaac ttccgcaatg caccactagc    2580
acatgtctgc gcctcaattc gcaaccggca agcaagcaag ccggcaagca gacagtcgcc    2640
atacggtttt taccaaacag ctagcgccca cagctgacta gctgaccacc gcaccaccca    2700
cactcctcct cgcgagtcgc gaggcaagcc gcaagctcct atatagagag gccccctccc    2760
tccccctgca tggacagcca ccgccttctt caaccctcct tccgtcttcc tcctctagtc    2820
ttacctcgtt gcacctcaag aaacttggcg cgcaaccagg aaaccccctc ttctctctct    2880
ctctctctct ctctctctgc cttctgattc caagctcccc aactgcccag caccaacctg    2940
ccgaactccc ctccttttg ttggtttgtc gaattataaa ttgagcccgg ccggctgact     3000
acc                                                                  3003
```

<210> SEQ ID NO 14
<211> LENGTH: 2001
<212> TYPE: DNA
<213> ORGANISM: Zea mays
<220> FEATURE:
<221> NAME/KEY: N_region
<222> LOCATION: (0)...(0)
<223> OTHER INFORMATION: ZmCkx3 promoter
<220> FEATURE:
<221> NAME/KEY: misc_feature
<222> LOCATION: 1366, 1626, 1629
<223> OTHER INFORMATION: n = A,T,C or G

<400> SEQUENCE: 14

```
ccggggtgtg acaggagcat tgaagcatgc atgctctgct cagcatataa ttaaagaaag      60
aagcatcaaa atgcactgga gcagttgacc aaaacttgca gctacgtcaa aatatatacg     120
agggctggca tcaaggtgtg ctcagcccga gccccgtcag gtaacttggt cttttgtttt     180
ctggccttgc ggcttcatta aaggccgccg gccgcgagcg aggcaaaaca gtgaagggga    240
ggggaggtgc ccgccactaa cctctcggtc ggatatatta gtattcaagc agttgacaaa    300
tctgtgcgga tttgatttgg tctgaggaaa atatatatat atatatatat agcccctcgt    360
cgttcatgca ccctctcgca gcctgcaacc ttacaatatt gttcttgcat ccggttttat    420 ttatatttt attttttaaa aaaaaaatcc atagtcctgc cgtcttgaag gatatgtttt     480 tctttacccca tgcacggcgg agtttaaatt tgcgctgacc cgactgctcg tgaacagaga    540
caagtatgac agatatcgtt gagttccaaa ttttaaaaaa aaaatcaata aaaaatttaa    600
```

```
aacagaatgt tgacgaggaa aaaaaatatg aaggtgcttg cacacctgtc actccatgcc      660
ggacatcaac aaattaattg ttcaagtggt gggagtcagc tgcttccagt ttaccttcct      720
gcgccagcgg ttggtagaca ggattgttgc cacgtggacg aaatctcctg ccgccagctg      780
gttgatcacg gcaggcagtc acatgcttct tgccaagatt accgcgggtt gtaatcatct      840
gaaatatatt aacctgagca cgtgatagag taaaaaaatt ggtcgactaa ggggtgtttt      900
ggtttctagg gactaatgtt tagtccctac attttattcc attttagttc taaaattacc      960
aaatatagaa actaaaactt tattttagtt tctatattag caatttatag actaaaaaag     1020
aataaaatga agggactaaa tattaatccc tagaaaccaa acacccccta actttaggta     1080
agttgtggca tgcattctct ggaacggcag ttctagagag cacttgagat gtcaacaggt     1140
gaagaattga agattggcca acacaggcgt tcaaggagat caaccaccc atccacatac      1200 cgcgcaaaca cttgggggc attcttgctg ctgccacatt tggaagaagc gcagcaatgt      1260
ggtgttcaga agaagcacag ctattttagc tcttgataac tatctttttt tttgcataga     1320
ttaatttatt tcttcgatat atactagctt gtaaaaaaat gttttncaga tatatgtata     1380
aaaatgtgta cctagtacct acgcatgtct tagttcaaca tacttgatag ctgtagtttt     1440
ctgaaaacct gttcaaatta acctttttcc taccctgatg gtgaatagag agaaaagctt     1500
tacctttgtc tgaataagaa aactaacaga aagcttacat tttggccact ctacctgccc     1560
gagtattttc taagcaagca aaggcgcatg aaaattttct cggaatccat gacctttac      1620 gcgcantgnw aaayawwgwm mattgmtcmg accaatgatc attttgatac tctccacaag     1680
tcaacatctc aaaaaaacca caagatgggg cccatcaaca taagttcacg agtgtgcctt     1740
caggtacatt gttctttttt tttgttttgc taaagtcaat cagctgcaaa atattcagaa     1800
caatttcaat aacccgaaag gctgttgtgc ctccatttgt caacgtttgc gaggccaaat     1860 ggtaccccg ctataaatac catggaagtt cttggcctct aggacacaca agcgatctct      1920
cctcctatag tttctataac cccacaaagc gtccaggtcc cgtagtcacc tccgattgca     1980
ttgcgttgcc gcaagacaag c                                              2001
```

<210> SEQ ID NO 15
<211> LENGTH: 2448
<212> TYPE: DNA
<213> ORGANISM: Zea mays
<220> FEATURE:
<221> NAME/KEY: misc_feature
<222> LOCATION: (0)...(0)
<223> OTHER INFORMATION: ZmCkx4 promoter

<400> SEQUENCE: 15

```
ctttatgttg tagccaagga aagtatactg ttaagatcag aatgaacctt ataggagttg       60
tatgggcata aagccagcaa gtatagccaa aggtacacaa ggctaatata gtcaagttgt      120
tgatgtgtga gacgttcaag gaagtgaact attggaggag tcgactaaaa gtacgattaa      180
taaggtagac atgatggtaa aatctttgat ctagaattta agtggtatgg atgcgagggt      240
gagaatggca agcacaactt caaatatagg gtgatgctta tgcttggctg agccatttca      300
ttcatgagca taggaacatg agacatggtg ggatatggat acttgcacaa aaaaaggaat      360
taagtttatg atattcacct cccagtcagt ttgcatggta aaaaaattcc tatcaatttg      420
gttctcaact agggcctaaa attctcaaaa tatctgttgg ggaccattat cgtcgacgat      480
cctcagaatc tgttattacc aaattaaaag gtgtgtttca ggtactgtgc aaagcagcag      540
cgaagctatc cttcgtcaaa agtggctcaa tgaaccaggt ggagaagcta tggagcttcg      600
```

```
tctgcgtaga gcgtgccgga ggaggaagct ttggctctga atgcatcgac ttacgaagca    660
tgggagaaga agactcagaa ggcttgtcca gcgtgggaat aaaaaggaga aaatacaatt    720
ttgcccttgt gggatttgta aatcatgtgc aaggctcatg gatatgtttg taatttata     780 tgatatgttt gtaaatcatg gatatgtttt gtaaatcagg tggactagag gagagggagg    840
gtggacatag tgacttgcat cttgatcatg gtagagtggt catggtagag ggaaaggggt    900
aggtcaattc tggagtgcgg ccacggtggc ttgagtgtcg gccacggtag gggaaagggg    960
tagcccaatt ctagggccgg catcggagaa ggccgacatg tgcacgtcag gaggtagtgt   1020
tagaggtttg aacggaaaaa attgaacatg ttagtatgat gagttgtgta attgctggga   1080
attgtggata atttccactt aactacggcc ctgtttattt accctagat tataaaatcc    1140 aacttaaaaa agttgagatg taaacaaaca acacatatta ttaggtggat tatgttatct   1200
agaaatctgg atgataataa tttataagtc ggttaatagg tgtttacata atcgataagc   1260
tggattatat aatcctggaa cacggctttc gcgagagcgt attaaaacag gattccgtga   1320
agcacactat ctgaggagct ccaccaaaag ctgaatctag cccgcactct tttttggagg   1380
attcaaattt ggtgtcactg gagcattcgg cattttgttt catggcgtga agctattttt    1440
actaattaca gaagctgttt caaatagacc tttaaatgat ggctgagtat aaaaggaggc   1500 aatttttta tctcgccgat ggagccaggt cgcgtcgcgc cgcggccgtg ctgcgctctc    1560
gacgcgatct agcggcgatg tgcacagtac agttttgcca tgccattggt taagcctgca   1620
tacaacacac cagcgtactg ccctgcacaa gatctcctcg gctcggcctc tcctgatgga   1680
acgttcagct tgaacagcgg agcgtggggg catcccgggg atgggcgccg cggccgagaa   1740
attttgcaac ctggcaaatc tgccctgtcg catactacca tccacctcca ggcgccaaga   1800
acgcctccga gtttcaggct tgcagctcag ctctgtgttg aattggaacg gcggagttt    1860 ctgggttcca gacttccagt acaaggcgat caattggtag ggcgaattac ttgcaggccc   1920
agatgcatgg cccatctatc tggttctcta tcggttgctt ttacttgcac aatagtggca   1980
gacaaactac aagtcagatc cgatcctatc catccatcca tctcgcagcg cgatgcaaat   2040
atgcaatcgt ctgtggaact cgaaaaaaaa cagaggtccg gcctcgcacg aggttaaggg   2100
aaaaaaaacg aagcgtttgg aactttggtt ggcattcgca gcatgctgtg ctgccaccgt   2160
atgtttttat ttttgctttg tttgtcttct ttgagaaacg tgagggagcc gcgtgtccgc   2220
tcgttataaa accccccggg cgacccaaac taccacgagc tcaagcctca agcctcaagc   2280
ctcaagcaag cagagcgccg tgacatcacg aaacaaacat atagagctag ctgctctgcc   2340
tctgcttcac caatcacctg cttggccgcg cggaggggag ggttccccc tttgacacag    2400 ctgagctccc ctccatcagc agccagctcc tcgtcgcaaa gcaagaag                2448
```

<210> SEQ ID NO 16
<211> LENGTH: 2346
<212> TYPE: DNA
<213> ORGANISM: Zea mays
<220> FEATURE:
<221> NAME/KEY: misc_feature
<222> LOCATION: (0)...(0)
<223> OTHER INFORMATION: ZmCkx5 promoter

<400> SEQUENCE: 16

```
tacagatttg cgttcatcaa tggcagcgcg ggatctcatg aggtcactgg gttcttgcaa     60
gtggggagag aaagggagat ctacgaaaga cttgttagtg ggccaccttt tccctctttc    120
cccacaagga cgagatcgtg gattagagta ggaaagtgat tccgcattgg tctcaaatct    180
```

```
tggcgaaaga ttgcattgtg tactctccac cactcgaccg gcaacgaggc attttgttat    240
tgcacgatgc atcctttgca catgagctag gcttgtgcct ttgagtattc agttagcatt    300
gcaaccccat ttcaattcac atgcttgtct ttccaaggaa ctttctaagc cacctaacag    360
acattagggt ttatatcaga atcgagctca tggcgtactt tatgctgcac gaacaatggg    420
ttgggggcgt cgtttcttgc atgagagcat gcgcatcctg gtaaggattt cgccaaaaga    480
actttagtcc tctaccgact tgtgttttgc gtgatctcgt gatttgaagc ctgtggtggt    540
gtgctgaggc agcatattgg aaggtatctc tgtgttgata tggcatccgt ccgtggacaa    600
atcgatacca catactgttc ttggattcta ttcttgggat tgctaaatga tctagataga    660
ttatattctc ttgttgcagc ccctattgct tcaatacgaa gaaaacccaa cgtttagaac    720
ttaataaaac catttgtgag cttagctgct taggcaattc attttatgc atgacaaata    780 tataataata ttagctatac tattattgat gcaacctgtg ggagcgtata aatggtact    840 tccccaattc taaattataa gacgttttga ctatatattc tacatacata tgtttaattt    900
tatatttaga taatcgctat gccttaatat atagtaaaaa gtagtatatc tagaaaagat    960
aaaacatctt ataatttaaa aatgggtaga gtattatatt agatatgaac agtgcttaga   1020
tgccaccaaa attttgccat gccatcctaa ggccagcaaa agtttgtgtc ttcttttgtt   1080
ttccaaacca ctagatgcca atatactatt tatcatcgat cgagatgtag gtcttagtta   1140
attgtgtcgg gtgcccttga gaaagaaaag aaaaaggtgg gattttgttt tcgcttagac   1200
gatgattgga tctcttggtc tctgaattcc atcccgaata aacaaatgaa gtaggtcctc   1260
agtcacccct gccctgttag ctgcaagaga gctcatggtt tccagccaca caatcagtcc   1320
atggctcctt cttcttggcc taagtggtgg ccaatcattg tgggtgatcg agtcttgggc   1380
cctctgaaca gtattacaca acagtaatcc tgcaaaagat ttggtatatc tagattctag   1440
agtgagcgcc gtgttgtgcc cagctaggaa tgggttgtca agtgcaacag gaggaggacc   1500
caggatggtc aggtgtaata ggctctcatt aaaagactgt tcagatggat tagagcaacg   1560
acggggaagc cgggaaaaaa tggttggttc tgctttcctc tcgctccccg gccgggttca   1620
tatatgaatc tgagaacgat attttttgct tcatttttca tttgctatat atttaaactg   1680 ttttttttgtg tgtgtgtgtg tgttcattga gctcaatact tgaggcttga tagggagagg   1740
agtgaggcag ctgatcacat ggacctccat ctgaggacag ttcctcttcc gaaacagaaa   1800
ggagagtgca gggaccagcg tggcctgtac agtattgtgt ttgccctttt cctttggcag   1860
ggacagagag cttcaggctt gtcctcttta tgtatgctgc tcgcctgctt cagagtcaga   1920
gcttcccctt ctcacttctc agagagagag agagagaaga gagagagagg agagccctcc   1980
acagctcccc tgtcctgccc tcaggcattc tttgtcacag ggggcgaggg ctgaagatca   2040
tcacatggtg gcctttttg ggtctgtggc ctttggtctt ttagtgcttc ttccttttac    2100
ctcctcatga catgaacccc ctttttaaac ctccctcaaa atcaaatcac cctccttctc   2160
ctttaagagc cctcaacccc ttcccctcat tttccttcat ccctcagcct ttgcacaaag   2220
ggcaagaata acgcagtatg atcatctgat catactcccg ccgccatcac aatcccacac   2280
gaacgtgaga caaaggtaac agacgcaaga agctagcagc tgcaggagat tgctcagccc   2340
atctcc                                                              2346

<210> SEQ ID NO 17
<211> LENGTH: 1470
<212> TYPE: DNA
<213> ORGANISM: Zea mays
<220> FEATURE:
```

```
<221> NAME/KEY: misc_feature
<222> LOCATION: (0)...(0)
<223> OTHER INFORMATION: ZmCkx1-2 promoter

<400> SEQUENCE: 17
gagctcgccc ttgcatgctt gagtcatatc ttggaaaaaa aaactgtaac ttaaagtatg      60
atctatatat ggattatttg gatgggatgt cattttcgta tcaccaacca aaattacagt     120
ttggtcgtgc gtagaaattc tacctactag ctgaaacaac ggctgctatg tataactact     180
ggtactggaa agaatattag tcattgactc aaaattagaa tgcatgtgta agtcatgcgt     240
gctaatttgt tctatcagca ttcggcgaat tccgaagtcc gtacgtgttg ttcgtggagg     300
agaggaaaac atcagaaatg acaaaactag acggcgtgtg cttctacact gaattcatca     360
acatttgttt tacttttact agagaatggc atcagatgga aaaccgctga aaaacaaga     420 aaacaattgg accccaaata tgtacagacg ctagctatag ccagccacac tgaagttgac     480
atgcggcaac tagctaacca ccttctctga aacactaaca tttgtacctt ggtcgtgtaa     540
gtgtagttag taacgtatgt tgacgcgact taccgaacaa aaatataatt gtcccaatca     600
agctagggac gattgtttgt ttccaaaatg ttgccatttg cttaatcaat cctatattga     660
ttcatggctg ttaaggtgag ataaagcgac aagaaatctc tctctatata tatatataag     720
atcccgaagg ctagcgacat ttttgatagc aaaatatgag aagttggcag gttctggtag     780
caaatcaaat aatatggcca gaataatcgt ggctagcttg attaaacctt cagcttggtg     840
tattttggaa gtcgaccaac cagctgggcc ggggctcgtc gtagtaccaa aattacagcc     900
tgcttccttc gtcgtcctgt acgtaatgca gtacagctgt ctgtctagta gagacgattt     960
tgagcaggca cacacattaa gtgataacat aaaagacggc ttcattttat ttcataacca    1020
aacgatatgg tcaacacaca cctatagcta ccaaatttgt acaactattt agtgcgaaaa    1080
ctatttcatt ctcaagaatt gatcgcttat atttattatt acaggttttt aaatgtataa    1140
atacgctata ttgcatggca aaggggggta ataattaggc aggactatat atataatagt    1200 ttttttttcct ttaaattctt gggaggatgg taaagttggt aactaggcac cttgtgcgca    1260 tattttctg tggtcaaaca gaataaaact agacgggatg cagaattttt ttttccttgg    1320
aaagcagctc atctctgtgt tcgagtacgt aattgaagaa gtatgtgatc gcactacacc    1380
tacacgtatg tgccgccgta tccgtcctat atatatacgg ggtgcaatca cctagttacc    1440
aaacactcac acataagggc ggatccatgg                                       1470

<210> SEQ ID NO 18
<211> LENGTH: 3317
<212> TYPE: DNA
<213> ORGANISM: Zea mays
<220> FEATURE:
<221> NAME/KEY: misc_feature
<222> LOCATION: (0)...(0)
<223> OTHER INFORMATION: ZmCkx1-2 promoter extended

<400> SEQUENCE: 18
tcttgttccc aagtgttttg taagcaaggc aagagacacc aagtgtgtgg tggtccttgc      60
ggggtctaag tgacccattt gattaaggag aaggctcact cggtctaagt gaccgtttga     120
gagagtgaaa gggttgaaag agacccggtc tttgtgacca cctcaatggg gactaggttc     180
tttagaaccg aacctcggta aaagaaatca tcgtgttcat ccgctttatt tcttggttga     240 tttgttttc ccctctctcc cgaactcgga tttaattcta acgctaaccc cggcttgtag     300 tttatgttttt aagttgtaaa tttcagatta cgcctattca cccctaggc aactttcagt     360
```

```
tccaccactc ctcccccacct tgtacttacg aaagattgtg ttagtagatc tcgagattta    420
caaacttacc ataagcaact aaaaataata taaacctaaa aatatgaaaa cccggaaaga    480
gcctaaaact tgaacccgga aaaaattcc tgcataatc ataatcaact aagttatgct     540
cacacattag gtctgcgttg ttgaattaac tttcaagacc agaaaacagg cacgcgtgca    600
tcgtacaagt ggaacttcca aacctttaag taaatagaga tagacacgcc cacatgtgga    660
acttcttggt acgtaatgcg tgacaagtta gaagtgaaca aggcaaccac gtcgctactt    720
gtgatgaata ctgggctgtg tgtgggtttt gtcgtcgcag gagtacatgt gttctctgaa    780
ttctaaatcg atcatgatgt ccgtcttttt tttattttag ccctttttta gttttttttc    840
ataaatatgc cctttctagt tttaactcaa aaaatggacc ctctggtcga caccattact    900
attggcggca acctaacacg tctaggcgcc tagacggcta gaccttgttc gtggcattga    960
cgtggtgcac ccgtggctag tgaggtggca gaggtaggcg ctaagaacta tagtgccgaa   1020
ggtaggcggc atatatcttg gcacaggccc cctttaatac gggcccacgt gtaatttttat   1080
tttcctttc ctcactctcc accctcgtcg ttcgcctggc tcaacatagc cgcccctctc    1140
cctctccgcg tctcgccatc gtcgcccctc tcctcgcagt gacttgccat ggtcgcggct   1200
caccgtggcc acgccatgcc agcgtcagcc cgctccctca tttatcgatg cgggctcggt   1260
ggtcggcgac gagcgcaagg ctgaggagcg tgggcgggcg acggtggtga gcgacgtagg   1320
acgccgacga cggtgacggg cgacttaggg caccgacgac gtatggcgtg ggcgggcgcc   1380
agcggcctca ccgacggagg atggcgcggg caacgctgga gagtggccga gcagcgaccg   1440
ggtcgaatgg aagagagaga aagaggaaaa gaacgtgaac cgattggtat atagagggtc   1500
ggcgctaaga tctatggcgt cgatccatac catgcctcag ggtccttcct ggccacgtca   1560
tcgatacata tgcgtcaatt gcattggcac caatacgtgt taggttggca ccaatagtga   1620
gagcgtcaac ctaagggtcc atattctgaa ttcaaacaaa aaataaccta tttgtgaaaa   1680
tgaaacacta aaaaggctaa aatagaaaaa aaatcggtcg cgatgcagac gcatcgtcgg   1740
tttcaccgcc gtcacgcgcg cgtctgtatg cgctgccagg agtcactgca agcggcaagc   1800
agccaaaaaa ataaaaattg gctgcatccg atctcgagac tccgacgaga ggaggctgcg   1860
catgcttgag tcatatcttg gaaaaaaaaa ctgtaactta agtatgatc tatatatgga   1920
ttatttggat gggatgtcat tttcgtatca ccaaccaaaa ttacagtttg gtcgtgcgta   1980
gaaattctac ctactagctg aaacaacggc tgctatgtat aactactggt actggaaaga   2040
atattagtca ttgactcaaa attagaatgc atgtgtaagt catgcgtgct aatttgttct   2100
atcagcattc ggcgaattcc gaagtccgta cgtgttgttc gtggaggaga ggaaaacatc   2160
agaaatgaca aaactagacg gcgtgtgctt ctacactgaa ttcatcaaca tttgttttac   2220
ttttactaga gaatggcatc agatggaaaa ccgctgaaaa aacaagaaaa caattggacc   2280
ccaaatatgt acagacgcta gctatagcca gccacactga agttgacatg cggcaactag   2340
ctaaccacct tctctgaaac actaacattt gtaccttggt cgtgtaagtg tagttagtaa   2400
cgtatgttga cgcgacttac cgaacaaaaa tataattgtc ccaatcaagc tagggacgat   2460
tgtttgtttc caaaatgttg ccatttgctt aatcaatcct atattgattc atggctgtta   2520
aggtgagata aagcgacaag aaatctctct ctatatatat atataagatc ccgaaggcta   2580
gcgacatttt tgatagcaaa atatgagaag ttggcaggtt ctggtagcaa atcaaataat   2640
atggccagaa taatcgtggc tagcttgatt aaaccttcag cttggtgtat tttggaagtc   2700
gaccaaccag ctgggccggg gctcgtcgta gtaccaaaat tacagcctgc ttccttcgtc   2760
```

-continued

| | | | | |
|---|---|---|---|---|
| gtcctgtacg | taatgcagta | cagctgtctg | tctagtagag | acgatttga  gcaggcacac | 2820 |
| acattaagtg | ataacataaa | agacggcttc | attttatttc | ataaccaaac  gatatggtca | 2880 |
| acacacacct | atagctacca | aatttgtaca | actatttagt | gcgaaaacta  tttcattctc | 2940 |
| aagaattgat | cgcttatatt | tattattaca | ggttttaaa | tgtataaata  cgctatattg | 3000 |
| catggcaaaa | gggggtaata | attaggcagg | actatatata | taatagtttt  ttttccttta | 3060 |
| aattcttggg | aggatggtaa | agttggtaac | taggcaccct | gtgcgcatat  ttttctgtgg | 3120 |
| tcaaacagaa | taaaactaga | cgggatgcag | aatttttttt | tccttggaaa  gcagctcatc | 3180 |
| tctgtgttcg | agtacgtaat | tgaagaagta | tgtgatcgca | ctacacctac  acgtatgtgc | 3240 |
| cgccgtatcc | gtcctatata | tatacgggt | gcaatcacct | agttaccaaa  cactcacaca | 3300 |
| taagggcgga | tccatgg | | | | 3317 |

<210> SEQ ID NO 19
<211> LENGTH: 25
<212> TYPE: DNA
<213> ORGANISM: Artificial Sequence
<220> FEATURE:
<223> OTHER INFORMATION: primer

<400> SEQUENCE: 19
ctgactacca tgaagccgcc atcat                                           25

<210> SEQ ID NO 20
<211> LENGTH: 29
<212> TYPE: DNA
<213> ORGANISM: Artificial Sequence
<220> FEATURE:
<223> OTHER INFORMATION: primer

<400> SEQUENCE: 20
ttgctctggt tatgatcccg aactgacca                                       29

<210> SEQ ID NO 21
<211> LENGTH: 24
<212> TYPE: DNA
<213> ORGANISM: Artificial Sequence
<220> FEATURE:
<223> OTHER INFORMATION: primer

<400> SEQUENCE: 21
atcctcaaca actggagggc gtcc                                            24

<210> SEQ ID NO 22
<211> LENGTH: 27
<212> TYPE: DNA
<213> ORGANISM: Artificial Sequence
<220> FEATURE:
<223> OTHER INFORMATION: primer

<400> SEQUENCE: 22
tcccaccttg ctccaaagtg ggttttc                                         27

<210> SEQ ID NO 23
<211> LENGTH: 27
<212> TYPE: DNA
<213> ORGANISM: Artificial Sequence
<220> FEATURE:
<223> OTHER INFORMATION: Primer

<400> SEQUENCE: 23
cgcaggtcag caatgtcaat caactgg                                         27

```
<210> SEQ ID NO 24
<211> LENGTH: 27
<212> TYPE: DNA
<213> ORGANISM: Artificial Sequence
<220> FEATURE:
<223> OTHER INFORMATION: Primer

<400> SEQUENCE: 24
agaggtgtgc accctgtcca aaaactc                                           27

<210> SEQ ID NO 25
<211> LENGTH: 32
<212> TYPE: DNA
<213> ORGANISM: Artificial Sequence
<220> FEATURE:
<223> OTHER INFORMATION: Primer

<400> SEQUENCE: 25
agagaagcca acgccawcgc ctcyatttcg tc                                     32

<210> SEQ ID NO 26
<211> LENGTH: 24
<212> TYPE: DNA
<213> ORGANISM: Artificial Sequence
<220> FEATURE:
<223> OTHER INFORMATION: Primer

<400> SEQUENCE: 26
ggagggtttc cccctttgac acag                                              24

<210> SEQ ID NO 27
<211> LENGTH: 27
<212> TYPE: DNA
<213> ORGANISM: Artificial Sequence
<220> FEATURE:
<223> OTHER INFORMATION: Primer

<400> SEQUENCE: 27
gggacgacaa agagcgcgat atgatga                                           27

<210> SEQ ID NO 28
<211> LENGTH: 28
<212> TYPE: DNA
<213> ORGANISM: Artificial Sequence
<220> FEATURE:
<223> OTHER INFORMATION: Primer

<400> SEQUENCE: 28
acgcacgctt cggcggcatt cattattt                                          28

<210> SEQ ID NO 29
<211> LENGTH: 28
<212> TYPE: DNA
<213> ORGANISM: Artificial Sequence
<220> FEATURE:
<223> OTHER INFORMATION: Primer

<400> SEQUENCE: 29
ggcaagcatg catggagcaa aaactcgt                                          28

<210> SEQ ID NO 30
<211> LENGTH: 29
<212> TYPE: DNA
<213> ORGANISM: Artificial Sequence
<220> FEATURE:
<223> OTHER INFORMATION: Primer
```

```
<400> SEQUENCE: 30
gcactactaa ctgactgacg ttgccattc                                    29

<210> SEQ ID NO 31
<211> LENGTH: 28
<212> TYPE: DNA
<213> ORGANISM: Artificial Sequence
<220> FEATURE:
<223> OTHER INFORMATION: Primer

<400> SEQUENCE: 31
gcaactcact tgctcttgag catagggt                                     28

<210> SEQ ID NO 32
<211> LENGTH: 32
<212> TYPE: DNA
<213> ORGANISM: Artificial Sequence
<220> FEATURE:
<223> OTHER INFORMATION: Primer

<400> SEQUENCE: 32
agagaagcca acgccawcgc ctcyatttcg tc                                32

<210> SEQ ID NO 33
<211> LENGTH: 534
<212> TYPE: PRT
<213> ORGANISM: Zea mays

<400> SEQUENCE: 33
```

Met Ala Val Val Tyr Tyr Leu Leu Leu Ala Gly Leu Ile Ala Cys Ser
 1               5                  10                  15

His Ala Leu Ala Ala Gly Thr Pro Ala Leu Gly Asp Asp Arg Gly Arg
            20                  25                  30

Pro Trp Pro Ala Ser Leu Ala Ala Leu Ala Leu Asp Gly Lys Leu Arg
        35                  40                  45

Thr Asp Ser Asn Ala Thr Ala Ala Ser Thr Asp Phe Gly Asn Ile
    50                  55                  60

Thr Ser Ala Leu Pro Ala Ala Val Leu Tyr Pro Ser Ser Thr Gly Asp
65                  70                  75                  80

Leu Val Ala Leu Leu Ser Ala Ala Asn Ser Thr Pro Gly Trp Pro Tyr
                85                  90                  95

Thr Ile Ala Phe Arg Gly Arg Gly His Ser Leu Met Gly Gln Ala Phe
            100                 105                 110

Ala Pro Gly Gly Val Val Asn Met Ala Ser Leu Gly Asp Ala Ala
        115                 120                 125

Ala Pro Pro Arg Ile Asn Val Ser Ala Asp Gly Arg Tyr Val Asp Ala
    130                 135                 140

Gly Gly Glu Gln Val Trp Ile Asp Val Leu Arg Ala Ser Leu Ala Arg
145                 150                 155                 160

Gly Val Ala Pro Arg Ser Trp Asn Asp Tyr Leu Tyr Leu Thr Val Gly
                165                 170                 175

Gly Thr Leu Ser Asn Ala Gly Ile Ser Gly Gln Ala Phe Arg His Gly
            180                 185                 190

Pro Gln Ile Ser Asn Val Leu Glu Met Asp Val Ile Thr Gly His Gly
        195                 200                 205

Glu Met Val Thr Cys Ser Lys Gln Leu Asn Ala Asp Leu Phe Asp Ala
    210                 215                 220

Val Leu Gly Gly Leu Gly Gln Phe Gly Val Ile Thr Arg Ala Arg Ile
225                 230                 235                 240

Ala Val Glu Pro Ala Pro Ala Arg Ala Arg Trp Val Arg Phe Val Tyr
                245                 250                 255

Thr Asp Phe Ala Ala Phe Ser Ala Asp Gln Glu Arg Leu Thr Ala Pro
            260                 265                 270

Arg Pro Gly Gly Gly Ala Ser Phe Gly Pro Met Ser Tyr Val Glu
        275                 280                 285

Gly Ser Val Phe Val Asn Gln Ser Leu Ala Thr Asp Leu Ala Asn Thr
    290                 295                 300

Gly Phe Phe Thr Asp Ala Asp Val Ala Arg Ile Val Ala Leu Ala Gly
305                 310                 315                 320

Glu Arg Asn Ala Thr Thr Val Tyr Ser Ile Glu Ala Thr Leu Asn Tyr
                325                 330                 335

Asp Asn Ala Thr Ala Ala Ala Ala Val Asp Gln Glu Leu Ala Ser
            340                 345                 350

Val Leu Gly Thr Leu Ser Tyr Val Glu Gly Phe Ala Phe Gln Arg Asp
        355                 360                 365

Val Ala Tyr Ala Ala Phe Leu Asp Arg Val His Gly Glu Glu Val Ala
    370                 375                 380

Leu Asn Lys Leu Gly Leu Trp Arg Val Pro His Pro Trp Leu Asn Met
385                 390                 395                 400

Phe Val Pro Arg Ser Arg Ile Ala Asp Phe Asp Arg Gly Val Phe Lys
                405                 410                 415

Gly Ile Leu Gln Gly Thr Asp Ile Val Gly Pro Leu Ile Val Tyr Pro
            420                 425                 430

Leu Asn Lys Ser Met Trp Asp Gly Met Ser Ala Ala Thr Pro Ser
        435                 440                 445

Glu Asp Val Phe Tyr Ala Val Ser Leu Leu Phe Ser Ser Val Ala Pro
    450                 455                 460

Asn Asp Leu Ala Arg Leu Gln Glu Gln Asn Arg Arg Ile Leu Arg Phe
465                 470                 475                 480

Cys Asp Leu Ala Gly Ile Gln Tyr Lys Thr Tyr Leu Ala Arg His Thr
                485                 490                 495

Asp Arg Ser Asp Trp Val Arg His Phe Gly Ala Ala Lys Trp Asn Arg
            500                 505                 510

Phe Val Glu Met Lys Asn Lys Tyr Asp Pro Lys Arg Leu Leu Ser Pro
        515                 520                 525

Gly Gln Asp Ile Phe Asn
    530

<210> SEQ ID NO 34
<211> LENGTH: 579
<212> TYPE: PRT
<213> ORGANISM: Artificial Sequence
<220> FEATURE:
<223> OTHER INFORMATION: Consensus Sequence
<220> FEATURE:
<221> NAME/KEY: VARIANT
<222> LOCATION: 2, 3, 21, 23, 26, 27, 30, 31, 32, 33, 35, 37, 39, 40,
      41, 42, 43, 46, 50, 63, 76, 87, 88, 90, 102, 107, 121, 127,
      128, 129, 130, 131, 132, 133, 134, 136, 137, 138, 139, 146,
      147, 155, 163, 169, 207, 225, 276, 280, 281, 282, 283, 284
<223> OTHER INFORMATION: Xaa = Any Amino Acid
<220> FEATURE:
<221> NAME/KEY: VARIANT
<222> LOCATION: 285, 286, 288, 289, 290, 303, 307, 309, 310, 311, 321,
      324, 329, 331, 332, 333, 345, 346, 350, 352, 353, 354, 355, 356,
      357, 368, 373, 375, 379, 392, 396, 400, 407, 433, 435, 436,
      437, 438, 439, 440, 455, 464, 465, 466, 467, 468, 469
<223> OTHER INFORMATION: Xaa = Any Amino Acid
<220> FEATURE:

```
<221> NAME/KEY: VARIANT
<222> LOCATION: 486, 487, 488, 489, 490, 491, 492, 493, 494, 495, 496,
      499, 500, 519, 529, 533, 567, 568, 569, 570, 575, 577, 578, 579
<223> OTHER INFORMATION: Xaa = Any Amino Acid

<400> SEQUENCE: 34
```

Val Xaa Xaa Phe Leu Leu Leu Val Leu Leu Leu Ser Ser Leu Ala
 1               5                  10                  15

Leu Ala Ala Gly Xaa Pro Xaa Asp Leu Xaa Xaa Leu Gly Xaa Xaa Xaa
            20              25                  30

Xaa Gly Xaa Leu Xaa Gly Xaa Xaa Xaa Xaa Arg Leu Xaa Thr Asp
        35              40                  45

Ala Xaa Ser Thr Ala Ala Ala Thr Asp Phe Gly Asn Ile Xaa Ser
    50              55                  60

Ala Leu Pro Ala Ala Val Leu His Pro Ala Ser Xaa Gly Asp Ile Ala
65              70                  75                  80

Ala Leu Val Arg Ala Ala Xaa Xaa Ser Xaa Ser Ala Ser Pro Leu Thr
            85                  90                  95

Val Ala Ala Arg Gly Xaa Gly His Ser Ile Xaa Gly Gln Ala Gln Ala
            100                 105                 110

Pro Gly Gly Val Val Asp Met Xaa Ser Leu Gly Ala Xaa Xaa
            115                 120                 125

Xaa Xaa Xaa Xaa Xaa Xaa Ile Xaa Xaa Xaa Xaa Val Ala Gly Gly Gly
            130                 135                 140

Arg Xaa Xaa Phe Val Asp Val Gly Gly Gly Xaa Leu Trp Ile Asp Val
145                 150                 155                 160

Leu Arg Xaa Thr Leu Lys His Gly Xaa Leu Ala Pro Arg Ser Trp Thr
            165                 170                 175

Asp Tyr Leu Tyr Leu Thr Val Gly Gly Thr Leu Ser Asn Ala Gly Ile
            180                 185                 190

Ser Gly Gln Ala Phe Arg His Gly Pro Gln Ile Ser Asn Val Xaa Glu
            195                 200                 205

Leu Asp Val Val Thr Gly Arg Gly Glu Met Val Thr Cys Ser Pro Ser
210                 215                 220

Xaa Asn Ala Asp Leu Phe Phe Ala Val Leu Gly Gly Leu Gly Gln Phe
225                 230                 235                 240

Gly Ile Ile Thr Arg Ala Arg Ile Ala Leu Glu Pro Ala Pro Lys Arg
            245                 250                 255

Val Arg Trp Val Arg Val Leu Tyr Ser Asp Phe Ala Ala Phe Thr Ala
            260                 265                 270

Asp Gln Glu Xaa Leu Ile Ser Xaa Xaa Xaa Xaa Xaa Xaa Ala Xaa
            275                 280                 285

Xaa Xaa Ser Phe Asp Tyr Val Glu Gly Phe Val Val Leu Asn Xaa Ser
            290                 295                 300

Leu Ile Xaa Asn Xaa Xaa Xaa Ser Ser Phe Phe Ser Pro Ala Asp Val
305                 310                 315                 320

Xaa Arg Leu Xaa Ser Leu Ala Ser Xaa Ser Xaa Xaa Xaa Val Leu Tyr
            325                 330                 335

Cys Leu Glu Val Thr Leu Asn Tyr Xaa Xaa Gly Thr Ala Xaa Ser Xaa
            340                 345                 350

Xaa Xaa Xaa Xaa Xaa Val Asp Gln Glu Val Ala Ala Leu Leu Gly Xaa
            355                 360                 365

Leu Ser Phe Val Xaa Gly Xaa Leu Phe Thr Xaa Asp Val Thr Tyr Val
            370                 375                 380

Asp Phe Leu Asp Arg Val His Xaa Glu Glu Leu Xaa Leu Arg Ala Xaa

```
                385                 390                 395                 400
Gly Leu Trp Glu Val Pro Xaa His Pro Trp Leu Asn Leu Phe Val Pro
                    405                 410                 415

Arg Ser Arg Ile Ala Asp Phe Asp Arg Gly Val Phe Lys Gly Ile Leu
                420                 425                 430

Xaa Asp Xaa Xaa Xaa Xaa Xaa Gly Pro Ile Leu Ile Tyr Pro Met
            435                 440                 445

Asn Lys Ser Lys Trp Asp Xaa Arg Thr Ser Val Val Thr Pro Asp Xaa
                450                 455                 460

Xaa Xaa Xaa Xaa Xaa Glu Glu Val Phe Tyr Leu Val Ala Phe Leu Arg
465                 470                 475                 480

Ser Ala Leu Ser Gly Xaa Xaa Xaa Xaa Xaa Xaa Xaa Xaa Xaa
                485                 490                 495

Ser Leu Xaa Xaa Leu Leu Arg Gln Asn Arg Arg Ile Leu Asp Phe Cys
            500                 505                 510

Asp Ala Ala Gly Ile Gly Xaa Lys Gln Tyr Leu Pro His His Thr Thr
                515                 520                 525

Xaa Ala Asp Trp Xaa Arg His Phe Gly Ala Ala Arg Trp Glu Arg Phe
            530                 535                 540

Ala Asp Arg Lys Ala Arg Tyr Asp Pro Leu Ala Ile Leu Ala Pro Gly
545                 550                 555                 560

Gln Arg Ile Phe Pro Arg Xaa Xaa Xaa Xaa Ala Ala Ile Ala Xaa Ala
                565                 570                 575

Xaa Xaa Xaa

<210> SEQ ID NO 35
<211> LENGTH: 575
<212> TYPE: PRT
<213> ORGANISM: Arabidopsis thaliana

<400> SEQUENCE: 35

Met Gly Leu Thr Ser Ser Leu Arg Phe His Arg Gln Asn Asn Lys Thr
1               5                   10                  15

Phe Leu Gly Ile Phe Met Ile Leu Val Leu Ser Cys Ile Pro Gly Arg
                20                  25                  30

Thr Asn Leu Cys Ser Asn His Ser Val Ser Thr Pro Lys Glu Leu Pro
            35                  40                  45

Ser Ser Asn Pro Ser Asp Ile Arg Ser Ser Leu Val Ser Leu Asp Leu
        50                  55                  60

Glu Gly Tyr Ile Ser Phe Asp Asp Val His Asn Val Ala Lys Asp Phe
65                  70                  75                  80

Gly Asn Arg Tyr Gln Leu Pro Pro Leu Ala Ile Leu His Pro Arg Ser
                85                  90                  95

Val Phe Asp Ile Ser Ser Met Met Lys His Ile Val His Leu Gly Ser
                100                 105                 110

Thr Ser Asn Leu Thr Val Ala Ala Arg Gly His Gly His Ser Leu Gln
            115                 120                 125

Gly Gln Ala Leu Ala His Gln Gly Val Val Ile Lys Met Glu Ser Leu
        130                 135                 140

Arg Ser Pro Asp Ile Arg Ile Tyr Lys Gly Lys Gln Pro Tyr Val Asp
145                 150                 155                 160

Val Ser Gly Gly Glu Ile Trp Ile Asn Ile Leu Arg Glu Thr Leu Lys
                165                 170                 175

Tyr Gly Leu Ser Pro Lys Ser Trp Thr Asp Tyr Leu His Leu Thr Val
            180                 185                 190
```

Gly Gly Thr Leu Ser Asn Ala Gly Ile Ser Gly Gln Ala Phe Lys His
            195                 200                 205

Gly Pro Gln Ile Asn Asn Val Tyr Gln Leu Glu Ile Val Thr Gly Lys
        210                 215                 220

Gly Glu Val Val Thr Cys Ser Glu Lys Arg Asn Ser Glu Leu Phe Phe
225                 230                 235                 240

Ser Val Leu Gly Gly Leu Gly Gln Phe Gly Ile Ile Thr Arg Ala Arg
                245                 250                 255

Ile Ser Leu Glu Pro Ala Pro His Met Val Lys Trp Ile Arg Val Leu
            260                 265                 270

Tyr Ser Asp Phe Ser Ala Phe Ser Arg Asp Gln Glu Tyr Leu Ile Ser
        275                 280                 285

Lys Glu Lys Thr Phe Asp Tyr Val Glu Gly Phe Val Ile Ile Asn Arg
        290                 295                 300

Thr Asp Leu Leu Asn Asn Trp Arg Ser Ser Phe Ser Pro Asn Asp Ser
305                 310                 315                 320

Thr Gln Ala Ser Arg Phe Lys Ser Asp Gly Lys Thr Leu Tyr Cys Leu
                325                 330                 335

Glu Val Val Lys Tyr Phe Asn Pro Glu Ala Ser Ser Met Asp Gln
            340                 345                 350

Glu Thr Gly Lys Leu Leu Ser Glu Leu Asn Tyr Ile Pro Ser Thr Leu
        355                 360                 365

Phe Ser Ser Glu Val Pro Tyr Ile Glu Phe Leu Asp Arg Val His Ile
        370                 375                 380

Ala Glu Arg Lys Leu Arg Ala Lys Gly Leu Trp Glu Val Pro His Pro
385                 390                 395                 400

Trp Leu Asn Leu Leu Ile Pro Lys Ser Ser Ile Tyr Gln Phe Ala Thr
                405                 410                 415

Glu Val Phe Asn Asn Ile Leu Thr Ser Asn Asn Asn Gly Pro Ile Leu
            420                 425                 430

Ile Tyr Pro Val Asn Gln Ser Lys Trp Lys Lys His Thr Ser Leu Ile
        435                 440                 445

Thr Pro Asn Glu Asp Ile Phe Tyr Leu Val Ala Phe Leu Pro Ser Ala
        450                 455                 460

Val Pro Asn Ser Ser Gly Lys Asn Asp Leu Glu Tyr Leu Leu Lys Gln
465                 470                 475                 480

Asn Gln Arg Val Met Asn Phe Cys Ala Ala Asn Leu Asn Val Lys
                485                 490                 495

Gln Tyr Leu Pro His Tyr Glu Thr Gln Lys Glu Trp Lys Ser His Phe
            500                 505                 510

Gly Lys Arg Trp Glu Thr Phe Ala Gln Arg Lys Gln Ala Tyr Asp Pro
        515                 520                 525

Leu Ala Ile Leu Ala Pro Gly Gln Arg Ile Phe Gln Lys Thr Thr Gly
530                 535                 540

Lys Leu Ser Pro Ile Gln Leu Ala Lys Ser Lys Ala Thr Gly Ser Pro
545                 550                 555                 560

Gln Arg Tyr His Tyr Ala Ser Ile Leu Pro Lys Pro Arg Thr Val
                565                 570                 575

<210> SEQ ID NO 36
<211> LENGTH: 501
<212> TYPE: PRT
<213> ORGANISM: Arabidopsis thaliana

<400> SEQUENCE: 36

-continued

Met Ala Asn Leu Arg Leu Met Ile Thr Leu Ile Thr Val Leu Met Ile
1               5                   10                  15

Thr Lys Ser Ser Asn Gly Ile Lys Ile Asp Leu Pro Lys Ser Leu Asn
            20                  25                  30

Leu Thr Leu Ser Thr Asp Pro Ser Ile Ile Ser Ala Ala Ser His Asp
        35                  40                  45

Phe Gly Asn Ile Thr Thr Val Thr Pro Gly Gly Val Ile Cys Pro Ser
    50                  55                  60

Ser Thr Ala Asp Ile Ser Arg Leu Leu Gln Tyr Ala Ala Asn Gly Lys
65                  70                  75                  80

Ser Thr Phe Gln Val Ala Ala Arg Gly Gln Gly His Ser Leu Asn Gly
            85                  90                  95

Gln Ala Ser Val Ser Gly Gly Val Ile Val Asn Met Thr Cys Ile Thr
            100                 105                 110

Asp Val Val Val Ser Lys Asp Lys Lys Tyr Ala Asp Val Ala Ala Gly
        115                 120                 125

Thr Leu Trp Val Asp Val Leu Lys Lys Thr Ala Glu Lys Gly Val Ser
    130                 135                 140

Pro Val Ser Trp Thr Asp Tyr Leu His Ile Thr Val Arg Gly Thr Leu
145                 150                 155                 160

Ser Asn Gly Gly Ile Gly Gly Gln Val Phe Arg Asn Gly Pro Leu Val
            165                 170                 175

Ser Asn Val Leu Glu Leu Asp Val Ile Thr Gly Lys Gly Glu Met Leu
            180                 185                 190

Thr Cys Ser Arg Gln Leu Asn Pro Glu Leu Phe Tyr Gly Val Leu Gly
        195                 200                 205

Gly Leu Gly Gln Phe Gly Ile Ile Thr Arg Ala Arg Ile Val Leu Asp
    210                 215                 220

His Ala Pro Lys Arg Ala Lys Trp Phe Arg Met Leu Tyr Ser Asp Phe
225                 230                 235                 240

Thr Thr Phe Thr Lys Asp Gln Glu Arg Leu Ile Ser Met Ala Asn Asp
            245                 250                 255

Ile Gly Val Asp Tyr Leu Glu Gly Gln Ile Phe Leu Ser Asn Gly Val
            260                 265                 270

Val Asp Thr Ser Phe Phe Pro Pro Ser Asp Gln Ser Lys Val Ala Asp
        275                 280                 285

Leu Val Lys Gln His Gly Ile Ile Tyr Val Leu Glu Val Ala Lys Tyr
    290                 295                 300

Tyr Asp Asp Pro Asn Leu Pro Ile Ile Ser Lys Val Ile Asp Thr Leu
305                 310                 315                 320

Thr Lys Thr Leu Ser Tyr Leu Pro Gly Phe Ile Ser Met His Asp Val
            325                 330                 335

Ala Tyr Phe Asp Phe Leu Asn Arg Val His Val Glu Glu Asn Lys Leu
            340                 345                 350

Arg Ser Leu Gly Leu Trp Glu Leu Pro His Pro Trp Leu Asn Leu Tyr
        355                 360                 365

Val Pro Lys Ser Arg Ile Leu Asp Phe His Asn Gly Val Val Lys Asp
    370                 375                 380

Ile Leu Leu Lys Gln Lys Ser Ala Ser Gly Leu Ala Leu Leu Tyr Pro
385                 390                 395                 400

Thr Asn Arg Asn Lys Trp Asp Asn Arg Met Ser Ala Met Ile Pro Glu
            405                 410                 415

Ile Asp Glu Asp Val Ile Tyr Ile Ile Gly Leu Leu Gln Ser Ala Thr

-continued

```
                420                 425                 430
Pro Lys Asp Leu Pro Glu Val Glu Ser Val Asn Glu Lys Ile Ile Arg
            435                 440                 445

Phe Cys Lys Asp Ser Gly Ile Lys Ile Lys Gln Tyr Leu Met His Tyr
        450                 455                 460

Thr Ser Lys Glu Asp Trp Ile Glu His Phe Gly Ser Lys Trp Asp Asp
465                 470                 475                 480

Phe Ser Lys Arg Lys Asp Leu Phe Asp Pro Lys Lys Leu Leu Ser Pro
                485                 490                 495

Gly Gln Asp Ile Phe
            500

<210> SEQ ID NO 37
<211> LENGTH: 523
<212> TYPE: PRT
<213> ORGANISM: Arabidopsis thaliana

<400> SEQUENCE: 37

Met Ala Ser Tyr Asn Leu Arg Ser Gln Val Arg Leu Ile Ala Ile Thr
1               5                   10                  15

Ile Val Ile Ile Ile Thr Leu Ser Thr Pro Ile Thr Thr Asn Thr Ser
            20                  25                  30

Pro Gln Pro Trp Asn Ile Leu Ser His Asn Glu Phe Ala Gly Lys Leu
        35                  40                  45

Thr Ser Ser Ser Ser Val Glu Ser Ala Ala Thr Asp Phe Gly His
    50                  55                  60

Val Thr Lys Ile Phe Pro Ser Ala Val Leu Ile Pro Ser Ser Val Glu
65                  70                  75                  80

Asp Ile Thr Asp Leu Ile Lys Leu Ser Phe Asp Ser Gln Leu Ser Phe
                85                  90                  95

Pro Leu Ala Ala Arg Gly His Gly His Ser His Arg Gly Gln Ala Ser
            100                 105                 110

Ala Lys Asp Gly Val Val Val Asn Met Arg Ser Met Val Asn Arg Asp
        115                 120                 125

Arg Gly Ile Lys Val Ser Arg Thr Cys Leu Tyr Val Asp Val Asp Ala
    130                 135                 140

Ala Trp Leu Trp Ile Glu Val Leu Asn Lys Thr Leu Glu Leu Gly Leu
145                 150                 155                 160

Thr Pro Val Ser Trp Thr Asp Tyr Leu Tyr Leu Thr Val Gly Gly Thr
                165                 170                 175

Leu Ser Asn Gly Gly Ile Ser Gly Gln Thr Phe Arg Tyr Gly Pro Gln
            180                 185                 190

Ile Thr Asn Val Leu Glu Met Asp Val Ile Thr Gly Lys Gly Glu Ile
        195                 200                 205

Ala Thr Cys Ser Lys Asp Met Asn Ser Asp Leu Phe Phe Ala Val Leu
    210                 215                 220

Gly Gly Leu Gly Gln Phe Gly Ile Ile Thr Arg Ala Arg Ile Lys Leu
225                 230                 235                 240

Glu Val Ala Pro Lys Arg Ala Lys Trp Leu Arg Phe Leu Tyr Ile Asp
                245                 250                 255

Phe Ser Glu Phe Thr Arg Asp Gln Glu Arg Val Ile Ser Lys Thr Asp
            260                 265                 270

Gly Val Asp Phe Leu Glu Gly Ser Ile Met Val Asp His Gly Pro Pro
        275                 280                 285

Asp Asn Trp Arg Ser Thr Tyr Tyr Pro Pro Ser Asp His Leu Arg Ile
```

```
                290                 295                 300
Ala Ser Met Val Lys Arg His Arg Val Ile Tyr Cys Leu Glu Val Val
305                 310                 315                 320

Lys Tyr Tyr Asp Glu Thr Ser Gln Tyr Thr Val Asn Glu Glu Met Glu
                325                 330                 335

Glu Leu Ser Asp Ser Leu Asn His Val Arg Gly Phe Met Tyr Glu Lys
                340                 345                 350

Asp Val Thr Tyr Met Asp Phe Leu Asn Arg Val Arg Thr Gly Glu Leu
                355                 360                 365

Asn Leu Lys Ser Lys Gly Gln Trp Asp Val Pro His Pro Trp Leu Asn
370                 375                 380

Leu Phe Val Pro Lys Thr Gln Ile Ser Lys Phe Asp Asp Gly Val Phe
385                 390                 395                 400

Lys Gly Ile Ile Leu Arg Asn Asn Ile Thr Ser Gly Pro Val Leu Val
                405                 410                 415

Tyr Pro Met Asn Arg Asn Lys Trp Asn Asp Arg Met Ser Ala Ala Ile
                420                 425                 430

Pro Glu Glu Asp Val Phe Tyr Ala Val Gly Phe Leu Arg Ser Ala Gly
                435                 440                 445

Phe Asp Asn Trp Glu Ala Phe Asp Gln Glu Asn Met Glu Ile Leu Lys
450                 455                 460

Phe Cys Glu Asp Ala Asn Met Gly Val Ile Gln Tyr Leu Pro Tyr His
465                 470                 475                 480

Ser Ser Gln Glu Gly Trp Val Arg His Phe Gly Pro Arg Trp Asn Ile
                485                 490                 495

Phe Val Glu Arg Lys Tyr Lys Tyr Asp Pro Lys Met Ile Leu Ser Pro
                500                 505                 510

Gly Gln Asn Ile Phe Gln Lys Ile Asn Ser Ser
                515                 520

<210> SEQ ID NO 38
<211> LENGTH: 524
<212> TYPE: PRT
<213> ORGANISM: Arabidopsis thaliana

<400> SEQUENCE: 38

Met Thr Asn Thr Leu Cys Leu Ser Leu Ile Thr Leu Ile Thr Phe Phe
1               5                   10                  15

Ile Ser Leu Thr Pro Thr Leu Ile Lys Ser Asp Glu Gly Ile Asp Val
                20                  25                  30

Phe Leu Pro Ile Ser Leu Asn Leu Thr Val Leu Thr Asp Pro Phe Ser
                35                  40                  45

Ile Ser Ala Ala Ser His Asp Phe Gly Asn Ile Thr Asp Glu Asn Pro
50                  55                  60

Gly Ala Val Leu Cys Pro Ser Ser Thr Thr Glu Val Ala Arg Leu Leu
65                  70                  75                  80

Arg Phe Ala Asn Gly Gly Phe Ser Tyr Asn Lys Gly Ser Thr Ser Pro
                85                  90                  95

Ala Ser Thr Phe Lys Val Ala Ala Arg Gly Gln Gly His Ser Leu Arg
                100                 105                 110

Gly Gln Ala Ser Ala Pro Gly Gly Val Val Val Asn Met Thr Cys Leu
                115                 120                 125

Ala Met Ala Ala Lys Pro Ala Ala Val Ile Ser Ala Asp Gly Thr
130                 135                 140

Tyr Ala Asp Val Ala Ala Gly Thr Met Trp Val Asp Val Leu Lys Ala
```

```
                145                 150                 155                 160
Ala Val Asp Arg Gly Val Ser Pro Val Thr Trp Thr Asp Tyr Leu Tyr
                    165                 170                 175

Leu Ser Val Gly Gly Thr Leu Ser Asn Ala Gly Ile Gly Gln Thr
            180                 185                 190

Phe Arg His Gly Pro Gln Ile Ser Asn Val His Glu Leu Asp Val Ile
            195                 200                 205

Thr Gly Lys Gly Glu Met Met Thr Cys Ser Pro Lys Leu Asn Pro Glu
    210                 215                 220

Leu Phe Tyr Gly Val Leu Gly Leu Gly Gln Phe Gly Ile Ile Thr
225                 230                 235                 240

Arg Ala Arg Ile Ala Leu Asp His Ala Pro Thr Arg Val Lys Trp Ser
                245                 250                 255

Arg Ile Leu Tyr Ser Asp Phe Ser Ala Phe Lys Arg Asp Gln Glu Arg
                260                 265                 270

Leu Ile Ser Met Thr Asn Asp Leu Gly Val Asp Phe Leu Glu Gly Gln
                275                 280                 285

Leu Met Met Ser Asn Gly Phe Val Asp Thr Ser Phe Phe Pro Leu Ser
    290                 295                 300

Asp Gln Thr Arg Val Ala Ser Leu Val Asn Asp His Arg Ile Ile Tyr
305                 310                 315                 320

Val Leu Glu Val Ala Lys Tyr Tyr Asp Arg Thr Thr Leu Pro Ile Ile
                325                 330                 335

Asp Gln Val Ile Asp Thr Leu Ser Arg Thr Leu Gly Phe Ala Pro Gly
                340                 345                 350

Phe Met Phe Val Gln Asp Val Pro Tyr Phe Asp Phe Leu Asn Arg Val
                355                 360                 365

Arg Asn Glu Glu Asp Lys Leu Arg Ser Leu Gly Leu Trp Glu Val Pro
            370                 375                 380

His Pro Trp Leu Asn Ile Phe Val Pro Gly Ser Arg Ile Gln Asp Phe
385                 390                 395                 400

His Asp Gly Val Ile Asn Gly Leu Leu Leu Asn Gln Thr Ser Thr Ser
                405                 410                 415

Gly Val Thr Leu Phe Tyr Pro Thr Asn Arg Asn Lys Trp Asn Asn Arg
                420                 425                 430

Met Ser Thr Met Thr Pro Asp Glu Asp Val Phe Tyr Val Ile Gly Leu
            435                 440                 445

Leu Gln Ser Ala Gly Gly Ser Gln Asn Trp Gln Glu Leu Glu Asn Leu
    450                 455                 460

Asn Asp Lys Val Ile Gln Phe Cys Glu Asn Ser Gly Ile Lys Ile Lys
465                 470                 475                 480

Glu Tyr Leu Met His Tyr Thr Arg Lys Glu Asp Trp Val Lys His Phe
                485                 490                 495

Gly Pro Lys Trp Asp Asp Phe Leu Arg Lys Lys Ile Met Phe Asp Pro
            500                 505                 510

Lys Arg Leu Leu Ser Pro Gly Gln Asp Ile Phe Asn
        515                 520

<210> SEQ ID NO 39
<211> LENGTH: 524
<212> TYPE: PRT
<213> ORGANISM: Arabidopsis thaliana

<400> SEQUENCE: 39

Met Ile Ala Tyr Ile Glu Pro Tyr Phe Leu Glu Asn Asp Ala Glu Ala
```

```
              1               5                  10                 15
Ala Ser Ala Ala Thr Ala Ala Gly Lys Ser Thr Asp Gly Val Ser Glu
                    20                  25                 30

Ser Leu Asn Ile Gln Gly Glu Ile Leu Cys Gly Gly Ala Ala Ala Asp
                    35                  40                 45

Ile Ala Gly Arg Asp Phe Gly Gly Met Asn Cys Val Lys Pro Leu Ala
 50                         55                     60

Val Val Arg Pro Val Gly Pro Glu Asp Ile Ala Gly Ala Val Lys Ala
 65                     70                  75                 80

Ala Leu Arg Ser Asp Lys Leu Thr Val Ala Ala Arg Gly Asn Gly His
                85                      90                 95

Ser Ile Asn Gly Gln Ala Met Ala Glu Gly Gly Leu Val Val Asp Met
                    100                 105                110

Ser Thr Thr Ala Glu Asn His Phe Glu Val Gly Tyr Leu Ser Gly Gly
                115                     120                125

Asp Ala Thr Ala Phe Val Asp Val Ser Gly Gly Ala Leu Trp Glu Asp
                130                     135                140

Val Leu Lys Arg Cys Val Ser Glu Tyr Gly Leu Ala Pro Arg Ser Trp
145                     150                 155                160

Thr Asp Tyr Leu Gly Leu Thr Val Gly Gly Thr Leu Ser Asn Ala Gly
                    165                 170                175

Val Ser Gly Gln Ala Phe Arg Tyr Gly Pro Gln Thr Ser Asn Val Thr
                180                     185                190

Glu Leu Asp Val Val Thr Gly Asn Gly Asp Val Thr Cys Ser Glu
                195                     200                205

Ile Glu Asn Ser Glu Leu Phe Phe Ser Val Leu Gly Gly Leu Gly Gln
                210                     215                220

Phe Gly Ile Ile Thr Arg Ala Arg Val Leu Leu Gln Pro Ala Pro Asp
225                     230                     235                240

Met Val Arg Trp Ile Arg Val Val Tyr Thr Glu Phe Asp Glu Phe Thr
                    245                 250                255

Gln Asp Ala Glu Trp Leu Val Ser Gln Lys Asn Glu Ser Ser Phe Asp
                260                     265                270

Tyr Val Glu Gly Phe Val Phe Val Asn Gly Ala Asp Pro Val Asn Gly
                275                     280                285

Trp Pro Thr Val Pro Leu His Pro Asp His Glu Phe Asp Pro Thr Arg
        290                     295                 300

Leu Pro Gln Ser Cys Gly Ser Val Leu Tyr Cys Leu Glu Leu Gly Leu
305                     310                     315                320

His Tyr Arg Asp Ser Asp Ser Asn Ser Thr Ile Asp Lys Arg Val Glu
                    325                 330                335

Arg Leu Ile Gly Arg Leu Arg Phe Asn Glu Gly Leu Arg Phe Glu Val
                340                     345                350

Asp Leu Pro Tyr Val Asp Phe Leu Leu Arg Val Lys Ser Glu Glu
                355                     360                365

Ile Ala Lys Glu Asn Gly Thr Trp Glu Thr Pro His Pro Trp Leu Asn
370                     375                     380

Leu Phe Val Ser Lys Arg Asp Ile Gly Asp Phe Asn Arg Thr Val Phe
385                     390                     395                400

Lys Glu Leu Val Lys Asn Gly Val Asn Gly Pro Met Leu Val Tyr Pro
                    405                 410                415

Leu Leu Arg Ser Arg Trp Asp Asp Arg Thr Ser Val Val Ile Pro Glu
                    420                 425                430
```

```
Glu Gly Glu Ile Phe Tyr Ile Val Ala Leu Leu Arg Phe Val Pro Pro
            435                 440                 445

Cys Ala Lys Val Ser Ser Val Glu Lys Met Val Ala Gln Asn Gln Glu
        450                 455                 460

Ile Val His Trp Cys Val Lys Asn Gly Ile Asp Tyr Lys Leu Tyr Leu
465                 470                 475                 480

Pro His Tyr Lys Ser Gln Glu Glu Trp Ile Arg His Phe Gly Asn Arg
                485                 490                 495

Trp Ser Arg Phe Val Asp Arg Lys Ala Met Phe Asp Pro Met Ala Ile
                500                 505                 510

Leu Ser Pro Gly Gln Lys Ile Phe Asn Arg Ser Leu
            515                 520

<210> SEQ ID NO 40
<211> LENGTH: 540
<212> TYPE: PRT
<213> ORGANISM: Arabidopsis thaliana

<400> SEQUENCE: 40

Met Asn Arg Glu Met Thr Ser Ser Phe Leu Leu Leu Thr Phe Ala Ile
1               5                   10                  15

Cys Lys Leu Ile Ile Ala Val Gly Leu Asn Val Gly Pro Ser Glu Leu
            20                  25                  30

Leu Arg Ile Gly Ala Ile Asp Val Asp Gly His Phe Thr Val His Pro
        35                  40                  45

Ser Asp Leu Ala Ser Val Ser Ser Asp Phe Gly Met Leu Lys Ser Pro
    50                  55                  60

Glu Glu Pro Leu Ala Val Leu His Pro Ser Ser Ala Glu Asp Val Ala
65                  70                  75                  80

Arg Leu Val Arg Thr Ala Tyr Gly Ser Ala Thr Ala Phe Pro Val Ser
                85                  90                  95

Ala Arg Gly His Gly His Ser Ile Asn Gly Gln Ala Ala Ala Gly Arg
            100                 105                 110

Asn Gly Val Val Val Glu Met Asn His Gly Val Thr Gly Thr Pro Lys
        115                 120                 125

Pro Leu Val Arg Pro Asp Glu Met Tyr Val Asp Val Trp Gly Gly Glu
    130                 135                 140

Leu Trp Val Asp Val Leu Lys Lys Thr Leu Glu His Gly Leu Ala Pro
145                 150                 155                 160

Lys Ser Trp Thr Asp Tyr Leu Tyr Leu Thr Val Gly Gly Thr Leu Ser
                165                 170                 175

Asn Ala Gly Ile Ser Gly Gln Ala Leu His His Gly Pro Gln Ile Ser
            180                 185                 190

Asn Val Leu Glu Leu Asp Val Val Thr Gly Lys Gly Glu Val Met Arg
        195                 200                 205

Cys Ser Glu Glu Glu Asn Thr Arg Leu Phe His Gly Val Leu Gly Gly
    210                 215                 220

Leu Gly Gln Phe Gly Ile Ile Thr Arg Ala Arg Ile Ser Leu Glu Pro
225                 230                 235                 240

Ala Pro Gln Arg Val Arg Trp Ile Arg Val Leu Tyr Ser Ser Phe Lys
                245                 250                 255

Val Phe Thr Glu Asp Gln Glu Tyr Leu Ile Ser Met His Gly Gln Leu
            260                 265                 270

Lys Phe Asp Tyr Val Glu Gly Phe Val Ile Val Asp Glu Gly Leu Val
        275                 280                 285
```

```
Asn Asn Trp Arg Ser Ser Phe Phe Ser Pro Arg Asn Pro Val Lys Ile
            290                 295                 300

Ser Ser Val Ser Ser Asn Gly Ser Val Leu Tyr Cys Leu Glu Ile Thr
305                 310                 315                 320

Lys Asn Tyr His Asp Ser Asp Ser Glu Ile Val Asp Gln Glu Val Glu
                325                 330                 335

Ile Leu Met Lys Lys Leu Asn Phe Ile Pro Thr Ser Val Phe Thr Thr
            340                 345                 350

Asp Leu Gln Tyr Val Asp Phe Leu Asp Arg Val His Lys Ala Glu Leu
                355                 360                 365

Lys Leu Arg Ser Lys Asn Leu Trp Glu Val Pro His Pro Trp Leu Asn
370                 375                 380

Leu Phe Val Pro Lys Ser Arg Ile Ser Asp Phe Asp Lys Gly Val Phe
385                 390                 395                 400

Lys Gly Ile Leu Gly Asn Lys Thr Ser Gly Pro Ile Leu Ile Tyr Pro
            405                 410                 415

Met Asn Lys Asp Lys Trp Asp Glu Arg Ser Ser Ala Val Thr Pro Asp
                420                 425                 430

Glu Glu Val Phe Tyr Leu Val Ala Leu Leu Arg Ser Ala Leu Thr Asp
            435                 440                 445

Gly Glu Thr Gln Lys Leu Glu Tyr Leu Lys Asp Gln Asn Arg Arg
450                 455                 460

Ile Leu Glu Phe Cys Glu Gln Ala Lys Ile Asn Val Lys Gln Tyr Leu
465                 470                 475                 480

Pro His His Ala Thr Gln Glu Glu Trp Val Ala His Phe Gly Asp Lys
                485                 490                 495

Trp Asp Arg Phe Arg Ser Leu Lys Ala Glu Phe Asp Pro Arg His Ile
                500                 505                 510

Leu Ala Thr Gly Gln Arg Ile Phe Gln Asn Pro Ser Leu Ser Leu Phe
                515                 520                 525

Pro Pro Ser Ser Ser Ser Ser Ala Ala Ser Trp
530                 535                 540
```

<210> SEQ ID NO 41
<211> LENGTH: 504
<212> TYPE: PRT
<213> ORGANISM: Arabidopsis thaliana

<400> SEQUENCE: 41

```
Met Leu Ile Val Arg Ser Phe Thr Ile Leu Leu Leu Ser Cys Ile Ala
1               5                   10                  15

Phe Lys Leu Ala Cys Cys Phe Ser Ser Ser Ile Ser Ser Leu Lys Ala
                20                  25                  30

Leu Pro Leu Val Gly His Leu Glu Phe Glu His Val His His Ala Ser
            35                  40                  45

Lys Asp Phe Gly Asn Arg Tyr Gln Leu Ile Pro Leu Ala Val Leu His
            50                  55                  60

Pro Lys Ser Val Ser Asp Ile Ala Ser Thr Ile Arg His Ile Trp Met
65                  70                  75                  80

Met Gly Thr His Ser Gln Leu Thr Val Ala Ala Arg Gly Arg Gly His
                85                  90                  95

Ser Leu Gln Gly Gln Ala Gln Thr Arg His Gly Ile Val Ile His Met
                100                 105                 110

Glu Ser Leu His Pro Gln Lys Leu Gln Val Tyr Ser Val Asp Ser Pro
            115                 120                 125
```

Ala Pro Tyr Val Asp Val Ser Gly Gly Glu Leu Trp Ile Asn Ile Leu
    130                 135                 140

His Glu Thr Leu Lys Tyr Gly Leu Ala Pro Lys Ser Trp Thr Asp Tyr
145                 150                 155                 160

Leu His Leu Thr Val Gly Gly Thr Leu Ser Asn Ala Gly Ile Ser Gly
                165                 170                 175

Gln Ala Phe Arg His Gly Pro Gln Ile Ser Asn Val His Gln Leu Glu
            180                 185                 190

Ile Val Thr Gly Lys Gly Glu Ile Leu Asn Cys Thr Lys Arg Gln Asn
        195                 200                 205

Ser Asp Leu Phe Asn Gly Val Leu Gly Leu Gly Gln Phe Gly Ile
    210                 215                 220

Ile Thr Arg Ala Arg Ile Ala Leu Glu Pro Ala Pro Thr Met Asp Gln
225                 230                 235                 240

Glu Gln Leu Ile Ser Ala Gln Gly His Lys Phe Asp Tyr Ile Glu Gly
                245                 250                 255

Phe Val Ile Ile Asn Arg Thr Gly Leu Leu Asn Ser Trp Arg Leu Ser
            260                 265                 270

Phe Thr Ala Glu Glu Pro Leu Glu Ala Ser Gln Phe Lys Phe Asp Gly
        275                 280                 285

Arg Thr Leu Tyr Cys Leu Glu Leu Ala Lys Tyr Leu Lys Gln Asp Asn
    290                 295                 300

Lys Asp Val Ile Asn Gln Glu Val Lys Glu Thr Leu Ser Glu Leu Ser
305                 310                 315                 320

Tyr Val Thr Ser Thr Leu Phe Thr Thr Glu Val Ala Tyr Glu Ala Phe
                325                 330                 335

Leu Asp Arg Val His Val Ser Glu Val Lys Leu Arg Ser Lys Gly Gln
            340                 345                 350

Trp Glu Val Pro His Pro Trp Leu Asn Leu Leu Val Pro Arg Ser Lys
        355                 360                 365

Ile Asn Glu Phe Ala Arg Gly Val Phe Gly Asn Ile Leu Thr Asp Thr
    370                 375                 380

Ser Asn Gly Pro Val Ile Val Tyr Pro Val Asn Lys Ser Lys Trp Asp
385                 390                 395                 400

Asn Gln Thr Ser Ala Val Thr Pro Glu Glu Val Phe Tyr Leu Val
                405                 410                 415

Ala Ile Leu Thr Ser Ala Ser Pro Gly Ser Ala Gly Lys Asp Gly Val
            420                 425                 430

Glu Glu Ile Leu Arg Arg Asn Arg Ile Leu Glu Phe Ser Glu Glu
        435                 440                 445

Ala Gly Ile Gly Leu Lys Gln Tyr Leu Pro His Tyr Thr Thr Arg Glu
    450                 455                 460

Glu Trp Arg Ser His Phe Gly Asp Lys Trp Gly Glu Phe Val Arg Arg
465                 470                 475                 480

Lys Ser Arg Tyr Asp Pro Leu Ala Ile Leu Ala Pro Gly His Arg Ile
                485                 490                 495

Phe Gln Lys Ala Val Ser Tyr Ser
            500

<210> SEQ ID NO 42
<211> LENGTH: 536
<212> TYPE: PRT
<213> ORGANISM: Dendrobium sonia

<400> SEQUENCE: 42

-continued

```
Met Asn Leu His Ala Met Pro Pro Phe Leu Asn Pro Thr Ser Leu Leu
  1               5                  10                  15

Leu Thr Thr Thr Leu Met Ser Ile Leu Ile Gln Ser Pro Asn Ser Leu
             20                  25                  30

Pro Thr Asn Leu Leu Thr His Pro Thr Ser Thr His Leu Arg Phe Asp
         35                  40                  45

Ser Leu Ser Leu Ser Ala Ala Ser Ser Asp Phe Gly Asp Ile Ile His
 50                  55                  60

Ser Leu Pro Ser Ala Val Phe Leu Pro Ser Ser Pro Ser Asp Ile Ala
 65                  70                  75                  80

Thr Leu Leu Arg Leu Ser His Phe Ser Pro His Ser Phe Thr Val Ser
                 85                  90                  95

Ala Arg Gly Leu Gly His Ser Thr Arg Gly Gln Ala Gln Ala Phe Gly
                100                 105                 110

Gly Ile Val Ile Asn Met Pro Ser Leu Asp Gly Gly Ile Thr Val Ser
                115                 120                 125

Ile Asp Gly Met Phe Val Asp Ala Gly Ala Glu Gln Met Trp Ile Asp
    130                 135                 140

Val Leu Arg Glu Thr Leu Arg His Gly Leu Thr Pro Lys Ser Trp Thr
145                 150                 155                 160

Asp Tyr Leu Tyr Leu Thr Leu Gly Gly Thr Leu Ser Asn Gly Gly Ile
                165                 170                 175

Ser Gly Gln Ala Phe Leu His Gly Pro Gln Ile Ser Asn Val His Glu
                180                 185                 190

Leu Asp Ile Val Thr Gly Lys Gly Glu Met Val Thr Cys Ser Glu Ser
                195                 200                 205

Asn Asn Pro Asp Leu Phe Phe Ser Val Leu Gly Gly Leu Gly Gln Phe
                210                 215                 220

Gly Ile Ile Thr Arg Ala Arg Ile Ala Leu Glu Lys Ala Pro Gln Ser
225                 230                 235                 240

Val Arg Trp Met Arg Leu Met Tyr Thr Asp Phe Glu Leu Phe Thr Lys
                245                 250                 255

Asp Gln Glu Leu Leu Ile Ser Ile Lys Ala Glu Gly Glu Gly Trp Lys
                260                 265                 270

Leu Asn Tyr Val Glu Gly Ser Leu Leu Met Glu His Ser Leu Lys Ser
                275                 280                 285

Asn Trp Arg Ser Pro Phe Phe Ser Glu Lys Asp Leu Lys Lys Ile Lys
                290                 295                 300

Lys Leu Ala Ser Gly Asn Glu Gly Val Ile Tyr Cys Leu Glu Ala Ser
305                 310                 315                 320

Phe Tyr Tyr Asp Tyr Gly His Glu Met Asn Phe Ser Arg Ala Asp Lys
                325                 330                 335

Ala Gln Met Asp Gln Asp Ile Glu Glu Leu Leu Arg Lys Leu Ser Phe
                340                 345                 350

Val Ser Gly Phe Ala Phe Arg Asn Asp Val Ser Tyr Met Gly Phe Leu
                355                 360                 365

Asn Arg Val His Asp Gly Glu Leu Lys Leu Arg Ala Met Gly Leu Trp
                370                 375                 380

Asp Val Pro His Pro Trp Leu Asn Leu Phe Val Ser Lys Ser Asn Ile
385                 390                 395                 400

Met Asp Phe His Ile Gly Val Phe Lys Gly Ile Met Lys Asn Ser Lys
                405                 410                 415

Ser Met Gly Pro Ile Leu Val Tyr Pro Thr Lys Arg Ser Lys Trp Asp
                420                 425                 430
```

-continued

Lys Arg Met Ser Thr Ser Ile Pro Asp Glu Val Phe Tyr Ser Ile
        435                 440                 445

Gly Ile Leu Leu Ser Ser Glu Met Asn Asp Leu Glu His Leu Glu Ser
450                 455                 460

His Asn Ala Glu Ile Leu Lys Phe Cys Asp Gln Gln Gly Met Asn Tyr
465                 470                 475                 480

Lys Gln Tyr Leu Pro His Tyr Thr Ser Ile Glu Asp Trp Lys Lys His
                485                 490                 495

Phe Gly Lys Lys Trp Glu Arg Phe Val Glu Met Lys Ser Arg Tyr Asp
                500                 505                 510

Pro Lys Ala Ile Leu Ser Pro Gly Gln Lys Ile Phe Thr His Leu Val
                515                 520                 525

Asp Glu Leu Cys Leu Ser Asp His
            530                 535

<210> SEQ ID NO 43
<211> LENGTH: 526
<212> TYPE: PRT
<213> ORGANISM: Hordeum vulgare

<400> SEQUENCE: 43

Met Arg Gln Leu Leu Gln Tyr Leu Lys Leu Phe Leu Leu Leu Gly
1                   5                   10                  15

Leu Gly Ala Val Thr Ala Glu His Val Leu Lys His Asp Val Leu Ala
                20                  25                  30

Ser Leu Gly Thr Leu Pro Leu Asp Gly His Phe Ser His Asp Leu
            35                  40                  45

Ser Ala Ala Ala Met Asp Phe Gly Asn Leu Ser Ser Phe Pro Pro Val
50                  55                  60

Ala Val Leu His Pro Gly Ser Val Ala Asp Ile Ala Thr Thr Val Arg
65                  70                  75                  80

His Val Phe Leu Met Gly Glu His Ser Ala Leu Thr Val Ala Ala Arg
                85                  90                  95

Gly His Gly His Ser Leu Tyr Gly Gln Ser Gln Ala Ala Gly Gly Ile
            100                 105                 110

Val Ile Arg Met Glu Ser Leu Arg Ser Val Lys Met Gln Val His Pro
        115                 120                 125

Gly Ala Ser Pro Tyr Val Asp Ala Ser Gly Gly Glu Leu Trp Ile Asn
130                 135                 140

Val Leu Asn Lys Thr Leu Lys Tyr Gly Leu Ala Pro Lys Ser Trp Thr
145                 150                 155                 160

Asp Tyr Leu His Leu Thr Val Gly Gly Thr Leu Ser Asn Ala Gly Val
                165                 170                 175

Ser Gly Gln Thr Phe Arg His Gly Pro Gln Ile Ser Asn Val Asn Glu
            180                 185                 190

Leu Glu Ile Val Thr Gly Arg Gly Asp Ile Val Thr Cys Ser Pro Glu
        195                 200                 205

Gln Asn Ser Asp Leu Phe Arg Ala Ala Leu Gly Gly Leu Gly Gln Phe
210                 215                 220

Gly Ile Ile Thr Arg Ala Arg Ile Ala Leu Glu Pro Ala Pro Gln Met
225                 230                 235                 240

Val Arg Trp Ile Arg Val Leu Tyr Leu Asp Phe Met Ser Phe Thr Glu
                245                 250                 255

Asp Gln Glu Met Leu Ile Ser Ala Glu Lys Thr Phe Asp Tyr Ile Glu
            260                 265                 270

```
Gly Phe Val Ile Ile Asn Arg Thr Gly Ile Leu Asn Asn Trp Arg Ser
            275                 280                 285

Ser Phe Asn Pro Gln Asp Pro Glu Arg Ala Ser Arg Phe Glu Thr Asp
            290                 295                 300

Arg Lys Val Leu Phe Cys Leu Glu Met Thr Lys Asn Phe Asn Pro Glu
305                 310                 315                 320

Glu Ala Asp Ile Met Glu Gln Glu Val His Ala Leu Leu Ser Gln Leu
            325                 330                 335

Arg Tyr Thr Pro Ala Ser Leu Phe His Thr Asp Val Thr Tyr Ile Glu
            340                 345                 350

Phe Leu Asp Arg Val His Ser Ser Glu Met Lys Leu Arg Ala Lys Gly
            355                 360                 365

Leu Trp Glu Val Pro His Pro Trp Leu Asn Leu Ile Pro Arg Ser
            370                 375                 380

Thr Ile His Thr Phe Ala Glu Gln Val Phe Gly Lys Ile Leu Glu Asp
385                 390                 395                 400

Asn Asn Asn Gly Pro Ile Leu Leu Tyr Pro Val Lys Lys Ser Arg Trp
            405                 410                 415

Asp Asn Arg Thr Ser Val Val Ile Pro Asp Glu Val Phe Tyr Leu
            420                 425                 430

Val Gly Phe Leu Ser Ser Ala Ile Gly Pro His Ser Ile Glu His Thr
            435                 440                 445

Leu Asn Leu Asn Asn Gln Ile Ile Glu Phe Ser Asn Lys Ala Ser Ile
            450                 455                 460

Gly Val Lys Gln Tyr Leu Pro Asn Tyr Thr Thr Glu Pro Glu Trp Lys
465                 470                 475                 480

Ala His Tyr Gly Ala Arg Trp Asp Ala Phe Gln Gln Arg Lys Asn Thr
            485                 490                 495

Tyr Asp Pro Leu Ala Ile Leu Ala Pro Gly Gln Lys Ile Phe Gln Lys
            500                 505                 510

Lys Pro Ala Ser Leu Pro Leu Ser Ser Leu Gln Tyr Leu Leu
            515                 520                 525

<210> SEQ ID NO 44
<211> LENGTH: 520
<212> TYPE: PRT
<213> ORGANISM: Hordeum vulgare

<400> SEQUENCE: 44

Met Lys Gln Leu Leu Gln Tyr Leu Lys Leu Phe Leu Leu Leu Gly
  1               5                  10                  15

Leu Ser Arg Val Thr Thr Glu His Val Pro Lys Tyr Asp Val Leu Ala
             20                  25                  30

Ser Leu Gly Thr Leu Pro Leu Asp Gly His Phe Ser Phe His Asp Leu
             35                  40                  45

Pro Ala Ala Ala Arg Asp Phe Gly Asn Leu Ser Ser Phe Pro Val
             50                  55                  60

Ala Val Leu His Pro Gly Ser Val Ala Asp Ile Ala Arg Thr Val Arg
 65                  70                  75                  80

His Val Phe Leu Met Gly Glu His Ser Thr Leu Thr Val Ala Ala Arg
             85                  90                  95

Gly His Gly His Ser Leu Tyr Gly Gln Ser Gln Ala Ala Gly Gly Ile
            100                 105                 110

Val Ile Arg Met Glu Ser Leu Gln Ser Val Lys Met Gln Val His Pro
            115                 120                 125
```

Gly Ala Ser Pro Tyr Val Asp Ala Ser Gly Gly Glu Leu Trp Ile Asn
    130                 135                 140

Val Leu Asn Lys Thr Leu Lys Tyr Gly Leu Ala Pro Lys Ser Trp Thr
145                 150                 155                 160

Asp Tyr Leu His Leu Thr Val Gly Gly Thr Leu Ser Asn Ala Gly Val
                165                 170                 175

Ser Gly Gln Thr Phe Arg His Gly Pro Gln Ile Ser Asn Val Asn Glu
            180                 185                 190

Leu Glu Ile Val Thr Gly Arg Gly Asp Ile Ile Thr Cys Ser Pro Glu
        195                 200                 205

Gln Asn Ser Asp Leu Phe His Ala Ala Leu Gly Gly Leu Gly Gln Phe
    210                 215                 220

Gly Ile Ile Thr Arg Ala Arg Ile Ala Leu Glu Pro Ala Pro Gln Met
225                 230                 235                 240

Val Arg Trp Ile Arg Val Leu Tyr Leu Asp Phe Met Ser Leu Thr Glu
                245                 250                 255

Asp Gln Glu Met Leu Ile Ser Ala Glu Lys Thr Phe Asp Tyr Ile Glu
            260                 265                 270

Gly Phe Val Ser Ile Asn Arg Thr Gly Ile Leu Asn Asn Trp Arg Ser
        275                 280                 285

Ser Phe Asn Pro Gln Asp Pro Glu Arg Ala Ser Gln Phe Glu Thr Asp
    290                 295                 300

Arg Lys Val Leu Phe Cys Leu Glu Met Thr Lys Asn Phe Asn Pro Glu
305                 310                 315                 320

Glu Ala Gly Ile Met Glu Gln Ile His Ala Leu Leu Ser Gln Leu Arg
                325                 330                 335

Tyr Thr Pro Pro Ser Leu Phe His Thr Asp Val Thr Tyr Met Glu Phe
            340                 345                 350

Leu Asp Arg Val His Ser Ser Glu Ile Lys Leu Arg Ala Lys Gly Leu
        355                 360                 365

Trp Glu Val Pro His Pro Trp Leu Asn Leu Ile Ile Pro Arg Ser Thr
    370                 375                 380

Val His Thr Phe Ala Lys Gln Val Phe Gly Lys Ile Leu Glu Asp Asn
385                 390                 395                 400

Asn Asn Gly Pro Ile Leu Leu Tyr Pro Val Asn Lys Ser Arg Trp Asp
                405                 410                 415

Asn Arg Thr Ser Val Val Leu Pro Asp Glu Glu Val Ser Tyr Leu Val
            420                 425                 430

Gly Phe Leu Pro Ser Ala Met Gly Pro His Ser Ile Lys Arg Thr Leu
        435                 440                 445

Asn Leu Asn Asn Gln Ile Ile Glu Phe Ser Asn Lys Ala Ser Ile Gly
    450                 455                 460

Val Lys Gln Tyr Leu Pro His Tyr Ser Thr Glu Pro Glu Trp Lys Ala
465                 470                 475                 480

His Tyr Gly Ala Arg Trp Asp Ala Phe Gln Gln Arg Lys Asn Thr Tyr
                485                 490                 495

Asp Pro Leu Ala Ile Leu Ala Pro Gly Gln Arg Ile Phe Gln Lys Thr
            500                 505                 510

Pro Ala Ser Leu Pro Leu Ser Ser
        515                 520

<210> SEQ ID NO 45
<211> LENGTH: 532
<212> TYPE: PRT

-continued

<213> ORGANISM: Oryza sativa

<400> SEQUENCE: 45

```
Met Ala Ala Ile Tyr Leu Leu Ile Ala Ala Leu Ile Ala Ser Ser His
 1               5                  10                  15
Ala Leu Ala Ala His Gly Ala Gly Gly Val Pro Leu Ala Ala Ala
            20                  25                  30
Ala Pro Leu Pro Phe Pro Gly Asp Leu Ala Ala Ser Gly Lys Leu Arg
        35                  40                  45
Thr Asp Pro Asn Ala Thr Val Pro Ala Ser Met Asp Phe Gly Asn Ile
    50                  55                  60
Thr Ala Ala Leu Pro Ala Ala Val Leu Phe Pro Gly Ser Pro Gly Asp
65                  70                  75                  80
Val Ala Glu Leu Leu Arg Ala Ala Tyr Ala Ala Pro Gly Arg Pro Phe
                85                  90                  95
Thr Val Ser Phe Arg Gly Arg Gly His Ser Thr Met Gly Gln Ala Leu
            100                 105                 110
Ala Ala Gly Gly Val Val His Met Gln Ser Met Gly Gly Gly
        115                 120                 125
Ala Pro Arg Ile Asn Val Ser Ala Asp Gly Ala Tyr Val Asp Ala Gly
    130                 135                 140
Gly Glu Gln Leu Trp Val Asp Val Leu Arg Ala Leu Ala Arg Gly
145                 150                 155                 160
Val Ala Pro Arg Ser Trp Thr Asp Tyr Leu His Leu Thr Val Gly Gly
                165                 170                 175
Thr Leu Ser Asn Ala Gly Val Ser Gly Gln Thr Tyr Arg His Gly Pro
            180                 185                 190
Gln Ile Ser Asn Val Leu Glu Leu Asp Val Ile Thr Gly His Gly Glu
        195                 200                 205
Thr Val Thr Cys Ser Lys Ala Val Asn Ser Asp Leu Phe Asp Ala Val
    210                 215                 220
Leu Gly Gly Leu Gly Gln Phe Gly Val Ile Thr Arg Ala Arg Val Ala
225                 230                 235                 240
Val Glu Pro Ala Pro Ala Arg Ala Arg Trp Val Arg Leu Val Tyr Ala
                245                 250                 255
Asp Phe Ala Phe Ser Ala Asp Gln Glu Arg Leu Val Ala Ala Arg
            260                 265                 270
Pro Asp Gly Ser His Gly Pro Trp Ser Tyr Val Glu Gly Ala Val Tyr
        275                 280                 285
Leu Ala Gly Arg Gly Leu Ala Val Ala Leu Lys Ser Ser Gly Gly Phe
    290                 295                 300
Phe Ser Asp Ala Asp Ala Ala Arg Val Val Ala Leu Ala Ala Ala Arg
305                 310                 315                 320
Asn Ala Thr Ala Val Tyr Ser Ile Glu Ala Thr Leu Asn Tyr Ala Ala
                325                 330                 335
Asn Ala Thr Pro Ser Ser Val Asp Ala Ala Val Ala Ala Ala Leu Gly
            340                 345                 350
Asp Leu His Phe Glu Glu Gly Phe Ser Phe Ser Arg Asp Val Thr Tyr
        355                 360                 365
Glu Glu Phe Leu Asp Arg Val Tyr Gly Glu Glu Ala Leu Glu Lys
    370                 375                 380
Ala Gly Leu Trp Arg Val Pro His Pro Trp Leu Asn Leu Phe Val Pro
385                 390                 395                 400
Gly Ser Arg Ile Ala Asp Phe Asp Arg Gly Val Phe Lys Gly Ile Leu
```

```
                    405                 410                 415
Gln Thr Ala Thr Asp Ile Ala Gly Pro Leu Ile Ile Tyr Pro Val Asn
            420                 425                 430
Lys Ser Lys Trp Asp Ala Ala Met Ser Ala Val Thr Pro Glu Gly Glu
        435                 440                 445
Glu Glu Val Phe Tyr Val Val Ser Leu Leu Phe Ser Ala Val Ala Asn
    450                 455                 460
Asp Val Ala Ala Leu Glu Ala Gln Asn Arg Arg Ile Leu Arg Phe Cys
465                 470                 475                 480
Asp Leu Ala Gly Ile Gly Tyr Lys Ala Tyr Leu Ala His Tyr Asp Ser
            485                 490                 495
Arg Gly Asp Trp Val Arg His Phe Gly Ala Lys Trp Asp Arg Phe Val
        500                 505                 510
Gln Arg Lys Asp Lys Tyr Asp Pro Lys Lys Leu Leu Ser Pro Gly Gln
    515                 520                 525
Asp Ile Phe Asn
    530

<210> SEQ ID NO 46
<211> LENGTH: 558
<212> TYPE: PRT
<213> ORGANISM: Oryza sativa

<400> SEQUENCE: 46

Met Ala Val Leu Leu Met Leu Asn Cys Phe Val Lys Ala Thr Ala Pro
1               5                   10                  15
Pro Pro Trp Pro Pro Ser Ala Ser Ser Ala Ser Phe Leu Asp Asp Leu
            20                  25                  30
Gly Asp Leu Gly Ile Ala Pro Leu Ile Arg Ala Asp Glu Ala Gly Thr
        35                  40                  45
Ala Arg Ala Ser Ala Asp Phe Gly Asn Leu Ser Val Ala Gly Val Gly
    50                  55                  60
Ala Pro Arg Leu Ala Ala Ala Ala Val Leu Tyr Pro Ser Arg Pro
65                  70                  75                  80
Ala Asp Ile Ala Ala Leu Leu Arg Ala Ser Cys Ala Arg Pro Ala Pro
                85                  90                  95
Phe Ala Val Ser Ala Arg Gly Cys Gly His Ser Val His Gly Gln Ala
            100                 105                 110
Ser Ala Pro Asp Gly Val Val Asp Met Ala Ser Leu Gly Arg Leu
        115                 120                 125
Gln Gly Gly Gly Ala Arg Arg Leu Ala Val Ser Val Glu Gly Arg Tyr
    130                 135                 140
Val Asp Ala Gly Gly Glu Gln Leu Trp Val Asp Val Leu Arg Ala Ser
145                 150                 155                 160
Met Ala His Gly Leu Thr Pro Val Ser Trp Thr Asp Tyr Leu His Leu
                165                 170                 175
Thr Val Gly Gly Thr Leu Ser Asn Ala Gly Ile Ser Gly Gln Ala Phe
            180                 185                 190
Arg His Gly Pro Gln Ile Ser Asn Val Leu Glu Leu Asp Val Ile Thr
        195                 200                 205
Gly Val Gly Glu Met Val Thr Cys Ser Lys Glu Lys Ala Pro Asp Leu
    210                 215                 220
Phe Asp Ala Val Leu Gly Gly Leu Gly Gln Phe Gly Val Ile Thr Arg
225                 230                 235                 240
Ala Arg Ile Pro Leu Ala Pro Ala Pro Ala Arg Ala Arg Trp Val Arg
```

```
                            245                 250                 255
            Phe Val Tyr Thr Thr Ala Ala Ala Met Thr Ala Asp Gln Glu Arg Leu
                            260                 265                 270

Ile Ala Val Asp Arg Ala Gly Gly Ala Gly Ala Val Gly Gly Leu Met
                            275                 280                 285

Asp Tyr Val Glu Gly Ser Val His Leu Asn Gln Gly Leu Val Glu Thr
                            290                 295                 300

Trp Arg Thr Gln Pro Gln Pro Pro Ser Pro Ser Ser Ser Ser Ser Ser
            305                 310                 315                 320

Ser Phe Phe Ser Asp Ala Asp Glu Ala Arg Val Ala Ala Leu Ala Lys
                            325                 330                 335

Glu Ala Gly Gly Val Leu Tyr Phe Leu Glu Gly Ala Ile Tyr Phe Gly
                            340                 345                 350

Gly Ala Ala Gly Pro Ser Ala Ala Asp Val Asp Lys Arg Met Asp Val
                            355                 360                 365

Leu Arg Arg Glu Leu Arg His Glu Arg Gly Phe Val Phe Ala Gln Asp
                            370                 375                 380

Val Ala Tyr Ala Gly Phe Leu Asp Arg Val His Asp Gly Glu Leu Lys
            385                 390                 395                 400

Leu Arg Ala Ala Gly Leu Trp Asp Val Pro His Pro Trp Leu Asn Leu
                            405                 410                 415

Phe Leu Pro Arg Ser Gly Val Leu Ala Phe Ala Asp Gly Val Phe His
                            420                 425                 430

Gly Ile Leu Ser Arg Thr Pro Ala Met Gly Pro Val Leu Ile Tyr Pro
                            435                 440                 445

Met Asn Arg Asn Lys Trp Asp Ser Asn Met Ser Ala Val Ile Thr Asp
                            450                 455                 460

Asp Asp Gly Asp Glu Val Phe Tyr Thr Val Gly Ile Leu Arg Ser Ala
            465                 470                 475                 480

Ala Ala Ala Gly Asp Val Gly Arg Leu Glu Gln Asn Asp Glu Ile
                            485                 490                 495

Leu Gly Phe Cys Glu Val Ala Gly Ile Ala Tyr Lys Gln Tyr Leu Pro
                            500                 505                 510

Tyr Tyr Gly Ser Gln Ala Glu Trp Gln Lys Arg His Phe Gly Ala Asn
                            515                 520                 525

Leu Trp Pro Arg Phe Val Gln Arg Lys Ser Lys Tyr Asp Pro Lys Ala
                            530                 535                 540

Ile Leu Ser Arg Gly Gln Gly Ile Phe Thr Ser Pro Leu Ala
            545                 550                 555

<210> SEQ ID NO 47
<211> LENGTH: 527
<212> TYPE: PRT
<213> ORGANISM: Oryza sativa

<400> SEQUENCE: 47

Met Glu Val Ala Met Val Cys Thr Arg Val Asn Leu Leu Ile Leu Ile
1               5                   10                  15

Leu Ser Leu Cys Ser Pro Tyr Lys Phe Ile Gln Ser Pro Met Asp Phe
                20                  25                  30

Gly Pro Leu Asn Leu Leu Pro Thr Thr Thr Ala Ser Ser Asp Phe
                35                  40                  45

Gly Arg Ile Leu Phe His Ser Pro Ser Ala Val Leu Lys Pro Gln Ala
            50                  55                  60

Pro Arg Asp Ile Ser Leu Leu Leu Ser Phe Leu Ser Ala Ser Pro Leu
```

```
              65                  70                  75                  80
Gly Lys Val Thr Val Ala Ala Arg Gly Ala Gly His Ser Ile His Gly
                        85                  90                  95
Gln Ala Gln Ala Leu Asp Gly Ile Val Val Glu Met Ser Ser Leu Pro
                100                 105                 110
Ser Glu Ile Glu Phe Tyr Arg Arg Gly Glu Gly Asp Val Ser Tyr Ala
            115                 120                 125
Asp Val Gly Gly Gly Ile Met Trp Ile Glu Leu Leu Glu Gln Ser Leu
        130                 135                 140
Lys Leu Gly Leu Ala Pro Arg Ser Trp Thr Asp Tyr Leu Tyr Leu Thr
145                 150                 155                 160
Ile Gly Gly Thr Leu Ser Asn Ala Gly Ile Ser Gly Gln Thr Phe Lys
                165                 170                 175
His Gly Pro Gln Ile Ser Asn Val Leu Gln Leu Glu Val Val Thr Gly
                180                 185                 190
Arg Gly Glu Ile Val Thr Cys Ser Pro Thr Lys Asp Ala Glu Leu Phe
            195                 200                 205
Asn Ala Val Leu Gly Gly Leu Gly Gln Phe Gly Ile Ile Thr Arg Ala
        210                 215                 220
Arg Ile Leu Leu Gln Glu Ala Pro Gln Lys Val Lys Trp Val Arg Ala
225                 230                 235                 240
Phe Tyr Asp Asp Phe Ala Thr Phe Thr Lys Asp Gln Glu Leu Leu Val
                245                 250                 255
Ser Met Pro Val Leu Val Asp Tyr Val Glu Gly Phe Ile Val Leu Asn
                260                 265                 270
Glu Gln Ser Leu His Ser Ser Ile Ala Phe Pro Thr Asn Val Asp
            275                 280                 285
Phe Asn Pro Asp Phe Gly Thr Lys Asn Asn Pro Lys Ile Tyr Tyr Cys
        290                 295                 300
Ile Glu Phe Ala Val His Asp Tyr Gln Asn Lys Asn Ile Asn Val Glu
305                 310                 315                 320
Gln Val Val Glu Val Ile Ser Arg Gln Met Ser His Ile Ala Ser His
                325                 330                 335
Leu Tyr Ser Val Glu Val Ser Tyr Phe Asp Phe Leu Asn Arg Val Arg
                340                 345                 350
Met Glu Glu Met Ser Leu Arg Asn Ser Gly Leu Trp Glu Val His His
            355                 360                 365
Pro Trp Leu Asn Met Phe Val Pro Ser Ala Gly Ile Ser Asp Phe Arg
        370                 375                 380
Asp Leu Leu Met Asp Ser Ile Ser Pro Asp Asn Phe Glu Gly Leu Ile
385                 390                 395                 400
Leu Ile Tyr Pro Leu Leu Arg His Lys Trp Asp Thr Asn Thr Ser Val
                405                 410                 415
Val Leu Pro Asp Ser Gly Ser Thr Asp Gln Val Met Tyr Ala Val Gly
                420                 425                 430
Ile Leu Arg Ser Ala Asn Pro Asp Asp Gly Cys Ser His His Cys Leu
            435                 440                 445
Gln Glu Leu Leu Leu Arg His Arg Leu Ala Gly Ala Ala Ser
        450                 455                 460
Gly Leu Gly Ala Lys Gln Tyr Leu Ala His Pro Thr Pro Ala Gly
465                 470                 475                 480
Trp Arg Arg His Phe Gly Arg Arg Trp Glu Arg Phe Ala Asp Arg Lys
                485                 490                 495
```

```
Ala Arg Phe Asp Pro Arg Cys Ile Leu Gly Pro Gly Gln Gly Ile Phe
            500                 505                 510

Pro Arg Asp Ser Ser Ser Asn Gly Ala Phe Ala Ser Tyr Ser
        515                 520                 525
```

<210> SEQ ID NO 48
<211> LENGTH: 525
<212> TYPE: PRT
<213> ORGANISM: Oryza sativa

<400> SEQUENCE: 48

```
Met Lys Pro Ser Ile Val His Cys Leu Lys Leu Leu Met Leu Leu Ala
  1               5                  10                  15

Leu Gly Gly Val Thr Met His Val Pro Asp Glu Asp Val Val Ala
             20                  25                  30

Ser Leu Gly Ala Leu Arg Leu Asp Gly His Phe Ser Phe Asp Asp Ala
             35                  40                  45

His Ala Ala Arg Asp Phe Gly Asn Arg Cys Ser Leu Leu Pro Ala
 50                  55                  60

Ala Val Leu His Pro Gly Ser Val Ser Asp Val Ala Ala Thr Val Arg
 65                  70                  75                  80

Arg Val Phe Gln Leu Gly Arg Ser Ser Pro Leu Thr Val Ala Ala Arg
                 85                  90                  95

Gly His Gly His Ser Leu Leu Gly Gln Ser Gln Ala Ala Gly Gly Ile
            100                 105                 110

Val Val Lys Met Glu Ser Leu Ala Ala Ala Ala Arg Ala Val Arg
            115                 120                 125

Val His Gly Gly Ala Ser Pro His Val Asp Ala Pro Gly Gly Glu Leu
130                 135                 140

Trp Ile Asn Val Leu His Glu Thr Leu Lys His Gly Leu Ala Pro Arg
145                 150                 155                 160

Ser Trp Thr Asp Tyr Leu His Leu Thr Val Gly Gly Thr Leu Ser Asn
                165                 170                 175

Ala Gly Val Ser Gly Gln Ala Phe Arg His Gly Pro Gln Val Ser Asn
            180                 185                 190

Val Asn Gln Leu Glu Ile Val Thr Gly Arg Gly Glu Val Val Thr Cys
            195                 200                 205

Ser His Glu Val Asn Ser Asp Leu Phe Tyr Ala Ala Leu Gly Gly Leu
210                 215                 220

Gly Gln Phe Gly Ile Ile Thr Arg Ala Arg Ile Ala Leu Glu Pro Ala
225                 230                 235                 240

Pro Lys Met Val Arg Trp Ile Arg Val Leu Tyr Ser Asp Phe Glu Thr
                245                 250                 255

Phe Thr Glu Asp Gln Glu Lys Leu Ile Ala Ser Glu Lys Thr Phe Asp
            260                 265                 270

Tyr Ile Glu Gly Phe Val Ile Asn Arg Thr Gly Ile Leu Asn Asn
            275                 280                 285

Trp Arg Thr Ser Phe Lys Pro Gln Asp Pro Val Gln Ala Ser Gln Phe
290                 295                 300

Gln Ser Asp Gly Arg Val Leu Tyr Cys Leu Glu Leu Thr Met Asn Phe
305                 310                 315                 320

Asn His Asp Glu Ala Asp Ile Met Glu Gln Glu Val Gly Ala Leu Leu
                325                 330                 335

Ser Arg Leu Arg Tyr Ile Ser Ser Thr Leu Phe Tyr Thr Asp Val Thr
            340                 345                 350
```

```
Tyr Leu Glu Phe Leu Asp Arg Val His Thr Ser Glu Leu Lys Leu Arg
            355                 360                 365

Ala Gln Gly Leu Trp Glu Val Pro His Pro Trp Leu Asn Leu Leu Ile
    370                 375                 380

Pro Arg Ser Thr Val His Lys Phe Ala Lys Glu Val Phe Gly Lys Ile
385                 390                 395                 400

Leu Lys Asp Ser Asn Asn Gly Pro Ile Leu Leu Tyr Pro Val Asn Arg
                405                 410                 415

Thr Lys Trp Asp Asn Arg Thr Ser Val Val Ile Pro Asp Glu Glu Ile
                420                 425                 430

Phe Tyr Leu Val Gly Phe Leu Ser Ser Ala Pro Ser Ser Ser Gly His
                435                 440                 445

Gly Ser Val Glu His Ala Met Asn Leu Asn Asn Lys Ile Val Asp Phe
450                 455                 460

Cys Glu Lys Asn Gly Val Gly Met Lys Gln Tyr Leu Ala Pro Tyr Thr
465                 470                 475                 480

Thr Gln Lys Gln Trp Lys Ala His Phe Gly Ala Arg Trp Glu Thr Phe
                485                 490                 495

Glu Arg Arg Lys His Thr Tyr Asp Pro Leu Ala Ile Leu Ala Pro Gly
                500                 505                 510

Gln Arg Ile Phe Pro Lys Ala Ser Leu Pro Met Ser Leu
                515                 520                 525

<210> SEQ ID NO 49
<211> LENGTH: 532
<212> TYPE: PRT
<213> ORGANISM: Oryza sativa

<400> SEQUENCE: 49

Met Ala Trp Cys Leu Val Phe Met Val Phe Leu Ile Tyr Cys Leu Ile
1               5                   10                  15

Ser Thr Val Gly Leu Pro Val Ala Pro Ala Asp Glu Ala Ala Met Gln
                20                  25                  30

Leu Gly Gly Val Gly Gly Gly Arg Leu Ser Val Glu Pro Ser Asp Val
            35                  40                  45

Met Glu Ala Ser Leu Asp Phe Gly Arg Leu Thr Ser Ala Glu Pro Leu
    50                  55                  60

Ala Val Phe His Pro Arg Gly Ala Gly Asp Val Ala Leu Val Lys
65                  70                  75                  80

Ala Ala Tyr Gly Ser Ala Ser Gly Ile Arg Val Ser Ala Arg Gly His
                85                  90                  95

Gly His Ser Ile Ser Gly Gln Ala Gln Ala Ala Gly Val Val Val
                100                 105                 110

Asp Met Ser His Gly Trp Arg Ala Glu Ala Ala Glu Arg Thr Leu Pro
    115                 120                 125

Val Tyr Ser Pro Ala Leu Gly Gly His Tyr Ile Asp Val Trp Gly Gly
    130                 135                 140

Glu Leu Trp Ile Asp Val Leu Asn Trp Thr Leu Ala His Gly Gly Leu
145                 150                 155                 160

Ala Pro Arg Ser Trp Thr Asp Tyr Leu Tyr Leu Ser Val Gly Gly Thr
                165                 170                 175

Leu Ser Asn Ala Gly Ile Ser Gly Gln Ala Phe His His Gly Pro Gln
            180                 185                 190

Ile Ser Asn Val Tyr Glu Leu Asp Val Val Thr Lys Gly Glu Val Val
            195                 200                 205
```

```
Thr Cys Ser Glu Ser Asn Asn Pro Asp Leu Phe Phe Gly Ala Leu Gly
    210                 215                 220
Gly Leu Gly Gln Leu Gly Ile Ile Thr Arg Ala Arg Ile Ala Leu Glu
225                 230                 235                 240
Pro Ala Pro His Arg Val Arg Trp Ile Arg Ala Leu Tyr Ser Asn Phe
                245                 250                 255
Thr Glu Phe Thr Ala Asp Gln Glu Arg Leu Ile Ser Leu Gln His Gly
            260                 265                 270
Gly Arg Arg Phe Asp Tyr Val Glu Gly Phe Val Val Ala Ala Glu Gly
        275                 280                 285
Leu Ile Asn Asn Trp Arg Ser Ser Phe Phe Ser Pro Gln Asn Pro Val
290                 295                 300
Lys Leu Ser Ser Leu Lys His His Ser Gly Val Leu Tyr Cys Leu Glu
305                 310                 315                 320
Val Thr Lys Asn Tyr Asp Asp Ser Thr Ala Val Thr Val Asp Gln Asp
                325                 330                 335
Val Glu Ala Leu Leu Gly Glu Leu Asn Phe Ile Pro Gly Thr Val Phe
            340                 345                 350
Thr Thr Asp Leu Pro Tyr Val Asp Phe Leu Asp Arg Val His Lys Ala
        355                 360                 365
Glu Leu Lys Leu Arg Gly Lys Gly Met Trp Glu Val Pro His Pro Trp
370                 375                 380
Leu Asn Leu Phe Val Pro Ala Ser Arg Ile Ala Asp Phe Asp Arg Gly
385                 390                 395                 400
Val Phe Arg Gly Val Leu Gly Ser Arg Thr Ala Gly Pro Ile Leu
                405                 410                 415
Ile Tyr Pro Met Asn Arg His Trp Asp Pro Arg Ser Ser Val Val Thr
            420                 425                 430
Pro Glu Glu Asp Val Phe Tyr Leu Val Ala Phe Leu Arg Ser Ala Val
        435                 440                 445
Pro Gly Ser Thr Asp Pro Ala Gln Ser Leu Glu Ala Leu Glu Arg Gln
450                 455                 460
Asn Arg Glu Ile Leu Glu Phe Cys Asp Glu Ala Gly Ile Gly Ala Lys
465                 470                 475                 480
Gln Tyr Leu Pro Asn His Lys Ala Gln Arg Glu Trp Glu Ala His Phe
                485                 490                 495
Gly Ala Arg Trp Ala Arg Phe Ala Arg Leu Lys Ala Glu Phe Asp Pro
            500                 505                 510
Arg Ala Met Leu Ala Thr Gly Gln Gly Ile Phe Asp Ser Pro Pro Leu
        515                 520                 525
Leu Ala Glu Ser
    530

<210> SEQ ID NO 50
<211> LENGTH: 650
<212> TYPE: PRT
<213> ORGANISM: Artificial Sequence
<220> FEATURE:
<223> OTHER INFORMATION: Consensus sequence
<220> FEATURE:
<221> NAME/KEY: VARIANT
<222> LOCATION: 1, 2, 3, 4, 5, 6, 7, 8, 9, 10, 11, 12, 13, 14, 15, 16,
      19, 20, 21, 24, 27, 28, 30, 31, 32, 33, 35, 36, 37, 38, 39,
      40, 41, 42, 43, 45, 47, 48, 50, 51, 52, 53, 54, 55, 56,
      57, 58, 59, 60, 61, 62, 63, 64, 65, 66, 67, 69, 70, 71,
      72
<223> OTHER INFORMATION: Xaa = Any Amino Acid
<220> FEATURE:
<221> NAME/KEY: VARIANT
```

-continued

```
<222> LOCATION: 73, 74, 80, 86, 87, 88, 89, 91, 92, 93, 94, 95, 96, 97,
      98, 105, 107, 108, 112, 116, 118, 119, 121, 122, 123, 124, 125,
      126, 127, 128, 129, 130, 131, 133, 141, 146, 150, 152, 154,
      159, 161, 164, 165, 166, 167, 168, 169, 170, 171, 172
<223> OTHER INFORMATION: Xaa = Any Amino Acid
<220> FEATURE:
<221> NAME/KEY: VARIANT
<222> LOCATION: 174, 175, 177, 178, 179, 180, 181, 183, 184, 185, 186,
      187, 192, 195, 203, 209, 247, 263, 264, 265, 295, 308, 309, 312,
      316, 320, 321, 322, 323, 324, 325, 326, 327, 328, 329, 330,
      331, 332, 344, 345, 346, 347, 348, 349, 350, 351, 352
<223> OTHER INFORMATION: Xaa = Any Amino Acid
<220> FEATURE:
<221> NAME/KEY: VARIANT
<222> LOCATION: 353, 354, 355, 356, 357, 358, 362, 369, 371, 373, 374,
      378, 380, 381, 382, 383, 384, 385, 397, 398, 399, 400, 401, 402,
      403, 404, 405, 406, 407, 408, 409, 410, 411, 418, 421, 422,
      424, 427, 429, 432, 433, 446, 447, 454, 458, 473, 475
<223> OTHER INFORMATION: Xaa = Any Amino Acid
<220> FEATURE:
<221> NAME/KEY: VARIANT
<222> LOCATION: 478, 479, 487, 488, 489, 490, 491, 492, 508, 516, 517,
      518, 519, 520, 521, 533, 536, 537, 538, 539, 540, 541, 542, 543,
      544, 545, 546, 547, 548, 549, 552, 555, 556, 558, 562, 566,
      581, 582, 585, 587, 591, 598, 599, 620, 621, 622, 623
<223> OTHER INFORMATION: Xaa = Any Amino Acid
<220> FEATURE:
<221> NAME/KEY: VARIANT
<222> LOCATION: (624)...(650)
<223> OTHER INFORMATION: Xaa = any amino acid

<400> SEQUENCE: 50

Xaa Xaa Xaa Xaa Xaa Xaa Xaa Xaa Xaa Xaa Xaa Xaa Xaa Xaa Xaa
 1               5                  10                  15

Leu Leu Xaa Xaa Xaa Leu Leu Xaa Leu Leu Xaa Xaa Leu Xaa Xaa Xaa
            20                  25                  30

Xaa Ala Xaa Xaa Xaa Xaa Xaa Xaa Xaa Xaa Ser Xaa Leu Xaa Xaa
        35                  40                  45

Leu Xaa Xaa Xaa Xaa Xaa Xaa Xaa Xaa Xaa Xaa Xaa Xaa Xaa Xaa
 50                  55                  60

Xaa Xaa Xaa Leu Xaa Xaa Xaa Xaa Xaa Val Ala Ala Ser Xaa
 65                  70                  75                  80

Asp Phe Gly Asn Ile Xaa Xaa Xaa Xaa Pro Xaa Xaa Xaa Xaa Xaa
                    85                  90                  95

Xaa Xaa Ala Ala Val Leu His Pro Xaa Ser Xaa Xaa Asp Ile Ala Xaa
                100                 105                 110

Leu Leu Arg Xaa Ala Xaa Xaa Ser Xaa Xaa Xaa Xaa Xaa Xaa Xaa
            115                 120                 125

Xaa Xaa Xaa Ser Xaa Leu Thr Val Ala Ala Arg Gly Xaa Gly His Ser
130                 135                 140

Leu Xaa Gly Gln Ala Xaa Ala Xaa Gly Xaa Gly Val Val Val Xaa Met
145                 150                 155                 160

Xaa Ser Leu Xaa Xaa Xaa Xaa Xaa Xaa Xaa Xaa Val Xaa Xaa Val
                165                 170                 175

Xaa Xaa Xaa Xaa Xaa Gly Xaa Xaa Xaa Xaa Xaa Tyr Val Asp Val Xaa
                180                 185                 190

Gly Gly Xaa Leu Trp Ile Asp Val Leu Arg Xaa Thr Leu Lys His Gly
            195                 200                 205

Xaa Leu Ala Pro Arg Ser Trp Thr Asp Tyr Leu His Leu Thr Val Gly
210                 215                 220

Gly Thr Leu Ser Asn Ala Gly Ile Ser Gly Gln Ala Phe Arg His Gly
225                 230                 235                 240

Pro Gln Ile Ser Asn Val Xaa Glu Leu Asp Val Val Thr Gly Lys Gly
                245                 250                 255
```

```
Glu Ile Val Thr Cys Ser Xaa Xaa Xaa Asn Ser Asp Leu Phe Phe Ala
                260                 265                 270

Val Leu Gly Gly Leu Gly Gln Phe Gly Ile Ile Thr Arg Ala Arg Ile
            275                 280                 285

Ala Leu Glu Pro Ala Pro Xaa Arg Val Arg Trp Ile Arg Val Leu Tyr
290                 295                 300

Ser Asp Phe Xaa Xaa Phe Thr Xaa Asp Gln Glu Xaa Leu Ile Ser Xaa
305                 310                 315                 320

Xaa Xaa Xaa Xaa Xaa Xaa Xaa Xaa Xaa Xaa Phe Asp Tyr Val
                325                 330                 335

Glu Gly Phe Val Ile Ile Asn Xaa Xaa Xaa Xaa Xaa Xaa Xaa
                340                 345                 350

Xaa Xaa Xaa Xaa Xaa Xaa Ile Leu Asn Xaa Trp Arg Ser Phe Phe
                355                 360                 365

Xaa Pro Xaa Asp Xaa Xaa Arg Ile Ser Xaa Leu Xaa Xaa Xaa Xaa
370                 375                 380

Xaa Val Leu Tyr Cys Leu Glu Val Ala Lys Tyr Tyr Xaa Xaa Xaa
385                 390                 395                 400

Xaa Xaa Xaa Xaa Xaa Xaa Xaa Xaa Xaa Val Asp Gln Glu Val
                405                 410                 415

Glu Xaa Leu Leu Xaa Xaa Leu Xaa Phe Ile Xaa Gly Xaa Leu Phe Xaa
                420                 425                 430

Xaa Asp Val Thr Tyr Val Asp Phe Leu Asp Arg Val His Xaa Xaa Glu
            435                 440                 445

Leu Lys Leu Arg Ala Xaa Gly Leu Trp Xaa Glu Val Pro His Pro Trp
450                 455                 460

Leu Asn Leu Phe Val Pro Arg Ser Xaa Ile Xaa Asp Phe Xaa Xaa Gly
465                 470                 475                 480

Val Phe Lys Gly Ile Leu Xaa Xaa Xaa Xaa Xaa Gly Gly Pro Ile
                485                 490                 495

Leu Ile Tyr Pro Val Asn Arg Ser Lys Trp Asp Xaa Arg Thr Ser Val
                500                 505                 510

Val Ile Pro Xaa Xaa Xaa Xaa Xaa Asp Glu Val Phe Tyr Leu
            515                 520                 525

Val Gly Leu Leu Xaa Ser Ala Xaa Xaa Xaa Xaa Xaa Xaa Xaa
            530                 535                 540

Xaa Xaa Xaa Xaa Xaa Val Glu Xaa Leu Leu Xaa Xaa Asn Xaa Arg Ile
545                 550                 555                 560

Leu Xaa Phe Cys Glu Xaa Ala Gly Ile Gly Val Lys Gln Tyr Leu Pro
            565                 570                 575

His Tyr Thr Thr Xaa Xaa Glu Trp Xaa Arg Xaa His Phe Gly Xaa Ala
                580                 585                 590

Arg Trp Asp Arg Phe Xaa Xaa Arg Lys Ala Arg Tyr Asp Pro Lys Ala
                595                 600                 605

Ile Leu Ala Pro Gly Gln Arg Ile Phe Gln Lys Xaa Xaa Xaa Xaa
            610                 615                 620

Xaa Xaa Xaa Xaa Xaa Xaa Xaa Xaa Xaa Xaa Xaa Xaa Xaa Xaa Xaa
625                 630                 635                 640

Xaa Xaa Xaa Xaa Xaa Xaa Xaa Xaa Xaa Xaa
                645                 650

<210> SEQ ID NO 51
<211> LENGTH: 7366
<212> TYPE: DNA
```

```
<213> ORGANISM: Zea mays
<220> FEATURE:
<221> NAME/KEY: misc_feature
<222> LOCATION: (1)...(7366)
<223> OTHER INFORMATION: ZmCkx6 genomic sequence

<400> SEQUENCE: 51
aaaaactgtg cagctagcta agagaagctg aaaaacagtt ttttttttta aaaaaaatct       60
gtctactctt agagcatctc caacaacgtg acctataaaa ttgccctata atttgaaaat      120
aagtatattt tatagaattt agggcaccaa caaaacacct cgctccaaca gtaaagtccc      180
aaatctagat tatagggcag accactacag tgtagtatat ttgagtcact tgagagggtg      240
ctctatagtt ttttgacaaa aaattatgaa atatggcact gttggagtag ttttcctgt       300
gtagagccct atatttcaat tttaggcact agtttaaggc attgttggag atgctcttat      360
tttttaacga aaagctgaaa aactggcctt cgattgataa aaaacattc agattaataa       420
tgttgtgagt ggtacctatg ccttctctta tttttttctt aatgatttat gagaaactat      480
aaattcttat attaacatat agagaaaaag gctctttgtt ttgcgaccga gcgagggagt      540
atacacggat acaccggtac ctccgctccg cacgtacctg gaggctggag cagacgtttg      600
actgggacgc gccgagtgtc cggccaatga gagcgacgca cgtagcgcgg gggcgccgct      660
gcggcggcac atcatcacgt gcatgcggcc acgcgcgcgg gcgacagaca acgcgcgagc      720
gacaggtcga cccccgtggc cgaaccgaat cgcgtagggg atctcgacct atggcagcaa      780
atttaacgcc gcgttccggt ggcggtcccg ctccagcgat ggccgcgtac cgtacctacg      840
gcgaccagac cacgggataa tgcgtgcgat tgttcttttg ggtggggag aatgctcgat       900
cgatcgcaaa tgccggtgct ccccggccgt tcgtcgtcgg ccggtcgatc acaggtacat      960
actggcagta aaaacagacg tgcaggttcc cgacctgtca tcgtattata ttcggcgtta     1020
ctgacaccat ggcaatggca tgcatggtac gaagccaagt aaggagcaga cgtgttcgta     1080
cgcctgtcgt cgtcttcgcg cgcgcgccca cgagcagcat gtctcacgcg cccagcaaat     1140
tcgcgcgcgc ggatgcagcc cgatcggtta tattcgatcg gttataatgc atcatcgtca     1200
acggcgtcaa acaacgcga gagaggacac ctacattttt cccctccgga aattaatctt      1260
aaaatttgcg cctcttatgc tattaatata cgtattaaaa tttgtataat ttaaaactca     1320
aaaaacattg ccaaatgcat tgacgcgatt aaaaagttaa aaaacaaaa aggataagaa      1380
taagtgtagc tacttttgaa ctttaaaacg tggtaaggct acagtgcagc tacctttgtc     1440
tagttactgc ctcgtgcgtg gaagattaga attccaccta gagtacgttt ttttccttct     1500
ttttgttagt tattactaac aataaagttc taactagaga caatttggct aattaaaaga     1560
aggaaagcag aggatgcaag ctgcctgttc tgtacagagc tgaatatgc acgtcatctc      1620
tgaagttact aaccgtaatt taggagagaa aatatagcag agacaggaaa atcgttcggt     1680
gtatctggaa actcacgaat gagttatgtt ttcagagaaa cttgctcgag aagcatggag     1740
ctgttactac acacgcgata agcggacttt cacagaaatg gaaaacttta cgcccgccag     1800
aaacgaaaga gcaattggag atcagatcac cgtggagaaa aataatagcg tgtttggttt     1860
gtaggttggg ctgcttctgg agccatccag acctgtgtcc gagcctacat cagcgtttgg     1920
tttgaatcgc agaatgatgt cgtccgccac tgtattgttc taataataaa ctagcatgcg     1980
ggttcaactc actccacaag gaactgccgg acggctccat ccggagccaa gccacgacgg     2040
atgagcgaaa ccgccggacc aaacgcgctg taaaagaatg cagataggtt aggttttggg     2100
agttgtgtga tcttcagctt tctgccgata ggctgtctgt aagaggtctt tcagttttgt     2160
```

```
ttggttctgt ttctggttgg aaccagttcc cttggcctca ggcttcagca caagtctagg    2220
tgtgatttaa actgcactgt attgaatact ttagtctttt gacaatactg tagttaaaag    2280 gccgggggt tttgccttgg aactctaaaa aaatatacag tattaaccat ggactctgaa     2340
ctctgtctgc gtccacaggc aagtcatctt tcttccttgc actggttatc ttattgaaac    2400
agaacggaaa tcttttttgg aacaagagaa tttcgtcaca tcttgcctgc agtaaagttt    2460
cccatctaga tgcatactcc ctccgtccaa gttttactgg cgttttagct tttctcagac    2520
ataaatacca gccaagagaa tagacgcatg tacccctgtg atctagcgtg aagtattaat    2580
tgcaattact gctgaggaca cgaaacggtt cacaacctcc agccctccac ggtggatgag    2640
aggagaccaa gagtccgttg gtgtgggaac gaagcgaacg ggtgtgtgaa acgaggagat    2700
aactataatg gcatcgaggt gtagaccacg aacgacacat aattctggac aaataaaatg    2760
agctaaaacg ccattaaact tggacggagg gagtatacta tcaacatttc gatcaaaagt    2820
tactatacaa aatttgcact gtccgaaaag cgatccttat caggaaggcg caggattcgt    2880
cccagctaag cgcaccggcc acaagtattc caccaccccc ggtcaatagc taaagaaatt    2940
gggcggcaag tgaaagtctc cgggatggga atgtgcatga gtcatgacgc gcctccgccc    3000
tccggcctcc gcagttgttt attcgcagcg cgcgggtggc ggcccgcccg tccgtgttct    3060
ctgctccctg tgttcggcac atcgtcaccc ccaccgtttc ctgtgcctct ctctcctatc    3120
ttcctcggtc tcctcccgta atcctttgcc tgataccccg ctctaccagg ccgccaccac    3180
ctccctccag gctccagcag cctataaata cgcccgcgtc gcccaccacc gcacaccact    3240
tgaatactcc atctcaactt cccttcctct cccgtgctgc gctgagctat atagctgctc    3300
ctcgacctcc aagaagcacg cgggcggagc ccggagcgag tgattagtga aaggcatagc    3360
ataaggccgc ccggccggga agtggtggca atgacgcggt gcctcatgtt cacgctgctg    3420
ttcctcgtct cctccctcat ctccaccgtg gggctcccg tcgagccgcc cgcggagctc     3480
ctgcagctgg gcggcgggga cgtcggcggc gggcgcctga cgtcgacgc gtccgacatc     3540 gcggaggcgt cgcgcgactt cggggggcgtc gcccgcgccg agcccatggc ggtgttccat    3600
ccgcgcgcgg ccggcgacgt ggcgggcctg gtcggcgccg cgttccggtc ggcgcgcggc    3660
ttccgcgtct cggcgcgggg ccacggccac tccatcagcg gccaggcgca ggcggccggc    3720
ggcgtggtcg tggacatgag ccgcggccgc ggccccggcg ccgccgtggc gcgggcattg    3780
cccgtgcact cggcggcgct gggcgggcac tacgtggacg tctggggcgg cgagctgtgg    3840
gtggacgtgc tcaactggac gctgtcccac ggcgggctgg cgccgcggtc gtggacggac    3900
tacctgtacc tgtccgtggg cggcaccctc tccaacgccg gcatcagcgg gcaggcgttc    3960
caccacgggc cacagatcag caatgtctac gagctcgacg tcgtcacagg tagcgtagca    4020
gctagctagg cgatcgagcc ggccgacgag tcgtagatgc aaggcgctgt ctctggcggg    4080
ccgatcgacg aatgaaccga ctgactgaca cacgtgcgct gtgcgttggc agggaaggga    4140
gaggtggtga cctgctcgga gacggagaac ccggacctgt tcttcggcgt cctgggcggg    4200
ctgggccagt tcggcatcat cacgcggggcg cgcatcgccc tggagcgtgc tcccaagagg    4260
gtaagtaaac agcttaggca gcccacaact gcgttctcct cgctcccttc tgctctctgt    4320
cgtgtctgga cctcccttca ggcgcgcgcc ctgatggatc accacctgca ccgattagat    4380
agcctttaat ttccctcccg tgagtcgtgt ctcgatcgtg tggcaccggg aaaggaacac    4440 agggcgggc gggcagtgca tctcctcccg tggcgtgtgt caccggcctc gctttccaac     4500
taatgaccga cccagcacac cggccggcca tgcaagtggc gagcgagcgc gctgctgatc    4560
```

```
cgttgaggaa agcgcccctc tgccgtccgc taataaaacg gctgccacat gtgtagcgtc    4620
cgaaaaaaga tccacgcgta gtacgtgtac gtcttgataa tcgccactgt agtatccgtg    4680
ggtctatcta taagcagggc ccccagccgc ccgggccagc catggccagt ccgacacata    4740
cgtacgcgtc atccggtcag gtgcatggtc cacggtgccc ctgctcaacg attagccgcc    4800
gccgccgtgt cgtcgtcatc gagtccgcct ttttcttttt gtttagctcg tgggatcttt    4860
cgcaagattt tgttcctctg ctaattaatc ggcctgtaat cttagtagca gctaagaatt    4920
gacgggcgga atgcatgggt ggtggtggtg gtggtggttg cttgcaggtt cggtggatcc    4980
gggcgctcta ctccaacttc agcgagttca cggcggacca ggagcgcctc atctccctcg    5040
gcagcggcgg cggacgccgg ttcgactacg tggagggctt cgtcgtcgcc gccgagggcc    5100
tcatcaacaa ctggaggtcc tccttcttct cgccgcagaa ccccgtgaag ctcacctcgc    5160
tcaagcacca ttccagcgtc ctctactgcc tcgaggtcac caagaactac gacgacgaaa    5220
ccgcagggtc ggtcgaccag gtaggtactc ggactcggag ccttgctttt cagttactag    5280
ccgtatgata acagtagcag gcagtgtact gtgtgtgcta atattttct tcttctctcc     5340 gttcaggacg tggatacgct gctgggcgag ctgaacttcc tccctggcac ggtgttcact    5400
acggacctgc cgtacgtgga cttcctggac cgcgtgcaca aggcggagct gaagctgcgc    5460
gccaagggga tgtgggaggt gccgcacccg tggctcaacc tcttcgtgcc ggcgtcccgc    5520
atcgccgact tcgaccgcgg cgtcttccgt ggcgtgctgg ggggccgcac cgccggcgcc    5580
ggcggccccg tcctcatcta ccccatgaac aagcacaagt aagtcgtcaa atcacaaagg    5640
cacacacgga ccacaagcca aaggccgcgc gcgctcatcg atctgccgcc acgcacgcgg    5700
aggcgcggcg cgtcgccctc gccgtccccg ccccgcccc gcgcttccaa ccaaccaacc     5760
ttccattcca ttccatccac atgcggcgct cgggacacgg ggacaggcgg acagcaccct    5820
ccctcacatg cgccgcccac acgcggacgg caccgcacgc gcagcgcagg tgccggctcg    5880
ctcatgtgtc atgtgttgcg attgcgatgg acttgtgccg cccattattg gcgccacgca    5940
cgcaaatcac cagccagccc atccgtagca gcggattatt atttgcccaa ctgcgcgagc    6000
cgaatctgga gccccgatag atagaatggc cgtggacaaa ccgcgcactc gcgcgacagg    6060
gcctactcta ttctgttgca atggacgcca cgcaactgcg gccggtgacg ccgacctgcc    6120
atttataaac cggcgccgcg acgagagctt tacagggcgc aacgagctcg gagcggtcag    6180
aatcggaatt ccttagctga gacctgctcg ccttttagta ctttgtttgc attggggtca    6240
gtgggccggg tagacgccta gacggcacca atttgtttgt tgctttcagc ttcagcgcat    6300
acacaaccaa cctaaaaaaa agacgtatca gaatcaccag acgatcctgc taaaaaccgc    6360
tgctttttta tttatttttt cccgtactct attctgtact agtatcgtgc agtatcccaa    6420
acccttttcg cgtcgattag cgactgcagc tctgagatct ggactgggcc gtgtggctga    6480
cgggctgctt cgtgcgcgca ggtgggaccc gaggagctcg gcggtgaccc cggacgagga    6540
ggtgttctac ctggtggcgt tcctgcggtc ggcgctgccg ggcgcgccgg agagcctgga    6600
ggcgctggcg cggcagaacc agcggatcct cgacttctgc gcgggcgcgg gcatcggcgc    6660
caagcagtac ctgccgggcc acaaggcgcg gcacgagtgg gcggagcact cggcgccgc     6720 gaggtgggac cggttcgcga ggctcaaggc cgagttcgac ccgcgggcca tcctggcgg     6780 ggggcagggc atcttcaggc cgcccggctc gccggcgctc gcggccgact cgtaacgtaa    6840
tccagctgct tatactaatt attaggcgcg tttagtgtaa ggtagaggta ctagctacag    6900
cagtaaccat acaggattgt ttagttagct ccggttggtt catgtacaaa tgtggggttg    6960
```

-continued

```
ttaatcgcgt gctctgccat ggctgctgtg atcggttctg tacaggggat gagggagcc      7020 aaatatgaac gtggcaaaat cgatacttct tataaagaaa aaatatctat ggtaaatact      7080
ggtgcctgcc tctgtttccc gtcaaactac agtgcagtgt attgttttct ccgtggtcca      7140
ctggatataa ggcattgcct gcaccttcat cctaaattat aattcatttg actttttctg      7200
tcacgtttga ccgatcttcc tatttattta ttttttaaaa taaatgaaaa ctcaaatata      7260
aagtatatta tgtgctaaac aatattacga taaaaaaata acaataatta tgatattttt      7320
taattcgaac gggttttcca agcacaaaaa cgcatatata tgtatg                    7366

<210> SEQ ID NO 52
<211> LENGTH: 1623
<212> TYPE: DNA
<213> ORGANISM: Zea mays
<220> FEATURE:
<221> NAME/KEY: CDS
<222> LOCATION: (1)...(1623)

<400> SEQUENCE: 52 atg acg cgg tgc ctc atg ttc acg ctg ctg ttc ctc gtc tcc tcc ctc      48
Met Thr Arg Cys Leu Met Phe Thr Leu Leu Phe Leu Val Ser Ser Leu
 1               5                  10                  15 atc tcc acc gtg ggg ctc ccc gtc gag ccg ccc gcg gag ctc ctg cag      96
Ile Ser Thr Val Gly Leu Pro Val Glu Pro Pro Ala Glu Leu Leu Gln
             20                  25                  30 ctg ggc ggc ggg gac gtc ggc ggc ggg cgc ctg agc gtc gac gcg tcc     144
Leu Gly Gly Gly Asp Val Gly Gly Gly Arg Leu Ser Val Asp Ala Ser
         35                  40                  45 gac atc gcg gag gcg tcg cgc gac ttc ggg ggc gtc gcc cgc gcc gag     192
Asp Ile Ala Glu Ala Ser Arg Asp Phe Gly Gly Val Ala Arg Ala Glu
     50                  55                  60 ccc atg gcg gtg ttc cat ccg cgc gcg gcc ggc gac gtg gcg ggc ctg     240
Pro Met Ala Val Phe His Pro Arg Ala Ala Gly Asp Val Ala Gly Leu
 65                  70                  75                  80 gtc ggc gcc gcg ttc cgg tcg gcg cgc ggc ttc cgc gtc tcg gcg cgg     288
Val Gly Ala Ala Phe Arg Ser Ala Arg Gly Phe Arg Val Ser Ala Arg
                 85                  90                  95 ggc cac ggc cac tcc atc agc ggc cag gcg cag gcg gcc ggc ggc gtg     336
Gly His Gly His Ser Ile Ser Gly Gln Ala Gln Ala Ala Gly Gly Val
            100                 105                 110 gtc gtg gac atg agc cgc ggc cgc ggc ccc ggc gcc gcc gtg gcg cgg     384
Val Val Asp Met Ser Arg Gly Arg Gly Pro Gly Ala Ala Val Ala Arg
        115                 120                 125 gca ttg ccc gtg cac tcg gcg gcg ctg ggc ggg cac tac gtg gac gtc     432
Ala Leu Pro Val His Ser Ala Ala Leu Gly Gly His Tyr Val Asp Val
    130                 135                 140 tgg ggc ggc gag ctg tgg gtg gac gtg ctc aac tgg acg ctg tcc cac     480
Trp Gly Gly Glu Leu Trp Val Asp Val Leu Asn Trp Thr Leu Ser His
145                 150                 155                 160 ggc ggg ctg gcg ccg cgg tcg tgg acg gac tac ctg tac ctg tcc gtg     528
Gly Gly Leu Ala Pro Arg Ser Trp Thr Asp Tyr Leu Tyr Leu Ser Val
                165                 170                 175 ggc ggc acc ctc tcc aac gcc ggc atc agc ggg cag gcg ttc cac cac     576
Gly Gly Thr Leu Ser Asn Ala Gly Ile Ser Gly Gln Ala Phe His His
            180                 185                 190 ggg cca cag atc agc aat gtc tac gag ctc gac gtc gtc aca ggg aag     624
Gly Pro Gln Ile Ser Asn Val Tyr Glu Leu Asp Val Val Thr Gly Lys
        195                 200                 205 gga gag gtg gtg acc tgc tcg gag acg gag aac ccg gac ctg ttc ttc     672
Gly Glu Val Val Thr Cys Ser Glu Thr Glu Asn Pro Asp Leu Phe Phe
    210                 215                 220
```

```
ggc gtc ctg ggc ggg ctg ggc cag ttc ggc atc atc acg cgg gcg cgc      720
Gly Val Leu Gly Gly Leu Gly Gln Phe Gly Ile Ile Thr Arg Ala Arg
225                 230                 235                 240 atc gcc ctg gag cgt gct ccc aag gtt cgg tgg atc cgg gcg ctc tac      768
Ile Ala Leu Glu Arg Ala Pro Lys Val Arg Trp Ile Arg Ala Leu Tyr
                245                 250                 255 tcc aac ttc agc gag ttc acg gcg gac cag gag cgc ctc atc tcc ctc      816
Ser Asn Phe Ser Glu Phe Thr Ala Asp Gln Glu Arg Leu Ile Ser Leu
            260                 265                 270 ggc agc ggc ggc gga cgc cgg ttc gac tac gtg gag ggc ttc gtc gtc      864
Gly Ser Gly Gly Gly Arg Arg Phe Asp Tyr Val Glu Gly Phe Val Val
        275                 280                 285 gcc gcc gag ggc ctc atc aac aac tgg agg tcc tcc ttc ttc tcg ccg      912
Ala Ala Glu Gly Leu Ile Asn Asn Trp Arg Ser Ser Phe Phe Ser Pro
    290                 295                 300 cag aac ccc gtg aag ctc acc tcg ctc aag cac cat tcc agc gtc ctc      960
Gln Asn Pro Val Lys Leu Thr Ser Leu Lys His His Ser Ser Val Leu
305                 310                 315                 320 tac tgc ctc gag gtc acc aag aac tac gac gac gaa acc gca ggg tcg     1008
Tyr Cys Leu Glu Val Thr Lys Asn Tyr Asp Asp Glu Thr Ala Gly Ser
                325                 330                 335 gtc gac cag gac gtg gat acg ctg ctg ggc gag ctg aac ttc ctc cct     1056
Val Asp Gln Asp Val Asp Thr Leu Leu Gly Glu Leu Asn Phe Leu Pro
            340                 345                 350 ggc acg gtg ttc act acg gac ctg ccg tac gtg gac ttc ctg gac cgc     1104
Gly Thr Val Phe Thr Thr Asp Leu Pro Tyr Val Asp Phe Leu Asp Arg
        355                 360                 365 gtg cac aag gcg gag ctg aag ctg cgc gcc aag ggg atg tgg gag gtg     1152
Val His Lys Ala Glu Leu Lys Leu Arg Ala Lys Gly Met Trp Glu Val
    370                 375                 380 ccg cac ccg tgg ctc aac ctc ttc gtg ccg gcg tcc cgc atc gcc gac     1200
Pro His Pro Trp Leu Asn Leu Phe Val Pro Ala Ser Arg Ile Ala Asp
385                 390                 395                 400 ttc gac cgc ggc gtc ttc cgt ggc gtg ctg ggg ggc cgc acc gcc ggc     1248
Phe Asp Arg Gly Val Phe Arg Gly Val Leu Gly Gly Arg Thr Ala Gly
                405                 410                 415 gcc ggc ggc ccc gtc ctc atc tac ccc atg aac aag cac aag tgg gac     1296
Ala Gly Gly Pro Val Leu Ile Tyr Pro Met Asn Lys His Lys Trp Asp
            420                 425                 430 ccg agg agc tcg gcg gtg acc ccg gac gag gag gtg ttc tac ctg gtg     1344
Pro Arg Ser Ser Ala Val Thr Pro Asp Glu Glu Val Phe Tyr Leu Val
        435                 440                 445 gcg ttc ctg cgg tcg gcg ctg ccg ggc gcg ccg gag agc ctg gag gcg     1392
Ala Phe Leu Arg Ser Ala Leu Pro Gly Ala Pro Glu Ser Leu Glu Ala
    450                 455                 460 ctg gcg cgg cag aac cag cgg atc ctc gac ttc tgc gcg ggc gcg ggc     1440
Leu Ala Arg Gln Asn Gln Arg Ile Leu Asp Phe Cys Ala Gly Ala Gly
465                 470                 475                 480 atc ggc gcc aag cag tac ctg ccg ggc cac aag gcg cgg cac gag tgg     1488
Ile Gly Ala Lys Gln Tyr Leu Pro Gly His Lys Ala Arg His Glu Trp
                485                 490                 495 gcg gag cac ttc ggc gcc gcg agg tgg gac cgg ttc gcg agg ctc aag     1536
Ala Glu His Phe Gly Ala Ala Arg Trp Asp Arg Phe Ala Arg Leu Lys
            500                 505                 510 gcc gag ttc gac ccg cgg gcc atc ctg gcg gcg ggg cag ggc atc ttc     1584
Ala Glu Phe Asp Pro Arg Ala Ile Leu Ala Ala Gly Gln Gly Ile Phe
        515                 520                 525 agg ccg ccc ggc tcg ccg gcg ctc gcg gcc gac tcg taa                 1623
Arg Pro Pro Gly Ser Pro Ala Leu Ala Ala Asp Ser
530                 535                 540
```

<210> SEQ ID NO 53
<211> LENGTH: 540
<212> TYPE: PRT
<213> ORGANISM: Zea mays

<400> SEQUENCE: 53

```
Met Thr Arg Cys Leu Met Phe Thr Leu Leu Phe Leu Val Ser Ser Leu
  1               5                  10                  15

Ile Ser Thr Val Gly Leu Pro Val Glu Pro Pro Ala Glu Leu Leu Gln
             20                  25                  30

Leu Gly Gly Gly Asp Val Gly Gly Arg Leu Ser Val Asp Ala Ser
         35                  40                  45

Asp Ile Ala Glu Ala Ser Arg Asp Phe Gly Gly Val Ala Arg Ala Glu
 50                  55                  60

Pro Met Ala Val Phe His Pro Arg Ala Ala Gly Asp Val Ala Gly Leu
 65                  70                  75                  80

Val Gly Ala Ala Phe Arg Ser Ala Arg Gly Phe Arg Val Ser Ala Arg
                 85                  90                  95

Gly His Gly His Ser Ile Ser Gly Gln Ala Gln Ala Ala Gly Gly Val
            100                 105                 110

Val Val Asp Met Ser Arg Gly Arg Gly Pro Gly Ala Ala Val Ala Arg
        115                 120                 125

Ala Leu Pro Val His Ser Ala Ala Leu Gly Gly His Tyr Val Asp Val
130                 135                 140

Trp Gly Gly Glu Leu Trp Val Asp Val Leu Asn Trp Thr Leu Ser His
145                 150                 155                 160

Gly Gly Leu Ala Pro Arg Ser Trp Thr Asp Tyr Leu Tyr Leu Ser Val
                165                 170                 175

Gly Gly Thr Leu Ser Asn Ala Gly Ile Ser Gly Gln Ala Phe His His
            180                 185                 190

Gly Pro Gln Ile Ser Asn Val Tyr Glu Leu Asp Val Thr Gly Lys
        195                 200                 205

Gly Glu Val Val Thr Cys Ser Glu Thr Glu Asn Pro Asp Leu Phe Phe
210                 215                 220

Gly Val Leu Gly Gly Leu Gly Gln Phe Gly Ile Ile Thr Arg Ala Arg
225                 230                 235                 240

Ile Ala Leu Glu Arg Ala Pro Lys Val Arg Trp Ile Arg Ala Leu Tyr
                245                 250                 255

Ser Asn Phe Ser Glu Phe Thr Ala Asp Gln Glu Arg Leu Ile Ser Leu
            260                 265                 270

Gly Ser Gly Gly Gly Arg Arg Phe Asp Tyr Val Glu Gly Phe Val Val
        275                 280                 285

Ala Ala Glu Gly Leu Ile Asn Asn Trp Arg Ser Ser Phe Phe Ser Pro
290                 295                 300

Gln Asn Pro Val Lys Leu Thr Ser Leu Lys His His Ser Ser Val Leu
305                 310                 315                 320

Tyr Cys Leu Glu Val Thr Lys Asn Tyr Asp Asp Glu Thr Ala Gly Ser
                325                 330                 335

Val Asp Gln Asp Val Asp Thr Leu Leu Gly Glu Leu Asn Phe Leu Pro
            340                 345                 350

Gly Thr Val Phe Thr Thr Asp Leu Pro Tyr Val Asp Phe Leu Asp Arg
        355                 360                 365

Val His Lys Ala Glu Leu Lys Leu Arg Ala Lys Gly Met Trp Glu Val
370                 375                 380
```

```
Pro His Pro Trp Leu Asn Leu Phe Val Pro Ala Ser Arg Ile Ala Asp
385                 390                 395                 400

Phe Asp Arg Gly Val Phe Arg Gly Val Leu Gly Gly Arg Thr Ala Gly
            405                 410                 415

Ala Gly Gly Pro Val Leu Ile Tyr Pro Met Asn Lys His Lys Trp Asp
        420                 425                 430

Pro Arg Ser Ser Ala Val Thr Pro Asp Glu Glu Val Phe Tyr Leu Val
        435                 440                 445

Ala Phe Leu Arg Ser Ala Leu Pro Gly Ala Pro Glu Ser Leu Glu Ala
    450                 455                 460

Leu Ala Arg Gln Asn Gln Arg Ile Leu Asp Phe Cys Ala Gly Ala Gly
465                 470                 475                 480

Ile Gly Ala Lys Gln Tyr Leu Pro Gly His Lys Ala Arg His Glu Trp
                485                 490                 495

Ala Glu His Phe Gly Ala Ala Arg Trp Asp Arg Phe Ala Arg Leu Lys
            500                 505                 510

Ala Glu Phe Asp Pro Arg Ala Ile Leu Ala Ala Gly Gln Gly Ile Phe
        515                 520                 525

Arg Pro Pro Gly Ser Pro Ala Leu Ala Ala Asp Ser
        530                 535                 540

<210> SEQ ID NO 54
<211> LENGTH: 1617
<212> TYPE: DNA
<213> ORGANISM: Zea mays
<220> FEATURE:
<221> NAME/KEY: misc_feature
<222> LOCATION: (1)...(1617)
<223> OTHER INFORMATION: ZmCkx3 cds

<400> SEQUENCE: 54
atggcaagaa ggactcgttt cgtggccatc gccgccctcc tcacaagctt cctcaacgtc      60
gcagccgggc attcccggcc actgtccggt gccggcctcc cgggcgatct tttcgggctg     120
ggcatcgcgt cgaggatccg cacggacagc aactcgacgg cgaaggcggc gacggacttc     180
ggccagatgg tgagggccgc gccggaggcc gtgttccacc ccgccacgcc ggccgacatc     240
gccgcgctcg tccggttctc cgccacgtcg cgggcgccgt tcccgttgc gccgcgcggg      300 cagggccact cctggcgcgg ccaggcgctc gccccgggcg cgtcgtcgt ggacatgggc      360 tcgctgggc gcggccccg catcaacgtg tccgccgtgg ccggcgcgga ccgttcgtc       420 gacgccggcg gggagcagct gtgggtcgac gtcctccgcg ccacgctgcg acacggcctg     480
gcgccccgcg tgtggaccga ctacctccgg ctcaccgtcg gcggcacgct ctccaacgcg     540
ggaatcggcg gcaggcgtt ccgacacggt ccgcagatcg ccaacgtgca tgaactcgac      600
gtcgtcacag gcacaggtga gatggtgaca tgctccatgg acgtgaactc ggacctgttc     660
atggcggctc taggcgggtt aggccagttc ggggtcataa ccagagcacg gatccggctt     720
gagccggcgc caagagggt gcgctgggtt cgacttgcct acaccgacgt cgctactttc      780
accaaggatc aggagtttct catatcaaac cgggctagcc aagtcgggtt cgactacgtc     840
gaaggccagg tccagctcag ccggtccttg gtcgaaggcc ccaaatcaac acccttcttc     900
tccggcgccg atgttgctag gcttgctgga ctcgcgtcca ggaccggacc tgctgcaatc     960
tactacatcg aaggcgccat gtactacacc aaggacaccg ccatatctgt ggacaagaaa    1020
atgaaggcac tcctggatca gctgagcttc gagccagggg ttgcgttcac caaggacgtg    1080
acgttcgtgc agttcctcga tcgggtgcgc gaggaggaga gggtgctccg gtcagccggc    1140
```

| | |
|---|---|
| gcgtgggagg tgccgcaccc atggctgaac ctcttcgtcc cacggtcgcg catcctcgac | 1200 |
| ttcgacgacg gagtgttcaa ggctctgctc aaggactcca acccagctgg gatcatcctc | 1260 |
| atgtacccca tgaacaagga taggtgggac gaccggatga cagcgatgac cccagccacg | 1320 |
| gacgacgacg acatgttcta tgccgttagt ttcctttggt cagcactgtc cgcagacgac | 1380 |
| gtgcccccagc tcgagagatg gaacaaggca gtgctggact tctgtgatcg gtcaggaata | 1440 |
| gaatgcaagc agtacctgcc acactacaca tctcaagacg ggtggcgacg gcatttcggg | 1500 |
| gcgaaatgga gcaggatcgc tgagctgaag gccagatatg accctcgggc attgttgtcg | 1560 |
| ccgggccaga ggattttttcc ggtgccagta gaggcatctg gcattgcttc tgcctga | 1617 |

<210> SEQ ID NO 55
<211> LENGTH: 1566
<212> TYPE: DNA
<213> ORGANISM: Zea mays
<220> FEATURE:
<221> NAME/KEY: misc_feature
<222> LOCATION: (1)...(1566)
<223> OTHER INFORMATION: ZmCkx4 cds

<400> SEQUENCE: 55

| | |
|---|---|
| atgatgctcg cgtacatgga ccgcgcgacg gcggccgccg agccagagga cgccggccgc | 60 |
| gagcccgcca ccatggcggg cgggtgcgcg gcggcggcga cggatttcgg cgggctgggg | 120 |
| agcgccatgc ccgcggccgt ggtccgcccg gcgagcgcgg acgacgtggc cagcgccatc | 180 |
| cgcgcggcgg cgctgacgcc gcacctcacc gtggccgccc gcgggaacgg gcactcggtg | 240 |
| gccggccagg ccatggccga gggcgggctg gtcctcgaca tgcgctcgct cgcggcgccg | 300 |
| tcccggcgcg cgcagatgca gctcgtcgtg cagtgccccg acggcggcgg cggccgccgc | 360 |
| tgcttcgccg acgtccccgg cggcgcgctc tgggaggagg tgctccactg ggccgtcgac | 420 |
| aaccacgggc tcgccccggc gtcctggacg gactacctcc gcctcaccgt gggcggcacg | 480 |
| ctctccaatg gcggcgtcag cggccagtcc ttccgctacg gccccaggt gtccaacgtg | 540 |
| gccgagctcg aggtggtcac cggcgacggc gagcgccgcg tctgctcgcc ctcctcccac | 600 |
| ccggacctct tcttcgccgt gctcggcggg ctcggccagt ttggcgtcat cacgcgcgcc | 660 |
| cgcatcccgc tccacagggc gcccaaggcg gtgcggtgga cgcgcgtggt gtacgcgagc | 720 |
| atcgcggact acacggcgga cgcggagtgg ctggtgacgc ggccccccga cgcggcgttc | 780 |
| gactacgtgg agggcttcgc gttcgtgaac agcgacgacc ccgtgaacgg ctggccgtcc | 840 |
| gtgcccatcc ccggcggcgc ccgcttcgac ccgtccctcc tccccgccgg cgccggcccc | 900 |
| gtcctctact gcctggaggt ggccctgtac cagtacgcgc accggccgga cgacgacgac | 960 |
| gaggaggacc aggcggcggt gaccgtgagc cggatgatgg cgccgctcaa gcacgtgcgg | 1020 |
| ggcctggagt tcgcgcgcga cgtcgggtac gtggacttcc tgtcccgcgt gaaccgggtg | 1080 |
| gaggaggagg cccggcgcaa cggcagctgg gacgcgccgc accgtggct caacctcttc | 1140 |
| gtctccgcgc gcgacatcgc cgacttcgac cgcgccgtca tcaagggcat gctcgccgac | 1200 |
| ggcatcgacg ggcccatgct cgtctaccct atgctcaaga gcaagtggga ccccaacacg | 1260 |
| tcggtggcgc tgccggaggg cgaggtcttc tacctggtgg cgctgctgcg gttctgccgg | 1320 |
| agcggcgggc cggcggtgga cgagctggtg gcgcagaacg cgccatcct ccgcgcctgc | 1380 |
| cgcgccaacg gctacgacta caaggcctac ttcccgagct accgcggcga ggccgactgg | 1440 |
| gcgcgccact tcggcgccgc caggtggagg cgcttcgtgg accgcaaggc ccggtacgac | 1500 |
| ccgctggcga tcctcgcgcc gggccagaag atcttccctc gggtcccggc gtccgtcgcc | 1560 |

```
gtgtag                                                      1566

<210> SEQ ID NO 56
<211> LENGTH: 173
<212> TYPE: PRT
<213> ORGANISM: Artificial Sequence
<220> FEATURE:
<223> OTHER INFORMATION: Consensus sequence of FAD domains of ZmCkx2,
      3, 4, and 5
<220> FEATURE:
<221> NAME/KEY: VARIANT
<222> LOCATION: 6, 11, 19, 20, 24, 26, 36, 40, 41, 58, 61, 63, 64, 65,
      66, 67, 69, 72, 73, 74, 80, 81, 83, 85, 86, 89, 97, 100, 126,
      137, 141, 142, 152, 159, 165, 167
<223> OTHER INFORMATION: Xaa = Any Amino Acid

<400> SEQUENCE: 56

Pro Ala Ala Val Leu Xaa Pro Ala Ser Pro Xaa Asp Ile Ala Ala Leu
1               5                   10                  15

Val Arg Xaa Xaa Phe Ser Ala Xaa Ser Xaa Ser Pro Leu Thr Val Ala
            20                  25                  30

Ala Arg Gly Xaa Gly His Ser Xaa Xaa Gly Gln Ala Gln Ala Pro Gly
        35                  40                  45

Gly Ile Val Val Asp Met Arg Ser Leu Xaa Arg Gly Xaa Arg Xaa Xaa
    50                  55                  60

Xaa Xaa Xaa Leu Xaa Val His Xaa Xaa Xaa Gly Gly Glu Gly Arg Xaa
65                  70                  75                  80

Xaa Phe Xaa Asp Xaa Xaa Gly Gly Xaa Leu Trp Ile Glu Val Leu Arg
                85                  90                  95

Xaa Thr Leu Xaa Lys His Gly Leu Ala Pro Arg Ser Trp Thr Asp Tyr
            100                 105                 110

Leu Arg Leu Thr Val Gly Gly Thr Leu Ser Asn Ala Gly Xaa Ser Gly
        115                 120                 125

Gln Ala Phe Arg His Gly Pro Gln Xaa Ser Asn Val Xaa Xaa Leu Glu
    130                 135                 140

Val Val Thr Gly Arg Gly Glu Xaa Val Thr Cys Ser Pro Ser Xaa Asn
145                 150                 155                 160

Ser Asp Leu Phe Xaa Ala Xaa Leu Gly Gly Leu Gly Gln
                165                 170

<210> SEQ ID NO 57
<211> LENGTH: 5737
<212> TYPE: DNA
<213> ORGANISM: Zea mays
<220> FEATURE:
<221> NAME/KEY: exon
<222> LOCATION: (1514)...(2183)
<220> FEATURE:
<221> NAME/KEY: exon
<222> LOCATION: (2317)...(2768)
<220> FEATURE:
<221> NAME/KEY: exon
<222> LOCATION: (4501)...(5127)
<220> FEATURE:
<221> NAME/KEY: misc_feature
<222> LOCATION: (0)...(0)
<223> OTHER INFORMATION: genomic sequence for ZmCkx7

<400> SEQUENCE: 57
gctcggattg tcgcacgcga gggtagtgta cgctacctgc cgcggtgact tcggaatggt      60
cgaaatactg aagactgtcg aaacggtctt tttttgacac gttgcgtctg agttttgttt    120
ttgtgggggc ttttgttggt atattacatg gctccgcctt gttaaaaacc tcaccccgg     180
```

```
ggggaaaaga gtgcgggccg gaataacatt gtttgctgga ttacaagggc gcatgggccc      240
tgatgattaa aaaaattgcg gtggttgtca atgttccagg agtgctctaa gtcttcacca      300
gatgtcgtta ctagcctata cgcgctgggg gatgccttcg acatgacgat gaatgggcct      360
tctcatttcg gctctagatt gccccgtgat tctgtctggg tggttcggac gagtacgagg      420
tctcctttgt cgaactctgt tgggacgacc gcgtggttgc gctaggcctt agtttgagcc      480
tgatatttgt tgagggcttg tagggcgagg acgcggtctc cgtcgatgag gtctttggac      540
attggttcgt cgacatcggg gaccgctgat gtgcttgttc ggggtgagcc atgctttatc      600
tcctgcggta tcatgacctc ggatccatac aatagacgaa aagtgtgaa tccggttgcc       660 cgacattctg tcgtgtttag ggcccagacc acttcaggta gttggttggc ccatttgccc      720
ttcttgtcat cgagatgtcg tttcttgatg gcagtgaaga tcttgccgtt ggcgcgctcc      780
accaatccaa cgcgcgcaac agcaatttac gtggacttgc aggcttggag caaggaacaa      840
caccaaaaca aaaagaaac atgcaacaag taatattgaa atttactttg aaacaggtat       900
gcatgtttat ttaatatatt ttgtacttga tgtttggact atttcatatt aacttgcata      960
ctaaattatt tatgaaaaat ttcttatggc atacctcatg aataaatcct agctacgcca      1020
ctattaccag tggttttttgg ttttttatgat ttttttaaat cttttgaatt tagaacgaat    1080
tttttaaaaa acgtgattt atcgaaaccg tatcccgact ggtttaccgt cagtttttac      1140
cggttttgta aaccatgcct acgctacaca tatatacata cggtattacg gtgtatgtac      1200
gtcgtatata tatcttagct tatatatctt attgcatggt tctgtacgtg tccgacgagt     1260
gacgacggct atcttagctt atactctctc cctctgtttt tttagttgtt gctggatagt     1320 ttaatttttac actatccagc gacaactaaa acgaaacgaa gggagtatat atcttactct   1380
caatcgttcg taacaataat aatggtaata ataacagcag tttaatctat atataggcca    1440
ccacggctct ccactgctgc gtgcgtgcgt gcgtacatcg tcaaaaacct ccatcaagca    1500
actgatcatg acgatggcta gagctacgac ctccacggtc gcagcactct gcttcctcct   1560
cagctgcgtc tccgcgaccc cttccacgct cgccgcgtcc tccgccatca tccacgacat   1620
catccgcggc ctcgcggaca ccacggcggc gcgcgtccgc acggacgccg aggccacggc   1680
gcgcgcgtcc accgacttcg gcaccaacgc gaccgcggac gacgcgaccc ggccggcggc   1740
cgtgttctac ccgtcgtgcg ccgccgacat cgccgcgctg ctgcgggcgt ccagcgcgag   1800
cgcctcgccg ttcccggtct ccgcgagggg ccgcgggcac tcgacccggg gccaggccac   1860
ggcccccggc ggcgtcgtcg tcgacatggc gtcgctagca gtagctgcag ggcgcgacga   1920
gaccgccacc accaacgcct cctccacctc cgcctccgca aggctcgccg tgtcggtgga   1980
cgggcgctac atcgacgccg gcggcgagca gctgtgggtg gacgtgctgc acgccgccct   2040
ggcgcacggc ctcacgcctc gctcctggac ggactacctc cgcctcaccg tcggcggcac   2100
gctctccaac gcaggcatca gcggccaggc cttccgccac ggcccgcaga tatccaacgt   2160
cctagagctc gacgtcgtca cgggtacgtg tacgtggctg tgcttatgat aagatcgatc   2220
aataacatgt ggagtatacg tcctatggaa tggacatgga cgtggaaacc gggtgatata   2280
tatagctagt tttggaactc gcgtgaaccc tcacaggaac aggtgacatg gtgacgtgct   2340
ccaaggagaa ggacgccgac ctcttcgacg ccgtgctggg agggctgggg cagttcggca   2400
tcataacgcg cgcgcggatc ccgctggcgc cggcgccggc gagggcgcgc tggctgcggc   2460
tcctctacac cggcgccgcc gacctcacgg ccgaccagga gcggctcatc gccgacgacg   2520
agcgccgcgg cggcgcgctg gccgggctca tggactacgt cgagggctcc gtcgtcaccg   2580
```

```
acctccagca gggcctcatc ggcagctggc gctcgcagcc gccgccgtcc tcctcgtcct    2640
tctactcggc taccgacgcc gcgcgcatcg cggcgctagc cgaggaggcc ggcggcgtcc    2700
tctacttcct cgagggcgcg gtgtactacg gcggcgccag cgacacgacc gccgcagacg    2760
ttgacaaggt aacacgatcg acgtacgacc caccgccggt ttctacgtgc atacgccagt    2820
gccaccgaag ccacgtgatc tgtggatggt tgatctggat tgtcgtcttc agcctttggc    2880
ttgtgatgca tgcatgtctg gtggggcagc atcggcagtc gtgcagcgtc aacatcgtac    2940
ttgcatggcc tgccgttgtc gggccctcgt cgtgcatatc attccaaagc ttttgggca     3000 tccccccccc ccctgctta cctatagttt tcaattttat aagacctgca cgcatccatt    3060
tgaagagtca aacctcgtg attttgaagc gacagttgta gcctgtacaa cagttttgtt     3120
gataccatat tttttatgg aactacgcca tccaaacagc tccgtaaact tttgctggat     3180
aataattaag tcgtagatgg ctagcgaatt aaaaccttat atattgcatc tattatatat    3240
aagaaaaaaa aacctagcta gtttactata ttaaggtgca taaaatacta ctatcatatt    3300
tcgtgaactc aaaacaaaga aataagaaat actctcgacg acaagttgat acaaatccta    3360
tgtaatttac attgctagta ccttaattca tcaactatgg tatatctgca tgcagttggc    3420
taatgttttt ggtaatacta ttccagttgg atgacaggaa caagtcatga ccactatgca    3480
tgcatggagc agctaacaaa agccagctcg atatagaact gattcaagta gtcatatgat    3540
aaggctagcg ctaaaaaagt aggaatatag ttacaaatgt ggcaagtatt ggtacttggc    3600
caatggccac atagaaacga gtcattcacc tatccaaata ttcttcaca atttcttagg     3660 gcgctaaatt aattttagtt cgaaaataaa taaaaataga gttcgatatt aatcagatct    3720
gatcttctgt aaaaatttat aacccattgt catccctac cctactagtt attagaggat     3780
actcttataa tagataatgc aagagatcta agcactgcac catccaagca aagctactgt    3840
agctcgacat gtgagtacac ttcactgtga ccaaccagat actgcacagc tcgcattcac    3900
aagcgctata gctagaagga cgaccgcatc agctctgcaa acgactcgga tctgttcgct    3960
gttcgcacca aggacagcaa cagtgctagt gtctctttct tttctgtttt tttatcgga     4020 gaggcaacac catatatttc cagacaaatc ttgagctata tatagagact ttcgtacata    4080
tgtgttttag acgaccgcat cctagcaact ttttttactt gagcagactt tcgtacattc    4140
tatattcaag gtcacaagaa gtcaagctcg atctcacatc aaattatgtt gtagtggtat    4200
ttttttagtc cccaaaatga aatggttttt ggacatcccc aacgaacgac gatcggttat    4260
atatgtgtca gttgggacag tcacgtttct cgatgaaagt gaccgtgcaa gcaaggtgca    4320
agttgacgtg tagtcgtgta gtcgcgcgcg catatcccta catatatgga cacatcacac    4380
acatgcaaag aaacactagt gaccaaatca tatacctttt gcacacaacg tgacactact    4440
tgtagagtat acgtagttag ttcctgcatg catggattaa cacaaaatgc gtacatgcag    4500
cgcgtggacg tgatgctgcg tgagctgcg tacgcgcggg ggttcgcgta cgtgcaggac    4560
gtgtcgtacg agcagttcct ggaccgcgtg agcgccggcg agcgcaggct ccgcggcgag    4620
ggcctctggg acgtgccgca cccgtggctc aacctcttcc tcccgcgctc ccgcatcctc    4680
gacttcgccg cgggcgtctt ccacggcgtg ctgctcccca cgcgcacggc tggcggcggc    4740
ggcggcgggc ccgtgctggt ctaccccatg aaccggggca gtgggacgg cgcgacgtcg     4800 gcggtgctcc cctacgacga tggcgacggc gacggcgacg aggtgttcta cacggtgggg    4860
atcctgcggt cggccgtggc ggacggcgac ctgcgccgca tggaggagca gaacgccgag    4920
gtggcgcgct tctgcgaggc cgccggcatc ccctgcacgc agtacctgcc ctcctacgcc    4980
```

-continued

```
acgcaggcgg actgggcggc gcgccacttc ggccccgccg gcagcggcag gtgggacacc    5040
ttcctccgcc gcaagaggaa atacgacccc atggcgatct tgtcgcgcgg ccagaggatt    5100
ttctcgtccc cgctacttgc ctcatgatcc gccggttccg gtctctcgat cgtcgtgtgt    5160
tgctgttgct ggcatgggct agctgcatga ataatagtg caagcaagca aaggcaaagc     5220
aagcttcaag gcatgactgt tttgctttag cgttttactg atcagtagtc aagtgacaca    5280
gttactacgt actacgatct gtctctgact ctcttccaga gggtcccaaa tatatgatgc    5340
tttttattaa ctttatttga ccgttattaa aaatatagtg atattgttta ctttaaacga    5400
gttattttat tgttacagaa ttttatcatt tacataaaaa tataaattta aataaatgat    5460
caaatacaat aatatctaaa aagtaaaaaa aaaccatcgt ctatgtcaaa agaaacatca    5520
tcaaaacgag ggaggaattt tactagtaat agacatgcat gcacgtgatc gagcaataat    5580
gcaacactac gataactata tatgcaagcg cgcgtgatac tgataagagt gtaccgtacg    5640
attgaagaac attgtacatg tactactgca cgtactcagc tgatgcctga cgatttgtaa    5700
tcttcacctt tgtgtttacg tacatagcgg tttgaac                            5737
```

<210> SEQ ID NO 58
<211> LENGTH: 1749
<212> TYPE: DNA
<213> ORGANISM: Zea mays
<220> FEATURE:
<221> NAME/KEY: CDS
<222> LOCATION: (1)...(1749)

<400> SEQUENCE: 58

```
atg gct aga gct acg acc tcc acg gtc gca gca ctc tgc ttc ctc ctc      48
Met Ala Arg Ala Thr Thr Ser Thr Val Ala Ala Leu Cys Phe Leu Leu
 1               5                  10                  15 agc tgc gtc tcc gcg acc cct tcc acg ctc gcc gcg tcc tcc gcc atc      96
Ser Cys Val Ser Ala Thr Pro Ser Thr Leu Ala Ala Ser Ser Ala Ile
             20                  25                  30 atc cac gac atc atc cgc ggc ctc gcg gac acc acg gcg gcg cgc gtc     144
Ile His Asp Ile Ile Arg Gly Leu Ala Asp Thr Thr Ala Ala Arg Val
         35                  40                  45 cgc acg gac gcc gag gcc acg gcg cgc gcg tcc acc gac ttc ggc acc     192
Arg Thr Asp Ala Glu Ala Thr Ala Arg Ala Ser Thr Asp Phe Gly Thr
     50                  55                  60 aac gcg acc gcg gac gac gcg acc cgg ccg gcg gcc gtg ttc tac ccg     240
Asn Ala Thr Ala Asp Asp Ala Thr Arg Pro Ala Ala Val Phe Tyr Pro
 65                  70                  75                  80 tcg tgc gcc gcc gac atc gcc gcg ctg ctg cgg gcg tcc agc gcg agc     288
Ser Cys Ala Ala Asp Ile Ala Ala Leu Leu Arg Ala Ser Ser Ala Ser
                 85                  90                  95 gcc tcg ccg ttc ccg gtc tcc gcg agg ggc cgc ggg cac tcg acc cgg     336
Ala Ser Pro Phe Pro Val Ser Ala Arg Gly Arg Gly His Ser Thr Arg
            100                 105                 110 ggc cag gcc acg gcc ccc ggc ggc gtc gtc gtc gac atg gcg tcg cta     384
Gly Gln Ala Thr Ala Pro Gly Gly Val Val Val Asp Met Ala Ser Leu
        115                 120                 125 gca gta gct gca ggg cgc gac gag acc gcc acc acc aac gcc tcc tcc     432
Ala Val Ala Ala Gly Arg Asp Glu Thr Ala Thr Thr Asn Ala Ser Ser
    130                 135                 140 acc tcc gcc tcc gca agg ctc gcc gtg tcg gtg gac ggg cgc tac atc     480
Thr Ser Ala Ser Ala Arg Leu Ala Val Ser Val Asp Gly Arg Tyr Ile
145                 150                 155                 160 gac gcc ggc ggc gag cag ctg tgg gtg gac gtg ctg cac gcc gcc ctg     528
Asp Ala Gly Gly Glu Gln Leu Trp Val Asp Val Leu His Ala Ala Leu
                165                 170                 175
```

| | | |
|---|---|---|
| gcg cac ggc ctc acg cct cgc tcc tgg acg gac tac ctc cgc ctc acc<br>Ala His Gly Leu Thr Pro Arg Ser Trp Thr Asp Tyr Leu Arg Leu Thr<br>180 185 190 | | 576 |
| gtc ggc ggc acg ctc tcc aac gca ggc atc agc ggc cag gcc ttc cgc<br>Val Gly Gly Thr Leu Ser Asn Ala Gly Ile Ser Gly Gln Ala Phe Arg<br>195 200 205 | | 624 |
| cac ggc ccg cag ata tcc aac gtc cta gag ctc gac gtc gtc acg gga<br>His Gly Pro Gln Ile Ser Asn Val Leu Glu Leu Asp Val Val Thr Gly<br>210 215 220 | | 672 |
| aca ggt gac atg gtg acg tgc tcc aag gag aag gac gcc gac ctc ttc<br>Thr Gly Asp Met Val Thr Cys Ser Lys Glu Lys Asp Ala Asp Leu Phe<br>225 230 235 240 | | 720 |
| gac gcc gtg ctg gga ggg ctg ggg cag ttc ggc atc ata acg cgc gcg<br>Asp Ala Val Leu Gly Gly Leu Gly Gln Phe Gly Ile Ile Thr Arg Ala<br>245 250 255 | | 768 |
| cgg atc ccg ctg gcg ccg gcg ccg gcg agg gcg cgc tgg ctg cgg ctc<br>Arg Ile Pro Leu Ala Pro Ala Pro Ala Arg Ala Arg Trp Leu Arg Leu<br>260 265 270 | | 816 |
| ctc tac acc ggc gcc gcc gac ctc acg gcc gac cag gag cgg ctc atc<br>Leu Tyr Thr Gly Ala Ala Asp Leu Thr Ala Asp Gln Glu Arg Leu Ile<br>275 280 285 | | 864 |
| gcc gac gac gag cgc cgc ggc ggc gcg ctg gcc ggg ctc atg gac tac<br>Ala Asp Asp Glu Arg Arg Gly Gly Ala Leu Ala Gly Leu Met Asp Tyr<br>290 295 300 | | 912 |
| gtc gag ggc tcc gtc gtc acc gac ctc cag cag ggc ctc atc ggc agc<br>Val Glu Gly Ser Val Val Thr Asp Leu Gln Gln Gly Leu Ile Gly Ser<br>305 310 315 320 | | 960 |
| tgg cgc tcg cag ccg ccg ccg tcc tcc tcg tcc ttc tac tcg gct acc<br>Trp Arg Ser Gln Pro Pro Pro Ser Ser Ser Ser Phe Tyr Ser Ala Thr<br>325 330 335 | | 1008 |
| gac gcc gcg cgc atc gcg gcg cta gcc gag gag gcc ggc ggc gtc ctc<br>Asp Ala Ala Arg Ile Ala Ala Leu Ala Glu Glu Ala Gly Gly Val Leu<br>340 345 350 | | 1056 |
| tac ttc ctc gag ggc gcg gtg tac tac ggc ggc gcc agc gac acg acc<br>Tyr Phe Leu Glu Gly Ala Val Tyr Tyr Gly Gly Ala Ser Asp Thr Thr<br>355 360 365 | | 1104 |
| gcc gca gac gtt gac aag cgc gtg gac gtg atg ctg cgt gag ctg cgg<br>Ala Ala Asp Val Asp Lys Arg Val Asp Val Met Leu Arg Glu Leu Arg<br>370 375 380 | | 1152 |
| tac gcg cgg ggg ttc gcg tac gtg cag gac gtg tcg tac gag cag ttc<br>Tyr Ala Arg Gly Phe Ala Tyr Val Gln Asp Val Ser Tyr Glu Gln Phe<br>385 390 395 400 | | 1200 |
| ctg gac cgc gtg agc gcc ggc gag cgc agg ctc cgc ggc gag ggc ctc<br>Leu Asp Arg Val Ser Ala Gly Glu Arg Arg Leu Arg Gly Glu Gly Leu<br>405 410 415 | | 1248 |
| tgg gac gtg ccg cac ccg tgg ctc aac ctc ttc ctc ccg cgc tcc cgc<br>Trp Asp Val Pro His Pro Trp Leu Asn Leu Phe Leu Pro Arg Ser Arg<br>420 425 430 | | 1296 |
| atc ctc gac ttc gcc gcg ggc gtc ttc cac ggc gtg ctg ctc ccc acg<br>Ile Leu Asp Phe Ala Ala Gly Val Phe His Gly Val Leu Leu Pro Thr<br>435 440 445 | | 1344 |
| cgc acg gct ggc ggc ggc ggc ggg ccc gtg ctg gtc tac ccc atg<br>Arg Thr Ala Gly Gly Gly Gly Gly Pro Val Leu Val Tyr Pro Met<br>450 455 460 | | 1392 |
| aac cgg ggc aag tgg gac ggc gcg acg tcg gcg gtg ctc ccc tac gac<br>Asn Arg Gly Lys Trp Asp Gly Ala Thr Ser Ala Val Leu Pro Tyr Asp<br>465 470 475 480 | | 1440 |
| gat ggc gac ggc gac ggc gac gag gtg ttc tac acg gtg ggg atc ctg<br>Asp Gly Asp Gly Asp Gly Asp Glu Val Phe Tyr Thr Val Gly Ile Leu<br>485 490 495 | | 1488 |

```
cgg tcg gcc gtg gcg gac ggc gac ctg cgc cgc atg gag gag cag aac    1536
Arg Ser Ala Val Ala Asp Gly Asp Leu Arg Arg Met Glu Glu Gln Asn
        500                 505                 510 gcc gag gtg gcg cgc ttc tgc gag gcc gcc ggc atc ccc tgc acg cag    1584
Ala Glu Val Ala Arg Phe Cys Glu Ala Ala Gly Ile Pro Cys Thr Gln
        515                 520                 525 tac ctg ccc tcc tac gcc acg cag gcg gac tgg gcg gcg cgc cac ttc    1632
Tyr Leu Pro Ser Tyr Ala Thr Gln Ala Asp Trp Ala Ala Arg His Phe
    530                 535                 540 ggc ccc gcc ggc agc ggc agg tgg gac acc ttc ctc cgc cgc aag agg    1680
Gly Pro Ala Gly Ser Gly Arg Trp Asp Thr Phe Leu Arg Arg Lys Arg
545                 550                 555                 560 aaa tac gac ccc atg gcg atc ttg tcg cgc ggc cag agg att ttc tcg    1728
Lys Tyr Asp Pro Met Ala Ile Leu Ser Arg Gly Gln Arg Ile Phe Ser
                565                 570                 575 tcc ccg cta ctt gcc tca tga                                        1749
Ser Pro Leu Leu Ala Ser
            580
```

<210> SEQ ID NO 59
<211> LENGTH: 582
<212> TYPE: PRT
<213> ORGANISM: Zea mays

<400> SEQUENCE: 59

```
Met Ala Arg Ala Thr Thr Ser Thr Val Ala Ala Leu Cys Phe Leu Leu
 1                5                  10                  15

Ser Cys Val Ser Ala Thr Pro Ser Thr Leu Ala Ala Ser Ser Ala Ile
             20                  25                  30

Ile His Asp Ile Ile Arg Gly Leu Ala Asp Thr Thr Ala Ala Arg Val
         35                  40                  45

Arg Thr Asp Ala Glu Ala Thr Ala Arg Ala Ser Thr Asp Phe Gly Thr
     50                  55                  60

Asn Ala Thr Ala Asp Asp Ala Thr Arg Pro Ala Ala Val Phe Tyr Pro
 65                  70                  75                  80

Ser Cys Ala Ala Asp Ile Ala Ala Leu Leu Arg Ala Ser Ser Ala Ser
                 85                  90                  95

Ala Ser Pro Phe Pro Val Ser Ala Arg Gly Arg Gly His Ser Thr Arg
            100                 105                 110

Gly Gln Ala Thr Ala Pro Gly Gly Val Val Asp Met Ala Ser Leu
        115                 120                 125

Ala Val Ala Ala Gly Arg Asp Glu Thr Ala Thr Asn Ala Ser Ser
    130                 135                 140

Thr Ser Ala Ser Ala Arg Leu Ala Val Ser Val Asp Gly Arg Tyr Ile
145                 150                 155                 160

Asp Ala Gly Gly Glu Gln Leu Trp Val Asp Val Leu His Ala Ala Leu
                165                 170                 175

Ala His Gly Leu Thr Pro Arg Ser Trp Thr Asp Tyr Leu Arg Leu Thr
            180                 185                 190

Val Gly Gly Thr Leu Ser Asn Ala Gly Ile Ser Gly Gln Ala Phe Arg
        195                 200                 205

His Gly Pro Gln Ile Ser Asn Val Leu Glu Leu Asp Val Val Thr Gly
    210                 215                 220

Thr Gly Asp Met Val Thr Cys Ser Lys Glu Lys Asp Ala Asp Leu Phe
225                 230                 235                 240

Asp Ala Val Leu Gly Gly Leu Gly Gln Phe Gly Ile Ile Thr Arg Ala
                245                 250                 255
```

```
Arg Ile Pro Leu Ala Pro Ala Pro Ala Arg Ala Arg Trp Leu Arg Leu
            260                 265                 270

Leu Tyr Thr Gly Ala Ala Asp Leu Thr Ala Asp Gln Glu Arg Leu Ile
        275                 280                 285

Ala Asp Asp Glu Arg Arg Gly Gly Ala Leu Ala Gly Leu Met Asp Tyr
    290                 295                 300

Val Glu Gly Ser Val Val Thr Asp Leu Gln Gln Gly Leu Ile Gly Ser
305                 310                 315                 320

Trp Arg Ser Gln Pro Pro Ser Ser Ser Phe Tyr Ser Ala Thr
                325                 330                 335

Asp Ala Ala Arg Ile Ala Ala Leu Ala Glu Glu Ala Gly Gly Val Leu
            340                 345                 350

Tyr Phe Leu Glu Gly Ala Val Tyr Tyr Gly Gly Ala Ser Asp Thr Thr
        355                 360                 365

Ala Ala Asp Val Asp Lys Arg Val Asp Val Met Leu Arg Glu Leu Arg
    370                 375                 380

Tyr Ala Arg Gly Phe Ala Tyr Val Gln Asp Val Ser Tyr Glu Gln Phe
385                 390                 395                 400

Leu Asp Arg Val Ser Ala Gly Glu Arg Arg Leu Arg Gly Glu Gly Leu
                405                 410                 415

Trp Asp Val Pro His Pro Trp Leu Asn Leu Phe Leu Pro Arg Ser Arg
            420                 425                 430

Ile Leu Asp Phe Ala Ala Gly Val Phe His Gly Val Leu Leu Pro Thr
        435                 440                 445

Arg Thr Ala Gly Gly Gly Gly Gly Pro Val Leu Val Tyr Pro Met
    450                 455                 460

Asn Arg Gly Lys Trp Asp Gly Ala Thr Ser Ala Val Leu Pro Tyr Asp
465                 470                 475                 480

Asp Gly Asp Gly Asp Gly Asp Glu Val Phe Tyr Thr Val Gly Ile Leu
                485                 490                 495

Arg Ser Ala Val Ala Asp Gly Asp Leu Arg Arg Met Glu Glu Gln Asn
            500                 505                 510

Ala Glu Val Ala Arg Phe Cys Glu Ala Ala Gly Ile Pro Cys Thr Gln
        515                 520                 525

Tyr Leu Pro Ser Tyr Ala Thr Gln Ala Asp Trp Ala Ala Arg His Phe
    530                 535                 540

Gly Pro Ala Gly Ser Gly Arg Trp Asp Thr Phe Leu Arg Arg Lys Arg
545                 550                 555                 560

Lys Tyr Asp Pro Met Ala Ile Leu Ser Arg Gly Gln Arg Ile Phe Ser
                565                 570                 575

Ser Pro Leu Leu Ala Ser
            580

<210> SEQ ID NO 60
<211> LENGTH: 8113
<212> TYPE: DNA
<213> ORGANISM: Zea mays
<220> FEATURE:
<221> NAME/KEY: exon
<222> LOCATION: (2080)...(2668)
<220> FEATURE:
<221> NAME/KEY: exon
<222> LOCATION: (2891)...(3018)
<220> FEATURE:
<221> NAME/KEY: exon
<222> LOCATION: (3144)...(3416)
<220> FEATURE:
<221> NAME/KEY: exon
```

```
<222> LOCATION: (3574)...(3836)
<220> FEATURE:
<221> NAME/KEY: exon
<222> LOCATION: (6286)...(6619)
<220> FEATURE:
<221> NAME/KEY: misc_feature
<222> LOCATION: (1)...(8113)
<223> OTHER INFORMATION: ZmCkx8 genomic

<400> SEQUENCE: 60
gaattctatc ttttcttgag ttattttatg atacaactgt tgctttgtct ggaatttatt      60
atcctacttc aacattgatg cttcatcata tacttaaaat tgctagacat ctaaatgctt     120
ttgaaaatga tgctttgctt agagatgcta ttgttcctat gaaaacaaaa tatttgaaat     180
attggaggaa gatacctgtt ttatattgct ttgcttttgt attggatcct agagcaaaaa     240
tgaggggtt taataagctt cttatgaggt tgtctggact taatgaact gattattcaa       300
ggtatcctac atacattcgg tctaaactaa ctaagatttt tcagatatat gaattgaaat     360
ttggtgaagt gtgcttgagt gcacaacaac ataagagtgc tggtacggca ggtaaggcta     420
cagaggcatg ggatgacata tatggggatg atatccttat gccttcccaa tctactagag     480
ctactcctac agctgtatca tctactgctg ctgctatatc tgagttgtca tcatatcttg     540
atagtgatac tgtcacccag tttgactctg atttcattct tctaaactgg tggcagcgac     600
acaagttgac atatcctgtg ctttctatac ttgctaaaga tgttataatt gtgcctgctt     660
ccactgtatc atcagagtcc actttcagtt tagctggcag ggtgcttgaa gaccgacggc     720
ggcgcctaac tcctgatatg gttgaagttt tgtcttgcat aaaggactgg gagcttgctg     780
acttgcatag tcagcacacg gtggagaaag ataccaaaga acttgaagtt gtttttgaag     840
caatgtacct agaagaaact ggtggaggca agaaagaag aggtggagga tctggtggag     900
cgggtagatc ttgagcagct gaattattgc tattactata ctctgttctt ctgttgtaac     960
ttgtgatgaa ctattaaact ctggacttaa attgaaccta taggagct ggctctactc       1020
ttttcttcc tagggttttc tcacgaggtg tgagttttta cctaggaagg tttttaatga     1080
ggcagcattg cactaaggct ccattagtat attgtttgca taaacttttg tgaactgtga     1140
ttttgtttct gagatgtttt gtgaactgtg tgaattgact gaaatctgat ataggaactg     1200
tgtgaaatct gatataggaa ctgtgtgaat tgactgaaat ttgatatatg aactgtgtga     1260
aatttgattc agctgtttat tgtgaaatta ctgtgcttcg ggtcagcccg gccctatggg     1320
ctgaccgggc cagaggcacg gcacgacaca acccgtttaa gccactttcg tgccgtgctt     1380
gtgccaacag tttagcccgc gggccagcac ggcacggcac ggaagtagga tcgtgccgtg     1440
cccggcacgc acagtaacgt gctgtgcttg gccgtgcccg tgccgtgccg gcccgacaca     1500
cacgaatgga catgtatagt cctgactgtc ccgtaaccaa acggacccca acatactcga     1560
tgttgtttag accgaccgac tgatcgtgcc acattgcact gcgcgtgaag aggtcgatac     1620
cgatcgttta gaccaccatg tcagctgatg gtactgtccc acgttggcat tggagcagct     1680
tacctatcat acatatcatc tattttttat ttaaaaattt actataaata gtgtagtata     1740
caatataaaa tagtatcata tgctcaatat gcttgagaca gctttaatag gatcaaacta     1800
agattctcgg gcccggcatc ggtagcgacg acaccggcta tatataatgc actcagtgag     1860
cttcctggtg gctcttgctg cttcttcctt gctgttccat ccgtccacag ttcttgtggg     1920
aacccaagat cgatcttgac ggggacggtga gcacggcacg tcgcgacctt attcttccgt     1980
cttggccccg tgcaccggca agcggcaacc aaatgcgcat gccctgtga aagctaatag      2040
tagctacatc acacagcaag acactatagc cagctagcca tggagggcaa ggtgctgtgc     2100
```

```
acgtacgccg ggatcgtggc cctactgctc tgctcgtcgg tgaatttcat acagagcccc    2160
tccgacgtgt tcggcccgt ggcgctgctg gagccgacag catccgcggc acgcgacttc     2220
ggcggcgtgg tctcggaggc ggccatcgcg gtcatgcagc ccgggtcccc cgccgacatc    2280
gcgcggctcc tgggcgcgct gtcgtcgacg gggccggggc cggggccgaa ggcggccgtg    2340
gcggcgcgcg gcgcggggca ctcgctccac gggcaggccc aggcgcgcgg cggcattgtg    2400
gtggagacgc gcgccctgcc gcgcctcgtg gaggtggtgc gacgcgggga cggggacggc    2460
ggcggcgcgg cgtacgcgga cgtgggcggc ggcgcgctgt gggtggaggt gctgaggag     2520 tgcctgaggg ccgggctggc gccgcggtcg tggacggact acctgtacct gaccgtgggc    2580
gggacgctgt cgaacggcgg catcagcggg caggcgttca gcacggccc gcagatcagc     2640 aacgtgctgc agctggaggt ggtcacaggt acgttacgcg cgccgtacac gcatcatgca    2700
cttccgcacg gcctcgctgc tcgcgtgcac catctgccgc gcgcctaatt gatctctctt    2760
ttccgtgtct ctctctctcc ctcccttttc ttcggtgaaa gaaagaaaga aagaaagaaa    2820
agatacgggt gatcggtggc cttgttcct ttgccggttg tttatgtgtt gtttgtcccg     2880
tcggttgcag gcacagggga ggtggtgaca tgctcgccca cccagagccc ggagcttttc    2940
ttcgccgtac ttggtgggct tggccagttc ggtatcataa cccgcgcaag gattccgctg    3000
caagttgctc cgcccaaggt acacagacac aattgcgcac gccctcgatc tgcttcctct    3060
ctagctggta gcagaaatag aaagaaatca ggaaagctgg taactaaaag cagctttggc    3120
cgataatttt ctatgattat taggtgagat gggtgagggc cttctacgac agcttcgaga    3180
cgttcaccaa ggaccaggag ctgctggtct caatgccaga gctggtggac tacgtggagg    3240
ggttcatggt cctgaacgag cagtccctcc gcagctcctc cgtggccttc cccgcccagg    3300
tcaacttcag accggacttc ggctccgacg acggcaccaa caagaaggtc tgctactact    3360
actgcatcga gttcgcggtg catgacttcc aacggcagga ctccgctgct gaccatgtca    3420
gtctctacta gctcatcgtc tctaccactc tatcaggagc gcgtgacagt atccccgtca    3480
cgttagcatc gtcaacagta gcctcgagaa ggaaagcact cactgaacga ccggccgggc    3540
ttgtggcctg cctccgaatt ttgctctgtg caggttgtgg acctggtgtc ggggaagctg    3600
agctatctga ggccccacgc gtacagcgtg gaggtggcct actgggattt cctcaacagg    3660
gtgcggatgg aggaggagag cctcaggagg cggggcctct gggacgtgcc gcacccctgg    3720
ctcaacctct tcgtgcccag gcatggcgtc gcgcggttca tggacctgct catggccacc    3780
atcgcgcagg gggacttcga ggggcccgtc ctcgtctacc ccctcctcac tcacaggtac    3840
ggtgcgaccc acgtccactc atattttttt tttattttat acgtatgaaa gacggcatgc    3900
ttggtccatt ggttgcatgg atgcatgaac tatagtggct taggatggat tagccagtca    3960
taaaagatgt tcatcatact gtactatata ttagtaagag tatatattta ttcataaaag    4020
tagttcttca aactgtaaaa agggttcagt ggtttattta ttttttgaaa aaaaaaagaa    4080
gtgatggcca cggccctcgt ggtcgtgggt gggtagataa aggagtccgt cccctttcaca   4140 ccacactggt attaatctgc atgatttttcc tgcgcaaaaa aaaacgtttt ggatggtgtg   4200
gccggcgtga tcgccttgtc atcacccgca gggaatctca agcattcca aaaacatgag     4260 acaaaagctc gtgcctcctt ttttttcttt catctgcgtg atctatgaac acggccaggc    4320
agattgcaca tcgtcaggtg cagcctagct cgaggtacct ggcccgttgt ttttcctccc    4380
agaaatgggt tgccaaacac caagcgcaac atgttggtcc aattgtgaca atgctatggc    4440
atatcgccgg ctctcccctct cagtcgtcgt cacaggggcg tcgtagcggt ggtcacctca   4500
```

```
taggccgtgt cctttcccag caggactgca cctttgcgtc gcttgtcaac gatcacactc    4560
acacgtcttt atgcacagtg aaaactagac attttatttt tttcactttc agaaaagaaa    4620
agaaactata cgtagccatt tcttctcgca aactttgcac tgcagtgtac gctgctgcta    4680
tagtagtgca caattaggat cggtaatgca tcacgattct aatgtttctt tacaattttg    4740
tttgagacat taataaattt tagtccaaaa ataaatagaa aataaactcg attctagtct    4800
aatccgattt tttatattgt aaaatttaga gactattatt gatccgatgc acaagccaag    4860
cccagccgtg atggccttgc atattttctg aaaggcgtcg tctctccata gctaccctac    4920
cttaggaata tcgtgaatct ctgtgtagtc gcctgggcgc ctggccttttt gcaagttgca    4980 gcgcttgctt gcacgtgacg gtataaatgg tcatataaaa tactatttgt aatgtagatt    5040
acactgtttg cgaagtgaaa tttgaaacaa ctggtaatag agtgtgatag tgattcttgt    5100
gaagataagc tactgagcta tgtgcagtcg cctggccttg ctaccactag ccatggcacg    5160
gctgcagcaa gtcgcgaggg caatcagtgc agtgcagtct cctcaaatgg cagtgccagt    5220
atggtggcag tggcactggc accctagcgt gtccacaccc ttcctggctg gctgactcgt    5280
cactttgata ggagaaagta ccgtggcaac atgatggtga ttattccccg tgtgcagtcg    5340
cctggtcggt tgcaaatcgc ttgacactga cttttgaaat gtgcgtaacc gtgtcgtgta    5400
attctatatc ttatcaaaaa aaaatcatgc aaaaggtatg ttaaaaaatt ttaccacgag    5460
aaagtagtgt ggcaacatga tgttgattac tcactccatc ttagaaaagc tgtgatttta    5520
gttttctgcc ggatcaatca atctgtctca actctaacac aatatatatg tactgaaatt    5580 cgaattttttt actaaataat ataattacat ttatcatgat ttttttaata gtgtaactgt    5640
ttagagtcat agaaattaat tatattttct acaaactgag acgaacttat taagaaagtt    5700
tgaccaatct aaatctgaaa ttccattatt tttggggac tgagaggttg tactacatgt    5760
ttcatgacat ttttttttgt aatgtacagt gccagtttcc ttcagttttg tttgcatgtg    5820
ggtgtgttaa gcaactcttg aacaaaagct gcagctcgtg aggttcagaa cccgggatta    5880
gcaggcctgg cccaggcgtt caggggtttt gtcacgttcg caggctctgc cgctatgctg    5940
gcaggcagca gcacaggatg cttgcacagc ctaccttttc tagtggtcaa attgcctttg    6000
agcctttccc agacagcgaa tctacatcct gccacaccac atggcagggc ctacgcccta    6060
caccctgacc ctgtcacggc ctcctcctcc tcctccatgc catttagga aggcgtcgca    6120 gggcacgcac cggcaccacc accgcccgaa agcctatagt cgggcataca ctgtcggatc    6180
atggcatcct ttataataac tctggttctc gtcatacgcc agctcgtgct gctaccgcac    6240
ccgtcatcct gctcatccac gcttggtgcg ctgcaatatt ttcaggtggg acggcaacat    6300
gtcggcggtg gttccggcgg cgccagacgg tgtgatgtac gtcttcagcg tgctacggtc    6360
gacggacccg gcgcggtgcg gccgcgcctg catggagagg atcctggagc agcaccgccg    6420
tgtcgccgac gaggcctgcc ggcgcctcgg cgccaagcag tacctggcca ggcagccgtc    6480
gctggcgcac tggcgcgacc acttcgggcc cagctgggac cgcttcgtgg ccaggaaggc    6540
ccgcttcgac cccatgaacg tgctcgggcc gggccaggga attttcccct ggacggactc    6600
ctcctcgagc ccgatgtgac ggcggctgtc gtgggctttg gtccacccac gtacggagga    6660
agtagctagg ctgatgagga gctgaagccg atgatgctag ttttgatgag attgtttatt    6720
attgttcatg tggaattcct atttaggttc ctaggtacta gtactatgtt ggcaagtggc    6780
tcaaggtaaa atgttcattc tttttttttcc ctacttctta tgtgctgtgt ttagctgatt    6840
agtggcctcc taaaattagt tgtttgccga gatgggcaaa taattcatcc tctcgtgttg    6900
```

-continued

```
ttccgtttcg atcattgaaa tgtctatcgt ttctctgcct aggttctttt tgtatttgat    6960
ctattatcat attcttgtct tctcatatta tttatttaa gctcaagatt tcgcagttta    7020
ttttataaat gatcatacag tgtttgcctt gttacattat ttatactcac aaaacgtaaa    7080
aatctagggc catgtgccgt cacccccgtc acacttggca ctggacagcc ctggccgtga    7140
agataataag tgtgagatta attttaagcg gctctttata tcattcataa ttgttagaaa    7200
tagatatctt acggcagagc actctccaac atctttttta aattggctat ccaagaatat    7260
cgtcatctat ttcaaaattc tcgctagcca cggatagaaa gttaaaataa ttctttagag    7320
tgtgtataag atatataaat gtcggaggat gaaaaaaatt taaaactatt tagagggtga    7380
gtttataaaa aactctaact acaaaatgat aatgatagaa ccaaaggtta aaaacaacaa    7440
gtctttggaa gaaataaaat ggctatctgt gtccgttctc atgagacacg ctaaaaaatc    7500
tataaaattt tcatagaggt aaaaaagatc tggcaaccaa ccaattctat atacattaat    7560
caccattcct cataataaca tctaattttt aaaaaaaata tccccttgtt aagaataacc    7620
taacataagc ccataaacat gtatctaaat tacccacctc acttaatata atcataatct    7680
aaagtgacgc acaaaattta cattttaatt gcctaactat gattataata tataatctaa    7740
gcaacacatt aagtttacat ctaaattgca agctcttata tttttcaaaa ttaaataaaa    7800
tatacaaatc aacaaaattt tgttatgaaa aatgtaaatt accataaatt atatttatgc    7860
atggttctaa gttgcccact tctatcgctg atggcctata aaaacatgtg ttttgcatgt    7920
tcaacattcc taaaagtgc cccttgaaag gctcatatga attcatctgc aattatattg    7980
atatccatca caaaaaattg taactacttt atataaatct atttctataa aattatgagg    8040
acattttaca attaataata taattataaa cacactgttt ttttaaatac tgctacacat    8100
tacttctagt taa                                                         8113
```

<210> SEQ ID NO 61
<211> LENGTH: 1587
<212> TYPE: DNA
<213> ORGANISM: Zea mays
<220> FEATURE:
<221> NAME/KEY: CDS
<222> LOCATION: (1)...(1587)
<223> OTHER INFORMATION: ZmCkx8 cds

<400> SEQUENCE: 61

```
atg gag ggc aag gtg ctg tgc acg tac gcc ggg atc gtg gcc cta ctg      48
Met Glu Gly Lys Val Leu Cys Thr Tyr Ala Gly Ile Val Ala Leu Leu
 1               5                  10                  15 ctc tgc tcg tcg gtg aat ttc ata cag agc ccc tcc gac gtg ttc ggc      96
Leu Cys Ser Ser Val Asn Phe Ile Gln Ser Pro Ser Asp Val Phe Gly
             20                  25                  30 ccc gtg gcg ctg ctg gag ccg aca gca tcc gcg gca cgc gac ttc ggc     144
Pro Val Ala Leu Leu Glu Pro Thr Ala Ser Ala Ala Arg Asp Phe Gly
         35                  40                  45 ggc gtg gtc tcg gag gcg gcc atc gcg gtc atg cag ccc ggg tcc ccc     192
Gly Val Val Ser Glu Ala Ala Ile Ala Val Met Gln Pro Gly Ser Pro
     50                  55                  60 gcc gac atc gcg cgg ctc ctg ggc gcg ctg tcg tcg acg ggg ccg ggg     240
Ala Asp Ile Ala Arg Leu Leu Gly Ala Leu Ser Ser Thr Gly Pro Gly
 65                  70                  75                  80 ccg ggg ccg aag gcg gcc gtg gcg gcg cgc ggc gcg ggg cac tcg ctc     288
Pro Gly Pro Lys Ala Ala Val Ala Ala Arg Gly Ala Gly His Ser Leu
                 85                  90                  95 cac ggg cag gcc cag gcg cgc ggc ggc att gtg gtg gag acg cgc gcc     336
```

-continued

| | |
|---|---|
| His Gly Gln Ala Gln Ala Arg Gly Gly Ile Val Val Glu Thr Arg Ala<br>                 100                           105                     110 | |
| ctg ccg cgc ctc gtg gag gtg gtg cga cgc ggg gac ggg gac ggc ggc<br>Leu Pro Arg Leu Val Glu Val Val Arg Arg Gly Asp Gly Asp Gly Gly<br>              115                         120                      125 | 384 |
| ggc gcg gcg tac gcg gac gtg ggc ggc gcg ctg tgg gtg gag gtg<br>Gly Ala Ala Tyr Ala Asp Val Gly Gly Ala Leu Trp Val Glu Val<br>    130                       135                     140 | 432 |
| ctg gag gag tgc ctg agg gcc ggg ctg gcg ccg cgg tcg tgg acg gac<br>Leu Glu Glu Cys Leu Arg Ala Gly Leu Ala Pro Arg Ser Trp Thr Asp<br>145                   150                       155                   160 | 480 |
| tac ctg tac ctg acc gtg ggc ggg acg ctg tcg aac ggc ggc atc agc<br>Tyr Leu Tyr Leu Thr Val Gly Gly Thr Leu Ser Asn Gly Gly Ile Ser<br>                   165                       170                   175 | 528 |
| ggg cag gcg ttc aag cac ggc ccg cag atc agc aac gtg ctg cag ctg<br>Gly Gln Ala Phe Lys His Gly Pro Gln Ile Ser Asn Val Leu Gln Leu<br>              180                       185                     190 | 576 |
| gag gtg gtc aca ggc aca ggg gag gtg gtg aca tgc tcg ccc acc cag<br>Glu Val Val Thr Gly Thr Gly Glu Val Val Thr Cys Ser Pro Thr Gln<br>          195                       200                     205 | 624 |
| agc ccg gag ctt ttc ttc gcc gta ctt ggt ggg ctt ggc cag ttc ggt<br>Ser Pro Glu Leu Phe Phe Ala Val Leu Gly Gly Leu Gly Gln Phe Gly<br>210                   215                       220 | 672 |
| atc ata acc cgc gca agg att ccg ctg caa gtt gct ccg ccc aag gtg<br>Ile Ile Thr Arg Ala Arg Ile Pro Leu Gln Val Ala Pro Pro Lys Val<br>225                   230                       235                   240 | 720 |
| aga tgg gtg agg gcc ttc tac gac agc ttc gag acg ttc acc aag gac<br>Arg Trp Val Arg Ala Phe Tyr Asp Ser Phe Glu Thr Phe Thr Lys Asp<br>                   245                       250                   255 | 768 |
| cag gag ctg ctg gtc tca atg cca gag ctg gtg gac tac gtg gag ggg<br>Gln Glu Leu Leu Val Ser Met Pro Glu Leu Val Asp Tyr Val Glu Gly<br>              260                       265                     270 | 816 |
| ttc atg gtc ctg aac gag cag tcc ctc cgc agc tcc tcc gtg gcc ttc<br>Phe Met Val Leu Asn Glu Gln Ser Leu Arg Ser Ser Ser Val Ala Phe<br>             275                       280                     285 | 864 |
| ccc gcc cag gtc aac ttc aga ccg gac ttc ggc tcc gac gac ggc acc<br>Pro Ala Gln Val Asn Phe Arg Pro Asp Phe Gly Ser Asp Asp Gly Thr<br>    290                       295                     300 | 912 |
| aac aag aag gtc tgc tac tac tac tgc atc gag ttc gcg gtg cat gac<br>Asn Lys Lys Val Cys Tyr Tyr Tyr Cys Ile Glu Phe Ala Val His Asp<br>305                   310                       315                   320 | 960 |
| ttc caa cgg cag gac tcc gct gct gac cat gtt gtg gac ctg gtg tcg<br>Phe Gln Arg Gln Asp Ser Ala Ala Asp His Val Val Asp Leu Val Ser<br>                   325                       330                   335 | 1008 |
| ggg aag ctg agc tat ctg agg ccc cac gcg tac agc gtg gag gtg gcc<br>Gly Lys Leu Ser Tyr Leu Arg Pro His Ala Tyr Ser Val Glu Val Ala<br>             340                       345                     350 | 1056 |
| tac tgg gat ttc ctc aac agg gtg cgg atg gag gag gag agc ctc agg<br>Tyr Trp Asp Phe Leu Asn Arg Val Arg Met Glu Glu Glu Ser Leu Arg<br>    355                       360                     365 | 1104 |
| agg cgg ggc ctc tgg gac gtg ccg cac ccc tgg ctc aac ctc ttc gtg<br>Arg Arg Gly Leu Trp Asp Val Pro His Pro Trp Leu Asn Leu Phe Val<br>370                   375                       380 | 1152 |
| ccc agg cat ggc gtc gcg cgg ttc atg gac ctg ctc atg gcc acc atc<br>Pro Arg His Gly Val Ala Arg Phe Met Asp Leu Leu Met Ala Thr Ile<br>385                   390                       395                   400 | 1200 |
| gcg cag ggg gac ttc gag ggg ccc gtc ctc gtc tac ccc ctc ctc act<br>Ala Gln Gly Asp Phe Glu Gly Pro Val Leu Val Tyr Pro Leu Leu Thr<br>                   405                       410                   415 | 1248 |
| cac agg tgg gac ggc aac atg tcg gcg gtg gtt ccg gcg gcg cca gac | 1296 |

```
His Arg Trp Asp Gly Asn Met Ser Ala Val Val Pro Ala Ala Pro Asp
            420                 425                 430 ggt gtg atg tac gtc ttc agc gtg cta cgg tcg acg gac ccg gcg cgg      1344
Gly Val Met Tyr Val Phe Ser Val Leu Arg Ser Thr Asp Pro Ala Arg
            435                 440                 445 tgc ggc cgc gcc tgc atg gag agg atc ctg gag cag cac cgc cgt gtc      1392
Cys Gly Arg Ala Cys Met Glu Arg Ile Leu Glu Gln His Arg Arg Val
            450                 455                 460 gcc gac gag gcc tgc cgg cgc ctc ggc gcc aag cag tac ctg gcc agg      1440
Ala Asp Glu Ala Cys Arg Arg Leu Gly Ala Lys Gln Tyr Leu Ala Arg
465                 470                 475                 480 cag ccg tcg ctg gcg cac tgg cgc gac cac ttc ggg gcc agc tgg gac      1488
Gln Pro Ser Leu Ala His Trp Arg Asp His Phe Gly Ala Ser Trp Asp
                485                 490                 495 cgc ttc gtg gcc agg aag gcc cgc ttc gac ccc atg aac gtg ctc ggg      1536
Arg Phe Val Ala Arg Lys Ala Arg Phe Asp Pro Met Asn Val Leu Gly
            500                 505                 510 ccg ggc cag gga att ttc ccc tgg acg gac tcc tcc tcg agc ccg atg      1584
Pro Gly Gln Gly Ile Phe Pro Trp Thr Asp Ser Ser Ser Ser Pro Met
        515                 520                 525 tga                                                                   1587

<210> SEQ ID NO 62
<211> LENGTH: 528
<212> TYPE: PRT
<213> ORGANISM: Zea mays

<400> SEQUENCE: 62

Met Glu Gly Lys Val Leu Cys Thr Tyr Ala Gly Ile Val Ala Leu Leu
 1               5                  10                  15

Leu Cys Ser Ser Val Asn Phe Ile Gln Ser Pro Ser Asp Val Phe Gly
                20                  25                  30

Pro Val Ala Leu Leu Glu Pro Thr Ala Ser Ala Ala Arg Asp Phe Gly
            35                  40                  45

Gly Val Val Ser Glu Ala Ala Ile Ala Val Met Gln Pro Gly Ser Pro
        50                  55                  60

Ala Asp Ile Ala Arg Leu Leu Gly Ala Leu Ser Ser Thr Gly Pro Gly
65                  70                  75                  80

Pro Gly Pro Lys Ala Ala Val Ala Ala Arg Gly Ala Gly His Ser Leu
                85                  90                  95

His Gly Gln Ala Gln Ala Arg Gly Gly Ile Val Val Glu Thr Arg Ala
            100                 105                 110

Leu Pro Arg Leu Val Glu Val Val Arg Arg Gly Asp Gly Asp Gly Gly
        115                 120                 125

Gly Ala Ala Tyr Ala Asp Val Gly Gly Gly Ala Leu Trp Val Glu Val
    130                 135                 140

Leu Glu Glu Cys Leu Arg Ala Gly Leu Ala Pro Arg Ser Trp Thr Asp
145                 150                 155                 160

Tyr Leu Tyr Leu Thr Val Gly Gly Thr Leu Ser Asn Gly Gly Ile Ser
                165                 170                 175

Gly Gln Ala Phe Lys His Gly Pro Gln Ile Ser Asn Val Leu Gln Leu
            180                 185                 190

Glu Val Val Thr Gly Thr Gly Glu Val Val Thr Cys Ser Pro Thr Gln
        195                 200                 205

Ser Pro Glu Leu Phe Phe Ala Val Leu Gly Gly Leu Gly Gln Phe Gly
    210                 215                 220

Ile Ile Thr Arg Ala Arg Ile Pro Leu Gln Val Ala Pro Pro Lys Val
```

```
                225                 230                 235                 240
Arg Trp Val Arg Ala Phe Tyr Asp Ser Phe Glu Thr Phe Thr Lys Asp
                    245                 250                 255
Gln Glu Leu Leu Val Ser Met Pro Glu Leu Val Asp Tyr Val Glu Gly
                260                 265                 270
Phe Met Val Leu Asn Glu Gln Ser Leu Arg Ser Ser Val Ala Phe
            275                 280                 285
Pro Ala Gln Val Asn Phe Arg Pro Asp Phe Gly Ser Asp Asp Gly Thr
        290                 295                 300
Asn Lys Lys Val Cys Tyr Tyr Cys Ile Glu Phe Ala Val His Asp
305                 310                 315                 320
Phe Gln Arg Gln Asp Ser Ala Ala Asp His Val Val Asp Leu Val Ser
                325                 330                 335
Gly Lys Leu Ser Tyr Leu Arg Pro His Ala Tyr Ser Val Glu Val Ala
            340                 345                 350
Tyr Trp Asp Phe Leu Asn Arg Val Arg Met Glu Glu Ser Leu Arg
        355                 360                 365
Arg Arg Gly Leu Trp Asp Val Pro His Pro Trp Leu Asn Leu Phe Val
    370                 375                 380
Pro Arg His Gly Val Ala Arg Phe Met Asp Leu Leu Met Ala Thr Ile
385                 390                 395                 400
Ala Gln Gly Asp Phe Glu Gly Pro Val Leu Val Tyr Pro Leu Leu Thr
                405                 410                 415
His Arg Trp Asp Gly Asn Met Ser Ala Val Pro Ala Ala Pro Asp
            420                 425                 430
Gly Val Met Tyr Val Phe Ser Val Leu Arg Ser Thr Asp Pro Ala Arg
        435                 440                 445
Cys Gly Arg Ala Cys Met Glu Arg Ile Leu Glu Gln His Arg Arg Val
    450                 455                 460
Ala Asp Glu Ala Cys Arg Arg Leu Gly Ala Lys Gln Tyr Leu Ala Arg
465                 470                 475                 480
Gln Pro Ser Leu Ala His Trp Arg Asp His Phe Gly Ala Ser Trp Asp
                485                 490                 495
Arg Phe Val Ala Arg Lys Ala Arg Phe Asp Pro Met Asn Val Leu Gly
            500                 505                 510
Pro Gly Gln Gly Ile Phe Pro Trp Thr Asp Ser Ser Ser Pro Met
        515                 520                 525

<210> SEQ ID NO 63
<211> LENGTH: 2080
<212> TYPE: DNA
<213> ORGANISM: Zea mays
<220> FEATURE:
<221> NAME/KEY: promoter
<222> LOCATION: (1)...(2080)
<223> OTHER INFORMATION: ZmCkx8 promoter region

<400> SEQUENCE: 63
gaattctatc ttttcttgag ttattttatg atacaactgt tgctttgtct ggaatttatt    60
atcctacttc aacattgatg cttcatcata tacttaaaat tgctagacat ctaaatgctt   120
ttgaaaatga tgctttgctt agagatgcta ttgttcctat gaaaacaaaa tatttgaaat   180
attggaggaa gatacctgtt ttatattgct ttgcttttgt attggatcct agagcaaaaa   240 tgaggggggtt taataagctt cttatgaggt tgtctggact taatgaaact gattattcaa   300
ggtatcctac atacattcgg tctaaactaa ctaagatttt tcagatatat gaattgaaat   360
```

-continued

| | |
|---|---|
| ttggtgaagt gtgcttgagt gcacaacaac ataagagtgc tggtacggca ggtaaggcta | 420 |
| cagaggcatg ggatgacata tatggggatg atatccttat gccttcccaa tctactagag | 480 |
| ctactcctac agctgtatca tctactgctg ctgctatatc tgagttgtca tcatatcttg | 540 |
| atagtgatac tgtcacccag tttgactctg atttcattct tctaaactgg tggcagcgac | 600 |
| acaagttgac atatcctgtg ctttctatac ttgctaaaga tgttataatt gtgcctgctt | 660 |
| ccactgtatc atcagagtcc actttcagtt tagctggcag ggtgcttgaa gaccgacggc | 720 |
| ggcgcctaac tcctgatatg gttgaagttt tgtcttgcat aaaggactgg gagcttgctg | 780 |
| acttgcatag tcagcacacg gtggagaaag ataccaaaga acttgaagtt gttttttgaag | 840 |
| caatgtacct agaagaaact ggtggaggca agaaagaag aggtggagga tctggtggag | 900 |
| cgggtagatc ttgagcagct gaattattgc tattactata ctctgttctt ctgttgtaac | 960 |
| ttgtgatgaa ctattaaact ctggacttaa attgaaccta tataggagct ggctctactc | 1020 |
| tttttcttcc tagggttttc tcacgagttg tgagttttta cctaggaagg ttttaatga | 1080 |
| ggcagcattg cactaaggct ccattagtat attgtttgca taaacttttg tgaactgtga | 1140 |
| ttttgtttct gagatgtttt gtgaactgtg tgaattgact gaaatctgat ataggaactg | 1200 |
| tgtgaaatct gatataggaa ctgtgtgaat tgactgaaat ttgatatatg aactgtgtga | 1260 |
| aatttgattc agctgtttat tgtgaaatta ctgtgcttcg ggtcagcccg gcccatgggg | 1320 |
| ctgaccgggc cagaggcacg gcacgacaca acccgtttaa gccactttcg tgccgtgctt | 1380 |
| gtgccaacag tttagcccgc gggccagcac ggcacggcac ggaagtagga tcgtgccgtg | 1440 |
| cccggcacgc acagtaacgt gctgtgcttg gccgtgcccg tgccgtgccg gcccgacaca | 1500 |
| cacgaatgga catgtatagt cctgactgtc ccgtaaccaa acggaccca acatactcga | 1560 |
| tgttgtttag accgaccgac tgatcgtgcc acattgcact gcgcgtgaag aggtcgatac | 1620 |
| cgatcgttta gaccaccatg tcagctgatg gtactgtccc acgttggcat tggagcagct | 1680 |
| tacctatcat acatatcatc tatttttat ttaaaaattt actataaata gtgtagtata | 1740 |
| caatataaaa tagtatcata tgctcaatat gcttgagaca gctttaatag gatcaaacta | 1800 |
| agattctcgg gcccggcatc ggtagcgacg acaccggcta tatataatgc actcagtgag | 1860 |
| cttcctggtg gctcttgctg cttcttcctt gctgttccat ccgtccacag ttcttgtggg | 1920 |
| aacccaagat cgatcttgac ggggacgtga gcacggcacg tcgcgacctt attcttccgt | 1980 |
| cttggccccg tgcaccggca agcggcaacc aaatgcgcat gcccctgtga agctaatag | 2040 |
| tagctacatc acacagcaag acactatagc cagctagcca | 2080 |

<210> SEQ ID NO 64
<211> LENGTH: 4365
<212> TYPE: DNA
<213> ORGANISM: Zea mays
<220> FEATURE:
<221> NAME/KEY: 5'UTR
<222> LOCATION: (3125)...(3226)
<220> FEATURE:
<221> NAME/KEY: intron
<222> LOCATION: (3227)...(4365)

<400> SEQUENCE: 64

| | |
|---|---|
| tagttgtcgt tcgctgatgc cttttgctgc aggggctgca cgtcagcctg atgcatttgt | 60 |
| tttgagattc atggcatgtc ttgcaggtca acttttgcct gattaataac atgctggtaa | 120 |
| acacggaggc tgggccacaa tgtctaagtt tagtaggtca aattgaagaa ctaactttag | 180 |
| actaaaaatt aaatcaaaca ggcctccaac ggtgcactaa atagcattcc taaccgtaca | 240 |

```
tacagtatga acagttcaat gtaaggagtc ctcgtatcta tagggagaag gaatctccct    300
gtatatatat agagtacgaa gcttcctcta tactttaata gagtcgtttc tttacggtat    360
taatcttatt taaatctcct aatatagtaa taatatatta tgatagtaca aatattatat    420
aactttttat ttttaaaaaa tgtaaataga tgttaattag ttgaatttta taatacatat    480
gaagaggtgt ataaggaaat ggttggaaac cttgtatatg tacgaggaga attttttaaa    540
atgagatagt aaaatatatt agaacgtaat ataaggagag atgtatatat gaaaagttgt    600
ataaagaaat agttggagac gtcatatatg tgagaagata attttaagat gagatagtaa    660
aatatattag aacgtagaga tgtataggaa aaatggttgg gagggtcatg tcatccgtca    720
accaccaacc ccggaggtag gagcacctac caccactgcc acggcccat tttgtcctcc     780 catgtgggcc ctaaagtggc caagtggggc gcctcatgtc tagtagtttt atgaggatta    840
tgatgggaga tcagctccaa ctccaatcta tgagttcgaa ttacatttat ttggttgaac    900
caggaagacg atgcgcatac actcatgcag tgtgttttga gtgtgatgta agccagattc    960
aagaaaaaaa aagtagctgg atgggagctt tcatggttgg tgggggctgg tgggccgagg   1020
agatgctcct actactccca caccgtttga gggttggtgg cacaaaatat tttctcgatc   1080
tgataatacc gttttgaac ataccataat attttagatt cattgacgtt tagaagcacg    1140
tttaaaactt gtgtattta aaccatggtt ttactaatac catagtattt ttttgggata    1200
aaaaactttg gtctaaacta ttttttttg cttgcacgca gctgcagttt tctcttttcc    1260
tacactaact aaaatattgt atcttcaaat atgtgttgga ttagacacat gtaaaatata   1320
ccctagtaay gtcacggtay acaataaacc atgatattgt aaactacggt tttaaaaaat   1380
agagttccta acagacatg tgtcatgatt ggctcgttgt ggaaaatcaa tttagacatc    1440
tttgaaactc aggaatctca tgagaatgct atagaaattt tacagaaatt agtttaaaaa   1500
tacagatatc cttttgatcc tgttcggact ttgggttgtc cgtagcttcg catgcaatta   1560
gttgtagttt catatgacta gccgctaaca atcttttta tccccactga cctagctaat    1620
tgttagctaa taactacttt actagttaca tcaaactagc taataacagt taatatagc    1680 tagtagctaa taattagcag ccaatagatg accaaaaaat gaagcataca aacaatacta   1740
caaactgaca tcggcttcat ttccaagtaa atcggctttt aaggttatca taagctatt    1800 ttttaaaaaa ataatcaaat ttataggaaa acaaacgta tttatgctac caaatcacag    1860
taattagata aatcatcaaaa tgtatttta cagtttattt acttagatta atagatattt    1920
atattggtat tctataaatt tggtcagaca taaaataaaa agcttcactc aaagacaatt   1980
ctttcggtgc ggatggtgta cctatcttta gtgtattcca tgaatatcaa ggcaatcaat   2040
gaagagcgtg ctgtaaacaa tcgtcatatc ttggccttat ttggttagaa ggaaattgcg   2100
gtgcatcaag tgcttgttg gttagaaatg aattaagtag gatttgaaat ctcatactat    2160
ttaaaaatta ataacaaga gatttaattt tcacaatcct ctataatccc tatacaaccg    2220
aacaagacat aagagctagt ttgaaaattc aaattctctc cgtggaattt aagtttctaa   2280
actagaatat atatcaacat tatcaacatc accaacaacc ccacatctgt attctgccct   2340
gctagctaag cacgtctcat tagctggcgt aagcgccttt ttttaataca ccatttttct   2400
acgatctgct gcttgccagt tgggcctttg tgcattcccc tctgtaaaat aataaaatac   2460
gaaatttccg tttccgtttc attagttggc attcgctgtg tagactgcaa aagtcagcct   2520
gttgctgttt ttttttctc ttccatggat gcgacagcta ctagcacggt cgttcagatt    2580
catcatatgg cgcactcgct tgccattcta acccaaatct cctgattaaa acgccaagat   2640
```

```
ttgtgccact cttattatag aaaattgttt gtttcacgcg aaattgttaa ttccaagttt    2700
ttagcaaagg cggagaggta cgtgtagacg tttcattgtt gctagtattt gggtctgctc    2760
attcgaacga attctgcaga aaatctagat tgcataaatt ttctaggagt ttccgatgcc    2820
gtagatccgg tttcttttg cctataatca attcgtttaa aaactgtcat gaggttttt    2880 tttattcttg attttcgatc gcactagctc aaaaaattta tgtagcaaga aaaagcagaa    2940
ataatcaaaa caaacgtttt tttttccaaa acaaaaaaga aagaaaacct caggcaccaa    3000
cggatctggc agatgggaaa tgggatctca ccaaatccca cgtactagcg cgcaccacct    3060
aacgcagacg atacacctt ttataaatga aacccacgaa cccctcagat ttcccgtgct    3120
catcatcacc agttcaccac ccacctccca ctcccagttc accccgtcgt cctcggcgcc    3180
accactcctc gtccccggc gctactcccc cgctccacgg tccaagggta agcgcgcctc    3240
cccaccgctc ccttgctcta tatagccctt cccactccac cgctcgccca ttccttcgct    3300
tccgctgtct ccccgcgcct cccggatcgc ctcggcgcgc ggtgagtctg gcgtgctgtt    3360
gggccgcctg cctgcctgcc cgtctctctt cggtctggat gcgtagccat tgtctccttc    3420
ccggtcgggg ttgctttgct gcgcgaggct gtgcggaatt ggtagttttt ttggtcgaga    3480
atggctggtt cgattttcgg gttccttttt gcacatgtcg ttgagatcgc cgctgggtca    3540
ctacgggatt agagcctgtt gccccctttt gtttctcgag gagatggttc gagtcgtaac    3600
tatatgaaat tcaggcccca gaattttgtt agcagcagaa cgggctttcc aaaactgttg    3660
ttacatctgt tggaaaattt agaatttctc catgtatgta tgtatgatcc gaaagttggg    3720
tggcagtttc agtgaatgga cagtgatatt tttatattg atgttgtttt ctgtggctgt    3780
agtttaatat atcatgcttc ctgtccaaac tatagtttct tacgatgtt atttgtagca    3840 tgatccctgc atgtctgaga gggaccttac ttcccttccg accgatttta gctctcctgt    3900
acccacatcc tggaaaggtt aggttgcaac ctaaatggaa gactgtagtg catacagcat    3960
acctccatgg tatggttaat ccttaccagt ttaaagaaac agccttgatt gaccagaggt    4020
atttctctgc atcgaatcat ttagatctta tgggagcaac acatgcagta tgaattcaga    4080
gtttcacatg gaaggataag aattcagttc agtttatgtt tcagtgaaat atatagaata    4140
tttttgtagc ttgtttgcag ctttgttcag ataaatattc agttatctgt tgcagtgaat    4200
caaagctgat tttaacattt ttgctgttat atagaaaggt ggtgtcccat attgttggat    4260
acacttgcat gagccccaag agggagctct tttagcttat ttgcagcttt gttgaggcaa    4320
atattcagct agcttctcta tttctgtgaa tcaacctgat cttaa                   4365
```

<210> SEQ ID NO 65
<211> LENGTH: 4215
<212> TYPE: DNA
<213> ORGANISM: Zea mays
<220> FEATURE:
<221> NAME/KEY: promoter
<222> LOCATION: (1)...(4215)

<400> SEQUENCE: 65

```
gatccctgtg gagaaatttt tacgtcgcgg ggatggtatg gggagttatt ccctgtagg     60 aaatgggtga cgcctaagag ggagggtgaa gtaggacttc taaaactttc actaaactag   120
gccacaaata attccctaga gcaaaaccta tgcaaatagt caaactagaa tgtgcaaacc   180
aagttttgtc taagtgttgc tatctctacc gcaatggcta agtttcaatc tacactatat   240
aagtatgaat acaagaatga aacttaaata cttaatataa atgcgaaaac ttaaagagca   300
aggtagagat gcaaattctc gtggatgacg cctgcatttt tatcgaggta tccggaacca   360
```

-continued

```
cgcaaggtcc cgactaatcc tcattggtgc ccctacgcaa agggaagccc acgcgagggc    420
caagcacctc ggtcgagtaa ctctatagag agccgtgggc cttctccacg cgcaagtggt    480
gctctgcttt cagctcctct cagaccctcc ccgctgtctc cactatcgag cttccggctg    540
aaaatgccat gggcctcgtt ccctccggta cacggtggcg gccgtgacac aaatgcggtt    600
atcacggtct cgcaagactc tcaccccac ttggtacaat ttcaatggct cgcacaagag     660
ccgaggggtt gatggtttat ctaatctcac tcaactaact aggattcatc taaagcaagc    720
gctagagcgg tctaactaac ctaagcactt cacaaagcac ctacgctaat caccgagtga    780
ttctatttag cacttgggtg caagagcact tgagaatgtc tactatatgc cttgctatgt    840
ctcttgggct cccaaacttg gaaatggccg gttggtggtg tatttatagc ccccaacaca    900
aaactagccg ttggaggaag ctgctgcttt ttgtggtgca ccggacagtc cggtggggtc    960
accagacagt ccgacgcccc tgtccggtgc cctgtccga tgcgcctagt tgttgggtct    1020
gtcagcgtag gtgaccgttg gcgcgcaggc ttttgcacc ggacagtccg gtggtcttcc     1080
ctcgacagtg ccacctggag ctagccgtta gggctactgt tcctggtgca ccggacagta    1140
gtccggtgct cttgtctgga cagtccgact gtggcaacac ttcttctttt cttggactttt   1200 acttgatctt catgatgtct tcttttgagg tgttgctttc ctaagtgcct tggtccaagt    1260
aacttatcat cctgtgaact acaaacacaa atagtagcaa acacattagt ccacaggtta    1320
tgttgatcat caaataccaa aatctattaa gccaaatggc ccagggtcca ttttccttac    1380
atccccgacg aagaattctc cgttgccatc cctatctgtg tacgcactac tggaatccgg    1440
gtctttgctg agtaccgcac tcggcaaagt cctactctcg gtaacgatgc cttttgccga    1500
gagcaggact ctcggcacag gaatacactc ggcgaagggc gggtctcggc aaaggccgtt    1560
agccaccgtc caaagctgac ggtcgttacc tatgccgagt ggtggaaaga tattgtgaag    1620
gcctaaggcc gatttcgtcc taagcagggc ccaaaggaag gaagtacttc agtggatcaa    1680
gatgttgatg ttccctgatg ggtatgcagc taacctgagt aggtggggtg aacttatcta    1740
ctctgtgagt cttagggatg aagagtcatg acttccacat atggattgaa cagattcttc    1800
tctgtgcatg gacaatctgg ggcggcatcc aacaaccctc atggatcgcc cggccaatcg    1860
ccgcaccagt ccatccgccc acctcgatga gacttatgtt cttagtgttg agacttcaga    1920
acttattgat aatgctgtat tggatactta tgtttgtgtt cgatacttat gtgagaactt    1980
gagacttatg agacttatgt tcttgatact tatgtttgtg ttgagaactt ggatatttat    2040
gtttgtgttg atacttatg tctgtgatga tatatgtgat gtatatatgt gatgtatatg     2100
tgacatatgt gatgtatatg tggtatcttt tgtttgtttg gatggaatag agaaagcaaa    2160
taaaaatgtg tatactggtc actttgtcga gtgtaacact cggcaaaaag gtgctttgcc    2220
gagtgttagg gccatagcac tcggtagaga accaatactt aggcaccggt aaagcttttt    2280
tgccgagtgt tgtggccctg gcactcagct ttgccgagtg cctcacagag cactcgacaa    2340
agaacctgac aaatggaccc gctggtaaat cctttaccga gtgcaggtca gtagacactc    2400
ggcaaaggta acttctttgc cgagtgccgc ttagaacatt tgacaaaggg tcatctccgt    2460
tacccggtgt cgtgacggcc gcttttcttt gccgagtgcc tgatagaaag tactcggcaa    2520
agaagtcgtt gccaatgtat tgttcgctga ggtctctttg tcaagtatta cactcggcaa    2580
agactgtgcc gagtgttttt cagactttgc cgagtggttt aagcactcag caaagcgctc    2640
gatttcggta gtgacggttg tttggcaata gtaaaatcca gccctctccc gtggggaaaa    2700
aactggtagg atctggctcg tggctaagat tctctttctt ccctttgtaa aaaaagagaa    2760
```

```
gaaaaaaaaa acgactgtca cggtgccttg tctggtaatg atcgcgcggt cggctctgtc    2820
ctaacccgta agatggacgg gagctgatga tagcgtgacc tccaaataaa caacaagggc    2880
gtgttccccg tggtcgaata ttttaagggc cactgattag gtgcggttga atacatcaac    2940
ttcacgaaca tcatctgatc tgatctgatt tggtctgata tgatctgggt agtcatttct    3000
gcaatgagca tctatcaggt gaaccaatta atattgatga cattatgagt tcgaagatat    3060
actctaaagt gttatctaaa tacagaagac attcgttcgt tctttgccta taactctaaa    3120
aggcttgtaa caccctcatt catcctctat atacgaagac tctctcctat cattttatc     3180 gatttatttt ttttatattt tagacaatgg aattaaatag aactaaaata tatataagaa    3240
tctgaggacc cgagatggta atggggactc gatcctcgat tctccacgga gaattcctct    3300
aggatatagg taatttgtcc ccacgaggat tgaaacgggg taatttggtc cccatgtgcc    3360
cgtcccgcga acttctcttg atctaaatta gtctatttcc atgttaaaac tatactaaaa    3420
atttaataca cagtctatta taaaatagca aactaaattc taaagttgat gcatcttgta    3480
attttaaatc tggtttgttc aagttatatt catttgatat aataaatttg aatttgactc    3540
ttaatatcgt atttttcct aacggggacg gattctccac ggggataaat tccatgatac     3600
agatgggatg aaagaaaaat ctcccgtatg aacttttgca ggaatgggga tgggccagag    3660 aaatttctc cctgcgggga cggggagcc atatcctcgg tggagaattt cccattatca     3720
tccttatttg tggtacatat atatgcataa tcttttttt ttgactgaca tgtgggaaag    3780
tatcccatct caatagtaga aaatcttggg aacggtagga tcgaacacaa agatcagcta    3840
gcttgtaatc accgagccat atagctagag ggtaatagat catgaatcaa atgtttttt    3900 cataaattat taaggctcta aattatttt aatttaaaaa taaataaaaa tatagttcga    3960
ttcttacatt ttatagtgta aaactttaaa gtctattatt accccctactt attgagttat   4020 ggttcagttc ttgtcgacgg agagtaatga gatatagaat aaggtaccct atagaataaa    4080
gaatctttct ctgaaaagtc tgacgtacgt aaataagata taataaaaaa aatacaaaga    4140
gaagcgctgg actggagatg ctcctatatg cggcaatgcc tgtgcttata aatagccacc    4200
tcggtcggca aggac                                                     4215

<210> SEQ ID NO 66
<211> LENGTH: 419
<212> TYPE: DNA
<213> ORGANISM: Zea mays
<220> FEATURE:
<221> NAME/KEY: 3'UTR
<222> LOCATION: (1)...(419)
<223> OTHER INFORMATION: ZmCkx2 TR1

<400> SEQUENCE: 66
gttgtacaaa agtgtaggta aaaagtatcc cctgtaaaga caatatctac ggaaggtagc      60
tagcctgaag aacacagcat agcgactttt tttatagtgg ccgaagacac ctcagagcaa     120
tacttcaaag tggagcaatg tcacctgaac tctgacacct ttggaggcaa tcactggagg    180
atcgtagcgg tccaagaaac ctgtatgttg ttacagcgtt gataattgag acgagctgtg    240
atgatcaact gatcactaac cagtatcccg gttatcaaca gtgcagaaag ttgcttgagg    300
gtagtagtgc cttgattaac aaataacact gcctgttatt tcacttgtaa ctagcatctc    360
atcccactca ggagtgcctg cgtaaatgta gcaggtttac attactttcc atgagtcag    419

<210> SEQ ID NO 67
<211> LENGTH: 2146
```

```
<212> TYPE: DNA
<213> ORGANISM: Zea mays
<220> FEATURE:
<221> NAME/KEY: CDS
<222> LOCATION: (68)...(1645)
<223> OTHER INFORMATION: ZmCkx2b or cko3; clone 2

<400> SEQUENCE: 67
tctctctctc tctctgcctt ctgtttccag gacgtcccaa ctgcccagcg ccgaccggcc      60 ggccacc atg aag ccg cca tca tca ctg gtg cac tac ttc aag ctg ctg       109
        Met Lys Pro Pro Ser Ser Leu Val His Tyr Phe Lys Leu Leu
        1               5                   10 gtc ctg ctg gcg ctc gcc agg ctg acc atg cac gtc ccc gac gag gac       157
Val Leu Leu Ala Leu Ala Arg Leu Thr Met His Val Pro Asp Glu Asp
15                  20                  25                  30 gtg ctc ttg tcc ctc ggc gcg ctc cgc ctc gac ggc cat ttc agt ttc       205
Val Leu Leu Ser Leu Gly Ala Leu Arg Leu Asp Gly His Phe Ser Phe
                35                  40                  45 cac gac gtc tcc gcc atg gcg cgg gac ttc ggc aac cag tgc agc ttc       253
His Asp Val Ser Ala Met Ala Arg Asp Phe Gly Asn Gln Cys Ser Phe
            50                  55                  60 ctg ccg gcc gcc gtg ctc cac cct ggc tcg gtc tcc gac atc gcc gcc       301
Leu Pro Ala Ala Val Leu His Pro Gly Ser Val Ser Asp Ile Ala Ala
        65                  70                  75 atc gtt agg cac gtc ttc tcc ctg ggc gag ggc tcg ccg ctc acg gtc       349
Ile Val Arg His Val Phe Ser Leu Gly Glu Gly Ser Pro Leu Thr Val
    80                  85                  90 gcg gcg cgc ggg cac ggg cac tcc ctc atg ggc cag tcc cag gcc gcc       397
Ala Ala Arg Gly His Gly His Ser Leu Met Gly Gln Ser Gln Ala Ala
95                  100                 105                 110 cag ggg atc gtg gtc agg atg gag tcg ctc cgg ggt cct agg ctt cag       445
Gln Gly Ile Val Val Arg Met Glu Ser Leu Arg Gly Pro Arg Leu Gln
                115                 120                 125 gtc aac gac gcc ggc gtg tcg cca ccg tct gtc gat gct ccc gga gga       493
Val Asn Asp Ala Gly Val Ser Pro Pro Ser Val Asp Ala Pro Gly Gly
            130                 135                 140 gag ctc tgg atc aac gtg ctg cgt gag acg ctc aag cac ggt ctg gca       541
Glu Leu Trp Ile Asn Val Leu Arg Glu Thr Leu Lys His Gly Leu Ala
        145                 150                 155 ccc aag tcg tgg acg gac tac ctc cat ctc acg gtc ggt ggc acc ttg       589
Pro Lys Ser Trp Thr Asp Tyr Leu His Leu Thr Val Gly Gly Thr Leu
    160                 165                 170 tct aat gcg ggg gtc agc ggg cag gcg ttc cgc cac gga ccg cag gtc       637
Ser Asn Ala Gly Val Ser Gly Gln Ala Phe Arg His Gly Pro Gln Val
175                 180                 185                 190 agc aat gtc aat caa ctg gag att gtg aca gga aga gga gat gtc gtt       685
Ser Asn Val Asn Gln Leu Glu Ile Val Thr Gly Arg Gly Asp Val Val
                195                 200                 205 acc tgc tca ccc gat gat aac gct gat ctc ttc tat gct gct ctc ggt       733
Thr Cys Ser Pro Asp Asp Asn Ala Asp Leu Phe Tyr Ala Ala Leu Gly
            210                 215                 220 gat ctt ggt cag ttc ggg atc atc acc aga gca agg att gca ctt gag       781
Asp Leu Gly Gln Phe Gly Ile Ile Thr Arg Ala Arg Ile Ala Leu Glu
        225                 230                 235 cct gct cca aag atg gtg agg tgg ata aga gtt ctt tac tcg gat ttt       829
Pro Ala Pro Lys Met Val Arg Trp Ile Arg Val Leu Tyr Ser Asp Phe
    240                 245                 250 gaa agc ttc acc gag gac cag gag atg ctg ata atg gca gag aac tcc       877
Glu Ser Phe Thr Glu Asp Gln Glu Met Leu Ile Met Ala Glu Asn Ser
255                 260                 265                 270 ttt gac tac gtt gaa ggt ttt gtc atc ata aac agg aca ggc gtc ctc       925
```

-continued

```
                Phe Asp Tyr Val Glu Gly Phe Val Ile Ile Asn Arg Thr Gly Val Leu
                                275                 280                 285 aac aac tgg agg gcg tcc ttc aag cca caa gac cca gtc gaa gca agc       973
Asn Asn Trp Arg Ala Ser Phe Lys Pro Gln Asp Pro Val Glu Ala Ser
            290                 295                 300 cat ttt cag tcg gat gga aga gta cta tac tgc ctc gag cta acc aag       1021
His Phe Gln Ser Asp Gly Arg Val Leu Tyr Cys Leu Glu Leu Thr Lys
        305                 310                 315 aac ttc aat agt gac gac act gat acc atg gaa cag gaa gtt act gta       1069
Asn Phe Asn Ser Asp Asp Thr Asp Thr Met Glu Gln Glu Val Thr Val
    320                 325                 330 ctg cta tct cga ctt aga ttc ata cag tct act cta ttc cac acc gat       1117
Leu Leu Ser Arg Leu Arg Phe Ile Gln Ser Thr Leu Phe His Thr Asp
335                 340                 345                 350 gtc acg tac ctg gag ttc ttg gac agg gtg cac acc tct gag ttg aaa       1165
Val Thr Tyr Leu Glu Phe Leu Asp Arg Val His Thr Ser Glu Leu Lys
                355                 360                 365 ctg agg gca caa ggc ctc tgg gaa gtt cca cat cct tgg ctg aat ctt       1213
Leu Arg Ala Gln Gly Leu Trp Glu Val Pro His Pro Trp Leu Asn Leu
            370                 375                 380 cta ata ccg agg agc tcc atc cgc aga ttt gct aag gaa gtc ttt ggc       1261
Leu Ile Pro Arg Ser Ser Ile Arg Arg Phe Ala Lys Glu Val Phe Gly
        385                 390                 395 aag atc ctg aaa gat agc aac aat ggt ccc ata ttg ctt tat cca gtg       1309
Lys Ile Leu Lys Asp Ser Asn Asn Gly Pro Ile Leu Leu Tyr Pro Val
    400                 405                 410 aac aaa tca aag tgg gac aac aga acg tca gta gtc ata cca gat gag       1357
Asn Lys Ser Lys Trp Asp Asn Arg Thr Ser Val Val Ile Pro Asp Glu
415                 420                 425                 430 gaa att ttc tac cta gtg ggg ttc ctt tct tca gca ccg tct ctc tca       1405
Glu Ile Phe Tyr Leu Val Gly Phe Leu Ser Ser Ala Pro Ser Leu Ser
                435                 440                 445 ggt tac ggc agc att gca cat tca atg aac ctg aac aaa cag ata gtg       1453
Gly Tyr Gly Ser Ile Ala His Ser Met Asn Leu Asn Lys Gln Ile Val
            450                 455                 460 gag ttc tgt gaa gag gct ggt att ggg atg aaa cag tat ctg gca ccc       1501
Glu Phe Cys Glu Glu Ala Gly Ile Gly Met Lys Gln Tyr Leu Ala Pro
        465                 470                 475 tac acc aca cag cag cag tgg aaa gcc cac ttt gga gca agg tgg gag       1549
Tyr Thr Thr Gln Gln Gln Trp Lys Ala His Phe Gly Ala Arg Trp Glu
    480                 485                 490 aca ttt gaa cgg agg aaa cac aga tat gat ccc cta gcc atc cta gcg       1597
Thr Phe Glu Arg Arg Lys His Arg Tyr Asp Pro Leu Ala Ile Leu Ala
495                 500                 505                 510 cca gga cag aga ata ttc cca aag gcg tca ctg cca ttg cct ttg tga       1645
Pro Gly Gln Arg Ile Phe Pro Lys Ala Ser Leu Pro Leu Pro Leu
                515                 520                 525 cagttcctgc tacttgaagg attctgtaga gcatacgttt acgttgtaca aaagtgtagg    1705
taaaaagtat cccctgtaaa gacaatatct acggaaggta gctagcctga agaacacagc    1765
atagcgactt tttttatagt ggccgaagac acctcagagc aatacttcaa agtggggcaa    1825
tgtcacctga actctgacac ctttggaggc aatcactgga ggatcgtagc ggtccaagaa    1885
acctgtatgt tgttacagcg ttgataattg agacgagctg tgatgatcaa ctgatcacta    1945
accagtatcc cggttatcaa cagtgcagaa agttgcttga gggtagtagt gccttgatta    2005
acaaataaca ctgcctgtta tttcacttgt aactagcatc tcatcccact caggagtgcc    2065
tgcgtaaatg tagcaggttt acattacttt ccatgagtca gaatattata tgctcatgca    2125
aaaacagtaa agtctcttat c                                              2146
```

<210> SEQ ID NO 68
<211> LENGTH: 525
<212> TYPE: PRT
<213> ORGANISM: Zea mays

<400> SEQUENCE: 68

```
Met Lys Pro Pro Ser Ser Leu Val His Tyr Phe Lys Leu Leu Val Leu
 1               5                  10                  15

Leu Ala Leu Ala Arg Leu Thr Met His Val Pro Asp Glu Asp Val Leu
            20                  25                  30

Leu Ser Leu Gly Ala Leu Arg Leu Asp Gly His Phe Ser Phe His Asp
        35                  40                  45

Val Ser Ala Met Ala Arg Asp Phe Gly Asn Gln Cys Ser Phe Leu Pro
    50                  55                  60

Ala Ala Val Leu His Pro Gly Ser Val Ser Asp Ile Ala Ala Ile Val
65                  70                  75                  80

Arg His Val Phe Ser Leu Gly Glu Gly Ser Pro Leu Thr Val Ala Ala
                85                  90                  95

Arg Gly His Gly His Ser Leu Met Gly Gln Ser Gln Ala Ala Gln Gly
           100                 105                 110

Ile Val Val Arg Met Glu Ser Leu Arg Gly Pro Arg Leu Gln Val Asn
       115                 120                 125

Asp Ala Gly Val Ser Pro Ser Val Asp Ala Pro Gly Gly Glu Leu
   130                 135                 140

Trp Ile Asn Val Leu Arg Glu Thr Leu Lys His Gly Leu Ala Pro Lys
145                 150                 155                 160

Ser Trp Thr Asp Tyr Leu His Leu Thr Val Gly Gly Thr Leu Ser Asn
               165                 170                 175

Ala Gly Val Ser Gly Gln Ala Phe Arg His Gly Pro Gln Val Ser Asn
           180                 185                 190

Val Asn Gln Leu Glu Ile Val Thr Gly Arg Gly Asp Val Val Thr Cys
       195                 200                 205

Ser Pro Asp Asp Asn Ala Asp Leu Phe Tyr Ala Ala Leu Gly Asp Leu
   210                 215                 220

Gly Gln Phe Gly Ile Ile Thr Arg Ala Arg Ile Ala Leu Glu Pro Ala
225                 230                 235                 240

Pro Lys Met Val Arg Trp Ile Arg Val Leu Tyr Ser Asp Phe Glu Ser
               245                 250                 255

Phe Thr Glu Asp Gln Glu Met Leu Ile Met Ala Glu Asn Ser Phe Asp
           260                 265                 270

Tyr Val Glu Gly Phe Val Ile Ile Asn Arg Thr Gly Val Leu Asn Asn
       275                 280                 285

Trp Arg Ala Ser Phe Lys Pro Gln Asp Pro Val Glu Ala Ser His Phe
   290                 295                 300

Gln Ser Asp Gly Arg Val Leu Tyr Cys Leu Glu Leu Thr Lys Asn Phe
305                 310                 315                 320

Asn Ser Asp Asp Thr Asp Thr Met Glu Gln Glu Val Thr Val Leu Leu
               325                 330                 335

Ser Arg Leu Arg Phe Ile Gln Ser Thr Leu Phe His Thr Asp Val Thr
           340                 345                 350

Tyr Leu Glu Phe Leu Asp Arg Val His Thr Ser Glu Leu Lys Leu Arg
       355                 360                 365

Ala Gln Gly Leu Trp Glu Val Pro His Pro Trp Leu Asn Leu Leu Ile
   370                 375                 380
```

```
Pro Arg Ser Ser Ile Arg Arg Phe Ala Lys Glu Val Phe Lys Ile
385                 390                 395                 400

Leu Lys Asp Ser Asn Asn Gly Pro Ile Leu Leu Tyr Pro Val Asn Lys
            405                 410                 415

Ser Lys Trp Asp Asn Arg Thr Ser Val Val Ile Pro Asp Glu Glu Ile
            420                 425                 430

Phe Tyr Leu Val Gly Phe Leu Ser Ser Ala Pro Ser Leu Ser Gly Tyr
            435                 440                 445

Gly Ser Ile Ala His Ser Met Asn Leu Asn Lys Gln Ile Val Glu Phe
            450                 455                 460

Cys Glu Glu Ala Gly Ile Gly Met Lys Gln Tyr Leu Ala Pro Tyr Thr
465                 470                 475                 480

Thr Gln Gln Gln Trp Lys Ala His Phe Gly Ala Arg Trp Glu Thr Phe
            485                 490                 495

Glu Arg Arg Lys His Arg Tyr Asp Pro Leu Ala Ile Leu Ala Pro Gly
            500                 505                 510

Gln Arg Ile Phe Pro Lys Ala Ser Leu Pro Leu Pro Leu
            515                 520                 525

<210> SEQ ID NO 69
<211> LENGTH: 3390
<212> TYPE: DNA
<213> ORGANISM: Zea mays
<220> FEATURE:
<221> NAME/KEY: promoter
<222> LOCATION: (1)...(3390)
<223> OTHER INFORMATION: ZmCkx6 promoter

<400> SEQUENCE: 69
aaaaactgtg cagctagcta agagaagctg aaaaacagtt ttttttttta aaaaaatct      60 gtctactctt agagcatctc caacaacgtg acctataaaa ttgccctata atttgaaaat   120
aagtatattt tatagaattt agggcaccaa caaaacacct cgctccaaca gtaaagtccc   180
aaatctagat tatagggcag accactacag tgtagtatat ttgagtcact tgagagggtg   240
ctctatagtt ttttgacaaa aaattatgaa atatggcact gttggagtag ttttttcctgt  300 gtagagccct atatttcaat tttaggcact agtttaaggc attgttggag atgctcttat   360
tttttaacga aaagctgaaa aactggcctt cgattgataa aaaaacattc agattaataa   420
tgttgtgagt ggtacctatg ccttctctta ttttttttctt aatgatttat gagaaactat    480
aaattcttat attaacatat agagaaaaag gctctttgtt ttgcgaccga gcagggagt    540 atacacggat acaccggtac ctccgctccg cacgtacctg gaggctggag cagacgtttg   600
actgggacgc gccgagtgtc cggccaatga gagcgacgca cgtagcgcgg gggcgccgct    660
gcggcggcac atcatcacgt gcatgcggcc acgcgcgcgg gcgacagaca acgcgcgagc    720
gacaggtcga cccccgtggc cgaaccgaat cgcgtagggg atctcgacct atggcagcaa    780
atttaacgcc gcgttccggt ggcggtcccg ctccagcgat ggccgcgtac cgtacctacg    840
gcgaccagac cacgggataa tgcgtgcgat tgttcttttg ggtgggggag aatgctcgat    900
cgatcgcaaa tgccggtgct ccccggccgt tcgtcgtcgg ccggtcgatc acaggtacat    960
actggcagta aaaacagacg tgcaggttcc cgacctgtca tcgtattata ttcggcgtta  1020
ctgacaccat ggcaatggca tgcatggtac gaagccaagt aaggagcaga cgtgttcgta  1080
cgcctgtcgt cgtcttcgcg cgcgcgccca cgagcagcat gtctcacgcg cccagcaaat  1140
tcgcgcgcgc ggatgcagcc cgatcggtta tattcgatcg gttataatgc atcatcgtca  1200
```

```
acggcgtcaa  acaacgcga  gagaggacac  ctacatttt  ccctccgga  aattaatctt  1260
aaaatttgcg  cctcttatgc  tattaatata  cgtattaaaa  tttgtataat  ttaaaactca  1320
aaaaacattg  ccaaatgcat  tgacgcgatt  aaaaagttaa  aaaaacaaaa  aggataagaa  1380
taagtgtagc  tactttttgaa  ctttaaaacg  tggtaaggct  acagtgcagc  tacctttgtc  1440
tagttactgc  ctcgtgcgtg  gaagattaga  attccaccta  gagtacgttt  ttttccttct  1500
ttttgttagt  tattactaac  aataaagttc  taactagaga  caatttggct  aattaaaaga  1560
aggaaagcag  aggatgcaag  ctgcctgttc  tgtacagagc  ctgaatatgc  acgtcatctc  1620
tgaagttact  aaccgtaatt  taggagagaa  aatatagcag  agacaggaaa  atcgttcggt  1680
gtatctggaa  actcacgaat  gagttatgtt  ttcagagaaa  cttgctcgag  aagcatggag  1740
ctgttactac  acacgcgata  agcggacttt  cacagaaatg  gaaaacttta  cgcccgccag  1800
aaacgaaaga  gcaattggag  atcagatcac  cgtggagaaa  aataatagcg  tgtttggttt  1860
gtaggttggg  ctgcttctgg  agccatccag  acctgtgtcc  gagcctacat  cagcgtttgg  1920
tttgaatcgc  agaatgatgt  cgtccgccac  tgtattgttc  taataataaa  ctagcatgcg  1980
ggttcaactc  actccacaag  gaactgccgg  acggctccat  ccggagccaa  gccacgacgg  2040
atgagcgaaa  ccgccggacc  aaacgcgctg  taaaagaatg  cagataggtt  aggttttggg  2100
agttgtgtga  tcttcagctt  tctgccgata  ggctgtctgt  aagaggtctt  tcagttttgt  2160
ttggttctgt  ttctggttgg  aaccagttcc  cttggcctca  ggcttcagca  caagtctagg  2220
tgtgatttaa  actgcactgt  attgaatact  ttagtctttt  gacaatactg  tagttaaaag  2280
gccgggggt  tttgccttgg  aactctaaaa  aaatatacag  tattaaccat  ggactctgaa  2340
ctctgtctgc  gtccacaggc  aagtcatctt  tcttccttgc  actggttatc  ttattgaaac  2400
agaacggaaa  tcttttttgg  aacaagagaa  tttcgtcaca  tcttgcctgc  agtaaagttt  2460
cccatctaga  tgcatactcc  ctccgtccaa  gttaactgg  cgttttagct  tttctcagac  2520
ataaatacca  gccaagagaa  tagacgcatg  taccctgtg  atctagcgtg  aagtattaat  2580
tgcaattact  gctgaggaca  cgaaacggtt  cacaacctcc  agccctccac  ggtggatgag  2640
aggagaccaa  gagtccgttg  gtgtgggaac  gaagcgaacg  ggtgtgtgaa  acgaggagat  2700
aactataatg  gcatcgaggt  gtagaccacg  aacgacacat  aattctggac  aaataaaatg  2760
agctaaaacg  ccattaaact  tggacggagg  gagtatacta  tcaacattc  gatcaaaagt  2820
tactatacaa  aatttgcact  gtccgaaaag  cgatccttat  caggaaggcg  caggattcgt  2880
cccagctaag  cgcaccggcc  acaagtattc  caccacccc  ggtcaatagc  taagaaaatt  2940
gggcggcaag  tgaaagtctc  cgggatggga  atgtgcatga  gtcatgacgc  gcctccgccc  3000
tccggcctcc  gcagttgttt  attccgcagcg  cgcgggtggc  ggcccgcccg  tccgtgttct  3060
ctgctccctg  tgttcggcac  atcgtcaccc  ccaccgtttc  ctgtgcctct  ctctcctatc  3120
ttcctcggtc  tcctcccgta  atcctttgcc  tgataccccg  ctctaccagg  ccgccaccac  3180
ctccctccag  gctccagcag  cctataaata  cgcccgcgtc  gcccaccacc  gcacaccact  3240
tgaatactcc  atctcaactt  cccttcctct  cccgtgctgc  gctgagctat  atagctgctc  3300
ctcgacctcc  aagaagcacg  cgggcggagc  ccggagcgag  tgattagtga  aaggcatagc  3360
ataaggccgc  ccggccggga  agtggtggca                                    3390
```

<210> SEQ ID NO 70
<211> LENGTH: 1507
<212> TYPE: DNA
<213> ORGANISM: Zea mays
<220> FEATURE:

```
<221> NAME/KEY: promoter
<222> LOCATION: (1)...(1507)
<223> OTHER INFORMATION: ZmCkx7 promoter

<400> SEQUENCE: 70
gctcggattg tcgcacgcga gggtagtgta cgctacctgc cgcggtgact tcggaatggt    60
cgaaatactg aagactgtcg aaacggtctt tttttgacac gttgcgtctg agttttgttt   120
ttgtgggggc ttttgttggt atattacatg gctccgcctt gttaaaaacc tcaccccgg    180
ggggaaaaga gtgcgggccg gaataacatt gtttgctgga ttacaagggc gcatgggccc   240
tgatgattaa aaaaattgcg gtggttgtca atgttccagg agtgctctaa gtcttcacca   300
gatgtcgtta ctagcctata cgcgctgggg gatgccttcg acatgacgat gaatgggcct   360
tctcatttcg gctctagatt gccccgtgat tctgtctggg tggttcggac gagtacgagg   420
tctcctttgt cgaactctgt tgggacgacc gcgtggttgc gctaggcctt agtttgagcc   480
tgatatttgt tgagggcttg tagggcgagg acgcggtctc cgtcgatgag gtctttggac   540
attggttcgt cgacatcggg gaccgctgat gtgcttgttc ggggtgagcc atgctttatc   600
tcctgcggta tcatgacctc ggatccatac aatagacgaa aagtgtgaa tccggttgcc    660
cgacattctg tcgtgtttag ggcccagacc acttcaggta gttggttggc ccatttgccc   720
ttcttgtcat cgagatgtcg tttcttgatg gcagtgaaga tcttgccgtt ggcgcgctcc   780
accaatccaa cgcgcgcaac agcaatttac gtggacttgc aggcttggag caaggaacaa   840
caccaaaaca aaaagaaac atgcaacaag taatattgaa atttactttg aaacaggtat    900
gcatgtttat ttaatatatt ttgtacttga tgtttggact atttcatatt aacttgcata   960
ctaaattatt tatgaaaaat ttcttatggc atacctcatg aataaatcct agctacgcca  1020
ctattaccag tggttttttgg ttttttatgat tttttttaaat cttttgaatt tagaacgaat 1080
tttttaaaaa acggtgattt atcgaaaccg tatcccgact ggtttaccgt cagttttttac 1140
cggttttgta aaccatgcct acgctacaca tatatacata cggtattacg gtgtatgtac  1200
gtcgtatata tatcttagct tatatatctt attgcatggt tctgtacgtg tccgacgagt  1260
gacgacggct atcttagctt atactctctc cctctgtttt tttagttgtt gctggatagt  1320
ttaattttac actatccagc gacaactaaa acgaaacgaa gggagtatat atcttactct  1380
caatcgttcg taacaataat aatggtaata ataacagcag tttaatctat ataaggcca   1440
ccacggctct ccactgctgc gtgcgtgcgt gcgtacatcg tcaaaaacct ccatcaagca  1500
actgatc                                                            1507

<210> SEQ ID NO 71
<211> LENGTH: 18
<212> TYPE: DNA
<213> ORGANISM: Artificial Sequence
<220> FEATURE:
<223> OTHER INFORMATION: primer

<400> SEQUENCE: 71
ggtgcacggc gaggaggt                                                  18

<210> SEQ ID NO 72
<211> LENGTH: 24
<212> TYPE: DNA
<213> ORGANISM: Artificial Sequence
<220> FEATURE:
<223> OTHER INFORMATION: primer

<400> SEQUENCE: 72
```

```
tcgccgccga catgccgtcg tccc                                           24
```

<210> SEQ ID NO 73
<211> LENGTH: 527
<212> TYPE: PRT
<213> ORGANISM: Oryza sativa
<220> FEATURE:
<221> NAME/KEY: PEPTIDE
<222> LOCATION: (1)...(527)
<223> OTHER INFORMATION: Os CKX6

<400> SEQUENCE: 73

```
Met Ala Ala Arg Cys Ser Ile Ala Phe Met Val Met Ala Ser Cys Leu
 1               5                  10                  15

Ser Val Val Ser Gly Gly Leu Pro Gly Asp Leu Phe Ala His Ser
            20                  25                  30

Val Ala Ser Lys Leu Arg Val Asp Arg Asp Thr Thr Ala Arg Ala Ser
        35                  40                  45

Ser Asp Phe Gly Arg Ile Val Ala Ala Pro Glu Ala Val Leu His
     50                  55                  60

Pro Ala Thr Pro Ala Glu Ile Ala Glu Leu Val Arg Phe Ser Ala Ser
 65                  70                  75                  80

Ser Pro Ser Pro Phe Pro Val Ala Pro Arg Gly Gln Gly His Ser Ala
                85                  90                  95

Arg Gly Gln Ser Leu Ala Pro Gly Gly Val Val Val Asp Met Arg Ala
            100                 105                 110

Leu Ala Ala Arg Arg Gly Arg Val Asn Val Ser Ala Gly Gly Ala Gly
        115                 120                 125

Ala Ala Pro Tyr Val Asp Ala Gly Gly Glu Gln Leu Trp Ala Asp Val
    130                 135                 140

Leu Arg Ala Thr Leu Glu His Gly Leu Ala Pro Arg Val Trp Thr Asp
145                 150                 155                 160

Tyr Leu Arg Ile Thr Val Ala Gly Thr Leu Ser Asn Ala Gly Ile Gly
                165                 170                 175

Gly Gln Ala Phe Arg His Gly Pro Gln Ile Ala Asn Val Leu Glu Leu
            180                 185                 190

Asp Val Ile Thr Gly Arg Gly Asp Met Val Thr Cys Ser Arg Asp Lys
        195                 200                 205

Glu Pro Asp Leu Phe Phe Ala Val Leu Gly Gly Leu Gly Gln Phe Gly
    210                 215                 220

Ile Ile Thr Arg Ala Arg Ile Gly Leu Glu Pro Ala Pro Lys Arg Val
225                 230                 235                 240

Arg Trp Val Arg Leu Ala Tyr Ser Asp Val Val Thr Phe Thr Arg Asp
                245                 250                 255

Gln Glu Leu Leu Ile Ser Lys Arg Ala Ser Glu Ala Gly Phe Asp Tyr
            260                 265                 270

Val Glu Gly Gln Val Gln Leu Asn Arg Thr Leu Thr Glu Gly Pro Lys
        275                 280                 285

Ser Thr Pro Phe Phe Ser Arg Phe Asp Ile Asp Arg Leu Ala Gly Leu
    290                 295                 300

Ala Ser Glu Ser Val Ser Gly Val Ile Tyr Phe Ile Glu Gly Ala Met
305                 310                 315                 320

Tyr Tyr Asn Glu Ser Thr Thr Ala Ser Val Asp Gln Lys Leu Thr Ser
                325                 330                 335

Val Leu Glu Gln Leu Ser Phe Asp Lys Gly Val Phe Val Thr Lys Asp
            340                 345                 350
```

```
Val Ser Tyr Val Gln Phe Leu Asp Arg Val Arg Glu Glu Arg Ile
        355                 360                 365

Leu Arg Ser Ile Gly Met Trp Asp Val Pro His Pro Trp Leu Asn Leu
370                 375                 380

Phe Val Pro Gln Ser Arg Ile Leu Asp Phe Asp Thr Gly Val Leu Lys
385                 390                 395                 400

Gly Val Phe Val Gly Ala Asn Pro Val Gly Val Ile Leu Met Tyr Pro
                405                 410                 415

Met Asn Arg Asn Met Trp Asp Asp Arg Met Thr Ala Val Ser Gly Asn
                420                 425                 430

Asp Asp Met Phe Tyr Val Val Gly Leu Leu Arg Ser Ala Val Val Pro
            435                 440                 445

Gly Asp Val Glu Arg Leu Glu Arg Glu Asn Glu Ala Val Leu Ala Phe
        450                 455                 460

Cys Asp Asn Glu Gly Ile Gly Cys Lys Gln Tyr Leu Pro His Tyr Ala
465                 470                 475                 480

Ser Gln Asp Gly Trp Arg Ser His Phe Gly Ala Lys Trp Ser Arg Val
                485                 490                 495

Thr Glu Leu Lys Val Lys Tyr Asp Pro Tyr Gly Ile Leu Ser Pro Gly
            500                 505                 510

Gln Arg Ile Phe Ser Ser Leu Thr Pro Met Ala Leu Val Ala Met
        515                 520                 525
```

<210> SEQ ID NO 74
<211> LENGTH: 524
<212> TYPE: PRT
<213> ORGANISM: Oryza sativa
<220> FEATURE:
<221> NAME/KEY: PEPTIDE
<222> LOCATION: (1)...(524)
<223> OTHER INFORMATION: OsCKX7

<400> SEQUENCE: 74

```
Met Ala Ala Arg Cys Ser Ile Ala Phe Met Ile Met Ala Ser Cys Leu
1               5                   10                  15

Ser Val Val Val Ser Gly Gly Leu Pro Gly Asp Leu Phe Ala Leu Ser
                20                  25                  30

Val Ala Ser Lys Leu Arg Val Asp Arg Asn Ser Thr Ala Arg Ala Ser
            35                  40                  45

Ser Asp Phe Gly Arg Ile Val Ala Ala Pro Glu Ala Val Leu His
50                  55                  60

Pro Ala Thr Pro Ala Glu Ile Ala Glu Leu Val Arg Phe Ser Ala Ser
65                  70                  75                  80

Ser Pro Ser Pro Phe Pro Val Ala Pro Arg Gly Gln Gly His Ser Ala
                85                  90                  95

Arg Gly Gln Ser Leu Ala Pro Gly Gly Val Val Val Asp Met Arg Ala
            100                 105                 110

Leu Ala Ser Arg Arg Gly Arg Val Asn Val Ser Ala Gly Ala Ala Pro
        115                 120                 125

Tyr Val Asp Ala Gly Gly Glu Gln Leu Trp Ala Asp Val Leu Arg Ala
    130                 135                 140

Thr Leu Glu His Gly Leu Ala Pro Arg Val Trp Thr Asp Tyr Leu Arg
145                 150                 155                 160

Ile Thr Val Ala Gly Thr Leu Ser Asn Ala Gly Ile Gly Gly Gln Ala
                165                 170                 175

Phe Arg His Gly Pro Gln Ile Ala Asn Val Leu Glu Leu Asp Val Ile
            180                 185                 190
```

Thr Gly Thr Gly Asp Met Val Thr Cys Ser Arg Asp Lys Asp Ser Asp
            195                 200                 205

Leu Phe Phe Ala Val Leu Gly Leu Gly Gln Phe Gly Ile Ile Thr
        210                 215                 220

Arg Ala Arg Ile Gly Leu Met Pro Ala Pro Lys Arg Val Arg Trp Val
225                 230                 235                 240

Arg Leu Ala Tyr Ser Asp Val Ala Thr Phe Thr Lys Asp Gln Glu Leu
                245                 250                 255

Leu Ile Ser Lys Arg Ala Ser Glu Ala Gly Phe Asp Tyr Val Glu Gly
            260                 265                 270

Gln Val Gln Leu Asn Arg Thr Leu Thr Glu Gly Pro Lys Ser Thr Pro
        275                 280                 285

Phe Phe Ser Ser Ser Asp Ile Gly Arg Leu Ala Gly Leu Ala Ser Lys
    290                 295                 300

Ser Val Ser Gly Val Ile Tyr Val Ile Glu Gly Thr Met Tyr Tyr Asn
305                 310                 315                 320

Glu Ser Thr Ser Thr Thr Met Asp Gln Lys Leu Glu Ser Ile Leu Gly
                325                 330                 335

Gln Leu Ser Phe Glu Glu Gly Phe Val Phe Thr Lys Asp Val Arg Tyr
            340                 345                 350

Val Gln Phe Leu Asp Arg Val Arg Glu Glu Arg Val Leu Arg Ser
        355                 360                 365

Ile Gly Met Trp Asp Val Pro His Pro Trp Leu Asn Leu Phe Val Pro
    370                 375                 380

Arg Ser Arg Ile Leu Asp Phe Asp Ala Gly Val Phe Lys Gly Val Phe
385                 390                 395                 400

Ala Gly Ala Asn Pro Val Gly Val Ile Leu Met Tyr Pro Met Asn Thr
                405                 410                 415

Asn Met Trp Asp Asp Cys Met Met Ala Val Ala Ser Asp Asp Val
            420                 425                 430

Phe Tyr Ala Val Gly Leu Leu Arg Ser Ala Ala Val Ile Gly Asp Val
        435                 440                 445

Glu Arg Leu Glu Lys Glu Asn Glu Ala Val Leu Ala Phe Cys His Asn
    450                 455                 460

Glu Asp Ile Gly Cys Lys Gln Tyr Leu Pro Tyr Tyr Thr Ser Gln Asp
465                 470                 475                 480

Gly Trp Gln Arg His Phe Gly Ala Lys Trp Ser Arg Val Ala Asp Leu
                485                 490                 495

Lys Ala Lys Tyr Asp Pro His Arg Ile Leu Ser Pro Gly Gln Arg Ile
            500                 505                 510

Phe Ser Ser Pro Ala Ser Met Val Val Ser Met
        515                 520

<210> SEQ ID NO 75
<211> LENGTH: 532
<212> TYPE: PRT
<213> ORGANISM: Oryza sativa
<220> FEATURE:
<221> NAME/KEY: PEPTIDE
<222> LOCATION: (1)...(532)
<223> OTHER INFORMATION: OsCKX8

<400> SEQUENCE: 75

Met Glu Leu Lys Ala Met Tyr Leu Tyr Ala Ala Val Leu Ala Val Leu
1               5                   10                  15

Leu Cys Ser Ser Val Asn Phe Ile Gln Ser Pro Thr Asp Val Leu Gly

```
            20                  25                  30
Pro Val Ala Leu Leu Glu Pro Thr Pro Ser Ser Ala Arg Asp Phe Gly
            35                  40                  45
Ala Val Val Ser Asp Ala Pro Phe Ala Val Met Arg Pro Glu Ser Pro
        50                  55                  60
Asp Asp Ile Ala Leu Leu Leu Gly Ala Leu Ser Ser Thr Ala Pro Ser
65                  70                  75                  80
Pro Arg Ala Thr Val Ala Ala Val Gly Ala Gly His Ser Leu His Gly
                85                  90                  95
Gln Ala Gln Ala Arg Asp Gly Ile Val Val Glu Thr Arg Ala Leu Pro
            100                 105                 110
Arg Asp Val His Val Val Ser Ala Arg Ala His Gly Gly Asp Asp Asp
        115                 120                 125
Ala Thr Val Arg Ala Tyr Ala Asp Val Gly Ala Gly Ala Leu Trp Val
        130                 135                 140
Glu Val Leu Glu Glu Cys Leu Lys Leu Gly Leu Ala Pro Pro Ser Trp
145                 150                 155                 160
Thr Asp Tyr Leu Tyr Leu Thr Val Gly Gly Thr Leu Ser Asn Gly Gly
                165                 170                 175
Ile Ser Gly Gln Thr Phe Lys His Gly Pro Gln Ile Ser Asn Val Leu
            180                 185                 190
Gln Leu Glu Val Val Thr Gly Lys Gly Glu Val Val Thr Cys Ser Pro
            195                 200                 205
Thr Glu Ile Pro Glu Leu Phe Phe Ala Val Leu Gly Gly Leu Gly Gln
        210                 215                 220
Phe Gly Ile Ile Thr Arg Ala Arg Ile Pro Leu Gln Leu Ala Pro Pro
225                 230                 235                 240
Lys Val Arg Trp Val Arg Ala Phe Tyr Asp Ser Phe Glu Thr Phe Thr
                245                 250                 255
Gly Asp Gln Glu Leu Leu Val Ser Met Pro Glu Gln Val Asp Tyr Val
            260                 265                 270
Glu Gly Phe Met Val Leu Asn Glu Gln Ser Leu His Ser Ser Ser Val
        275                 280                 285
Ala Phe Pro Ala Gln Leu Asn Phe Ser Pro Asp Phe Gly Ser Lys Gly
        290                 295                 300
Arg Lys Lys Val Tyr Tyr Cys Ile Glu Phe Ala Val His Asp Phe Gln
305                 310                 315                 320
Gln Asp Ser Ser Arg Ala Asp His Val Val Lys Leu Val Ser Ala Lys
                325                 330                 335
Leu Ser Tyr Leu Arg Pro His Val Tyr Ser Val Glu Val Ser Tyr Phe
            340                 345                 350
Asp Phe Leu Asn Arg Val Arg Met Glu Glu Glu Ser Leu Arg Ser Arg
        355                 360                 365
Gly Leu Trp Asp Val Pro His Pro Trp Leu Asn Val Phe Val Pro Lys
        370                 375                 380
His Gly Ile Thr Gln Phe Lys Gly Leu Leu Met Asp Thr Val Ser Ala
385                 390                 395                 400
Asp Asp Phe Glu Gly Pro Ile Leu Val Tyr Pro Leu Leu Thr Asp Lys
                405                 410                 415
Trp Asp Gly Asn Thr Ser Ala Val Val Pro Ala Ala Pro Asp Gly Val
            420                 425                 430
Met Tyr Ile Phe Gly Val Leu Arg Ser Thr Asp Pro Ala Arg Cys Gly
            435                 440                 445
```

```
Arg Ala Cys Val Asp Ser Ile Met Ala Arg His Arg Arg Val Ala Asp
    450                 455                 460

Glu Ala Cys Arg Asp Gly Gly Gly Gly Arg Gly Ile Gly Ala Lys
465                 470                 475                 480

Gln Tyr Leu Ala Arg Gln Pro Ser Pro Ala Arg Trp Arg Asp His Phe
                485                 490                 495

Gly Ala Gly Trp Gly Arg Phe Ala Ala Arg Lys Ala Arg Phe Asp Pro
            500                 505                 510

Leu His Val Leu Gly Pro Gly Gln Gly Ile Phe Pro Arg Thr Asp Ser
        515                 520                 525

Ala Gly Ser Met
        530

<210> SEQ ID NO 76
<211> LENGTH: 521
<212> TYPE: PRT
<213> ORGANISM: Oryza sativa
<220> FEATURE:
<221> NAME/KEY: PEPTIDE
<222> LOCATION: (1)...(521)
<223> OTHER INFORMATION: OsCKX9

<400> SEQUENCE: 76

Met Arg Pro Ser Leu Leu Gln Tyr Leu Lys Leu Leu Leu Leu Leu Ala
1               5                   10                  15

Leu Gly Gly Val Thr Thr Met His Val Pro Lys Gln Asp Val Pro Ser
            20                  25                  30

Ser Leu Glu Glu Leu Thr Leu Asp Gly His Phe Ser Phe His Asp Val
        35                  40                  45

Ser Ala Ala Gln Asp Phe Gly Asn Leu Ser Ser Phe Pro Pro Val
    50                  55                  60

Ala Val Leu His Pro Gly Ser Val Ala Asp Ile Ala Thr Thr Ile Arg
65                  70                  75                  80

His Val Phe Leu Met Gly Glu His Ser Thr Leu Thr Val Ala Ala Arg
                85                  90                  95

Gly His Gly His Ser Leu Tyr Gly Gln Ser Gln Ala Ala Glu Gly Ile
            100                 105                 110

Ile Ile Ser Met Glu Ser Leu Gln Ser Asn Thr Met Arg Val Asn Pro
        115                 120                 125

Gly Val Ser Pro Tyr Val Asp Ala Ser Gly Gly Glu Leu Trp Ile Asn
    130                 135                 140

Val Leu His Glu Thr Leu Lys Tyr Gly Leu Ala Pro Lys Ser Trp Thr
145                 150                 155                 160

Asp Tyr Leu His Leu Thr Val Gly Gly Thr Leu Ser Asn Ala Gly Val
                165                 170                 175

Ser Gly Gln Thr Phe Arg His Gly Pro Gln Ile Ser Asn Val Asn Glu
            180                 185                 190

Leu Glu Ile Val Thr Gly Arg Gly Asp Val Ile Thr Cys Ser Pro Glu
        195                 200                 205

Gln Asn Ser Asp Leu Phe His Ala Ala Leu Gly Gly Leu Gly Gln Phe
    210                 215                 220

Gly Val Ile Thr Arg Ala Arg Ile Pro Leu Glu Pro Ala Pro Lys Met
225                 230                 235                 240

Val Arg Trp Leu Arg Val Leu Tyr Leu Asp Phe Thr Ser Phe Thr Glu
                245                 250                 255

Asp Gln Glu Met Leu Ile Ser Ala Glu Lys Thr Phe Asp Tyr Ile Glu
            260                 265                 270
```

Gly Phe Val Ile Ile Asn Arg Thr Gly Ile Leu Asn Trp Arg Ser
            275                 280                 285

Ser Phe Asn Pro Gln Asp Pro Val Arg Ser Ser Gln Phe Glu Ser Asp
        290                 295                 300

Gly Lys Val Leu Phe Cys Leu Glu Met Thr Lys Asn Phe Asn Pro Asp
305                 310                 315                 320

Glu Ala Asp Val Met Glu Gln Glu Val Asn Thr Leu Leu Ser Gln Leu
                325                 330                 335

Arg Tyr Met Pro Ser Ser Leu Phe His Thr Asp Val Thr Tyr Ile Glu
            340                 345                 350

Phe Leu Asp Arg Val His Ser Ser Glu Met Lys Leu Arg Ala Lys Gly
        355                 360                 365

Met Trp Glu Val Pro His Pro Trp Leu Asn Ile Ile Pro Arg Ser
370                 375                 380

Met Ile His Lys Phe Ala Lys Glu Val Phe Gly Lys Ile Leu Lys Asp
385                 390                 395                 400

Ser Asn Asn Gly Pro Ile Leu Leu Tyr Pro Val Asn Lys Ser Arg Trp
                405                 410                 415

Asp Asn Arg Thr Ser Val Val Ile Pro Asp Glu Glu Val Phe Tyr Leu
            420                 425                 430

Val Ala Phe Leu Ser Ser Ala Leu Gly Pro His Asn Ile Lys His Thr
        435                 440                 445

Leu Asp Leu Asn Tyr Arg Ile Ile Glu Phe Ser Asp Lys Ala Gly Ile
450                 455                 460

Gly Val Lys Gln Tyr Leu Pro Asn Tyr Thr Thr Glu Gln Glu Trp Gln
465                 470                 475                 480

Ser His Phe Gly Ala Arg Trp Asp Thr Phe Gln Gln Arg Lys Lys Ala
                485                 490                 495

Tyr Asp Pro Leu Ala Ile Leu Ala Pro Gly Gln Arg Ile Phe Gln Lys
            500                 505                 510

Ala Ser Ala Ser Leu Pro Leu Pro Ser
        515                 520

<210> SEQ ID NO 77
<211> LENGTH: 550
<212> TYPE: PRT
<213> ORGANISM: Oryza sativa
<220> FEATURE:
<221> NAME/KEY: PEPTIDE
<222> LOCATION: (1)...(550)
<223> OTHER INFORMATION: OsCKX10

<400> SEQUENCE: 77

Met Met Pro Arg Ala Gln Leu Thr Thr Phe Leu Ile Val Thr Ser Phe
1               5                   10                  15

Leu Ser Thr Val Pro Tyr Leu Arg Ala Pro Val His Gly Gly Val Leu
            20                  25                  30

Thr Ser Tyr Asp Val Ser Ser Leu Asp Ile Met Ser Lys Ile His Thr
        35                  40                  45

Asp His Asp Ala Thr Thr Lys Ala Ser Ser Asp Phe Gly His Ile Val
    50                  55                  60

His Ala Thr Pro Asn Gly Val Phe Arg Pro Thr Phe Pro Ala Asp Ile
65                  70                  75                  80

Ala Ala Leu Ile Arg Leu Ser Leu Ser Gln Pro Thr Pro Phe Thr Val
                85                  90                  95

Ala Pro Arg Gly Lys Gly His Ser Ser Arg Gly Gln Ala Phe Ala Pro

-continued

```
                100                 105                 110
Gly Gly Ile Val Val Asp Met Ser Ala Leu Gly Asp His Gly His His
            115                 120                 125

Thr Ser His Arg Ile Asp Val Ser Val Asp Arg Met Tyr Val Asp Ala
130                 135                 140

Gly Gly Glu Gln Leu Trp Ile Asp Val Leu His Thr Ala Leu Lys His
145                 150                 155                 160

Gly Leu Thr Pro Arg Val Trp Thr Asp Tyr Leu Arg Ile Thr Val Gly
                165                 170                 175

Gly Thr Leu Ser Asn Ala Gly Ile Gly Gly Gln Ala Phe Arg His Gly
            180                 185                 190

Pro Gln Ile Ser Asn Val His Glu Leu Asp Val Val Thr Gly Met Gly
            195                 200                 205

Glu Met Ile Thr Cys Ser Pro Glu Val Asn Ser Ala Leu Phe Phe Ala
        210                 215                 220

Val Leu Gly Gly Leu Gly Gln Phe Gly Val Ile Thr Arg Ala Arg Ile
225                 230                 235                 240

Arg Leu Glu Pro Ala Pro Lys Arg Val Lys Trp Val Arg Ile Ala Tyr
                245                 250                 255

Ser Asp Val His Pro Phe Thr Thr Asp Gln Glu Leu Leu Ile Ser Lys
            260                 265                 270

Trp Ala Ser Gly Ser Gly Phe Asp Tyr Val Glu Gly Gln Val Gln Leu
        275                 280                 285

Asn Arg Thr Leu Thr Gln Gly Arg Arg Ser Ser Phe Phe Ser Ala
        290                 295                 300

Thr Asp Leu Ala Arg Leu Thr Gly Leu Ala Ile Asp Thr Gly Ser Val
305                 310                 315                 320

Ala Ile Tyr Tyr Ile Glu Gly Ala Met Tyr Tyr Asp Asn Thr Ala
                325                 330                 335

Ala Ser Val Asp Gln Lys Leu Asp Ala Leu Leu Glu Glu Leu Ser Phe
            340                 345                 350

Val Arg Gly Phe Val Phe Val Arg Asp Ala Ser Tyr Val Glu Phe Leu
        355                 360                 365

Asp Arg Val Gly Arg Glu Glu Gln Asn Leu Arg Ser Ala Gly Ala Trp
370                 375                 380

Asp Val Pro His Pro Trp Leu Asn Leu Phe Val Pro Arg Ser Arg Ile
385                 390                 395                 400

Leu His Phe Asp Ala Ala Val Phe Lys Gly Ile Leu Arg Asn Ala Asn
                405                 410                 415

Pro Val Gly Leu Ile Leu Met Tyr Pro Met Asn Lys Asp Met Trp Asp
            420                 425                 430

Asp Arg Met Thr Ala Met Thr Pro Asp Glu Asp Val Phe Tyr Ala Val
        435                 440                 445

Gly Leu Leu Arg Ser Ala Val Ala Gly Ser Gly Gly Asp Val Glu
        450                 455                 460

Gln Leu Glu Arg Glu Asn Ala Ala Val Leu Glu Leu Cys Asp Leu Ala
465                 470                 475                 480

Gly Gly Gly Ile Gly Cys Arg Gln Tyr Leu Pro His His Ala Ser Arg
                485                 490                 495

Asp Gly Trp Arg Arg His Phe Gly Ala Lys Trp Gly Arg Val Ala Asp
            500                 505                 510

Leu Lys Ala Arg Tyr Asp Pro Arg Ala Ile Leu Ser Pro Gly Gln Gly
            515                 520                 525
```

```
Ile Phe Pro Pro Pro Pro Pro Ser Pro Pro Pro Ala Ala Gly
        530                 535                 540

Glu Pro Ile Thr Ala Ser
545                 550

<210> SEQ ID NO 78
<211> LENGTH: 518
<212> TYPE: PRT
<213> ORGANISM: Oryza sativa
<220> FEATURE:
<221> NAME/KEY: PEPTIDE
<222> LOCATION: (1)...(518)
<223> OTHER INFORMATION: OsCKX11

<400> SEQUENCE: 78

Met Met Leu Ala Tyr Met Asp His Ala Ala Ala Ala Glu Pro Asp
  1               5                  10                  15

Ala Gly Ala Glu Pro Ala Val Ala Ala Asp Ala Ala Glu Phe Ala
             20                  25                  30

Ala Ala Met Asp Phe Gly Gly Leu Val Ser Ala Arg Pro Ala Ala Val
         35                  40                  45

Val Arg Pro Ala Ser Ser Asp Asp Val Ala Ser Ala Ile Arg Ala Ala
 50                  55                  60

Ala Arg Thr Ala His Leu Thr Val Ala Ala Arg Gly Asn Gly His Ser
 65                  70                  75                  80

Val Ala Gly Gln Ala Met Ala Arg Gly Gly Leu Val Leu Asp Met Arg
                 85                  90                  95

Ala Leu Pro Arg Arg Met Gln Leu Val Val Ala Pro Ser Gly Glu Lys
            100                 105                 110

Phe Ala Asp Val Pro Gly Gly Ala Leu Trp Glu Glu Val Leu His Trp
        115                 120                 125

Ala Val Ser Lys His Gly Leu Ala Pro Ala Ser Trp Thr Asp Tyr Leu
130                 135                 140

Arg Leu Thr Val Gly Gly Thr Leu Ser Asn Gly Gly Val Ser Gly Gln
145                 150                 155                 160

Ser Phe Arg Tyr Gly Pro Gln Val Ser Asn Val Ala Gln Leu Glu Val
                165                 170                 175

Val Thr Gly Asp Gly Glu Cys His Val Cys Ser Arg Ser Ala Asp Pro
            180                 185                 190

Asp Leu Phe Phe Ala Val Leu Gly Gly Leu Gly Gln Phe Gly Val Ile
        195                 200                 205

Thr Arg Ala Arg Ile Pro Leu Ser Pro Ala Pro Gln Thr Val Arg Trp
210                 215                 220

Thr Arg Val Val Tyr Ala Ser Phe Ala Asp Tyr Ala Ala Asp Ala Glu
225                 230                 235                 240

Trp Leu Val Thr Arg Pro Pro His Glu Ala Phe Asp Tyr Val Glu Gly
                245                 250                 255

Phe Ala Phe Val Arg Ser Asp Asp Pro Val Asn Gly Trp Pro Thr Val
            260                 265                 270

Pro Ile Pro Asp Gly Ala His Phe Asp Ala Ser Leu Leu Pro Ala Asn
        275                 280                 285

Ala Gly Pro Val Leu Tyr Cys Leu Glu Val Ala Leu Tyr Gln Arg Gly
    290                 295                 300

Gly Gly Gly Asp Gly Gly Asp Asp Met Asp Lys Arg Val Gly Glu
305                 310                 315                 320

Met Met Arg Gln Leu Lys Tyr Val Arg Gly Leu Glu Phe Ala Ala Gly
                325                 330                 335
```

```
Val Gly Tyr Val Asp Phe Leu Ser Arg Val Asn Arg Val Glu Asp Glu
            340                 345                 350

Ala Arg Arg Asn Gly Ser Trp Ala Ala Pro His Pro Trp Leu Asn Leu
        355                 360                 365

Phe Ile Ser Ser Arg Asp Ile Ala Ala Phe Asp Arg Ala Val Leu Asn
370                 375                 380

Gly Met Leu Ala Asp Gly Val Asp Gly Pro Met Leu Ile Tyr Pro Met
385                 390                 395                 400

Leu Lys Ser Lys Trp Asp Pro Ala Thr Ser Val Ala Leu Pro Asn Gly
                405                 410                 415

Glu Ile Phe Tyr Leu Val Ala Leu Leu Arg Phe Cys Arg Pro Tyr Pro
            420                 425                 430

Gly Gly Gly Pro Pro Val Asp Glu Leu Val Ala Gln Asn Asn Ala Ile
                435                 440                 445

Ile Asp Ala Cys Arg Ser Asn Gly Tyr Asp Tyr Lys Ile Tyr Phe Pro
450                 455                 460

Ser Tyr His Ala Gln Ser Asp Trp Ser Arg His Phe Gly Ala Lys Trp
465                 470                 475                 480

Ser Arg Phe Val Asp Arg Lys Ala Arg Tyr Asp Pro Leu Ala Ile Leu
                485                 490                 495

Ala Pro Gly Gln Asn Ile Phe Ala Arg Thr Pro Ser Val Ala Ala
            500                 505                 510

Ala Ala Ala Val Ile Val
        515

<210> SEQ ID NO 79
<211> LENGTH: 142
<212> TYPE: PRT
<213> ORGANISM: Zea mays
<220> FEATURE:
<221> NAME/KEY: DOMAIN
<222> LOCATION: (1)...(142)
<223> OTHER INFORMATION: ZmCkx2a PF01565.13.1s domain per Figure 9

<400> SEQUENCE: 79

Pro Ala Ala Val Val Arg Pro Glu Ser Glu Glu Val Ala Ala Ile
1               5                   10                  15

Val Arg Leu Ala Arg Glu His Gly Ile Pro Val Thr Pro Arg Gly Gly
            20                  25                  30

Gly His Ser Leu Ser Phe Gly Gly Ala Val Pro Leu Asn Thr Gly Gly
        35                  40                  45

Val Val Leu Asp Leu Ser Arg Lys Leu Asn Arg Ile Ile Leu Glu Ile
    50                  55                  60

Asp Pro Glu Thr Asp Gly Thr Ala Thr Val Glu Ala Gly Val Thr Leu
65                  70                  75                  80

Asp Leu Asn Arg Ala Leu Ala Ala Lys Gly Leu Phe Leu Pro Leu Asp
                85                  90                  95

Pro Gly Ser Gly Ile Pro Gly Thr Val Gly Gly Ala Ile Ala Thr Asn
            100                 105                 110

Ala Gly Gly Tyr Gly Ser Glu Lys Tyr Gly Leu Thr Arg Asp Asn Val
        115                 120                 125

Leu Gly Leu Glu Val Val Leu Ala Asp Gly Glu Val Val Arg
    130                 135                 140

<210> SEQ ID NO 80
<211> LENGTH: 120
<212> TYPE: PRT
```

```
<213> ORGANISM: Zea mays
<220> FEATURE:
<221> NAME/KEY: DOMAIN
<222> LOCATION: (1)...(120)
<223> OTHER INFORMATION: ZmCkx2a PF01565.13.fs domain per Figure 9

<400> SEQUENCE: 80

Ile Pro Val Thr Pro Arg Gly Gly His Ser Leu Ser Phe Gly Gly
 1               5                  10                  15

Ala Val Pro Leu Asn Thr Gly Val Val Leu Asp Leu Ser Arg Lys
             20                  25                  30

Leu Asn Arg Ile Ile Leu Glu Ile Asp Pro Glu Thr Asp Gly Thr Ala
         35                  40                  45

Thr Val Glu Ala Gly Val Thr Leu Asp Leu Asn Arg Ala Leu Ala Ala
     50                  55                  60

Lys Gly Leu Phe Leu Pro Leu Asp Pro Gly Ser Gly Ile Pro Gly Thr
 65                  70                  75                  80

Val Gly Gly Ala Ile Ala Thr Asn Ala Gly Gly Tyr Gly Ser Glu Lys
                 85                  90                  95

Tyr Gly Leu Thr Arg Asp Asn Val Leu Gly Leu Glu Val Val Leu Ala
            100                 105                 110

Asp Gly Glu Val Val Arg Leu Ser
            115                 120

<210> SEQ ID NO 81
<211> LENGTH: 297
<212> TYPE: PRT
<213> ORGANISM: Zea mays
<220> FEATURE:
<221> NAME/KEY: DOMAIN
<222> LOCATION: (1)...(297)
<223> OTHER INFORMATION: ZmCkx2a PF09265.1.fs domain per Figure 9

<400> SEQUENCE: 81

Pro Lys Arg Val Arg Trp Val Arg Val Leu Tyr Ser Asp Phe Ala Ala
 1               5                  10                  15

Phe Thr Lys Asp Gln Glu Arg Leu Ile Ser Lys Glu Asn Gly Gly Gly
             20                  25                  30

Gly Ala Lys Val Gly Phe Asp Tyr Val Glu Gly Phe Val Ile Leu Asn
         35                  40                  45

Arg Thr Gly Leu Val Asn Asn Trp Arg Ser Ser Phe Ser Pro Ser
     50                  55                  60

Asp Pro Ala Arg Ile Ala Ser Leu Ala Ser Lys Asn Asn Gly Gly Val
 65                  70                  75                  80

Leu Tyr Cys Leu Glu Val Ala Lys Tyr Tyr Asp Tyr Ala Asp Ser Asp
                 85                  90                  95

Ala Ala Thr Val Asp Gln Glu Val Glu Glu Leu Leu Arg Gln Leu Ser
            100                 105                 110

Phe Val Pro Gly Phe Leu Phe Ser Thr Asp Val Ser Tyr Val Asp Phe
            115                 120                 125

Leu Asp Arg Val His Arg Glu Glu Leu Lys Leu Arg Ser Lys Gly Leu
        130                 135                 140

Trp Asp Val Pro His Pro Trp Leu Asn Leu Phe Val Pro Lys Ser Arg
145                 150                 155                 160

Ile Leu Asp Phe Asp Arg Gly Val Phe Lys Gly Ile Leu Leu Lys Asn
                165                 170                 175

Thr Asn Asn Ser Gly Pro Ile Leu Val Tyr Pro Met Asn Arg Ser Lys
            180                 185                 190
```

```
Trp Asp Asp Arg Met Ser Ala Val Ile Pro Asp Glu Asp Val
        195                 200                 205

Phe Tyr Leu Val Gly Leu Leu Arg Ser Ala Val Pro Tyr Ser Ala Gly
    210                 215                 220

Pro Gly Asp Leu Glu Glu Leu Glu Asn Gln Asn Arg Arg Ile Leu Glu
225                 230                 235                 240

Phe Cys Glu Lys Ala Gly Ile Gly Tyr Lys Gln Tyr Leu Pro His Tyr
                245                 250                 255

Leu Thr Ser Gln Glu Asp Asn Tyr Trp Lys Arg His Phe Gly Ala Ala
                260                 265                 270

Lys Trp Asp Arg Phe Val Asp Arg Lys Ala Arg Tyr Asp Pro Lys Ala
                275                 280                 285

Ile Leu Ser Pro Gly Gln Gly Ile Phe
                290                 295

<210> SEQ ID NO 82
<211> LENGTH: 297
<212> TYPE: PRT
<213> ORGANISM: Zea mays
<220> FEATURE:
<221> NAME/KEY: DOMAIN
<222> LOCATION: (1)...(297)
<223> OTHER INFORMATION: ZmCkx2a PF09265.1.1s domain per Figure 9

<400> SEQUENCE: 82

Pro Lys Arg Val Arg Trp Val Arg Val Leu Tyr Ser Asp Phe Ala Ala
1               5                   10                  15

Phe Thr Lys Asp Gln Glu Arg Leu Ile Ser Lys Glu Asn Gly Gly Gly
            20                  25                  30

Gly Ala Lys Val Gly Phe Asp Tyr Val Glu Gly Phe Val Ile Leu Asn
        35                  40                  45

Arg Thr Gly Leu Val Asn Asn Trp Arg Ser Ser Phe Phe Ser Pro Ser
    50                  55                  60

Asp Pro Ala Arg Ile Ala Ser Leu Ala Ser Lys Asn Asn Gly Gly Val
65                  70                  75                  80

Leu Tyr Cys Leu Glu Val Ala Lys Tyr Tyr Asp Tyr Ala Asp Ser Asp
                85                  90                  95

Ala Ala Thr Val Asp Gln Glu Val Glu Glu Leu Leu Arg Gln Leu Ser
                100                 105                 110

Phe Val Pro Gly Phe Leu Phe Ser Thr Asp Val Ser Tyr Val Asp Phe
            115                 120                 125

Leu Asp Arg Val His Arg Glu Glu Leu Lys Leu Arg Ser Lys Gly Leu
130                 135                 140

Trp Asp Val Pro His Pro Trp Leu Asn Leu Phe Val Pro Lys Ser Arg
145                 150                 155                 160

Ile Leu Asp Phe Asp Arg Gly Val Phe Lys Gly Ile Leu Leu Lys Asn
                165                 170                 175

Thr Asn Asn Ser Gly Pro Ile Leu Val Tyr Pro Met Asn Arg Ser Lys
            180                 185                 190

Trp Asp Asp Arg Met Ser Ala Val Ile Pro Asp Glu Asp Val
        195                 200                 205

Phe Tyr Leu Val Gly Leu Leu Arg Ser Ala Val Pro Tyr Ser Ala Gly
    210                 215                 220

Pro Gly Asp Leu Glu Glu Leu Glu Asn Gln Asn Arg Arg Ile Leu Glu
225                 230                 235                 240

Phe Cys Glu Lys Ala Gly Ile Gly Tyr Lys Gln Tyr Leu Pro His Tyr
                245                 250                 255
```

Leu Thr Ser Gln Glu Asp Asn Tyr Trp Lys Arg His Phe Gly Ala Ala
            260                 265                 270

Lys Trp Asp Arg Phe Val Asp Arg Lys Ala Arg Tyr Asp Pro Lys Ala
            275                 280                 285

Ile Leu Ser Pro Gly Gln Gly Ile Phe
        290                 295

<210> SEQ ID NO 83
<211> LENGTH: 144
<212> TYPE: PRT
<213> ORGANISM: Zea mays
<220> FEATURE:
<221> NAME/KEY: DOMAIN
<222> LOCATION: (1)...(144)
<223> OTHER INFORMATION: ZmCkx2b PF01565.13.fs domain per Figure 9

<400> SEQUENCE: 83

Pro Ala Ala Val Val Arg Pro Glu Ser Glu Glu Val Ala Ala Ile
 1               5                  10                  15

Val Arg Leu Ala Arg Glu His Gly Ile Pro Val Thr Pro Arg Gly Gly
            20                  25                  30

Gly His Ser Leu Ser Phe Gly Ala Val Pro Leu Asn Thr Gly Gly
            35                  40                  45

Val Val Leu Asp Leu Ser Arg Lys Leu Asn Arg Ile Ile Leu Glu Ile
        50                  55                  60

Asp Pro Glu Thr Asp Gly Thr Ala Thr Val Glu Ala Gly Val Thr Leu
65                  70                  75                  80

Asp Leu Asn Arg Ala Leu Ala Ala Lys Gly Leu Phe Leu Pro Leu Asp
                85                  90                  95

Pro Gly Ser Gly Ile Pro Gly Thr Val Gly Gly Ala Ile Ala Thr Asn
            100                 105                 110

Ala Gly Gly Tyr Gly Ser Glu Lys Tyr Gly Leu Thr Arg Asp Asn Val
        115                 120                 125

Leu Gly Leu Glu Val Val Leu Ala Asp Gly Glu Val Val Arg Leu Ser
    130                 135                 140

<210> SEQ ID NO 84
<211> LENGTH: 144
<212> TYPE: PRT
<213> ORGANISM: Zea mays
<220> FEATURE:
<221> NAME/KEY: DOMAIN
<222> LOCATION: (1)...(144)
<223> OTHER INFORMATION: ZmCkx2b PF01565.13.ls domain per Figure 9

<400> SEQUENCE: 84

Pro Ala Ala Val Val Arg Pro Glu Ser Glu Glu Val Ala Ala Ile
 1               5                  10                  15

Val Arg Leu Ala Arg Glu His Gly Ile Pro Val Thr Pro Arg Gly Gly
            20                  25                  30

Gly His Ser Leu Ser Phe Gly Ala Val Pro Leu Asn Thr Gly Gly
            35                  40                  45

Val Val Leu Asp Leu Ser Arg Lys Leu Asn Arg Ile Ile Leu Glu Ile
        50                  55                  60

Asp Pro Glu Thr Asp Gly Thr Ala Thr Val Glu Ala Gly Val Thr Leu
65                  70                  75                  80

Asp Leu Asn Arg Ala Leu Ala Ala Lys Gly Leu Phe Leu Pro Leu Asp
                85                  90                  95

Pro Gly Ser Gly Ile Pro Gly Thr Val Gly Gly Ala Ile Ala Thr Asn

-continued

```
                  100                 105                 110
Ala Gly Gly Tyr Gly Ser Glu Lys Tyr Gly Leu Thr Arg Asp Asn Val
            115                 120                 125

Leu Gly Leu Glu Val Val Leu Ala Asp Gly Glu Val Val Arg Leu Ser
        130                 135                 140

<210> SEQ ID NO 85
<211> LENGTH: 297
<212> TYPE: PRT
<213> ORGANISM: Zea mays
<220> FEATURE:
<221> NAME/KEY: DOMAIN
<222> LOCATION: (1)...(297)
<223> OTHER INFORMATION: ZmCkx2b PF09265.1.fs domain per Figure 9

<400> SEQUENCE: 85

Pro Lys Arg Val Arg Trp Val Arg Val Leu Tyr Ser Asp Phe Ala Ala
 1               5                  10                  15

Phe Thr Lys Asp Gln Glu Arg Leu Ile Ser Lys Glu Asn Gly Gly Gly
            20                  25                  30

Gly Ala Lys Val Gly Phe Asp Tyr Val Glu Gly Phe Val Ile Leu Asn
        35                  40                  45

Arg Thr Gly Leu Val Asn Asn Trp Arg Ser Ser Phe Phe Ser Pro Ser
    50                  55                  60

Asp Pro Ala Arg Ile Ala Ser Leu Ala Ser Lys Asn Asn Gly Gly Val
65                  70                  75                  80

Leu Tyr Cys Leu Glu Val Ala Lys Tyr Tyr Asp Tyr Ala Asp Ser Asp
                85                  90                  95

Ala Ala Thr Val Asp Gln Glu Val Glu Glu Leu Leu Arg Gln Leu Ser
            100                 105                 110

Phe Val Pro Gly Phe Leu Phe Ser Thr Asp Val Ser Tyr Val Asp Phe
        115                 120                 125

Leu Asp Arg Val His Arg Glu Glu Leu Lys Leu Arg Ser Lys Gly Leu
    130                 135                 140

Trp Asp Val Pro His Pro Trp Leu Asn Leu Phe Val Pro Lys Ser Arg
145                 150                 155                 160

Ile Leu Asp Phe Asp Arg Gly Val Phe Lys Gly Ile Leu Leu Lys Asn
                165                 170                 175

Thr Asn Asn Ser Gly Pro Ile Leu Val Tyr Pro Met Asn Arg Ser Lys
            180                 185                 190

Trp Asp Asp Arg Met Ser Ala Val Ile Pro Asp Glu Asp Glu Asp Val
        195                 200                 205

Phe Tyr Leu Val Gly Leu Leu Arg Ser Ala Val Pro Tyr Ser Ala Gly
    210                 215                 220

Pro Gly Asp Leu Glu Glu Leu Glu Asn Gln Asn Arg Arg Ile Leu Glu
225                 230                 235                 240

Phe Cys Glu Lys Ala Gly Ile Gly Tyr Lys Gln Tyr Leu Pro His Tyr
                245                 250                 255

Leu Thr Ser Gln Glu Asp Asn Tyr Trp Lys Arg His Phe Gly Ala Ala
            260                 265                 270

Lys Trp Asp Arg Phe Val Asp Arg Lys Ala Arg Tyr Asp Pro Lys Ala
        275                 280                 285

Ile Leu Ser Pro Gly Gln Gly Ile Phe
    290                 295

<210> SEQ ID NO 86
<211> LENGTH: 297
```

```
<212> TYPE: PRT
<213> ORGANISM: Zea mays
<220> FEATURE:
<221> NAME/KEY: DOMAIN
<222> LOCATION: (1)...(297)
<223> OTHER INFORMATION: ZmCkx2b PF09265.1.ls domain per Figure 9

<400> SEQUENCE: 86

Pro Lys Arg Val Arg Trp Val Arg Val Leu Tyr Ser Asp Phe Ala Ala
  1               5                  10                  15

Phe Thr Lys Asp Gln Glu Arg Leu Ile Ser Lys Glu Asn Gly Gly Gly
                 20                  25                  30

Gly Ala Lys Val Gly Phe Asp Tyr Val Glu Gly Phe Val Ile Leu Asn
             35                  40                  45

Arg Thr Gly Leu Val Asn Asn Trp Arg Ser Ser Phe Phe Ser Pro Ser
 50                  55                  60

Asp Pro Ala Arg Ile Ala Ser Leu Ala Ser Lys Asn Asn Gly Gly Val
 65                  70                  75                  80

Leu Tyr Cys Leu Glu Val Ala Lys Tyr Tyr Asp Tyr Ala Asp Ser Asp
                 85                  90                  95

Ala Ala Thr Val Asp Gln Glu Val Glu Leu Leu Arg Gln Leu Ser
                100                 105                 110

Phe Val Pro Gly Phe Leu Phe Ser Thr Asp Val Ser Tyr Val Asp Phe
            115                 120                 125

Leu Asp Arg Val His Arg Glu Glu Leu Lys Leu Arg Ser Lys Gly Leu
130                 135                 140

Trp Asp Val Pro His Pro Trp Leu Asn Leu Phe Val Pro Lys Ser Arg
145                 150                 155                 160

Ile Leu Asp Phe Asp Arg Gly Val Phe Lys Gly Ile Leu Leu Lys Asn
                165                 170                 175

Thr Asn Asn Ser Gly Pro Ile Leu Val Tyr Pro Met Asn Arg Ser Lys
            180                 185                 190

Trp Asp Asp Arg Met Ser Ala Val Ile Pro Asp Glu Asp Glu Asp Val
        195                 200                 205

Phe Tyr Leu Val Gly Leu Leu Arg Ser Ala Val Pro Tyr Ser Ala Gly
    210                 215                 220

Pro Gly Asp Leu Glu Glu Leu Glu Asn Gln Asn Arg Arg Ile Leu Glu
225                 230                 235                 240

Phe Cys Glu Lys Ala Gly Ile Gly Tyr Lys Gln Tyr Leu Pro His Tyr
                245                 250                 255

Leu Thr Ser Gln Glu Asp Asn Tyr Trp Lys Arg His Phe Gly Ala Ala
            260                 265                 270

Lys Trp Asp Arg Phe Val Asp Arg Lys Ala Arg Tyr Asp Pro Lys Ala
        275                 280                 285

Ile Leu Ser Pro Gly Gln Gly Ile Phe
    290                 295

<210> SEQ ID NO 87
<211> LENGTH: 144
<212> TYPE: PRT
<213> ORGANISM: Zea mays
<220> FEATURE:
<221> NAME/KEY: DOMAIN
<222> LOCATION: (1)...(144)
<223> OTHER INFORMATION: ZmCkx3 PF01565.13.fs domain per Figure 9

<400> SEQUENCE: 87

Pro Ala Ala Val Val Arg Pro Glu Ser Glu Glu Glu Val Ala Ala Ile
  1               5                  10                  15
```

```
Val Arg Leu Ala Arg Glu His Gly Ile Pro Val Thr Pro Arg Gly Gly
         20                  25                  30

Gly His Ser Leu Ser Phe Gly Gly Ala Val Pro Leu Asn Thr Gly Gly
         35                  40                  45

Val Val Leu Asp Leu Ser Arg Lys Leu Asn Arg Ile Ile Leu Glu Ile
 50                  55                  60

Asp Pro Glu Thr Asp Gly Thr Ala Thr Val Glu Ala Gly Val Thr Leu
 65                  70                  75                  80

Asp Leu Asn Arg Ala Leu Ala Ala Lys Gly Leu Phe Leu Pro Leu Asp
                 85                  90                  95

Pro Gly Ser Gly Ile Pro Gly Thr Val Gly Ala Ile Ala Thr Asn
                100                 105                 110

Ala Gly Gly Tyr Gly Ser Glu Lys Tyr Gly Leu Thr Arg Asp Asn Val
            115                 120                 125

Leu Gly Leu Glu Val Val Leu Ala Asp Gly Glu Val Val Arg Leu Ser
    130                 135                 140
```

<210> SEQ ID NO 88
<211> LENGTH: 144
<212> TYPE: PRT
<213> ORGANISM: Zea mays
<220> FEATURE:
<221> NAME/KEY: DOMAIN
<222> LOCATION: (1)...(144)
<223> OTHER INFORMATION: ZmCkx3 PF01565.13.ls domain per Figure 9

<400> SEQUENCE: 88

```
Pro Ala Ala Val Val Arg Pro Glu Ser Glu Glu Val Ala Ala Ile
 1               5                  10                  15

Val Arg Leu Ala Arg Glu His Gly Ile Pro Val Thr Pro Arg Gly Gly
         20                  25                  30

Gly His Ser Leu Ser Phe Gly Gly Ala Val Pro Leu Asn Thr Gly Gly
         35                  40                  45

Val Val Leu Asp Leu Ser Arg Lys Leu Asn Arg Ile Ile Leu Glu Ile
 50                  55                  60

Asp Pro Glu Thr Asp Gly Thr Ala Thr Val Glu Ala Gly Val Thr Leu
 65                  70                  75                  80

Asp Leu Asn Arg Ala Leu Ala Ala Lys Gly Leu Phe Leu Pro Leu Asp
                 85                  90                  95

Pro Gly Ser Gly Ile Pro Gly Thr Val Gly Ala Ile Ala Thr Asn
                100                 105                 110

Ala Gly Gly Tyr Gly Ser Glu Lys Tyr Gly Leu Thr Arg Asp Asn Val
            115                 120                 125

Leu Gly Leu Glu Val Val Leu Ala Asp Gly Glu Val Val Arg Leu Ser
    130                 135                 140
```

<210> SEQ ID NO 89
<211> LENGTH: 297
<212> TYPE: PRT
<213> ORGANISM: Zea mays
<220> FEATURE:
<221> NAME/KEY: DOMAIN
<222> LOCATION: (1)...(297)
<223> OTHER INFORMATION: ZmCkx3 PF09265.1.fs domain per Figure 9

<400> SEQUENCE: 89

```
Pro Lys Arg Val Arg Trp Val Arg Val Leu Tyr Ser Asp Phe Ala Ala
 1               5                  10                  15

Phe Thr Lys Asp Gln Glu Arg Leu Ile Ser Lys Glu Asn Gly Gly Gly
```

```
                    20                  25                  30

Gly Ala Lys Val Gly Phe Asp Tyr Val Glu Gly Phe Val Ile Leu Asn
            35                  40                  45

Arg Thr Gly Leu Val Asn Asn Trp Arg Ser Ser Phe Phe Ser Pro Ser
        50                  55                  60

Asp Pro Ala Arg Ile Ala Ser Leu Ala Ser Lys Asn Asn Gly Gly Val
 65                  70                  75                  80

Leu Tyr Cys Leu Glu Val Ala Lys Tyr Tyr Asp Tyr Ala Asp Ser Asp
                85                  90                  95

Ala Ala Thr Val Asp Gln Glu Val Glu Leu Leu Arg Gln Leu Ser
            100                 105                 110

Phe Val Pro Gly Phe Leu Phe Ser Thr Asp Val Ser Tyr Val Asp Phe
            115                 120                 125

Leu Asp Arg Val His Arg Glu Glu Leu Lys Leu Arg Ser Lys Gly Leu
        130                 135                 140

Trp Asp Val Pro His Pro Trp Leu Asn Leu Phe Val Pro Lys Ser Arg
145                 150                 155                 160

Ile Leu Asp Phe Asp Arg Gly Val Phe Lys Gly Ile Leu Leu Lys Asn
                165                 170                 175

Thr Asn Asn Ser Gly Pro Ile Leu Val Tyr Pro Met Asn Arg Ser Lys
            180                 185                 190

Trp Asp Asp Arg Met Ser Ala Val Ile Pro Asp Glu Asp Glu Asp Val
        195                 200                 205

Phe Tyr Leu Val Gly Leu Leu Arg Ser Ala Val Pro Tyr Ser Ala Gly
            210                 215                 220

Pro Gly Asp Leu Glu Glu Leu Glu Asn Gln Asn Arg Arg Ile Leu Glu
225                 230                 235                 240

Phe Cys Glu Lys Ala Gly Ile Gly Tyr Lys Gln Tyr Leu Pro His Tyr
                245                 250                 255

Leu Thr Ser Gln Glu Asp Asn Tyr Trp Lys Arg His Phe Gly Ala Ala
            260                 265                 270

Lys Trp Asp Arg Phe Val Asp Arg Lys Ala Arg Tyr Asp Pro Lys Ala
        275                 280                 285

Ile Leu Ser Pro Gly Gln Gly Ile Phe
    290                 295

<210> SEQ ID NO 90
<211> LENGTH: 297
<212> TYPE: PRT
<213> ORGANISM: Zea mays
<220> FEATURE:
<221> NAME/KEY: DOMAIN
<222> LOCATION: (1)...(297)
<223> OTHER INFORMATION: ZmCkx3 PF09265.1.1s domain per Figure 9

<400> SEQUENCE: 90

Pro Lys Arg Val Arg Trp Val Arg Val Leu Tyr Ser Asp Phe Ala Ala
 1               5                  10                  15

Phe Thr Lys Asp Gln Glu Arg Leu Ile Ser Lys Glu Asn Gly Gly Gly
            20                  25                  30

Gly Ala Lys Val Gly Phe Asp Tyr Val Glu Gly Phe Val Ile Leu Asn
            35                  40                  45

Arg Thr Gly Leu Val Asn Asn Trp Arg Ser Ser Phe Phe Ser Pro Ser
        50                  55                  60

Asp Pro Ala Arg Ile Ala Ser Leu Ala Ser Lys Asn Asn Gly Gly Val
 65                  70                  75                  80
```

```
Leu Tyr Cys Leu Glu Val Ala Lys Tyr Tyr Asp Tyr Ala Asp Ser Asp
            85                  90                  95

Ala Ala Thr Val Asp Gln Glu Val Glu Leu Leu Arg Gln Leu Ser
        100                 105                 110

Phe Val Pro Gly Phe Leu Phe Ser Thr Asp Val Ser Tyr Val Asp Phe
            115                 120                 125

Leu Asp Arg Val His Arg Glu Glu Leu Lys Leu Arg Ser Lys Gly Leu
        130                 135                 140

Trp Asp Val Pro His Pro Trp Leu Asn Leu Phe Val Pro Lys Ser Arg
145                 150                 155                 160

Ile Leu Asp Phe Asp Arg Gly Val Phe Lys Gly Ile Leu Leu Lys Asn
                165                 170                 175

Thr Asn Asn Ser Gly Pro Ile Leu Val Tyr Pro Met Asn Arg Ser Lys
            180                 185                 190

Trp Asp Asp Arg Met Ser Ala Val Ile Pro Asp Glu Asp Glu Asp Val
            195                 200                 205

Phe Tyr Leu Val Gly Leu Leu Arg Ser Ala Val Pro Tyr Ser Ala Gly
            210                 215                 220

Pro Gly Asp Leu Glu Glu Leu Glu Asn Gln Asn Arg Arg Ile Leu Glu
225                 230                 235                 240

Phe Cys Glu Lys Ala Gly Ile Gly Tyr Lys Gln Tyr Leu Pro His Tyr
                245                 250                 255

Leu Thr Ser Gln Glu Asp Asn Tyr Trp Lys Arg His Phe Gly Ala Ala
            260                 265                 270

Lys Trp Asp Arg Phe Val Asp Arg Lys Ala Arg Tyr Asp Pro Lys Ala
            275                 280                 285

Ile Leu Ser Pro Gly Gln Gly Ile Phe
    290                 295

<210> SEQ ID NO 91
<211> LENGTH: 57
<212> TYPE: PRT
<213> ORGANISM: Zea mays
<220> FEATURE:
<221> NAME/KEY: DOMAIN
<222> LOCATION: (1)...(57)
<223> OTHER INFORMATION: ZmCkx4 PF01565.13.fs domain per Figure 9

<400> SEQUENCE: 91

Pro Ala Ala Val Val Arg Pro Glu Ser Glu Glu Val Ala Ala Ile
1               5                   10                  15

Val Arg Leu Ala Arg Glu His Gly Ile Pro Val Thr Pro Arg Gly Gly
            20                  25                  30

Gly His Ser Leu Ser Phe Gly Gly Ala Val Pro Leu Asn Thr Gly Gly
        35                  40                  45

Val Val Leu Asp Leu Ser Arg Lys Leu
    50                  55

<210> SEQ ID NO 92
<211> LENGTH: 144
<212> TYPE: PRT
<213> ORGANISM: Zea mays
<220> FEATURE:
<221> NAME/KEY: DOMAIN
<222> LOCATION: (1)...(144)
<223> OTHER INFORMATION: ZmCkx4 PF01565.13.ls domain per Figure 9

<400> SEQUENCE: 92

Pro Ala Ala Val Val Arg Pro Glu Ser Glu Glu Val Ala Ala Ile
1               5                   10                  15
```

Val Arg Leu Ala Arg Glu His Gly Ile Pro Val Thr Pro Arg Gly Gly
        20                  25                  30

Gly His Ser Leu Ser Phe Gly Ala Val Pro Leu Asn Thr Gly Gly
        35                  40                  45

Val Val Leu Asp Leu Ser Arg Lys Leu Asn Arg Ile Ile Leu Glu Ile
50                  55                  60

Asp Pro Glu Thr Asp Gly Thr Ala Thr Val Glu Ala Gly Val Thr Leu
65                  70                  75                  80

Asp Leu Asn Arg Ala Leu Ala Ala Lys Gly Leu Phe Leu Pro Leu Asp
            85                  90                  95

Pro Gly Ser Gly Ile Pro Gly Thr Val Gly Gly Ala Ile Ala Thr Asn
        100                 105                 110

Ala Gly Gly Tyr Gly Ser Glu Lys Tyr Gly Leu Thr Arg Asp Asn Val
        115                 120                 125

Leu Gly Leu Glu Val Val Leu Ala Asp Gly Glu Val Val Arg Leu Ser
130                 135                 140

<210> SEQ ID NO 93
<211> LENGTH: 73
<212> TYPE: PRT
<213> ORGANISM: Zea mays
<220> FEATURE:
<221> NAME/KEY: DOMAIN
<222> LOCATION: (1)...(73)
<223> OTHER INFORMATION: ZmCkx4 PF01565.13.fs domain per Figure 9

<400> SEQUENCE: 93

Ala Thr Val Glu Ala Gly Val Thr Leu Asp Leu Asn Arg Ala Leu Ala
1               5                   10                  15

Ala Lys Gly Leu Phe Leu Pro Leu Asp Pro Gly Ser Gly Ile Pro Gly
            20                  25                  30

Thr Val Gly Gly Ala Ile Ala Thr Asn Ala Gly Gly Tyr Gly Ser Glu
        35                  40                  45

Lys Tyr Gly Leu Thr Arg Asp Asn Val Leu Gly Leu Glu Val Val Leu
    50                  55                  60

Ala Asp Gly Glu Val Val Arg Leu Ser
65                  70

<210> SEQ ID NO 94
<211> LENGTH: 297
<212> TYPE: PRT
<213> ORGANISM: Zea mays
<220> FEATURE:
<221> NAME/KEY: DOMAIN
<222> LOCATION: (1)...(297)
<223> OTHER INFORMATION: ZmCKx4 PF09265.1.fs domain per Figure 9

<400> SEQUENCE: 94

Pro Lys Arg Val Arg Trp Val Arg Val Leu Tyr Ser Asp Phe Ala Ala
1               5                   10                  15

Phe Thr Lys Asp Gln Glu Arg Leu Ile Ser Lys Glu Asn Gly Gly Gly
            20                  25                  30

Gly Ala Lys Val Gly Phe Asp Tyr Val Glu Gly Phe Val Ile Leu Asn
        35                  40                  45

Arg Thr Gly Leu Val Asn Asn Trp Arg Ser Ser Phe Phe Ser Pro Ser
    50                  55                  60

Asp Pro Ala Arg Ile Ala Ser Leu Ala Ser Lys Asn Asn Gly Gly Val
65                  70                  75                  80

Leu Tyr Cys Leu Glu Val Ala Lys Tyr Tyr Asp Tyr Ala Asp Ser Asp

```
Ala Ala Thr Val Asp Gln Glu Val Glu Glu Leu Leu Arg Gln Leu Ser
                100                 105                 110

Phe Val Pro Gly Phe Leu Phe Ser Thr Asp Val Ser Tyr Val Asp Phe
            115                 120                 125

Leu Asp Arg Val His Arg Glu Glu Leu Lys Leu Arg Ser Lys Gly Leu
        130                 135                 140

Trp Asp Val Pro His Pro Trp Leu Asn Leu Phe Val Pro Lys Ser Arg
145                 150                 155                 160

Ile Leu Asp Phe Asp Arg Gly Val Phe Lys Gly Ile Leu Leu Lys Asn
                165                 170                 175

Thr Asn Asn Ser Gly Pro Ile Leu Val Tyr Pro Met Asn Arg Ser Lys
            180                 185                 190

Trp Asp Arg Met Ser Ala Val Ile Pro Asp Glu Asp Glu Asp Val
        195                 200                 205

Phe Tyr Leu Val Gly Leu Leu Arg Ser Ala Val Pro Tyr Ser Ala Gly
        210                 215                 220

Pro Gly Asp Leu Glu Glu Leu Glu Asn Gln Asn Arg Arg Ile Leu Glu
225                 230                 235                 240

Phe Cys Glu Lys Ala Gly Ile Gly Tyr Lys Gln Tyr Leu Pro His Tyr
                245                 250                 255

Leu Thr Ser Gln Glu Asp Asn Tyr Trp Lys Arg His Phe Gly Ala Ala
            260                 265                 270

Lys Trp Asp Arg Phe Val Asp Arg Lys Ala Arg Tyr Asp Pro Lys Ala
        275                 280                 285

Ile Leu Ser Pro Gly Gln Gly Ile Phe
        290                 295

<210> SEQ ID NO 95
<211> LENGTH: 297
<212> TYPE: PRT
<213> ORGANISM: Zea mays
<220> FEATURE:
<221> NAME/KEY: DOMAIN
<222> LOCATION: (1)...(297)
<223> OTHER INFORMATION: ZmCkx4 PF09265.1.1s domain per Figure 9

<400> SEQUENCE: 95

Pro Lys Arg Val Arg Trp Val Arg Val Leu Tyr Ser Asp Phe Ala Ala
 1               5                  10                  15

Phe Thr Lys Asp Gln Glu Arg Leu Ile Ser Lys Glu Asn Gly Gly Gly
            20                  25                  30

Gly Ala Lys Val Gly Phe Asp Tyr Val Glu Gly Phe Val Ile Leu Asn
        35                  40                  45

Arg Thr Gly Leu Val Asn Asn Trp Arg Ser Ser Phe Phe Ser Pro Ser
 50                  55                  60

Asp Pro Ala Arg Ile Ala Ser Leu Ala Ser Lys Asn Asn Gly Gly Val
65                  70                  75                  80

Leu Tyr Cys Leu Glu Val Ala Lys Tyr Tyr Asp Tyr Ala Asp Ser Asp
                85                  90                  95

Ala Ala Thr Val Asp Gln Glu Val Glu Glu Leu Leu Arg Gln Leu Ser
                100                 105                 110

Phe Val Pro Gly Phe Leu Phe Ser Thr Asp Val Ser Tyr Val Asp Phe
            115                 120                 125

Leu Asp Arg Val His Arg Glu Glu Leu Lys Leu Arg Ser Lys Gly Leu
        130                 135                 140
```

-continued

```
Trp Asp Val Pro His Pro Trp Leu Asn Leu Phe Val Pro Lys Ser Arg
145                 150                 155                 160

Ile Leu Asp Phe Asp Arg Gly Val Phe Lys Gly Ile Leu Leu Lys Asn
            165                 170                 175

Thr Asn Asn Ser Gly Pro Ile Leu Val Tyr Pro Met Asn Arg Ser Lys
        180                 185                 190

Trp Asp Asp Arg Met Ser Ala Val Ile Pro Asp Glu Asp Glu Asp Val
    195                 200                 205

Phe Tyr Leu Val Gly Leu Leu Arg Ser Ala Val Pro Tyr Ser Ala Gly
210                 215                 220

Pro Gly Asp Leu Glu Glu Leu Glu Asn Gln Asn Arg Arg Ile Leu Glu
225                 230                 235                 240

Phe Cys Glu Lys Ala Gly Ile Gly Tyr Lys Gln Tyr Leu Pro His Tyr
                245                 250                 255

Leu Thr Ser Gln Glu Asp Asn Tyr Trp Lys Arg His Phe Gly Ala Ala
            260                 265                 270

Lys Trp Asp Arg Phe Val Asp Arg Lys Ala Arg Tyr Asp Pro Lys Ala
                275                 280                 285

Ile Leu Ser Pro Gly Gln Gly Ile Phe
            290                 295

<210> SEQ ID NO 96
<211> LENGTH: 144
<212> TYPE: PRT
<213> ORGANISM: Zea mays
<220> FEATURE:
<221> NAME/KEY: DOMAIN
<222> LOCATION: (1)...(144)
<223> OTHER INFORMATION: ZmCkx5 PF01565.13.fs domain per Figure 9

<400> SEQUENCE: 96

Pro Ala Ala Val Val Arg Pro Glu Ser Glu Glu Val Ala Ala Ile
1               5                   10                  15

Val Arg Leu Ala Arg Glu His Gly Ile Pro Val Thr Pro Arg Gly Gly
            20                  25                  30

Gly His Ser Leu Ser Phe Gly Gly Ala Val Pro Leu Asn Thr Gly Gly
        35                  40                  45

Val Val Leu Asp Leu Ser Arg Lys Leu Asn Arg Ile Ile Leu Glu Ile
    50                  55                  60

Asp Pro Glu Thr Asp Gly Thr Ala Thr Val Glu Ala Gly Val Thr Leu
65                  70                  75                  80

Asp Leu Asn Arg Ala Leu Ala Ala Lys Gly Leu Phe Leu Pro Leu Asp
                85                  90                  95

Pro Gly Ser Gly Ile Pro Gly Thr Val Gly Gly Ala Ile Ala Thr Asn
            100                 105                 110

Ala Gly Gly Tyr Gly Ser Glu Lys Tyr Gly Leu Thr Arg Asp Asn Val
        115                 120                 125

Leu Gly Leu Glu Val Val Leu Ala Asp Gly Glu Val Val Arg Leu Ser
    130                 135                 140

<210> SEQ ID NO 97
<211> LENGTH: 144
<212> TYPE: PRT
<213> ORGANISM: Zea mays
<220> FEATURE:
<221> NAME/KEY: DOMAIN
<222> LOCATION: (1)...(144)
<223> OTHER INFORMATION: ZmCkx5 PF01565.13.ls domain per Figure 9

<400> SEQUENCE: 97
```

```
Pro Ala Ala Val Val Arg Pro Glu Ser Glu Glu Val Ala Ala Ile
 1               5                  10                  15

Val Arg Leu Ala Arg Glu His Gly Ile Pro Val Thr Pro Arg Gly Gly
             20                  25                  30

Gly His Ser Leu Ser Phe Gly Gly Ala Val Pro Leu Asn Thr Gly Gly
             35                  40                  45

Val Val Leu Asp Leu Ser Arg Lys Leu Asn Arg Ile Ile Leu Glu Ile
     50                  55                  60

Asp Pro Glu Thr Asp Gly Thr Ala Thr Val Glu Ala Gly Val Thr Leu
 65                  70                  75                  80

Asp Leu Asn Arg Ala Leu Ala Ala Lys Gly Leu Phe Leu Pro Leu Asp
                 85                  90                  95

Pro Gly Ser Gly Ile Pro Gly Thr Val Gly Ala Ile Ala Thr Asn
                100                 105                 110

Ala Gly Gly Tyr Gly Ser Glu Lys Tyr Gly Leu Thr Arg Asp Asn Val
            115                 120                 125

Leu Gly Leu Glu Val Val Leu Ala Asp Gly Glu Val Val Arg Leu Ser
    130                 135                 140
```

<210> SEQ ID NO 98
<211> LENGTH: 297
<212> TYPE: PRT
<213> ORGANISM: Zea mays
<220> FEATURE:
<221> NAME/KEY: DOMAIN
<222> LOCATION: (1)...(297)
<223> OTHER INFORMATION: ZmCkx5 PF09265.1.fs domain per Figure 9

<400> SEQUENCE: 98

```
Pro Lys Arg Val Arg Trp Val Arg Val Leu Tyr Ser Asp Phe Ala Ala
 1               5                  10                  15

Phe Thr Lys Asp Gln Glu Arg Leu Ile Ser Lys Glu Asn Gly Gly Gly
             20                  25                  30

Gly Ala Lys Val Gly Phe Asp Tyr Val Glu Gly Phe Val Ile Leu Asn
             35                  40                  45

Arg Thr Gly Leu Val Asn Asn Trp Arg Ser Ser Phe Phe Ser Pro Ser
     50                  55                  60

Asp Pro Ala Arg Ile Ala Ser Leu Ala Ser Lys Asn Asn Gly Gly Val
 65                  70                  75                  80

Leu Tyr Cys Leu Glu Val Ala Lys Tyr Asp Tyr Ala Asp Ser Asp
                 85                  90                  95

Ala Ala Thr Val Asp Gln Glu Val Glu Glu Leu Leu Arg Gln Leu Ser
                100                 105                 110

Phe Val Pro Gly Phe Leu Phe Ser Thr Asp Val Ser Tyr Val Asp Phe
            115                 120                 125

Leu Asp Arg Val His Arg Glu Glu Leu Lys Leu Arg Ser Lys Gly Leu
    130                 135                 140

Trp Asp Val Pro His Pro Trp Leu Asn Leu Phe Val Pro Lys Ser Arg
145                 150                 155                 160

Ile Leu Asp Phe Asp Arg Gly Val Phe Lys Gly Ile Leu Leu Lys Asn
                165                 170                 175

Thr Asn Asn Ser Gly Pro Ile Leu Val Tyr Pro Met Asn Arg Ser Lys
            180                 185                 190

Trp Asp Asp Arg Met Ser Ala Val Ile Pro Asp Glu Asp Glu Asp Val
        195                 200                 205

Phe Tyr Leu Val Gly Leu Leu Arg Ser Ala Val Pro Tyr Ser Ala Gly
```

-continued

```
                    210                 215                 220
Pro Gly Asp Leu Glu Glu Leu Glu Asn Gln Asn Arg Arg Ile Leu Glu
225                 230                 235                 240

Phe Cys Glu Lys Ala Gly Ile Gly Tyr Lys Gln Tyr Leu Pro His Tyr
                245                 250                 255

Leu Thr Ser Gln Glu Asp Asn Tyr Trp Lys Arg His Phe Gly Ala Ala
                260                 265                 270

Lys Trp Asp Arg Phe Val Asp Lys Ala Arg Tyr Asp Pro Lys Ala
                275                 280                 285

Ile Leu Ser Pro Gly Gln Gly Ile Phe
                290                 295

<210> SEQ ID NO 99
<211> LENGTH: 297
<212> TYPE: PRT
<213> ORGANISM: Zea mays
<220> FEATURE:
<221> NAME/KEY: DOMAIN
<222> LOCATION: (1)...(297)
<223> OTHER INFORMATION: ZmCkx5 PF09265.1.ls domain per Figure 9

<400> SEQUENCE: 99

Pro Lys Arg Val Arg Trp Val Arg Val Leu Tyr Ser Asp Phe Ala Ala
1               5                   10                  15

Phe Thr Lys Asp Gln Glu Arg Leu Ile Ser Lys Glu Asn Gly Gly Gly
                20                  25                  30

Gly Ala Lys Val Gly Phe Asp Tyr Val Glu Gly Phe Val Ile Leu Asn
                35                  40                  45

Arg Thr Gly Leu Val Asn Asn Trp Arg Ser Ser Phe Phe Ser Pro Ser
50                  55                  60

Asp Pro Ala Arg Ile Ala Ser Leu Ala Ser Lys Asn Asn Gly Gly Val
65                  70                  75                  80

Leu Tyr Cys Leu Glu Val Ala Lys Tyr Tyr Asp Tyr Ala Asp Ser Asp
                85                  90                  95

Ala Ala Thr Val Asp Gln Glu Val Glu Glu Leu Leu Arg Gln Leu Ser
                100                 105                 110

Phe Val Pro Gly Phe Leu Phe Ser Thr Asp Val Ser Tyr Val Asp Phe
                115                 120                 125

Leu Asp Arg Val His Arg Glu Glu Leu Lys Leu Arg Ser Lys Gly Leu
130                 135                 140

Trp Asp Val Pro His Pro Trp Leu Asn Leu Phe Val Pro Lys Ser Arg
145                 150                 155                 160

Ile Leu Asp Phe Asp Arg Gly Val Phe Lys Gly Ile Leu Leu Lys Asn
                165                 170                 175

Thr Asn Asn Ser Gly Pro Ile Leu Val Tyr Pro Met Asn Arg Ser Lys
                180                 185                 190

Trp Asp Asp Arg Met Ser Ala Val Ile Pro Asp Glu Asp Val
                195                 200                 205

Phe Tyr Leu Val Gly Leu Leu Arg Ser Ala Val Pro Tyr Ser Ala Gly
                210                 215                 220

Pro Gly Asp Leu Glu Glu Leu Glu Asn Gln Asn Arg Arg Ile Leu Glu
225                 230                 235                 240

Phe Cys Glu Lys Ala Gly Ile Gly Tyr Lys Gln Tyr Leu Pro His Tyr
                245                 250                 255

Leu Thr Ser Gln Glu Asp Asn Tyr Trp Lys Arg His Phe Gly Ala Ala
                260                 265                 270
```

```
Lys Trp Asp Arg Phe Val Asp Arg Lys Ala Arg Tyr Asp Pro Lys Ala
    275                 280                 285

Ile Leu Ser Pro Gly Gln Gly Ile Phe
    290                 295
```

<210> SEQ ID NO 100
<211> LENGTH: 144
<212> TYPE: PRT
<213> ORGANISM: Zea mays
<220> FEATURE:
<221> NAME/KEY: DOMAIN
<222> LOCATION: (1)...(144)
<223> OTHER INFORMATION: ZmCkx6 PF01565.13.fs domain per Figure 9

<400> SEQUENCE: 100

```
Pro Ala Ala Val Val Arg Pro Glu Ser Glu Glu Val Ala Ala Ile
1               5                   10                  15

Val Arg Leu Ala Arg Glu His Gly Ile Pro Val Thr Pro Arg Gly Gly
                20                  25                  30

Gly His Ser Leu Ser Phe Gly Gly Ala Val Pro Leu Asn Thr Gly Gly
                35                  40                  45

Val Val Leu Asp Leu Ser Arg Lys Leu Asn Arg Ile Ile Leu Glu Ile
    50                  55                  60

Asp Pro Glu Thr Asp Gly Thr Ala Thr Val Glu Ala Gly Val Thr Leu
65                  70                  75                  80

Asp Leu Asn Arg Ala Leu Ala Ala Lys Gly Leu Phe Leu Pro Leu Asp
                85                  90                  95

Pro Gly Ser Gly Ile Pro Gly Thr Val Gly Gly Ala Ile Ala Thr Asn
                100                 105                 110

Ala Gly Gly Tyr Gly Ser Glu Lys Tyr Gly Leu Thr Arg Asp Asn Val
                115                 120                 125

Leu Gly Leu Glu Val Val Leu Ala Asp Gly Glu Val Val Arg Leu Ser
            130                 135                 140
```

<210> SEQ ID NO 101
<211> LENGTH: 144
<212> TYPE: PRT
<213> ORGANISM: Zea mays
<220> FEATURE:
<221> NAME/KEY: DOMAIN
<222> LOCATION: (1)...(144)
<223> OTHER INFORMATION: ZmCkx6 PF01565.13.ls domain per Figure 9

<400> SEQUENCE: 101

```
Pro Ala Ala Val Val Arg Pro Glu Ser Glu Glu Val Ala Ala Ile
1               5                   10                  15

Val Arg Leu Ala Arg Glu His Gly Ile Pro Val Thr Pro Arg Gly Gly
                20                  25                  30

Gly His Ser Leu Ser Phe Gly Gly Ala Val Pro Leu Asn Thr Gly Gly
                35                  40                  45

Val Val Leu Asp Leu Ser Arg Lys Leu Asn Arg Ile Ile Leu Glu Ile
    50                  55                  60

Asp Pro Glu Thr Asp Gly Thr Ala Thr Val Glu Ala Gly Val Thr Leu
65                  70                  75                  80

Asp Leu Asn Arg Ala Leu Ala Ala Lys Gly Leu Phe Leu Pro Leu Asp
                85                  90                  95

Pro Gly Ser Gly Ile Pro Gly Thr Val Gly Gly Ala Ile Ala Thr Asn
                100                 105                 110

Ala Gly Gly Tyr Gly Ser Glu Lys Tyr Gly Leu Thr Arg Asp Asn Val
                115                 120                 125
```

Leu Gly Leu Glu Val Val Leu Ala Asp Gly Glu Val Val Arg Leu Ser
        130                 135                 140

<210> SEQ ID NO 102
<211> LENGTH: 297
<212> TYPE: PRT
<213> ORGANISM: Zea mays
<220> FEATURE:
<221> NAME/KEY: DOMAIN
<222> LOCATION: (1)...(297)
<223> OTHER INFORMATION: ZmCkx6 PF09265.1.fs domain per Figure 9

<400> SEQUENCE: 102

Pro Lys Arg Val Arg Trp Val Arg Val Leu Tyr Ser Asp Phe Ala Ala
  1               5                  10                  15

Phe Thr Lys Asp Gln Glu Arg Leu Ile Ser Lys Glu Asn Gly Gly Gly
             20                  25                  30

Gly Ala Lys Val Gly Phe Asp Tyr Val Glu Gly Phe Val Ile Leu Asn
         35                  40                  45

Arg Thr Gly Leu Val Asn Asn Trp Arg Ser Ser Phe Phe Ser Pro Ser
 50                  55                  60

Asp Pro Ala Arg Ile Ala Ser Leu Ala Ser Lys Asn Asn Gly Gly Val
 65                  70                  75                  80

Leu Tyr Cys Leu Glu Val Ala Lys Tyr Tyr Asp Tyr Ala Asp Ser Asp
                 85                  90                  95

Ala Ala Thr Val Asp Gln Glu Val Glu Glu Leu Leu Arg Gln Leu Ser
            100                 105                 110

Phe Val Pro Gly Phe Leu Phe Ser Thr Asp Val Ser Tyr Val Asp Phe
        115                 120                 125

Leu Asp Arg Val His Arg Glu Glu Leu Lys Leu Arg Ser Lys Gly Leu
    130                 135                 140

Trp Asp Val Pro His Pro Trp Leu Asn Leu Phe Val Pro Lys Ser Arg
145                 150                 155                 160

Ile Leu Asp Phe Asp Arg Gly Val Phe Lys Gly Ile Leu Leu Lys Asn
                165                 170                 175

Thr Asn Asn Ser Gly Pro Ile Leu Val Tyr Pro Met Asn Arg Ser Lys
            180                 185                 190

Trp Asp Asp Arg Met Ser Ala Val Ile Pro Asp Glu Asp Glu Asp Val
        195                 200                 205

Phe Tyr Leu Val Gly Leu Leu Arg Ser Ala Val Pro Tyr Ser Ala Gly
    210                 215                 220

Pro Gly Asp Leu Glu Glu Leu Glu Asn Gln Asn Arg Arg Ile Leu Glu
225                 230                 235                 240

Phe Cys Glu Lys Ala Gly Ile Gly Tyr Lys Gln Tyr Leu Pro His Tyr
                245                 250                 255

Leu Thr Ser Gln Glu Asp Asn Tyr Trp Lys Arg His Phe Gly Ala Ala
            260                 265                 270

Lys Trp Asp Arg Phe Val Asp Arg Lys Ala Arg Tyr Asp Pro Lys Ala
        275                 280                 285

Ile Leu Ser Pro Gly Gln Gly Ile Phe
    290                 295

<210> SEQ ID NO 103
<211> LENGTH: 297
<212> TYPE: PRT
<213> ORGANISM: Zea mays
<220> FEATURE:
<221> NAME/KEY: DOMAIN

```
<222> LOCATION: (1)...(297)
<223> OTHER INFORMATION: ZmCkx6 PF09265.1.1s domain per Figure 9

<400> SEQUENCE: 103
```

Pro Lys Arg Val Arg Trp Val Arg Val Leu Tyr Ser Asp Phe Ala Ala
 1               5                  10                  15

Phe Thr Lys Asp Gln Glu Arg Leu Ile Ser Lys Glu Asn Gly Gly Gly
             20                  25                  30

Gly Ala Lys Val Gly Phe Asp Tyr Val Glu Gly Phe Val Ile Leu Asn
         35                  40                  45

Arg Thr Gly Leu Val Asn Asn Trp Arg Ser Ser Phe Phe Ser Pro Ser
 50                  55                  60

Asp Pro Ala Arg Ile Ala Ser Leu Ala Ser Lys Asn Asn Gly Gly Val
 65                  70                  75                  80

Leu Tyr Cys Leu Glu Val Ala Lys Tyr Tyr Asp Tyr Ala Asp Ser Asp
                 85                  90                  95

Ala Ala Thr Val Asp Gln Glu Val Glu Leu Leu Arg Gln Leu Ser
             100                 105                 110

Phe Val Pro Gly Phe Leu Phe Ser Thr Asp Val Ser Tyr Val Asp Phe
             115                 120                 125

Leu Asp Arg Val His Arg Glu Glu Leu Lys Leu Arg Ser Lys Gly Leu
     130                 135                 140

Trp Asp Val Pro His Pro Trp Leu Asn Leu Phe Val Pro Lys Ser Arg
145                 150                 155                 160

Ile Leu Asp Phe Asp Arg Gly Val Phe Lys Gly Ile Leu Leu Lys Asn
                 165                 170                 175

Thr Asn Asn Ser Gly Pro Ile Leu Val Tyr Pro Met Asn Arg Ser Lys
             180                 185                 190

Trp Asp Asp Arg Met Ser Ala Val Ile Pro Asp Glu Asp Glu Asp Val
         195                 200                 205

Phe Tyr Leu Val Gly Leu Leu Arg Ser Ala Val Pro Tyr Ser Ala Gly
     210                 215                 220

Pro Gly Asp Leu Glu Glu Leu Glu Asn Gln Asn Arg Arg Ile Leu Glu
225                 230                 235                 240

Phe Cys Glu Lys Ala Gly Ile Gly Tyr Lys Gln Tyr Leu Pro His Tyr
                 245                 250                 255

Leu Thr Ser Gln Glu Asp Asn Tyr Trp Lys Arg His Phe Gly Ala Ala
             260                 265                 270

Lys Trp Asp Arg Phe Val Asp Arg Lys Ala Arg Tyr Asp Pro Lys Ala
         275                 280                 285

Ile Leu Ser Pro Gly Gln Gly Ile Phe
    290                 295

```
<210> SEQ ID NO 104
<211> LENGTH: 57
<212> TYPE: PRT
<213> ORGANISM: Zea mays
<220> FEATURE:
<221> NAME/KEY: DOMAIN
<222> LOCATION: (1)...(57)
<223> OTHER INFORMATION: ZmCKx7 PF01565.13.fs domain per Figure 9

<400> SEQUENCE: 104
```

Pro Ala Ala Val Val Arg Pro Glu Ser Glu Glu Val Ala Ala Ile
 1               5                  10                  15

Val Arg Leu Ala Arg Glu His Gly Ile Pro Val Thr Pro Arg Gly Gly
             20                  25                  30

Gly His Ser Leu Ser Phe Gly Gly Ala Val Pro Leu Asn Thr Gly Gly
         35                  40                  45

Val Val Leu Asp Leu Ser Arg Lys Leu
 50                  55

<210> SEQ ID NO 105
<211> LENGTH: 144
<212> TYPE: PRT
<213> ORGANISM: Zea mays
<220> FEATURE:
<221> NAME/KEY: DOMAIN
<222> LOCATION: (1)...(144)
<223> OTHER INFORMATION: ZmCkx7 PF01565.13.ls domain per Figure 9

<400> SEQUENCE: 105

Pro Ala Ala Val Val Arg Pro Glu Ser Glu Glu Val Ala Ala Ile
 1               5                  10                  15

Val Arg Leu Ala Arg Glu His Gly Ile Pro Val Thr Pro Arg Gly Gly
             20                  25                  30

Gly His Ser Leu Ser Phe Gly Gly Ala Val Pro Leu Asn Thr Gly Gly
         35                  40                  45

Val Val Leu Asp Leu Ser Arg Lys Leu Asn Arg Ile Ile Leu Glu Ile
 50                  55                  60

Asp Pro Glu Thr Asp Gly Thr Ala Thr Val Glu Ala Gly Val Thr Leu
65                  70                  75                  80

Asp Leu Asn Arg Ala Leu Ala Ala Lys Gly Leu Phe Leu Pro Leu Asp
                 85                  90                  95

Pro Gly Ser Gly Ile Pro Gly Thr Val Gly Gly Ala Ile Ala Thr Asn
            100                 105                 110

Ala Gly Gly Tyr Gly Ser Glu Lys Tyr Gly Leu Thr Arg Asp Asn Val
        115                 120                 125

Leu Gly Leu Glu Val Val Leu Ala Asp Gly Glu Val Val Arg Leu Ser
    130                 135                 140

<210> SEQ ID NO 106
<211> LENGTH: 83
<212> TYPE: PRT
<213> ORGANISM: Zea mays
<220> FEATURE:
<221> NAME/KEY: DOMAIN
<222> LOCATION: (1)...(83)
<223> OTHER INFORMATION: ZmCkx7 PF01565.13.fs domain per Figure 9

<400> SEQUENCE: 106

Leu Glu Ile Asp Pro Glu Thr Asp Gly Thr Ala Thr Val Glu Ala Gly
 1               5                  10                  15

Val Thr Leu Asp Leu Asn Arg Ala Leu Ala Ala Lys Gly Leu Phe Leu
             20                  25                  30

Pro Leu Asp Pro Gly Ser Gly Ile Pro Gly Thr Val Gly Gly Ala Ile
         35                  40                  45

Ala Thr Asn Ala Gly Gly Tyr Gly Ser Glu Lys Tyr Gly Leu Thr Arg
     50                  55                  60

Asp Asn Val Leu Gly Leu Glu Val Val Leu Ala Asp Gly Glu Val Val
65                  70                  75                  80

Arg Leu Ser

<210> SEQ ID NO 107
<211> LENGTH: 297
<212> TYPE: PRT
<213> ORGANISM: Zea mays
<220> FEATURE:

```
<221> NAME/KEY: DOMAIN
<222> LOCATION: (1)...(297)
<223> OTHER INFORMATION: ZmCkx7 PF09265.1.fs domain per Figure 9

<400> SEQUENCE: 107

Pro Lys Arg Val Arg Trp Val Arg Val Leu Tyr Ser Asp Phe Ala Ala
 1               5                  10                  15

Phe Thr Lys Asp Gln Glu Arg Leu Ile Ser Lys Glu Asn Gly Gly Gly
            20                  25                  30

Gly Ala Lys Val Gly Phe Asp Tyr Val Glu Gly Phe Val Ile Leu Asn
        35                  40                  45

Arg Thr Gly Leu Val Asn Asn Trp Arg Ser Ser Phe Phe Ser Pro Ser
 50                  55                  60

Asp Pro Ala Arg Ile Ala Ser Leu Ala Ser Lys Asn Asn Gly Gly Val
65                  70                  75                  80

Leu Tyr Cys Leu Glu Val Ala Lys Tyr Tyr Asp Tyr Ala Asp Ser Asp
                85                  90                  95

Ala Ala Thr Val Asp Gln Glu Val Glu Leu Leu Arg Gln Leu Ser
            100                 105                 110

Phe Val Pro Gly Phe Leu Phe Ser Thr Asp Val Ser Tyr Val Asp Phe
            115                 120                 125

Leu Asp Arg Val His Arg Glu Glu Leu Lys Leu Arg Ser Lys Gly Leu
        130                 135                 140

Trp Asp Val Pro His Pro Trp Leu Asn Leu Phe Val Pro Lys Ser Arg
145                 150                 155                 160

Ile Leu Asp Phe Asp Arg Gly Val Phe Lys Gly Ile Leu Leu Lys Asn
                165                 170                 175

Thr Asn Asn Ser Gly Pro Ile Leu Val Tyr Pro Met Asn Arg Ser Lys
            180                 185                 190

Trp Asp Asp Arg Met Ser Ala Val Ile Pro Asp Glu Asp Glu Asp Val
        195                 200                 205

Phe Tyr Leu Val Gly Leu Leu Arg Ser Ala Val Pro Tyr Ser Ala Gly
210                 215                 220

Pro Gly Asp Leu Glu Glu Leu Glu Asn Gln Asn Arg Arg Ile Leu Glu
225                 230                 235                 240

Phe Cys Glu Lys Ala Gly Ile Gly Tyr Lys Gln Tyr Leu Pro His Tyr
                245                 250                 255

Leu Thr Ser Gln Glu Asp Asn Tyr Trp Lys Arg His Phe Gly Ala Ala
            260                 265                 270

Lys Trp Asp Arg Phe Val Asp Arg Lys Ala Arg Tyr Pro Lys Ala
        275                 280                 285

Ile Leu Ser Pro Gly Gln Gly Ile Phe
    290                 295

<210> SEQ ID NO 108
<211> LENGTH: 297
<212> TYPE: PRT
<213> ORGANISM: Zea mays
<220> FEATURE:
<221> NAME/KEY: DOMAIN
<222> LOCATION: (1)...(297)
<223> OTHER INFORMATION: ZmCkx7 PF09265.1.ls domain per Figure 9

<400> SEQUENCE: 108

Pro Lys Arg Val Arg Trp Val Arg Val Leu Tyr Ser Asp Phe Ala Ala
 1               5                  10                  15

Phe Thr Lys Asp Gln Glu Arg Leu Ile Ser Lys Glu Asn Gly Gly Gly
            20                  25                  30
```

```
Gly Ala Lys Val Gly Phe Asp Tyr Val Glu Gly Phe Val Ile Leu Asn
         35                  40                  45

Arg Thr Gly Leu Val Asn Asn Trp Arg Ser Ser Phe Phe Ser Pro Ser
 50                  55                  60

Asp Pro Ala Arg Ile Ala Ser Leu Ala Ser Lys Asn Asn Gly Gly Val
 65                  70                  75                  80

Leu Tyr Cys Leu Glu Val Ala Lys Tyr Tyr Asp Tyr Ala Asp Ser Asp
                 85                  90                  95

Ala Ala Thr Val Asp Gln Glu Val Glu Glu Leu Leu Arg Gln Leu Ser
            100                 105                 110

Phe Val Pro Gly Phe Leu Phe Ser Thr Asp Val Ser Tyr Val Asp Phe
        115                 120                 125

Leu Asp Arg Val His Arg Glu Glu Leu Lys Leu Arg Ser Lys Gly Leu
    130                 135                 140

Trp Asp Val Pro His Pro Trp Leu Asn Leu Phe Val Pro Lys Ser Arg
145                 150                 155                 160

Ile Leu Asp Phe Asp Arg Gly Val Phe Lys Gly Ile Leu Leu Lys Asn
                165                 170                 175

Thr Asn Asn Ser Gly Pro Ile Leu Val Tyr Pro Met Asn Arg Ser Lys
            180                 185                 190

Trp Asp Asp Arg Met Ser Ala Val Ile Pro Asp Glu Asp Glu Asp Val
        195                 200                 205

Phe Tyr Leu Val Gly Leu Leu Arg Ser Ala Val Pro Tyr Ser Ala Gly
    210                 215                 220

Pro Gly Asp Leu Glu Glu Leu Glu Asn Gln Asn Arg Arg Ile Leu Glu
225                 230                 235                 240

Phe Cys Glu Lys Ala Gly Ile Gly Tyr Lys Gln Tyr Leu Pro His Tyr
                245                 250                 255

Leu Thr Ser Gln Glu Asp Asn Tyr Trp Lys Arg His Phe Gly Ala Ala
            260                 265                 270

Lys Trp Asp Arg Phe Val Asp Arg Lys Ala Arg Tyr Asp Pro Lys Ala
        275                 280                 285

Ile Leu Ser Pro Gly Gln Gly Ile Phe
    290                 295

<210> SEQ ID NO 109
<211> LENGTH: 144
<212> TYPE: PRT
<213> ORGANISM: Zea mays
<220> FEATURE:
<221> NAME/KEY: DOMAIN
<222> LOCATION: (1)...(144)
<223> OTHER INFORMATION: ZmCkx8 PF01565.13.fs domain per Figure 9

<400> SEQUENCE: 109

Pro Ala Ala Val Val Arg Pro Glu Ser Glu Glu Glu Val Ala Ala Ile
 1               5                  10                  15

Val Arg Leu Ala Arg Glu His Gly Ile Pro Val Thr Pro Arg Gly Gly
            20                  25                  30

Gly His Ser Leu Ser Phe Gly Gly Ala Val Pro Leu Asn Thr Gly Gly
        35                  40                  45

Val Val Leu Asp Leu Ser Arg Lys Leu Asn Arg Ile Ile Leu Glu Ile
    50                  55                  60

Asp Pro Glu Thr Asp Gly Thr Ala Thr Val Glu Ala Gly Val Thr Leu
 65                  70                  75                  80

Asp Leu Asn Arg Ala Leu Ala Ala Lys Gly Leu Phe Leu Pro Leu Asp
```

85                  90                  95

Pro Gly Ser Gly Ile Pro Gly Thr Val Gly Gly Ala Ile Ala Thr Asn
            100                 105                 110

Ala Gly Gly Tyr Gly Ser Glu Lys Tyr Gly Leu Thr Arg Asp Asn Val
        115                 120                 125

Leu Gly Leu Glu Val Val Leu Ala Asp Gly Glu Val Val Arg Leu Ser
    130                 135                 140

<210> SEQ ID NO 110
<211> LENGTH: 144
<212> TYPE: PRT
<213> ORGANISM: Zea mays
<220> FEATURE:
<221> NAME/KEY: DOMAIN
<222> LOCATION: (1)...(144)
<223> OTHER INFORMATION: ZmCkx8 PF01565.13.ls domain per Figure 9

<400> SEQUENCE: 110

Pro Ala Ala Val Val Arg Pro Glu Ser Glu Glu Val Ala Ala Ile
1               5                   10                  15

Val Arg Leu Ala Arg Glu His Gly Ile Pro Val Thr Pro Arg Gly Gly
            20                  25                  30

Gly His Ser Leu Ser Phe Gly Ala Val Pro Leu Asn Thr Gly Gly
        35                  40                  45

Val Val Leu Asp Leu Ser Arg Lys Leu Asn Arg Ile Ile Leu Glu Ile
    50                  55                  60

Asp Pro Glu Thr Asp Gly Thr Ala Thr Val Gly Ala Gly Val Thr Leu
65                  70                  75                  80

Asp Leu Asn Arg Ala Leu Ala Ala Lys Gly Leu Phe Leu Pro Leu Asp
                85                  90                  95

Pro Gly Ser Gly Ile Pro Gly Thr Val Gly Gly Ala Ile Ala Thr Asn
            100                 105                 110

Ala Gly Gly Tyr Gly Ser Glu Lys Tyr Gly Leu Thr Arg Asp Asn Val
        115                 120                 125

Leu Gly Leu Glu Val Val Leu Ala Asp Gly Glu Val Val Arg Leu Ser
    130                 135                 140

<210> SEQ ID NO 111
<211> LENGTH: 297
<212> TYPE: PRT
<213> ORGANISM: Zea mays
<220> FEATURE:
<221> NAME/KEY: DOMAIN
<222> LOCATION: (1)...(297)
<223> OTHER INFORMATION: ZmCkx8 PF09265.1.fs domain per Figure 9

<400> SEQUENCE: 111

Pro Lys Arg Val Arg Trp Val Arg Val Leu Tyr Ser Asp Phe Ala Ala
1               5                   10                  15

Phe Thr Lys Asp Gln Glu Arg Leu Ile Ser Lys Glu Asn Gly Gly Gly
            20                  25                  30

Gly Ala Lys Val Gly Phe Asp Tyr Val Glu Gly Phe Val Ile Leu Asn
        35                  40                  45

Arg Thr Gly Leu Val Asn Asn Trp Arg Ser Ser Phe Phe Ser Pro Ser
    50                  55                  60

Asp Pro Ala Arg Ile Ala Ser Leu Ala Ser Lys Asn Asn Gly Gly Val
65                  70                  75                  80

Leu Tyr Cys Leu Glu Val Ala Lys Tyr Tyr Asp Tyr Ala Asp Ser Asp
                85                  90                  95

```
Ala Ala Thr Val Asp Gln Glu Val Glu Leu Leu Arg Gln Leu Ser
            100                 105                 110

Phe Val Pro Gly Phe Leu Phe Ser Thr Asp Val Ser Tyr Val Asp Phe
        115                 120                 125

Leu Asp Arg Val His Arg Glu Glu Leu Lys Leu Arg Ser Lys Gly Leu
    130                 135                 140

Trp Asp Val Pro His Pro Trp Leu Asn Leu Phe Val Pro Lys Ser Arg
145                 150                 155                 160

Ile Leu Asp Phe Asp Arg Gly Val Phe Lys Gly Ile Leu Leu Lys Asn
                165                 170                 175

Thr Asn Asn Ser Gly Pro Ile Leu Val Tyr Pro Met Asn Arg Ser Lys
            180                 185                 190

Trp Asp Asp Arg Met Ser Ala Val Ile Pro Asp Glu Asp Glu Asp Val
        195                 200                 205

Phe Tyr Leu Val Gly Leu Leu Arg Ser Ala Val Pro Tyr Ser Ala Gly
    210                 215                 220

Pro Gly Asp Leu Glu Glu Leu Glu Asn Gln Asn Arg Arg Ile Leu Glu
225                 230                 235                 240

Phe Cys Glu Lys Ala Gly Ile Gly Tyr Lys Gln Tyr Leu Pro His Tyr
                245                 250                 255

Leu Thr Ser Gln Glu Asp Asn Tyr Trp Lys Arg His Phe Gly Ala Ala
            260                 265                 270

Lys Trp Asp Arg Phe Val Asp Arg Lys Ala Arg Tyr Asp Pro Lys Ala
        275                 280                 285

Ile Leu Ser Pro Gly Gln Gly Ile Phe
    290                 295

<210> SEQ ID NO 112
<211> LENGTH: 297
<212> TYPE: PRT
<213> ORGANISM: Zea mays
<220> FEATURE:
<221> NAME/KEY: DOMAIN
<222> LOCATION: (1)...(297)
<223> OTHER INFORMATION: ZmCkx8 PF09265.1.ls domain per Figure 9

<400> SEQUENCE: 112

Pro Lys Arg Val Arg Trp Val Arg Val Leu Tyr Ser Asp Phe Ala Ala
1               5                   10                  15

Phe Thr Lys Asp Gln Glu Arg Leu Ile Ser Lys Glu Asn Gly Gly Gly
            20                  25                  30

Gly Ala Lys Val Gly Phe Asp Tyr Val Glu Gly Phe Val Ile Leu Asn
        35                  40                  45

Arg Thr Gly Leu Val Asn Asn Trp Arg Ser Ser Phe Phe Ser Pro Ser
    50                  55                  60

Asp Pro Ala Arg Ile Ala Ser Leu Ala Ser Lys Asn Asn Gly Gly Val
65                  70                  75                  80

Leu Tyr Cys Leu Glu Val Ala Lys Tyr Tyr Asp Tyr Ala Asp Ser Asp
                85                  90                  95

Ala Ala Thr Val Asp Gln Glu Val Glu Glu Leu Leu Arg Gln Leu Ser
            100                 105                 110

Phe Val Pro Gly Phe Leu Phe Ser Thr Asp Val Ser Tyr Val Asp Phe
        115                 120                 125

Leu Asp Arg Val His Arg Glu Glu Leu Lys Leu Arg Ser Lys Gly Leu
    130                 135                 140

Trp Asp Val Pro His Pro Trp Leu Asn Leu Phe Val Pro Lys Ser Arg
145                 150                 155                 160
```

```
Ile Leu Asp Phe Asp Arg Gly Val Phe Lys Gly Ile Leu Leu Lys Asn
            165                 170                 175

Thr Asn Asn Ser Gly Pro Ile Leu Val Tyr Pro Met Asn Arg Ser Lys
            180                 185                 190

Trp Asp Asp Arg Met Ser Ala Val Ile Pro Asp Glu Asp Glu Asp Val
        195                 200                 205

Phe Tyr Leu Val Gly Leu Leu Arg Ser Ala Val Pro Tyr Ser Ala Gly
        210                 215                 220

Pro Gly Asp Leu Glu Glu Leu Glu Asn Gln Asn Arg Arg Ile Leu Glu
225                 230                 235                 240

Phe Cys Glu Lys Ala Gly Ile Gly Tyr Lys Gln Tyr Leu Pro His Tyr
                245                 250                 255

Leu Thr Ser Gln Glu Asp Asn Tyr Trp Lys Arg His Phe Gly Ala Ala
            260                 265                 270

Lys Trp Asp Arg Phe Val Asp Arg Lys Ala Arg Tyr Asp Pro Lys Ala
            275                 280                 285

Ile Leu Ser Pro Gly Gln Gly Ile Phe
290                 295
```

CYTOKININ OXIDASE SEQUENCES AND METHODS OF USE

This application is a continuation-in-part of utility application Ser. No. 11/094,917, filed Mar. 31, 2005, now abandoned, which claims the benefit of provisional application 60/559,252 filed Apr. 2, 2004, both of which are hereby incorporated by reference.

FIELD OF THE INVENTION

The invention relates to the field of the genetic manipulation of plants, particularly the modulation of gene activity and development in plants.

BACKGROUND OF THE INVENTION

Cytokinins are a class of $N^6$ substituted purine derivative plant hormones that regulate cell division, as well as a large number of developmental events, such as shoot development, root branching, control of apical dominance in the shoot, leaf development, chloroplast development, and leaf senescence (Mok, et al., (1994) *Cytokinins. Chemistry, Action and Function* CRC Press, Boca Raton, Fla., pp. 155-166). Active cytokinin pools are regulated by the rate of synthesis, storage, and/or degradation. In maize, cytokinins were found to play a role in establishing seed size, decreasing tip kernel abortion, and increasing seed set during unfavorable environmental conditions (Cheikh and Jones, (1994) *Plant Physiol* 106:45-51; Dietrich and Morris, (1995) *Plant Physiol Biochem* 33(5): 327-336).

The irreversible degradation of cytokinins, catalyzed by cytokinin oxidase, is an important mechanism by which plants modulate their cytokinin levels (Houba-Herin, (1999) *Plant Journal* 17:615-626; Morris, et al., (1999) *Biochemical and Biophysical Research Communications* 255:328-333; Brugière, et al., (2003) *Plant Physiol* 132:1228-1240). The catabolic enzyme cytokinin oxidase (CKX) plays a major role in controlling cytokinin levels in plant tissues, and CKX activity has been found in a great number of plant tissues. The CKX enzyme is a FAD-containing oxidoreductase that catalyzes the degradation of cytokinins bearing unsaturated isoprenoid side chains. The CKX enzymes irreversibly inactivate most cytokinins by cleaving the isoprenoid side chain from the adenine ring (Armstrong, et al., (1994) *Cytokinins. Chemistry, Action and Function*. CRC Press, Boca Raton, Fla., pp. 139-154).

It was earlier shown that ZmCkx1 gene expression is inducible in various organs by synthetic and natural cytokinins. ZmCkx1 is also induced by abscisic acid, which may control cytokinin oxidase expression in the kernel under abiotic stress. Under non-stress conditions, cytokinin oxidase in maize may play a role in controlling growth and development via regulation of cytokinin levels transiting in the xylem. Under environmental stress conditions, cytokinin oxidase gene induction by abscisic acid results in aberrant degradation of cytokinins, therefore impairing normal development (Brugière, et al., 2003, supra).

In view of the influence of cytokinins on a wide variety of plant developmental processes, including root architecture, shoot and leaf development, and seed set, the ability to manipulate cytokinin levels in higher plant cells, and thereby affect plant growth and productivity, is of great commercial value.

BRIEF SUMMARY OF THE INVENTION

Compositions of the invention include cytokinin oxidase (CKX) polypeptides and polynucleotides that are involved in modulating plant development, morphology, and physiology. Compositions include isolated polypeptides comprising an amino acid sequence selected from the group consisting of: (a) the amino acid sequence comprising SEQ ID NO: 3, 6, 9, 12, 53, 59, 62 or 68; (b) the amino acid sequence comprising at least 70% sequence identity to SEQ ID NO: 3, 6, 9, 12, 53, 59, 62 or 68, wherein said polypeptide has cytokinin oxidase activity; (c) the amino acid sequence encoded by a nucleotide sequence that hybridizes under stringent conditions to the complement of SEQ ID NO: 2, 5, 8, 11, 52, 58, 61 or 67, wherein said stringent conditions comprise hybridization in 50% formamide, 1 M NaCl, 1% SDS at 37° C., and a wash in 0.1×SSC at 60° C. to 65° C.; and, (d) the amino acid sequence comprising at least 30 consecutive amino acids of SEQ ID NO: 3, 6, 9, 12, 53, 59, 62 or 68, wherein said polypeptide retains cytokinin oxidase activity.

Compositions further include isolated polynucleotides comprising a nucleotide sequence selected from the group consisting of: (a) a nucleotide sequence comprising SEQ ID NO: 1, 2, 4, 5, 7, 8, 10, 11, 51, 52, 54, 55, 57, 58, 60, 61 or 67; (b) a nucleotide sequence encoding an amino acid sequence comprising SEQ ID NO: 3, 6, 9, 12, 53, 59, 62 or 68; (c) a nucleotide sequence comprising at least 60% sequence identity to SEQ ID NO: 1, 2, 4, 5, 7, 8, 10, 11, 51, 52, 54, 55, 57, 58, 60, 61 or 67, wherein said polynucleotide encodes a polypeptide having cytokinin oxidase activity; (d) a nucleotide sequence comprising at least 50 consecutive nucleotides of SEQ ID NO: 1, 2, 4, 5, 7, 8, 10, 11, 51, 52, 54, 55, 57, 58, 60, 61 or 67, or a complement thereof; and (e) a nucleotide sequence that hybridizes under stringent conditions to the complement of a nucleotide sequence of a), wherein said stringent conditions comprise hybridization in 50% formamide, 1 M NaCl, 1% SDS at 37° C., and a wash in 0.1×SSC at 60° C. to 65° C.

Compositions also include plants comprising a CKX polypeptide of the invention operably linked to a promoter that drives expression in the plant. The plants of the invention can have a modulated cytokinin level compared to a control plant. In some plants, the cytokinin level is modulated in a vegetative tissue, a reproductive tissue, or a vegetative tissue and a reproductive tissue. Plants of the invention may have at least one of the following phenotypes: modulated floral development, modulated flowering time, modulated root development, an altered shoot-to-root ratio, increased seed size and/or increased seed weight, increased plant yield and/or plant vigor, improved or maintained stress tolerance, or a decrease in shoot growth, when compared to a control plant.

Compositions further include plants that have been genetically modified at a genomic locus, wherein the genomic locus encodes a CKX polypeptide of the invention.

Methods for increasing the level or activity of a CKX polypeptide in a plant are provided, which may decrease the level of cytokinin in the plant. The method can comprise introducing into the plant a CKX polynucleotide of the invention. In certain methods, the activity of the CKX polypeptide is increased in a vegetative tissue, a reproductive tissue, or a vegetative tissue and a reproductive tissue. In certain embodiments, increasing the activity of the CKX polypeptide modulates root development, alters the shoot-to-root ratio, and/or modulates floral development.

Methods for reducing or eliminating the level of a CKX polypeptide in a plant are also provided. The method can comprise introducing into said plant a CKX polynucleotide of the invention using techniques to result in downregulation. Reducing the level or activity of the CKX polypeptide can increase the level of a cytokinin in the plant. The level or activity of the polypeptide is reduced or eliminated in a vegetative tissue, a reproductive tissue, or a vegetative tissue and a reproductive tissue. In certain methods, reducing the level and/or activity of the CKX polypeptide maintains or improves the stress tolerance of the plant, increases seed size and/or seed weight, increases the shoot growth of the plant, and/or delays leaf senescence.

Methods and compositions for regulating gene expression in a plant are also provided. Polynucleotides comprising promoter sequences are provided. Compositions include isolated polynucleotides comprising a nucleotide sequence selected from the group consisting of: (a) a nucleotide sequence comprising SEQ ID NO: 13, 14, 15, 16, 17, 18, 63, 69 or 70; b) a nucleotide sequence comprising at least 60% sequence identity to SEQ ID NO: 13, 14, 15, 16, 17, 18, 63, 69 or 70, wherein said polynucleotide retains the ability to regulate transcription; (c) a nucleotide sequence comprising at least 20 consecutive nucleotides of SEQ ID NO: 13, 14, 15, 16, 17, 18, 63, 69 or 70, wherein said polynucleotide retains the ability to regulate transcription; and, (d) a nucleotide sequence that hybridizes under stringent conditions to the complement of the nucleotide sequence of a), wherein said stringent conditions comprise hybridization in 50% formamide, 1 M NaCl, 1% SDS at 37° C., and a wash in 0.1×SSC at 60° C. to 65° C., wherein said sequence retains the ability to regulate transcription. Compositions further include plants and seed having a DNA construct comprising a nucleotide sequence of interest operably linked to a CKX promoter of the invention. In specific embodiments, the DNA construct is stably integrated into the genome of the plant. Other methods may comprise use of a fragment of the promoter in a hairpin construct designed to target the promoter and hence downregulate expression of an operably-linked polynucleotide.

Methods for regulating the expression of a nucleotide sequence of interest are also provided. The method comprises introducing into a plant a nucleotide sequence of interest operably linked to a CKX promoter of the invention.

BRIEF DESCRIPTION OF THE DRAWINGS

FIG. 1 provides a phylogenetic tree of maize and rice cytokinin oxidase protein sequences. The phylogenetic tree was calculated using the Unweighted Pair Group Method with Arithmetic Mean (UPGMA) method with Phylip (Phylogenetic Inference Package) Version 3.573c (Felsenstein, (1989) *Cladistics* 5:164-166) based on a ClustalW alignment using the Blosum matrix. The resulting radial tree was displayed using TreeView (Page, (1996) *Comput Appl Biosci* 12:357-358).

FIG. 2 provides a diagram of the structure of each of the ZmCkx genes.

FIG. 3 provides expression data for ZmCkx2a, ZmCkx2b, ZmCkx3, ZmCkx4, ZmCkx5, ZmCkx6, ZmCkx7, and ZmCkx8 in various maize tissues using Pioneer's Lynx database.

FIG. 4 (A-D) provides schematic representations of various Mu insertions in ZmCkx2a, ZmCkx2b, ZmCkx4, and ZmCkx7.

FIG. 5 shows increased in vitro root growth of Ubi:ZmCkx2a calli relative to control calli FIG. 6 provides data as to number of shoots formed in transgenic Ubi:ZmCkx2a and control maize calli during the regeneration process.

FIG. 7 provides data as to phenotypic characteristics of transgenic Ubi:ZmCkx2a and control maize plants.

FIG. 9 (A-M) provides the HmmerPfam (see, Bateman, et al., (2002) *Nucleic Acids Research* 30(1):276-280) FAD domain identification for ZmCkx2a, ZmCkx2b, ZmCkx3, ZmCkx4, ZmCkx5, ZmCkx6, ZmCkx7, and ZmCkx8. A Pfam consensus sequence is provided in SEQ ID NO: 56.

FIG. 10 provides InterPro data for ZmCkx2, ZmCkx3, ZmCkx4, ZmCkx5, ZmCkx6, ZmCkx7, and ZmCkx8.

FIG. 11 provides an amino acid alignment of AtCkx1 (SEQ ID NO: 35), AtCkx2 (SEQ ID NO: 36), AtCkx3 (SEQ ID NO: 37), AtCkx4 (SEQ ID NO: 38), AtCkx5 (SEQ ID NO: 39), AtCkx6 (SEQ ID NO: 40), AtCkx7 (SEQ ID NO: 41), DsCkx1 (SEQ ID NO: 42), HvCkx2 (SEQ ID NO: 43), HvCkx3 (SEQ ID NO: 44), OsCkx1 (SEQ ID NO: 45), OsCkx2 (SEQ ID NO: 46), OsCkx3 (SEQ ID NO: 47), OsCkx4 (SEQ ID NO: 48), OsCkx5 (SEQ ID NO: 49), OsCkx6 (SEQ ID NO: 73), OsCkx7 (SEQ ID NO: 74), OsCkx8 (SEQ ID NO: 75), OsCkx9 (SEQ ID NO: 76), OsCkx10 (SEQ ID NO: 77), OsCkx11 (SEQ ID NO: 78), ZmCkx1 (SEQ ID NO: 33), ZmCkx2a (SEQ ID NO: 3), ZmCkx2b (SEQ ID NO: 68), ZmCkx3 (SEQ ID NO: 6), ZmCkx4 (SEQ ID NO: 9) ZmCkx5 (SEQ ID NO: 12), ZmCkx6 (SEQ ID NO: 53), ZmCkx7 (SEQ ID NO: 59), and ZmCkx8 (SEQ ID NO: 62). The alignment was generated with AlignX from the VNTI suite using the blosum62mt2 matrix, a gap opening penalty of 10 and gap extension penalty of 0.05, a gap separation penalty range of 8 and a % identity for alignment delay of 40. Also see, Ashikari, et al., 2005 (*Science* 309:741-745) for rice cytokinin oxidase sequences.

FIG. 12A is a map of the PHP24558 plasmid showing the "head-to-tail" arrangement of the Ubi-ZmCkx1 PRO inverted repeat construct relative to the 35S promoter of the cauliflower mosaic virus (CaMV).

FIG. 12B is a map of the PHP24773 plasmid showing the "head-to-head" arrangement of the Ubi-ZmCkx1 PRO inverted repeat construct relative to the 35S promoter of the cauliflower mosaic virus (CaMV).

FIGS. 13-17 provide data on ZmCkx1 promoter hairpin expression as described in Example 10.

FIG. 18 shows details of the 3' UTR hairpin for ZmCkx2b.

FIG. 19 shows details of constructs PHP28930 and PHP28937.

FIG. 20 (A-B) shows root growth of PHP28930 and PHP28937 transgenic plants.

FIG. 21 shows data for height, leaf length, and leaf width for transgenic plants.

FIG. 22 provides details of optimized constructs.

FIG. 23 provides identity levels for ZmCkx1, ZmCkx2a, ZmCkx2b, ZmCkx3, ZmCkx4, ZmCkx5, ZmCkx6, ZmCkx7, ZmCkx8, OsCkx1, OsCkx2, OsCkx3, OsCkx4, OsCkx5, OsCkx6, OsCkx7, OsCkx8, OsCkx9, OsCkx10, and OsCkx11 polypeptides, calculated using the Multiple Sequences Pairwise Relationships Tool for global alignments using the Needleman-Wunsch Algorithm as implemented in the Needle program (EMBOSS tool suite), with a GAP creation penalty of 8 and a GAP extension penalty of 2.

FIG. 24 provides plant growth data (Z-scores) for Ckx2 RNAi events.

FIG. 25 (A-B) provides Northern data for PHP28930 and 28937.

FIG. 26 provides PHP28930 and PHP28937 ear phenotypes.

FIG. 27 provides data showing that improved yield under limited nitrogen conditions is associated with root-preferred overexpression of ZmCkx2.

DETAILED DESCRIPTION OF THE INVENTION

Figure 8B:
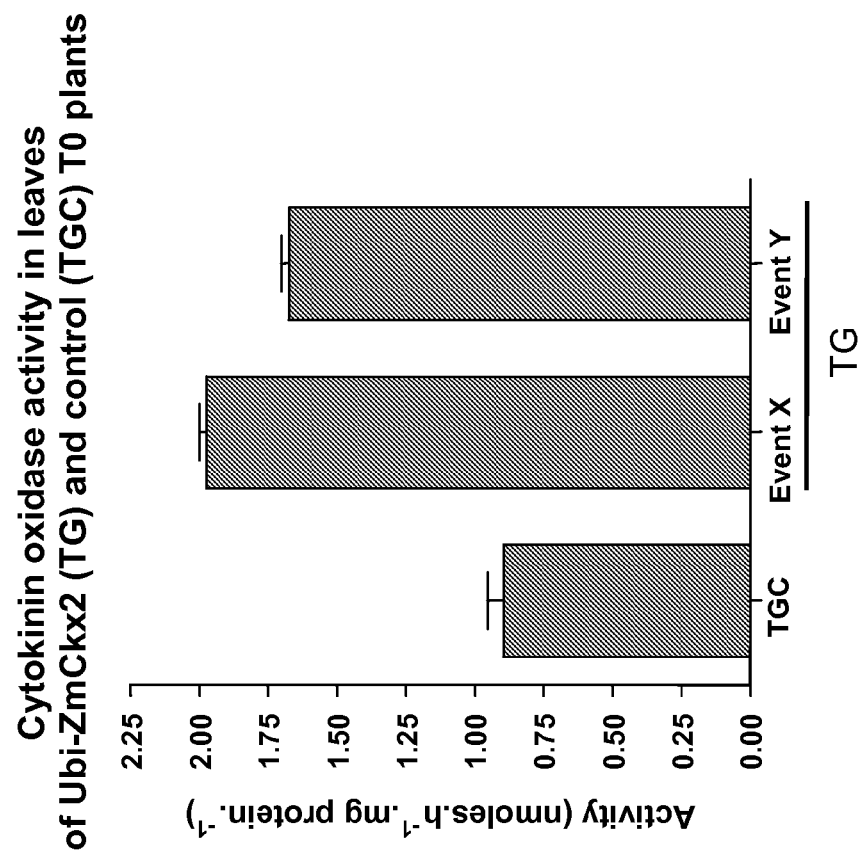
FIG. 8B shows the level of cytokinin oxidase activity in leaves of transgenic plants expressing Ubi-ZmCkx2a compared to transgenic controls.

The present invention now will be described more fully hereinafter with reference to the accompanying drawings, in which some, but not all, embodiments of the invention are shown. Indeed, the invention may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the invention set forth herein will come to mind to one skilled in the art to which these inventions pertain, having the benefit of the teachings presented in the foregoing descriptions and the associated drawings. Therefore, it is to be understood that the invention is not to be limited to the specific embodiments disclosed, and that modifications and other embodiments are intended to be included within the scope of the appended claims. Although specific terms are employed herein, they are used in a generic and descriptive sense only and not for purposes of limitation.

Compositions

Compositions of the invention include cytokinin oxidase (CKX) polypeptides and polynucleotides that are involved in modulating plant development, morphology, and physiology. Compositions of the invention further include CKX promoters that are capable of regulating transcription. In particular, the present invention provides for isolated polynucleotides comprising nucleotide sequences encoding the amino acid sequence shown in SEQ ID NO: 3, 6, 9, 12, 53, 59, 62 or 68. Further provided are polypeptides having an amino acid sequence encoded by a polynucleotide described herein, for example those set forth in SEQ ID NO: 1, 2, 4, 5, 7, 8, 10, 11, 51, 52, 54, 55, 57, 58, 60, 61 or 67. Additional compositions include the promoter sequences for ZmCkx2, ZmCkx3, ZmCkx4, ZmCkx5, ZmCkx8, ZmCkx6, and ZmCkx7, set forth in SEQ ID NO: 13, 14, 15, 16, 63, 69 and 70, respectively.

The cytokinin oxidase polypeptides of the invention share sequence identity with members of the cytokinin oxidase family of proteins. Changes in cytokinin oxidase activity alter the cytokinin concentration in tissues, and thus cytokinin oxidase enzymes are important in controlling local cytokinin-dependent processes. The cytokinin oxidase enzyme is a FAD-containing oxidoreductase that catalyzes the degradation of cytokinins bearing unsaturated isoprenoid side chains. The free bases, isopentenyl-adenine (iP) and zeatin (Z), and their respective ribosides, are exemplary substrates.

The CKX polypeptides of the invention contain a predicted FAD-binding domain (PFAM Accession Number PF01565), and are members of the recently identified PF09265 family of protein. Members of this family adopt an alpha+beta sandwich structure with an antiparallel beta-sheet, in a ferredoxin-like fold. They are predominantly found in plant cytokinin oxidase/dehydrogenases, where they are capable of binding both FAD and cytokinin substrates. The PF01565 and PF09265 domains of ZmCkx2a, ZmCkx2b, ZmCkx3, ZmCkx4, ZmCkx5, ZmCkx6, ZmCkx7, and ZmCkx8 are identified in FIG. 9. The CKX polypeptides of the invention also share homology with several polypeptides in the CKX family. FIG. 10 provides a graphic representation of the identified domains in ZmCkx2, ZmCkx3, ZmCkx4, ZmCkx5, ZmCkx6, ZmCkx7, and ZmCkx8. (Results for ZmCkx2a and ZmCkx2b were very similar due to their high level of identity.) This figure was prepared using InterPro, a program of the European Bioinformatics Institute, which integrates numerous protein signature databases to provide a unique, non-redundant characterization of a given protein family, domain or functional site. FIG. 23 provides a summary of identity of rice and maize cytokinin oxidase polypeptide sequences.

The invention encompasses isolated or substantially purified polynucleotide or protein compositions. An "isolated" or "purified" polynucleotide or protein, or biologically active portion thereof, is substantially or essentially free from components that normally accompany or interact with the polynucleotide or protein as found in its naturally occurring environment. Thus, an isolated or purified polynucleotide or protein is substantially free of other cellular material, or culture medium when produced by recombinant techniques, or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, 4 kb, 3 kb, 2 kb, 1 kb, 0.5 kb or 0.1 kb of nucleotide sequence that naturally flank the polynucleotide in genomic DNA of the cell from which the polynucleotide is derived. A protein that is substantially free of cellular material includes preparations of protein having less than about 30%, 20%, 10%, 5% or 1% (by dry weight) of contaminating protein. When the protein of the invention or biologically active portion thereof is recombinantly produced, optimally culture medium represents less than about 30%, 20%, 10%, 5% or 1% (by dry weight) of chemical precursors or non-protein-of-interest chemicals.

Fragments and variants of the disclosed polynucleotides and proteins encoded thereby are also encompassed by the present invention. By "fragment" is intended a portion of the polynucleotide or a portion of the amino acid sequence and hence of the protein encoded thereby. Fragments of a polynucleotide may encode protein fragments that retain the biological activity of the native protein and hence exhibit cytokinin oxidase activity. Alternatively, fragments of a polynucleotide that are useful as hybridization probes generally do not encode protein fragments retaining biological activity. Thus, fragments of a nucleotide sequence may range from at least about 20 nucleotides, about 50 nucleotides, about 100 nucleotides and up to a full-length polynucleotide encoding a protein of the invention.

A fragment of a CKX polynucleotide that encodes a biologically active portion of a CKX protein of the invention will encode at least 15, 25, 30, 50, 100, 150, 200, 250, 300, 350, 400, 450, 500, 525 or 537 contiguous amino acids, or up to the total number of amino acids present in a full-length CKX protein of the invention (for example, 519 amino acids, 538 amino acids, 521 amino acids and 542 amino acids for SEQ ID NO:3, 6, 9 and 12, respectively). Fragments of a CKX polynucleotide that are useful as hybridization probes or PCR primers generally need not encode a biologically active portion of a CKX protein.

Thus, a fragment of a CKX polynucleotide may encode a biologically active portion of a CKX protein, or it may be a fragment that can be used as a hybridization probe or PCR primer using methods disclosed below. A biologically active portion of a CKX protein can be prepared by isolating a portion of one of the CKX polynucleotides of the invention, expressing the encoded portion of the CKX protein (e.g., by recombinant expression in vitro), and assessing the activity of the encoded portion of the CKX protein. Polynucleotides that are fragments of a CKX nucleotide sequence comprise at least 16, 20, 50, 75, 100, 150, 200, 250, 300, 350, 400, 450, 500, 550, 600, 650, 700, 800, 900, 1000, 1100, 1200, 1300, 1400, 1500, 1600 or 1629 nucleotides, or up to the number of nucleotides present in a full-length CKX polynucleotide disclosed herein (for example, 3200 nucleotides, 1560 nucleotides, 3258 nucleotides, 2635 nucleotides, 1617 nucleotides, 6177 nucleotides, 1816 nucleotides, 1566 nucleotides, 5108 nucleotides or 1629 nucleotides for SEQ ID NO: 1, 2, 4, 5, 54, 7, 8, 55, 10 or 11, respectively).

"Variants" is intended to mean substantially similar sequences. For polynucleotides, a variant comprises a deletion and/or addition of one or more nucleotides at one or more sites within the native polynucleotide and/or a substitution of one or more nucleotides at one or more sites in the native polynucleotide. As used herein, a "native" polynucleotide or polypeptide comprises a naturally occurring nucleotide sequence or amino acid sequence, respectively. For polynucleotides, conservative variants include those sequences that, because of the degeneracy of the genetic code, encode the amino acid sequence of one of the cytokinin oxidase polypeptides of the invention. Naturally occurring allelic variants such as these can be identified with the use of well-known molecular biology techniques, as, for example, with polymerase chain reaction (PCR) and hybridization techniques as outlined below. Variant polynucleotides also include synthetically derived polynucleotides, such as those generated, for example, by using site-directed mutagenesis but which still encode a CKX protein of the invention. Generally, variants of a particular polynucleotide of the invention will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular polynucleotide as determined by sequence alignment programs and parameters described elsewhere herein.

Variants of a particular polynucleotide of the invention (i.e., the reference polynucleotide) can also be evaluated by comparison of the percent sequence identity between the polypeptide encoded by a variant polynucleotide and the polypeptide encoded by the reference polynucleotide. Thus, for example, isolated polynucleotides that encode a polypeptide with a given percent sequence identity to the polypeptide of SEQ ID NO: 3, 6, 9, 12, 53, 59, 62 or 68 are disclosed. Percent sequence identity between any two polypeptides can be calculated using sequence alignment programs and parameters described elsewhere herein. Where any given pair of polynucleotides of the invention is evaluated by comparison of the percent sequence identity shared by the two polypeptides they encode, the percent sequence identity between the two encoded polypeptides is at least about 40%, 45%, 50%, 55%, 60%, 65%, 70%, 75%, 80%, 85%, 90%, 91%, 92%, 93%, 94%, 95%, 96%, 97%, 98%, 99% or more sequence identity.

"Variant" protein is intended to mean a protein derived from the native protein by deletion or addition of one or more amino acids at one or more sites in the native protein and/or substitution of one or more amino acids at one or more sites in the native protein. Variant proteins encompassed by the present invention are biologically active, that is they continue to possess the desired biological activity of the native protein, that is, cytokinin oxidase activity as described herein. Such variants may result from, for example, genetic polymorphism or from human manipulation. Biologically active variants of a native CKX protein of the invention will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to the amino acid sequence for the native protein as determined by sequence alignment programs and parameters described elsewhere herein. A biologically active variant of a protein of the invention may differ from that protein by as few as 1-15 amino acid residues, as few as 1-10, such as 6-10, as few as 5, as few as 4, 3, 2 or even 1 amino acid residue. The upper limit of variation for an amino acid sequence of the invention which retains biological activity can be determined empirically, i.e., by testing variants in an assay for cytokinin oxidase activity as described elsewhere herein. A biologically active variant of a protein of the invention may differ from that protein by as much as 100, 200 or 300 amino acids. One of skill in the art would note that conservation of functional motifs, such as the FAD binding domain identified in FIG. 9 or cytokinin binding domains, is preferred.

The proteins of the invention may be altered in various ways including amino acid substitutions, deletions, truncations, and insertions. Methods for such manipulations are generally known in the art. For example, amino acid sequence variants and fragments of the CKX proteins can be prepared by mutations in the DNA. Methods for mutagenesis and polynucleotide alterations are well known in the art. See, for example, Kunkel, (1985) *Proc. Natl. Acad. Sci. USA* 82:488-492; Kunkel, et al., (1987) *Methods in Enzymol* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff, et al., (1978) *Atlas of Protein Sequence and Structure* (Natl. Biomed. Res. Found., Washington, D.C.), herein incorporated by reference. Conservative substitutions, such as exchanging one amino acid with another having similar properties, may be optimal.

Thus, the genes and polynucleotides of the invention include both the naturally occurring sequences as well as mutant forms. Likewise, the proteins of the invention encompass both naturally occurring proteins as well as variations and modified forms thereof. Such variants will continue to possess the desired cytokinin oxidase activity. The mutations that will be made in the DNA encoding the variant must not place the sequence out of reading frame and optimally will not create complementary regions that could produce secondary mRNA structure. See, EP Patent Application Publication Number 0075444.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. That is, the activity can be evaluated by assaying for cytokinin oxidase activity.

Cytokinin oxidase activity can be assayed in a variety of ways. For example, a variety of cytokinin derivatives can be used as substrates to measure cytokinin oxidase activity. For instance, the polypeptide having CKX activity can be mixed with a cytokinin, for example, zeatin, and the net change of absorbance at 590 nm can be measured. See, U.S. Pat. No. 6,229,066. Alternatively, cytokinin oxidase activity can be measured by assaying for the conversion of $[2-^3H]iP$ to adenine. See, for example, Faiss, et al., (1997) *Plant J.* 12:401-415, herein incorporated by reference. For additional assays, see, Morris, et al., (1999) *Biochem Biophys Res Comm* 255:328-333, Bilyeu, et al., (2001) *Plant Physiol* 125: 378-386, Jones, et al., (1990) *Proceedings of the Plant*

*Growth Regulation Society of America*: (17$^{th}$), pp 183-196, Dietrich, et al., (1995) *Plant Physiol. Bioch.* 268:327-336, Motyka, et al., (1996) *Plant Physiol.* 112:1035-1043, and Frebort, et al., (2002) *Annu Biochem* 306:1-7, each of which is herein incorporated by reference. In addition, a photospectrometric initial rate method which results in the formation of a formazan dye has been used to assay for cytokinin oxidase activity. See, for example, Frebort, et al., (2002) *Annu Biochem* 306:1-7. In addition, cytokinin oxidase activity can be measured by assaying for a decrease in cytokinin levels in vivo. Such a decrease in cytokinin levels can produce one or more symptoms of a cytokinin-deficiency syndrome. The various phenotypes associated with cytokinin-deficiency syndrome are known in the art. See, for example, Schmulling, et al., (2003) *J. Plant Res* 116:241-252, herein incorporated by reference.

Variant polynucleotides and proteins also encompass sequences and proteins derived from a mutagenic and recombinogenic procedure such as DNA shuffling. With such a procedure, one or more different CKX sequences can be manipulated to create a new CKX polypeptide possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the CKX gene of the invention and other known CKX genes to obtain a new gene coding for a protein with an improved property of interest, such as an increased $K_m$ in the case of an enzyme. Strategies for such DNA shuffling are known in the art. See, for example, Stemmer, (1994) *Proc. Natl. Acad. Sci. USA* 91:10747-10751; Stemmer, (1994) *Nature* 370:389-391; Crameri, et al., (1997) *Nature Biotech.* 15:436-438; Moore, et al., (1997) *J. Mol. Biol.* 272: 336-347; Zhang, et al., (1997) *Proc. Natl. Acad. Sci. USA* 94:4504-4509; Crameri, et al., (1998) *Nature* 391:288-291; and U.S. Pat. Nos. 5,605,793 and 5,837,458.

The compositions of the invention also include isolated polynucleotides comprising the CKX promoter nucleotide sequences set forth in SEQ ID NOS: 13, 14, 15, 16, 63, 69 and 70. By "promoter" is intended a regulatory region of DNA usually comprising a TATA box capable of directing RNA polymerase II to initiate RNA synthesis at the appropriate transcription initiation site for a particular polynucleotide sequence. A promoter may additionally comprise other recognition sequences generally positioned upstream or 5' to the TATA box, referred to as upstream promoter elements, which influence the transcription initiation rate. The promoter sequences of the present invention regulate (i.e., repress or activate) transcription from the promoter region.

It is recognized that additional domains can be added to the promoter sequences of the invention and thereby modulate the level of expression, the developmental timing of expression, or tissue type in which expression occurs. See particularly, U.S. Pat. Nos. 5,466,785 and 5,635,618.

Fragments and variants of the disclosed CKX promoter polynucleotides are also encompassed by the present invention. Fragments of a promoter polynucleotide may retain biological activity and hence retain transcriptional regulatory activity. Alternatively, fragments of a polynucleotide that are useful as hybridization probes generally do not retain biological activity. Thus, fragments of a promoter nucleotide sequence may range from at least about 20 nucleotides, about 50 nucleotides, about 100 nucleotides, and up to the full-length polynucleotide of the invention.

Thus, a fragment of a CKX promoter polynucleotide may encode a biologically active portion of a CKX promoter, or it may be a fragment that can be used as a hybridization probe or PCR primer using methods disclosed below. A biologically active portion of a CKX promoter polynucleotide can be prepared by isolating a portion of one of the CKX promoter polynucleotides of the invention, and assessing the activity of the portion of the CKX promoter. Polynucleotides that are fragments of a CKX promoter polynucleotide comprise at least 16, 20, 50, 75, 100, 150, 200, 250, 300, 350, 400, 450, 500, 550, 600, 650, 700, 800, 900, 1,000, 1,100, 1,200, 1,300, 1,400, 1,500, 1,600, 1,700, 1,800, 1,900 or 2000 nucleotides, or up to the number of nucleotides present in a full-length CKX promoter polynucleotide disclosed herein (for example, 3003, 2001, 2448 or 2346 nucleotides for SEQ ID NO: 13, 14, 15 or 16, respectively).

For a promoter polynucleotide, a variant comprises a deletion and/or addition of one or more nucleotides at one or more sites within the native polynucleotide and/or a substitution of one or more nucleotides at one or more sites in the native polynucleotide. Generally, variants of a particular promoter polynucleotide of the invention will have at least about 40%, 45%, 50%, 55%, 60%, 65%, 70%, 75%, 80%, 85%, 90%, 91%, 92%, 93%, 94%, 95%, 96%, 97%, 98% or 99% sequence identity to that particular polynucleotide as determined by sequence alignment programs and parameters described elsewhere herein.

Variant promoter polynucleotides also encompass sequences derived from a mutagenic and recombinogenic procedure such as DNA shuffling. With such a procedure, one or more different promoter sequences can be manipulated to create a new CKX promoter possessing the desired properties. Strategies for such DNA shuffling are described elsewhere herein.

Methods are available in the art for determining if a promoter sequence retains the ability to regulate transcription. Such activity can be measured by Northern blot analysis. See, for example, Sambrook, et al., (1989) *Molecular Cloning: A Laboratory Manual* (2d ed., Cold Spring Harbor Laboratory Press, Plainview, N.Y.), herein incorporated by reference. Alternatively, biological activity of the promoter can be measured using assays specifically designed for measuring the activity and/or level of the polypeptide being expressed from the promoter. Such assays are known in the art.

The polynucleotides of the invention (i.e., the CKX sequences and the CKX promoter sequences) can be used to isolate corresponding sequences from other organisms, particularly other plants, and more particularly other monocots. In this manner, methods such as PCR, hybridization, and the like can be used to identify such sequences based on their sequence homology to the sequences set forth herein. Sequences isolated based on their sequence identity to the entire CKX sequences or the CKX promoter sequences set forth herein or to variants and fragments thereof are encompassed by the present invention. Such sequences include sequences that are orthologs of the disclosed sequences. "Orthologs" is intended to mean genes derived from a common ancestral gene and which are found in different species as a result of speciation. Genes found in different species are considered orthologs when their nucleotide sequences and/or their encoded protein sequences share at least 60%, 70%, 75%, 80%, 85%, 90%, 91%, 92%, 93%, 94%, 95%, 96%, 97%, 98%, 99% or greater sequence identity. Functions of orthologs are often highly conserved among species. Thus, isolated polynucleotides that encode a CKX protein and which hybridize under stringent conditions to the CKX sequences disclosed herein, or to variants or fragments or complements thereof, are encompassed by the present invention.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook, et al., (1989) *Molecular Cloning: A Laboratory Manual* (2d ed., Cold Spring Harbor Laboratory Press, Plainview, N.Y.). See also, Innis, et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known polynucleotide is used as a probe that selectively hybridizes to other corresponding polynucleotides present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}$P, or any other detectable marker. Thus, for example, probes for hybridization can be made by labeling synthetic oligonucleotides based on the CKX polynucleotides or the CKX promoter sequences of the invention. Methods for preparation of probes for hybridization and for construction of cDNA and genomic libraries are generally known in the art and are disclosed in Sambrook, et al., (1989) *Molecular Cloning: A Laboratory Manual* (2d ed., Cold Spring Harbor Laboratory Press, Plainview, N.Y.).

For example, an entire CKX polynucleotide or an entire CKX promoter sequence disclosed herein, or one or more portions thereof, may be used as a probe capable of specifically hybridizing to corresponding CKX polynucleotides and messenger RNAs. To achieve specific hybridization under a variety of conditions, such probes include sequences that are unique among CKX polynucleotide sequences and are optimally at least about 10 nucleotides in length, and most optimally at least about 20 nucleotides in length. Such probes may be used to amplify corresponding CKX polynucleotides from a chosen plant by PCR. This technique may be used to isolate additional coding sequences from a desired plant or as a diagnostic assay to determine the presence of coding sequences in a plant. Hybridization techniques include hybridization screening of plated DNA libraries (either plaques or colonies; see, for example, Sambrook, et al., (1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, optimally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

Specificity is typically the function of post-hybridization washes, the critical factors being the ionic strength and temperature of the final wash solution. For DNA-DNA hybrids, the $T_m$ can be approximated from the equation of Meinkoth and Wahl, (1984) *Anal. Biochem.* 138:267-284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≥90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3 or 4° C. lower than the thermal melting point ($T_m$); moderately stringent conditions can utilize a hybridization and/or wash at 6, 7, 8, 9 or 10° C. lower than the thermal melting point ($T_m$); low stringency conditions can utilize a hybridization and/or wash at 11, 12, 13, 14, 15 or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is optimal to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, N.Y.); and Ausubel, et al., eds. (1995) *Current Protocols in Molecular Biology*, Chapter 2 (Greene Publishing and Wiley-Interscience, New York). See, Sambrook, et al., (1989) *Molecular Cloning: A Laboratory Manual* (2d ed., Cold Spring Harbor Laboratory Press, Plainview, N.Y.).

The following terms are used to describe the sequence relationships between two or more polynucleotides or polypeptides: (a) "reference sequence", (b) "comparison window", (c) "sequence identity", and, (d) "percentage of sequence identity."

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two polynucleotides. Generally, the comparison window is at least 20 contiguous nucleotides in length, and optionally can be 30, 40, 50, 100 or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11-17; the local alignment algorithm of Smith, et al., (1981) *Adv. Appl. Math.* 2:482; the global alignment algorithm of Needleman and Wunsch, (1970) *J. Mol. Biol.* 48:443-453; the search-for-local alignment method of Pearson and Lipman, (1988) *Proc. Natl. Acad. Sci.* 85:2444-2448; the algorithm of Karlin and Altschul, (1990) *Proc. Natl. Acad. Sci. USA* 872264, modified as in Karlin and Altschul, (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA). Alignments using these programs can be performed using the default parameters. The CLUSTAL program is well described by Higgins, et al., (1988) *Gene* 73:237-244 (1988); Higgins, et al., (1989) *CABIOS* 5:151-153; Corpet, et al., (1988) *Nucleic Acids Res.* 16:10881-90; Huang, et al., (1992) *CABIOS* 8:155-65; and Pearson, et al., (1994) *Meth. Mol. Biol.* 24:307-331. The ALIGN program is based on the algorithm of Myers and Miller, (1988) supra. A PAM120 weight residue table, a gap length penalty of 12, and a gap penalty of 4 can be used with the ALIGN program when comparing amino acid sequences. The BLAST programs of Altschul, et al., (1990) *J. Mol. Biol.* 215:403 are based on the algorithm of Karlin and Altschul, (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul, et al., (1997) *Nucleic Acids Res.* 25:3389. Alternatively, PSI-BLAST (in BLAST 2.0) can be used to perform an iterated search that detects distant relationships between molecules. See, Altschul, et al., (1997) supra. When utilizing BLAST, Gapped BLAST, PSI-BLAST, the default parameters of the respective programs (e.g., BLASTN for nucleotide sequences, BLASTX for proteins) can be used. See www.ncbi.nlm.nih.gov. Alignment may also be performed manually by inspection.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman and Wunsch, (1970) *J. Mol. Biol.* 48:443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the GCG Wisconsin Genetics Software Package is BLOSUM62 (see, Henikoff and Henikoff, (1989) *Proc. Natl. Acad. Sci. USA* 89:10915).

(c) As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The invention further provides plants having altered levels and/or activities of the CKX polypeptides of the invention. In some embodiments, the plants of the invention have stably incorporated into their genomes the CKX sequences of the invention. In certain embodiments, plants that are genetically modified at a genomic locus encoding a CKX polypeptide of the invention are provided. By "native genomic locus" is intended a naturally occurring genomic sequence. In some embodiments, the genomic locus is set forth in SEQ ID NO: 1, 4, 7, 10, 51, 57 or 60. In still further embodiments, the genomic locus is modified to reduce or eliminate the activity of the CKX polypeptide. The term "genetically modified" as used herein refers to a plant or plant part that is modified in its genetic information by the introduction of one or more foreign polynucleotides, and that the insertion of the foreign polynucleotide leads to a phenotypic change in the plant. By "phenotypic change" is intended a measurable change in one or more cell functions. For example, plants having the genetic modification at the genomic locus encoding the CKX polypeptide can show reduced or eliminated expression or activity of the CKX polypeptide. Various methods to generate such a genetically modified genomic locus are described elsewhere herein, as are the variety of phenotypes that can result from the modulation of the level and/or activity of the CKX sequences of the invention.

As used herein, the term plant includes plant cells, plant protoplasts, plant cell tissue cultures from which a plant can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, grain and the like. As used herein, by "grain" is intended the mature seed produced by commercial growers for purposes other than growing or reproducing the species. Progeny, variants, and mutants of the regenerated plants are also included within the scope of the invention, provided that these parts comprise the introduced nucleic acid sequences.

A "subject plant" or "subject plant cell" is one in which genetic alteration, such as transformation, has been effected as to a gene of interest, or is a plant or plant cell which is descended from a plant or plant cell so altered and which comprises the alteration. A "control" or "control plant" or "control plant cell" provides a reference point for measuring changes in the subject plant or plant cell.

A control plant or control plant cell may comprise, for example: (a) a wild-type plant or plant cell, i.e., of the same genotype as the starting material for the genetic alteration which resulted in the subject plant or subject plant cell; (b) a plant or plant cell of the same genotype as the starting material but which has been transformed with a null construct (i.e., with a construct which has no known effect on the trait of interest, such as a construct comprising a marker gene); (c) a plant or plant cell which is a non-transformed segregant among progeny of a subject plant or subject plant cell; (d) a plant or plant cell genetically identical to the subject plant or subject plant cell but which is not exposed to conditions or stimuli that would induce expression of the gene of interest; or (e) the subject plant or subject plant cell itself, under conditions in which the gene of interest is not expressed.

In the present case, for example, in various embodiments, changes in ctyokinin oxidase activity, cytokinin oxidase levels, cytokinin activity, cytokinin levels, cytokinin ratios, cytokinin distribution, and/or changes in one or more traits such as flowering time, seed set, branching, senescence, stress tolerance, or root mass, could be measured by comparing a subject plant or subject plant cell to a control plant or control plant cell.

Methods

I. Providing Sequences

The sequences of the present invention can be introduced/expressed in a host cell such as bacteria, yeast, insect, mammalian, or optimally plant cells. It is expected that those of skill in the art are knowledgeable in the numerous systems available for the introduction of a polypeptide or a nucleotide sequence of the present invention into a host cell. No attempt to describe in detail the various methods known for providing proteins in prokaryotes or eukaryotes will be made.

By "host cell" is meant a cell which comprises a heterologous nucleic acid sequence of the invention. Host cells may be prokaryotic cells such as *E. coli*, or eukaryotic cells such as yeast, insect, amphibian, or mammalian cells. Host cells can also be monocotyledonous or dicotyledonous plant cells. In one embodiment, the monocotyledonous host cell is a maize host cell.

The use of the term "polynucleotide" is not intended to limit the present invention to polynucleotides comprising DNA. Those of ordinary skill in the art will recognize that polynucleotides can comprise ribonucleotides and combinations of ribonucleotides and deoxyribonucleotides. Such deoxyribonucleotides and ribonucleotides include both naturally occurring molecules and synthetic analogues. The polynucleotides of the invention also encompass all forms of sequences including, but not limited to, single-stranded forms, double-stranded forms, hairpins, stem-and-loop structures, and the like.

The CKX polynucleotide or CKX promoter sequences of the invention can be provided in expression cassettes for expression in the organism of interest. The cassette may include 5' and 3' regulatory sequences operably linked to a CKX polynucleotide of the invention. "Operably linked" is intended to mean a functional linkage between two or more elements. For example, an operable linkage between a polynucleotide of interest and a regulatory sequence (i.e., a promoter) is a functional link that allows for expression of the polynucleotide of interest. Operably linked elements may be contiguous or non-contiguous. When used to refer to the joining of two protein coding regions, by "operably linked" is intended that the coding regions are in the same reading frame. The cassette may additionally contain at least one additional gene to be cotransformed into the organism. Alternatively, any additional gene(s) can be provided on multiple expression cassettes. Such an expression cassette is provided with a plurality of restriction sites and/or recombination sites for insertion of the CKX polynucleotide to be under the transcriptional regulation of the regulatory regions. The expression cassette may additionally contain selectable marker genes.

The expression cassette may include in the 5'-3' direction of transcription, a transcriptional and translational initiation region (i.e., a promoter), a CKX polynucleotide of the invention, and a transcriptional and translational termination region (i.e., termination region) functional in the host cell (i.e., the plant). The regulatory regions (i.e., promoters, transcriptional regulatory regions, and translational termination regions) and/or the CKX polynucleotide of the invention may be native/analogous to the host cell or to each other. Alternatively, the regulatory regions and/or the CKX polynucleotide of the invention may be heterologous to the host cell or to each other. As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide. As used herein, a chimeric gene comprises a coding sequence operably linked to a transcription initiation region that is heterologous to the coding sequence.

While heterologous promoters can be used to express the sequences, the native promoter sequences (i.e., SEQ ID NOS: 13, 14, 15, 16, 63, 69 and 70) also may be used. Such constructs can change expression levels of CKX in the plant or plant cell. Thus, the phenotype of the plant or plant cell can be altered. Alternatively, in other methods, any CKX promoter sequence of the invention can be used to express a CKX sequence. In addition, other CKX promoters can be used, such as SEQ ID NOS: 17 and 18 herein; see also WO 02/0708438; U.S. Pat. Nos. 6,921,815 and 7,371,925; and U.S. patent application Ser. No. 12/051,893 (SEQ ID NOS: 17 and 18 herein).

A termination region may be native with the transcriptional initiation region, may be native with the operably linked CKX polynucleotide of interest or with the CKX promoter sequences, may be native with the plant host, or may be derived from another source (i.e., foreign or heterologous) to the promoter, the CKX polynucleotide of interest, the plant host, or any combination thereof. Convenient termination regions are available from the Ti-plasmid of *A. tumefaciens*, such as the octopine synthase and nopaline synthase termination regions. See also, Guerineau, et al., (1991) *Mol. Gen. Genet.* 262:141-144; Proudfoot, (1991) *Cell* 64:671-674; Sanfacon, et al., (1991) *Genes Dev.* 5:141-149; Mogen, et al., (1990) *Plant Cell* 2:1261-1272; Munroe, et al., (1990) *Gene* 91:151-158; Ballas, et al., (1989) *Nucleic Acids Res.* 17:7891-7903; and Joshi, et al., (1987) *Nucleic Acids Res.* 15:9627-9639.

Where appropriate, the polynucleotides may be optimized for increased expression in the transformed plant. That is, the polynucleotides can be synthesized using plant-preferred codons for improved expression. See, for example, Campbell and Gowri, (1990) *Plant Physiol.* 92:1-11 for a discussion of host-preferred codon usage. Methods are available in the art for synthesizing plant-preferred genes. See, for example, U.S. Pat. Nos. 5,380,831 and 5,436,391, and Murray, et al., (1989) *Nucleic Acids Res.* 17:477-498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences. Such leader sequences can act to enhance translation. Translation leaders are known in the art and include: picornavirus leaders, for example, EMCV leader (Encephalomyocarditis 5' noncoding region) (Elroy-Stein, et al., (1989) *Proc. Natl. Acad. Sci. USA* 86:6126-6130); potyvirus leaders, for example, TEV leader (Tobacco Etch Virus) (Gallie, et al., (1995) *Gene* 165(2):233-238), MDMV leader (Maize Dwarf Mosaic Virus) (Johnson, et al., (1986) *Virology* 154:9-20), and human immunoglobulin heavy-chain binding protein (BiP) (Macejak, et al., (1991) *Nature* 353:90-94); untranslated leader from the coat protein mRNA of alfalfa mosaic virus (AMV RNA 4) (Jobling, et al., (1987) *Nature* 325:622-625); tobacco mosaic virus leader (TMV) (Gallie, et al., (1989) in *Molecular Biology of RNA*, ed. Cech (Liss, New York), pp. 237-256); and maize chlorotic mottle virus leader (MCMV) (Lommel, et al., (1991) *Virology* 81:382-385). See also, Della-Cioppa, et al., (1987) *Plant Physiol.* 84:965-968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

The expression cassette can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). Additional selectable markers include phenotypic markers such as β-galactosidase and fluorescent proteins such as green fluorescent protein (GFP) (Su, et al., (2004) *Biotechnol Bioeng* 85:610-9 and Fetter, et al., (2004) *Plant Cell* 16:215-

28), cyan florescent protein (CYP) (Bolte, et al., (2004) *J. Cell Science* 117:943-54 and Kato, et al., (2002) *Plant Physiol* 129:913-42), and yellow florescent protein (PhiYFP™ from Evrogen, see, Bolte, et al., (2004) *J. Cell Science* 117:943-54). For additional selectable markers, see generally, Yarranton, (1992) *Curr. Opin. Biotech.* 3:506-511; Christopherson, et al., (1992) *Proc. Natl. Acad. Sci. USA* 89:6314-6318; Yao, et al., (1992) *Cell* 71:63-72; Reznikoff, (1992) *Mol. Microbiol.* 6:2419-2422; Barkley, et al., (1980) in *The Operon*, pp. 177-220; Hu, et al., (1987) *Cell* 48:555-566; Brown, et al., (1987) *Cell* 49:603-612; Figge, et al., (1988) *Cell* 52:713-722; Deuschle, et al., (1989) *Proc. Natl. Acad. Aci. USA* 86:5400-5404; Fuerst, et al., (1989) *Proc. Natl. Acad. Sci. USA* 86:2549-2553; Deuschle, et al., (1990) *Science* 248:480-483; Gossen (1993) Ph.D. Thesis, University of Heidelberg; Reines, et al., (1993) *Proc. Natl. Acad. Sci. USA* 90:1917-1921; Labow, et al., (1990) *Mol. Cell. Biol.* 10:3343-3356; Zambretti, et al., (1992) *Proc. Natl. Acad. Sci. USA* 89:3952-3956; Baim, et al., (1991) *Proc. Natl. Acad. Sci. USA* 88:5072-5076; Wyborski, et al., (1991) *Nucleic Acids Res.* 19:4647-4653; Hillenand-Wissman, (1989) *Topics Mol. Struc. Biol.* 10:143-162; Degenkolb, et al., (1991) *Antimicrob. Agents Chemother.* 35:1591-1595; Kleinschnidt, et al., (1988) *Biochemistry* 27:1094-1104; Bonin, (1993) Ph.D. Thesis, University of Heidelberg; Gossen, et al., (1992) *Proc. Natl. Acad. Sci. USA* 89:5547-5551; Oliva, et al., (1992) *Antimicrob. Agents Chemother.* 36:913-919; Hlavka, et al., (1985) *Handbook of Experimental Pharmacology*, Vol. 78 (Springer-Verlag, Berlin); Gill, et al., (1988) *Nature* 334:721-724. Such disclosures are herein incorporated by reference. The above list of selectable marker genes is not meant to be limiting. Any selectable marker gene can be used in the present invention.

A number of promoters can be used in the practice of the invention, including the native promoter of the polynucleotide sequence of interest. The promoters can be selected based on the desired outcome. The nucleic acids can be combined with constitutive, tissue-preferred, or other promoters for expression in plants.

Such constitutive promoters include, for example, the core promoter of the Rsyn7 promoter and other constitutive promoters disclosed in WO 99/43838 and U.S. Pat. No. 6,072,050; the core CaMV 35S promoter (Odell, et al., (1985) *Nature* 313:810-812); rice actin (McElroy, et al., (1990) *Plant Cell* 2:163-171); ubiquitin (Christensen, et al., (1989) *Plant Mol. Biol.* 12:619-632 and Christensen, et al., (1992) *Plant Mol. Biol.* 18:675-689); PEMU (Last, et al., (1991) *Theor. Appl. Genet.* 81:581-588); MAS (Velten, et al., (1984) *EMBO J.* 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142 and 6,177,611.

Tissue-preferred promoters can be utilized to target enhanced CKX expression within a particular plant tissue. Tissue-preferred promoters include those disclosed by Yamamoto, et al., (1997) *Plant J.* 12(2):255-265; Kawamata, et al., (1997) *Plant Cell Physiol.* 38(7):792-803; Hansen, et al., (1997) *Mol. Gen. Genet.* 254(3):337-343; Russell, et al., (1997) *Transgenic Res.* 6(2):157-168; Rinehart, et al., (1996) *Plant Physiol.* 112(3):1331-1341; Van Camp, et al., (1996) *Plant Physiol.* 112(2):525-535; Canevascini, et al., (1996) *Plant Physiol.* 112(2):513-524; Yamamoto, et al., (1994) *Plant Cell Physiol.* 35(5):773-778; Lam, (1994) *Results Probl. Cell Differ.* 20:181-196; Orozco, et al., (1993) *Plant Mol. Biol.* 23(6):1129-1138; Matsuoka, et al., (1993) *Proc Natl. Acad. Sci. USA* 90(20):9586-9590; and Guevara-Garcia, et al., (1993) *Plant J.* 4(3):495-505. Such promoters can be modified, if necessary, for weak expression. See, also, US Patent Application Publication Number 2003/0074698, herein incorporated by reference. Promoters active in maternal plant tissues, such as female florets, ovaries, aleurone, pedicel, and pedicel-forming region, either pre-pollination or upon pollination, may be of particular interest.

Leaf-preferred promoters are known in the art. See, for example, Yamamoto, et al., (1997) *Plant J.* 12(2):255-265; Kwon, et al., (1994) *Plant Physiol.* 105:357-67; Yamamoto, et al., (1994) *Plant Cell Physiol.* 35(5):773-778; Gotor, et al., (1993) *Plant J.* 3:509-18; Orozco, et al., (1993) *Plant Mol. Biol.* 23(6):1129-1138; Baszczynski, et al., (1988) *Nucl. Acid Res.* 16:4732; Mitra, et al., (1994) *Plant Molecular Biology* 26:35-93; Kayaya, et al., (1995) *Molecular and General Genetics* 248:668-674; and Matsuoka, et al., (1993) *Proc. Natl. Acad. Sci. USA* 90(20):9586-9590. Senescence regulated promoters are also of use, such as SAM22 (Crowell, et al., (1992) *Plant Mol. Biol.* 18:459-466).

Root-preferred or root-specific promoters are known and can be selected from the many available from the literature or isolated de novo from various compatible species. See, for example, Hire, et al., (1992) *Plant Mol. Biol.* 20(2):207-218 (soybean root-specific glutamine synthetase gene); Keller and Baumgartner, (1991) *Plant Cell* 3(10):1051-1061 (root-specific control element in the GRP 1.8 gene of French bean); Sanger, et al., (1990) *Plant Mol. Biol.* 14(3):433-443 (root-specific promoter of the mannopine synthase (MAS) gene of *Agrobacterium tumefaciens*); and Miao, et al., (1991) *Plant Cell* 3(1):11-22 (full-length cDNA clone encoding cytosolic glutamine synthetase (GS), which is expressed in roots and root nodules of soybean). See also, Bogusz, et al., (1990) *Plant Cell* 2(7):633-641, where two root-specific promoters isolated from hemoglobin genes from the nitrogen-fixing nonlegume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-specific promoter activity was preserved. Leach and Aoyagi, (1991) describe their analysis of the promoters of the highly expressed rolC and rolD root-inducing genes of *Agrobacterium rhizogenes* (see, *Plant Science* (Limerick) 79(1):69-76). They concluded that enhancer and tissue-preferred DNA determinants are dissociated in those promoters. Teeri, et al., (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see, *EMBO J.* 8(2):343-350). The TR1' gene, fused to nptII (neomycin phosphotransferase II) showed similar characteristics. Additional root-preferred promoters include the VfENOD-GRP3 gene promoter (Kuster, et al., (1995) *Plant Mol. Biol.* 29(4):759-772); rolB promoter (Capana, et al., (1994) *Plant Mol. Biol.* 25(4):681-691; and the CRWAQ81 root-preferred promoter with the ADH first intron (U.S. patent application Ser. No. 10/961,629, filed Oct. 8, 2004, herein incorporated by reference). See also, U.S. Pat. Nos. 5,837,876; 5,750,386; 5,633,363; 5,459,252; 5,401,836; 5,110,732 and 5,023,179. Promoters associated with the Ckx1 gene from maize may also be useful in modifying CKX activity in roots; see SEQ ID NOS: 17 and 18 herein and U.S. Pat. Nos. 6,921,815 and 7,371,925, and U.S. patent application Ser. No. 12/051,893. Other root-preferred promoters include Zm-NAS2 (U.S. patent application Ser. No. 12/030, 455, filed Feb. 13, 2008), Zm-Cyclo1 promoter (U.S. Pat. No. 7,268,226), Zm-Metallothionein promoters (U.S. Pat. Nos. 6,774,282; 7,214,854 and 7,214,855 (also known as Root-MET2)), Zm-MSY promoter (SEQ ID NO: 64; U.S. patent application Ser. No. 60/971,310 filed Sep. 11, 2007), or MsZRP promoter (SEQ ID NO: 65; see, U.S. Pat. No. 5,633, 363); constructs may also include one or more of the CaMV35S enhancer, Odell, et al., (1988) *Plant Mol. Biol.* 10:263-272, the ADH1 INTRON1 (Callis, et al., (1987) *Genes and Dev.* 1:1183-1200), the UBI1ZM INTRON (PHI) as an enhancer, and PINII terminator.

"Seed-preferred" promoters include those promoters active during seed development, such as those expressed preferentially in female reproductive tissues, and those regulating seed storage proteins, as well as those promoters active during seed germination. See, Thompson, et al., (1989) *BioEssays* 10:108, herein incorporated by reference. Such seed-preferred promoters include, but are not limited to, maize zag2.1 promoter, (GenBank X80206); maize Zap promoter, also known as ZmMADS (US Patent Application Publication Number 2004/0025206); maize eep1 promoter (US Patent Publication Number 2004/0237147); maize lec1 promoter (U.S. patent application Ser. No. 09/718,754); maize F3.7 promoter (Baszczynski, et al., (1997) *Maydica* 42:189-201; maize tb1 promoter (Hubbarda, et al., (2002) *Genetics* 162: 1927-1935); maize Zm40 promoter (U.S. Pat. No. 6,403,862 and WO 01/21783); maize mLIP15 promoter, U.S. Pat. No. 6,479,734; maize ESR promoter, US Patent Application Publication Number 2004/0210960; maize PCNA 2 promoter (U.S. patent application Ser. No. 10/388,359 and WO 03/078591); Cim1 (cytokinin-induced message); cZ19B1 (maize 19 kDa zein); milps (myo-inositol-1-phosphate synthase) (see, WO 00/11177 and U.S. Pat. No. 6,225,529, herein incorporated by reference); and a BETL (basal endosperm transfer layer) promoter, for example, see, U.S. Pat. No. 7,119,251. Several gamma-zein promoters are known to drive endosperm-specific expression. Globulin-1 (Glob-1) is a representative embryo-specific promoter. For dicots, seed-specific promoters include, but are not limited to, bean β-phaseolin, napin, β-conglycinin, soybean lectin, cruciferin, and the like. For monocots, seed-specific promoters include, but are not limited to, maize 15 kDa zein, 22 kDa zein, 27 kDa zein, gamma-zein, waxy, shrunken 1, shrunken 2, globulin 1, etc. See also, WO 00/12733 and U.S. Pat. No. 6,528,704, where seed-preferred promoters from end1 and end2 genes are disclosed; herein incorporated by reference. Additional embryo specific promoters are disclosed in Sato, et al., (1996) *Proc. Natl. Acad. Sci.* 93:8117-8122; Nakase, et al., (1997) *Plant J* 12:235-46; and Postma-Haarsma, et al., (1999) *Plant Mol. Biol.* 39:257-71. Additional endosperm specific promoters are disclosed in Albani, et al., (1984) *EMBO* 3:1405-15; Albani, et al., (1999) *Theor. Appl. Gen.* 98:1253-62; Albani, et al., (1993) *Plant J.* 4:343-55; Mena, et al., (1998) *The Plant Journal* 116:53-62, and Wu, et al., (1998) *Plant Cell Physiology* 39:885-889.

Shoot-preferred promoters include shoot meristem-preferred promoters such as promoters disclosed in Weigal, et al., (1992) *Cell* 69:843-859; Accession Number AJ131822; Accession Number Z71981; Accession Number AF049870 and shoot-preferred promoters disclosed in McAvoy, et al., (2003) *Acta Hort.* (ISHS) 625:379-385.

Dividing cell or meristematic tissue-preferred promoters have been disclosed in Ito, et al., (1994) *Plant Mol. Biol.* 24:863-878; Reyad, et al., (1995) *Mo. Gen. Genet.* 248:703-711; Shaul, et al., (1996) *Proc. Natl. Acad. Sci.* 93:4868-4872; Ito, et al., (1997) *Plant J.* 11:983-992; and Treh in, et al., (1997) *Plant Mol. Biol.* 35:667-672.

Inflorescence-preferred promoters include the promoter of chalcone synthase (Van der Meer, et al., (1990) *Plant Mol. Biol.* 15:95-109), LAT52 (Twell, et al., (1989) *Mol. Gen. Genet.* 217:240-245), pollen specific genes (Albani et al (1990) *Plant Mol. Biol.* 15:605, Zml3 (Buerrero, et al., (1993) *Mol. Gen. Genet.* 224:161-168), maize pollen-specific gene (Hamilton, et al., (1992) *Plant Mol. Biol.* 18:211-218), sunflower pollen expressed gene (Baltz, et al., (1992) *The Plant Journal* 2:713-721), *B. napus* pollen specific genes (Arnoldo, et al., (1992) *J. Cell. Biochem*, Abstract Number Y101204).

Stress inducible promoters include salt/water stress-inducible promoters such as P5CS (Zang, et al., (1997) *Plant Sciences* 129:81-89); cold-inducible promoters, such as cor15a (Hajela, et al., (1990) *Plant Physiol.* 93:1246-1252), cor15b (Wlihelm, et al., (1993) *Plant Mol Biol* 23:1073-1077), wsc120 (Ouellet, et al., (1998) *FEBS Lett.* 423:324-328), ci7 (Kirch, et al., (1997) *Plant Mol. Biol.* 33:897-909), ci21A (Schneider, et al., (1997) *Plant Physiol.* 113:335-45); drought-inducible promoters, such as, Trg-31 (Chaudhary, et al., (1996) *Plant Mol. Biol.* 30:1247-57), rd29 (Kasuga, et al., (1999) *Nature Biotechnology* 18:287-291); osmotic inducible promoters, such as, Rab17 (Vilardell, et al., (1991) *Plant Mol. Biol.* 17:985-93) and osmotin (Raghothama, et al., (1993) *Plant Mol Biol* 23:1117-28); and heat inducible promoters, such as heat shock proteins (Barros, et al., (1992) *Plant Mol.* 19:665-75; Marrs, et al., (1993) *Dev. Genet.* 14:27-41), and smHSP (Waters, et al., (1996) *J. Experimental Botany* 47:325-338). Other stress-inducible promoters include rip2 (U.S. Pat. No. 5,332,808 and US Patent Application Publication Number 2003/0217393) and rd29a (Yamaguchi-Shinozaki, et al., (1993) *Mol. Gen. Genetics* 236:331-334).

The methods of the invention comprise introducing a polypeptide or polynucleotide into a host cell (i.e., a plant). "Introducing" is intended to mean presenting to the plant the polynucleotide or polypeptide in such a manner that the sequence gains access to the interior of a cell. The methods of the invention do not depend on a particular method for introducing a sequence into the host cell, only that the polynucleotide or polypeptides gains access to the interior of at least one cell of the host. Methods for introducing polynucleotide or polypeptides into host cells (i.e., plants) are known in the art and include, but are not limited to, stable transformation methods, transient transformation methods, and virus-mediated methods.

"Stable transformation" is intended to mean that the nucleotide construct introduced into a host (i.e., a plant) integrates into the genome of the plant and is capable of being inherited by the progeny thereof. "Transient transformation" is intended to mean that a polynucleotide is introduced into the host (i.e., a plant) and expressed temporally or a polypeptide is introduced into a host (i.e., a plant).

Transformation protocols as well as protocols for introducing polypeptides or polynucleotide sequences into plants may vary depending on the type of plant or plant cell, i.e., monocot or dicot, targeted for transformation. Suitable methods of introducing polypeptides and polynucleotides into plant cells include microinjection (Crossway, et al., (1986) *Biotechniques* 4:320-334), electroporation (Riggs, et al., (1986) *Proc. Natl. Acad. Sci. USA* 83:5602-5606, *Agrobacterium*-mediated transformation (Townsend, et al., U.S. Pat. No. 5,563,055; Zhao, et al., U.S. Pat. No. 5,981,840), direct gene transfer (Paszkowski, et al., (1984) *EMBO J.* 3:2717-2722), and ballistic particle acceleration (see, for example, Sanford, et al., U.S. Pat. No. 4,945,050; Tomes, et al., U.S. Pat. No. 5,879,918; Tomes, et al., U.S. Pat. No. 5,886,244; Bidney, et al., U.S. Pat. No. 5,932,782; Tomes, et al., (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); McCabe, et al., (1988) *Biotechnology* 6:923-926); and Lec1 transformation (WO 00/28058). Also see, Weissinger, et al., (1988) *Ann. Rev. Genet.* 22:421-477; Sanford, et al., (1987) *Particulate Science and Technology* 5:27-37 (onion); Christou, et al., (1988) *Plant Physiol.* 87:671-674 (soybean); McCabe, et al., (1988) *Bio/Technology* 6:923-926 (soybean); Finer and McMullen, (1991) *In Vitro Cell Dev. Biol.* 27P:175-182 (soybean); Singh, et al., (1998) *Theor. Appl. Genet.* 96:319-324 (soybean); Datta, et al., (1990) *Biotechnology* 8:736-740 (rice); Klein, et al., (1988) *Proc. Natl. Acad. Sci. USA* 85:4305-4309 (maize); Klein, et al., (1988) *Biotechnology* 6:559-563 (maize); Tomes, U.S. Pat. No. 5,240,855; Buising, et al., U.S. Pat. Nos. 5,322,783 and 5,324,646; Tomes, et al., (1995) "Direct DNA Transfer into Intact Plant Cells via Microprojectile Bombardment," in *Plant Cell, Tissue, and Organ Culture: Fundamental Methods*, ed. Gamborg, (Springer-Verlag, Berlin) (maize); Klein, et al., (1988) *Plant Physiol.* 91:440-444 (maize); Fromm, et al., (1990) *Biotechnology* 8:833-839 (maize); Hooykaas-Van Slogteren, et al., (1984) *Nature* (London) 311:763-764; Bowen, et al., U.S. Pat. No. 5,736,369 (cereals); Bytebier, et al., (1987) *Proc. Natl. Acad. Sci. USA* 84:5345-5349 (Liliaceae); De Wet, et al., (1985) in *The Experimental Manipulation of Ovule Tissues*, ed. Chapman, et al., (Longman, N.Y.), pp. 197-209 (pollen); Kaeppler, et al., (1990) *Plant Cell Reports* 9:415-418 and Kaeppler, et al., (1992) *Theor. Appl. Genet.* 84:560-566 (whisker-mediated transformation); D'Halluin, et al., (1992) *Plant Cell* 4:1495-1505 (electroporation); Li, et al., (1993) *Plant Cell Reports* 12:250-255 and Christou and Ford, (1995) *Annals of Botany* 75:407-413 (rice); Osjoda, et al., (1996) *Nature Biotechnology* 14:745-750 (maize via *Agrobacterium tumefaciens*); all of which are herein incorporated by reference.

In specific embodiments, the CKX sequences of the invention can be provided to a plant using a variety of transient transformation methods. Such transient transformation methods include, but are not limited to, the introduction of the CKX protein or variants or fragments thereof directly into the plant, or the introduction of a CKX transcript into the plant. Such methods include, for example, microinjection or particle bombardment. See, for example, Crossway, et al., (1986) *Mol. Gen. Genet.* 202:179-185; Nomura, et al., (1986) *Plant Sci.* 44:53-58; Hepler, et al., (1994) *Proc. Natl. Acad. Sci.* 91: 2176-2180 and Hush, et al., (1994) *The Journal of Cell Science* 107:775-784, all of which are herein incorporated by reference. Alternatively, the CKX polynucleotide can be transiently transformed into the plant using techniques known in the art. Such techniques include viral vector system and the precipitation of the polynucleotide in a manner that precludes subsequent release of the DNA. Thus, the transcription from the particle-bound DNA can occur, but the frequency with which it is released to become integrated into the genome is greatly reduced. Such methods include the use particles coated with polyethylimine (PEI; Sigma #P3143).

In certain embodiments, the polynucleotide of the invention may be introduced into plants by contacting plants with a virus or viral nucleic acids. Generally, such methods involve incorporating a nucleotide construct of the invention within a viral DNA or RNA molecule. It is recognized that the a CKX sequence of the invention may be initially synthesized as part of a viral polyprotein, which later may be processed by proteolysis in vivo or in vitro to produce the desired recombinant protein. Further, it is recognized that promoters of the invention also encompass promoters utilized for transcription by viral RNA polymerases. Methods for introducing polynucleotides into plants and expressing a protein encoded therein, involving viral DNA or RNA molecules, are known in the art. See, for example, U.S. Pat. Nos. 5,889,191, 5,889,190, 5,866, 785, 5,589,367, 5,316,931 and Porta, et al., (1996) *Molecular Biotechnology* 5:209-221; herein incorporated by reference.

Methods are known in the art for the targeted insertion of a polynucleotide at a specific location in the plant genome. In one embodiment, the insertion of the polynucleotide at a desired genomic location is achieved using a site-specific recombination system. See, for example, WO99/25821, WO99/25854, WO99/25840, WO99/25855, and WO99/25853; also, U.S. Pat. Nos. 6,552,248, 6,624,297, 6,573,425, 6,455,315 and 6,458,594, all of which are herein incorporated by reference. Briefly, the polynucleotide of the invention can be contained in a transfer cassette flanked by two non-identical recombination sites. The transfer cassette is introduced into a plant having stably incorporated into its genome a target site which is flanked by two non-identical recombination sites that correspond to the sites of the transfer cassette. An appropriate recombinase is provided and the transfer cassette is integrated at the target site. The polynucleotide of interest is thereby integrated at a specific chromosomal position in the plant genome.

The cells that have been transformed may be grown into plants in accordance with conventional ways. See, for example, McCormick, et al., (1986) *Plant Cell Reports* 5:81-84. These plants may then be grown, and either pollinated with the same transformed strain or different strains, and the resulting progeny having appropriate expression of the desired phenotypic characteristic identified. Two or more generations may be grown to ensure that expression of the desired phenotypic characteristic is stably maintained and inherited, and then seeds harvested to ensure expression of the desired phenotypic characteristic has been achieved. In this manner, the present invention provides transformed seed (also referred to as "transgenic seed") having a polynucleotide of the invention, for example, an expression cassette of the invention, stably incorporated into its genome.

Pedigree breeding starts with the crossing of two genotypes, such as an elite line of interest and one other line having one or more desirable characteristics (e.g., having stably incorporated a polynucleotide of the invention, having a modulated activity and/or level of the polypeptide of the invention, etc.) which complements the elite line of interest. If the two original parents do not provide all the desired characteristics, other sources can be included in the breeding population. In the pedigree method, superior plants are selfed and selected in successive filial generations. In the succeeding filial generations the heterozygous condition gives way to homogeneous lines as a result of self-pollination and selection. Typically in the pedigree method of breeding, five or more successive filial generations of selfing and selection are practiced: F1→F2; F2→F3; F3→F4; F4→F5, etc. After a sufficient amount of inbreeding, successive filial generations will serve to increase seed of the developed inbred. Preferably, the inbred line comprises homozygous alleles at about 95% or more of its loci.

Backcrossing can be used to transfer one or more specifically desirable traits from one line, the donor parent, to an inbred called the recurrent parent, which has overall good agronomic characteristics yet lacks that desirable trait or traits. Backcrossing may be used in combination with pedigree breeding to modify an elite line of interest, and a hybrid is made using the modified elite line. However, the same procedure can be used to move the progeny toward the genotype of the recurrent parent but at the same time retain many components of the non-recurrent parent, by stopping the backcrossing at an early stage and proceeding with selfing and selection. For example, an F1, such as a commercial hybrid, is created. This commercial hybrid may be backcrossed to one of its parent lines to create a BC1 or BC2. Progeny are selfed and selected so that the newly developed inbred has many of the attributes of the recurrent parent and yet several of the desired attributes of the non-recurrent parent. This approach leverages the value and strengths of the recurrent parent for use in new hybrids and breeding.

Therefore, one embodiment of this invention is a method of making a backcross conversion of a maize inbred line of interest, comprising the steps of crossing a plant of the maize inbred line of interest with a donor plant comprising a mutant gene or transgene conferring a desired trait, selecting an F1 progeny plant comprising the mutant gene or transgene conferring the desired trait, and backcrossing the selected F1 progeny plant to a plant of the maize inbred line of interest. This method may further comprise the step of obtaining a molecular marker profile of the maize inbred line of interest and using the molecular marker profile to select for a progeny plant with the desired trait and the molecular marker profile of the inbred line of interest. In the same manner, this method may be used to produce F1 hybrid seed by adding a final step of crossing the desired trait-converted maize inbred line of interest with a different maize plant to make F1 hybrid maize seed comprising a mutant gene or transgene conferring the desired trait.

Recurrent selection is a method used in a plant breeding program to improve a population of plants. The method entails individual plants cross pollinating with each other to form progeny. The progeny are grown and the superior progeny selected by any number of selection methods, which include individual plant, half-sib progeny, full-sib progeny, selfed progeny and topcrossing. The selected progeny are cross-pollinated with each other to form progeny for another population. This population is planted and again superior plants are selected to cross pollinate with each other. Recurrent selection is a cyclical process and therefore can be repeated as many times as desired. The objective of recurrent selection is to improve the traits of a population. The improved population can then be used as a source of breeding material to obtain inbred lines to be used in hybrids or used as parents for a synthetic cultivar. A synthetic cultivar is the resultant progeny formed by the intercrossing of several selected inbreds.

Mass selection is a useful technique especially when used in conjunction with molecular marker enhanced selection. In mass selection seeds from individuals are selected based on phenotype and/or genotype. These selected seeds are then bulked and used to grow the next generation. Bulk selection requires growing a population of plants in a bulk plot, allowing the plants to self-pollinate, harvesting the seed in bulk and then using a sample of the seed harvested in bulk to plant the next generation. Instead of self pollination, directed pollination could be used as part of the breeding program.

Mutation breeding is one of many methods that could be used to introduce new traits into an elite line. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation (such as X-rays, Gamma rays (e.g., cobalt 60 or cesium 137), neutrons, (product of nuclear fission by uranium 235 in an atomic reactor), Beta radiation (emitted from radioisotopes such as phosphorus 32 or carbon 14), or ultraviolet radiation (preferably from 2500 to 2900 nm)), or chemical mutagens (such as base analogues (5-bromo-uracil), related compounds (8-ethoxy caffeine), antibiotics (streptonigrin), alkylating agents (sulfur mustards, nitrogen mustards, epoxides, ethylenamines, sulfates, sulfonates, sulfones, lactones), azide, hydroxylamine, nitrous acid, or acridines. Once a desired trait is observed through mutagenesis the trait may then be incorporated into existing germplasm by traditional breeding techniques, such as backcrossing. Details of mutation breeding can be found in Fehr's "Principles of Cultivar Development," 1993, Macmillan Publishing Company, the disclosure of which is incorporated herein by reference. In addition, mutations created in other lines may be used to produce a backcross conversion of an elite line comprising such mutations.

The present invention may be used for transformation of any plant species, including, but not limited to, monocots and dicots. Examples of plant species of interest include, but are not limited to, corn or maize (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassaya (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, grasses and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum. Turfgrasses include, but are not limited to: annual bluegrass (*Poa annua*); annual ryegrass (*Lolium multiflorum*); Canada bluegrass (*Poa compressa*); Chewings fescue (*Festuca rubra*); colonial bentgrass (*Agrostis tenuis*); creeping bentgrass (*Agrostis palustris*); crested wheatgrass (*Agropyron desertorum*); fairway wheatgrass (*Agropyron cristatum*); hard fescue (*Festuca longifolia*); Kentucky bluegrass (*Poa pratensis*); orchardgrass (*Dactylis glomerata*); perennial ryegrass (*Lolium perenne*); red fescue (*Festuca rubra*); redtop (*Agrostis alba*); rough bluegrass (*Poa trivialis*); sheep fescue (*Festuca ovina*); smooth bromegrass (*Bromus inermis*); tall fescue (*Festuca arundinacea*); timothy (*Phleum pratense*); velvet bentgrass (*Agrostis canina*); weeping alkaligrass (*Puccinellia distans*); western wheatgrass (*Agropyron smithii*); Bermuda grass (*Cynodon* spp.); St. Augustine grass (*Stenotaphrum secundatum*); zoysia grass (*Zoysia* spp.); Bahia grass (*Paspalum notatum*); carpet grass (*Axonopus affinis*); centipede grass (*Eremochloa ophiuroides*); kikuyu grass (*Pennisetum clandesinum*); seashore paspalum (*Paspalum vaginatum*); blue grama (*Bouteloua gracilis*); buffalo grass (*Buchloe dactyloids*); sideoats grama (*Bouteloua curtipendula*).

In specific embodiments, plants of the present invention are crop plants (for example, corn (maize), alfalfa, sunflower, *Brassica*, soybean, cotton, safflower, peanut, sorghum, wheat, millet, tobacco, etc.).

Other plants of interest include grain plants that provide seeds of interest, oil-seed plants, and leguminous plants. Seeds of interest include grain seeds, such as corn, wheat, barley, rice, sorghum, rye, etc. Oil-seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

Typically, an intermediate host cell will be used in the practice of this invention to increase the copy number of the cloning vector. With an increased copy number, the vector containing the nucleic acid of interest can be isolated in significant quantities for introduction into the desired plant cells. In one embodiment, plant promoters that do not cause expression of the polypeptide in bacteria are employed.

Prokaryotes most frequently are represented by various strains of *E. coli* however, other microbial strains may also be used. Commonly used prokaryotic control sequences, which are defined herein to include promoters for transcription initiation, optionally with an operator, along with ribosome binding sequences, include such commonly used promoters as the beta lactamase (penicillinase) and lactose (lac) promoter systems (Chang, et al., (1977) *Nature* 198:1056), the tryptophan (trp) promoter system (Goeddel, et al., (1980) *Nucleic Acids Res.* 8:4057) and the lambda derived P L promoter and N-gene ribosome binding site (Shimatake, et al., (1981) *Nature* 292:128). The inclusion of selection markers in DNA vectors transfected in *E. coli*. is also useful. Examples of such markers include genes specifying resistance to ampicillin, tetracycline, or chloramphenicol.

The vector is selected to allow introduction into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for expressing a protein of the present invention are available using *Bacillus* sp. and *Salmonella* (Palva, et al., (1983) *Gene* 22:229-235); Mosbach, et al., (1983) *Nature* 302:543-545).

A variety of eukaryotic expression systems such as yeast, insect cell lines, plant and mammalian cells, are known to those of skill in the art. As explained briefly below, a polynucleotide of the present invention can be expressed in these eukaryotic systems. In some embodiments, transformed/transfected plant cells, as discussed infra, are employed as expression systems for production of the proteins of the instant invention.

Synthesis of heterologous polynucleotides in yeast is well known (Sherman, et al., (1982) *Methods in Yeast Genetics*, Cold Spring Harbor Laboratory). Two widely utilized yeasts for production of eukaryotic proteins are *Saccharomyces cerevisiae* and *Pichia pastoris*. Vectors, strains, and protocols for expression in *Saccharomyces* and *Pichia* are known in the art and available from commercial suppliers (e.g., Invitrogen). Suitable vectors usually have expression control sequences, such as promoters, including 3-phosphoglycerate kinase or alcohol oxidase, and an origin of replication, termination sequences and the like as desired.

A protein of the present invention, once expressed, can be isolated from yeast by lysing the cells and applying standard protein isolation techniques to the lysate. The monitoring of the purification process can be accomplished by using Western blot techniques or radioimmunoassay or other standard immunoassay techniques.

The sequences of the present invention can also be ligated to various expression vectors for use in transfecting cell cultures of, for instance, mammalian, insect, or plant origin. Illustrative cell cultures useful for the production of the peptides are mammalian cells. A number of suitable host cell lines capable of expressing intact proteins have been developed in the art, and include the HEK293, BHK21, and CHO cell lines. Expression vectors for these cells can include expression control sequences, such as an origin of replication, a promoter (e.g., the CMV promoter, a HSV tk promoter or pgk (phosphoglycerate kinase) promoter), an enhancer (Queen, et al., (1986) *Immunol. Rev.* 89:49), and necessary processing information sites, such as ribosome binding sites, RNA splice sites, polyadenylation sites (e.g., an SV40 large T Ag poly A addition site), and transcriptional terminator sequences. Other animal cells useful for production of proteins of the present invention are available, for instance, from the American Type Culture Collection.

Appropriate vectors for expressing proteins of the present invention in insect cells are usually derived from the SF9 baculovirus. Suitable insect cell lines include mosquito larvae, silkworm, armyworm, moth and *Drosophila* cell lines such as a Schneider cell line (See, Schneider, (1987) *J. Embryol. Exp. Morphol.* 27:353-365).

As with yeast, when higher animal or plant host cells are employed, polyadenylation or transcription terminator sequences are typically incorporated into the vector. An example of a terminator sequence is the polyadenylation sequence from the bovine growth hormone gene. Sequences for accurate splicing of the transcript may also be included. An example of a splicing sequence is the VP1 intron from SV40 (Sprague, et al., (1983) *J. Virol.* 45:773-781). Additionally, gene sequences to control replication in the host cell may be incorporated into the vector such as those found in bovine papilloma virus type-vectors (Saveria-Campo, (1985) *DNA Cloning Vol. II a Practical Approach*, D. M. Glover, Ed., IRL Press, Arlington, Va., pp. 213-238).

Animal and lower eukaryotic (e.g., yeast) host cells are competent or rendered competent for transfection by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextrin, electroporation, biolistics, and micro-injection of the DNA directly into the cells. The transfected cells are cultured by means well known in the art (Kuchler, (1997) *Biochemical Methods in Cell Culture and Virology*, Dowden, Hutchinson and Ross, Inc.).

In certain embodiments, the polynucleotides of the present invention can be stacked with any combination of other polynucleotide sequences of interest in order to create a plant with a desired phenotype with respect to one or more traits. The combinations generated may include multiple copies of any one or more of the polynucleotides of interest.

These stacked combinations can be created by any method including, but not limited to, cross breeding plants by any conventional or TopCross methodology, or genetic transformation. If the traits are stacked by genetically transforming the plants, the polynucleotide sequences of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of a polynucleotide of interest. This may be combined with any combination of other suppression cassettes or overexpression cassettes to generate the desired combination of traits in the plant.

II. Modulating the Concentration and/or Activity of a CKX Polypeptide

A method for modulating the concentration and/or activity of a polypeptide of the present invention in a plant is provided. In general, concentration and/or activity is increased or decreased by at least 1%, 5%, 10%, 20%, 30%, 40%, 50%, 60%, 70%, 80% or 90% relative to a native control plant, plant part, or cell which did not have the sequence of the invention introduced. Modulation in the present invention may occur during and/or subsequent to growth of the plant to the desired stage of development. In specific embodiments, the polypeptides of the present invention are modulated in monocots, particularly maize.

A variety of methods can be employed to assay for a modulation in the concentration and/or activity of a CKX polypeptide. For instance, the expression level of the CKX polypeptide may be measured directly, for example, by assaying for the level of the CKX polypeptide in the plant (i.e., Western or Northern blot), or indirectly, for example, by assaying the cytokinin oxidase activity of the CKX polypeptide in the plant. Methods for measuring the cytokinin oxidase activity are described elsewhere herein. In specific embodiments, modulation of CKX polypeptide concentration and/or activity comprises the modulation (i.e., an increase or a decrease) in the level of cytokinin in the plant. Methods to measure the level and/or activity of cytokinin are known in the art and are discussed elsewhere herein. In still other embodiments, the level and/or activity of the CKX polypeptide is modulated in vegetative tissue, in reproductive tissue, or in both vegetative and reproductive tissue.

In one embodiment, the activity and/or concentration of the CKX polypeptide is modulated by introducing the polypeptide or the polynucleotide of the invention into the plant. Subsequently, a plant having the introduced sequence of the invention is selected using methods known to those of skill in the art such as, but not limited to, Southern blot analysis, DNA sequencing, PCR analysis, or phenotypic analysis. A plant or plant part altered or modified by the foregoing embodiments is grown under plant forming conditions for a time sufficient to modulate the concentration and/or activity of the CKX polypeptide in the plant. Plant forming conditions are well known in the art and discussed briefly elsewhere herein.

It is also recognized that the level and/or activity of the polypeptide may be modulated by employing a polynucleotide that is not capable of directing, in a transformed plant, the expression of a protein or an RNA. For example, the polynucleotides of the invention may be used to design polynucleotide constructs that can be employed in methods for altering or mutating a genomic nucleotide sequence in an organism. Such polynucleotide constructs include, but are not limited to, RNA:DNA vectors, RNA:DNA mutational vectors, RNA:DNA repair vectors, mixed-duplex oligonucleotides, self-complementary RNA:DNA oligonucleotides, and recombinogenic oligonucleobases. Such nucleotide constructs and methods of use are known in the art. See, U.S. Pat. Nos. 5,565,350; 5,731,181; 5,756,325; 5,760,012; 5,795,972 and 5,871,984, all of which are herein incorporated by reference. See also, WO 98/49350, WO 99/07865, WO 99/25821 and Beetham, et al., (1999) *Proc. Natl. Acad. Sci. USA* 96:8774-8778; herein incorporated by reference. It is therefore recognized that methods of the present invention do not depend on the incorporation of the entire polynucleotide into the genome, only that the plant or cell thereof is altered as a result of the introduction of the polynucleotide into a cell. In one embodiment of the invention, the genome may be altered following the introduction of the polynucleotide into a cell. For example, the polynucleotide, or any part thereof, may be incorporated into the genome of the plant. Alterations to the genome of the present invention include, but are not limited to, additions, deletions, and substitutions of nucleotides into the genome. While the methods of the present invention do not depend on additions, deletions, and substitutions of any particular number of nucleotides, it is recognized that such additions, deletions, or substitutions comprise at least one nucleotide.

Genetic constructs providing reduced expression of cytokinin oxidase genes may be used in combination with constructs providing further modulation of effective levels of cytokinin in a plant, including increased biosynthesis of cytokinins, as described in co-pending U.S. patent application Ser. No. 09/545,334 filed Apr. 16, 1999, and US Patent Application Publication Number 2004/0237147, published Nov. 24, 2004, herein incorporated by reference.

A Increasing the Activity and/or Level of a CKX Polypeptide

Methods are provided to increase the activity and/or level of a CKX polypeptide of the invention in a plant. Such increase in the level and/or activity of a CKX polypeptide of the invention can be achieved by providing to the plant a CKX polypeptide. The CKX polypeptide can be provided by introducing the amino acid sequence encoding the CKX polypeptide into the plant, introducing into the plant a nucleotide sequence encoding a CKX polypeptide, or by modifying a genomic locus encoding the CKX polypeptide of the invention.

As discussed elsewhere herein, many methods are known in the art for providing a polypeptide to a plant including, but not limited to, direct introduction of the polypeptide into the plant, and introducing into the plant (transiently or stably) a polynucleotide construct encoding a polypeptide having cytokinin oxidase activity. It is also recognized that the methods of the invention may employ a polynucleotide that is not capable of directing, in the transformed plant, the expression of a protein or an RNA. Thus, the level and/or activity of a CKX polypeptide may be increased by altering the gene encoding the CKX polypeptide or by altering or affecting its promoter. See, e.g., Kmiec, U.S. Pat. No. 5,565,350; Zarling, et al., PCT/US93/03868. Therefore mutagenized plants that carry mutations in CKX genes, where the mutations increase expression of the CKX gene or increase the cytokinin oxidase activity of the encoded CKX polypeptide, are provided.

B. Reducing the Activity and/or Level of a CKX Polypeptide

Methods are provided to reduce or eliminate the activity of a CKX polypeptide of the invention by transforming a plant cell with an expression cassette that expresses a polynucleotide that inhibits the expression of the CKX polypeptide. The polynucleotide may inhibit the expression of the CKX polypeptide directly, by preventing translation of the CKX messenger RNA, or indirectly, by encoding a polypeptide that inhibits the transcription or translation of a CKX gene encoding a CKX polypeptide. Methods for inhibiting or eliminating the expression of a gene in a plant are well known in the art, and any such method may be used in the present invention to inhibit the expression of a CKX polypeptide.

In accordance with the present invention, the expression of a CKX polypeptide is inhibited if the protein level of the CKX polypeptide is less than the protein level of the same CKX polypeptide in a plant or plant part that has not been genetically modified or mutagenized to inhibit the expression of that CKX polypeptide. In particular embodiments of the invention, the protein level of the CKX polypeptide in a modified plant or plant part according to the invention is less than 70%, less than 60%, less than 50%, less than 40%, less than 30%, less than 20%, less than 10%, less than 5% or less than 2% of the protein level of the same CKX polypeptide in a plant or plant part that is not a mutant or that has not been genetically modified to inhibit the expression of that CKX polypeptide. The expression level of the CKX polypeptide may be measured directly, for example, by assaying for the level of CKX polypeptide expressed in the plant cell or plant, or indirectly, for example, by measuring the cytokinin oxidase activity of the CKX polypeptide in the plant cell or plant, or by measuring the cytokinin level or activity in the plant or plant cell. Methods for performing such assays are described elsewhere herein.

In certain embodiments of the invention, the activity of the CKX polypeptides is reduced or eliminated by transforming a plant cell with an expression cassette comprising a polynucleotide encoding a polypeptide that inhibits the activity of a CKX polypeptide. The cytokinin oxidase activity of a CKX polypeptide is inhibited according to the present invention if the cytokinin oxidase activity of the CKX polypeptide is less than the cytokinin oxidase activity of the same CKX polypeptide in a plant that has not been modified to inhibit the cytokinin oxidase activity of that CKX polypeptide. In particular embodiments of the invention, the cytokinin oxidase activity of the CKX polypeptide in a modified plant according to the invention is less than 70%, less than 60%, less than 50%, less than 40%, less than 30%, less than 20%, less than 10% or less than 5% of the cytokinin oxidase activity of the same CKX polypeptide in a plant that that has not been modified to inhibit the expression of that CKX polypeptide. The cytokinin oxidase activity of a CKX polypeptide is "eliminated" according to the invention when it is not detectable by the assay methods described elsewhere herein. Methods of determining the cytokinin oxidase activity of a CKX polypeptide are described elsewhere herein.

In other embodiments, the activity of a CKX polypeptide may be reduced or eliminated by disrupting the gene encoding the CKX polypeptide. The invention encompasses mutagenized plants that carry mutations in CKX genes, where the mutations reduce expression of the CKX gene or inhibit the cytokinin oxidase activity of the encoded CKX polypeptide.

Thus, many methods may be used to reduce or eliminate the activity of a CKX polypeptide. In addition, more than one method may be used to reduce the activity of a single CKX polypeptide. Non-limiting examples of methods of reducing or eliminating the expression of a CKX polypeptides are given below.

1. Polynucleotide-Based Methods:

In some embodiments of the present invention, a plant is transformed with an expression cassette that is capable of expressing a polynucleotide that inhibits the expression of a CKX polypeptide of the invention. The term "expression" as used herein refers to the biosynthesis of a gene product, including the transcription and/or translation of said gene product. For example, for the purposes of the present invention, an expression cassette capable of expressing a polynucleotide that inhibits the expression of at least one CKX polypeptide is an expression cassette capable of producing an RNA molecule that inhibits the transcription and/or translation of at least one CKX polypeptide of the invention. The "expression" or "production" of a protein or polypeptide from a DNA molecule refers to the transcription and translation of the coding sequence to produce the protein or polypeptide, while the "expression" or "production" of a protein or polypeptide from an RNA molecule refers to the translation of the RNA coding sequence to produce the protein or polypeptide.

Examples of polynucleotides that inhibit the expression of a CKX polypeptide are given below.

i. Sense Suppression/Cosuppression

In some embodiments of the invention, inhibition of the expression of a CKX polypeptide may be obtained by sense suppression or cosuppression. For cosuppression, an expression cassette is designed to express an RNA molecule corresponding to all or part of a messenger RNA encoding a CKX polypeptide in the "sense" orientation. Overexpression of this RNA molecule can result in reduced expression of the native gene. Accordingly, multiple plant lines transformed with the cosuppression expression cassette are screened to identify those that show the greatest inhibition of CKX polypeptide expression.

The polynucleotide used for cosuppression may correspond to all or part of the sequence encoding the CKX polypeptide, all or part of the 5' and/or 3' untranslated region of a CKX polypeptide transcript, or all or part of both the coding sequence and the untranslated regions of a transcript encoding a CKX polypeptide. In some embodiments where the polynucleotide comprises all or part of the coding region for the CKX polypeptide, the expression cassette is designed to eliminate the start codon of the polynucleotide so that no protein product will be translated.

Cosuppression may be used to inhibit the expression of plant genes to produce plants having undetectable protein levels for the proteins encoded by these genes. See, for example, Broin, et al., (2002) *Plant Cell* 14:1417-1432. Cosuppression may also be used to inhibit the expression of multiple proteins in the same plant. See, for example, U.S. Pat. No. 5,942,657. Methods for using cosuppression to inhibit the expression of endogenous genes in plants are described in Flavell, et al., (1994) *Proc. Natl. Acad. Sci. USA* 91:3490-3496; Jorgensen, et al., (1996) *Plant Mol. Biol.* 31:957-973; Johansen and Carrington, (2001) *Plant Physiol.* 126:930-938; Broin, et al., (2002) *Plant Cell* 14:1417-1432; Stoutjesdijk, et al., (2002) *Plant Physiol.* 129:1723-1731; Yu, et al., (2003) *Phytochemistry* 63:753-763; and U.S. Pat. Nos. 5,034,323, 5,283,184 and 5,942,657, each of which is herein incorporated by reference. The efficiency of cosuppression may be increased by including a poly-dT region in the expression cassette at a position 3' to the sense sequence and 5' of the polyadenylation signal. See, US Patent Application Publication Number 2002/0048814, herein incorporated by reference. Typically, such a nucleotide sequence has substantial sequence identity to the sequence of the transcript of the endogenous gene, optimally greater than about 65% sequence identity, more optimally greater than about 85% sequence identity, most optimally greater than about 95% sequence identity. See, U.S. Pat. Nos. 5,283,184 and 5,034, 323, herein incorporated by reference.

ii. Antisense Suppression

In some embodiments of the invention, inhibition of the expression of the CKX polypeptide may be obtained by antisense suppression. For antisense suppression, the expression cassette is designed to express an RNA molecule complementary to all or part of a messenger RNA encoding the CKX polypeptide. Overexpression of the antisense RNA molecule can result in reduced expression of the native gene. Accordingly, multiple plant lines transformed with the antisense suppression expression cassette are screened to identify those that show the greatest inhibition of CKX polypeptide expression.

The polynucleotide for use in antisense suppression may correspond to all or part of the complement of the sequence encoding the CKX polypeptide, all or part of the complement of the 5' and/or 3' untranslated region of the CKX transcript, or all or part of the complement of both the coding sequence and the untranslated regions of a transcript encoding the CKX polypeptide. In addition, the antisense polynucleotide may be fully complementary (i.e., 100% identical to the complement of the target sequence) or partially complementary (i.e., less than 100% identical to the complement of the target sequence) to the target sequence. Antisense suppression may be used to inhibit the expression of multiple proteins in the same plant. See, for example, U.S. Pat. No. 5,942,657. Furthermore, portions of the antisense nucleotides may be used to disrupt the expression of the target gene. Generally, sequences of at least 50 nucleotides, 100 nucleotides, 200 nucleotides, 300, 400, 450, 500, 550 or greater may be used. Methods for using antisense suppression to inhibit the expression of endogenous genes in plants are described, for example, in Liu, et al., (2002) *Plant Physiol.* 129:1732-1743 and U.S. Pat. Nos. 5,759,829 and 5,942,657, each of which is herein incorporated by reference. Efficiency of antisense suppression may be increased by including a poly-dT region in the expression cassette at a position 3' to the antisense sequence and 5' of the polyadenylation signal. See, US Patent Application Publication Number 2002/0048814, herein incorporated by reference.

iii. Double-Stranded RNA Interference

In some embodiments of the invention, inhibition of the expression of a CKX polypeptide may be obtained by double-stranded RNA (dsRNA) interference. For dsRNA interference, a sense RNA molecule like that described above for cosuppression and an antisense RNA molecule that is fully or partially complementary to the sense RNA molecule are expressed in the same cell, resulting in inhibition of the expression of the corresponding endogenous messenger RNA.

Expression of the sense and antisense molecules can be accomplished by designing the expression cassette to comprise both a sense sequence and an antisense sequence. Alternatively, separate expression cassettes may be used for the sense and antisense sequences. Multiple plant lines transformed with the dsRNA interference expression cassette or expression cassettes are then screened to identify plant lines that show the greatest inhibition of CKX polypeptide expression. Methods for using dsRNA interference to inhibit the expression of endogenous plant genes are described in Waterhouse, et al., (1998) *Proc. Natl. Acad. Sci. USA* 95:13959-13964, Liu, et al., (2002) *Plant Physiol.* 129:1732-1743, and WO 99/49029, WO 99/53050, WO 99/61631 and WO 00/49035; each of which is herein incorporated by reference.

iv. Hairpin RNA Interference and Intron-Containing Hairpin RNA Interference

In some embodiments of the invention, inhibition of the expression of one or more CKX polypeptides may be obtained by hairpin RNA (hpRNA) interference or intron-containing hairpin RNA (ihpRNA) interference. These methods are highly efficient at inhibiting the expression of endogenous genes. See, Waterhouse and Helliwell, (2003) *Nat. Rev. Genet.* 4:29-38 and the references cited therein.

For hpRNA interference, the expression cassette is designed to express an RNA molecule that hybridizes with itself to form a hairpin structure that comprises a single-stranded loop region and a base-paired stem. The base-paired stem region comprises a sense sequence corresponding to all or part of the endogenous messenger RNA encoding the gene whose expression is to be inhibited, and an antisense sequence that is fully or partially complementary to the sense sequence. Thus, the base-paired stem region of the molecule generally determines the specificity of the RNA interference. Alternatively, the base-paired stem region may comprise complementary sequences corresponding to a selected promoter region, resulting in silencing of a coding sequence operably linked to said selected promoter. See, for example, Mette, et al., (2000) *EMBO J.* 19(19):5194-5201. hpRNA molecules are highly efficient at inhibiting the expression of endogenous genes, and the RNA interference they induce is inherited by subsequent generations of plants. See, for example, Chuang and Meyerowitz, (2000) *Proc. Natl. Acad. Sci. USA* 97:4985-4990; Stoutjesdijk, et al., (2002) *Plant Physiol.* 129:1723-1731 and Waterhouse and Helliwell, (2003) *Nat. Rev. Genet.* 4:29-38. Methods for using hpRNA interference to inhibit or silence the expression of genes are described, for example, in Chuang and Meyerowitz, (2000) *Proc. Natl. Acad. Sci. USA* 97:4985-4990; Stoutjesdijk, et al., (2002) *Plant Physiol.* 129:1723-1731; Waterhouse and Helliwell, (2003) *Nat. Rev. Genet.* 4:29-38; Pandolfini, et al., *BMC Biotechnology* 3:7, and US Patent Application Publication Number 2003/0175965; each of which is herein incorporated by reference. A transient assay for the efficiency of hpRNA constructs to silence gene expression in vivo has been described by Panstruga, et al., (2003) *Mol. Biol. Rep.* 30:135-140, herein incorporated by reference.

For ihpRNA, the interfering molecules have the same general structure as for hpRNA, but the RNA molecule additionally comprises an intron that is capable of being spliced in the cell in which the ihpRNA is expressed. The use of an intron minimizes the size of the loop in the hairpin RNA molecule following splicing, and this increases the efficiency of interference. See, for example, Smith, et al., (2000) *Nature* 407: 319-320. In fact, Smith, et al., show 100% suppression of endogenous gene expression using ihpRNA-mediated interference. Methods for using ihpRNA interference to inhibit the expression of endogenous plant genes are described, for example, in Smith, et al., (2000) *Nature* 407:319-320; Wesley, et al., (2001) *Plant J.* 27:581-590; Wang and Waterhouse, (2001) *Curr. Opin. Plant Biol.* 5:146-150; Waterhouse and Helliwell, (2003) *Nat. Rev. Genet.* 4:29-38; Helliwell and Waterhouse, (2003) *Methods* 30:289-295 and US Patent Application Publication Number 2003/0180945, each of which is herein incorporated by reference. See also, Cigan, et al., (2005) *Plant Journal* 43:929-940, demonstrating downregulation using a hairpin construct which targets the DNA regulating expression of a gene of interest.

The expression cassette for hpRNA interference may also be designed such that the sense sequence and the antisense sequence do not correspond to an endogenous RNA. In this embodiment, the sense and antisense sequence flank a loop sequence that comprises a nucleotide sequence corresponding to all or part of the endogenous messenger RNA of the target gene. Thus, it is the loop region that determines the specificity of the RNA interference. See, for example, WO 02/00904, herein incorporated by reference.

v. Amplicon-Mediated Interference

Amplicon expression cassettes comprise a plant virus-derived sequence that contains all or part of the target gene but generally not all of the genes of the native virus. The viral sequences present in the transcription product of the expression cassette allow the transcription product to direct its own replication. The transcripts produced by the amplicon may be either sense or antisense relative to the target sequence (i.e., the messenger RNA for the CKX polypeptide). Methods of using amplicons to inhibit the expression of endogenous plant genes are described, for example, in Angell and Baulcombe, (1997) *EMBO J.* 16:3675-3684, Angell and Baulcombe, (1999) *Plant J.* 20:357-362 and U.S. Pat. No. 6,646,805, each of which is herein incorporated by reference.

vi. Ribozymes

In some embodiments, the polynucleotide expressed by the expression cassette of the invention is catalytic RNA or has ribozyme activity specific for the messenger RNA of the CKX polypeptide. Thus, the polynucleotide causes the degradation of the endogenous messenger RNA, resulting in reduced expression of the CKX polypeptide. This method is described, for example, in U.S. Pat. No. 4,987,071, herein incorporated by reference.

vii. Small Interfering RNA or Micro RNA

In some embodiments of the invention, inhibition of the expression of a CKX polypeptide may be obtained by RNA interference by expression of a gene encoding a micro RNA (miRNA). miRNAs are regulatory agents consisting of about 22 ribonucleotides. miRNA are highly efficient at inhibiting the expression of endogenous genes. See, for example, Javier, et al., (2003) *Nature* 425:257-263, herein incorporated by reference.

For miRNA interference, the expression cassette is designed to express an RNA molecule that is modeled on an endogenous miRNA gene. The miRNA gene encodes an RNA that forms a hairpin structure containing a 22-nucleotide sequence that is complementary to another endogenous gene (target sequence). For suppression of CKX expression, the 22-nucleotide sequence is selected from a CKX transcript sequence and contains 22 nucleotides of said CKX sequence in sense orientation and 21 nucleotides of a corresponding antisense sequence that is complementary to the sense sequence. miRNA molecules are highly efficient at inhibiting the expression of endogenous genes, and the RNA interference they induce is inherited by subsequent generations of plants.

2. Polypeptide-Based Inhibition of Gene Expression

In one embodiment, the polynucleotide encodes a zinc finger protein that binds to a gene encoding a CKX polypeptide, resulting in reduced expression of the gene. In particular embodiments, the zinc finger protein binds to a regulatory region of a CKX gene. In other embodiments, the zinc finger protein binds to a messenger RNA encoding a CKX polypeptide and prevents its translation. Methods of selecting sites for targeting by zinc finger proteins have been described, for example, in U.S. Pat. No. 6,453,242, and methods for using zinc finger proteins to inhibit the expression of genes in plants are described, for example, in US Patent Application Publication Number 2003/0037355; each of which is herein incorporated by reference.

3. Polypeptide-Based Inhibition of Protein Activity

In some embodiments of the invention, the polynucleotide encodes an antibody that binds to at least one CKX polypeptide, and reduces the cytokinin oxidase activity of the CKX polypeptide. In another embodiment, the binding of the antibody results in increased turnover of the antibody-CKX complex by cellular quality control mechanisms. The expression of antibodies in plant cells and the inhibition of molecular pathways by expression and binding of antibodies to proteins in plant cells are well known in the art. See, for example, Conrad and Sonnewald, (2003) *Nature Biotech.* 21:35-36, incorporated herein by reference.

4. Gene Disruption

In some embodiments of the present invention, the activity of a CKX polypeptide is reduced or eliminated by disrupting the gene encoding the CKX polypeptide. The gene encoding the CKX polypeptide may be disrupted by any method known in the art. For example, in one embodiment, the gene is disrupted by transposon tagging. In another embodiment, the gene is disrupted by mutagenizing plants using random or targeted mutagenesis, and selecting for plants that have reduced cytokinin oxidase activity.

i. Transposon Tagging

In one embodiment of the invention, transposon tagging is used to reduce or eliminate the CKX activity of one or more CKX polypeptides. Transposon tagging comprises inserting a transposon within an endogenous CKX gene to reduce or eliminate expression of the CKX polypeptide. "CKX gene" is intended to mean the gene that encodes a CKX polypeptide according to the invention.

In this embodiment, the expression of one or more CKX polypeptide is reduced or eliminated by inserting a transposon within a regulatory region or coding region of the gene encoding the CKX polypeptide. A transposon that is within an exon, intron, 5' or 3' untranslated sequence, a promoter, or any other regulatory sequence of a CKX gene may be used to reduce or eliminate the expression and/or activity of the encoded CKX polypeptide.

Methods for the transposon tagging of specific genes in plants are well known in the art. See, for example, Maes, et al., (1999) *Trends Plant Sci.* 4:90-96; Dharmapuri and Sonti, (1999) *FEMS Microbiol. Lett.* 179:53-59; Meissner, et al., (2000) *Plant J.* 22:265-274; Phogat, et al., (2000) *J. Biosci.* 25:57-63; Walbot, (2000) *Curr. Opin. Plant Biol.* 2:103-107; Gai, et al., (2000) *Nucleic Acids Res.* 28:94-96; Fitzmaurice, et al., (1999) *Genetics* 153:1919-1928). In addition, the TUSC process for selecting Mu insertions in selected genes has been described in Bensen, et al., (1995) *Plant Cell* 7:75-84; Mena, et al., (1996) *Science* 274:1537-1540 and U.S. Pat. No. 5,962,764; each of which is herein incorporated by reference.

ii. Mutant Plants with Reduced Activity

Additional methods for decreasing or eliminating the expression of endogenous genes in plants are also known in the art and can be similarly applied to the instant invention. These methods include other forms of mutagenesis, such as ethyl methanesulfonate-induced mutagenesis, deletion mutagenesis, and fast neutron deletion mutagenesis used in a reverse genetics sense (with PCR) to identify plant lines in which the endogenous gene has been deleted. For examples of these methods see, Ohshima, et al., (1998) *Virology* 243: 472-481; Okubara, et al., (1994) *Genetics* 137:867-874; and Quesada, et al., (2000) *Genetics* 154:421-436; each of which is herein incorporated by reference. In addition, a fast and automatable method for screening for chemically induced mutations, TILLING (Targeting Induced Local Lesions In Genomes), using denaturing HPLC or selective endonuclease digestion of selected PCR products is also applicable to the instant invention. See, McCallum, et al., (2000) *Nat. Biotechnol.* 18:455-457, herein incorporated by reference.

Mutations that impact gene expression or that interfere with the function (cytokinin oxidase activity) of the encoded protein are well known in the art. Insertional mutations in gene exons usually result in null-mutants. Mutations in conserved residues are particularly effective in inhibiting the cytokinin oxidase activity of the encoded protein. Conserved residues of plant CKX polypeptides suitable for mutagenesis with the goal to eliminate cytokinin oxidase activity have been described. See, for example, FIGS. 4, 9 and 10, and Example 3. Such mutants can be isolated according to well-known procedures, and mutations in different CKX loci can be stacked, for example by genetic crossing. See, for example, Gruis, et al., (2002) *Plant Cell* 14:2863-2882.

In another embodiment of this invention, dominant mutants can be used to trigger RNA silencing due to gene inversion and recombination of a duplicated gene locus. See, for example, Kusaba, et al., (2003) *Plant Cell* 15:1455-1467.

The invention encompasses additional methods for reducing or eliminating the activity of one or more CKX polypeptides. Examples of other methods for altering or mutating a genomic nucleotide sequence in a plant are known in the art and include, but are not limited to, the use of RNA:DNA vectors, RNA:DNA mutational vectors, RNA:DNA repair vectors, mixed-duplex oligonucleotides, self-complementary RNA:DNA oligonucleotides, and recombinogenic oligonucleobases. Such vectors and methods of use are known in the art. See, for example, U.S. Pat. Nos. 5,565,350; 5,731, 181; 5,756,325; 5,760,012; 5,795,972 and 5,871,984; each of which are herein incorporated by reference. See also, WO 98/49350, WO 99/07865, WO 99/25821 and Beetham, et al., (1999) *Proc. Natl. Acad. Sci. USA* 96:8774-8778; each of which is herein incorporated by reference.

iii. Modulating Cytokinin Level/Activity

As used herein a "cytokinin" refers to a class of plant-specific hormones that play a central role during the cell cycle and influence numerous developmental programs. Cytokinins comprise an $N^6$-substituted purine derivative. Representative cytokinins include isopentenyladenine ($N^6$-($\Delta^2$-isopentenyl)adenine (hereinafter, iP), zeatin (6-(4-hydroxy-3methylbut-trans-2-enylamino) purine) (hereinafter, Z), and dihydrozeatin (DZ). The free bases and their ribosides (iPR, ZR, and DZR) are believed to be the active compounds. Additional cytokinins are known. See, for example, U.S. Pat. No. 5,211,738.

"Modulating the level and/or activity of cytokinin" includes any decrease or increase in cytokinin level and/or activity in the plant. For example, modulating the level and/or activity can comprise either an increase or a decrease in overall cytokinin content of about 0.1%, 0.5%, 1%, 3% 5%, 10%, 15%, 20%, 25%, 30%, 35%, 40%, 45%, 50%, 55%, 60%, 65%, 70%, 75%, 80%, 85%, 90%, 95% or greater when compared to a control plant or plant part. Alternatively, the modulated level and/or activity of the cytokinin can include about a 0.5 fold, 1 fold, 2 fold, 4 fold, 8 fold, 16 fold or 32 fold increase or decrease in cytokinin level/activity in the plant or a plant part when compared to a control plant or plant part.

It is further recognized that the modulation of the cytokinin level/activity need not be an overall increase/decrease in cytokinin level and/or activity, but also includes a change in tissue distribution of the cytokinin. For example, CKX polypeptides may influence the amount of cytokinin imported into specific tissues or exported from a cytokinin producing tissue. For example, import of cytokinin in sink tissues may involve an apoplastic transport step, where CKX polypeptides control the level of physiologically active cytokinins. See, for example, Jones, et al., (1997) *Plant Growth Regul* 23:123-134, Turner, et al., (1985) *Plant Physiol* 79:321-322, and Mok, et al., (2001) *Annu Rev Plant Physiol Plant Mol Biol* 52:89-118, each of which are herein incorporated by reference.

Moreover, the modulation of the cytokinin level/activity need not be an overall increase/decrease in cytokinins, but also includes a change in the ratio of various cytokinin derivatives. For example, the ratio of various cytokinin derivatives such as isopentenyladenine-type, zeatin-type, or dihydrozeatin-type cytokinins, and the like, could be altered and thereby modulate the level/activity of the cytokinin of the plant or plant part when compared to a control plant.

Methods for assaying for a modulation in cytokinin level and/or activity are known in the art. For example, representative methods for cytokinin extraction, immunopurification, HPLC separation, and quantification by ELISA methods can be found in Faiss, et al., (1997) *Plant J.* 12:401-415. See also, Werner, et al., (2001) *PNAS* 98:10487-10492) and Dewitte, et al., (1999) *Plant Physiol.* 119:111-121. Each of these references is herein incorporated by reference.

In specific methods, the level and/or activity of a cytokinin in a plant is decreased by increasing the level or activity of the CKX polypeptide in the plant. Methods for increasing the level and/or activity of CKX polypeptides in a plant are discussed elsewhere herein. Briefly, such methods comprise providing a CKX polypeptide of the invention to a plant and thereby increasing the level and/or activity of the CKX polypeptide. In other embodiments, a CKX nucleotide sequence encoding a CKX polypeptide can be provided by introducing into the plant a polynucleotide comprising a CKX nucleotide sequence of the invention, expressing the CKX sequence, increasing the activity of the CKX polypeptide, and thereby decreasing the level and/or activity of a cytokinin in the plant or plant part. In certain embodiments, the CKX nucleotide construct introduced into the plant is stably incorporated into the genome of the plant.

In other methods, the level and/or activity of a cytokinin in a plant is increased by decreasing the level and/or activity of the CKX polypeptide in the plant. Such methods are disclosed in detail elsewhere herein. In one such method, a CKX nucleotide sequence is introduced into the plant and expression of said CKX nucleotide sequence decreases the activity of the CKX polypeptide, and thereby increasing the level and/or activity of a cytokinin in the plant or plant part. In certain embodiments, the CKX nucleotide construct introduced into the plant is stably incorporated into the genome of the plant.

As discussed above, one of skill will recognize the appropriate promoter to use to modulate the level/activity of a cytokinin in the plant. Exemplary promoters for this embodiment have been disclosed elsewhere herein.

Accordingly, the present invention further provides plants having a modulated level/activity of a cytokinin when compared to the cytokinin level/activity of a control plant. In one embodiment, the plant of the invention has an increased level/activity of the CKX polypeptide of the invention and thus has a decreased level/activity of cytokinin. In other embodiments, the plant of the invention has a reduced or eliminated level of the CKX polypeptide of the invention and thus has an increased level/activity of a cytokinin. In certain embodiments, such plants have stably incorporated into their genome a nucleic acid molecule comprising a CKX nucleotide sequence of the invention operably linked to a promoter that drives expression in the plant cell.

iv. Modulating Root Development

Methods for modulating root development in a plant are provided. By "modulating root development" is intended any alteration in the development of the plant root when compared to a control plant. Such alterations in root development include, but are not limited to, alterations in the growth rate of the primary root, the fresh root weight, the extent of lateral and adventitious root formation, the vasculature system, meristem development, or radial expansion.

Methods for modulating root development in a plant are provided. The methods comprise modulating the level and/or activity of the CKX polypeptide in the plant. In one method, a CKX sequence of the invention is provided to the plant. In another method, the CKX nucleotide sequence is provided by introducing into the plant a polynucleotide comprising a CKX nucleotide sequence of the invention, expressing the CKX sequence, and thereby modifying root development. In still other methods, the CKX nucleotide construct introduced into the plant is stably incorporated into the genome of the plant.

In other methods, root development is modulated by increasing the level or activity of the CKX polypeptide in the plant. An increase in CKX activity can result in one or more alterations to root development, including, but not limited to, larger root meristems, increased root growth, enhanced radial expansion, an enhanced vasculature system, increased root branching, more adventitious roots, and/or an increase in fresh root weight when compared to a control plant.

As used herein, "root growth" encompasses all aspects of growth of the different parts that make up the root system at different stages of its development in both monocotyledonous and dicotyledonous plants. It is to be understood that enhanced root growth can result from enhanced growth of one or more of its parts including the primary root, lateral roots, adventitious roots, etc.

Methods of measuring such developmental alterations in the root system are known in the art. See, for example, US Patent Application Publication Number 2003/0074698 and Werner, et al., (2001) *PNAS* 18:10487-10492, both of which are herein incorporated by reference.

As discussed above, one of skill will recognize the appropriate promoter to use to modulate root development in the plant. Exemplary promoters for this embodiment include constitutive promoters and root-preferred promoters. Exemplary root-preferred promoters have been disclosed elsewhere herein.

Stimulating root growth and increasing root mass by increasing the activity and/or level of the CKX polypeptide also finds use in improving the standability of a plant. The term "resistance to lodging" or "standability" refers to the ability of a plant to fix itself to the soil. For plants with an erect or semi-erect growth habit, this term also refers to the ability to maintain an upright position under adverse conditions, such as adverse environments. This trait relates to the size, depth and morphology of the root system. In addition, stimulating root growth and increasing root mass by increasing the level and/or activity of the CKX polypeptide also finds use in promoting in vitro propagation of explants.

Furthermore, higher root biomass production due to an increased level and/or activity of CKX has a direct effect on the yield and an indirect effect on production of compounds produced by root cells or transgenic root cells or cell cultures of said transgenic root cells. One example of an interesting compound produced in root cultures is shikonin, the yield of which can be advantageously enhanced by said methods.

Higher root biomass production resulting from an increased level and/or activity of CKX may also impact the plant's assimilation of water and/or nutrients, favorably impacting yield of vegetative and/or reproductive tissues, including seed. Further, improved root structure may result in increased tolerance to drought, or improved nitrogen use efficiency, or improved disease resistance, or improved insect resistance, particularly when combined with an insecticidal trait. Such characteristics may be apparent at various points throughout the plant life cycle, affecting, for example, flowering, early seed development, and/or senescence. Modified plants may be more productive with current fertilizer application rates, or may maintain their productivity even under significantly reduced fertilizer input or on less fertile soils. Increased nitrogen use efficiency can result from enhanced uptake and assimilation of nitrogen fertilizer and/or the subsequent remobilization and reutilization of accumulated nitrogen reserves, enhancing yield. Improving nitrogen use efficiency in maize would increase corn harvestable yield per unit of input nitrogen, both in developing nations where access to nitrogen fertilizer is limited and in developed nations where the level of nitrogen use is high. Nitrogen utilization improvement also allows decreases in on-farm input costs, reduces dependence on non-renewable energy sources required for synthetic nitrogen fertilizer production, and decreases the environmental impact of nitrogen fertilizer manufacturing and its agricultural use.

Evaluation for improved nitrogen use efficiency may include testing in field plots where yield is limited by reducing fertilizer application by 30% or more. Improvement in nitrogen utilization resulting from expression of transgenic events is measured by assessing yield, yield components, or other agronomic traits of transgenic plants compared to non-transgenic plants in these reduced-nitrogen-fertility plots. Similar comparisons are made in plots supplemented with recommended nitrogen fertility rates. Effective transgenic events may achieve similar yields in the nitrogen-limited and normal-nitrogen environments.

Accordingly, the present invention further provides plants having modulated root development when compared to the root development of a control plant. In some embodiments, the plant of the invention has an increased level/activity of the CKX polypeptide of the invention and has enhanced root growth and/or root biomass. In certain embodiments, such plants have stably incorporated into their genome a nucleic acid molecule comprising a CKX nucleotide sequence of the invention operably linked to a promoter that drives expression in the plant cell. The CKX sequence may be preferentially expressed in cells of root tissues.

v. Modulating Shoot and Leaf Development

Methods are also provided for modulating shoot and leaf development in a plant. By "modulating shoot and/or leaf development" is intended any alteration in the development of the plant shoot and/or leaf. Such alterations in shoot and/or leaf development include, but are not limited to, alterations in shoot meristem development, in leaf number, leaf size, leaf and stem vasculature, internode length, and leaf senescence. As used herein, "leaf development" and "shoot development" encompasses all aspects of growth of the different parts that make up the leaf system and the shoot system, respectively, at different stages of their development, both in monocotyledonous and dicotyledonous plants. Methods for measuring such developmental alterations in the shoot and leaf system are known in the art. See, for example, Werner, et al., (2001) *PNAS* 98:10487-10492 and US Patent Application Publication Number 2003/0074698, each of which is herein incorporated by reference.

The method for modulating shoot and/or leaf development in a plant comprises modulating the activity and/or level of a CKX polypeptide of the invention. In one embodiment, a CKX polypeptide sequence of the invention is provided. In other embodiments, the CKX nucleotide sequence can be provided by introducing into the plant a polynucleotide comprising a CKX nucleotide sequence of the invention, expressing the CKX sequence, and thereby modifying shoot and/or leaf development. In certain embodiments, the CKX nucleotide construct introduced into the plant is stably incorporated into the genome of the plant.

In specific embodiments, shoot or leaf development is modulated by increasing the level and/or activity of the CKX polypeptide in the plant. An increase in CKX activity can result in one or more alterations in shoot and/or leaf development, including, but not limited to, smaller apical meristems, reduced leaf number, reduced leaf surface, reduced vasculature, shorter internodes and stunted growth, and retarded leaf senescence, when compared to a control plant. Thus, the methods of the invention may find use in producing dwarf plants.

In certain embodiments, the level and/or activity of the CKX polypeptide in the plant is decreased to result in higher cytokinin levels. As discussed elsewhere herein, targeted reduction in CKX polypeptide level and/or activity may result in one or more of modulated floral development, modulated flowering time, increased seed size and/or increased seed weight, increased plant yield and/or plant vigor, improved or maintained stress tolerance, altered root/shoot ratio, or an increase in shoot growth, when compared to a control plant.

As discussed above, one of skill will recognize the appropriate promoter to use to modulate shoot and leaf development of the plant. Exemplary promoters for this embodiment include constitutive promoters, shoot-preferred promoters, shoot meristem-preferred promoters, and leaf-preferred promoters. Exemplary promoters have been disclosed elsewhere herein.

Accordingly, the present invention further provides plants having modulated shoot and/or leaf development when compared to a control plant. In some embodiments, the plant of the invention has an increased level/activity of the CKX polypeptide of the invention. In other embodiments, the plant of the invention has a decreased level/activity of the CKX polypeptide of the invention.

vi. Modulating Reproductive Tissue Development

Methods for modulating reproductive tissue development are provided. In one embodiment, methods are provided to modulate floral development in a plant. By "modulating floral development" is intended any alteration in a structure of a plant's reproductive tissue as compared to a control plant in which the activity or level of the CKX polypeptide has not been modulated. "Modulating floral development" further includes any alteration in the timing of the development of a plant's reproductive tissue (i.e., a delayed or a accelerated timing of floral development) when compared to a control plant in which the activity or level of the CKX polypeptide has not been modulated. Macroscopic alterations may include changes in size, shape, number, or location of reproductive organs, the developmental time period over which these structures form, and/or the ability to maintain or proceed through the flowering process in times of environmental stress. Microscopic alterations may include changes to the types or shapes of cells that make up the reproductive organs.

The method for modulating floral development in a plant comprises modulating CKX activity in a plant. In one method, a CKX sequence of the invention is provided. A CKX nucleotide sequence can be provided by introducing into the plant a polynucleotide comprising a CKX nucleotide sequence of the invention, expressing the CKX sequence, and thereby modifying floral development. In certain embodiments, the CKX nucleotide construct introduced into the plant is stably incorporated into the genome of the plant.

In specific methods, floral development is modulated by increasing the level or activity of the CKX polypeptide in the plant. An increase in CKX activity can result in one or more alterations in floral development, including, but not limited to, retarded flowering, reduced number of flowers, partial male sterility, and reduced seed set, when compared to a control plant. Inducing delayed flowering or inhibiting flowering can be used to enhance yield in forage crops such as alfalfa. Methods for measuring such developmental alterations in floral development are known in the art. See, for example, Mouradov, et al., (2002) *The Plant Cell* S11-S130, herein incorporated by reference.

As discussed above, one of skill will recognize the appropriate promoter to use to modulate floral development of the plant. Exemplary promoters for this embodiment include constitutive promoters, inducible promoters, shoot-preferred promoters, and inflorescence-preferred promoters.

In other methods, floral development is modulated by decreasing the level and/or activity of the CKX sequence of the invention. Such methods can comprise introducing a CKX nucleotide sequence into the plant and decreasing the activity of the CKX polypeptide. In other methods, the CKX nucleotide construct introduced into the plant is stably incorporated into the genome of the plant. Decreasing expression of the CKX sequence of the invention can modulate floral development during periods of stress. Such methods are described elsewhere herein.

Accordingly, the present invention further provides plants having modulated floral development when compared to the floral development of a control plant. Compositions include plants having an increased level/activity of the CKX polypeptide of the invention and having an altered floral development. Compositions also include plants having a decreased level/activity of the CKX polypeptide of the invention wherein the plant maintains or proceeds through the flowering process in times of stress.

Methods are also provided for the use of the CKX sequences of the invention to increase seed size and/or weight. The method comprises decreasing the activity of the CKX sequences in a plant or plant part, such as the seed, by means of downregulation techniques described elsewhere herein. An increase in seed size and/or weight comprises an increased size or weight of the seed and/or an increase in the size or weight of one or more seed parts including, for example, the embryo, endosperm, seed coat, aleurone, and/or cotyledon.

As discussed above, one of skill will recognize an appropriate promoter to use to increase seed size and/or seed weight. Exemplary promoters of this embodiment include constitutive promoters, inducible promoters, seed-preferred promoters, embryo-preferred promoters, endosperm-preferred promoters, and promoters active in female reproductive tissues immediately pre- and post-pollination.

It is further recognized that increasing seed size and/or weight can also be accompanied by an increase in the speed of growth of seedlings or an increase in early vigor. As used herein, the term "early vigor" refers to the ability of a plant to grow rapidly during early development, and relates to the successful establishment, after germination, of a well-developed root system and a well-developed photosynthetic apparatus. In addition, an increase in seed size and/or weight can result in an increase in plant yield when compared to a control.

Accordingly, the present invention further provides plants having an increased seed weight and/or seed size when compared to a control plant. In other embodiments, plants having an increased vigor and plant yield are also provided. In some embodiments, the plant of the invention has a decreased level/activity of the CKX polypeptide of the invention and has an increased seed weight and/or seed size. In certain embodiments, such plants have stably incorporated into their genome a nucleic acid molecule comprising a CKX nucleotide sequence of the invention operably linked to a promoter that drives expression in the plant cell.

vii. Modulating the Stress Tolerance of a Plant

Methods are provided for the use of the CKX sequences of the invention to modify the tolerance of a plant to abiotic stress. Increases in the growth of seedlings or early vigor are often associated with increase in stress tolerance. For example, faster development of seedlings, including the root system of seedlings upon germination, is critical for survival, particularly under adverse conditions such as drought or low temperatures. Promoters that can be used in this method are described elsewhere herein and include constitutive, root-preferred, or stress-induced promoters. Accordingly, in one method of the invention, a plant's tolerance to stress is increased or maintained when compared to a control plant by decreasing the level of CKX activity in one or more parts of the plant. In other methods, a CKX nucleotide sequence is provided by introducing into the plant a polynucleotide comprising a CKX nucleotide sequence of the invention, expressing the CKX sequence, and thereby increasing the plant's tolerance to stress. In certain embodiments, the CKX nucleotide construct introduced into the plant is stably incorporated into the genome of the plant.

Methods are also provided to increase or maintain seed set during abiotic stress episodes. During periods of stress (i.e., drought, salt, heavy metals, temperature extremes, etc.) embryo development is often aborted. In maize, halted embryo development results in aborted kernels on the ear. Preventing this kernel loss will maintain yield. Accordingly, methods are provided to increase the stress resistance in a plant (for example, by targeted downregulation of cytokinin oxidase in an early developing embryo or endosperm). Decreasing expression of the CKX sequence of the invention in appropriate tissues can also modulate floral development during periods of stress, and thus methods are provided to maintain or improve the flowering process in plants under stress. The method comprises decreasing the level and/or activity of the CKX sequence of the invention by means of downregulation techniques described elsewhere herein.

Significant yield instability can occur as a result of unfavorable environments, especially during the lag phase of seed development. During this period, seeds undergo dramatic changes in ultra structure, biochemistry, and sensitivity to environmental perturbation, yet demonstrate little change in dry mass accumulation. Two important events that occur during the lag phase are initiation and division of endosperm cells and amyloplasts (which are the sites for starch deposition). It has been demonstrated that during the lag phase (in maize, from pollination to about 10 to 12 days after pollination (DAP)), a dramatic increase in cytokinin concentration immediately precedes maximum rates of endosperm cell division and amyloplast formation, indicating that this hormone plays a central role in these processes and in what is called the 'sink strength' of the developing seed. Cytokinins have been demonstrated to play an important role in establishing seed size, decreasing tip kernel abortion, and increasing seed set during unfavorable environmental conditions. See, for example, Brugière, et al., (2003) *Plant Physiology* 132:1228-1240; Setter, et al., (2001) *Crop Sci.* 41:1530-1540.

Methods are therefore provided to decrease activity and/or level of CKX polypeptides in the developing female inflorescence, thereby elevating cytokinin levels and allowing developing seed to achieve their full genetic potential for size, minimizing tip kernel abortion, and buffering seed set during unfavorable environments. The methods further allow the plant to maintain and/or improve the flowering process during unfavorable environments.

In this embodiment, a variety of promoters could be used to direct the expression of a sequence capable of decreasing the level and/or activity of the CKX polypeptide. In one method, a stress insensitive/lag phase/developing kernel-preferred promoter is used. By "insensitive to stress" is intended that the expression level of a sequence operably linked to the promoter is not altered or only minimally altered under stress conditions. Such promoters are known in the art and include Zag2.1 (Schmidt, et al., (1993) *Plant Cell* 5:729-737, Genbank Accession Number X80206). Also useful are ZmCkx1-2 promoter (U.S. Pat. Nos. 6,921,815 and 7,371,925 and U.S. patent application Ser. No. 12/051,893), ZmCkx2 promoter (SEQ ID NO: 13), ZmCkx3 promoter (SEQ ID NO: 14), ZmCkx4 promoter (SEQ ID NO: 15), ZmCkx5 promoter (SEQ ID NO: 16), ZmCkx6 promoter (SEQ ID NO: 69), ZmCkx7 promoter (SEQ ID NO: 70), ZmCkx8 promoter (SEQ ID NO: 63) any other CKX promoter, and mzE40 (Zm40) (U.S. Pat. No. 6,403,862 and WO01/2178). Alternatively, a stress-responsive promoter may be used, such as rd29a (Yamaguchi-Shinozaki, et al., (1993) *Mol. Gen. Genetics* 236:331-334). Also of interest are promoters directing expression preferentially within seed tissues such as the endosperm or the basal endosperm transfer layer, as listed elsewhere herein. Methods to assay for an increase in seed set during abiotic stress are known in the art. For example, plants having the reduced CKX activity can be monitored under various stress conditions and compared to control plants. For instance, the plant having the reduced CKX activity can be subjected to various degrees of stress during flowering and seed set. Under identical conditions, the genetically modified plant having the reduced CKX activity will have a higher number of developing kernels than will a wild type (non-transformed) plant.

Accordingly, the present invention further provides plants having increased yield or maintained yield and/or an increased or maintained flowering process during periods of abiotic stress (e.g., drought, salt, heavy metals, temperature extremes, etc.). In some embodiments, the plants having an increased or maintained yield during abiotic stress have a decreased level/activity of the CKX polypeptide of the invention. In other embodiments, the plant comprises a CKX nucleotide sequence of the invention operably linked to a promoter that drives expression in the plant cell. In certain embodiments, such plants have stably incorporated into their genome a nucleic acid molecule comprising a CKX nucleotide sequence of the invention operably linked to a promoter that drives expression in the plant cell.

viii. Modulating Pathogen Resistance

Methods for modulating pathogen resistance in a plant are provided. Plant pathogens can produce cytokinins (Mills, et al., (1978) *Physiol Plant Pathol* 13:73-80 and Angra, et al., (1990) *Mycopathologia* 109:177-182). Accordingly, increasing CKX activity in a plant or plant part can increase the plant's resistance to the pathogen. See, for example, Bilyeu, et al., (2001) *Plant Physiol.* 125:378-386. Thus, compositions and methods for inducing resistance in a plant to plant pests are provided. In specific embodiments, the CKX polypeptide is provided to the developing seed and thereby increases the pathogen resistance of the seed. Accordingly, the compositions and methods are also useful in protecting plants against fungal pathogens, viruses, nematodes, insects and the like.

By "disease resistance" is intended that the plants avoid the disease symptoms that are the outcome of plant-pathogen interactions. That is, pathogens are prevented from causing plant diseases and the associated disease symptoms, or alternatively, the disease symptoms caused by the pathogen are minimized or lessened. By "antipathogenic compositions" is intended that the compositions of the invention have antipathogenic activity and thus are capable of suppressing, controlling, and/or killing the invading pathogenic organism. An antipathogenic composition of the invention will reduce the disease symptoms resulting from pathogen challenge by at least about 2% to about 6%, at least about 5% to about 50%, at least about 10% to about 60%, at least about 30% to about 70%, at least about 40% to about 80% or at least about 50% to about 90% or greater. Hence, the methods of the invention can be utilized to protect plants from disease, particularly those diseases that are caused by plant pathogens.

The method for increasing pathogen resistance in a plant comprises increasing the level or activity of the CKX polypeptides of the invention. In specific methods, a CKX sequence of the invention is provided. A CKX nucleotide sequence can be provided by introducing into the plant a polynucleotide comprising a CKX nucleotide sequence of the invention, expressing the CKX sequence, and thereby increasing pathogen resistance in the plant. In certain embodiments, the CKX nucleotide construct introduced into the plant is stably incorporated into the genome of the plant.

As discussed above, one of skill will recognize the appropriate promoter to use to increase pathogen resistance in the plant. Exemplary promoters for this embodiment include constitutive promoters, tissue-preferred promoters, pathogen-inducible promoters, and seed-preferred promoters.

Assays that measure antipathogenic activity are commonly known in the art, as are methods to quantitate disease resistance in plants following pathogen infection. See, for example, U.S. Pat. No. 5,614,395, herein incorporated by reference. Such techniques include measuring over time the average lesion diameter, the pathogen biomass, and the overall percentage of decayed plant tissues. For example, a plant either expressing an antipathogenic polypeptide or having an antipathogenic composition applied to its surface shows a decrease in tissue necrosis (i.e., lesion diameter) or a decrease in plant death following pathogen challenge when compared to a control plant that was not exposed to the antipathogenic polypeptide or composition. Alternatively, antipathogenic activity can be measured by a decrease in pathogen biomass. For example, a plant expressing an antipathogenic polypeptide or exposed to an antipathogenic composition is challenged with a pathogen of interest. Over time, tissue samples from the pathogen-inoculated tissues are obtained and RNA is extracted. The percent of a specific pathogen RNA transcript relative to the level of a plant specific transcript allows the level of pathogen biomass to be determined. See, for example, Thomma, et al., (1998) *Plant Biology* 95:15107-15111, herein incorporated by reference.

Pathogens of the invention include, but are not limited to, viruses or viroids, bacteria, insects, nematodes, fungi, and the like. Viruses include any plant virus, for example, tobacco or cucumber mosaic virus, ringspot virus, necrosis virus, or maize dwarf mosaic virus.

ix. Method of Use for CKX Promoter Polynucleotides

The polynucleotides comprising the CKX promoters disclosed in the present invention, as well as variants and fragments thereof, are useful in the genetic manipulation of any host cell, preferably plant cell, when assembled with a DNA construct such that the promoter sequence is operably linked to a nucleotide sequence comprising a polynucleotide of interest. In this manner, the CKX promoter polynucleotides of the invention are provided in expression cassettes along with a polynucleotide sequence of interest for expression in the host cell of interest. As discussed in Example 2 below, the CKX promoter sequences of the invention drive native expression in a variety of tissues and thus the promoter sequences can find use in regulating temporal and/or spatial expression of polynucleotides of interest.

Synthetic hybrid promoter regions are known in the art. Such regions comprise upstream promoter elements of one polynucleotide operably linked to the promoter element of another polynucleotide. In an embodiment of the invention, heterologous sequence expression is controlled by a synthetic hybrid promoter comprising a CKX promoter sequence of the invention, or a variant or fragment thereof, operably linked to upstream promoter element(s) from a heterologous promoter. Upstream promoter elements that are involved in the plant defense system have been identified and may be used to generate a synthetic promoter. See, for example, Rushton, et al., (1998) *Curr. Opin. Plant Biol.* 1:311-315. Alternatively, a synthetic CKX promoter sequence may comprise duplications of the upstream promoter elements found within the CKX promoter sequences.

It is recognized that a promoter sequence of the invention may be used with its native CKX coding sequence. A DNA construct comprising a CKX promoter operably linked with its native CKX gene may be used to transform any plant of interest to bring about a desired phenotypic change, such as modulating cytokinin levels, modulating root, shoot, leaf, floral, and embryo development, stress tolerance and any other phenotype described elsewhere herein.

The promoter nucleotide sequences and methods disclosed herein are useful in regulating expression of any nucleotide sequence in a host plant in order to vary the phenotype of a plant. Various changes in phenotype are of interest including modifying the fatty acid composition in a plant, altering the amino acid content of a plant, altering a plant's pathogen defense mechanism, and the like. These results can be achieved by providing expression of heterologous products or increased expression of endogenous products in plants. Alternatively, the results can be achieved by providing for a reduction of expression of one or more endogenous products, particularly enzymes or cofactors in the plant. These changes result in a change in phenotype of the transformed plant.

Genes of interest are reflective of the commercial markets and interests of those involved in the development of the crop. Crops and markets of interest change, and as developing nations open up world markets, new crops and technologies will emerge also. In addition, as our understanding of agronomic traits and characteristics such as yield and heterosis increases, the choice of genes for transformation will change accordingly. General categories of genes of interest include, for example, those genes involved in information, such as zinc fingers, those involved in communication, such as kinases, and those involved in housekeeping, such as heat shock proteins. More specific categories of transgenes, for example, include genes encoding important traits for agronomics, insect resistance, disease resistance, herbicide resistance, sterility, grain characteristics, and commercial products. Genes of interest include, generally, those involved in oil, starch, carbohydrate, or nutrient metabolism, particularly nitrogen assimilation, as well as those affecting kernel size, sucrose loading, and the like.

In one embodiment, sequences of interest improve plant growth and/or crop yields. In more specific embodiments, expression of the nucleotide sequence of interest improves the plant's response to stress induced under high density growth conditions. For example, sequences of interest include agronomically important genes that result in improved primary or lateral root systems. Such genes include, but are not limited to, nutrient/water transporters and growth inducers. Examples of such genes include, but are not limited to, maize plasma membrane $H^+$-ATPase (MHA2) (Frias, et al., (1996) *Plant Cell* 8:1533-44); AKT1, a component of the potassium uptake apparatus in *Arabidopisis*, (Spalding, et al., (1999) *J Gen Physiol* 113:909-18); RML genes which activate cell division cycle in the root apical cells (Cheng, et al., (1995) *Plant Physiol* 108:881); maize glutamine synthetase genes (Sukanya, et al., (1994) *Plant Mol Biol* 26:1935-46) and hemoglobin (Duff, et al., (1997) *J. Biol. Chem.* 27:16749-16752, Arredondo-Peter, et al., (1997) *Plant Physiol.* 115: 1259-1266; Arredondo-Peter, et al., (1997) *Plant Physiol* 114:493-500 and references cited therein); and isopentenyl transferase, or ipt (Strabala, et al., (1989) *Mol. Gen. Genet.* 216:388-394, (Agrobacterium); U.S. Patent Application Ser. Nos. 60/610,656 filed Sep. 17, 2004 and 60/637,230 filed Dec. 17, 2004 (maize); Takei, et al., (2001) *J. Biol. Chem.* 276:26405-26410 (Arabidopsis); Zubko, et al., (2002) *Plant J.* 29(6):797-808 (petunia); Sakano, et al., (2004) *Phytochem* 65:2439-2446 (hop); and GenBank Accession Number XM_477138 (rice, 2004)). The sequence of interest may also be useful in expressing antisense nucleotide sequences of genes that negatively affect root development.

Additional, agronomically important traits such as oil, starch, and protein content can be genetically altered in addition to using traditional breeding methods. Modifications include increasing content of oleic acid, saturated and unsaturated oils, increasing levels of lysine and sulfur, providing essential amino acids, and also modification of starch. Hordothionin protein modifications are described in U.S. Pat. Nos. 5,703,049, 5,885,801, 5,885,802 and 5,990,389, herein incorporated by reference. Another example is lysine and/or sulfur rich seed protein encoded by the soybean 2S albumin described in U.S. Pat. No. 5,850,016, and the chymotrypsin inhibitor from barley, described in Williamson, et al., (1987) *Eur. J. Biochem.* 165:99-106, the disclosures of which are herein incorporated by reference.

Derivatives of the coding sequences can be made by site-directed mutagenesis to increase the level of preselected amino acids in the encoded polypeptide. For example, the gene encoding the barley high lysine polypeptide (BHL) is derived from barley chymotrypsin inhibitor, U.S. patent application Ser. No. 08/740,682, filed Nov. 1, 1996, and WO 98/20133, the disclosures of which are herein incorporated by reference. Other proteins include methionine-rich plant proteins such as from sunflower seed (Lilley, et al., (1989) *Proceedings of the World Congress on Vegetable Protein Utilization in Human Foods and Animal Feedstuffs*, ed. Applewhite (American Oil Chemists Society, Champaign, Ill.), pp. 497-502; herein incorporated by reference); corn (Pedersen, et al., (1986) *J. Biol. Chem.* 261:6279; Kirihara, et al., (1988) *Gene* 71:359; both of which are herein incorporated by reference); and rice (Musumura, et al., (1989) *Plant Mol. Biol.* 12:123, herein incorporated by reference). Other agronomically important genes encode latex, Floury 2, growth factors, seed storage factors, and transcription factors.

Insect resistance genes may encode resistance to pests that cause significant yield penalty such as rootworm, cutworm, European Corn Borer, and the like. Such genes include, for example, *Bacillus thuringiensis* toxin genes (see, for example, U.S. Pat. Nos. 5,366,892 5,747,450; 5,736,514; 5,723,756; 5,593,881; 5,188,960; 5,689,052; 5,880,275; 7,105,332; WO 91/14778; WO 99/31248; WO 01/12731; WO 99/24581; WO 97/40162 and U.S. patent application Ser. Nos. 10/032,717; 10/414,637; 10/746,914 and 11/224,624 and Geiser, et al., (1986) *Gene* 48:109). Other insect resistance genes may encode an insect-specific hormone or pheromone such as an ecdysteroid and juvenile hormone, a variant thereof, a mimetic based thereon, or an antagonist or agonist thereof; an insect-specific peptide which, upon expression, disrupts the physiology of the affected pest (for example, see, Regan, (1994) *J. Biol. Chem.* 269:9; Pratt, et al., (1989) *Biochem. Biophys. Res. Comm.* 163:1243; Chattopadhyay, et al., (2004) *Critical Reviews in Microbiology* 30(1):33-54 2004; Zjawiony, (2004) *J Nat Prod* 67(2):300-310; Carlini and Grossi-de-Sa, (2002) *Toxicon,* 40(11):1515-1539; Ussuf, et al., (2001) *Curr Sci.* 80(7):847-853; and Vasconcelos and Oliveira, (2004) *Toxicon* 44(4):385-403 and U.S. Pat. No. 5,266,317); an enzyme responsible for a hyperaccumulation of a monoterpene, a sesquiterpene, a steroid, hydroxycinnamic acid, a phenylpropanoid derivative or another non-protein molecule with insecticidal activity; or an enzyme involved in the modification, including the post-translational modification, of a biologically active molecule, such as a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic (for example, see, WO 93/02197; Kramer, et al., (1993) *Insect Biochem. Molec. Biol.* 23:691, Kawalleck, et al., (1993) *Plant Molec. Biol.* 21:673, U.S. Pat. Nos. 6,563,020, 7,145,060 and 7,087,810.

Genes encoding disease resistance traits include detoxification genes, such as against fumonosin (U.S. Pat. No. 5,792, 931); avirulence (avr) and disease resistance (R) genes (Jones, et al., (1994) *Science* 266:789; Martin, et al., (1993) *Science* 262:1432; and Mindrinos, et al., (1994) *Cell* 78:1089); and the like.

Herbicide resistance traits may include genes coding for resistance to herbicides that act to inhibit the action of acetolactate synthase (ALS), in particular the sulfonylurea-type herbicides (e.g., the acetolactate synthase (ALS) gene containing mutations leading to such resistance, in particular the S4 and/or Hra mutations), genes coding for resistance to herbicides that act to inhibit action of glutamine synthase, such as phosphinothricin or basta (e.g., the bar gene), genes encoding proteins which break down glyphosate, or other such genes known in the art. The bar gene encodes resistance to the herbicide basta, the nptII gene encodes resistance to the antibiotics kanamycin and geneticin, and the ALS-gene mutants encode resistance to the herbicide chlorsulfuron.

Sterility genes can also be encoded in an expression cassette and provide an alternative to physical detasseling. Examples of genes used in such ways include male tissue-preferred genes and genes with male sterility phenotypes such as QM, described in U.S. Pat. No. 5,583,210. Other genes include kinases and those encoding compounds toxic to either male or female gametophytic development.

The quality of grain is reflected in traits such as levels and types of oils, saturated and unsaturated, quality and quantity of essential amino acids, and levels of cellulose. In corn, modified hordothionin proteins are described in U.S. Pat. Nos. 5,703,049, 5,885,801, 5,885,802 and 5,990,389.

Commercial traits can also be encoded on a gene or genes that could increase for example, starch for ethanol production, or provide expression of proteins. Another important commercial use of transformed plants is the production of polymers and bioplastics such as described in U.S. Pat. No. 5,602,321. Genes such as β-Ketothiolase, PHBase (polyhydroxyburyrate synthase), and acetoacetyl-CoA reductase (see, Schubert, et al., (1988) *J. Bacteriol.* 170:5837-5847) facilitate expression of polyhyroxyalkanoates (PHAs).

Exogenous products include plant enzymes and products as well as those from other sources including procaryotes and other eukaryotes. Such products include enzymes, cofactors, hormones, and the like. The level of proteins, particularly modified proteins having improved amino acid distribution to improve the nutrient value of the plant, can be increased. This is achieved by the expression of such proteins having enhanced amino acid content.

All publications and patents herein referred to are hereby incorporated by reference to the same extent as if each was individually so incorporated.

The following examples are intended to illustrate but not to limit the invention.

EXPERIMENTAL

Example 1

Analysis of CKX Sequences

The CKX polypeptides of the invention share sequence similarity with a number of CKX polypeptides. FIG. 23 provides identity values for ZmCkx1-8 and OsCkx 1-11 polypeptides compared to each other.

The amino acid alignment of the CKX polypeptides of the invention with other known CKX polypeptides is provided in FIG. 11. Specifically, the alignment provides the sequence relationship of AtCkx1 (SEQ ID NO: 35), AtCkx2 (SEQ ID NO: 36), AtCkx3 (SEQ ID NO: 37), AtCkx4 (SEQ ID NO: 38), AtCkx5 (SEQ ID NO: 39), AtCkx6 (SEQ ID NO: 40), AtCkx7 (SEQ ID NO: 41), DsCkx1 (SEQ ID NO: 42), HvCkx2 (SEQ ID NO: 43), HvCkx3 (SEQ ID NO: 44), OsCkx1 (SEQ ID NO: 45), OsCkx2 (SEQ ID NO: 46), OsCkx3 (SEQ ID NO: 47), OsCkx4 (SEQ ID NO: 48), OsCkx5 (SEQ ID NO: 49), OsCkx6 (SEQ ID NO: 73), OsCkx7 (SEQ ID NO: 74), OsCkx8 (SEQ ID NO: 75), OsCkx9 (SEQ ID NO: 76), OsCkx10 (SEQ ID NO: 77), OsCkx11 (SEQ ID NO: 78), ZmCkx1 (SEQ ID NO: 33), ZmCkx2 or 2a (SEQ ID NO: 3), ZmCkx2b (SEQ ID NO: 68) ZmCkx3 (SEQ ID NO: 6), ZmCkx4 (SEQ ID NO: 9) ZmCkx5 (SEQ ID NO: 12), ZmCkx6 (SEQ ID NO: 53), ZmCkx7 (SEQ ID NO: 59), and ZmCkx8 (SEQ ID NO: 62).

The CKX polypeptides of the invention contain a predicted FAD-binding domain (PFAM Accession Number PF01565). The PFAM consensus sequence is provided in SEQ ID NO: 56.

Analysis of the subcellular location of the CKX polypeptides of the invention was also performed using ProtComp (Softberry, Inc.; version 5 or 6.1) trained onto plants. The program is based on complex neural-network recognizers, which identify probability of subcellular localization in nuclear, plasma membrane, extracellular, cytoplasmic, mitochondrial, chloroplast, endoplasmic reticulum, peroxisomal, lysosomal or Golgi compartments.

The results of these analyses are set forth below.

A. Analysis of ZmCkx2:

The results for ZmCkx2a follow and predict that the ZmCkx2a polypeptide is extracellularly localized.

ProtComp Version 5. Identifying sub-cellular location (Plants)
Seq name: ZmCkx2a 519
Significant similarity in Location DB - Location: Extracellular (Secreted)
Database sequence: AC=Q9T0N8 Location: Extracellular (Secreted)
DE Cytokinin oxidase 1 precursor (EC
Score=11145, Sequence length=534, Alignment length=392
Predicted by Neural Nets - Plasma membrane with score 0.9
******** Transmembrane segments are found: .-325 : 337+.
Integral Prediction of protein location: Membrane bound Extracellular (Secreted) with score 4.3

| Location weights: | LocDB | PotLocDB | Neural Nets | Integral |
|---|---|---|---|---|
| Nuclear | 0.0 | 0.0 | 0.74 | 0.74 |
| Plasma membrane | 0.0 | 0.0 | 0.92 | 0.92 |
| Extracellular | 11145.0 | 9230.0 | 0.81 | 4.31 |
| Cytoplasmic | 0.0 | 0.0 | 0.64 | 0.64 |
| Mitochondrial | 0.0 | 0.0 | 0.76 | 0.76 |
| Chloroplast | 0.0 | 0.0 | 0.73 | 0.73 |
| Endoplasm. retic. | 0.0 | 0.0 | 0.77 | 0.77 |
| Peroxisomal | 0.0 | 0.0 | 0.76 | 0.76 |

SPScan in SeqWeb
1. 1 mkppslvhcfkllvllalarltmh^vp 26
Score: 7.7
Probability: 7.225E−01
SP Length: 24
McGeoch scan succeeded:
Charged-region statistics:
Length: 11 Charge: 2
Hydrophobic-region statistics:
Length: 8 Offset: 12 Total hydropathy: 62.3
Maximum 8-residue hydropathy: 62.3, starting at 13

The results for ZmCkx2b follow and predict that the ZmCkx2b polypeptide is extracellularly localized.

ProtComp Version 6.1. Identifying sub-cellular location (Plants)
Seq name: ZmCkx2b 525
Significant similarity in Location DB - Location:Extracellular (Secreted)
Database sequence: AC=Q9T0N8 Location:Extracellular (Secreted)
DE Cytokinin dehydrogenase 1 precurso
Score=11240, Sequence length=534, Alignment length=384
Predicted by Neural Nets - Endoplasmic reticulum with score 1.1
Integral Prediction of protein location: Extracellular (Secreted) with score 5.3

| Location weights: | LocDB | PotLocDB | Neural Nets | Pentamers | Integral |
|---|---|---|---|---|---|
| Nuclear | 0.0 | 0.0 | 0.74 | 0.00 | 0.74 |
| Plasma membrane | 0.0 | 0.0 | 0.72 | 0.63 | 1.35 |
| Extracellular | 11240.0 | 15415.0 | 0.77 | 0.31 | 5.29 |
| Cytoplasmic | 0.0 | 0.0 | 0.78 | 0.05 | 0.84 |
| Mitochondrial | 0.0 | 0.0 | 0.77 | 0.22 | 1.00 |
| Chloroplast | 0.0 | 0.0 | 0.73 | 0.00 | 0.73 |
| Endoplasm. retic. | 0.0 | 0.0 | 1.13 | 0.00 | 1.13 |
| Peroxisomal | 0.0 | 0.0 | 0.75 | 0.00 | 0.75 |

SPScan in SeqWeb
1. 1 mkppsslvhyfkllvllalarltmh^vp 27
Score: 7.7
Probability: 8.044E−01
SP length: 25
McGeoch scan succeeded:
Charged-region statistics:
Length: 2 Charge: 1
Hydrophobic-region statistics:
Length: 15 Offset: 3 Total hydropathy: 83.7
Maximum 8-residue hydropathy: 52.5, starting at 11

B. Analysis of ZmCkx3:

The results for ZmCkx3 follow and predict that the ZmCkx3 polypeptide is extracellularly localized.

ProtComp Version 5. Identifying sub-cellular location (Plants)
Seq name: ZmCkx3 538
Significant similarity in Location DB - Location: Extracellular (Secreted)
Database sequence: AC=Q9T0N8 Location: Extracellular (Secreted)
DE Cytokinin oxidase
Score=13520, Sequence length=534, Alignment length=500
Predicted by Neural Nets - Plasma membrane with score 1.3
Integral Prediction of protein location: Extracellular (Secreted) with score 5.3

| Location weights: | LocDB | PotLocDB | Neural Nets | Integral |
|---|---|---|---|---|
| Nuclear | 0.0 | 0.0 | 1.18 | 1.18 |
| Plasma membrane | 0.0 | 0.0 | 1.32 | 1.32 |
| Extracellular | 13520.0 | 11200.0 | 1.07 | 5.32 |
| Cytoplasmic | 0.0 | 0.0 | 0.72 | 0.72 |
| Mitochondrial | 0.0 | 0.0 | 0.98 | 0.98 |
| Chloroplast | 0.0 | 0.0 | 0.71 | 0.71 |
| Endoplasm. retic. | 0.0 | 0.0 | 0.56 | 0.56 |
| Peroxisomal | 0.0 | 0.0 | 0.42 | 0.42 |

ZmCkx3
SPScan in SeqWeb
1 marrtrfvaiaalltsflnvaag^hs 25
Score: 8.7
Probability: 4.497E−01
SP length: 23

C. Analysis of ZmCkx4:

The results for ZmCkx4 follow and predict that the ZmCkx4 polypeptide is extracellularly localized.

ProtComp Version 5. Identifying sub-cellular location (Plants)
Seq name: ZmCkx4 521
Significant similarity in Location DB - Location: Extracellular (Secreted)
Database sequence: AC=Q9LTS3 Location: Extracellular (Secreted)
DE Cytokinin oxidase
Score=10155, Sequence length=523, Alignment length=360
Predicted by Neural Nets - Plasma membrane with score 1.3
Integral Prediction of protein location: Extracellular (Secreted) with score 4.4

| Location weights: | LocDB | PotLocDB | Neural Nets | Integral |
|---|---|---|---|---|
| Nuclear | 0.0 | 0.0 | 1.18 | 1.18 |
| Plasma membrane | 0.0 | 0.0 | 1.32 | 1.32 |
| Extracellular | 10155.0 | 9925.0 | 1.07 | 4.43 |
| Cytoplasmic | 0.0 | 0.0 | 0.72 | 0.72 |
| Mitochondrial | 0.0 | 0.0 | 0.95 | 0.95 |
| Chloroplast | 0.0 | 0.0 | 0.71 | 0.71 |
| Endoplasm. retic. | 0.0 | 0.0 | 0.56 | 0.56 |
| Peroxisomal | 0.0 | 0.0 | 0.42 | 0.42 |

ZmCkx4
SPScan in SeqWeb
1 mlaymdrataaaepedagrepatmaggcaaaatdfgglgsampaavvrpasa^dd 54
Score: 6.7
Probability: 9.945E−01
SP length: 52
McGeoch scan succeeded:
Charged-region statistics:
Length: 7 Charge: 0
Hydrophobic-region statistics:
Length: 8 Offset: 8 Total hydropathy: 33.9
Maximum 8-residue hydropathy: 33.9, starting at 9

D. Analysis of ZmCkx5:

The results for ZmCkx5 follow and predict that the ZmCkx5 polypeptide is extracellularly localized.

ProtComp Version 5. Identifying sub-cellular location (Plants)
Seq name: ZmCkx5 542
Significant similarity in Location DB - Location: Extracellular (Secreted)
Database sequence: AC=Q9LTS3 Location: Extracellular (Secreted)
DE Cytokinin oxidase
Score=9405, Sequence length=523, Alignment length=390
Predicted by Neural Nets - Plasma membrane with score 1.3
Integral Prediction of protein location: Extracellular (Secreted) with score 4.3

| Location weights: | LocDB | PotLocDB | Neural Nets | Integral |
|---|---|---|---|---|
| Nuclear | 0.0 | 0.0 | 1.18 | 1.18 |
| Plasma membrane | 0.0 | 0.0 | 1.32 | 1.32 |
| Extracellular | 9405.0 | 10020.0 | 1.08 | 4.28 |
| Cytoplasmic | 0.0 | 0.0 | 0.72 | 0.72 |
| Mitochondrial | 0.0 | 0.0 | 0.98 | 0.98 |
| Chloroplast | 0.0 | 0.0 | 0.71 | 0.71 |
| Endoplasm. retic. | 0.0 | 0.0 | 0.56 | 0.56 |
| Peroxisomal | 0.0 | 0.0 | 0.42 | 0.42 |

ZmCkx5
SPScan in SeqWeb
1 MEVAMWSARASLLILVLSLCSP^YK 25
Score: 7.4
Probability: 9.387E−01
SP length: 23
McGeoch scan succeeded:
Charged-region statistics:
Length: 10 Charge: 0
Hydrophobic-region statistics:
Length: 10 Offset: 11 Total hydropathy: 72.2
Maximum 8-residue hydropathy: 62.3, starting at 14

E. Analysis of ZmCkx6:

The results for ZmCkx6 follow and predict that the ZmCkx6 polypeptide is extracellularly localized.

Seq name: ZmCkx6 540
Significant similarity in Location DB - Location:Extracellular (Secreted)
Database sequence: AC=Q9T0N8 Location:Extracellular (Secreted)
DE Cytokinin dehydrogenase 1 precurso
Score=12595, Sequence length=534, Alignment length=439
Predicted by Neural Nets - Chloroplast with score 1.6
******** Signal 1-47 is found
******** Transmembrane segments are found: .−348:360+.
Integral Prediction of protein location: Membrane bound Extracellular (Secreted) with score 6.3

| Location weights: | LocDB | PotLocDB | Neural Nets | Pentamers | Integral |
|---|---|---|---|---|---|
| Nuclear | 0.0 | 0.0 | 0.73 | 0.05 | 0.78 |
| Plasma membrane | 0.0 | 0.0 | 1.31 | 0.73 | 2.04 |
| Extracellular | 12595.0 | 17440.0 | 1.11 | 0.49 | 6.34 |
| Cytoplasmic | 0.0 | 0.0 | 0.66 | 0.06 | 0.72 |
| Mitochondrial | 0.0 | 0.0 | 0.72 | 0.04 | 0.76 |
| Chloroplast | 0.0 | 0.0 | 1.58 | 0.00 | 1.63 |
| Endoplasm. retic. | 0.0 | 0.0 | 1.04 | 0.05 | 1.04 |
| Peroxisomal | 0.0 | 0.0 | 0.71 | 0.00 | 0.71 |

ZmCkx6
SPScan in SeqWeb
1 mtrclmftllflvsslistvg^lp 23
Score: 8.8
Probability: 4.377E−01
SP length: 21
McGeoch scan succeeded:
Charged-region statistics:
Length: 3 Charge: 1
Hydrophobic-region statistics:
Length: 10 Offset: 4 Total hydropathy: 73.1
Maximum 8-residue hydropathy: 57.9, starting at 7

E. Analysis of ZmCkx7:

The results for ZmCkx7 follow and predict that the ZmCkx7 polypeptide is extracellularly localized.

Seq name: ZmCkx7 582
Significant similarity in Location DB - Location:Extracellular (Secreted)
Database sequence: AC=Q9T0N8 Location:Extracellular (Secreted)
DE Cytokinin dehydrogenase 1 precurso
Score=13695, Sequence length=534, Alignment length = 481
Predicted by Neural Nets - Mitochondrial with score 1.7
Integral Prediction of protein location: Extracellular
(Secreted) with score 6.2

| Location weights: | LocDB | PotLocDB | Neural Nets | Pentamers | Integral |
|---|---|---|---|---|---|
| Nuclear | 0.0 | 0.0 | 0.71 | 0.19 | 0.90 |
| Plasma membrane | 0.0 | 0.0 | 0.72 | 0.37 | 1.09 |
| Extracellular | 13695.0 | 12375.0 | 1.27 | 0.54 | 6.23 |
| Cytoplasmic | 0.0 | 0.0 | 0.70 | 0.35 | 1.05 |
| Mitochondrial | 0.0 | 0.0 | 1.74 | 0.00 | 1.74 |
| Chloroplast | 0.0 | 0.0 | 1.40 | 0.00 | 1.40 |
| Endoplasm. retic. | 0.0 | 0.0 | 0.72 | 0.00 | 0.72 |
| Peroxisomal | 0.0 | 0.0 | 0.48 | 0.00 | 0.48 |

ZmCkx7
SPScan in SeqWeb
1 marattstvaalcfllscvsa^tp 23
Score: 11.3
Probability: 7.910E−03
SP length: 21
McGeoch scan succeeded:
Charged-region statistics:
Length: 3 Charge: 1
Hydrophobic-region statistics:
Length: 13 Offset: 4 Total hydropathy: 81.4
Maximum 8-residue hydropathy: 60.1, starting at 10

F. Analysis of ZmCkx8:

The results for ZmCkx8 follow and predict that the ZmCkx8 polypeptide is extracellularly localized.

Seq name: ZmCkx8 528
Significant similarity in Location DB - Location:Extracellular (Secreted)
Database sequence: AC=Q9T0N8 Location:Extracellular (Secreted)
DE Cytokinin dehydrogenase 1 precurso
Score=9365, Sequence length=534, Alignment length=350
Predicted by Neural Nets - Mitochondrial with score 1.3
******** Signal 1-17 is found
******** Transmembrane segments are found: .o133:146–.
Integral Prediction of protein location: Membrane bound Extracellular
(Secreted) with score 4.8

| Location weights: | LocDB | PotLocDB | Neural Nets | Pentamers | Integral |
|---|---|---|---|---|---|
| Nuclear | 0.0 | 0.0 | 0.73 | 0.04 | 0.78 |
| Plasma membrane | 0.0 | 0.0 | 1.26 | 0.30 | 1.56 |
| Extracellular | 9365.0 | 10875.0 | 1.11 | 0.37 | 4.78 |
| Cytoplasmic | 0.0 | 0.0 | 0.73 | 0.00 | 0.73 |
| Mitochondrial | 0.0 | 0.0 | 1.31 | 0.13 | 1.45 |
| Chloroplast | 0.0 | 0.0 | 0.72 | 0.00 | 0.72 |
| Endoplasm. retic. | 0.0 | 0.0 | 1.01 | 0.00 | 1.01 |
| Peroxisomal | 0.0 | 0.0 | 1.13 | 0.00 | 1.13 |

ZmCkx8
SPScan in SeqWeb
1 megkvlctyagivalllcssvnfiqspsdvfgpvalleptasa^ar 45
Score: 6.7
Probability: 9.988E−01
SP length: 43
McGeoch scan succeeded:
Charged-region statistics:
Length: 4 Charge: 0
Hydrophobic-region statistics:
Length: 14 Offset: 5 Total hydropathy: 96.9
Maximum 8-residue hydropathy: 59.7, starting at 12

Example 2

Expression Profiles of Cytokinin Oxidase Genes

Several cytokinin oxidase ESTs were identified and genomic sequences isolated from corresponding BAC clones. Expression profiles of the CKX sequences were studied using Northern blots and RT-PCR for ZmCkx2, ZmCkx3, ZmCkx4, ZmCkx5, and ZmCkx6. In addition, expression of ZmCkx2-8 was evaluated using a proprietary Lynx database (Lynx Therapeutics, Hayward Calif., USA; see, for example, Brenner, et al., (2000) *Nature Biotechnology* 18:630-634).

A. Analysis of ZmCkx2

Northern analysis of ZmCkx2 was performed using ExpressHyb™ Hybridization Solution from BD Biosciences Clontech (Palo Alto, Calif.) with a final wash in 0.1×SSC, 0.1% SDS at 65° C. for 20 minutes.

ZmCkx2 exists as a duplicated gene in maize, identified on Chromosome 3 (ZmCkx2a, SEQ ID NO: 1-3; NCBI CAE55200) and on Chromosome 8 (ZmCkx2b, SEQ ID NO: 67-68; NCBI CAE55201) (Massoneau, et al., 2004). The ZmCkx2b polypeptide (GenBank entry AJ606944) is 94% identical to the ZmCkx2a polypeptide of SEQ ID NO: 3. Because of the high degree of identity between the two ZmCkx2 sequences, analysis of expression will likely reflect activity of both ZmCkx2a and ZmCkx2b.

A tight relationship exists between Lynx and Northern data for ZmCkx2. This provided confidence when the Lynx database was mined for ZmCkx2 expression in various plant parts. For example, both Northern and Lynx analyses showed that ZmCkx2 had a 2-fold increase in expression in leaf discs incubated with 10 μM benzyladenine (a synthetic cytokinin). Lynx data in FIG. 3 show that expression is highest in leaves, stalk, whorl, roots and seedlings. Similarly, Northern data indicated strongest signals from ear leaf and midrib tissues; intermediate levels in tassel, husk leaves, young leaves, stalk, and pulvini; and lower levels in cob and ovary tissue. Little to no ZmCkx2 activity was detected by Northern analysis of roots or silks.

In addition, analyses of the Lynx data revealed that expression of ZmCkx2 increases during root aging and is induced 4-fold in seedlings submitted to a freezing stress. In the stalk, expression is 3-fold higher in the pith than in the rind.

RT-PCR was performed to determine the expression profile of ZmCkx2 in various maize tissues. RT-PCR was performed on maize mature and seedling tissue employing the following PCR parameters: 94° C. for 45 sec, 60° C. for 1 min, 72° C. for 3 min, for 30 cycles. ZmCkx2 expression was strongest in mature stalk tissue and in seedling leaf and mesocotyl. Weaker expression was noted in midribs and young and mature leaves of mature plants, as well as seedling roots. Similar RT-PCR studies were also performed during various stages of maize kernel development, including 0, 5, 10, 15, 20, 25 and 30 days after pollination. An expression peak was detected at 5 DAP.

A proprietary Agilent database (Agilent Technologies, Palo Alto, Calif.) was also analyzed to identify trends in ZmCkx2 expression. Tissues that showed the most dramatic differences in ZmCkx2 expression are from stalk. These samples were collected from the internodal zone of the $3^{rd}$ or $4^{th}$ internode below the ear before and after flowering. It was found that ZmCkx2 expression goes up more than 10-fold in the stalk after flowering (Table 1).

TABLE 1

| Experiment Id | Experiment Name | Ratio | Fold Change | P-value |
|---|---|---|---|---|
| 2340 | Pt#1 preflowering at 59K vs Pt#2 postflowering at 59K | 0.08 | −12.8 | 1.73E−27 |
| 2364 | Pt#2 preflowering at 27K vs Pt#2 postflowering at 59K | 0.09 | −11.3 | 7.77E−26 |
| 2349 | Pt#1 preflowering at 27K vs Pt#3 postflowering at 59K | 0.09 | −11.1 | 5.73E−23 |
| 2336 | Pt#3 preflowering at 59K vs Pt#1 postflowering at 59K | 0.09 | −10.7 | 7.05E−25 |
| 2345 | Pt#3 preflowering at 27K vs Pt33 postflowering at 27K | 0.1 | −10.3 | 3.67E−24 |
| 2332 | Pt#2 postflowering at 27K vs Pt#1 preflowering at 59K | 6.82 | 6.82 | 7.37E−17 |
| 2359 | Pt#1 postflowering at 59K vs Pt#2 preflowering at 27K | 9.16 | 9.16 | 6.71E−22 |
| 2368 | Pt#2 postflowering at 27K vs Pt#3 preflowering at 59K | 11.17 | 11.17 | 1.07E−25 |
| 2366 | Pt#1 postflowering at 27K vs Pt#3 preflowering at 59K | 11.78 | 11.78 | 2.04E−26 |
| 2333 | Pt#3 postflowering at 27K vs Pt#1 preflowering at 27K | 17.7 | 17.7 | 1.72E−31 |

Table 1 shows fold changes identified in stalk samples collected from the internodal zone of the 3rd or 4th internode below ear, before and after flowering. This increase in ZmCkx2 expression could be associated with the flowering process. An increase of cytokinin flux from roots to shoots is often regarded as a flowering signal and is consistent with previous findings that increased cytokinin levels induce ZmCkx1 and ZmCkx2 expression. ZmCkx2 expression was also found to increase an average of 10-fold during ear development. Thus, manipulation of ZmCkx2 expression may be useful in modulation of flowering time.

B. Analysis of ZmCkx3

Expression of ZmCkx3 could not be detected using Northern blots. Mining of the Agilent and Lynx database confirmed that the gene is expressed at extremely low levels. The EST for ZmCkx3 came from a tassel library and it is believed that this gene could be tightly expressed in a particular cell type at a particular stage of tassel development. It remains possible that ZmCkx3 expresses during another development at very low levels. The only tags from Lynx are from roots at an average of 4-5 ppm (See, FIG. 3).

C. Analysis of ZmCkx4

Analysis of the Lynx database for ZmCkx4 showed low constitutive expression of the gene in most organs, with higher levels observed in ear, silk and vascular bundles as well as intermediate levels in leaf and pedicels (FIG. 3). Interestingly, in 15-20 mm ears, ZmCkx4 is expressed at higher levels at the base of the ear than at the ear tip. This stage of ear growth coincides with the appearance of silk structure on the ear, which, taken together with strong expression in the silk, suggests a role for this gene in silk development.

D. Analysis of ZmCkx5

Analysis of the Lynx database for ZmCkx5 showed highest levels of expression to be in root and vascular bundles. (See, FIG. 3)

E. Analysis of ZmCkx6

Analysis of the Lynx database showed that ZmCkx6 is expressed at low levels in most maize tissues with stronger expression in anthers and pedicels. (See, FIG. 3)

F. Analysis of ZmCkx7

Analysis of the Lynx database showed that ZmCkx7 is also expressed at low levels in most tissues but with stronger levels in endosperm and pedicel. (See, FIG. 3)

G. Analysis of ZmCkx8

Analysis of the Lynx database showed that ZmCkx8 is expressed at low levels with stronger levels in anther, endosperm, and meristems. (See FIG. 3)

Example 3

Identification of ZmCkx2a, ZmCkx2b. ZmCkx4, and ZmCkx7 TUSC Events

In order to better define the roles of ZmCkx genes in plant development, knockout mutants were obtained for ZmCkx2a, ZmCkx2b, ZmCkx4, and ZmCkx7 using methods previously described (see, U.S. Pat. Nos. 5,962,764 and 6,300,542; Trait Utility System for Corn (TUSC)).

A. ZmCkx2a TUSC Summary

Two genomic sequences for cytokinin oxidase orthologues were provided for knockout screening. ZmCkx2a is a ~3200 bp genomic sequence with five exons and four introns. Using this annotation, six PCR primers were designed across various intervals of the ZmCkx2a gene and then tested in control reactions against wild type maize (B73) gDNA. Primers were identified as 71936 (SEQ ID NO: 19), 71937 (SEQ ID NO: 20), 71938 (SEQ ID NO: 21), 71939 (SEQ ID NO: 22), 71940 (SEQ ID NO: 23), 71941 (SEQ ID NO: 24) and 9242 MuTIR (SEQ ID NO: 25). Verification and clean results were obtained for 71936+71937, 71940+71937, 71940+71941, 71940+71939, 71938+71941 and 71938+71939. No amplification results were observed for 71936+71941 and 71936+71939.

The 71936+71937 and 71938+71939 amplification products were cut out of the agarose gel, purified, and used as probes for hybridization. These two intervals effectively segment the ZmCkx2a gene into 5' and 3' halves for insertion screening. Primer sequences are shown below along with the expected and observed amplicon sizes for each primer combination.

TABLE 2

| Primer Pair | cDNA (bp) | observed (bp) |
|---|---|---|
| 71936 + 71937 | 798 | ~800 |
| 71936 + 71941 | 1350 | No product |
| 71936 + 71939 | 1841 | No product |
| 71940 + 71937 | 245 | ~250 |
| 71940 + 71941 | 797 | ~800 |
| 71940 + 71939 | 1288 | ~1300 |
| 71938 + 71941 | 310 | ~300 |
| 71938 + 71939 | 801 | ~800 |

The pooled TUSC population was screened with gene primers 71936, 71937, 71938, and 71939 each in combination with the Mutator TIR primer 9242. Results of the pool hybridizations were fair with some PCR-positive pools detected by hybridization. Overall, hybridization signals were cross-confirmed between the primers.

Pools were selected for fragment sizing analysis based on hybridization signal intensity and reproducibility of the pool dot blots. In this phase of the screen, sizes of target::Mu PCR products are determined by reamplification, electrophoresis, and Southern analysis. Fourteen positive pools for primer 71936, fifty-one positive pools for primer 71937, forty-four positive pools for primer 71939, and thirty-seven positive pools for 71938 were screened through fragment-sizing. A number of pools were identified with strong EtBr and Southern bands.

Eight pools were selected for individual analysis based on the putative Mutator insertion location within ZmCKX2a, determined from the size data, and the overall quality of the hybridization signals throughout the screening process. The pools are shown in the table below, along with their size data. Each plate listed consists of individuals from two pools: those assayed in the sizing analysis (highlighted in bold type), as well as individuals from its companion pools. Individuals in the companion pools are often, but not necessarily, related to those in the targeted pools.

TABLE 3

| Plate | Pools | Size (Bp) for Pool |
|---|---|---|
| PV03 60 | 119 and 120 | 350 |
| PV03 70 | 139 and 140 | 425 |
| PV03 71 | 141 and 142 | 600 |
| PV03 94 | 187 and 188 | 750 |
| PV03 118 | 235 and 236 | 750 |
| PV03 119 | 237 and 238 | 225 |
| PV03 159 | 317 and 318 | 350 |
| BT94 166 | 841 and 842 | 425 |

71937

Individual DNAs were arrayed, and a dot blot screen conducted with 71936 and 71937. Note that these selections are focused on the best candidates from the 5' half of the gene, targeting primarily the first large exon. In individual screens, PCR-positive individuals were identified for all of the targeted pools. To ensure germinal transmission of target::Mu alleles, F2 transmission testing was performed on thirty individual families harboring putative ZmCKX2a::Mu alleles. F2 genomic DNA was isolated from dry kernels (5K/individual) and amplified with the appropriate primers. Template controls on these preps were also performed using the gene-specific pair 71936+71937.

FIG. 4 provides a schematic of various Mu insertions in ZmCkx2 and ZmCkx4. Results indicate the genetic transmission of five ZmCkx2::Mu alleles.

1) Insertion A: This insertion is inherited uniquely by this F2 family in Pool 139. The insertion is cross-confirmed from both flanks of the insertion, producing strong EtBr and hybridization signals in F2 tests. The allele amplifies a ~625 fragment with 71936+9242, cross-confirmed with a ~375 bp fragment using 71937+9242. This provides evidence for a knockout allele in the first exon of ZmCkx2, near nt 800 of the genomic reference sequence.

2) Insertion B: Several related sibling families inherit the same insertion allele, suggesting a pre-meiotic origin for this allele; a parental insertion would have been evident in many more positive families. Five strong positive individuals were subjected to F2 tests; all were positive for the insertion allele. This insertion is cross-confirmed by amplification from both flanks. The 71936+9242 combination produces a small product of ~150 bp, and the 3' flank primer pair 71937+9242 produces a fragment of ~800 bp. The insertion site is thus predicted to be near the beginning of Exon I, and may be in the untranslated region. A Mu-suppressible phenotype may be one outcome of an insertion in this position.

3) Insertion C: This is a uniquely inherited Mu insertion in the 5' end of ZmCkx2. The allele is of a distinct pedigree from that of Allele 2, yet it produces very similar PCR product sizes as those listed above from 5' and 3' flanks.

4) Insertion D: This is another uniquely inherited and cross-confirmed insertion in the 5' end of the ZmCKX2a gene. This insertion produces fragments of ~775 bp and ~225 bp with 5' (71936) and 3' (71937) primer combinations, respectively. Based on the genomic annotation, this insertion occurs in Intron I of the gene, and thus may not provide a strong knockout allele. DNA sequence confirmation will be necessary to substantiate the expectations for this allele.

5) Insertion E: This is a uniquely inherited insertion, again cross-confirmed by amplification from both flanks of the insertion site. The allele produces strong EtBr and hybridization fragments of ~525 bp with the 71936+9242 combination, and ~475 bp with the 71937+9242 combination. This insertion position appears to squarely interrupt Exon I of the gene, and is perhaps the best candidate for a good null in the ZmCkx2a gene.

B. ZmCKX4 TUSC Summary

As for ZmCkx2, a complete genomic sequence for ZmCkx4 was provided to facilitate knockout screening. Alignments of the two genes were used, and known intron sequences identified to enable the design of primers specific for insertions in ZmCkx4. Following these analyses, six PCR primers were designed across various intervals of ZmCkx4 and tested in control pairs against wild-type (wt) maize (B73) gDNA. Primers were identified as 71942 (SEQ ID NO: 26), 71943 (SEQ ID NO: 27), 71944 (SEQ ID NO: 28), 71945 (SEQ ID NO: 29), 71946 (SEQ ID NO: 30), 71947 (SEQ ID NO: 31), and 9249 MuTIR (SEQ ID NO: 32). Verification and clean results were obtained solely for the 71944+71947 primer combination. Further screening targeted Exon IV.

For Exon IV screening, the 71944+71947 amplification product was cut out of the agarose gel, purified, and used as probe for hybridization. Primer sequences are shown below along with the expected and observed amplicon sizes for each primer combination.

TABLE 4

| Primer Pair | cDNA (bp) | observed by |
|---|---|---|
| 71942 + 71943 | 1575 | No product |
| 71942 + 71947 | 2072 | No product |
| 71942 + 71945 | 3075 | No product |
| 71946 + 71943 | 763 | No product |
| 71946 + 71947 | 1260 | No product |
| 71946 + 71945 | 2263 | No product |
| 71944 + 71947 | 448 | 450 |
| 71944 + 71945 | 1451 | No product |

The pooled TUSC population was screened with gene primers 71944 and 71947, each in combination with the Mutator TIR primer 9242. Results of the pool hybridizations were fair with some PCR-positive pools detected by hybridization: some signals were reproducible, and were cross-confirmed between the primers.

Pools were selected for fragment sizing analysis based on hybridization signal intensity and reproducibility of the pool dot blots. In this phase of the screen, sizes of target::Mu PCR products are determined by reamplification, electrophoresis, and Southern analysis. Forty-five positive pools for primer 71944 and seven positive pools for primer 71947 were screened through fragment-sizing. A number of pools were identified with strong EtBr and Southern bands.

Six pools were selected for individual analysis based on the putative Mutator insertion location within ZmCkx4, determined from the size-data, and the overall quality of the hybridization signals throughout the screening process. The pools are shown in the table below, along with their size data. Insertions detected outside the bounds of the primer interval are useful to expand the search for insertions beyond exon IV. Each plate listed consists of individuals from two pools: those assayed in the sizing analysis (highlighted in bold type), as well as individuals from its companion pools. Individuals in the companion pools are often, but not necessarily, related to those in the targeted pools.

TABLE 5

| Plate | Pools | Size (bp) for Pool |
|---|---|---|
| PV03 47 | 93 and 94 | 1800 |
| PV03 119 | 237 and 238 | 1550 |
| PV03 170 | 339 and 340 | 400; 225 |
| PV03 253 | 505 and 506 | 175 |
| BT94 19 | 547 and 548 | 1675, 775, 350 |
| BT94 96 | 705 and 706 | 1175, 350 |

71944
71947

Individual DNAs were arrayed, and a dot blot screen conducted with 71944 and 71947. PCR-positive individuals were identified for all of the targeted pools. To ensure germinal transmission of target::Mu alleles, F2 transmission testing was performed on thirty individual families harboring putative ZmCkx4::Mu alleles. F2 genomic DNA was isolated from dry kernels (5K/individual) and amplified with the appropriate primers. Template controls on these preps were also performed using the gene-specific pair 71944+71947.

FIG. 4 provides a schematic of various Mu insertions in ZmCkx4. Results indicate the genetic transmission of three ZmCKX4::Mu alleles.

1) Insertion A: This unique insertion allele is detected solely with primer 71947+9242, and produces a large fragment of >1600 bp. This is a positive signal and likely represents an insertion into Exon I of the ZmCkx4 gene. Further characterization of this allele will include DNA sequencing and the design and testing of alternative 5' primers.

2) Insertion B: A uniquely inherited insertion, this is cross-confirmed by amplification with both F and R primers from Exon IV. As such, this represents an excellent candidate for a knockout. The allele produces a strong product of ~200 bp with 71944+9242; cross-confirmed by the ~400 bp product with 71947+9242. These primers may be useful for genotyping assays during propagation.

3) Insertion C: This is another uniquely inherited insertion into Exon IV. This insertion is near that of Allele 2. The insertion produces a small ~175 bp product with the 71944+9242 combination and is cross-confirmed by a ~425 bp product with the right flank combination 71947+9242.

All three of these alleles are excellent candidates for ZmCkx4 knockouts.

C. ZmCKX2b TUSC Summary

Mu-insertion mutants have been isolated using gene-specific primers for ZmCkx2b and techniques similar to those described above. Insertions are diagrammed in FIG. 4.

D. ZmCkx7 TUSC Summary

Mu-insertion mutants have been isolated using gene-specific primers for ZmCkx7 and techniques similar to those described above. Insertions are diagrammed in FIG. 4.

Example 4

Altered Expression of ZmCkx2 Modulates Plant Development

A DNA construct comprising ZmCkx2a operably linked to the ubiquitin promoter was introduced into maize plants as described in Zhao, et al., U.S. Pat. No. 5,981,840 and PCT Publication Number WO98/32326, herein incorporated by reference, and herein at Example 7.

Maize plants comprising a plasmid containing the ZmCkx2a sequence operably linked to a ubiquitin promoter were obtained (PHP21533). As a control, a non-cytokinin-related construct was also introduced into maize plants using the transformation method outlined above. Northern analysis indicated elevated levels of ZmCkx2a expression in transgenic events. The phenotypes of these transgenic maize plants having an elevated level of the ZmCkx2a polypeptide were further studied.

Callus cultures of the transgenic maize tissue produced significantly more roots (see, FIG. 5) and only one-sixth as many shoots as control plants during the regeneration process. (See FIG. 6) In addition, transgenic roots cultured in vitro and leaves of T0 plants in the greenhouse showed a 2-fold increase in cytokinin oxidase activity. (See, FIG. 8)

Plants growing in the greenhouse and expressing the ZmCkx2a sequence at high levels showed a phenotype typical of plants with lower cytokinin levels, including developmental problems as shorter plants with thinner leaves and a green/gray color. These differences were evident through the vegetative growth period. Out of 23 plants expressing the Ubi:ZmCkx2a sequence, 6 transgenic plants appeared to be of normal size, 8 transgenic plants displayed a medium size, 6 transgenic plants were small but viable, and 3 transgenic plants were very small. FIG. 7 provides data as to plant height, leaf length, and leaf width of transgenic plants compared to controls, showing a strong difference in plant height and leaf width but very similar leaf length relative to control plants.

Certain Ubi:ZmCkx2a plants produced tassels lacking spikelets but generated silks capable of setting seed.

Example 5

Assaying for Cytokinin Oxidase Activity

The level of cytokinin oxidase activity in the maize plants generated in Example 4 was measured. The assay to determine the level of cytokinin oxidase activity was carried out as described in Brugière, et al., (2003) *Plant Physiol.* 132:1228-1240, herein incorporated by reference.

Figure 8A:
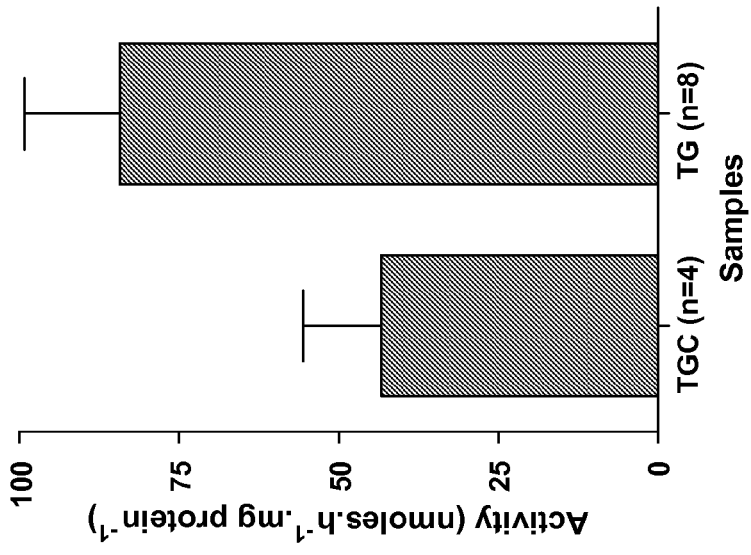
FIG. 8A shows the level of cytokinin oxidase activity in roots produced by calli expressing Ubi-ZmCkx2a compared to roots produced by control calli.

As demonstrated in FIG. 8A, cytokinin oxidase activity in transgenic root tissue is significantly higher than cytokinin oxidase activity in control root tissue. In addition, as demonstrated in FIG. 8B, cytokinin oxidase activity in leaves is higher in plants expressing ZmCkx2 than in the control plants.

Example 6

Maintaining or Increasing Seed Set During Stress

Immature maize embryos from greenhouse donor plants are bombarded with a plasmid designed to achieve post-transcriptional gene silencing (PTGS) with an appropriate promoter. For example, the plasmid may comprise the ZmCkx2 promoter (SEQ ID NO: 13) operably linked to a sequence encoding a hairpin structure corresponding to at least a portion of the coding sequence of the ZmCkx2 polynucleotide (SEQ ID NO: 2 or SEQ ID NO: 67). The plasmid may also contain the selectable marker gene PAT (Wohlleben, et al., (1988) *Gene* 70:25-37), which confers resistance to the herbicide Bialaphos.

Transformation is performed as follows. Media recipes follow below.

The ears are husked and surface sterilized in 30% Clorox™ bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5 cm target zone in preparation for bombardment.

A plasmid vector is made comprising the ZmCkx2 promoter sequence operably linked to a sequence encoding a hairpin structure corresponding to the CDS of the ZmCkx2 polynucleotide. This plasmid DNA plus plasmid DNA containing a PAT selectable marker is precipitated onto 1.1 μm (average diameter) tungsten pellets using a $CaCl_2$ precipitation procedure as follows: 100 μl prepared tungsten particles in water; 10 μl (1 μg) DNA in Tris EDTA buffer (1 μg total DNA); 100 μl 2.5 M $CaCl_2$; and, 10 μl 0.1 M spermidine.

Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 μl 100% ethanol is added to the final tungsten particle pellet. For particle gun bombardment, the tungsten/DNA particles are briefly sonicated and 10 μl spotted onto the center of each macrocarrier and allowed to dry about 2 minutes before bombardment.

The sample plates are bombarded at level #4 in particle gun #HE34-1 or #HE34-2. All samples receive a single shot at 650 PSI, with a total of ten aliquots taken from each tube of prepared particles/DNA.

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2-4 weeks), well-developed somatic embryos are transferred to medium for germination and transferred to the lighted culture room. Approximately 7-10 days later, developing plantlets are transferred to 272V hormone-free medium in tubes for 7-10 days until plantlets are well established. Plants are then transferred to inserts in flats (equivalent to 2.5" pot) containing potting soil and grown for 1 week in a growth chamber, subsequently grown an additional 1-2 weeks in the greenhouse, then transferred to classic 600 pots (1.6 gallon) and grown to maturity. Plants are monitored and scored under various stress conditions and compared to control plants. The maintenance of or an increase in seed set during an abiotic stress episode is monitored.

Bombardment medium (560Y) comprises 4.0 g/l N6 basal salts (SIGMA C-1416), 1.0 ml/l Eriksson's Vitamin Mix (1000X SIGMA-1511), 0.5 mg/l thiamine HCl, 120.0 g/l sucrose, 1.0 mg/l 2,4-D, and 2.88 g/l L-proline (brought to volume with D-I $H_2O$ following adjustment to pH 5.8 with KOH); 2.0 g/l Gelrite™ (added after bringing to volume with D-I $H_2O$); and 8.5 mg/l silver nitrate (added after sterilizing the medium and cooling to room temperature). Selection medium (560R) comprises 4.0 g/l N6 basal salts (SIGMA C-1416), 1.0 ml/l Eriksson's Vitamin Mix (1000X SIGMA-1511), 0.5 mg/l thiamine HCl, 30.0 g/l sucrose, and 2.0 mg/l 2,4-D (brought to volume with D-I $H_2O$ following adjustment to pH 5.8 with KOH); 3.0 g/l Gelrite™ (added after bringing to volume with D-I $H_2O$); and 0.85 mg/l silver nitrate and 3.0 mg/l bialaphos (both added after sterilizing the medium and cooling to room temperature).

Plant regeneration medium (288J) comprises 4.3 g/l MS salts (GIBCO 11117-074), 5.0 ml/l MS vitamins stock solution (0.100 g nicotinic acid, 0.02 g/l thiamine HCL, 0.10 g/l pyridoxine HCL, and 0.40 g/l glycine brought to volume with polished D-I $H_2O$) (Murashige and Skoog, (1962) *Physiol. Plant.* 15:473), 100 mg/l myo-inositol, 0.5 mg/l zeatin, 60 g/l sucrose, and 1.0 ml/l of 0.1 mM abscisic acid (brought to volume with polished D-I $H_2O$ after adjusting to pH 5.6); 3.0 g/l Gelrite™ (added after bringing to volume with D-I $H_2O$); and 1.0 mg/l indoleacetic acid and 3.0 mg/l bialaphos (added after sterilizing the medium and cooling to 60° C.). Hormone-free medium (272V) comprises 4.3 g/l MS salts (GIBCO 11117-074), 5.0 ml/l MS vitamins stock solution (0.100 g/l nicotinic acid, 0.02 g/l thiamine HCL, 0.10 g/l pyridoxine HCL, and 0.40 g/l glycine brought to volume with polished D-I $H_2O$), 0.1 g/l myo-inositol, and 40.0 g/l sucrose (brought to volume with polished D-I $H_2O$ after adjusting pH to 5.6); and 6 g/l Bacto™-agar (added after bringing to volume with polished D-I $H_2O$), sterilized and cooled to 60° C.

Example 7

Modulating Root Development

For *Agrobacterium*-mediated transformation of maize with the ZmCkx4 sequence operably linked to the CRWAQ81 root-preferred promoter::ADH intron, the method of Zhao is employed (U.S. Pat. No. 5,981,840, and PCT Patent Publication Number WO98/32326, the contents of which are hereby incorporated by reference). Briefly, immature embryos are isolated from maize and the embryos contacted with a suspension of *Agrobacterium*, where the bacteria are capable of transferring the ZmCkx4 to at least one cell of at least one of the immature embryos (step 1: the infection step). In this step the immature embryos are immersed in an *Agrobacterium* suspension for the initiation of inoculation. The embryos are co-cultured for a time with the *Agrobacterium* (step 2: the co-cultivation step). The immature embryos are cultured on solid medium following the infection step. Following this co-cultivation period an optional "resting" step is contemplated. In this resting step, the embryos are incubated in the presence of at least one antibiotic known to inhibit the growth of *Agrobacterium* without the addition of a selective agent for plant transformants (step 3: resting step). The immature embryos are cultured on solid medium with antibiotic, but without a selecting agent, for elimination of *Agrobacterium* and for a resting phase for the infected cells. Next, inoculated embryos are cultured on medium containing a selective agent and growing transformed callus is recovered (step 4: the selection step). The immature embryos are cultured on solid medium with a selective agent resulting in the selective growth of transformed cells. The callus is then regenerated into plants (step 5: the regeneration step), and calli grown on selective medium are cultured on solid medium to regenerate the plants.

Plants are monitored and scored for a modulation in root development. The modulation in root development includes monitoring for enhanced root growth of one or more root parts including the primary root, lateral roots, adventitious roots, etc. Methods of measuring such developmental alterations in the root system are known in the art. See, for example, US Patent Application Publication Number 2003/0074698 and Werner, et al., (2001) *PNAS* 18:10487-10492, both of which are herein incorporated by reference.

Example 8

Soybean Embryo Transformation

Soybean embryos are bombarded with a plasmid containing the ZmCkx3 sequence operably linked to a root-preferred promoter. To induce somatic embryos, cotyledons, 3-5 mm in length dissected from surface-sterilized, immature seeds of the soybean cultivar A2872, are cultured in the light or dark at 26° C. on an appropriate agar medium for six to ten weeks. Somatic embryos producing secondary embryos are then excised and placed into a suitable liquid medium. After repeated selection for clusters of somatic embryos that multiplied as early, globular-staged embryos, the suspensions are maintained as described below.

Soybean embryogenic suspension cultures can maintained in 35 ml liquid media on a rotary shaker, 150 rpm, at 26° C. with florescent lights on a 16:8 hour day/night schedule. Cultures are subcultured every two weeks by inoculating approximately 35 mg of tissue into 35 ml of liquid medium.

Soybean embryogenic suspension cultures may then be transformed by the method of particle gun bombardment (Klein, et al., (1987) Nature (London) 327:70-73, U.S. Pat. No. 4,945,050). A Du Pont Biolistic PDS1000/HE instrument (helium retrofit) can be used for these transformations.

A selectable marker gene that can be used to facilitate soybean transformation is a transgene composed of the 35S promoter from Cauliflower Mosaic Virus (Odell, et al., (1985) Nature 313:810-812), the hygromycin phosphotransferase gene from plasmid pJR225 (from E. coli; Gritz, et al., (1983) Gene 25:179-188), and the 3' region of the nopaline synthase gene from the T-DNA of the Ti plasmid of Agrobacterium tumefaciens. The expression cassette comprising the ZmCkx2 sequence operably linked to the root-preferred promoter can be isolated as a restriction fragment. This fragment can then be inserted into a unique restriction site of the vector carrying the marker gene.

To 50 µl of a 60 mg/ml 1 µm gold particle suspension is added (in order): 5 µl DNA (1 µg/µl), 20 µl spermidine (0.1 M), and 50 µl CaCl$_2$ (2.5 M). The particle preparation is then agitated for three minutes, spun in a microfuge for 10 seconds and the supernatant removed. The DNA-coated particles are then washed once in 400 µl 70% ethanol and resuspended in 40 µl of anhydrous ethanol. The DNA/particle suspension can be sonicated three times for one second each. Five microliters of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi, and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post-bombardment with fresh media containing 50 mg/ml hygromycin. This selective media can be refreshed weekly. Seven to eight weeks post-bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 9

Variants of CKX Sequences

A. Variant Nucleotide Sequences of CKX (SEQ ID NO: 2, 5, 8, 11, 52, 58, 61 or 67) That do not Alter the Encoded Amino Acid Sequence The CKX nucleotide sequences set forth in SEQ ID NO: 2, 5, 8, 11, 52, 58, 61 and 67 are used to generate variant nucleotide sequences having the nucleotide sequence of the open reading frame with about 70%, 75%, 80%, 85%, 90% and 95% nucleotide sequence identity when compared to the starting unaltered ORF nucleotide sequence of the corresponding SEQ ID NO. These functional variants are generated using a standard codon table. While the nucleotide sequence of the variants are altered, the amino acid sequence encoded by the open reading frames do not change.

B. Variant Amino Acid Sequences of CKX Polypeptides

Variant amino acid sequences of the CKX polypeptides are generated. In this example, one amino acid is altered. Specifically, the open reading frames set forth in SEQ ID NOS: 3, 6, 9, 12, 53, 59, 62 and 68 are reviewed to determine the appropriate amino acid alteration. The selection of the amino acid to change is made by consulting the protein alignment (with the other orthologs and other gene family members from various species). See, FIG. 11. An amino acid is selected that is deemed not to be under high selection pressure (not highly conserved) and which is rather easily substituted by an amino acid with similar chemical characteristics (i.e., similar functional side-chain). Using the protein alignment set forth in FIG. 11, an appropriate amino acid can be changed. Once the targeted amino acid is identified, the procedure outlined in Example 9A is followed. Variants having about 70%, 75%, 80%, 85%, 90% and 95% sequence identity to each of SEQ ID NO: 3, 6, 9, 12, 53, 59, 62 or 68 are generated using this method.

C. Additional Variant Amino Acid Sequences of CKX Polypeptides

In this example, artificial protein sequences are created having 80%, 85%, 90% and 95% identity relative to the reference protein sequence. This latter effort requires identifying conserved and variable regions from the alignments and analyses set forth in FIGS. 9, 10, and 11, and then the judicious application of an amino acid substitution table. These parts will be discussed in more detail below.

Largely, the determination of which amino acid sequences are altered is made based on the conserved regions among CKX protein or among the other CKX polypeptides. See, FIGS. 9, 10 and 11. Based on the sequence alignment, the various regions of the CKX polypeptide that can likely be altered are represented in lower case letters, while the conserved regions are represented by capital letters. It is recognized that conservative substitutions can be made in the conserved regions below without altering function. In addition, one of skill will understand that functional variants of the CKX sequence of the invention can have minor non-conserved amino acid alterations in the conserved domain.

Artificial protein sequences are then created that are different from the original in the intervals of 80-85%, 85-90%, 90-95% and 95-100% identity. Midpoints of these intervals are targeted, with liberal latitude of plus or minus 1%, for example. The amino acids substitutions will be effected by a custom Perl script. The substitution table is provided below in Table 6.

TABLE 6

Substitution Table

| Amino Acid | Strongly Similar and Optimal Substitution | Rank of Order to Change | Comment |
|---|---|---|---|
| I | L, V | 1 | 50:50 substitution |
| L | I, V | 2 | 50:50 substitution |
| V | I, L | 3 | 50:50 substitution |
| A | G | 4 | |
| G | A | 5 | |
| D | E | 6 | |
| E | D | 7 | |
| W | Y | 8 | |
| Y | W | 9 | |
| S | T | 10 | |
| T | S | 11 | |
| K | R | 12 | |
| R | K | 13 | |
| N | Q | 14 | |
| Q | N | 15 | |
| F | Y | 16 | |
| M | L | 17 | First methionine cannot change |
| H | | Na | No good substitutes |
| C | | Na | No good substitutes |
| P | | Na | No good substitutes |

First, any conserved amino acids in the protein that should not be changed is identified and "marked off" for insulation from the substitution. The start methionine will of course be added to this list automatically. Next, the changes are made.

H, C, and P are not changed in any circumstance. The changes will occur with isoleucine first, sweeping N-terminal to C-terminal. Then leucine, and so on down the list until the desired target it reached. Interim number substitutions can be made so as not to cause reversal of changes. The list is ordered 1-17, so start with as many isoleucine changes as needed before leucine, and so on down to methionine. Clearly many amino acids will in this manner not need to be changed. L, I and V will involve a 50:50 substitution of the two alternate optimal substitutions.

The variant amino acid sequences are written as output. Perl script is used to calculate the percent identities. Using this procedure, variants of the CKX polypeptides are generating having about 80%, 85%, 90% and 95% amino acid identity to the starting unaltered ORF nucleotide sequence of SEQ ID NO: 3, 6, 9, 12, 53, 59, 62 or 68.

Example 10

Downregulation of Cytokinin Catabolism

The promoters of the present invention can be used in constructs designed to downregulate cytokinin oxidase activity to prevent the adverse effects of cytokinin oxidase expression on plant performance under normal or stress conditions. For example, certain embodiments comprise a construct comprising a segment of an endogenous cytokinin oxidase promoter such that, upon expression, self-hybridization of the RNA results in formation of hairpin RNA (hpRNA), resulting in transcriptional gene silencing of the native cytokinin oxidase gene. Thus, the embodiment comprises a nucleotide sequence which, when expressed in a cell, forms a hairpin RNA molecule (hpRNA), which suppresses (i.e., reduces or eliminates) expression of the endogenous cytokinin oxidase gene from its endogenous promoter. The ability of hpRNAs to suppress expression of a gene has been described (see, e.g., Matzke, et al., (2001) Curr. Opin. Genet. Devel. 11:221-227; Scheid, et al., (2002) Proc. Natl. Acad. Sci., USA 99:13659-13662; Waterhouse and Helliwell, (2003) Nature Reviews Genetics 4:29-38; Aufsaftz, et al., (2002) Proc. Nat'l. Acad. Sci. 99(4):16499-16506; Sijen, et al., (2001) Curr. Biol. 11:436-440).

The promoter which is operably linked to the nucleotide sequence encoding the hpRNA can be any promoter that is active in plant cells, particularly a promoter that is active (or can be activated) in reproductive tissues of a plant. As such, the promoter can be, for example, a constitutively active promoter, an inducible promoter, a tissue-specific promoter, a tissue-preferred promoter, a developmental-stage-specific promoter, or a developmental-stage-preferred promoter.

A hairpin may target a single promoter or may target two or more promoters by means of a single transcribed RNA. The hairpin-encoding region may be located in any appropriate position within the construct, such as within an intron of an encoded gene or within 5' or 3' non-coding regions, or may be the sole expressed element of the construct.

Methods for preparing said constructs and transforming plants may be as previously described (for example, see, Cigan, et al., (2001) Sex Plant Reprod. 14:135-142).

Said construct for downregulating cytokinin oxidase expression may be used in combination with other constructs or methods, such as those which result in increased cytokinin biosynthesis activity.

This example demonstrates the effectiveness of this approach at down-regulating cytokinin-induced expression of ZmCkx1 in leaves. The inverted repeat constructs were prepared using a strategy designed by Cigan, et al., (2005, The Plant Journal 43:929-940).

An approximately 500 bp fragment, nucleotides 942-1470 of the ZmCkx1 promoter (Accession Number CQ895592; U.S. Pat. No. 6,921,815) was PCR amplified and cloned in inverse orientations separated by a portion of the Nos gene (nucleotide 259-568, accession number V00087). The ZmCkx1 PRO-Nos-ZmCkx1 PRO fragment was placed under transcriptional control of the Ubiquitin promoter (Ubiquitin-1) (Christensen, et al., (1992) Plant Molecular Biology 18:675) in a plasmid containing the 35S::PAT selectable marker (Unger, et al., (2001) Transgenic Research 10:409) to yield PHP24558 (FIG. 12A). A second version of the construct, PHP24773 (FIG. 12B), was obtained by inversion of the HindIII fragment by digestion and re-ligation, and screening for the inversion by restriction digests. Plasmids PHP24558 and PHP24773 were used to build corresponding co-integrate vectors PHP24865 and PHP24866, respectively, in Agrobacterium. Plasmids were introduced in Agrobacterium strain LBA4404 and used for transformation as described earlier (Zhao, et al., (1998) Maize Genetics Cooperation Newsletter 72:34-37) and at Example 7 herein.

RNA Isolation, RT-PCR and Northern Blot

Total RNA extractions were performed as previously described (Brugière, et al., (2003) Plant Physiol. 132:1228-1240). Hybridizations were performed overnight at 65° C. using the procedure previously described (Brugière, et al., (1999) Plant Cell 11:1995-2012; Abarca, (2001) Physiologia Plantarum 113:409-415). Successive washes were performed as follows: twice at 25° C. for 10 min each with 2×SSC; 0.1% (w/v) SDS (1×SSC is 150 mM NaCl and 15 mM sodium citrate), and twice for 20 min at 65° C. with 0.1×SSC; 0.1% (w/v) SDS. Blots were hybridized with $\alpha$-$^{32}$P-dCTP labeled probes corresponding to the fragment of Nos gene present in the inverted repeat or ZmCkx1. Relative mRNA abundance was quantified using a phosphor imager (Typhoon™, Molecular Dynamics, Sunnyvale, Calif.) with imaging software (ImageQuant™, Molecular Dynamics). RNA was quantified using a spectrophotometer. Semi-quantitative RT-PCR was carried out from 5 µg of total RNA using Superscript III kit from Invitrogen (Carlsbad, Calif.) according to the manufacturer's instructions. PCR was carried out using the following primers, 5'-GGTGCACGGCGAG-GAGGT-3' (SEQ ID NO: 71) and 5' TCGCCGCCGACAT-GCCGTCGTCCC-3' (SEQ ID NO: 72) using the following conditions: 94° C. 2 min, 25 cycles of 94° C. for 1 min, 62° C. for 1 min and 72° C. for 1.5 min, followed by 7 min at 72° C. After electrophoresis, the DNA amplification products were quantified by density using LabWorks analysis software (UVP, Inc., Upland, Calif.).

Cytokinin Treatment

Leaf discs (5 mm in diameter) were collected from fully expanded leaves of 8-week-old transgenic and non-transgenic plants and incubated in petri dishes containing water or water supplemented with 10 µM benzyladenine (BA). Approximately 100 discs per sample collected from individual T0 plants were used for each treatment, and discs were incubated at 25° C. for 24 h.

Expression of the Inverted Repeat Construct in T0 Plants

FIGS. 16 and 17 show the pattern of expression of the ZmCkx1 PRO-Nos-ZmCkx1 PRO inverted repeat in transgenic T0 PHP24865 and PHP24866 plants corresponding to the constructs described in FIGS. 12A and 12B, respectively. Total RNA was extracted from leaf of T0 plants harvested at the V8 stage in the greenhouse. After electrophoresis and transfer to nylon membrane, blots were probed with a DNA probe corresponding to the Nos sequence present in the hairpin. As previously seen when constitutively expressing this kind of inverted repeat in corn (Cigan, et al., (2005) supra), two major transcripts were identified in plants transformed with the constructs, most likely being the result of the absence of terminator at the 3'-end of the inverted repeat construct.

Induction of ZmCkx1 Expression by BA in Transgenic Ubi-ZmCkx1 PRO hHairpin Compared to Transgenic Control Plants Because native ZmCkx1 expression is high only in developing kernels (Brugière, et al., (2003) supra) and destructive sampling of T0 plants is undesirable, the effect of the inverted repeat constructs on ZmCkx1 cytokinin-induced expression in leaves was studied. Using the technique described in Brugière, et al., (2003, supra), leaf discs of selected PHP24865 and PHP24866 transgenic T0 plants, as well as leaf discs of transgenic control plants, were treated with 10 µM of the cytokinin benzyladenine (BA) for 24 h, and induction of ZmCkx1 was compared. The Northern blot of FIG. 15 shows a strong down-regulation of BA-induced ZmCkx1 expression in leaf discs of PHP24865 and PHP24866 transgenics compared to transgenic controls.

In order to quantify the degree of down-regulation of BA-induced ZmCkx1 expression in transgenic plants compared to controls, the radioactive signal of FIG. 15 was quantified with a phosphor imager and compared to the signal obtained after hybridization of the same blot with a probe corresponding to the ubiquitously expressed 18S RNA. The ratio of ZmCkx1 vs. 18S RNA expression was calculated, and results are presented in FIG. 16. Results show that ZmCkx1 was down-regulated by between 18% and 61% depending on the construct and the event considered. On the average, down-regulation was 50% in PHP24865 and 44% in PHP24866 (54% if not considering Event 14). As seen in FIG. 17, similar results were obtained using a semi-quantitative RT-PCR procedure with PHP24865 samples (PHP24866 samples were not tested). Results show down-regulation ranging from 58 to 69% with an average of 65% compared to transgenic control.

The promoter inverted repeat strategy was previously found to be effective for transcriptional gene silencing (Cigan, et al., (2005) supra). Here, we show that this approach is efficacious to down-regulate BA-induced ZmCkx1 expression in leaves by a measurable and reproducible extent. Expression levels were reduced by 50-60% as measured by Northern blot or semi-quantitative RT-PCR. Optimization of the construct, for example by using different sections of the promoter in hairpin configurations, and/or by using alternative promoters, may result in a stronger down-regulation effect and/or in a more tissue-preferred downregulation.

Example 11

Yield Improvement Through ZmCkx2b 3'UTR-RNAi

ZmCkx2 exists as a duplicated gene in maize, identified on Chromosome 3 (ZmCkx2a, SEQ ID NO: 1-3; NCBI CAE55200) and on Chromosome 8 (ZmCkx2b, SEQ ID NO: 67-68; NCBI CAE55201) (Massoneau, et al., 2004). The ZmCkx2b polypeptide (GenBank entry AJ606943) is 94% identical to the ZmCkx2a polypeptide of SEQ ID NO: 3.

The ZmCkx2b(TR1) genetic element (SEQ ID NO: 66) corresponds to the 3'-UTR of ZmCkx2b. The ZmCKx2b (TR1) element can be used in a hairpin construct to down-regulate the expression of ZmCkx2, improving seed yield, for example, in maize. The ZmCkx2b(TR1) sequence (SEQ ID NO: 66; see also, NM_001111693) is over 99% identical to the corresponding 3' region of ZmCkx2b (SEQ ID NO: 67). While not being bound by any particular mode of action, Applicants propose that targeted downregulation results from the activity of small interfering RNAs produced from the double-stranded RNA of a hairpin construct with significant complentarity to the target sequence, as has been previously described (McManus and Sharp, (2002) *Nature Reviews Genetics* 3:737-747; Johnston and Hobert, (2003) *Nature* 426:845-849; Brugière, et al., (1999) supra).

Data were gathered from maize plants transformed with a construct comprising the ubiquitin promoter operably linked to a 447-base-pair portion of the ZmCkx2b genomic locus (a 3' UTR segment, designated p0081.chcag31r in plasmid PHP27911; see, FIG. 18) in direct and reverse orientations, separated by a 539-base-pair Adh1 intron sequence, to produce a hairpin configuration when transcribed. The construct also comprises the UBI1Zm intron (PHI) as an enhancer and PINII as terminator. This hairpin, or a similar one, could also be expressed under the control of a drought-inducible promoter such as Rab17 (Vilardell, et al., (1991) *Plant Molecular Biology* 17(5):985-993.) Similar constructs could be created using fragments of the ZmCkx2a and/or b coding sequence in inverted repeats separated by a fragment of the Adh1 intron driven by UBI1Zm PRO. Each such exemplary construct is designed to suppress expression of the endogenous gene(s) using a hairpin strategy.

The plants were of the fast-cycling type (Gaspe/Flint) described in U.S. Patent Application Publication Number 2003/0221212. Ten plants transformed with PHP27911 were scored for (1) rate of growth to half of maximum volume ("rt halfmaxvol"); (2) rate of growth to maximum volume ("rt maxvolume"); and (3) estimated seed yield ("yield estimate") using a high-throughput system (Functional Analysis System for Traits or FASTcorn). These scores were then compared to the scores obtained for 13,968 other FASTcorn transgenic plants tested with the same system. Each of the FASTcorn plants in the pool represents an independent transformation event for an assortment of proprietary constructs tested for improved agronomic traits.

The total pool of 13,968 FASTcorn transgenic plants for which a Zscore was available for the rate to half maximum volume (Zscore rt half max vol) was first filtered to retain only those events with a Zscore>1. A Zscore of 1 indicates a value that is two standard deviations away from the mean and is therefore substantially different. Seven events out of ten events transformed with the PHP27911 construct met this criterion (FIG. 24).

A second filter was then applied to retain only those events which had a Zscore>1 for the trait rt maxvolume. Seven out of ten events corresponding to the PHP27911 construct, met this criterion alone.

Six events out of the ten generated were retained when both filters were applied (FIG. 24). Thus, a significant improvement in growth rate was observed in more than half of the PHP27911 events tested.

The total volume growth rate was determined for the ten PHP27911 events. For the six identified in FIG. 24 as meeting both criteria, a clear growth rate advantage was demonstrated relative to all FASTcorn transgenics.

FASTcorn events remaining in the pool following application of the two filters as described above (1557 events total) were further filtered to identify those with a Zscore>1 for the "yield estimate" trait. Yield estimate is calculated based on seed count and single kernel mass. Four of the six PHP27911 events retained based on the previous filters were again retained after filtering for improved yield estimate (FIG. 24). (For one of the six events, no Zscore for yield estimate was available.) These data strongly suggest that the improved growth rate observed in the PHP27911 events generally translates to improved yield estimate.

Example 12

Root-Preferred Overexpression of ZmCkx2a for Increased Root Biomass and Improved Nitrogen Use Efficiency As described in Example 4 and shown in FIGS. 5, 6 and 7, constitutive overexpression of a genomic ZmCkx2a sequence resulted in increased root growth but had negative effects on overall plant growth. In contrast, over-expression of ZmCkx2a genomic or cDNA sequences in maize using a root-specific or root-preferred promoter improves root biomass and yield of transgenic plants growing in drought-stressed or low-nitrogen conditions compared to control plants. The improved root biomass may improve the plant's ability to mine for water and/or essential nutrients, such as nitrogen, in the soil. Improved root growth may also improve resistance to insects and other biotic or abiotic stresses. Delayed leaf senescence may also result.

Preferred promoters include Zm-NAS2 promoter (U.S. patent application Ser. No. 12/030,455); Zm-Cyclo1 promoter (U.S. Pat. No. 7,268,226); Zm-Metallothionein promoters (U.S. Pat. Nos. 6,774,282, 7,214,854 and 7,214,855 (also known as RootMET2)); ZM-MSY promoter (SEQ ID NO: 64; U.S. Patent Application Ser. No. 60/971,310 filed Sep. 11, 2007) or ZRP promoter (SEQ ID NO: 65; see, U.S. Pat. No. 5,633,363); constructs may also include one or more of the CaMV35S enhancer, Odell, et al., (1988) *Plant Mol. Biol.* 10:263-272, the ADH1 INTRON1 (Callis, et al., (1987) *Genes and Dev.* 1:1183-1200), the UBI1ZM INTRON (PHI) as an enhancer, and PINII as terminator.

Maize was transformed as described in Zhao, et al., (1998) *Maize Genetics Cooperation Newsletter* 72:34-37, and at Example 7 herein, but with a construct comprising either the ZmCyclo1 promoter (plasmid PHP28930) or the ZmROOT-MET2 promoter (plasmid PHP28937) operably linked to the ZmCkx2a genomic sequence (SEQ ID NO: 1) and the PinII terminator (FIG. 19). Plants were regenerated and pollinated, and next-generation plants were observed in the field. Both constructs resulted in increased branching on brace roots (FIG. 20A) and increased root mass overall (FIG. 20B), with no (PHP28937) or minimal (PHP28930) reduction in above-ground biomass (FIG. 21). Northern data indicated ROOT-MET2-driven expression (FIG. 25A) was more tightly targeted to root tissue than was ZmCyclo1-driven expression (FIG. 25B). Ears (FIG. 26) harvested from the transgenic plants confirmed that more favorable ear phenotypes and yield result from more highly specific root overexpression of ZmCkx2a. Optimization of the constructs (FIG. 22) will further improve the positive effect on roots while avoiding negative impact on above-ground growth.

Also, maize was transformed as described in Zhao, et al., (1998) *Maize Genetics Cooperation Newsletter* 72:34-37, but with a construct comprising either the NAS2 promoter (PHP22524) or the ZRP promoter and Adh1 intron (PHP22532) operably linked to ZmCkx2a cDNA (SEQ ID NO: 2). This root-specific overexpression of ZmCkx2 resulted in yield improvement under conditions of limited nitrogen. FIG. 27 shows the increase in hybrid grain yield for two events of PHP22514 (ZM-NAS2 PRO::ZM-CKX2) in limited nitrogen environments at Iowa and California test locations. Yield data from 6 replicates of each event per location are compared to that of the bulked transgenic nulls for the construct (NULL). Asterisks (*) mark those that are significantly different from the NULL at P<0.1. The yield data from hybrid 3245 (WT) are also included and shown to be not different from that of the NULL.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. An isolated polynucleotide comprising a nucleotide sequence selected from the group consisting of:
   (a) a nucleotide sequence comprising SEQ ID NO: 1;
   (b) a nucleotide sequence encoding an amino acid sequence comprising SEQ ID NO: 3; and
   (c) a nucleotide sequence comprising at least 95% sequence identity to the coding sequence of SEQ ID NO: 1, wherein said polynucleotide encodes a polypeptide having cytokinin oxidase activity.

2. An expression cassette comprising the polynucleotide of claim 1 operably linked to a root-preferred promoter that drives expression in a plant.

3. A *Zea mays* plant comprising the expression cassette of claim 2.

4. The plant of claim 3, wherein said plant produces more numerous and/or larger ears compared to a control plant.

5. The expression cassette of claim 2, wherein said root-preferred promoter is the NAS2 promoter or the ROOTMET2 promoter.

6. The plant of claim 3, wherein said plant has increased total seed weight when compared to a control plant.

7. The plant of claim 3, wherein stress tolerance of said plant is improved when compared to a control plant.

8. A transformed seed of the plant of claim 3, wherein said seed comprises the isolated polynucleotide introduced into said plant.

9. A method for increasing the number and/or size of ears harvested from a *Zea mays* plant, comprising introducing into said plant a polynucleotide comprising a nucleotide sequence selected from the group consisting of:
   (a) a nucleotide sequence comprising the coding sequence of SEQ ID NO:1;
   (b) a nucleotide sequence encoding an amino acid sequence comprising SEQ ID NO: 3; and
   (c) a nucleotide sequence having at least 95% sequence identity to the full length of the coding sequence of SEQ ID NO: 1, wherein said polynucleotide encodes a polypeptide having cytokinin oxidase activity and wherein said polynucleotide is operably linked to a root-preferred promoter.

10. The method of claim 9, wherein the promoter is the NAS2 promoter or the ROOTMET2 promoter.

11. The method of claim 10, wherein the promoter is operably linked to a polynucleotide encoding a polypeptide at least 95% identical to SEQ ID NO: 3, and wherein said polypeptide has cytokinin oxidase activity.

12. The plant of claim 7, wherein said stress tolerance is reflected in yield improvement under conditions of limited nitrogen, compared to yield of a control plant.

* * * * *